United States Patent
Efremov et al.

(10) Patent No.: US 11,590,111 B2
(45) Date of Patent: *Feb. 28, 2023

(54) MACROCYCLIC AZOLOPYRIDINE DERIVATIVES AS EED AND PRC2 MODULATORS

(71) Applicant: Fulcrum Therapeutics, Inc., Cambridge, MA (US)

(72) Inventors: Ivan Viktorovich Efremov, Chestnut Hill, MA (US); Steven Kazmirski, Sherborn, MA (US); Qingyi Li, Somerville, MA (US); Lorin A. Thompson, III, Cohasset, MA (US); Owen Brendan Wallace, Brookline, MA (US); Shawn Donald Johnstone, Saint-Lazare (CA); Feng Zhou, Dollard-des-Ormeaux (CA); Peter Rahl, Natick, MA (US)

(73) Assignee: Fulcrum Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/178,637

(22) Filed: Feb. 18, 2021

(65) Prior Publication Data

US 2022/0160686 A1    May 26, 2022

Related U.S. Application Data

(63) Continuation of application No. 16/858,404, filed on Apr. 24, 2020, now Pat. No. 10,973,805, which is a continuation of application No. PCT/US2020/022724, filed on Mar. 13, 2020.

(60) Provisional application No. 62/819,064, filed on Mar. 15, 2019.

(51) Int. Cl.
| | |
|---|---|
| *A61K 31/4355* | (2006.01) |
| *A61K 31/437* | (2006.01) |
| *A61K 45/06* | (2006.01) |
| *C07D 498/16* | (2006.01) |
| *C07D 498/22* | (2006.01) |

(52) U.S. Cl.
CPC ........ *A61K 31/4355* (2013.01); *A61K 31/437* (2013.01); *A61K 45/06* (2013.01); *C07D 498/16* (2013.01); *C07D 498/22* (2013.01)

(58) Field of Classification Search
CPC .. A61K 31/4355; A61K 31/437; A61K 45/06; C07D 498/16; C07D 498/22
See application file for complete search history.

(56) References Cited

U.S. PATENT DOCUMENTS

| | | | |
|---|---|---|---|
| 9,730,925 B2 | 8/2017 | Creasy et al. | |
| 10,342,786 B2 | 7/2019 | Cacace et al. | |
| 10,537,560 B2 | 1/2020 | Cacace et al. | |
| 10,689,378 B2 | 6/2020 | Chan et al. | |
| 10,973,805 B2 * | 4/2021 | Efremov | A61K 31/437 |
| 2015/0366886 A1 | 12/2015 | Smith | |
| 2018/0289677 A1 | 10/2018 | Wang et al. | |
| 2020/0255451 A1 | 8/2020 | Braje et al. | |
| 2020/0360353 A1 | 11/2020 | Efremov et al. | |

FOREIGN PATENT DOCUMENTS

| | | |
|---|---|---|
| WO | WO-2017221092 A1 | 12/2017 |
| WO | WO-2017221100 A1 | 12/2017 |
| WO | 2018013929 A1 | 1/2018 |
| WO | WO-2018/140934 A1 | 8/2018 |
| WO | 2020106876 A2 | 5/2020 |
| WO | 2022212746 A1 | 10/2022 |

(Continued)

OTHER PUBLICATIONS

Kotzin, Nature, vol. 537, 239-243, Sep. 2016. (Year: 2016).*
Matson, Blood, vol. 13 (Supplement 1), Nov. 2021, 2018. (Year: 2021).*
Shi, Oncogene, Feb. 2013, vol. 32(7), 930-938. (Year: 2013).*
International Search Report and Written Opinion dated May 28, 2020 for International Application No. PCT/US2020/022724, 12 pages.
Blobel, G. A et al., "An international effort to cure a global health problem: A report on the 19th Hemoglobin Switching Conference," Experimental Hematology, 43:821-837 (2015).

(Continued)

*Primary Examiner* — D Margaret M Seaman
(74) *Attorney, Agent, or Firm* — Goodwin Procter LLP

(57) ABSTRACT

The invention relates to modulators of Embryonic Ectoderm Development (EED) and/or Polycomb Repressive Complex 2 (PRC2) useful in the treatment of disorders and diseases associated with EEC and PRC2, being macrocyclic azolopyridine derivatives and compositions thereof of Formula I:

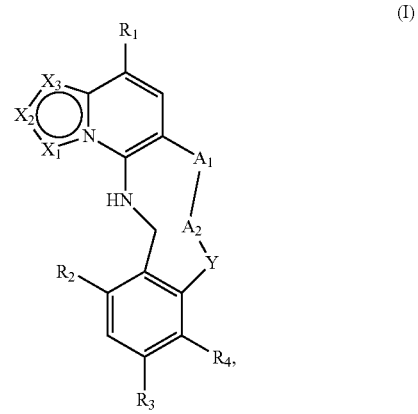

(I)

or a pharmaceutically acceptable salt, prodrug, solvate, hydrate, enantiomer, isomer, or tautomer thereof, wherein $X_1$, $X_2$, $X_3$, $A_1$, $A_2$, Y, $R_1$, $R_2$, $R_3$, and $R_4$ are as described herein.

10 Claims, No Drawings

Specification includes a Sequence Listing.

(56) References Cited

FOREIGN PATENT DOCUMENTS

| WO | 2022212748 A1 | 10/2022 |
| WO | 2022232435 A1 | 11/2022 |

OTHER PUBLICATIONS

Lettre, G. & Bauer, D. E., "Fetal haemoglobin in sickle-cell disease: from genetic epidemiology to new therapeutic strategies," Lancet, 387:2554-2564 (2016).

Letvin, N. L. et al., "Augmentation of Fetal-Hemoglobin Production in Anemic Monkeys by Hydroxyurea," N Engl J Med, 310(14):869-873 (1984).

Li, Q. et al., "Locus control regions," Blood, 100:3077-3086 (2002).

Margueron, R. & Reinberg, D., "The Polycomb complex PRC2 and its mark in life," Nature, 469:343-349 (2011).

Moutouh-De Parseval, L. A et al., "Pomalidomide and lenalidomide regulate erythropoiesis and fetal hemoglobin production in human CD34+ cells," J Clin Invest., 118(1):248-258 (2008).

Paikari, A & Sheehan, V. A, "Fetal haemoglobin induction in sickle cell disease," British Journal of Haematology, 180: 189-200 (2018). First published on line Nov. 16, 2017 doi: 10.1111/bjh.15021.

Renneville, A et al., "EHMT1 and EHMT2 inhibition induces fetal hemoglobin expression," Blood,126(16): 1930-1939 (2015).

Shi, Y. et al., "Structure of the PRC2 complex and application to drug discovery," Acta Pharmacologica Sinica, 38:963-976 (2017).

Stamatoyannopoulos, G., "Control of globin gene expression during development and erythroid differentiation," Experimental Hematology, 33:259-271 (2005).

Abkowitz, JL. "Retrovirus-induced feline pure red blood cell aplasia pathogenesis and response to suramin," Blood, 77(7): 1442-1451.

International Search Report and Written Opinion dated Jun. 24, 2020 for Internation Application Np. PCT/US2019/062461, 21 pages.

Zhou, H et al.,"A potent small-molecule inhibitor of the DCN1-UBC12 interaction that selectively blocks cullin 3 neddylation," Nature Communications, 8(1:)1150.

Florence, Alastair J., "Polymorph screening in pharmaceutical development", European Pharmaceutical Review, Aug. 19, 2010,<https://www.europeanpharmaceuticalreview.com/article/3659/polymorph-screening-in-pharmaceutical-development/>.

Lee, Eun Hee, "A practical guide to pharmaceutical polymorph screening & selection", Asian Journal of Pharmaceutical Sciences, vol. 9, No. 4, Mar. 16, 2014, pp. 163-175.

Morissette, Sherry L. et al., "High-throughput crystallization: polymorphs, salts, co-crystals and solvates of pharmaceutical solids", Advaned Drug Delivery Reviews, vol. 56, No. 3, Feb. 23, 2004, pp. 275-300.

Bastin, Richard J. et al., "Salt Selection and Optimisation Procedures for Pharmaceutical New Chemical Entities", Organic Process Research & Development, American Chemical Society, US, vol. 4, No. 5, Jul. 19, 2000, pp. 427-435.

International Search Report and Written Opinion for International Application No. PCT/US2022/022893 dated Jun. 24, 2022. 10 pages.

International Search Report and Written Opinion for International Application No. PCT/US2022/026795 dated Aug. 2, 2022. 13 pages.

Lesney, Mark S., "Unique oral drug candidate designed to overcome sickle cell disease", MDedge, Federal Practitioner, Apr. 16, 2021, <https://www.mdedge.com/fedprac/article/238801/anemia/unique-oral-drug-candidate-designed-overcome-sickle-cell-disease>.

Efremov, Ivan V., et al., "Discovery of clinical candidate FTX-6058: a potent, orally bioavailable upregulator of fetal emoglobin for treatment of sickle cell disease", 2021 Spring ACS National Meeting, Apr. 16, 2021, <https://vww.fulcrumtx.com/wp-content/uploads/Discovery_of_clinical_candidate_FTX-6058.pdf>.

Eich, Marie-Lisa et al., "F/H2-Targeted Therapies in Cancer: Hype or a Reality", Cancer Research, vol. 80, No. 24, Dec. 15, 2020, pp. 5449-5458.

Yin, Jiawei et al., "BCL11 A: a potential diagnostic biomarker and therapeutic target in human diseases", Cell Death and Disease, vol. 39, No. 11, Nov. 29, 2019, p. 20190604.

Moody, Rebecca Reed, et al., "Probing the interaction between the histone methyltransferase/deacetylase subunit RBBP4/7 and the transcription factor BCL11A in epigenetic complexes", Journal of Biological Chemistry, vol. 293, No. 6, Feb. 1, 2018, pp. 2125-2136.

Anonymous, "Fulcrum Therapeutics Announces Additional HBG mRNA", Dec. 6, 2021, <https://www. globenewswire.com/Ne/news-release/2021/12/06/2346419/0/en/Fulcrum-Therapeutics-Announces-Additional-HBG-mRNA-lnduction-from-Higher-Dose-Cohorts-in-Phase-1-Healthy-Adult-Volunteer-Trial-of-FTX-6058-for-Sickle-Cell-Disease-and-New-Preclinic.html>.

International Search Report and Written Opinion for International Application No. PCT/US2022/022895 dated Jun. 23, 2022. 10 pages.

\* cited by examiner

SEQUENCE LISTING

<160> NUMBER OF SEQ ID NOS: 4

<210> SEQ ID NO 1
<211> LENGTH: 147
<212> TYPE: PRT
<213> ORGANISM: Homo sapiens

<400> SEQUENCE: 1

```
Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45
```

```
Leu Ser Ser Ala Ser Ala Ile Met Gly Asn Pro Lys Val Lys Ala His
        50                  55                  60

Gly Lys Lys Val Leu Thr Ser Leu Gly Asp Ala Ile Lys His Leu Asp
 65                  70                  75                  80

Asp Leu Lys Gly Thr Phe Ala Gln Leu Ser Glu Leu His Cys Asp Lys
                 85                  90                  95

Leu His Val Asp Pro Glu Asn Phe Lys Leu Leu Gly Asn Val Leu Val
                100                 105                 110

Thr Val Leu Ala Ile His Phe Gly Lys Glu Phe Thr Pro Glu Val Gln
                115                 120                 125

Ala Ser Trp Gln Lys Met Val Thr Ala Val Ala Ser Ala Leu Ser Ser
        130                 135                 140

Arg Tyr His
145

<210> SEQ ID NO 2
<211> LENGTH: 147
<212> TYPE: PRT
<213> ORGANISM: Homo sapiens

<400> SEQUENCE: 2

Met Gly His Phe Thr Glu Glu Asp Lys Ala Thr Ile Thr Ser Leu Trp
 1               5                  10                  15

Gly Lys Val Asn Val Glu Asp Ala Gly Gly Glu Thr Leu Gly Arg Leu
                 20                  25                  30

Leu Val Val Tyr Pro Trp Thr Gln Arg Phe Phe Asp Ser Phe Gly Asn
             35                  40                  45

Leu Ser Ser Ala Ser Ala Ile Met Gly Asn Pro Lys Val Lys Ala His
        50                  55                  60

Gly Lys Lys Val Leu Thr Ser Leu Gly Asp Ala Ile Lys His Leu Asp
 65                  70                  75                  80

Asp Leu Lys Gly Thr Phe Ala Gln Leu Ser Glu Leu His Cys Asp Lys
                 85                  90                  95

Leu His Val Asp Pro Glu Asn Phe Lys Leu Leu Gly Asn Val Leu Val
                100                 105                 110

Thr Val Leu Ala Ile His Phe Gly Lys Glu Phe Thr Pro Glu Val Gln
                115                 120                 125

Ala Ser Trp Gln Lys Met Val Thr Gly Val Ala Ser Ala Leu Ser Ser
        130                 135                 140

Arg Tyr His
145

<210> SEQ ID NO 3
<211> LENGTH: 142
<212> TYPE: PRT
<213> ORGANISM: Homo sapiens

<400> SEQUENCE: 3

Met Val Leu Ser Pro Ala Asp Lys Thr Asn Val Lys Ala Ala Trp Gly
 1               5                  10                  15

Lys Val Gly Ala His Ala Gly Glu Tyr Gly Ala Glu Ala Leu Glu Arg
                 20                  25                  30

Met Phe Leu Ser Phe Pro Thr Thr Lys Thr Tyr Phe Pro His Phe Asp
             35                  40                  45

Leu Ser His Gly Ser Ala Gln Val Lys Gly His Gly Lys Lys Val Ala
        50                  55                  60
```

```
Asp Ala Leu Thr Asn Ala Val Ala His Val Asp Asp Met Pro Asn Ala
 65                  70                  75                  80

Leu Ser Ala Leu Ser Asp Leu His Ala His Lys Leu Arg Val Asp Pro
                 85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140

<210> SEQ ID NO 4
<211> LENGTH: 142
<212> TYPE: PRT
<213> ORGANISM: Homo sapiens

<400> SEQUENCE: 4

Met Val Leu Ser Pro Ala Asp Lys Thr Asn Val Lys Ala Ala Trp Gly
  1               5                  10                  15

Lys Val Gly Ala His Ala Gly Glu Tyr Gly Ala Glu Ala Leu Glu Arg
             20                  25                  30

Met Phe Leu Ser Phe Pro Thr Thr Lys Thr Tyr Phe Pro His Phe Asp
         35                  40                  45

Leu Ser His Gly Ser Ala Gln Val Lys Gly His Gly Lys Lys Val Ala
     50                  55                  60

Asp Ala Leu Thr Asn Ala Val Ala His Val Asp Asp Met Pro Asn Ala
 65                  70                  75                  80

Leu Ser Ala Leu Ser Asp Leu His Ala His Lys Leu Arg Val Asp Pro
                 85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140
```

MACROCYCLIC AZOLOPYRIDINE DERIVATIVES AS EED AND PRC2 MODULATORS

RELATED APPLICATIONS

This application is a continuation of U.S. patent application Ser. No. 16/858,404, filed Apr. 24, 2020, which is a continuation of International Patent Application No. PCT/US2020/022724, filed Mar. 13, 2020, which claims the benefit of, and priority to, U.S. Provisional Patent Application No. 62/819,064, filed on Mar. 15, 2019, the entire contents of each of which are incorporated by reference in their entireties.

DESCRIPTION OF THE TEXT FILE SUBMITTED ELECTRONICALLY

The present application contains a Sequence Listing, which has been submitted in ASCII format via EFS-Web and is hereby incorporated by reference in its entirety. Said ASCII copy, created on Mar. 11, 2020, is named "FULC-034-01WO_SeqList.txt" and is 6 KB in size.

FIELD OF INVENTION

The present disclosure relates to macrocyclic azolopyridine derivatives, compositions comprising these compounds, methods of treating diseases or disorders associated with Embryonic Ectoderm Development (EED) and/or Polycomb Repressive Complex 2 (PRC2), e.g., by modulating gene expression, and methods of synthesis of these compounds.

BACKGROUND OF THE INVENTION

Polycomb group (PcG) proteins are a family of chromatin modifying enzymes that play a key role in gene expression and are dysregulated in many human diseases. The PcG family includes two classes of Polycomb Repressive Complexes (PRCs), namely Polycomb Repressive Complex 1 (PRC1) and Polycomb Repressive Complex 2 (PRC2). PRC2 includes SUZ12 (suppressor of zeste 12), EED (embryonic ectoderm development) and the catalytic subunit, EZH2 (enhancer of zeste homolog 2), and represses genes by methylating histone H3 lysine 27 (H3K27me3) at and around the promoter regions of genes. This critical component of chromatin regulation is involved in modulation of gene transcription and plays crucial function in development, differentiation, and regeneration. Although EZH2 is the catalytic subunit, PRC2 minimally requires EED and SUZ12 for its methyltransferase activity. EED, SUZ12 and EZH2 have been found to be overexpressed in many cancers, which include but are not limited to hepatocellular carcinoma, breast cancer, prostate cancer, etc. Activating mutations in EZH2 have been found in FL (follicular lymphoma) and DLBCL (diffuse large B cell lymphoma) patients. EED normally mediates repression of gene activity by binding to di- and trimethylated lysine 27 of histone 3 where it allosterically activates EZH2 activity of PRC2. EED has also been reported to recruit PRC1 to H3K27me3 loci and to enhance PRC1 mediated H2A ubiquitin E3 ligase activity.

Taken together, EED is a critical regulator of PRC2 in the silencing of expression of genes and gene clusters involved in development including but not limited to fetal orthologues (i.e. gamma globin), Hox genes, X chromosome inactivation, etc. Thus, EED provides a pharmacologic target for the treatment of diseases or disorders to impact transcription of specific target genes in blood and other tissues. The need exists for small molecules that modulate EED and/or PRC2.

SUMMARY OF THE INVENTION

A first aspect of the invention relates to compounds of Formula I:

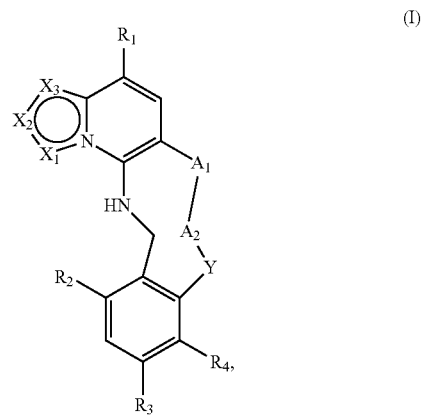

(I)

and pharmaceutically acceptable salts, prodrugs, solvates, hydrates, enantiomers, isomers, and tautomers thereof, wherein:

$X_1$, $X_2$, and $X_3$ are independently N or $C(R_5)$, provided that $X_1$, $X_2$, and $X_3$ are not all N and at least one of $X_1$, $X_2$, or $X_3$ is N;

$A_1$ is a bond, —$C(R_8)(R_9)$—, —O—, —NRs, —S—, —S(O)—, or —$SO_2$—;

$A_2$ and Y are independently at each occurrence —$C(R_8)(R_9)$—, —O—, —NRs, —S—, —S(O)—, or —$SO_2$—;

$R_1$ is H, halogen, —$NR_8R_9$, —$P(O)(OR_8)(OR_9)$, —$C(O)R_8$, —$C(O)NR_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl, wherein the alkyl, alkoxy, alkenyl, alkynyl, cycloalkyl, cycloalkenyl, spirocycloalkyl, spiroheterocyclyl, heterocyclyl, aryl, or heteroaryl is optionally substituted with one or more $R_6$;

$R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$;

$R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, or $R_4$ and $R_9$ when taken together can form $C_3$-$C_{10}$ cycloalkyl, $C_5$-$C_8$ cycloalkenyl, heterocyclyl, aryl, or heteroaryl, wherein the cycloalkyl, cycloalkenyl, heterocyclyl, aryl, or heteroaryl is optionally substituted with one or more $R_{10}$;

$R_5$ is H, halogen, —CN, —$OR_8$, —$NR_8R_9$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, wherein alkyl, alkenyl, alkynyl, cycloalkyl, cycloalkenyl, heterocyclyl, aryl, or heteroaryl is optionally substituted with one or more $R_7$;

$R_6$ is independently at each occurrence oxo, halogen, —CN, OH, —$NR_8R_9$, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkenyl, alkynyl, cycloalkyl, heterocyclyl, aryl, or heteroaryl is optionally substituted with one or more $R_{10}$; or two $R_6$ can combine to form $C_3$-$C_{10}$ cycloalkyl, $C_5$-$C_8$ cycloalkenyl, heterocyclyl, aryl, or heteroaryl, wherein the cycloalkyl, cycloalkenyl, heterocyclyl, aryl, or heteroaryl is optionally substituted with one or more $R_{10}$;

$R_7$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl;

$R_8$ is independently at each occurrence H, OH, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$;

$R_9$ is independently at each occurrence H, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$;

or $R_8$ and $R_9$ when taken together form a $C_3$-$C_6$ cycloalkyl or heterocyclyl, wherein the cycloalkyl or heterocyclyl is optionally substituted with $R_{10}$; and $R_{10}$ is independently at each occurrence oxo, halogen, —CN, —$OR_{11}$, —$C(O)R_{11}$, —$C(O)OR_{11}$, —$C(O)NR_{11}R_{12}$, —$NR_{11}R_{12}$, —$NR_{11}C(O)R_{12}$, —$S(O)R_{11}$, —$S(O)_2R_{11}$, —$NR_{11}S(O)_2R_{12}$, —$S(O)_2NR_{11}R_{12}$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl; and $R_{11}$ and $R_{12}$ are independently H, $C_1$-$C_6$ alkyl, $C_1$-$C_6$ haloalkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

Another aspect of the invention relates to a pharmaceutical composition comprising a compound of Formula I and a pharmaceutically acceptable carrier. The pharmaceutically acceptable carrier may further include an excipient, diluent, or surfactant.

Another aspect of the invention is directed to a method of treating a disease or disorder associated with modulation of embryonic ectoderm development (EED). The method involves administering to a patient in need thereof an effective amount of the compound of Formula I.

Another aspect of the invention relates to a method of treating a disease or disorder associated with modulation of Polycomb Repressive Complex 2 (PRC2). The method comprises administering to a patient in need thereof an effective amount of the compound of Formula I.

The present invention further provides methods of treating a cancer selected from diffused large B cell lymphoma, follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neuroblastoma, schwannoma, glioma, glioblastoma and astrocytoma, cervical cancer, colon cancer, melanoma, endometrial cancer, esophageal cancer, head and neck cancer, lung cancer, nasopharyngeal carcinoma, ovarian cancer, pancreatic cancer, renal cell carcinoma, rectal cancer, thyroid cancers, parathyroid tumors, uterine tumors, and soft tissue sarcomas.

The present invention further provides methods of a blood disorder selected from Acute lymphoblastic leukemia (ALL), Acute myeloid leukemia (AML) (e.g., acute promyelocytic leukemia, APL), Amyloidosis, Anemia, Aplastic anemia, Bone marrow failure syndromes, Chronic lymphocytic leukemia (CLL), Chronic myeloid leukemia (CML), Deep vein thrombosis (DVT), Diamond-Blackfan anemia, Dyskeratosis congenita (DKC), Eosinophilic disorder, Essential thrombocythemia, Fanconi anemia, Gaucher disease, Hemochromatosis, Hemolytic anemia, Hemophilia, Hereditary spherocytosis, Hodgkin's lymphoma, Idiopathic thrombocytopenic purpura (ITP), Inherited bone marrow failure syndromes, Iron-deficiency anemia, Langerhans cell histiocytosis, Large granular lymphocytic (LGL) leukemia, Leukemia, Leukopenia, Mastocytosis, Monoclonal gammopathy, Multiple myeloma, Myelodysplastic syndromes (MDS), Myelofibrosis, Myeloproliferative neoplasms (MPN), Non-Hodgkin's lymphoma, Paroxysmal nocturnal hemoglobinuria (PNH), Pernicious anemia (B12 deficiency), Polycythemia vera, *Porphyria*, Post-transplant lymphoproliferative disorder (PTLD), Pulmonary embolism (PE), Shwachman-Diamond syndrome (SDS), sickle cell disease (SCD), Thalassemia (e.g., β-thalassemia), Thrombocytopenia, Thrombotic thrombocytopenic purpura (TTP), Venous thromboembolism, Von Willebrand disease, and Waldenstrom's macroglobulinemia (lymphoplasmacytic lymphoma).

The present invention further provides methods of treating sickle cell disease (SCD) or β-thalassemia. The method comprises administering to a patient in need thereof an effective amount of the compound of Formula I.

The present invention further provides methods of treating thoracic aortic aneurysm, coronary heart disease, stenotic disease, pulmonary artery hypertension (PAH), liver fibrosis, allergic inflammation, retinitis pigmentosa, septic shock, herpes simplex virus, human cytomegalovirus, α-thalassemia, familial atrial fibrillation, common variable immunodeficiency, aneurysm-osteoarthritis syndrome, and acquired immunodeficiency syndrome. The method comprises administering to a patient in need thereof an effective amount of the compound of Formula I.

The present invention further provides use of a compound of Formula I for treating a disease or disorder associated with the modulation of embryonic ectoderm development (EED).

The present invention further provides use of a compound of Formula I for treating a disease or disorder associated with the modulation of Polycomb Repressive Complex 2 (PRC2).

The present invention further provides a compound of Formula I for use in the manufacture of a medicament for treating a disorder or disease associated with embryonic ectoderm development (EED).

The present invention further provides a compound of Formula I for use in the manufacture of a medicament for treating a disorder or disease associated with Polycomb Repressive Complex 2 (PRC2).

DETAILED DESCRIPTION OF THE INVENTION

EED mediates repression of gene activity by binding to di- and trimethylated lysine 27 of histone 3 where it allosterically activates the methyltransferase activity of PRC2, functions to recruit PRC1 to H3K27me3 loci, enhances PRC1 mediated H2A ubiquitin E3 ligase activity and regulates PRC2 in the silencing of expression of genes and gene clusters involved in development, i.e., Hox genes, and in X chromosome inactivation. Thus, EED and/or PRC2 provides a pharmacological target for the diseases or disorders, including cancers, to impact transcription.

Hemoglobin is the critical protein involved in oxygen transport throughout the body of vertebrates. It is found in red blood cells and consists of two α subunits and two β subunits. The composition of hemoglobin is developmentally regulated where the human genome encodes multiple versions of these proteins that are expressed during distinct stages of development (Blobel et al., Exp. Hematol. 2015, incorporated herein by reference; Stamatoyannopoulos G, Exp. Hematol. 2005, incorporated herein by reference). In general, fetal hemoglobin (HbF) is composed of two subunits of hemoglobin γ (HBγ) and two subunits of hemoglobin α (HBα) and adult hemoglobin (HbA) is composed of two subunits of hemoglobin β (HBβ) and two subunits of HBα. Thus, the β subunit utilized during the fetal stage of development is (HBγ) and switches to hemoglobin β (HBβ) after birth. Red blood cell disorders like sickle cell disease (SCD) and β-thalassemias are caused by alterations within the gene for the hemoglobin β (HBβ) subunit. SCD is an autosomal recessive disease caused by a single mutation in both copies of the HBB gene (E6V). A fetal ortholog of HBβ, hemoglobin γ (HBγ) can reverse disease-related pathophysiology in these disorders by also forming complexes with the required hemoglobin α subunit (Paikari and Sheehan, Br. J. Haematol. 2018, incorporated herein by reference; Lettre and Bauer, Lancet 2016, incorporated herein by reference). Because β-like globin expression is developmentally regulated, with a reduction in the fetal ortholog (γ) occurring shortly after birth concomitantly with an increase in the adult ortholog (β), it has been postulated that maintaining expression of the anti-sickling γ ortholog may be of therapeutic benefit in children and adults.

The developmental regulation of the expression of β-like subunits has been the focus of intense studies for decades (Li et al. Blood 2002, incorporated herein by reference). All five β-like subunits in humans reside on chromosome 11 where their genomic location corresponds to their temporal expression pattern. A distal cluster of enhancer elements, called the locus control region (LCR), coordinates the expression pattern at the R globin locus where multiple transcription factors including GATA1, GATA2, KLF1, KLF2, and MYB and TAL1 bind at specific locations within the LCR at specific times in development. The five human β-like subunits are epsilon (HBE1; ε), gammaG (HBG2; γ), gammaA (HBG1; γ), delta (HBD; δ) and beta (HBB; β). HBE1 is expressed during embryonic development, HBG1 and HBG2 are expressed during fetal development, and HBD and HBB are expressed in adults. The HBG1 and HBG2 genes encode identical proteins except for a single amino acid change at residue 136 (HBG1=gly; HBG2=ala). Functionally, however, upregulation of either gene can compensate for mutant or defect adult HBβ.

Sickle cell disease (SCD) is caused by homozygous mutations in the HBB gene product (E6V) that results in a mutant hemoglobin protein (HbS). Under deoxygenated conditions, the HbS protein polymerizes which leads to abnormal red blood cell morphology. This abnormal morphology can lead to multiple pathologic symptoms including vaso-occlusion, pain crises, pulmonary hypertension, organ damage, and stroke. Expression of the fetal hemoglobin protein can reverse the SCD pathophysiology through inhibiting HbS polymerization and morphologically defective red blood cells. SCD affects millions of people worldwide and is the most common inherited blood disorder in the United States (70,000-80,000 Americans). SCD has a high incidence in African Americans where it is estimated to occur in 1 in 500 individuals. β-thalassemia is caused by mutations in the HBB gene and is the result of reduced hemoglobin production. The mutations in the HBB gene typically reduce the production of adult β-globin protein which leads to low levels of adult hemoglobin, HbA. This leads to a shortage of red blood cells and a lack of oxygen distribution throughout the body. Patients with β-thalassemias can have weakness, fatigue and are at risk of developing abnormal blood clots. Thousands of infants are born with β-thalassemia each year where symptoms are typically detected within the first two years of life. The identification of factors that regulate the expression of fetal hemoglobin could be useful targets for the treatment of SCD and β-thalassemias as upregulation of fetal hemoglobin could compensate for mutant HbS protein in SCD or a lack of HbA in β-thalassemias.

Based on clinical and preclinical studies, upregulation of hemoglobin γ (HBγ) is the proposed mechanism for compounds including Palmolidomide and Hydroxyurea and targets including EHMT1/EHMT2 and LSD1 (Moutouh-de Parseval et al. J. Clin. Invest. 2008, incorporated herein by reference; Letvin et al. NEJM 1984, incorporated herein by reference; Renneville et al. Blood 2015, incorporated herein by reference; Shi et al. Nature Med. 2015, incorporated herein by reference). We discovered that treatment with inhibitors of Polycomb Repressive Complex 2 (PRC2) function through targeting the EED subunit leads to HBγupregulation.

The PRC2 complex is an evolutionarily conserved multi-subunit chromatin regulatory complex that functions in repression of gene expression (Margueron and Reinberg, Nature 2011, incorporated herein by reference). The four core PRC2 subunits are EED, SUZ12, RbAp48 and EZH1 or EZH2. EZH1 and EZH2 contain methyltransferase activity and catalyze trimethylation of lysine 27 on histone H3 (H3K27me3). The EED subunit can bind to the H3K27me3 mark and stimulate EZH2 methyltransferase activity. Additional subunits can associate with PRC2 that may impact complex localization on chromatin in specific regions of the genome which leads to the formation of H3K27me3-marked chromatin domains. The deposition of the H3K27me3 modification is typically associated with the repression of gene expression.

The present invention provides, inter alia, modulators of EED and/or PRC2, and prophylactic measures to treat diseases and disorders associated with EED and/or PRC2.

In a first aspect, the invention provides compounds of Formula I:

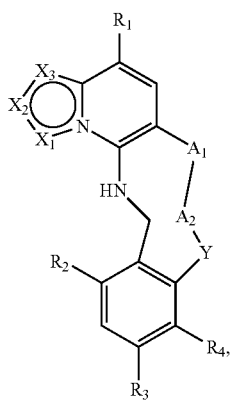
(I)

and pharmaceutically acceptable salts, prodrugs, solvates, hydrates, enantiomers, isomers, and tautomers thereof, wherein $X_1$, $X_2$, $X_3$, $A_1$, $A_2$, Y, $R_1$, $R_2$, $R_3$, and $R_4$ are as described above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, CN, —COOH, —CH$_2$CN, —O—C$_1$-C$_6$ alkyl, C$_1$-C$_6$ alkyl, —OC$_2$-C$_6$ alkenyl, —OC$_2$-C$_6$ alkynyl, —C$_2$-C$_6$ alkenyl, —C$_2$-C$_6$ alkynyl, —OH, —OP(O)(OH)$_2$, —OC(O)C$_1$-C$_6$ alkyl, —C(O)C$_1$-C$_6$ alkyl, —OC(O)OC$_1$-C$_6$ alkyl, NH$_2$, NH(C$_1$-C$_6$ alkyl), N(C$_1$-C$_6$ alkyl)$_2$, —NHC(O)C$_1$-C$_6$ alkyl, —C(O)NHC$_1$-C$_6$ alkyl, —S(O)$_2$—C$_1$-C$_6$ alkyl, —S(O)NHC$_1$-C$_6$ alkyl, and S(O)N(C$_1$-C$_6$ alkyl)$_2$.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$ alkyl, C$_1$-C$_6$ alkyl, —OC$_2$-C$_6$ alkenyl, —OC$_2$-C$_6$ alkynyl, —C$_2$-C$_6$ alkenyl, —C$_2$-C$_6$ alkynyl, —OH, —OP(O)(OH)$_2$, —OC(O)C$_1$-C$_6$ alkyl, —C(O)C$_1$-C$_6$ alkyl, —OC(O)OC$_1$-C$_6$ alkyl, NH$_2$, NH(C$_1$-C$_6$ alkyl), N(C$_1$-C$_6$ alkyl)$_2$, —S(O)$_2$—C$_1$-C$_6$ alkyl, —S(O)NHC$_1$-C$_6$ alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

Halogen or "halo" refers to fluorine, chlorine, bromine and iodine.

Alkyl refers to a straight or branched chain saturated hydrocarbon containing 1-12 carbon atoms. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain. Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

"Cycloalkyl" means monocyclic or bicyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[1.1.1]pentyl, or bicyclo[2.2.2]octenyl.

"Heterocyclyl" or "heterocycloalkyl" means a monocyclic or polycyclic radical of 3 to 24-membered ring containing carbon and heteroatoms taken from containing one or more ring heteroatoms selected from N, O, S, P, or B and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. In accordance with the present invention, heterocyclyl refers to saturated or partially saturated non aromatic rings structures in which there is at least one heteroatoms selected from the group N, O, or S. In some embodiments, the one or more heteroatoms in the heterocyclyl are presented at an oxidated state (e.g.,).

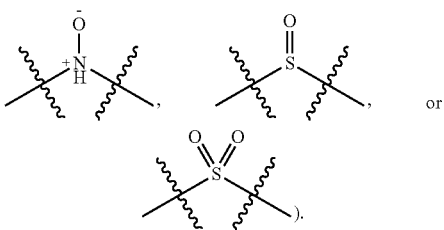

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A ($C_5$-$C_{12}$) spirocycloalkyl is a spirocycle containing between 5 and 12 carbon atoms. One or more of the carbon atoms can be substituted with a heteroatom.

The term "spiroheterocycloalkyl" or "spiroheterocyclyl" is understood to mean a spirocycle wherein at least one of the atoms in one of the rings is a heteroatom. In some embodiments, at least one of the atoms in one of the rings is O, N, S, or P.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I may have one or more asymmetric atom and may occur as racemates, racemic mixtures and as individual enantiomers or diastereomers. The term stereoisomer may also encompass atropisomers, which arise from hindered rotation about a single bond, e.g., in compounds having a substituted biphenyl moiety.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

In one embodiment, $X_1$ is N or $C(R_5)$. In one embodiment, $X_1$ is N. In one embodiment, $X_1$ is $C(R_5)$. In one embodiment, $X_2$ is N. In one embodiment, $X_2$ is $C(R_5)$. In one embodiment, $X_3$ is N. In one embodiment, $X_3$ is $C(R_5)$.

In one embodiment, $A_1$ is a bond, —$C(R_8)(R_9)$—, —O—, —$NR_8$—, —S—, —S(O)—, or —$SO_2$—.

In one embodiment, $A_2$ and Y are independently at each occurrence —$C(R_8)(R_9)$—, —O—, —$NR_8$—, or —$SO_2$—.

In one embodiment, $A_1$ is —$C(R_8)(R_9)$—, —O—, —$NR_8$—, —S—, —S(O)—, or —$SO_2$—. In one embodiment, $A_1$ is a bond. In one embodiment, $A_1$ is —$C(R_8)(R_9)$— or —O—. In one embodiment, $A_1$ is —$C(R_8)(R_9)$—. In one embodiment, $A_1$ is —O—. In one embodiment, $A_1$ is —$NR_8$—. In one embodiment, $A_1$ is —S—. In one embodiment, $A_1$ is —S(O)—. In one embodiment, $A_1$ is —$SO_2$—.

In one embodiment, $A_2$ is —$C(R_8)(R_9)$—, —O—, —$NR_8$—, or —$SO_2$—. In one embodiment, $A_2$ is —$C(R_8)(R_9)$— or —O—. In one embodiment, $A_2$ is —$C(R_8)(R_9)$—. In one embodiment, $A_2$ is —O—. In one embodiment, $A_2$ is —$NR_8$—. In one embodiment, $A_2$ is —S—. In one embodiment, $A_2$ is —S(O)—. In one embodiment, $A_2$ is —$SO_2$—.

In one embodiment, Y is —$C(R_8)(R_9)$—, —O—, —$NR_8$—, or —$SO_2$—. In one embodiment, Y is —$C(R_8)(R_9)$— or —O—. In one embodiment, Y is —$C(R_8)(R_9)$—. In one embodiment, Y is —O—. In one embodiment, Y is —$NR_8$—. In one embodiment, Y is —S—. In one embodiment, Y is —S(O)—. In one embodiment, Y is —$SO_2$—.

In one embodiment, $R_1$ is H, halogen, —$NR_8R_9$, —$P(O)(OR_8)(OR_9)$, —$C(O)R_8$, —$C(O)NR_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl. In one embodiment, $R_1$ is H. In one embodiment, $R_1$ is —$NR_8R_9$. In one embodiment, $R_1$ is —$P(OR_8)(OR_9)$. In one embodiment, $R_1$ is —$C(O)R_8$. In one embodiment, $R_1$ is —$C(O)NR_8R_9$. In one embodiment, $R_1$ is —CN. In one embodiment, $R_1$ is $C_1$-$C_6$ alkyl. In one embodiment, $R_1$ is $C_1$-$C_6$ alkoxy. In one embodiment, $R_1$ is $C_2$-$C_6$ alkenyl. In one embodiment, $R_1$ is $C_2$-$C_6$ alkynyl. In one embodiment, $R_1$ is $C_3$-$C_{10}$ cycloalkyl. In one embodiment, $R_1$ is $C_5$-$C_8$ cycloalkenyl. In one embodiment, $R_1$ is $C_3$-$C_8$ spirocycloalkyl. In one embodiment, $R_1$ is spiroheterocyclyl. In one embodiment, $R_1$ is heterocyclyl. In one embodiment, $R_1$ is aryl. In one embodiment, $R_1$ is heteroaryl.

In one embodiment, $R_1$ is $C_1$-$C_6$ alkyl is optionally substituted with one or more $R_6$. In one embodiment, $R_1$ is $C_1$-$C_6$ alkoxy is optionally substituted with one or more $R_6$. In one embodiment, $R_1$ is $C_2$-$C_6$ alkenyl is optionally substituted with one or more $R_6$. In one embodiment, $R_1$ is $C_2$-$C_6$ alkynyl is optionally substituted with one or more $R_6$. In one embodiment, $R_1$ is $C_3$-$C_{10}$ cycloalkyl is optionally substituted with one or more $R_6$. In one embodiment, $R_1$ is $C_5$-$C_8$ cycloalkenyl is optionally substituted with one or more $R_6$. In one embodiment, $R_1$ is $C_3$-$C_8$ spirocycloalkyl is optionally substituted with one or more $R_6$. In one embodiment, $R_1$ is spiroheterocyclyl is optionally substituted with one or more $R_6$. In one embodiment, $R_1$ is heterocyclyl is optionally substituted with one or more $R_6$. In one embodiment, $R_1$ is aryl is optionally substituted with one or more $R_6$. In one embodiment, $R_1$ is heteroaryl is optionally substituted with one or more $R_6$.

In another embodiment, $R_1$ is

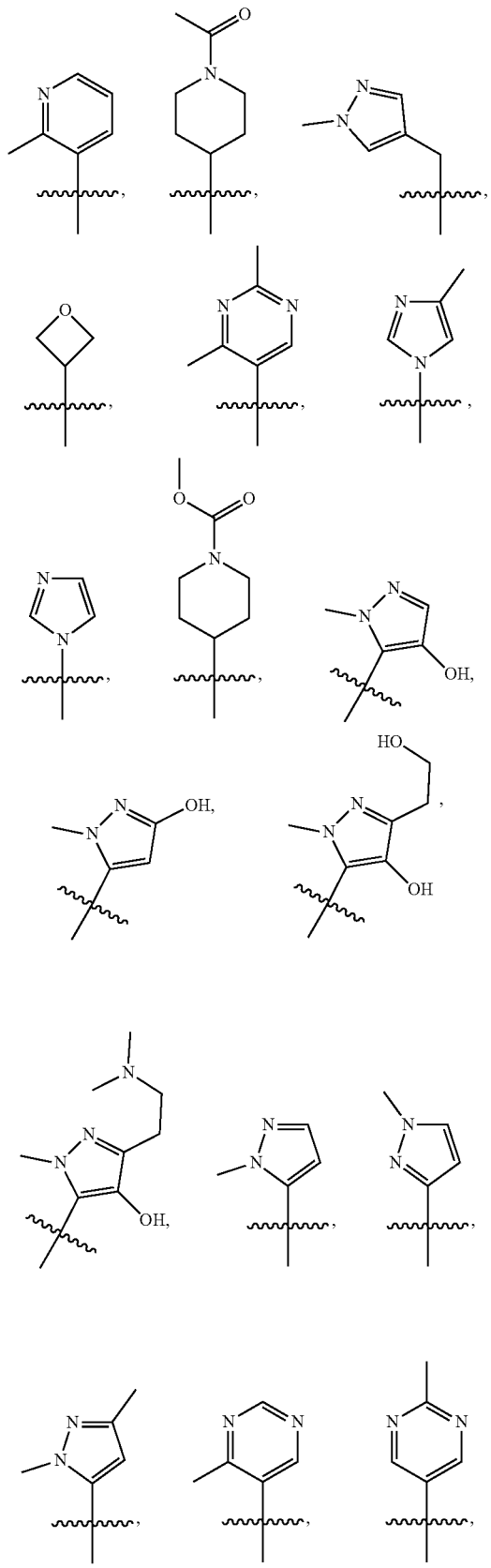

-continued
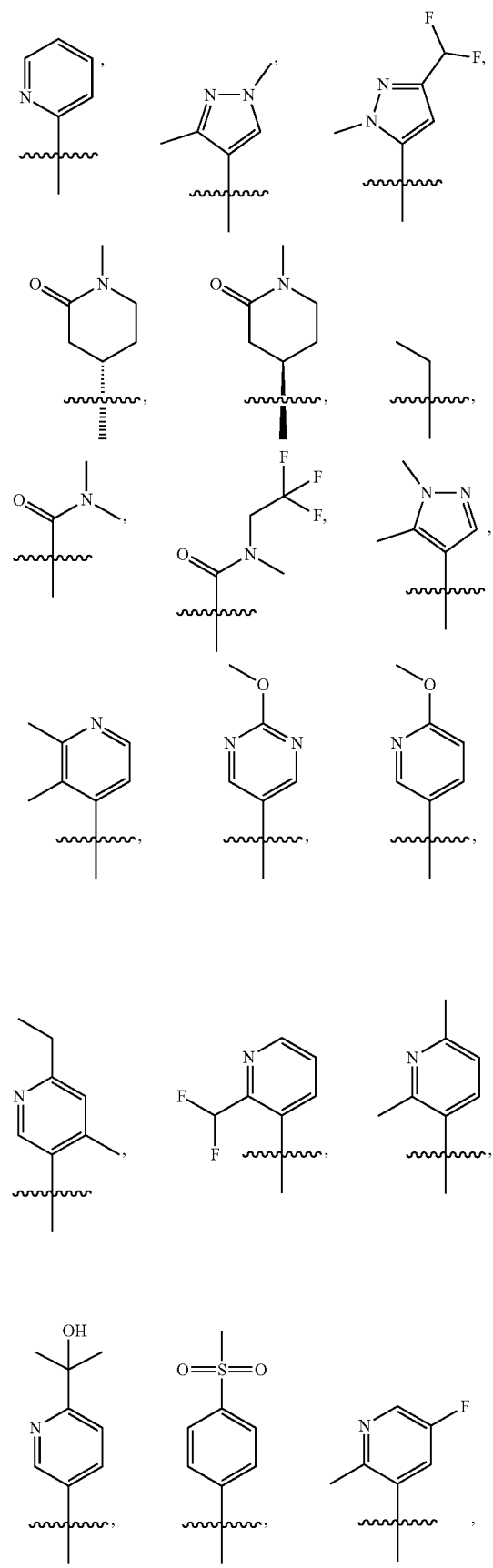
-continued
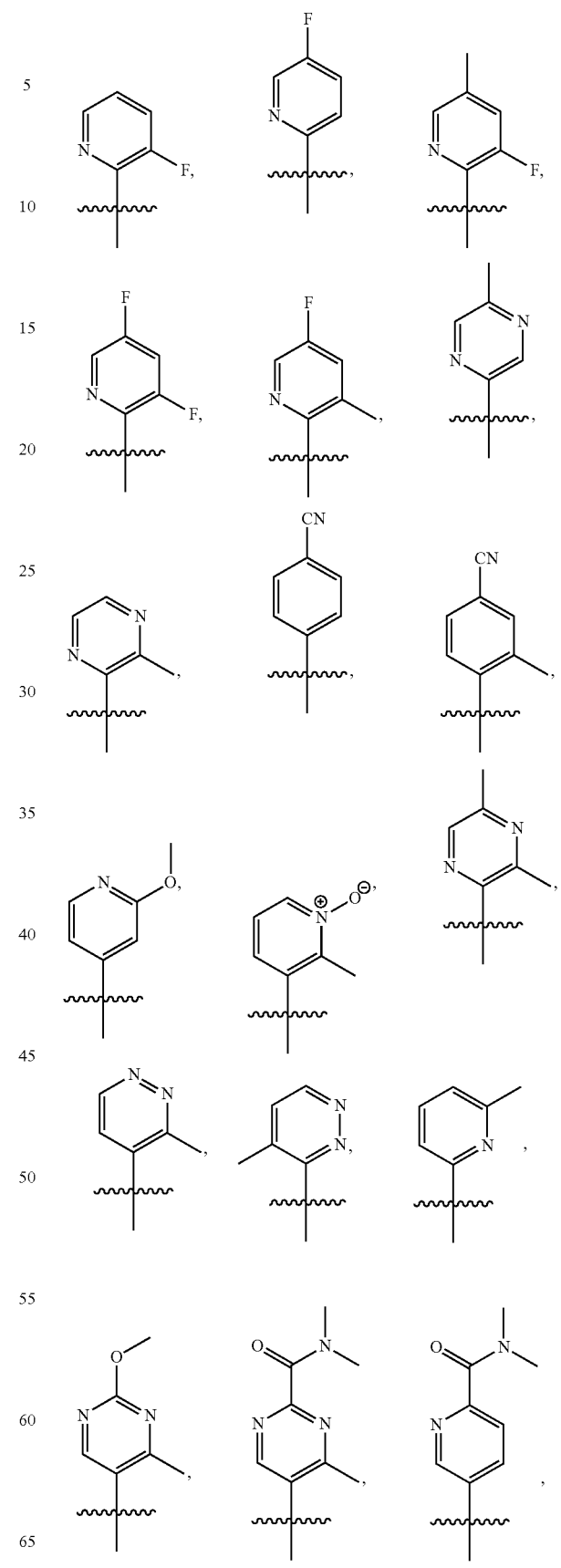

-continued
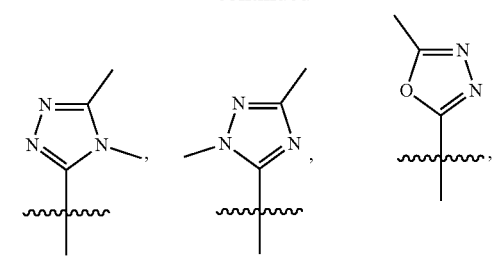
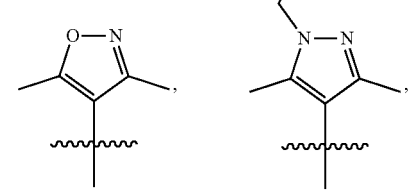
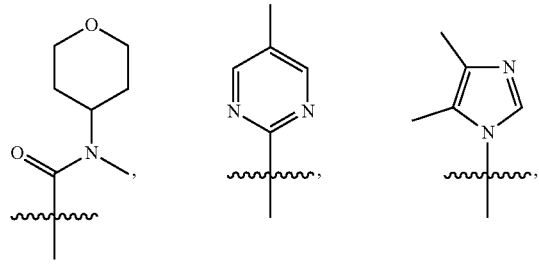
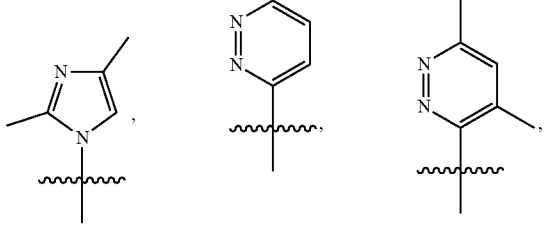
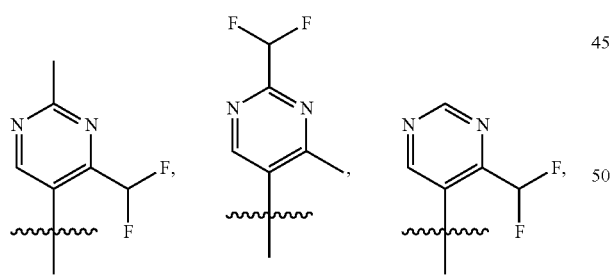
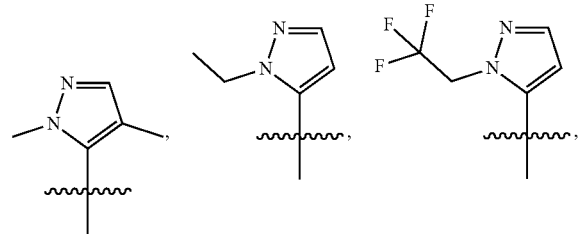
-continued
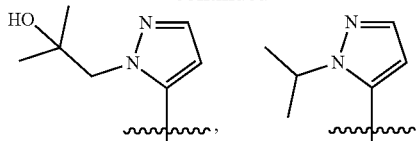
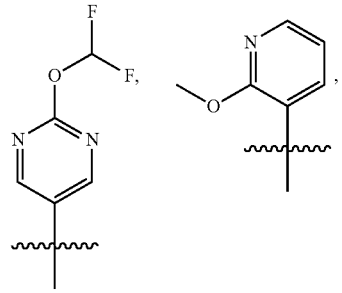
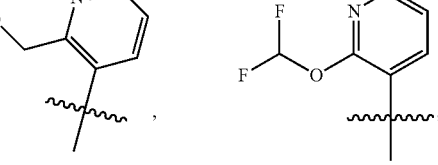
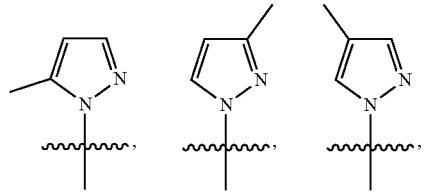
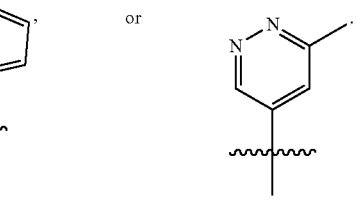
In another embodiment, $R_1$ is
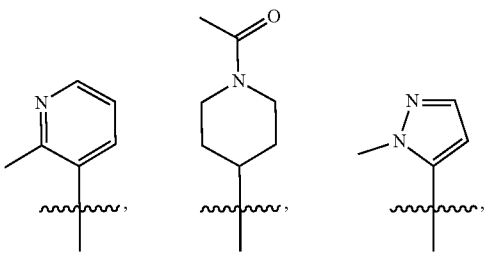
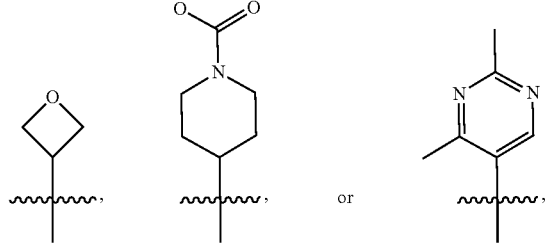

In another embodiment, $R_1$ is

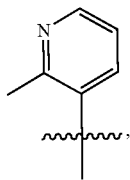 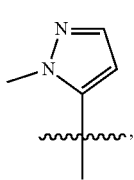 or 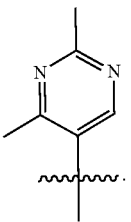.

In one embodiment, $R_1$ is

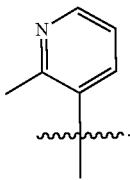

In one embodiment, $R_1$ is

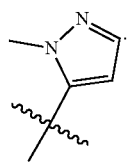 [SMILES: *c1ccnn1C]

In one embodiment, $R_1$ is

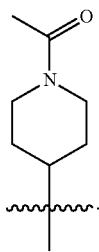.

In one embodiment, $R_2$ is independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl. In one embodiment, $R_2$ is H. In one embodiment, $R_2$ is halogen. In one embodiment, $R_2$ is —OH. In one embodiment, $R_2$ is —NH$_2$. In one embodiment, $R_2$ is —CN. In one embodiment, $R_2$ is $C_1$-$C_6$ alkyl. In one embodiment, $R_2$ is $C_1$-$C_6$ alkoxy. In one embodiment, $R_2$ is $C_2$-$C_6$ alkenyl. In one embodiment, $R_2$ is $C_2$-$C_6$ alkynyl.

In one embodiment, $R_2$ is $C_1$-$C_6$ alkyl optionally substituted with one or more $R_7$. In one embodiment, $R_2$ is $C_1$-$C_6$ alkoxy optionally substituted with one or more $R_7$. In one embodiment, $R_2$ is $C_2$-$C_6$ alkenyl optionally substituted with one or more $R_7$. In one embodiment, $R_2$ is $C_2$-$C_6$ alkynyl optionally substituted with one or more $R_7$.

In one embodiment, $R_3$ is independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl. In one embodiment, $R_3$ is H. In one embodiment, $R_3$ is halogen. In one embodiment, $R_3$ is —OH. In one embodiment, $R_3$ is —NH$_2$. In one embodiment, $R_3$ is —CN. In one embodiment, $R_3$ is $C_1$-$C_6$ alkyl. In one embodiment, $R_3$ is $C_1$-$C_6$ alkoxy. In one embodiment, $R_3$ is $C_2$-$C_6$ alkenyl. In one embodiment, $R_3$ is $C_2$-$C_6$ alkynyl.

In one embodiment, $R_3$ is $C_1$-$C_6$ alkyl optionally substituted with one or more $R_7$. In one embodiment, $R_3$ is $C_1$-$C_6$ alkoxy optionally substituted with one or more $R_7$. In one embodiment, $R_3$ is $C_2$-$C_6$ alkenyl optionally substituted with one or more $R_7$. In one embodiment, $R_3$ is $C_2$-$C_6$ alkynyl optionally substituted with one or more $R_7$.

In one embodiment, $R_4$ is independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl. In one embodiment, $R_4$ is H. In one embodiment, $R_4$ is halogen. In one embodiment, $R_4$ is —OH. In one embodiment, $R_4$ is —NH$_2$. In one embodiment, $R_4$ is —CN. In one embodiment, $R_4$ is $C_1$-$C_6$ alkyl. In one embodiment, $R_4$ is $C_1$-$C_6$ alkoxy. In one embodiment, $R_4$ is $C_2$-$C_6$ alkenyl. In one embodiment, $R_4$ is $C_2$-$C_6$ alkynyl.

In one embodiment, $R_4$ is $C_1$-$C_6$ alkyl optionally substituted with one or more $R_7$. In one embodiment, $R_4$ is $C_1$-$C_6$ alkoxy optionally substituted with one or more $R_7$. In one embodiment, $R_4$ is $C_2$-$C_6$ alkenyl optionally substituted with one or more $R_7$. In one embodiment, $R_4$ is $C_2$-$C_6$ alkynyl optionally substituted with one or more $R_7$.

In one embodiment, $R_4$ and $R_9$ can form $C_3$-$C_{10}$ cycloalkyl, $C_5$-$C_8$ cycloalkenyl, heterocyclyl, aryl, or heteroaryl. In one embodiment, $R_4$ and $R_9$ can form $C_3$-$C_{10}$ cycloalkyl, $C_5$-$C_8$ cycloalkenyl, heterocyclyl, aryl, or heteroaryl, wherein the cycloalkyl, cycloalkenyl, heterocyclyl, aryl, or heteroaryl is optionally substituted with one or more $R_{10}$.

In one embodiment, $R_4$ and $R_9$ can form $C_3$-$C_{10}$ cycloalkyl. In one embodiment, $R_4$ and $R_9$ can form $C_5$-$C_8$ cycloalkenyl. In one embodiment, $R_4$ and $R_9$ can form heterocyclyl. In one embodiment, $R_4$ and $R_9$ can form aryl. In one embodiment, $R_4$ and $R_9$ can form heteroaryl.

In one embodiment, $R_4$ and $R_9$ can form $C_3$-$C_{10}$ cycloalkyl optionally substituted with one or more $R_{10}$. In one embodiment, $R_4$ and $R_9$ can form $C_5$-$C_8$ cycloalkenyl optionally substituted with one or more $R_{10}$. In one embodiment, $R_4$ and $R_9$ can form heterocyclyl optionally substituted with one or more $R_{10}$. In one embodiment, $R_4$ and $R_9$ can form aryl optionally substituted with one or more $R_{10}$. In one embodiment, $R_4$ and $R_9$ can form heteroaryl optionally substituted with one or more $R_{10}$.

In one embodiment, $R_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, wherein alkyl, alkenyl, alkynyl, cycloalkyl, cycloalkenyl, heterocyclyl, aryl, or heteroaryl is optionally substituted with one or more $R_7$.

In one embodiment, $R_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl. In one embodiment, $R_5$ is H. In one embodiment, $R_5$ is halogen. In one embodiment, $R_5$ is CN. In one embodiment, $R_5$ is —OR$_8$. In one embodiment, $R_5$ is —NR$_8$R$_9$. In one embodiment, $R_5$ is —C(O)R$_8$. In one embodiment, $R_5$ is —C(O)OR$_8$. In one embodiment, $R_5$ is —C(O)NR$_8$R$_9$. In one embodiment, $R_5$ is —NR$_8$C(O)R$_9$. In one embodiment, $R_5$ is —S(O)R$_8$. In one embodiment, $R_5$ is —S(O)$_2$R$_8$. In one embodiment, $R_5$ is —NR$_8$S $(O)_2R_9$. In one embodiment, $R_5$ is $-S(O)_2NR_8R_9$. In one embodiment, $R_5$ is $C_1$-$C_6$ alkyl. In one embodiment, $R_5$ is $C_1$-$C_6$ haloalkyl. In one embodiment, $R_5$ is $C_2$-$C_6$ alkenyl. In one embodiment, $R_5$ is $C_2$-$C_6$ alkynyl. In one embodiment, $R_5$ is $C_3$-$C_{10}$ cycloalkyl. In one embodiment, $R_5$ is $C_5$-$C_8$ cycloalkenyl. In one embodiment, $R_5$ is heterocyclyl. In one embodiment, $R_5$ is aryl. In one embodiment, $R_5$ is heteroaryl.

In one embodiment, $R_5$ is $C_1$-$C_6$ alkyl, $C_1$-$C_6$ haloalkyl, $C_2$-$C_6$ alkenyl, or $C_2$-$C_6$ alkynyl.

In one embodiment, $R_5$ is $C_1$-$C_6$ alkyl. In one embodiment, $R_5$ is methyl. In one embodiment, $R_5$ is ethyl. In one embodiment, $R_5$ is propyl. In one embodiment, $R_5$ is butyl. In one embodiment, $R_5$ is pentyl. In one embodiment, $R_5$ is hexyl.

In one embodiment, $R_5$ is $C_1$-$C_6$ alkyl optionally substituted with one or more $R_7$. In one embodiment, $R_5$ is methyl optionally substituted with one or more $R_7$. In one embodiment, $R_5$ is ethyl optionally substituted with one or more $R_7$. In one embodiment, $R_5$ is propyl optionally substituted with one or more $R_7$. In one embodiment, $R_5$ is butyl optionally substituted with one or more $R_7$. In one embodiment, $R_5$ is pentyl optionally substituted with one or more $R_7$. In one embodiment, $R_5$ is hexyl optionally substituted with one or more $R_7$.

In one embodiment, $R_5$ is $C_1$-$C_6$ haloalkyl. In one embodiment, $R_5$ is halomethyl. In one embodiment, $R_5$ is haloethyl. In one embodiment, $R_5$ is halopropyl. In one embodiment, $R_5$ is halobutyl. In one embodiment, $R_5$ is halopentyl. In one embodiment, $R_5$ is halohexyl.

In one embodiment, $R_5$ is $C_2$-$C_6$ alkenyl. In one embodiment, $R_5$ is $C_2$-$C_6$ alkynyl.

In one embodiment, $R_5$ is $C_2$-$C_6$ alkenyl optionally substituted with one or more $R_7$. In one embodiment, $R_5$ is $C_2$-$C_6$ alkynyl optionally substituted with one or more $R_7$.

In one embodiment, $R_5$ is $C_3$-$C_{10}$ cycloalkyl or $C_5$-$C_8$ cycloalkenyl.

In one embodiment, $R_5$ is $C_3$-$C_{10}$ cycloalkyl or $C_5$-$C_8$ cycloalkenyl, wherein the cycloalkyl or cycloalkenyl is optionally substituted with one or more $R_7$.

In one embodiment, $R_5$ is $C_3$-$C_{10}$ cycloalkyl. In one embodiment, $R_5$ is monocylic $C_3$-$C_{10}$ cycloalkyl. In one embodiment, $R_5$ is bicyclic $C_3$-$C_{10}$ cycloalkyl. In one embodiment, $R_5$ is polycyclic $C_3$-$C_{10}$ cycloalkyl.

In one embodiment, $R_5$ is $C_3$-$C_{10}$ cycloalkyl optionally substituted with one or more $R_7$. In one embodiment, $R_5$ is monocylic $C_3$-$C_{10}$ cycloalkyl optionally substituted with one or more $R_7$. In one embodiment, $R_5$ is bicyclic $C_3$-$C_{10}$ cycloalkyl optionally substituted with one or more $R_7$. In one embodiment, $R_5$ is polycyclic $C_3$-$C_{10}$ cycloalkyl optionally substituted with one or more $R_7$.

In one embodiment, $R_5$ is $C_5$-$C_8$ cycloalkenyl. In one embodiment, $R_5$ is heterocyclyl, aryl, or heteroaryl. In one embodiment, $R_5$ is heterocyclyl. In one embodiment, $R_5$ is aryl. In one embodiment, $R_5$ is phenyl.

In one embodiment, $R_5$ is $C_5$-$C_8$ cycloalkenyl optionally substituted with one or more $R_7$. In one embodiment, $R_5$ is heterocyclyl, aryl, or heteroaryl, wherein the heterocyclyl, aryl, or heteroaryl is optionally substituted with one or more $R_7$. In one embodiment, $R_5$ is heterocyclyl optionally substituted with one or more $R_7$. In one embodiment, $R_5$ is aryl optionally substituted with one or more $R_7$. In one embodiment, $R_5$ is phenyl optionally substituted with one or more $R_7$.

In one embodiment, $R_5$ is heteroaryl. In one embodiment, $R_5$ is pyridine. In one embodiment, $R_5$ is imidazolyl. In one embodiment, $R_5$ is pyrazolyl. In one embodiment, $R_5$ is pyrimidinyl.

In one embodiment, $R_5$ is heteroaryl optionally substituted with one or more $R_7$. In one embodiment, $R_5$ is pyridine optionally substituted with one or more $R_7$. In one embodiment, $R_5$ is imidazolyl optionally substituted with one or more $R_7$. In one embodiment, $R_5$ is pyrazolyl optionally substituted with one or more $R_7$. In one embodiment, $R_5$ is pyrimidinyl optionally substituted with one or more $R_7$.

In one embodiment, $R_5$ is $-CF_3$. In one embodiment, $R_5$ is $-CHF_2$. In one embodiment, $R_5$ is $-CH_2F$.

In one embodiment, $R_6$ is independently at each occurrence oxo, halogen, $-CN$, OH, $-NR_8R_9$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl. In one embodiment, $R_6$ is oxo. In one embodiment, $R_6$ is halogen. In one embodiment, $R_6$ is CN. In one embodiment, $R_6$ is OH. In one embodiment, $R_6$ is $-NR_8R_9$. In one embodiment, $R_6$ is $-OR_8$. In one embodiment, $R_6$ is $-NR_8R_9$. In one embodiment, $R_6$ is $-C(O)R_8$. In one embodiment, $R_6$ is $-C(O)OR_8$. In one embodiment, $R_6$ is $-C(O)NR_8R_9$. In one embodiment, $R_6$ is $-NR_8C(O)R_9$. In one embodiment, $R_6$ is $-S(O)R_8$. In one embodiment, $R_6$ is $-S(O)_2R_8$. In one embodiment, $R_6$ is $-NR_8S(O)_2R_9$. In one embodiment, $R_6$ is $-S(O)_2NR_8R_9$. In one embodiment, $R_6$ is $C_1$-$C_6$ alkyl. In one embodiment, $R_6$ is $C_1$-$C_6$ haloalkyl. In one embodiment, $R_6$ is $C_2$-$C_6$ alkenyl. In one embodiment, $R_6$ is $C_2$-$C_6$ alkynyl. In one embodiment, $R_6$ is $C_3$-$C_{10}$ cycloalkyl. In one embodiment, $R_6$ is $C_5$-$C_8$ cycloalkenyl. In one embodiment, $R_6$ is heterocyclyl. In one embodiment, $R_6$ is aryl. In one embodiment, $R_6$ is heteroaryl.

In one embodiment, $R_6$ is $C_1$-$C_6$ alkyl optionally substituted with one or more $R_{10}$. In one embodiment, $R_6$ is $C_1$-$C_6$ haloalkyl optionally substituted with one or more $R_{10}$. In one embodiment, $R_6$ is $C_2$-$C_6$ alkenyl optionally substituted with one or more $R_{10}$. In one embodiment, $R_6$ is $C_2$-$C_6$ alkynyl optionally substituted with one or more $R_{10}$. In one embodiment, $R_6$ is $C_3$-$C_{10}$ cycloalkyl optionally substituted with one or more $R_{10}$. In one embodiment, $R_6$ is $C_5$-$C_8$ cycloalkenyl optionally substituted with one or more $R_{10}$. In one embodiment, $R_6$ is heterocyclyl optionally substituted with one or more $R_{10}$. In one embodiment, $R_6$ is aryl optionally substituted with one or more $R_{10}$. In one embodiment, $R_6$ is heteroaryl optionally substituted with one or more $R_{10}$.

In another embodiment, two $R_6$ may combine to form $C_3$-$C_{10}$ cycloalkyl, $C_5$-$C_8$ cycloalkenyl, heterocyclyl, aryl, or heteroaryl. In another embodiment, two $R_6$ may combine to form $C_3$-$C_{10}$ cycloalkyl. In another embodiment, two $R_6$ may combine to form $C_5$-$C_8$ cycloalkenyl. In another embodiment, two $R_6$ may combine to form a heteroaryl. In another embodiment, two $R_6$ may combine to form a heterocyclyl. In another embodiment, two $R_6$ may combine to form an aryl. In another embodiment, two $R_6$ may combine to form $C_3$-$C_{10}$ cycloalkyl, wherein the cycloalkyl is optionally substituted with one or more $R_{10}$. In another embodiment, two $R_6$ may combine to form $C_5$-$C_8$ cycloalkenyl, wherein the cycloalkenyl is optionally substituted with one or more $R_{10}$. In another embodiment, two $R_6$ may combine to form a heteroaryl, wherein the heteroaryl is optionally substituted with one or more $R_{10}$. In another embodiment, two $R_6$ may combine to form a heterocyclyl, wherein the heterocyclyl is optionally substituted with one or more $R_{10}$.

In another embodiment, two $R_6$ may combine to form an aryl wherein the aryl is optionally substituted with one or more $R_{10}$.

In one embodiment, $R_7$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_7$ is independently at each occurrence oxo, halogen, or —CN. In one embodiment, $R_7$ is oxo. In one embodiment, $R_7$ is halogen. In one embodiment, $R_7$ is F, $C_1$, Br, or I. In one embodiment, $R_7$ is F or $C_1$. In one embodiment, $R_7$ is F. In one embodiment, $R_7$ is $C_1$. In one embodiment, $R_7$ is —CN.

In one embodiment, $R_7$ is independently at each occurrence —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, or —$S(O)_2NR_8R_9$. In one embodiment, $R_7$ is —$OR_8$. In one embodiment, $R_7$ is —$C(O)R_8$. In one embodiment, $R_7$ is —$C(O)OR_8$. In one embodiment, $R_7$ is —$C(O)NR_8R_9$. In one embodiment, $R_7$ is —$NR_8C(O)R_9$. In one embodiment, $R_7$ is —$S(O)R_8$. In one embodiment, $R_7$ is —$S(O)_2R_8$. In one embodiment, $R_7$ is —$NR_8S(O)_2R_9$. In one embodiment, $R_7$ is —$S(O)_2NR_8R_9$.

In one embodiment, $R_7$ is independently at each occurrence $C_1$-$C_6$ alkyl, $C_1$-$C_6$ haloalkyl, $C_2$-$C_6$ alkenyl, or $C_2$-$C_6$ alkynyl.

In one embodiment, $R_7$ is $C_1$-$C_6$ alkyl. In one embodiment, $R_7$ is methyl. In one embodiment, $R_7$ is ethyl. In one embodiment, $R_7$ is propyl. In one embodiment, $R_7$ is butyl. In one embodiment, $R_7$ is pentyl. In one embodiment, $R_7$ is hexyl.

In one embodiment, $R_7$ is $C_1$-$C_6$ haloalkyl. In one embodiment, $R_7$ is halomethyl. In one embodiment, $R_7$ is haloethyl. In one embodiment, $R_7$ is halopropyl. In one embodiment, $R_7$ is halobutyl. In one embodiment, $R_7$ is halopentyl. In one embodiment, $R_7$ is halohexyl.

In one embodiment, $R_7$ is $C_2$-$C_6$ alkenyl. In one embodiment, $R_7$ is $C_2$-$C_6$ alkynyl.

In one embodiment, $R_7$ is independently at each occurrence $C_3$-$C_8$ cycloalkyl or heterocyclyl. In one embodiment, $R_7$ is $C_3$-$C_8$ cycloalkyl. In one embodiment, $R_7$ is heterocyclyl.

In one embodiment, $R_7$ is independently at each occurrence aryl or heteroaryl. In one embodiment, $R_7$ is aryl. In one embodiment, $R_7$ is heteroaryl.

In one embodiment, $R_8$ is independently at each occurrence H, OH, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_9$ is independently at each occurrence H, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_8$ and $R_9$ are independently at each occurrence H, $C_1$-$C_6$ alkyl, $C_1$-$C_6$ alkoxy, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_8$ and $R_9$ are independently at each occurrence H.

In one embodiment, $R_8$ and $R_9$ are independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

In one embodiment, $R_8$ and $R_9$ are independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_8$ is independently at each occurrence H, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_8$ is independently at each occurrence H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

In one embodiment, $R_8$ is H.

In one embodiment, $R_8$ is halogen.

In one embodiment, $R_8$ is independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

In one embodiment, $R_8$ is independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_8$ is independently at each occurrence $C_1$-$C_6$ alkyl, $C_1$-$C_6$ alkoxy, $C_2$-$C_6$ alkenyl or $C_2$-$C_6$ alkynyl.

In one embodiment, $R_8$ is independently at each occurrence $C_1$-$C_6$ alkyl, $C_1$-$C_6$ alkoxy, $C_2$-$C_6$ alkenyl or $C_2$-$C_6$ alkynyl, wherein each alkyl, alkoxy, alkenyl or alkynyl is optionally substituted with one or more $R_{10}$.

In one embodiment, $R_8$ is $C_1$-$C_6$ alkyl. In one embodiment, $R_8$ is methyl. In one embodiment, $R_8$ is ethyl. In one embodiment, $R_8$ is propyl. In one embodiment, $R_8$ is butyl. In one embodiment, $R_8$ is pentyl. In one embodiment, $R_8$ is hexyl.

In one embodiment, $R_8$ is $C_1$-$C_6$ alkyl optionally substituted with one or more $R_{10}$. In one embodiment, $R_8$ is methyl optionally substituted with one or more $R_{10}$. In one embodiment, $R_8$ is ethyl optionally substituted with one or more $R_{10}$. In one embodiment, $R_8$ is propyl optionally substituted with one or more $R_{10}$. In one embodiment, $R_8$ is butyl optionally substituted with one or more $R_{10}$. In one embodiment, $R_8$ is pentyl optionally substituted with one or more $R_{10}$. In one embodiment, $R_8$ is hexyl optionally substituted with one or more $R_{10}$.

In one embodiment, $R_8$ is $C_1$-$C_6$ alkoxy. In one embodiment, $R_8$ is methoxy. In one embodiment, $R_8$ is ethoxy. In one embodiment, $R_8$ is propoxy. In one embodiment, $R_8$ is butoxy. In one embodiment, $R_8$ is pentoxy. In one embodiment, $R_8$ is hexoxy.

In one embodiment, $R_8$ is $C_1$-$C_6$ alkoxy optionally substituted with one or more $R_{10}$. In one embodiment, $R_8$ is methoxy optionally substituted with one or more $R_{10}$. In one embodiment, $R_8$ is ethoxy optionally substituted with one or more $R_{10}$. In one embodiment, $R_8$ is propoxy optionally substituted with one or more $R_{10}$. In one embodiment, $R_8$ is butoxy optionally substituted with one or more $R_{10}$. In one embodiment, $R_8$ is pentoxy optionally substituted with one or more $R_{10}$. In one embodiment, $R_8$ is hexoxy optionally substituted with one or more $R_{10}$.

In one embodiment, $R_8$ is $C_2$-$C_6$ alkenyl. In one embodiment, $R_8$ is $C_2$-$C_6$ alkynyl.

In one embodiment, $R_8$ is $C_2$-$C_6$ alkenyl optionally substituted with one or more $R_{10}$. In one embodiment, $R_8$ is $C_2$-$C_6$ alkynyl optionally substituted with one or more $R_{10}$.

In one embodiment, $R_8$ is independently at each occurrence $C_3$-$C_8$ cycloalkyl, heterocyclyl, aryl, or heteroaryl.

In one embodiment, $R_8$ is independently at each occurrence $C_3$-$C_8$ cycloalkyl, heterocyclyl, aryl, or heteroaryl, wherein each $C_3$-$C_8$ cycloalkyl, heterocyclyl, aryl, or heteroaryl is optionally substituted with one or more $R_{10}$.

In one embodiment, $R_8$ is $C_3$-$C_8$ cycloalkyl. In one embodiment, $R_8$ is heterocyclyl. In one embodiment, $R_8$ is aryl. In one embodiment, $R_8$ is heteroaryl.

In one embodiment, $R_8$ is $C_3$-$C_8$ cycloalkyl optionally substituted with one or more $R_{10}$. In one embodiment, $R_8$ is heterocyclyl optionally substituted with one or more $R_{10}$. In one embodiment, $R_8$ is aryl optionally substituted with one or more $R_{10}$. In one embodiment, $R_8$ is heteroaryl optionally substituted with one or more $R_{10}$.

In one embodiment, $R_9$ is independently at each occurrence H, halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_9$ is independently at each occurrence H, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

In one embodiment, $R_9$ is H.

In one embodiment, $R_9$ is halogen.

In one embodiment, $R_9$ is independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl.

In one embodiment, $R_9$ is independently at each occurrence $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl is optionally substituted with one or more $R_{10}$.

In one embodiment, $R_9$ is independently at each occurrence $C_1$-$C_6$ alkyl, $C_1$-$C_6$ alkoxy, $C_2$-$C_6$ alkenyl or $C_2$-$C_6$ alkynyl.

In one embodiment, $R_9$ is independently at each occurrence $C_1$-$C_6$ alkyl, $C_1$-$C_6$ alkoxy, $C_2$-$C_6$ alkenyl or $C_2$-$C_6$ alkynyl, wherein each alkyl, alkoxy, alkenyl, or alkynyl is optionally substituted with one or more $R_{10}$.

In one embodiment, $R_9$ is $C_1$-$C_6$ alkyl. In one embodiment, $R_9$ is methyl. In one embodiment, $R_9$ is ethyl. In one embodiment, $R_9$ is propyl. In one embodiment, $R_9$ is butyl. In one embodiment, $R_9$ is pentyl. In one embodiment, $R_9$ is hexyl.

In one embodiment, $R_9$ is $C_1$-$C_6$ alkyl optionally substituted with one or more $R_{10}$. In one embodiment, $R_9$ is methyl optionally substituted with one or more $R_{10}$. In one embodiment, $R_9$ is ethyl optionally substituted with one or more $R_{10}$. In one embodiment, $R_9$ is propyl optionally substituted with one or more $R_{10}$. In one embodiment, $R_9$ is butyl optionally substituted with one or more $R_{10}$. In one embodiment, $R_9$ is pentyl optionally substituted with one or more $R_{10}$. In one embodiment, $R_9$ is hexyl optionally substituted with one or more $R_{10}$.

In one embodiment, $R_9$ is $C_1$-$C_6$ alkoxy. In one embodiment, $R_9$ is methoxy. In one embodiment, $R_9$ is ethoxy. In one embodiment, $R_9$ is propoxy. In one embodiment, $R_9$ is butoxy. In one embodiment, $R_9$ is pentoxy. In one embodiment, $R_9$ is hexoxy.

In one embodiment, $R_9$ is $C_1$-$C_6$ alkoxy optionally substituted with one or more $R_{10}$. In one embodiment, $R_9$ is methoxy optionally substituted with one or more $R_{10}$. In one embodiment, $R_9$ is ethoxy optionally substituted with one or more $R_{10}$. In one embodiment, $R_9$ is propoxy optionally substituted with one or more $R_{10}$. In one embodiment, $R_9$ is butoxy optionally substituted with one or more $R_{10}$. In one embodiment, $R_9$ is pentoxy optionally substituted with one or more $R_{10}$. In one embodiment, $R_9$ is hexoxy optionally substituted with one or more $R_{10}$.

In one embodiment, $R_9$ is $C_2$-$C_6$ alkenyl. In one embodiment, $R_9$ is $C_2$-$C_6$ alkynyl.

In one embodiment, $R_9$ is $C_2$-$C_6$ alkenyl optionally substituted with one or more $R_{10}$. In one embodiment, $R_9$ is $C_2$-$C_6$ alkynyl optionally substituted with one or more $R_{10}$.

In one embodiment, $R_9$ is independently at each occurrence $C_3$-$C_8$ cycloalkyl, heterocyclyl, aryl, or heteroaryl.

In one embodiment, $R_9$ is independently at each occurrence $C_3$-$C_8$ cycloalkyl, heterocyclyl, aryl, or heteroaryl, wherein each cycloalkyl, heterocyclyl, aryl, or heteroaryl is optionally substituted with one or more $R_{10}$.

In one embodiment, $R_9$ is $C_3$-$C_8$ cycloalkyl. In one embodiment, $R_9$ is heterocyclyl. In one embodiment, $R_9$ is aryl. In one embodiment, $R_9$ is heteroaryl.

In one embodiment, $R_9$ is $C_3$-$C_8$ cycloalkyl optionally substituted with one or more $R_{10}$. In one embodiment, $R_9$ is heterocyclyl optionally substituted with one or more $R_{10}$. In one embodiment, $R_9$ is aryl optionally substituted with one or more $R_{10}$. In one embodiment, $R_9$ is heteroaryl optionally substituted with one or more $R_{10}$.

In one embodiment, $R_8$ and $R_9$ when taken together form a $C_3$-$C_6$ cycloalkyl or heterocycle, wherein the cycloalkyl or heterocycle is optionally substituted with $R_{10}$.

In one embodiment, $R_8$ and $R_9$ when taken together form a $C_3$-$C_6$ cycloalkyl, wherein the cycloalkyl is optionally substituted with $R_{10}$. In one embodiment, $R_8$ and $R_9$ when taken together form a $C_3$-$C_6$ cycloalkyl. In one embodiment, $R_8$ and $R_9$ when taken together form cyclopropyl, wherein the cyclopropyl is optionally substituted with $R_{10}$. In one embodiment, $R_8$ and $R_9$ when taken together form cyclopropyl.

In one embodiment, $R_8$ and $R_9$ when taken together form a heterocycle, wherein the heterocycle is optionally substituted with $R_{10}$. In one embodiment, $R_8$ and $R_9$ when taken together form a 4-membered heterocycle optionally substituted with $R_{10}$. In one embodiment, $R_8$ and $R_9$ when taken together form azetidinyl optionally substituted with $R_{10}$. In one embodiment, $R_8$ and $R_9$ when taken together form oxetanyl optionally substituted with $R_{10}$.

In one embodiment, $R_{10}$ is independently at each occurrence oxo, halogen, —CN, —$OR_{11}$, —$C(O)R_{11}$, —$C(O)OR_{11}$, —$C(O)NR_{11}R_{12}$, —$NR_{11}C(O)R_{12}$, —$S(O)R_{11}$, —$S(O)_2R_{11}$, —$NR_{11}S(O)_2R_{12}$, —$S(O)_2NR_{11}R_{12}$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_{10}$ is independently at each occurrence oxo, halogen, —CN, —$OR_{11}$, —$C(O)R_{11}$, —$C(O)OR_{11}$, —$C(O)NR_{11}R_{12}$, —$NR_{11}R_{12}$, —$NR_{11}C(O)R_{12}$, —$S(O)R_{11}$, —$S(O)_2R_{11}$, —$NR_{11}S(O)_2R_{12}$, —$S(O)_2NR_{11}R_{12}$, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_{10}$ is independently at each occurrence oxo, halogen, or —CN. In one embodiment, $R_{10}$ is oxo. In one embodiment, $R_{10}$ is halogen. In one embodiment, $R_{10}$ is F, $C_1$, Br, or I. In one embodiment, $R_{10}$ is F or $C_1$. In one embodiment, $R_{10}$ is F. In one embodiment, $R_{10}$ is $C_1$. In one embodiment, $R_{10}$ is —CN.

In one embodiment, $R_{10}$ is independently at each occurrence —$OR_{11}$, —$C(O)R_{11}$, —$C(O)OR_{11}$, —$C(O)NR_{11}R_{12}$, —$NR_{11}C(O)R_{12}$, —$S(O)R_{11}$, —$S(O)_2R_{11}$, —$NR_{11}S(O)_2R_{12}$, or —$S(O)_2NR_{11}R_{12}$. In one embodiment, $R_{10}$ is —$OR_{11}$. In one embodiment, $R_{10}$ is —$C(O)R_{11}$. In one embodiment, $R_{10}$ is —$C(O)OR_{11}$. In one embodiment, $R_{10}$ is —$C(O)NR_{11}R_{12}$. In one embodiment, $R_{10}$ is —$NR_{11}C(O)R_{12}$. In one embodiment, $R_{10}$ is —$S(O)R_{11}$. In one embodiment, $R_{10}$ is —$S(O)_2R_{11}$. In one embodiment, $R_{10}$ is —$NR_{11}S(O)_2R_{12}$. In one embodiment, $R_{10}$ is —$S(O)_2NR_{11}R_{12}$.

In one embodiment, $R_{10}$ is independently at each occurrence $C_1$-$C_6$ alkyl, $C_1$-$C_6$ haloalkyl, $C_2$-$C_6$ alkenyl, or $C_2$-$C_6$ alkynyl.

In one embodiment, $R_{10}$ is $C_1$-$C_6$ alkyl. In one embodiment, $R_{10}$ is methyl. In one embodiment, $R_{10}$ is ethyl. In one embodiment, $R_{10}$ is propyl. In one embodiment, $R_{10}$ is butyl. In one embodiment, $R_{10}$ is pentyl. In one embodiment, $R_{10}$ is hexyl.

In one embodiment, $R_{10}$ is $C_1$-$C_6$ haloalkyl. In one embodiment, $R_{10}$ is halomethyl. In one embodiment, $R_{10}$ is haloethyl. In one embodiment, $R_{10}$ is halopropyl. In one embodiment, $R_{10}$ is halobutyl. In one embodiment, $R_{10}$ is halopentyl. In one embodiment, $R_{10}$ is halohexyl.

In one embodiment, $R_{10}$ is $C_2$-$C_6$ alkenyl. In one embodiment, $R_{10}$ is $C_2$-$C_6$ alkynyl.

In one embodiment, $R_{10}$ is independently at each occurrence $C_3$-$C_8$ cycloalkyl or heterocyclyl. In one embodiment, $R_{10}$ is $C_3$-$C_8$ cycloalkyl. In one embodiment, $R_{10}$ is heterocyclyl.

In one embodiment, $R_{10}$ is independently at each occurrence aryl or heteroaryl. In one embodiment, $R_{10}$ is aryl. In one embodiment, $R_{10}$ is heteroaryl.

In one embodiment, $R_{10}$ is —OH.

In one embodiment, Ru and $R_{12}$ are independently H, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, Ru and $R_{12}$ are independently H.

In one embodiment, Ru and $R_{12}$ are independently $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, Ru is H, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, Ru is H.

In one embodiment, Ru is $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, Ru is $C_1$-$C_6$ alkyl, $C_1$-$C_6$ haloalkyl, $C_2$-$C_6$ alkenyl, or $C_2$-$C_6$ alkynyl.

In one embodiment, Ru is $C_1$-$C_6$ alkyl. In one embodiment, Ru is methyl. In one embodiment, Ru is ethyl. In one embodiment, Ru is propyl. In one embodiment, Ru is butyl. In one embodiment, Ru is pentyl. In one embodiment, Ru is hexyl.

In one embodiment, Ru is $C_1$-$C_6$ haloalkyl. In one embodiment, Ru is halomethyl. In one embodiment, Ru is haloethyl. In one embodiment, Ru is halopropyl. In one embodiment, Ru is halobutyl. In one embodiment, Ru is halopentyl. In one embodiment, Ru is halohexyl.

In one embodiment, Ru is $C_2$-$C_6$ alkenyl. In one embodiment, Ru is $C_2$-$C_6$ alkynyl.

In one embodiment, Ru is $C_3$-$C_8$ cycloalkyl, heterocyclyl, aryl, or heteroaryl. In one embodiment, Ru is $C_3$-$C_8$ cycloalkyl. In one embodiment, Ru is heterocyclyl. In one embodiment, Ru is aryl. In one embodiment, Ru is heteroaryl.

In one embodiment, $R_{12}$ is H, $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_{12}$ is H.

In one embodiment, $R_{12}$ is $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, heterocyclyl, aryl, or heteroaryl.

In one embodiment, $R_{12}$ is $C_1$-$C_6$ alkyl, $C_1$-$C_6$ haloalkyl, $C_2$-$C_6$ alkenyl, or $C_2$-$C_6$ alkynyl.

In one embodiment, $R_{12}$ is $C_1$-$C_6$ alkyl. In one embodiment, $R_{12}$ is methyl. In one embodiment, $R_{12}$ is ethyl. In one embodiment, $R_{12}$ is propyl. In one embodiment, $R_{12}$ is butyl. In one embodiment, $R_{12}$ is pentyl. In one embodiment, $R_{12}$ is hexyl.

In one embodiment, $R_{12}$ is $C_1$-$C_6$ haloalkyl. In one embodiment, $R_{12}$ is halomethyl. In one embodiment, $R_{12}$ is haloethyl. In one embodiment, $R_{12}$ is halopropyl. In one embodiment, $R_{12}$ is halobutyl. In one embodiment, $R_{12}$ is halopentyl. In one embodiment, $R_{12}$ is halohexyl.

In one embodiment, $R_{12}$ is $C_2$-$C_6$ alkenyl. In one embodiment, $R_{12}$ is $C_2$-$C_6$ alkynyl.

In one embodiment, $R_{12}$ is $C_3$-$C_8$ cycloalkyl, heterocyclyl, aryl, or heteroaryl. In one embodiment, $R_{12}$ is $C_3$-$C_8$ cycloalkyl. In one embodiment, $R_{12}$ is heterocyclyl. In one embodiment, $R_{12}$ is aryl. In one embodiment, $R_{12}$ is heteroaryl.

In one embodiment, the compounds of the present disclosure are represented by compounds of Formula II:

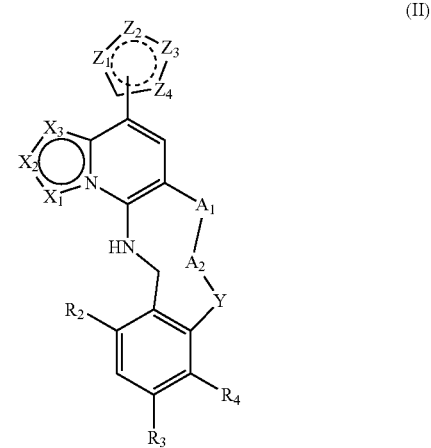

(II)

or pharmaceutically acceptable salts, prodrugs, solvates, hydrates, enantiomers, isomers, or tautomers thereof, wherein:

------ represents optional double bonds which can form an aromatic when present;

$Z_1$, $Z_2$, $Z_3$, and $Z_4$ are independently C, N, S, O, $N(R_{10})$, or $C(R_{10})$; and $X_1$, $X_2$, $X_3$, $A_1$, $A_2$, Y, $R_2$, $R_3$, $R_4$, $R_{10}$ are described as herein.

In one embodiment, the compounds of the present disclosure are represented by compounds of Formula III:

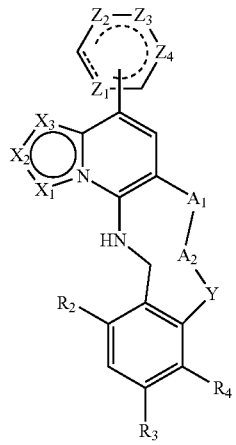

(III)

or pharmaceutically acceptable salts, prodrugs, solvates, hydrates, enantiomers, isomers, or tautomers thereof, wherein:

------ straight or curved represents optional double bonds that form a partially unsaturated ring or an aromatic ring when present;

$Z_1$, $Z_2$, $Z_3$, and $Z_4$ are independently C, N, O, $N(R_{10})$, or $C(R_{10})$, provided $Z_1$, $Z_2$, $Z_3$, and $Z_4$ are not all N or $N(R_{10})$ when ------ is present and aromatic; provided that no three N or $N(R_{10})$ are adjacent; provided that $Z_1$, $Z_2$, $Z_3$, and $Z_4$ are not O when ------ is present and aromatic; and $X_1$, $X_2$, $X_3$, $A_1$, $A_2$, Y, $R_2$, $R_3$, $R_4$, $R_{10}$ are described as herein.

In one embodiment, the compound is of formula Ia:

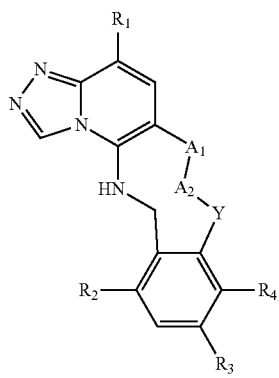

(Ia)

or a pharmaceutically acceptable salt, prodrug, solvate, hydrate, enantiomer, isomer, or tautomer thereof.

In one embodiment, the compound is of formula Ib:

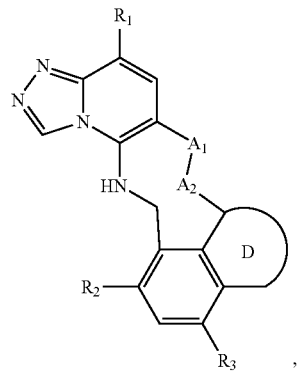

(Ib)

or a pharmaceutically acceptable salt, prodrug, solvate, hydrate, enantiomer, isomer, or tautomer thereof, wherein the D ring represents a $C_3$-$C_{10}$ cycloalkyl, $C_5$-$C_8$ cycloalkenyl, heterocyclyl, aryl, or heteroaryl.

In one embodiment, the compound is of formula Ic:

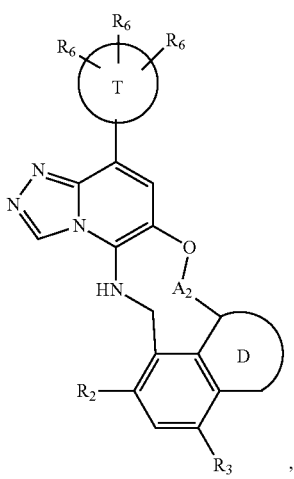

(Idc)

or a pharmaceutically acceptable salt, prodrug, solvate, hydrate, enantiomer, isomer, or tautomer thereof, wherein the D ring represents a $C_3$-$C_{10}$ cycloalkyl, $C_5$-$C_8$ cycloalkenyl, heterocyclyl, aryl, or heteroaryl; and the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Id:

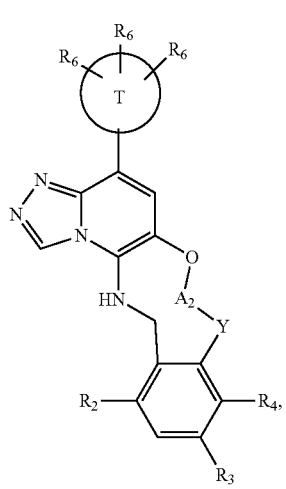

(Id)

or a pharmaceutically acceptable salt, prodrug, solvate, hydrate, enantiomer, isomer, or tautomer thereof, wherein the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Ie:

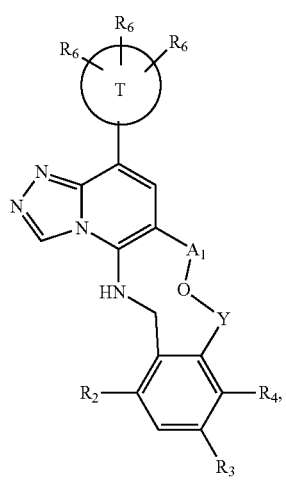

(Ie)

or a pharmaceutically acceptable salt, prodrug, solvate, hydrate, enantiomer, isomer, or tautomer thereof, wherein the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula If;

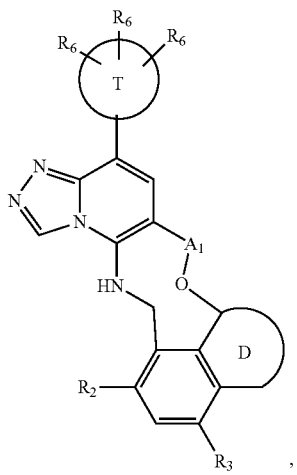

(If)

or a pharmaceutically acceptable salt, prodrug, solvate, hydrate, enantiomer, isomer, or tautomer thereof, wherein the D ring represents a $C_3$-$C_{10}$ cycloalkyl, $C_5$-$C_8$ cycloalkenyl, heterocyclyl, aryl, or heteroaryl; and the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Ig;

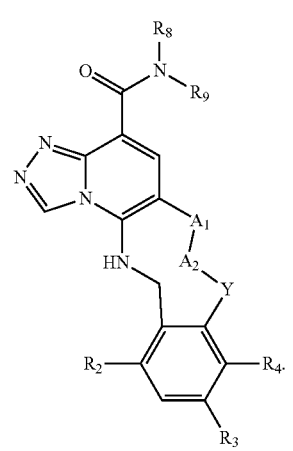

(Ig)

or a pharmaceutically acceptable salt, prodrug, solvate, hydrate, enantiomer, isomer, or tautomer thereof.

In one embodiment, the compound is of formula Ih:

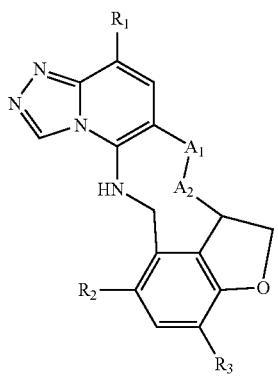
(Ih)

or a pharmaceutically acceptable salt, prodrug, solvate, hydrate, enantiomer, isomer, or tautomer thereof.

In one embodiment, the compound is of formula Ih-a:

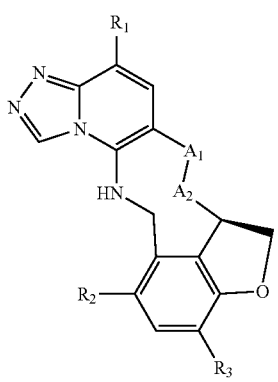
(Ih-a)

or a pharmaceutically acceptable salt, prodrug, solvate, hydrate, enantiomer, isomer, or tautomer thereof.

In one embodiment, the compound is of formula Ii:

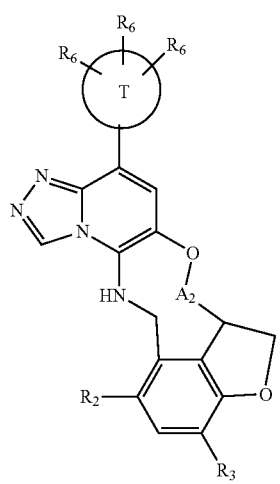
(Ii)

or a pharmaceutically acceptable salt, prodrug, solvate, hydrate, enantiomer, isomer, or tautomer thereof, wherein the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Ii-a:

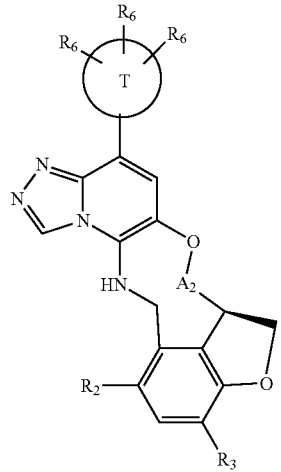
(Ii-a)

or a pharmaceutically acceptable salt, prodrug, solvate, hydrate, enantiomer, isomer, or tautomer thereof, wherein the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Ii or a pharmaceutically acceptable salt, prodrug, solvate, hydrate, enantiomer, isomer, or tautomer thereof, wherein the T ring represents a heterocyclyl.

In one embodiment, the compound is of formula Ii-a or a pharmaceutically acceptable salt, prodrug, solvate, hydrate, enantiomer, isomer, or tautomer thereof, wherein the T ring represents a heterocyclyl.

In one embodiment, the compound is of formula Ij:

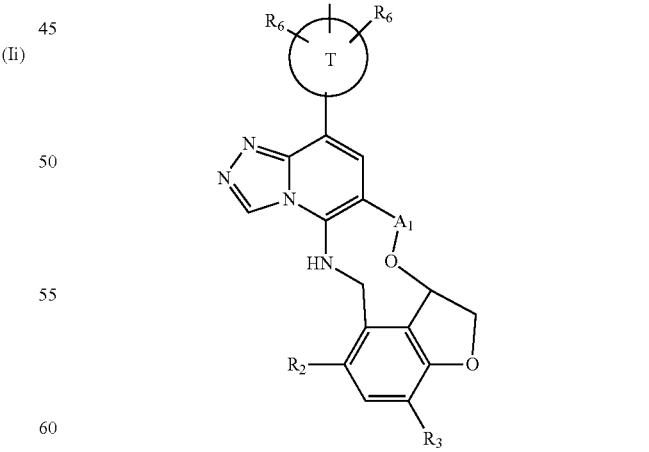
(Ij)

or a pharmaceutically acceptable salt, prodrug, solvate, hydrate, enantiomer, isomer, or tautomer thereof, wherein the T ring represents a $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl.

In one embodiment, the compound is of formula Ij or a pharmaceutically acceptable salt, prodrug, solvate, hydrate, enantiomer, isomer, or tautomer thereof, wherein the T ring represents a heterocyclyl.

In one embodiment, the compound is of formula Ik:

(Ik)

or a pharmaceutically acceptable salt, prodrug, solvate, hydrate, enantiomer, isomer, or tautomer thereof.

In one embodiment, the compound is of formula Ik-a:

(Ik-a)

or a pharmaceutically acceptable salt, prodrug, solvate, hydrate, enantiomer, isomer, or tautomer thereof.

In one embodiment, at least one of $X_1$, $X_2$, or $X_3$ is N, $A_1$ is —O—, $A_2$ is —C($R_8$)($R_9$)—, and Y is —C($R_8$)($R_9$)—.

In one embodiment, at least one of $X_1$, $X_2$, or $X_3$ is N, $A_1$ is —C($R_8$)($R_9$)—, $A_2$ is —O—, and Y is —C($R_8$)($R_9$)—.

In one embodiment, one of $X_1$, $X_2$, $X_3$ is C($R_5$), $A_1$ is —O—, $A_2$ is —C($R_8$)($R_9$)—, and Y is —C($R_8$)($R_9$)—.

In one embodiment, one of $X_1$, $X_2$, $X_3$ is C($R_5$), $A_1$ is —C($R_8$)($R_9$)—, $A_2$ is —O—, and Y is —C($R_8$)($R_9$)—.

In one embodiment, at least one of $X_1$, $X_2$, or $X_3$ is N, $A_1$ is —O—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, and Y is —C($R_8$)($R_9$)—, wherein $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, and Y is —C($R_8$)($R_9$)—, wherein $R_4$ and $R_9$ can form heterocyclyl.

In one embodiment, at least one of $X_1$, $X_2$, or $X_3$ is N, $A_1$ is —S—, $A_2$ is —C($R_8$)($R_9$)—, and Y is —C($R_8$)($R_9$)—.

In one embodiment, at least one of $X_1$, $X_2$, or $X_3$ is N, $A_1$ is —C($R_8$)($R_9$)—, $A_2$ is —S—, and Y is —C($R_8$)($R_9$)—.

In one embodiment, one of $X_1$, $X_2$, $X_3$ is C($R_5$), $A_1$ is —S—, $A_2$ is —C($R_8$)($R_9$)—, and Y is —C($R_8$)($R_9$)—.

In one embodiment, one of $X_1$, $X_2$, $X_3$ is C($R_5$), $A_1$ is —C($R_8$)($R_9$)—, $A_2$ is —S—, and Y is —C($R_8$)($R_9$)—.

In one embodiment, at least one of $X_1$, $X_2$, or $X_3$ is N, $A_1$ is —S—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —S—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —S—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —S—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —S—, $A_2$ is —C($R_8$)($R_9$)—, and Y is —C($R_8$)($R_9$)—, wherein $R_4$ and $R_9$ can form heterocyclyl.

In one embodiment, at least one of $X_1$, $X_2$, or $X_3$ is N, $A_1$ is —C($R_8$)($R_9$)—, $A_2$ is —S—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —S—, $A_2$ is —C($R_8$)($R_9$)—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —S—, and Y is —C($R_8$)($R_9$)—, wherein $R_4$ and $R_9$ can form heterocyclyl.

In one embodiment, at least one of $X_1$, $X_2$, or $X_3$ is N, $A_1$ is —S(O)—, $A_2$ is —C($R_8$)($R_9$)—, and Y is —C($R_8$)($R_9$)—.

In one embodiment, at least one of $X_1$, $X_2$, or $X_3$ is N, $A_1$ is —C($R_8$)($R_9$)—, $A_2$ is —S(O)—, and Y is —C($R_8$)($R_9$)—.

In one embodiment, one of $X_1$, $X_2$, $X_3$ is C($R_5$), $A_1$ is —S(O)—, $A_2$ is —C($R_8$)($R_9$)—, and Y is —C($R_8$)($R_9$)—.

In one embodiment, one of $X_1$, $X_2$, $X_3$ is C($R_5$), $A_1$ is —C($R_8$)($R_9$)—, $A_2$ is —S(O)—, and Y is —C($R_8$)($R_9$)—.

In one embodiment, at least one of $X_1$, $X_2$, or $X_3$ is N, $A_1$ is —S(O)—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —S(O)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —S(O)—, $A_2$ is —C($R_8$)($R_9$)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —S(O)—, and Y is —C($R_8$)($R_9$)—, wherein $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —S(O)—, $A_2$ is —C($R_8$)($R_9$)—, and Y is —C($R_8$)($R_9$)—, wherein $R_4$ and $R_9$ can form heterocyclyl.

In one embodiment, at least one of $X_1$, $X_2$, or $X_3$ is N, $A_1$ is —C($R_8$)($R_9$)—, $A_2$ is —S(O)—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —S(O)—, $A_2$ is —C($R_8$)($R_9$)—, and Y is —C($R_8$)($R_9$)—, wherein $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —S(O)—, and Y is —C($R_8$)($R_9$)—, wherein $R_4$ and $R_9$ can form heterocyclyl.

In one embodiment, at least one of $A_1$, $A_2$, and Y is —C($R_8$)($R_9$)—, wherein $R_8$ and $R_9$ are halogen.

In one embodiment, at least one of $A_1$, $A_2$, and Y is —C($R_8$)($R_9$)—, wherein $R_8$ and $R_9$ are F.

In one embodiment, at least two of $A_1$, $A_2$, and Y is —C($R_8$)($R_9$)—, wherein $R_8$ and $R_9$ are halogen.

In one embodiment, at least two of $A_1$, $A_2$, and Y is —C($R_8$)($R_9$)—, wherein $R_8$ and $R_9$ are F.

In one embodiment, $A_1$, $A_2$, and Y are —C($R_8$)($R_9$)—, wherein $R_8$ and $R_9$ are halogen.

In one embodiment, $A_1$, $A_2$, and Y are —C($R_8$)($R_9$)—, wherein $R_8$ and $R_9$ are F.

In one embodiment, $A_1$ is —C($R_8$)($R_9$)—, wherein $R_8$ and $R_9$ are halogen.

In one embodiment, $A_1$ is —C($R_8$)($R_9$)—, wherein $R_8$ and $R_9$ are F.

In one embodiment, $A_2$ is —C($R_8$)($R_9$)—, wherein $R_8$ and $R_9$ are halogen.

In one embodiment, $A_2$ is —C($R_8$)($R_9$)—, wherein $R_8$ and $R_9$ are F.

In one embodiment, Y is —C($R_8$)($R_9$)—, wherein $R_8$ and $R_9$ are halogen.

In one embodiment, Y is —C($R_8$)($R_9$)—, wherein $R_8$ and $R_9$ are F.

In one embodiment, at least one of $X_1$, $X_2$, or $X_3$ is N, $A_1$ is —O—, $A_2$ is —C($R_8$)($R_9$)—, Y is —C($R_8$)($R_9$)—, and $R_1$ is H, —N$R_8R_9$, —P(O)(O$R_8$)(O$R_9$), —C(O)$R_8$, —C(O)N$R_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl, wherein the alkyl, alkoxy, alkenyl, alkynyl, cycloalkyl, cycloalkenyl, spirocycloalkyl, spiroheterocyclyl, heterocyclyl, aryl, or heteroaryl is optionally substituted with one or more $R_6$.

In one embodiment, at least one of $X_1$, $X_2$, or $X_3$ is N, $A_1$ is —C($R_8$)($R_9$)—, $A_2$ is —O—, Y is —C($R_8$)($R_9$)—, and $R_1$ is H, —N$R_8R_9$, —P(O)(O$R_8$)(O$R_9$), —C(O)$R_8$, —C(O)N$R_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl, wherein the alkyl, alkoxy, alkenyl, alkynyl, cycloalkyl, cycloalkenyl, spirocycloalkyl, spiroheterocyclyl, heterocyclyl, aryl, or heteroaryl is optionally substituted with one or more $R_6$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, and $R_1$ is H, —N$R_8R_9$, —P(O)(O$R_8$)(O$R_9$), —C(O)$R_8$, —C(O)N$R_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl, wherein the alkyl, alkoxy, alkenyl, alkynyl, cycloalkyl, cycloalkenyl, spirocycloalkyl, spiroheterocyclyl, heterocyclyl, aryl, or heteroaryl is optionally substituted with one or more $R_6$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, and $R_1$ is H, —N$R_8R_9$, —P(O)(O$R_8$)(O$R_9$), —C(O)$R_8$, —C(O)N$R_8R_9$, —CN, $C_1$-$C_6$ alkyl, $C_1$-$C_6$ alkoxy, $C_2$-$C_6$ alkenyl, $C_2$-$C_6$ alkynyl, $C_3$-$C_{10}$ cycloalkyl, $C_5$-$C_8$ cycloalkenyl, $C_3$-$C_8$ spirocycloalkyl, spiroheterocyclyl, heterocyclyl, aryl, or heteroaryl, wherein the alkyl, alkoxy, alkenyl, alkynyl, cycloalkyl, cycloalkenyl, spirocycloalkyl, spiroheterocyclyl, heterocyclyl, aryl, or heteroaryl is optionally substituted with one or more $R_6$.

In one embodiment, at least one of $X_1$, $X_2$, or $X_3$ is N, $A_1$ is —O—, $A_2$ is —C($R_8$)($R_9$)—, Y is —C($R_8$)($R_9$)—, and $R_1$ is heterocyclyl, aryl, or heteroaryl, wherein the heterocyclyl, aryl, or heteroaryl is optionally substituted with one or more $R_6$.

In one embodiment, at least one of $X_1$, $X_2$, or $X_3$ is N, $A_1$ is —C($R_8$)($R_9$)—, $A_2$ is —O—, Y is —C($R_8$)($R_9$)—, and $R_1$ is heterocyclyl, aryl, or heteroaryl, wherein the heterocyclyl, aryl, or heteroaryl is optionally substituted with one or more $R_6$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, and $R_1$ is heterocyclyl, aryl, or heteroaryl, wherein the heterocyclyl, aryl, or heteroaryl is optionally substituted with one or more $R_6$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, and $R_1$ is heterocyclyl, aryl, or heteroaryl, wherein the heterocyclyl, aryl, or heteroaryl is optionally substituted with one or more $R_6$.

In one embodiment, at least one of $X_1$, $X_2$, or $X_3$ is N, $A_1$ is —O—, $A_2$ is —C($R_8$)($R_9$)—, Y is —C($R_8$)($R_9$)—, and $R_1$ is heterocyclyl optionally substituted with one or more $R_6$.

In one embodiment, at least one of $X_1$, $X_2$, or $X_3$ is N, $A_1$ is —C($R_8$)($R_9$)—, $A_2$ is —O—, Y is —C($R_8$)($R_9$)—, and $R_1$ is heterocyclyl optionally substituted with one or more $R_6$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, and $R_1$ is heterocyclyl optionally substituted with one or more $R_6$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, and $R_1$ is heterocyclyl optionally substituted with one or more $R_6$.

In one embodiment, at least one of $X_1$, $X_2$, or $X_3$ is N, $A_1$ is —O—, $A_2$ is —C($R_8$)($R_9$)—, Y is —C($R_8$)($R_9$)—, and $R_1$ is heteroaryl optionally substituted with one or more $R_6$.

In one embodiment, at least one of $X_1$, $X_2$, or $X_3$ is N, $A_1$ is —C($R_8$)($R_9$)—, $A_2$ is —O—, Y is —C($R_8$)($R_9$)—, and $R_1$ is heteroaryl optionally substituted with one or more $R_6$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, and $R_1$ is heteroaryl optionally substituted with one or more $R_6$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, and $R_1$ is heteroaryl optionally substituted with one or more $R_6$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$ In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$ In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$ In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, and $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, and $R_2$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, and $R_2$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, and $R_2$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, and $R_2$ is H.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl optionally substituted with one or more $R_6$, and $R_2$ is H.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heteroaryl optionally substituted with one or more $R_6$, and $R_2$ is H.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heteroaryl optionally substituted with one or more $R_6$, and $R_2$ is H.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heteroaryl optionally substituted with one or more $R_6$, and $R_2$ is H.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heteroaryl optionally substituted with one or more $R_6$, and $R_2$ is H.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, and $R_2$ is halogen.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, and $R_2$ is halogen.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, and $R_2$ is halogen.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, and $R_2$ is halogen.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl optionally substituted with one or more $R_6$, and $R_2$ is halogen.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl optionally substituted with one or more $R_6$, and $R_2$ is halogen.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl optionally substituted with one or more $R_6$, and $R_2$ is halogen.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl optionally substituted with one or more $R_6$, and $R_2$ is halogen.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heteroaryl optionally substituted with one or more $R_6$, and $R_2$ is halogen.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heteroaryl optionally substituted with one or more $R_6$, and $R_2$ is halogen.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heteroaryl optionally substituted with one or more $R_6$, and $R_2$ is halogen.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heteroaryl optionally substituted with one or more $R_6$, and $R_2$ is halogen.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is H, and $R_3$ is H.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is H, and $R_3$ is H.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is H, and $R_3$ is H.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is H, and $R_3$ is H.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl optionally substituted with one or more $R_6$, $R_2$ is H, and $R_3$ is H.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl optionally substituted with one or more $R_6$, $R_2$ is H, and $R_3$ is H.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl optionally substituted with one or more $R_6$, $R_2$ is H, and $R_3$ is H.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl optionally substituted with one or more $R_6$, $R_2$ is H, and $R_3$ is H.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heteroaryl optionally substituted with one or more $R_6$, $R_2$ is H, and $R_3$ is H.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heteroaryl optionally substituted with one or more $R_6$, $R_2$ is H, and $R_3$ is H.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heteroaryl optionally substituted with one or more $R_6$, $R_2$ is H, and $R_3$ is H.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heteroaryl optionally substituted with one or more $R_6$, $R_2$ is H, and $R_3$ is H.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is halogen, and $R_3$ is H.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, $R_2$ is halogen, and $R_3$ is H.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, and $R_3$ is H.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, and $R_3$ is H.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, and $R_3$ is H.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, and $R_3$ is H.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, and $R_3$ is H.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, and $R_3$ is H.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, and $R_3$ is H.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, and $R_3$ is H.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, and $R_3$ is H.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, and $R_3$ is H.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ —O—, $A_2$ is —$C(R_8)(R_9)$—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, X is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ is H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ is H.

In one embodiment, X is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ is H.

In one embodiment, X is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ and $R_9$ can form $C_3$-$C_{10}$ cycloalkyl, $C_5$-$C_8$ cycloalkenyl, heterocyclyl, aryl, or heteroaryl In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is $C(R_5)$, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, one of $X_1$, $X_2$, $X_3$ is $C(R_5)$, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ and $R_9$ can form $C_3$-$C_{10}$ cycloalkyl, $C_5$-$C_8$ cycloalkenyl, heterocyclyl, aryl, or heteroaryl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), wherein $R_8$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more P $R_7$, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is C($R_5$), wherein $R_8$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $R_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is C($R_5$), wherein $R_8$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is H, $R_3$ is H, and $R_4$ is H.

In one embodiment, one of $X_1$, $X_2$, $X_3$ is C($R_5$), wherein $R_8$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is H, $R_3$ is H, and $R_4$ is H.

In one embodiment, one of $X_1$, $X_2$, $X_3$ is C($R_5$), wherein $R_8$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is C($R_5$), wherein $R_8$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$—$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is C($R_5$), wherein $R_5$ is H, halogen, —CN, —O$R_8$, —N$R_8R_9$, —C(O)$R_8$, —C(O)O$R_8$, —C(O)N$R_8R_9$, —N$R_8$C(O)$R_9$, —S(O)$R_8$, —S(O)$_2R_8$, —N$R_8$S(O)$_2R_9$, —S(O)$_2$N$R_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is C($R_5$), wherein $R_8$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is C($R_5$), wherein $R_8$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_8$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—$R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), wherein $R_8$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —O—, $A_2$ is —C($R_8$)($R_9$)—, Y is —C($R_8$)($R_9$)—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is C($R_5$), wherein $R_5$ is H, halogen, —CN, —$OR_8$, —$NR_8R_9$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_5$-$C_8$ cycloalkenyl, heterocyclyl, aryl, or heteroaryl, $A_1$ is —C($R_8$)($R_9$)—, $A_2$ is —O—, Y is —C($R_8$)

(R$_9$)—, R$_1$ is heterocyclyl optionally substituted with one or more R$_6$, R$_2$ is H, R$_3$ is H, and R$_4$ and R$_9$ can form heterocyclyl.

In one embodiment, one of X$_1$, X$_2$, X$_3$ is C(R$_5$), wherein R$_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —O—, A$_2$ is —C(R$_8$)(R$_9$)—, Y is —C(R$_8$)(R$_9$)—, R$_1$ is heteroaryl optionally substituted with one or more R$_6$, R$_2$ is H, R$_3$ is H, and R$_4$ and R$_9$ can form heterocyclyl.

In one embodiment, one of X$_1$, X$_2$, X$_3$ is C(R$_5$), wherein R$_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —C(R$_8$)(R$_9$)—, A$_2$ is —O—, Y is —C(R$_8$)(R$_9$)—, R$_1$ is heteroaryl optionally substituted with one or more R$_6$, R$_2$ is H, R$_3$ is H, and R$_4$ and R$_9$ can form heterocyclyl.

In one embodiment, one of X$_1$, X$_2$, X$_3$ is C(R$_5$), wherein R$_8$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, R$_2$ is halogen, R$_3$ is H, and R$_4$ and R$_9$ can form heterocyclyl.

In one embodiment, one of X$_1$, X$_2$, X$_3$ is C(R$_5$), wherein R$_8$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —C(R$_8$)(R$_9$)—, A$_2$ is —O—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, R$_2$ is halogen, R$_3$ is H, and R$_4$ and R$_9$ can form heterocyclyl.

In one embodiment, one of X$_1$, X$_2$, X$_3$ is C(R$_5$), wherein R$_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —O—, A$_2$ is —C(R$_8$)(R$_9$)—, Y is —C(R$_8$)(R$_9$)—, R$_1$ is heterocyclyl optionally substituted with one or more R$_6$, R$_2$ is halogen, R$_3$ is H, and R$_4$ and R$_9$ can form heterocyclyl.

In one embodiment, one of X$_1$, X$_2$, X$_3$ is C(R$_5$), wherein R$_5$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —C(R$_8$)(R$_9$)—, A$_2$ is —O—, Y is —C(R$_8$)(R$_9$)—, R$_1$ is heteroaryl optionally substituted with one or more R$_6$, R$_2$ is halogen, R$_3$ is H, and R$_4$ and R$_9$ can form heterocyclyl.

In one embodiment, one of X$_1$, X$_2$, X$_3$ is C(R$_5$), wherein R$_8$ is H, halogen, —CN, —OR$_8$, —NR$_8$R$_9$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_1$-C$_6$ haloalkyl, C$_2$-C$_6$ alkenyl, C$_2$-C$_6$ alkynyl, C$_3$-C$_{10}$ cycloalkyl, C$_5$-C$_8$ cycloalkenyl, heterocyclyl, aryl, or heteroaryl, A$_1$ is —C(R$_8$)(R$_9$)—, A$_2$ is —O—, Y is —C(R$_8$)(R$_9$)—, R$_1$ is heteroaryl optionally substituted with one or more R$_6$, R$_2$ is halogen, R$_3$ is H, and R$_4$ and R$_9$ can form heterocyclyl.

In one embodiment, one of X$_1$, X$_2$, X$_3$ is C(R$_5$), wherein R$_8$ is H, A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), wherein R$_5$ is H, A$_1$ is —C(R$_8$)(R$_9$)—, A$_2$ is —O—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), wherein R$_5$ is H, A$_1$ is —O—, A$_2$ is —C(R$_8$)(R$_9$)—, Y is —C(R$_8$)(R$_9$)—, R$_1$ is heterocyclyl optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), wherein R$_5$ is H, A$_1$ is —C(R$_8$)(R$_9$)—, A$_2$ is —O—, Y is —C(R$_8$)(R$_9$)—, R$_1$ is heterocyclyl optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), wherein R$_5$ is H, A$_1$ is —O—, A$_2$ is —C(R$_8$)(R$_9$)—, Y is —C(R$_8$)(R$_9$)—, R$_1$ is heteroaryl optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), wherein R$_5$ is H, A$_1$ is —C(R$_8$)(R$_9$)—, A$_2$ is —O—, Y is —C(R$_8$)(R$_9$)—, R$_1$ is heteroaryl optionally substituted with one or more R$_6$, R$_2$ and R$_3$ are independently at each occurrence H, halogen, —OH, —NH$_2$, —CN, C$_1$-C$_6$ alkyl, C$_1$-C$_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ H, $A_1$ is —$C(R_8)(R_9)$—, $A_2$ is —O, Y is —$C(R_8)(R_9)$—, $R_1$ is heteroaryl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ H, $A_1$ is —$C(R_8)(R_9)$—, $A_2$ is —O—, Y is —$C(R_8)$ $(R_9)$—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is H, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is H, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, $R_3$ is H, and $R_4$ is H.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is H, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heterocyclyl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heterocyclyl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —O—, $A_2$ is —$C(R_8)(R_9)$—, Y is —$C(R_8)(R_9)$—, $R_1$ is heteroaryl optionally substituted with one or more $R_6$, $R_2$ is halogen, $R_3$ is H, and $R_4$ and $R_9$ can form heterocyclyl.

In one embodiment, one of $X_1$, $X_2$, $X_3$ is $C(R_5)$, wherein $R_5$ is $C_1$-$C_6$ alkyl, $A_1$ is —$C(R_8)(R_9)$—, $A_2$ is —O—, Y is —$C(R_8)(R_9)$—, $R_1$ is heteroaryl optionally substituted with one or more $R_6$, $R_2$ is halogen, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, one of X$_1$, X$_2$, X$_3$ is C(R$_5$), A$_1$ is —C(R$_8$)(R$_9$)—, A$_2$ is —O—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ is H.

In one embodiment, at least one of X$_1$, X$_2$, or X$_3$ is N, A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, at least one of X$_1$, X$_2$, or X$_3$ is N, A$_1$ is —C(R$_8$)(R$_9$)—, A$_2$ is —O—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O) NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O) NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, one of X$_1$, X$_2$, X$_3$ is C(R$_5$), A$_1$ is —C(R$_8$)(R$_9$)—, A$_2$ is —O—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O) NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, at least one of X$_1$, X$_2$, or X$_3$ is N, A$_1$ is —O—, A$_2$ is —C(R$_8$)(R$_9$)—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, at least one of X$_1$, X$_2$, or X$_3$ is N, A$_1$ is —C(R$_8$)(R$_9$)—, A$_2$ is —O—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, one of X$_1$, X$_2$, X$_3$ is C(R$_5$), A$_1$ is —C(R$_8$)(R$_9$)—, A$_2$ is —O—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence oxo, halogen, —CN, —$OR_8$, —C(O)$R_8$, —C(O)$OR_8$, —C(O)$NR_8R_9$, —$NR_8$C(O)$R_9$, —S(O)$R_8$, —S(O)$_2R_8$, —$NR_8$S(O)$_2R_9$, —S(O)$_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, one of X$_1$, X$_2$, X$_3$ is C(R$_5$), A$_1$ is —C(R$_8$)(R$_9$)—, A$_2$ is —O—, Y is —C(R$_8$)(R$_9$)—, R$_1$ is heterocyclyl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, at least one of X$_1$, X$_2$, or X$_3$ is N, A$_1$ is —O—, A$_2$ is —C(R$_8$)(R$_9$)—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, at least one of X$_1$, X$_2$, or X$_3$ is N, A$_1$ is —C(R$_8$)(R$_9$)—, A$_2$ is —O—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, one of X$_1$, X$_2$, X$_3$ is C(R$_5$), A$_1$ is —C(R$_8$)(R$_9$)—, A$_2$ is —O—, Y is —C(R$_8$)(R$_9$)—, R$_1$ is heteroaryl optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ and R$_3$ are independently at each occurrence H, halogen, —OH, —NH$_2$, —CN, C$_1$-C$_6$ alkyl, C$_1$-C$_6$ alkoxy, C$_2$-C$_6$ alkenyl, or C$_2$-C$_6$ alkynyl, wherein the alkyl, alkoxy, alkenyl, or alkynyl is optionally substituted with one or more R$_7$, and R$_4$ and R$_9$ can form heterocyclyl.

In one embodiment, at least one of X$_1$, X$_2$, or X$_3$ is N, A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ and R$_9$ can form heterocyclyl.

In one embodiment, at least one of X$_1$, X$_2$, or X$_3$ is N, A$_1$ is —C(R$_8$)(R$_9$)—, A$_2$ is —O—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence oxo, halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —NR$_8$S(O)$_2$R$_9$, —S(O)$_2$NR$_8$R$_9$, C$_1$-C$_6$ alkyl, C$_2$-C$_6$ alkenyl, C$_2$-C$_6$ alkynyl, C$_3$-C$_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more R$_{10}$, R$_2$ is H, R$_3$ is H, and R$_4$ and R$_9$ can form heterocyclyl.

In one embodiment, one of X$_1$, X$_2$, X$_3$ is C(R$_5$), A$_1$ is —O—, A$_2$ is —C(R$_8$)(R$_9$)—, Y is —C(R$_8$)(R$_9$)—, R$_1$ is heterocyclyl, aryl, or heteroaryl, wherein the heterocyclyl, aryl, or heteroaryl is optionally substituted with one or more R$_6$, wherein R$_6$ is independently at each occurrence halogen, —CN, —OR$_8$, —C(O)R$_8$, —C(O)OR$_8$, —C(O)NR$_8$R$_9$, —NR$_8$C(O)R$_9$, —S(O)R$_8$, —S(O)$_2$R$_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —$C(O)R_8$, —$C(O)OR_8$, —$C(O)NR_8R_9$, —$NR_8C(O)R_9$, —$S(O)R_8$, —$S(O)_2R_8$, —$NR_8S(O)_2R_9$, —$S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, —CN, —$OR_8$, —$C(O)R_8$, —$C(O)OR_8$, —$C(O)$ $NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl, aryl, or heteroaryl, wherein the heterocyclyl, aryl, or heteroaryl is optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heterocyclyl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heterocyclyl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heterocyclyl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is $-C(R_8)(R_9)-$, $A_2$ is $-O-$, Y is $-C(R_8)(R_9)-$, $R_1$ is heteroaryl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-O-$, $A_2$ is $-C(R_8)(R_9)-$, Y is $-C(R_8)(R_9)-$, $R_1$ is heteroaryl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is $-C(R_8)(R_9)-$, $A_2$ is $-O-$, Y is $-C(R_8)(R_9)-$, $R_1$ is heteroaryl optionally substituted with one or more $R_6$, wherein $R_6$ is independently at each occurrence oxo, halogen, $-CN$, $-OR_8$, $-C(O)R_8$, $-C(O)OR_8$, $-C(O)NR_8R_9$, $-NR_8C(O)R_9$, $-S(O)R_8$, $-S(O)_2R_8$, $-NR_8S(O)_2R_9$, $-S(O)_2NR_8R_9$, $C_1$-$C_6$ alkyl, $C_2$-$C_6$ alkenyl, $C_2$-$C_6$ alkynyl, $C_3$-$C_8$ cycloalkyl, heterocyclyl, aryl, or heteroaryl, wherein each alkyl, alkoxy, alkenyl, alkynyl, cycloalkyl, heterocyclyl, aryl, or heteroaryl can be optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is $-O-$, $A_2$ is $-C(R_8)(R_9)-$, Y is $-C(R_8)(R_9)-$, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —NH$_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —O—, $A_2$ is —C($R_8$)($R_9$)—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, one of $X_1$, $X_2$, $X_3$ is C($R_5$), $A_1$ is —C($R_8$)($R_9$)—, $A_2$ is —O—, Y is —C($R_8$)($R_9$)—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ is H.

In one embodiment, at least one of $X_1$, $X_2$, or $X_3$ is N, $A_1$ is —O—, $A_2$ is —C($R_8$)($R_9$)—, Y is —C($R_8$)($R_9$)—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ and $R_3$ are independently at each occurrence H, halogen, —OH, —$NH_2$, —CN, $C_1$-$C_6$ alkyl, $C_1$-$C_6$ alkoxy, $C_2$-$C_6$ alkenyl, or $C_2$-$C_6$ alkynyl, wherein the alkyl, alkoxy, alkenyl, or alkynyl is optionally substituted with one or more $R_7$, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is H, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl, aryl, or heteroaryl, wherein the heterocyclyl, aryl, or heteroaryl is optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heterocyclyl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, at least one of $X_1$, $X_2$, or $X_3$ is N, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —O—, $A_2$ is —$C(R_8)(R_9)$—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, one of $X_1$, $X_2$, $X_3$ is $C(R_5)$, $A_1$ is —$C(R_8)(R_9)$—, $A_2$ is —O—, Y is —$C(R_8)(R_9)$—, $R_1$ is heteroaryl optionally substituted with one or more $R_6$, wherein $R_6$ is independently at each occurrence $C_1$-$C_6$ alkyl optionally substituted with one or more $R_{10}$, $R_2$ is halogen, $R_3$ is H, and $R_4$ and $R_9$ can form heterocyclyl.

In one embodiment, suitable compounds of the disclose are and pharmaceutically acceptable salts, prodrugs, solvates, hydrates, enantiomers, isomers, and tautomers thereof are described in Table 1.

TABLE 1

| Compound No. | Compound Name |
|---|---|
| 1 | (15R)-10-(2-methyl-3-pyridyl)-13,17-dioxa-3,5,7,8-tetrazapentacyclo [13.6.1.04,12.05,9.018,22] docosa-1(22),4(12),6,8,10,18,20-heptaene |
| 3 | (S)-1-(4-(7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one |
| 4 | 1-(4-(12-fluoro-7,8,13,14-tetrahydro-[1,2,4]triazolo[4',3':1,6]pyrido[3,2-b]benzo[f][1,4]oxazonin-4-yl)piperidin-1-yl)ethan-1-one |
| 5 | 12-fluoro-4-(2-methylpyridin-3-yl)-7,8,13,14-tetrahydro-[1,2,4]triazolo[4',3':1,6]pyrido[3,2-b]benzo[f][1,4]oxazonine |
| 6 | 12-fluoro-4-(2-methylpyridin-3-yl)-6,8,13,14-tetrahydro-[1,2,4]triazolo[4',3':1,6]pyrido[3,2-c]benzo[g][1,5]oxazonine |
| 7 | (S)-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine |
| 8 | (S)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 9 | (S)-1-(4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one |
| 10 | (S)-12-fluoro-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine |
| 11 | (S)-7a,8,13,14-tetrahydro-7H-[1,2,4]triazolo[4',3':1,6]pyrido[3,2-b]benzofuro[4,3-fg][1,4]oxazonine |
| 12 | (S)-12-fluoro-4-(oxetan-3-yl)-7a,8,13,14-tetrahydro-7H-[1,2,4]triazolo[4',3':1,6]pyrido[3,2-b]benzofuro[4,3-fg][1,4]oxazonine |
| 13 | (S)-4-(2,4-dimethylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 14 | 4-(2,4-dimethylpyrimidin-5-yl)-12-fluoro-7,8,13,14-tetrahydro-[1,2,4]triazolo[4',3':1,6]pyrido[3,2-b]benzo[f][1,4]oxazonine |
| 15 | (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine |
| 16 | methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate |
| 17 | (S)-12-fluoro-4-(1-methyl-1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 18 | (S)-4-(1,3-dimethyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 19 | (S)-12-fluoro-4-(4-methylpyrimidin-5-yl)-7a,8,13,14-tetrahydro-7H-[1,2,4]triazolo[4',3':1,6]pyrido[3,2-b]benzofuro[4,3-fg][1,4]oxazonine |
| 20 | (S)-12-fluoro-4-(2-methylpyrimidin-5-yl)-7a,8,13,14-tetrahydro-7H-[1,2,4]triazolo[4',3':1,6]pyrido[3,2-b]benzofuro[4,3-fg][1,4]oxazonine |
| 21 | (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine |
| 22 | (S)-4-(1,3-dimethyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 23 | (S)-4-(3-(difluoromethyl)-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 24 | (S)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one |
| 25 | (R)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one |
| 26 | (S)-4-ethyl-12-fluoro-7a,8,13,14-tetrahydro-7H-[1,2,4]triazolo[4',3':1,6]pyrido[3,2-b]benzofuro[4,3-fg][1,4]oxazonine |
| 27 | (S)-12-fluoro-4-(1H-pyrazol-1-yl)-7a,8,13,14-tetrahydro-7H-[1,2,4]triazolo[4',3':1,6]pyrido[3,2-b]benzofuro[4,3-fg][1,4]oxazonine |
| 28 | (S)-4-(1,5-dimethyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 29 | (S)-4-(2,3-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 30 | (S)-12-fluoro-4-(2-methoxypyrimidin-5-yl)-7a,8,13,14-tetrahydro-7H-[1,2,4]triazolo[4',3':1,6]pyrido[3,2-b]benzofuro[4,3-fg][1,4]oxazonine |
| 31 | (S)-12-fluoro-4-(6-methoxypyridin-3-yl)-7a,8,13,14-tetrahydro-7H-[1,2,4]triazolo[4',3':1,6]pyrido[3,2-b]benzofuro[4,3-fg][1,4]oxazonine |
| 32 | (S)-4-(6-ethyl-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 33 | (S)-4-(2-(difluoromethyl)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |

TABLE 1-continued

| Compound No. | Compound Name |
|---|---|
| 34 | (S)-4-(2,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 35 | (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)propan-2-ol |
| 36 | (S)-12-fluoro-4-(4-(methylsulfonyl)phenyl)-7a,8,13,14-tetrahydro-7H-[1,2,4]triazolo[4',3':1,6]pyrido[3,2-b]benzofuro[4,3-fg][1,4]oxazonine |
| 37 | (S)-12-fluoro-N,N-dimethyl-7a,8,13,14-tetrahydro-7H-[1,2,4]triazolo[4',3':1,6]pyrido[3,2-b]benzofuro[4,3-fg][1,4]oxazonine-4-carboxamide |
| 38 | (S)-12-fluoro-N-methyl-N-(2,2,2-trifluoroethyl)-7a,8,13,14-tetrahydro-7H-[1,2,4]triazolo[4',3':1,6]pyrido[3,2-b]benzofuro[4,3-fg][1,4]oxazonine-4-carboxamide |
| 39 | (S)-12-fluoro-4-(1-methyl-1H-pyrazol-3-yl)-7a,8,13,14-tetrahydro-7H-[1,2,4]triazolo[4',3':1,6]pyrido[3,2-b]benzofuro[4,3-fg][1,4]oxazonine |
| 40 | (S)-12-fluoro-4-(5-fluoro-2-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 41 | (S)-12-fluoro-4-(3-fluoropyridin-2-yl)-7a,8,13,14-tetrahydro-7H-[1,2,4]triazolo[4',3':1,6]pyrido[3,2-b]benzofuro[4,3-fg][1,4]oxazonine |
| 42 | (S)-12-fluoro-4-(5-fluoropyridin-2-yl)-7a,8,13,14-tetrahydro-7H-[1,2,4]triazolo[4',3':1,6]pyrido[3,2-b]benzofuro[4,3-fg][1,4]oxazonine |
| 43 | (S)-12-fluoro-4-(3-fluoro-5-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 44 | (S)-4-(3,5-difluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 45 | (S)-12-fluoro-4-(5-fluoro-3-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 46 | (S)-12-fluoro-4-(5-methylpyrazin-2-yl)-7a,8,13,14-tetrahydro-7H-[1,2,4]triazolo[4',3':1,6]pyrido[3,2-b]benzofuro[4,3-fg][1,4]oxazonine |
| 47 | (S)-12-fluoro-4-(3-methylpyrazin-2-yl)-7a,8,13,14-tetrahydro-7H-[1,2,4]triazolo[4',3':1,6]pyrido[3,2-b]benzofuro[4,3-fg][1,4]oxazonine |
| 48 | (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)benzonitrile |
| 49 | (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)-3-methylbenzonitrile |
| 50 | (S)-12-fluoro-4-(2-methoxypyridin-4-yl)-7a,8,13,14-tetrahydro-7H-[1,2,4]triazolo[4',3':1,6]pyrido[3,2-b]benzofuro[4,3-fg][1,4]oxazonine |
| 51 | (S)-3-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridine 1-oxide |
| 52 | (S)-4-(3,5-dimethylpyrazin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 53 | (S)-12-fluoro-4-(3-methylpyridazin-4-yl)-7a,8,13,14-tetrahydro-7H-[1,2,4]triazolo[4',3':1,6]pyrido[3,2-b]benzofuro[4,3-fg][1,4]oxazonine |
| 54 | (S)-12-fluoro-4-(4-methylpyridazin-3-yl)-7a,8,13,14-tetrahydro-7H-[1,2,4]triazolo[4',3':1,6]pyrido[3,2-b]benzofuro[4,3-fg][1,4]oxazonine |
| 55 | (S)-12-fluoro-4-(6-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 56 | (S)-12-fluoro-4-(2-methylpyrimidin-4-yl)-7a,8,13,14-tetrahydro-7H-[1,2,4]triazolo[4',3':1,6]pyrido[3,2-b]benzofuro[4,3-fg][1,4]oxazonine |
| 57 | (S)-12-fluoro-4-(2-methoxy-4-methylpyrimidin-5-yl)-7a,8,13,14-tetrahydro-7H-[1,2,4]triazolo[4',3':1,6]pyrido[3,2-b]benzofuro[4,3-fg][1,4]oxazonine |
| 58 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,4-trimethylpyrimidine-2-carboxamide |
| 59 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpicolinamide |
| 60 | (S)-4-(1,3-dimethyl-1H-1,2,4-triazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 61 | (S)-12-fluoro-4-(5-methyl-1,3,4-oxadiazol-2-yl)-7a,8,13,14-tetrahydro-7H-[1,2,4]triazolo[4',3':1,6]pyrido[3,2-b]benzofuro[4,3-fg][1,4]oxazonine |
| 62 | (S)-4-(3,5-dimethylisoxazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 63 | (S)-12-fluoro-4-(1-(2-methoxyethyl)-3,5-dimethyl-1H-pyrazol-4-yl)-7a,8,13,14-tetrahydro-7H-[1,2,4]triazolo[4',3':1,6]pyrido[3,2-b]benzofuro[4,3-fg][1,4]oxazonine |
| 64 | (S)-12-fluoro-N-methyl-N-(tetrahydro-2H-pyran-4-yl)-7a,8,13,14-tetrahydro-7H-[1,2,4]triazolo[4',3':1,6]pyrido[3,2-b]benzofuro[4,3-fg][1,4]oxazonine-4-carboxamide |
| 65 | (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine |
| 66 | (S)-12-fluoro-4-(6-methylpyridazin-3-yl)-7a,8,13,14-tetrahydro-7H-[1,2,4]triazolo[4',3':1,6]pyrido[3,2-b]benzofuro[4,3-fg][1,4]oxazonine |
| 67 | (S)-4-(4,6-dimethylpyridazin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 68 | (S)-4-(4-(difluoromethyl)-2-methylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |

TABLE 1-continued

| Compound No. | Compound Name |
|---|---|
| 69 | (S)-4-(2-(difluoromethyl)-4-methylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 70 | (S)-4-(4-(difluoromethyl)pyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 71 | (S)-4-(1,4-dimethyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 72 | (S)-4-(1-ethyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 73 | (S)-12-fluoro-4-(1-(2,2,2-trifluoroethyl)-1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 74 | (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol |
| 75 | (S)-12-fluoro-4-(1-isopropyl-1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 76 | (S)-4-(2-(difluoromethoxy)pyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 77 | (S)-12-fluoro-4-(2-methoxypyridin-3-yl)-7a,8,13,14-tetrahydro-7H-[1,2,4]triazolo[4',3':1,6]pyrido[3,2-b]benzofuro[4,3-fg][1,4]oxazonine |
| 78 | (S)-4-(2-(difluoromethoxy)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 79 | (S)-12-fluoro-4-(3-methyl-1H-pyrazol-1-yl)-7a,8,13,14-tetrahydro-7H-[1,2,4]triazolo[4',3':1,6]pyrido[3,2-b]benzofuro[4,3-fg][1,4]oxazonine |
| 80 | (S)-12-fluoro-4-(4-methyl-1H-pyrazol-1-yl)-7a,8,13,14-tetrahydro-7H-[1,2,4]triazolo[4',3':1,6]pyrido[3,2-b]benzofuro[4,3-fg][1,4]oxazonine |
| 81 | (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)-2-methylpropan-2-ol |
| 82 | (S)-4-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)-2-methylbutan-2-ol |
| 83 | (S)-12-fluoro-4-(2-(trifluoromethoxy)pyridin-3-yl)-7a,8,13,14-tetrahydro-7H-[1,2,4]triazolo[4',3':1,6]pyrido[3,2-b]benzofuro[4,3-fg][1,4]oxazonine |
| 84 | (S)-4-(6-(difluoromethyl)-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 85 | (S)-4-(2-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 86 | (S)-4-(4,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 87 | (S)-12-fluoro-4-(3-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine |
| 88 | (S)-4-(4-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 89 | (S)-12-fluoro-4-(5-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine |
| 90 | (S)-4-(6-(difluoromethyl)-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 91 | (S)-12-fluoro-4-(pyrimidin-5-yl)-7a,8,13,14-tetrahydro-7H-[1,2,4]triazolo[4',3':1,6]pyrido[3,2-b]benzofuro[4,3-fg][1,4]oxazonine |
| 92 | (S)-12-fluoro-4-(3-methylisoxazol-4-yl)-7a,8,13,14-tetrahydro-7H-[1,2,4]triazolo[4',3':1,6]pyrido[3,2-b]benzofuro[4,3-fg][1,4]oxazonine |
| 93 | (S)-12-fluoro-4-(thiazol-5-yl)-7a,8,13,14-tetrahydro-7H-[1,2,4]triazolo[4',3':1,6]pyrido[3,2-b]benzofuro[4,3-fg][1,4]oxazonine |
| 94 | (S)-12-fluoro-4-(6-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 95 | (S)-12-fluoro-4-(3-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 96 | (S)-4-(2-ethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 97 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2(1H)-one |
| 98 | (S)-12-fluoro-4-(6-methoxypyridin-2-yl)-7a,8,13,14-tetrahydro-7H-[1,2,4]triazolo[4',3':1,6]pyrido[3,2-b]benzofuro[4,3-fg][1,4]oxazonine |
| 99 | (S)-12-fluoro-4-(1,3,5-trimethyl-1H-pyrazol-4-yl)-7a,8,13,14-tetrahydro-7H-[1,2,4]triazolo[4',3':1,6]pyrido[3,2-b]benzofuro[4,3-fg][1,4]oxazonine |
| 100 | (S)-4-(3-ethyl-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 101 | (S)-4-(5-chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 102 | (S)-4-(4-cyclopropylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 103 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpyridin-2-amine |
| 104 | (S)-12-fluoro-4-(6-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine |

TABLE 1-continued

| Compound No. | Compound Name |
|---|---|
| 105 | (S)-12-fluoro-4-(2-methoxy-6-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 106 | (S)-12-fluoro-4-(6-methoxy-2-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 107 | (S)-12-fluoro-4-(2-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 108 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpyrimidin-2-amine |
| 109 | (S)-4-(2-ethoxypyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 110 | (S)-12-fluoro-4-(5-fluoro-6-methoxypyridin-3-yl)-7a,8,13,14-tetrahydro-7H-[1,2,4]triazolo[4',3':1,6]pyrido[3,2-b]benzofuro[4,3-fg][1,4]oxazonine |
| 111 | (S)-12-fluoro-4-(5-fluoro-2-methoxypyridin-3-yl)-7a,8,13,14-tetrahydro-7H-[1,2,4]triazolo[4',3':1,6]pyrido[3,2-b]benzofuro[4,3-fg][1,4]oxazonine |
| 112 | (S)-12-fluoro-4-(6-(trifluoromethyl)pyridin-3-yl)-7a,8,13,14-tetrahydro-7H-[1,2,4]triazolo[4',3':1,6]pyrido[3,2-b]benzofuro[4,3-fg][1,4]oxazonine |
| 113 | (S)-12-fluoro-4-(5-(trifluoromethyl)pyridin-2-yl)-7a,8,13,14-tetrahydro-7H-[1,2,4]triazolo[4',3':1,6]pyrido[3,2-b]benzofuro[4,3-fg][1,4]oxazonine |
| 114 | (S)-12-fluoro-4-(2-(trifluoromethyl)pyrimidin-5-yl)-7a,8,13,14-tetrahydro-7H-[1,2,4]triazolo[4',3':1,6]pyrido[3,2-b]benzofuro[4,3-fg][1,4]oxazonine |
| 115 | (S)-12-fluoro-4-(1-methyl-3-(trifluoromethyl)-1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 116 | (S)-12-fluoro-4-(6-morpholinopyridin-3-yl)-7a,8,13,14-tetrahydro-7H-[1,2,4]triazolo[4',3':1,6]pyrido[3,2-b]benzofuro[4,3-fg][1,4]oxazonine |
| 117 | (S)-12-fluoro-4-(6-(4-methylpiperazin-1-yl)pyridin-3-yl)-7a,8,13,14-tetrahydro-7H-[1,2,4]triazolo[4',3':1,6]pyrido[3,2-b]benzofuro[4,3-fg][1,4]oxazonine |
| 118 | (S)-12-fluoro-4-(2-(4-methylpiperazin-1-yl)pyrimidin-5-yl)-7a,8,13,14-tetrahydro-7H-[1,2,4]triazolo[4',3':1,6]pyrido[3,2-b]benzofuro[4,3-fg][1,4]oxazonine |
| 119 | (S)-12-fluoro-4-(2-(trifluoromethyl)pyridin-3-yl)-7a,8,13,14-tetrahydro-7H-[1,2,4]triazolo[4',3':1,6]pyrido[3,2-b]benzofuro[4,3-fg][1,4]oxazonine |
| 120 | (S)-12-fluoro-4-(5-fluoro-6-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 121 | (S)-12-fluoro-4-(2-methylpyridin-3-yl)-7a,8,13,14-tetrahydro-7H-[1,2,4]triazolo[r,5':1,6]pyrido[3,2-b]benzofuro[4,3-fg][1,4]oxazonine |
| 122 | (S)-12-fluoro-4-(1-(2,2,2-trifluoroethyl)-1H-pyrazol-3-yl)-7a,8,13,14-tetrahydro-7H-[1,2,4]triazolo[4',3':1,6]pyrido[3,2-b]benzofuro[4,3-fg][1,4]oxazonine |
| 123 | (S)-12-fluoro-4-(6-methylpyridazin-4-yl)-7a,8,13,14-tetrahydro-7H-[1,2,4]triazolo[4',3':1,6]pyrido[3,2-b]benzofuro[4,3-fg][1,4]oxazonine |
| 124 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-amine |
| 125 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,1-dimethyl-1H-pyrazol-3-amine |
| 126 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,1-trimethyl-1H-pyrazol-3-amine |
| 127 | (S)-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)methanamine |
| 128 | (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N-methylmethanamine |
| 129 | (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylmethanamine |
| 130 | (S)-4-(3-(difluoromethyl)-1-methyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 131 | (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-ol |
| 132 | (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylethan-1-amine |
| 133 | (S)-4-(1,2-dimethyl-1H-imidazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 134 | (S)-4-(1,4-dimethyl-1H-imidazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 135 | (S)-4-(1,4-dimethyl-1H-imidazol-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 136 | (S)-4-(1,5-dimethyl-1H-imidazol-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 137 | (S)-12-fluoro-4-(1-methyl-1H-imidazol-2-yl)-7a,8,13,14-tetrahydro-7H-[1,2,4]triazolo[4',3':1,6]pyrido[3,2-b]benzofuro[4,3-fg][1,4]oxazonine |
| 138 | (S)-12-fluoro-4-(1-methyl-1H-imidazol-4-yl)-7a,8,13,14-tetrahydro-7H-[1,2,4]triazolo[4',3':1,6]pyrido[3,2-b]benzofuro[4,3-fg][1,4]oxazonine |
| 139 | (S)-4-(1,5-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 140 | (S)-4-(1,2-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine |

TABLE 1-continued

| Compound No. | Compound Name |
|---|---|
| 141 | (S)-4-(5-(difluoromethyl)-6-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 142 | (S)-12-fluoro-4-(1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 143 | (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol |
| 144 | (S)-4-(3-(difluoromethyl)-6-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 145 | (S)-4-(3-ethyl-1-methyl-1H-1,2,4-triazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 146 | (S)-4-(3-ethyl-1-methyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 147 | (S)-12-fluoro-4-(1,2,4-trimethyl-1H-imidazol-5-yl)-7a,8,13,14-tetrahydro-7H-[1,2,4]triazolo[4',3':1,6]pyrido[3,2-b]benzofuro[4,3-fg][1,4]oxazonine |
| 148 | (S)-12-fluoro-4-(1,4,5-trimethyl-1H-imidazol-2-yl)-7a,8,13,14-tetrahydro-7H-[1,2,4]triazolo[4',3':1,6]pyrido[3,2-b]benzofuro[4,3-fg][1,4]oxazonine |
| 149 | (S)-12-fluoro-4-(4-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 150 | (S)-12-fluoro-4-(5-methylpyridin-2-yl)-7a,8,13,14-tetrahydro-7H-[1,2,4]triazolo[4',3':1,6]pyrido[3,2-b]benzofuro[4,3-fg][1,4]oxazonine |
| 151 | (S)-4-(3-chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 152 | (S)-4-(5-chloro-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 153 | (S)-4-(5-chloro-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 154 | (S)-12-fluoro-4-(5-fluoro-6-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 155 | (S)-12-fluoro-4-(2-methylpyridin-4-yl)-7a,8,13,14-tetrahydro-7H-[1,2,4]triazolo[4',3':1,6]pyrido[3,2-b]benzofuro[4,3-fg][1,4]oxazonine |
| 156 | (S)-4-(2,5-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 157 | (S)-4-(3-chloro-2-methylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 158 | (S)-4-(3-chloro-5-fluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 159 | (S)-12-fluoro-4-(3-methoxypyridin-2-yl)-7a,8,13,14-tetrahydro-7H-[1,2,4]triazolo[4',3':1,6]pyrido[3,2-b]benzofuro[4,3-fg][1,4]oxazonine |
| 160 | (S)-12-fluoro-4-(pyrimidin-4-yl)-7a,8,13,14-tetrahydro-7H-[1,2,4]triazolo[4',3':1,6]pyrido[3,2-b]benzofuro[4,3-fg][1,4]oxazonine |
| 161 | (S)-12-fluoro-4-(6-methylpyrimidin-4-yl)-7a,8,13,14-tetrahydro-7H-[1,2,4]triazolo[4',3':1,6]pyrido[3,2-b]benzofuro[4,3-fg][1,4]oxazonine |
| 162 | (S)-12-fluoro-4-(5-methylpyrimidin-4-yl)-7a,8,13,14-tetrahydro-7H-[1,2,4]triazolo[4',3':1,6]pyrido[3,2-b]benzofuro[4,3-fg][1,4]oxazonine |
| 163 | (S)-4-(5-chloropyrimidin-4-yl)-12-fluoro-7a,8,13,14-tetrahydro-7H-[1,2,4]triazolo[4',3':1,6]pyrido[3,2-b]benzofuro[4,3-fg][1,4]oxazonine |
| 164 | (S)-12-fluoro-4-(5-fluoropyrimidin-4-yl)-7a,8,13,14-tetrahydro-7H-[1,2,4]triazolo[4',3':1,6]pyrido[3,2-b]benzofuro[4,3-fg][1,4]oxazonine |
| 165 | (S)-4-bromo-12-fluoro-7a,8,13,14-tetrahydro-7H-[1,2,4]triazolo[4',3':1,6]pyrido[3,2-b]benzofuro[4,3-fg][1,4]oxazonine |
| 166 | (S)-4-(5-chloro-3-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine |
| 167 | (S)-4-(3-(difluoromethoxy)-1-methyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 168 | (S)-12-fluoro-4-(3-fluoro-1-methyl-1H-pyrazol-5-yl)-7a,8,13,14-tetrahydro-7H-[1,2,4]triazolo[4',3':1,6]pyrido[3,2-b]benzofuro[4,3-fg][1,4]oxazonine |
| 169 | (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-2-methylpropanenitrile |
| 170 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazole-4-carbonitrile |
| 171 | (S)-4-(5,6-dihydro-4H-pyrrolo[1,2-b]pyrazol-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 172 | (S)-5-fluoro-12-(1-methyl-1H-pyrazol-5-yl)-6,7,15,15a-tetrahydro-1H-benzofuro[4,3-fg]imidazo[r,2':1,6]pyrido[3,2-b][1,4]oxazonine-10-carbonitrile |
| 174 | (S)-5-fluoro-12-(1-methyl-1H-pyrazol-5-yl)-6,7,15,15a-tetrahydro-1H-benzofuro[4,3-fg]imidazo[r,2':1,6]pyrido[3,2-b][1,4]oxazonine-10-carboxylic acid |
| 175 | (S)-5-fluoro-12-(1-methyl-1H-pyrazol-5-yl)-6,7,15,15a-tetrahydro-1H-benzofuro[4,3-fg]imidazo[r,2':1,6]pyrido[3,2-b][1,4]oxazonine-10-carboxamide |
| 176 | (S)-5-fluoro-12-(2-methylpyridin-3-yl)-6,7,15,15a-tetrahydro-1H-benzofuro[4,3-fg]imidazo[r,2':1,6]pyrido[3,2-b][1,4]oxazonine-10-carboxamide |
| 177 | (S)-5-fluoro-12-(2-methylpyridin-3-yl)-6,7,15,15a-tetrahydro-1H-benzofuro[4,3-fg]imidazo[r,2':1,6]pyrido[3,2-b][1,4]oxazonine-10-carboxylic acid |

TABLE 1-continued

| Compound No. | Compound Name |
|---|---|
| 178 | (S)-4-(2-cyclopropylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 179 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-3-amine |
| 181 | methyl 4-(12-fluoro-6,8,13,14-tetrahydro-[1,2,4]triazolo[4',3':1,6]pyrido[3,2-c]benzo[g][1,5]oxazonin-4-yl)piperidine-1-carboxylate |
| 182 | 4-(2,4-dimethylpyrimidin-5-yl)-12-fluoro-6,8,13,14-tetrahydro-[1,2,4]triazolo[4',3':1,6]pyrido[3,2-c]benzo[g][1,5]oxazonine |
| 183 | 12-fluoro-4-((1-methyl-1H-pyrazol-4-yl)methyl)-6,8,13,14-tetrahydro-[1,2,4]triazolo[4',3':1,6]pyrido[3,2-c]benzo[g][1,5]oxazonine |
| 184 | (S)-4-(4,5-dimethyl-4H-1,2,4-triazol-3-yl)-12-fluoro-7a,8,13,14-tetrahydro-7H-[1,2,4]triazolo[4',3':1,6]pyrido[3,2-b]benzofuro[4,3-fg][1,4]oxazonine |
| 185 | (R)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine |
| 186 | (S)-5-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carbonitrile |
| 187 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-ol |
| 188 | (S)-12-fluoro-4-(oxazol-5-yl)-7a,8,13,14-tetrahydro-7H-[1,2,4]triazolo[4',3':1,6]pyrido[3,2-b]benzofuro[4,3-fg][1,4]oxazonine |
| 189 | (S)-12-fluoro-4-(4-methyloxazol-5-yl)-7a,8,13,14-tetrahydro-7H-[1,2,4]triazolo[4',3':1,6]pyrido[3,2-b]benzofuro[4,3-fg][1,4]oxazonine |
| 190 | (S)-4-(2-cyclopropyl-4-methylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine |
| 191 | (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)-N-methylpropanamide |
| 192 | (S)-3-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-4-ol |
| 193 | (S)-1-(4-(12-fluoro-7a,8,13,14-tetrahydro-7H-[1,2,4]triazolo[4',3':1,6]pyrido[3,2-b]benzofuro[4,3-fg][1,4]oxazonin-4-yl)-3,6-dihydropyridin-1(2H)-yl)ethan-1-one |
| 194 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-3-ol |
| 195 | (S)-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)methanol |
| 196 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-4-ol |
| 197 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-ol |
| 198 | 1-(4-(12-fluoro-6,8,13,14-tetrahydro-[1,2,4]triazolo[4',3':1,6]pyrido[3,2-c]benzo[g][1,5]oxazonin-4-yl)piperidin-1-yl)ethan-1-one |

In another embodiment of the invention, the compounds of Formula I are enantiomers. In some embodiments the compounds are (S)-enantiomer. In other embodiments the compounds may also be (R)-enantiomer. In yet other embodiments, the compounds of Formula I may be (+) or (−) enantiomers.

In another embodiment of the invention, the compounds of Formula I contain isotopes of atoms forming the structure of Formula I. Isotopes herein means, each of two or more forms of the same element (e.g., H and D; $^{12}C$ and $^{13}C$) that contain equal numbers of protons but different numbers of neutrons in their nuclei, and hence differ in relative atomic mass.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis or trans configuration. All tautomeric forms are also intended to be included.

Methods of Using the Disclosed Compounds

Another aspect of the invention relates to a method of a disease or disorder associated with modulation of embryonic ectoderm development (EED) and/or Polycomb Repressive Complex 2 (PRC2). The method involves administering to a patient in need thereof an effective amount of the composition or compound of Formula I.

Another aspect of the invention relates to a method of a disease or disorder associated with modulation of embryonic ectoderm development (EED). The method involves administering to a patient in need thereof an effective amount of the composition or compound of Formula I.

Another aspect of the invention is directed to a method treating a disease or disorder associated with modulation of Polycomb Repressive Complex 2 (PRC2). The method involves administering to a patient in need thereof an effective amount of the composition or compound of Formula I.

Another aspect of the invention is directed to a method treating a disease or disorder associated with modulation of Polycomb Repressive Complex 2 (PRC2). The method involves administering to a patient in need thereof an effective amount of the composition or compound of Formula I.

In one embodiment, the disease or disorder is a blood disorder.

In one embodiment, the blood disorder is Acute lymphoblastic leukemia (ALL), Acute myeloid leukemia (AML) (e.g., acute promyelocytic leukemia, APL), Amyloidosis, Anemia, Aplastic anemia, Bone marrow failure syndromes, Chronic lymphocytic leukemia (CLL), Chronic myeloid leukemia (CML), Deep vein thrombosis (DVT), Diamond-Blackfan anemia, Dyskeratosis congenita (DKC), Eosinophilic disorder, Essential thrombocythemia, Fanconi anemia, Gaucher disease, Hemochromatosis, Hemolytic anemia, Hemophilia, Hereditary spherocytosis, Hodgkin's lymphoma, Idiopathic thrombocytopenic purpura (ITP), Inherited bone marrow failure syndromes, Iron-deficiency anemia, Langerhans cell histiocytosis, Large granular lymphocytic (LGL) leukemia, Leukemia, Leukopenia, Mastocytosis, Monoclonal gammopathy, Multiple myeloma, Myelodysplastic syndromes (MDS), Myelofibrosis, Myeloproliferative neoplasms (MPN), Non-Hodgkin's lymphoma, Paroxysmal nocturnal hemoglobinuria (PNH), Pernicious anemia (B12 deficiency), Polycythemia vera, *Porphyria*, Post-transplant lymphoproliferative disorder (PTLD), Pulmonary embolism (PE), Shwachman-Diamond syndrome (SDS), sickle cell disease (SCD), Thalassemia, Thrombocytopenia, Thrombotic thrombocytopenic purpura (TTP), Venous thromboembolism, Von Willebrand disease, or Waldenstrom's macroglobulinemia (lymphoplasmacytic lymphoma).

In one embodiment, the blood disorder is sickle cell disease.

In one embodiment, the blood disorder is thalassemia (e.g., β-thalassemia).

In one embodiment, the disease or disorder is cancer. In one embodiment, the disease or disorder is selected from diffused large B cell lymphoma, follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neuroblastoma, schwannoma, glioma, glioblastoma and astrocytoma, cervical cancer, colon cancer, melanoma, endometrial cancer, esophageal cancer, head and neck cancer, lung cancer, nasopharyngeal carcinoma, ovarian cancer, pancreatic cancer, renal cell carcinoma, rectal cancer, thyroid cancers, parathyroid tumors, uterine tumors, and soft tissue sarcomas.

The present invention further provides a method of treating sickle cell disease (SCD) or β-thalassemia. The method comprises administering to a patient in need thereof an effective amount of the compound of Formula I. In one embodiment, the administration results in modulation of EED regulated expression of a fetal orthologue (e.g., fetal hemoglobin (e.g., HbF or α2γ2)) in the blood of the patient. In one embodiment, the modulation results in compensation for the function of one or more mutations affecting the β-globin genes in adult hemoglobin A (α2γ2).

In one embodiment, the disease or disorder is a disease or disorder capable of being treated by reactivation of a developmentally regulated fetal ortholog in another disease or another tissue.

The present invention further provides a method of treating sickle cell disease (SCD) or β-thalassemia. The method comprises administering to a patient in need thereof an effective amount of the composition or compound of Formula I. In one embodiment, the administration results in modulation of EED regulated expression of a fetal orthologue (e.g., fetal hemoglobin (e.g., HbF or α2γ2)) in the blood of the patient. In one embodiment, the modulation results in compensation for the function of one or more mutations affecting the β-globin genes in adult hemoglobin A (α2β2).

The present invention further provides methods of treating thoracic aortic aneurysm, coronary heart disease, stenotic disease, pulmonary artery hypertension (PAH), liver fibrosis, allergic inflammation, retinitis pigmentosa, septic shock, herpes simplex virus, human cytomegalovirus, α-thalassemia, familial atrial fibrillation, common variable immunodeficiency, aneurysm-osteoarthritis syndrome, and acquired immunodeficiency syndrome. The method comprises administering to a patient in need thereof an effective amount of the compound of Formula I.

In one embodiment, the method of the present disclosure further comprises administering to a patient in need thereof an effective amount of at least one additional therapeutic agent. In one embodiment, at least one therapeutic agent is selected from anti-cancer agents, immunomodulators, anti-allergic agents, anti-emetics, pain relievers, cytoprotective agents, or combinations thereof. In one embodiment, at least one therapeutic agent is hydroxyurea, L-glutamine, gene therapies (e.g., CRISPR and AAV or other viral HBG delivery), PDE9 inhibitors, RBC anti-adhension therapies (e.g., P-selectin), or other compounds targeting transcriptional regulation. In one embodiment, at least one therapeutic agent is an EZH2 inhibitor. In one embodiment, at least one therapeutic agent is N-((4,6-dimethyl-2-oxo-1,2-dihydropyridin-3-yl)methyl)-S—(ethyl(tetrahydro-2H-pyran-4-yl)amino)-4-methyl-4'-(morpholinomethyl)-[1,1'-biphenyl]-3-carboxamide (tazemetostat), (2R)-7-chloro-2-[4-(dimethylamino)cyclohexyl]-N-[(4,6-dimethyl-2-oxo-1H-pyridin-3-yl)methyl]-2,4-dimethyl-1,3-benzodioxole-5-carboxamide (valemetostat, DS-3201b), N-[(4-methoxy-6-methyl-2-oxo-1H-pyridin-3-yl)methyl]-2-methyl-1-[(1R)-1-[1-(2,2,2-trifluoroethyl)piperidin-4-yl]ethyl]indole-3-carboxamide (CPI-1205), (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide (GSK2816126), or (R)-5,8-dichloro-7-(methoxy(oxetan-3-yl)methyl)-2-((4-methoxy-6-methyl-2-oxo-1,2-dihydropyridin-3-yl)methyl)-3,4-dihydroisoquinolin-1 (2H)-one (PF-06821497), or SHR2554, or a combination thereof. In one embodiment, at least one therapeutic agent is hydroxyurea. In one embodiment, at least one therapeutic agent is 2-hydroxy-6-((2-(1-isopropyl-1H-pyrazol-5-yl)pyridin-3-yl)methoxy)benzaldehyde (voxelotor, GBT-440), P-Selectin antibodies, or L-Glutamine, or a combination thereof. In one embodiment, the at least one therapeutic agent is selected from anti-adhesion agents. In one embodiment, the at least one therapeutic agent is crizanlizumab (SEG101), (2S)-2-[(2R,3R,4S,5S,6R)-3-benzoyloxy-2-[(1R,2R,3S,5R)-3-[(2,4-dioxo-1H-pyrimidine-6-carbonyl)amino]-S—[2-[[2-[2-[2-oxo-2-[(3,6,8-trisulfonaphthalen-1-yl)amino]ethoxy]ethoxy]acetyl]amino]ethylcarbamoyl]-2-[(2S,3S,4R,5S,6S)-3,4,5-trihydroxy-6-methyloxan-2-yl]oxycyclohexyl]oxy-S-hydroxy-6-(hydroxymethyl)oxan-4-yl]oxy-3-cyclohexylpropanoic acid (rivipansel, GMI-1070), sevuparin, 6-[(3S,4S)-4-methyl-1-(pyrimidin-2-ylmethyl)pyrrolidin-3-yl]-1-(oxan-4-yl)-5H-pyrazolo[3,4-d]pyrimidin-4-one (PF-04447943), inclacumab (LC1004-002), or 3-[3-[4-(1-aminocyclobutyl)phenyl]-S-phenylimidazo[4,5-b]pyridin-2-yl]pyridin-2-amine (miransertib, ARQ 092), or combinations thereof. In one embodiment, the at least one therapeutic agent is selected from other anti-sickling agents. In one embodiment, at least one therapeutic agent is 2-hydroxy-6-((2-(1-isopropyl-1H-pyrazol-S-yl)pyridin-3-yl)methoxy)benzaldehyde (voxelotor, GBT-440) or 6-[(3S,4S)-4-Methyl-1-(2-pyrimidinylmethyl)-3-pyrrolidinyl]-3-(tetrahydro-2H-pyran-4-yl)imidazo[1,5-a]pyrazin-8 (7H)-one (IMR-687), or combinations thereof. In one embodiment, at least one therapeutic agent is selected from detoxification agents. In one embodiment, at least one therapeutic agent is LJPC-401. In one embodiment, at least one therapeutic agent is selected from anti-inflammatory agents, anti-thrombiotic agents, or combinations thereof. In one embodiment, the at least one therapeutic agent is (1S, 2S,3R,5S)-3-[7-{[(1R,2S)-2-(3,4-difluorophenyl)cyclopropyl]amino}-5(propylthio)-3H-[1,2,3]-triazolo[4,5-d]pyrimidin-3-yl]-S-(2-hydroxyethoxy)cyclopentane-1,2-diol (Brilinta, tricagrelor), (2R)-3,3,3-trifluoro-2-[[[5-fluoro-2-[1-[(2-fluorophenyl)methyl]-S-(1,2-oxazol-3-yl)pyrazol-3-yl]pyrimidin-4-yl]amino]methyl]-2-hydroxypropanamide (olinciguat), orNKTT120, or combinations thereof. In one embodiment, at least one therapeutic agent is sanguinate. In one embodiment, at least one therapeutic agent causes disruption of PRC2. In one embodiment, at least one therapeutic agent is AZD9291.

Another aspect of the invention is directed to a method of inducing fetal hemoglobin (hemoglobin γ (HB7), or HbF) expression in erythroid cells. The method involves administering to a patient in need thereof an effective amount of the composition or compound of Formula I.

In one embodiment, the composition or compound of Formula I induces upregulation of mRNA levels (e.g., HBG1 or HBG2, with sequences shown herein) or upregulation of fetal hemoglobin protein (HB7) that results in an elevation in HbF protein.

In one embodiment, the method further involves administering to a patient in need thereof one or more additional therapeutic agents that upregulate HbF and/or reduce or alleviate one or more symptoms of SCD and/or β-thalassemia (e.g., vaso-occlusion and anemia).

Hemoglobin Subunit Gamma-1 (HBG1) Sequence (SEQ ID NO: 1): MGHFTEEDKATITSLWGKVNVEDAGGETLGRLLVVYPWTQRFFDSFGNLSSASAIMGNPKVKAHGKKVLTSLGDAIKHLD-DLKGTFAQLSELHCDKLHVDPENFKLLGNVLVTV-LAI HFGKEFTPEVQASWQKMVTAVASALSSRYH Hemoglobin Subunit Gamma-2 (HBG2) sequence (SEQ ID NO: 2): MGHFTEEDKATITSLWGKVNVEDAGGETLGRLLVVYPWTQRFFDSFGNLSSASAIMGNPKVKAHGKKVLTSLGDAIKHLD-DLKGTFAQLSELHCDKLHVDPENFKLLGNVLVTV-LAI HFGKEFTPEVQASWQKMVTGVASALSSRYH Hemoglobin Subunit Alpha-1 (HBA1) amino acid sequence (SEQ ID NO: 3): MVLSPADKTNV-KAAWGKVGAHAGEYGAEALER-MFLSFPTTKTYFPHFDLSHGSAQVK GHGKK-VADALTNAVAHVDDMPNALSALSDLHAHKLRV DPVNFKLLSHCLLVTLAAHL PAEFTPAVHASLDK-FLASVSTVLTSKYR Hemoglobin Subunit Alpha-2 (HBA2) amino acid sequence (SEQ ID NO: 4) MVLSPADKTNV-KAAWGKVGAHAGEYGAEALER-MFLSFPTTKTYFPHFDLSHGSAQVK GHGKK-VADALTNAVAHVDDMPNALSALSDLHAHKLR VDPVNFKLLSHCLLVTLAAHL PAEFTPAVHASLDK-FLASVSTVLTSKYR Another aspect of the invention is directed to use of a compound of Formula I for treating a disease or disorder associated with the modulation of embryonic ectoderm development (EED) and/or Polycomb Repressive Complex 2 (PRC2).

Another aspect of the invention is directed to use of a compound of Formula I for treating a disease or disorder associated with the modulation of embryonic ectoderm development (EED).

Another aspect of the invention is directed to use of a compound of Formula I for treating a disease or disorder associated with the modulation of Polycomb Repressive Complex 2 (PRC2).

Another aspect of the invention is directed to a compound of Formula I for use in the manufacture of a medicament for treating a disorder or disease associated with embryonic ectoderm development (EED) and/or Polycomb Repressive Complex 2 (PRC2).

Another aspect of the invention is directed to a compound of Formula I for use in the manufacture of a medicament for treating a disorder or disease associated with embryonic ectoderm development (EED).

Another aspect of the invention is directed to a compound of Formula I for use in the manufacture of a medicament for treating a disorder or disease associated with Polycomb Repressive Complex 2 (PRC2).

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Another aspect of the invention is directed to pharmaceutical compositions comprising a compound of Formula I and a pharmaceutically acceptable carrier. The pharmaceutical acceptable carrier may further include an excipient, diluent, or surfactant.

In one embodiment, the pharmaceutical composition further comprises at least one additional therapeutic agent. In one embodiment, the at least one therapeutic agent is selected from other anti-cancer agents, immunomodulators, anti-allergic agents, anti-emetics, pain relievers, cytoprotective agents, and combinations thereof. In one embodiment, the at least one therapeutic agent is selected from hydroxyurea, L-glutamine, gene therapies (e.g., CRISPR and AAV or other viral HBG delivery), PDE9 inhibitors, RBC anti-adhesion therapies (e.g., β-selectin), and other compounds targeting transcriptional regulation.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.1 mg to about 5000 mg of the disclosed compound as needed to treat the condition. Compositions for in vivo or in vitro use can contain about 0.1, 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Method of Synthesizing the Compounds

The compounds of the present invention may be made by a variety of methods, including standard chemistry. Suitable synthetic routes are depicted in the Schemes given below.

The compounds of Formula I may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. General methods include but are not limited to those methods described below. Moreover, the suitable starting material readily available and known by one of skilled in the art can be selected to arrive at specific compounds of the present disclosure. Compounds of the present invention Formula I can be synthesized by following the steps outlined in Schemes 1-4, wherein $R_1$, $R_2$, and $R_3$ are defined in Formula I. Starting materials are either commercially available or made by known procedures in the reported literature or as illustrated.

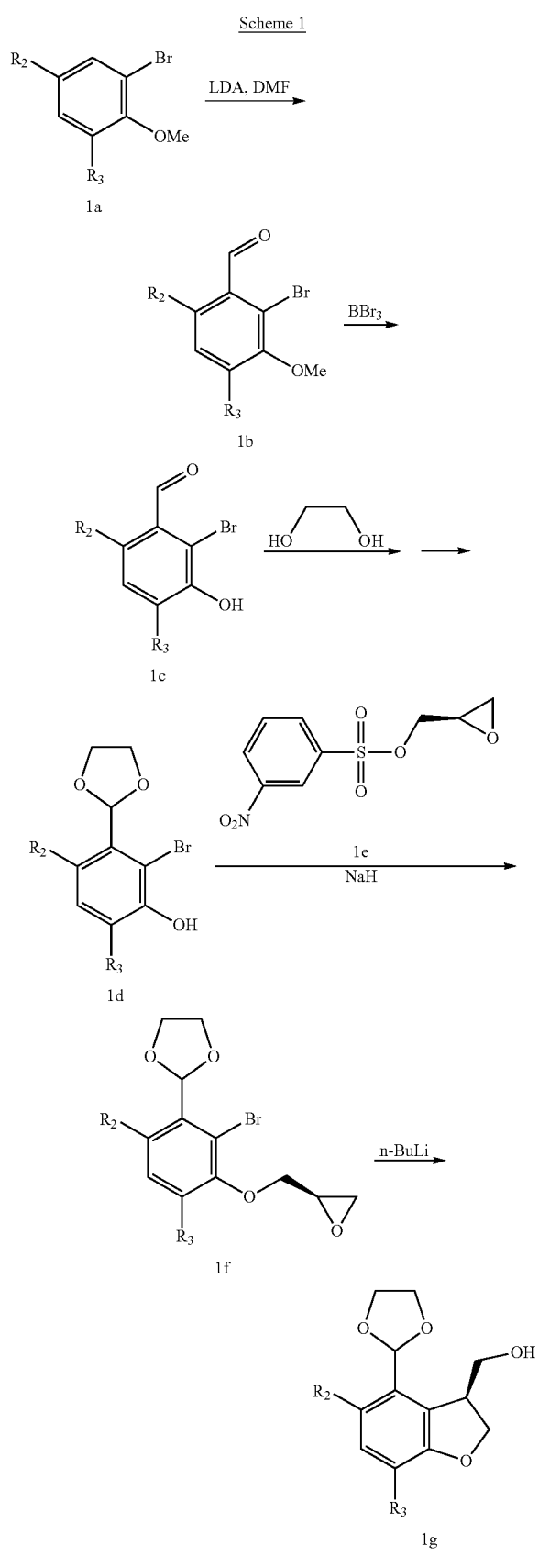

The general way of preparing a common intermediate 1g is outlined in Scheme 1, wherein $R_2$ and $R_3$ are defined in Formula 1. Deprotonation of 1a followed by a reaction with a formylation agent, such as DMF, yields intermediate 1b which can be treated with boron tribromide to deprotect the phenolic moiety to afford 1c. Protection of the alhedyde results in intermediate 1d which can be reacted with commercially available epoxide 1e to afford 1f. Treatment with a strong base, such as n-butyl lithium, yields the common intermediate 1g that can be converted in a number of ways to the final compounds.

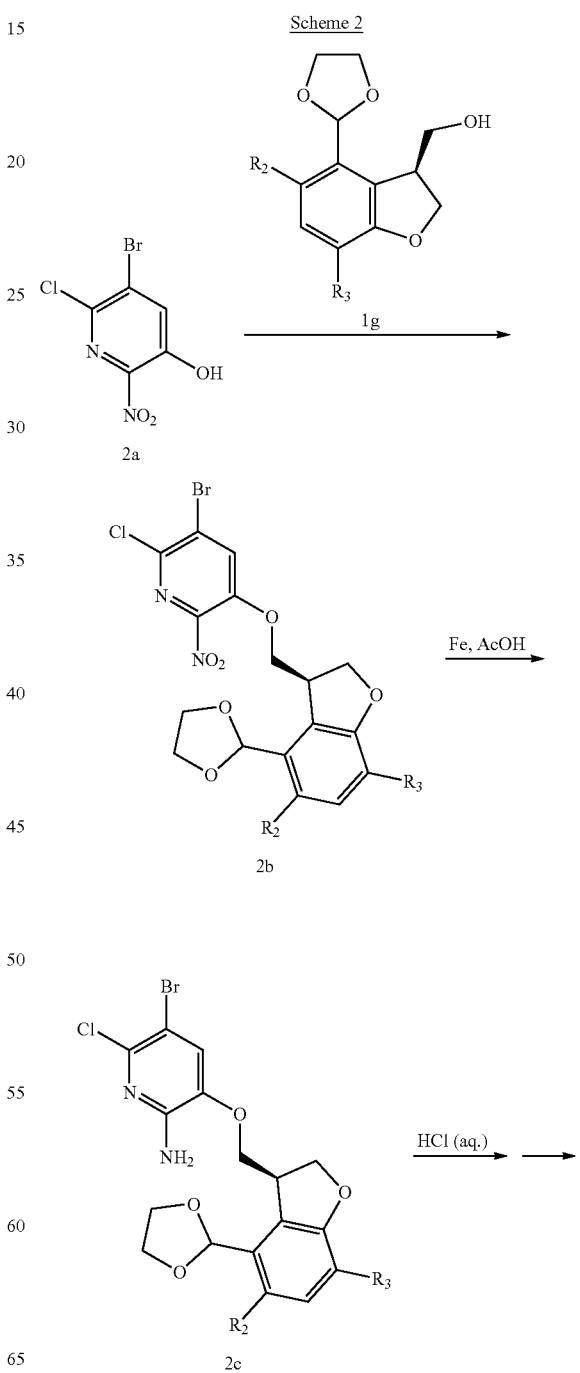

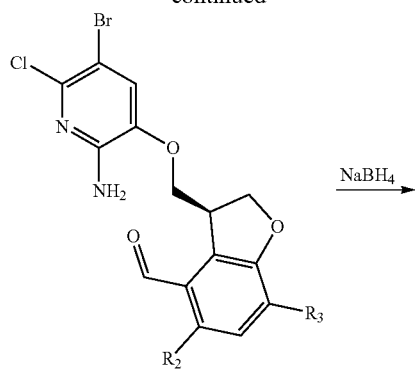
2d
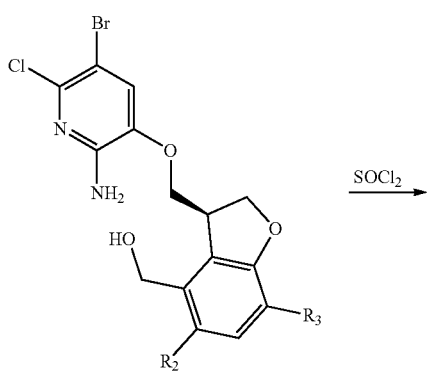
2e
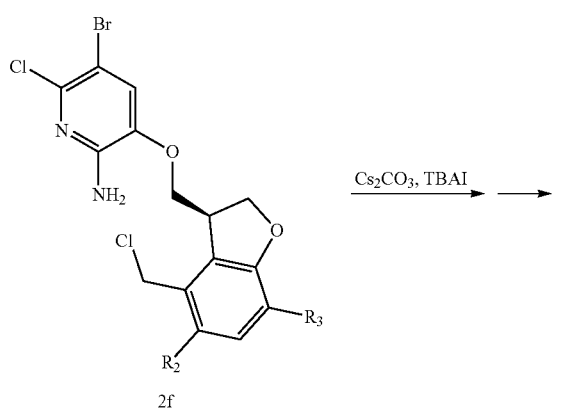
2f
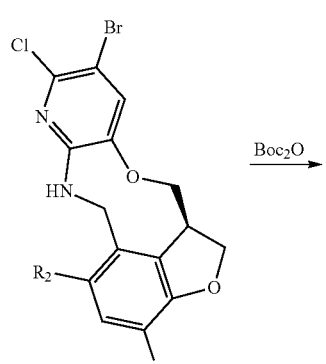
2g
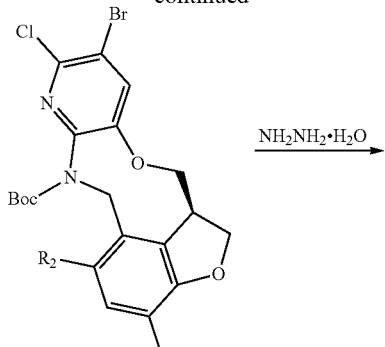
2h
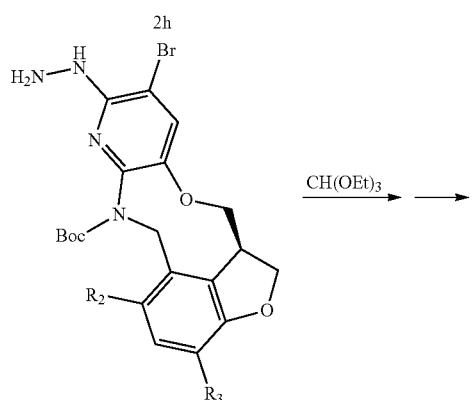
2i
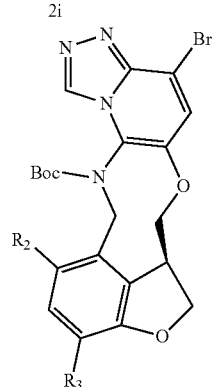
2j
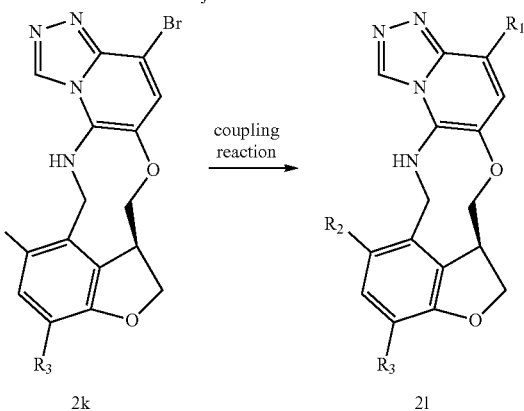
2k        2l
The general way of preparing target compound 2l is outlined in Scheme 2, wherein $R_1$, $R_2$ and $R_3$ are defined in Formula 1. 5-Bromo-6-chloro-2-nitropyridin-3-ol (Example 2) is reacted with the alcohol 1g under Mitsunobu conditions. Nitro group reduction followed by the aldehyde deprotection step affords intermediate 2d which can be converted into an alcohol and subsequently into a leaving group such as chloride 2f. The cyclization step can be conducted, for example, with cesium carbonate and tetrabutyl ammonium iodide. Boc protection affords intermediate 2h which then can be reacted with hydrazine hydrate to afford intermediate 2i. The triazole ring formation can be accomplished, for example, by means of triethyl orthoformate, thus affording a common intermediate 2j. The Boc group can be removed in acidic conditions followed by coupling steps with a variety of reagents to result in final products 21. Alternatively, the coupling step can be performed on the Boc-protected intermediate 2j with a subsequent Boc-deprotection step.

Scheme 3

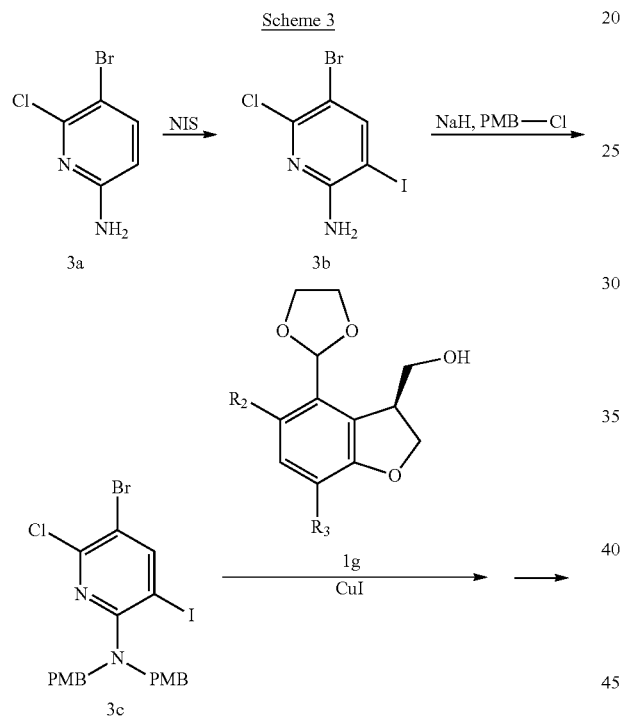

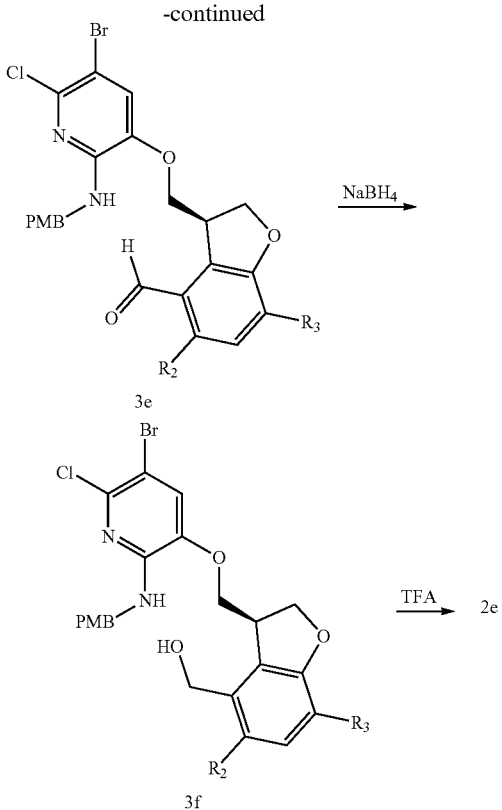

Another general way of preparing cyclization precursor 2e is outlined in Scheme 3, wherein $R_2$ and $R_3$ are defined in Formula 1. Iodide 3b is obtained from 5-bromo-6-chloropyridin-2-amine by means of N-iodosuccinimide and the amino group is protected by alkylation with, for example, p-methoxybenzyl chloride. The resulting intermediate 3c can be coupled with the alcohol of 1g under copper-mediated conditions, for example. The dioxolane moiety is cleaved under acidic conditions, for example with aqueous HCl, and the resulting aldehyde is converted into alcohol 3f with a reducing agent, such as sodium borohydride. Full deprotection of the amino group with a strong acid, such as TFA, results in intermediate 2e, which can then be converted into the final products as described in Scheme 2.

Scheme 4

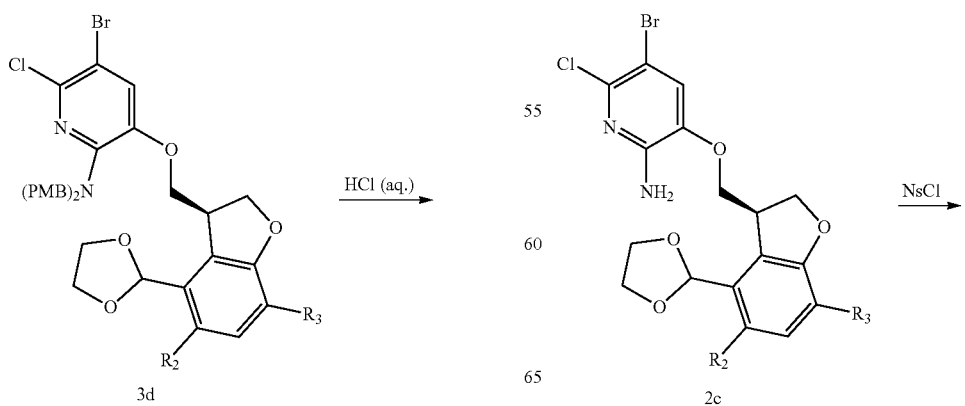

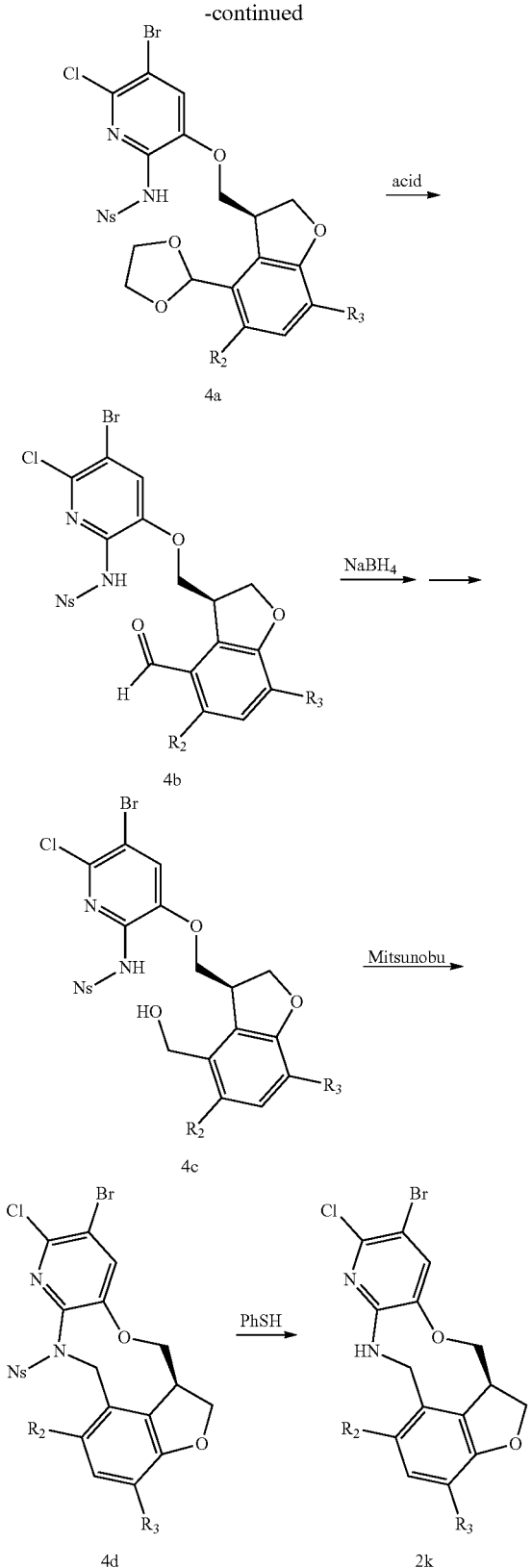

Another general way of preparing the common intermediate 2k is outlined in Scheme 4, wherein $R_2$ and $R_3$ are defined in Formula 1. Nosyl protection of the amino group in intermediate 2c with a subsequent aldehyde deprotection affords compound 4b, which can be reduced to provide alcohol 4c. The cyclization can be accomplished under Mitsunobu conditions to result in intermediate 4d. Removal of the nosyl protecting group with PhSH affords common intermediate 2k which can then be converted into the final products as described in Scheme 2.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.
Abbreviations Used in the Following Examples and Elsewhere Herein are:
23° C. room temperature;
Ac$_2$O acetic anhydride
ACN acetonitrile
AcOH or HOAc acetic acid
aq aqueous
Boc$_2$O di-tert-butyl dicarbonate
BOP ammonium 4-(3-(pyridin-3-ylmethyl)ureido)benzenesulfinate
(Bpin)$_2$ bis(pinacolato)diboron;
CDCl$_3$ deuterated chloroform
CD$_3$OD deuterated methanol
Comins' reagent N-bis(trifluoromethanesulfonimide);
δ chemical shift
DBDMH 1,3-dibromo-5,5-dimethylhydantoin
DCM dichloromethane or methylene chloride
DCE 1,2-dichloroethane
DEAD diethyl azodicarboxylate
DIAD diisopropyl azodicarboxylate
DIBAL-H diisobutylaluminum hydride
DIEA N,N-diisopropylethylamine
DMA N,N-dimethylacetamide
DME dimethoxyethane
DMF N,N-dimethylformamide
DMP Dess-Martin Periodinane
DMSO dimethylsulfoxide
DMSO-d$_6$ deuterated dimethylsulfoxide
DPPA diphenyl phosphoryl azide
dppf 1,1'-Bis(diphenylphosphino)ferrocene
EDCI N-(3-dimethylaminopropyl)-N'-ethylcarbodiimide hydrochloride
EDTA ethylenediaminetetraacetic acid
ee enantiomeric excess
eq. or equiv. equivalent
Et$_2$O diethyl ether
EtOAc ethyl acetate
EtOH ethanol
FA formate
Fe iron
h or hr hour(s)
$^1$H NMR proton nuclear magnetic resonance
HATU 2-(3H-[1,2,3]triazolo[4,5-b]pyridin-3-yl)-1,1,3,3-tetramethylisouronium hexafluorophosphate
HFIP hexafluoroisopropanol
HOBT 1H-benzo[d][1,2,3]triazol-1-ol hydrate
HPLC high performance liquid chromatography Hz hertz
IPA isopropyl alcohol
KOAc potassium acetate
LAH lithium aluminum hydride
LCMS liquid chromatography/mass spectrometry
LC-MS liquid chromatography/mass spectrometry
LiHMDS lithium bis(trimethylsilyl)amide
m minute(s)
(M+1) mass+1
m-CPBA m-chloroperbenzoic acid
MBTE methyl tert-butyl ether
MeOH methanol
MeMgBr methyl magnesium bromide
MPLC medium-pressure liquied chromatography
MS mass spectrometry
NaHMDS sodium bis(trimethylsilyl)amide
NCS N-chlorosuccinimide
NMP N-methylpyrrolidone
NMR nuclear magnetic resonance
Ns nosyl (4-nitrobenzenesulfonyl)
Pd(dppf)Cl$_2$ [1,1'-Bis(diphenylphosphino)ferrocene]dichloropalladium(II)
Palladium tetrakis Tetrakis(triphenylphosphine)palladium (0)
PMB para-methoxybenzyl
tR retention time
sat. saturated
SFC supercritical fluid chromatography
TBAI tetrabutylammonium iodide
TBDMS-C$_1$ tert-butyl dimethylsilyl chloride
TBME tert-butyl methyl ether
TEA trimethylamine
TFA trifluoroacetic acid
TFAA trifluoroacetic anhydride
HFIP hexafluoroisopropanol
THF tetrahydrofuran
TLC thin layer chromatography
OTf trifluoromethanesulfonate
Xantphos 4,5-Bis(diphenylphosphino)-9,9-dimethylxanthene General Methods All temperatures are in degrees Celsius (° C.) and are uncorrected. Reagent grade chemicals and anhydrous solvent were purchased from commercial sources and unless otherwise mentioned, were used without further purification. Silica gel chromatography was performed on Teledyne Isco instruments using pre-packaged disposable SiO$_2$ stationary phase columns with eluent flow rate range of 15 to 200 mL/min, UV detection (254 and 280 nm). Reverse phase preparative HPLC was carried out using C18 columns, UV detection (214 and 254 nm) eluting with gradients of MeCN in water (0.03% (NH$_4$)$_2$CO$_3$/0.375% NH$_4$OH) or MeCN in water (0.1% HCOOH). The analytical HPLC chromatograms were performed using an Agilent 1100 series instrument with DAD detector (190 nm to 300 nm). The mass spectra were recorded with a Waters Micromass ZQ detector at 130° C. The mass spectrometer was equipped with an electrospray ion source (ESI) operated in a positive ion mode and was set to scan between m/z 150-750 with a scan time of 0.3 s. Unless otherwise specified, products and intermediates were analyzed by HPLC/MS on a Gemini-NX (5 μM, 2.0×30 mm) using a high pH buffer gradient of 5% to 100% of MeCN in water (0.03% (NH$_4$)$_2$CO$_3$/0.375% NH$_4$OH) over 2.5 min at 1.8 mL/min for a 3.5 min run (B05) and EVO C18 (5 μM, 3.0×50 mm) using a low pH buffer gradient of 5% to 100% of MeCN in water (0.1% HCOOH) over 2.5 min at 2.2 mL/min for a 3.5 min run (A$_{05}$). Unless otherwise specified, prep-HPLC purification was performed using the following eluents: MeCN/10 mM aqueous NH$_4$HCO$_3$ for the "neutral conditions" method, MeCN/0.04% aqueous HCl for the "HCl conditions" method, and MeCN/0.2% aqueous HCOOH for the "FA conditions" method. The $^1$H NMR chemical shifts are referenced to solvent peaks, which in $^1$H NMR appear at 7.26 ppm for CDCl$_3$, 2.50 for DMSO-d6, and 3.31 ppm for CD$_3$OD.

Example 1: 5-bromo-6-chloropyridin-3-ol

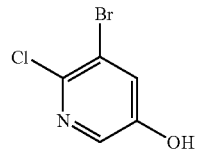

A mixture of NaNO$_2$ (31.9 g, 4620 mmol, 1.20 eq) in water (80.0 mL) was added to an ice-cooled solution of 5-bromo-6-chloropyridin-3-amine (80.0 g, 386 mmol, 1.00 eq) in H$_2$SO$_4$ (567 g, 2.89 mol, 308 mL, 50% purity, 7.50 eq) at 0° C., and then the mixture was stirred at 25° C. for 30 mins. The mixture was added to AcOH (400 mL) at 100° C. The mixture was stirred at 100° C. for 12 h. LCMS showed the reaction was complete. The mixture was concentrated under reduced pressure. The mixture was added to ice-water (2000 mL) and adjusted the pH to 6-7 using sat. aq. Na$_2$CO$_3$. The mixture was extracted with EtOAc (5000 mL). The organic layer was washed with brine (2000 mL), dried over Na$_2$CO$_3$, filtered and concentrated under reduced pressure. The residue was purified by column chromatography (SiO$_2$, Petroleum ether/Ethyl acetate=1/0 to 4/1, Petroleum ether/Ethyl acetate=2/1, R$_f$=0.56). 5-bromo-6-chloropyridin-3-ol (52.0 g, crude) was obtained as a yellow solid. $^1$H NMR CDCl$_3$ 400 MHz, δ=ppm 7.95 (d, J=2.6 Hz, 1H), 7.45 (d, J=2.6 Hz, 1H).

Example 2: 5-bromo-6-chloro-2-nitropyridin-3-ol

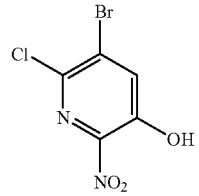 [SMILES: O=[N+]([O-])c1nc(Cl)c(Br)cc1O]

The reaction was set up in two separate batches. A mixture of 5-bromo-6-chloropyridin-3-ol (46.0 g, 220 mmol, 1.00 eq) in H$_2$SO$_4$ (138 mL, 98% purity) was stirred at 0° C. for 75 min. H$_2$SO$_4$ (42.3 g, 423 mmol, 23.0 mL, 98% purity, 1.92 eq) and fuming HNO$_3$ (19.3 g, 294 mmol, 13.8 mL, 96% purity, 1.33 eq) was added to the reaction mixture at 0° C. The mixture was stirred at 0° C. for 2 h. After stirring for 2 h, the mixture was stirred at 20° C. for 12 h. LCMS showed that a small amount of 5-bromo-6-chloropyridin-3-ol remained and the desired mass was detected. The two reaction mixtures were combined and added to ice-water (3000 mL) and stirred at 20° C. for 1 hr. The mixture was filtered and the filter cake was dried under reduced pressure to give 5-bromo-6-chloro-2-nitropyridin-3-ol (83.0 g, crude) as a yellow solid. $^1$H NMR DMSO-$d_6$ 400 MHz, δ=ppm 7.97 (s, 1H).

Example 3:
2-bromo-6-fluoro-3-methoxybenzaldehyde

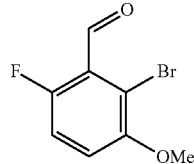 [SMILES: COc1ccc(F)c(C=O)c1Br]

The reaction was set up in 3 separate batches. To a solution of 2-bromo-4-fluoro-1-methoxybenzene (170 g, 829 mmol, 1.00 eq) in THF (2500 mL) was added LDA (2 M, 456 mL, 1.10 eq) at −78° C. under nitrogen. The mixture was stirred at −78° C. for 1 hr, then DMF (121 g, 1.66 mol, 128 mL, 2.00 eq) was added under −65° C. The reaction mixture was stirred at −65° C. for 1 hr. TLC (Petroleum ether:Ethyl acetate=3:1, $R_f$=0.6) detected one major new spot with larger polarity. Each batch was quenched by addition of water (700 mL) and then the organic solvent was evaporated. The three batches of the remaining aqueous phase were combined and extracted with EtOAc (1000 mL*3). The combined organic layers were washed with brine (1000 mL) and dried over $Na_2SO_4$, filtered and concentrated under reduced pressure. The residue was triturated with MTBE (1000 mL) and filtered to afford 2-bromo-6-fluoro-3-methoxybenzaldehyde (600 g, crude) as a yellow solid. $^1$H NMR CDCl$_3$ 400 MHz, δ=ppm 10.39 (s, 1H), 7.19-7.03 (m, 2H), 3.93 (s, 3H).

Example 4:
2-bromo-6-fluoro-3-hydroxybenzaldehyde

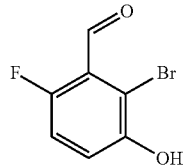

The reaction was set up in 3 separate batches. To a solution of 2-bromo-6-fluoro-3-methoxybenzaldehyde (165 g, 708 mmol, 1.00 eq) in DCM (2000 mL) was added BBr$_3$ (408 g, 1.63 mol, 157 mL, 2.30 eq) dropwise over 0.5 hr while keeping inner temperature between 0-10° C. under N$_2$. The mixture was stirred at 25° C. for 2 h under N$_2$. TLC (Petroleum ether:Ethyl acetate=3:1, $R_f$=0.25) detected one major new spot with higher polarity. The reaction mixture was quenched with water (2500 mL) and extracted with EtOAc (1000 mL*3). The organic layers from the three batches were combined, washed with brine (800 mL), dried over Na$_2$SO$_4$, filtered and then concentrated under reduced pressure. The residue was washed with PE/EtOAc (1/1, 600 mL) and filtered, the filter cake was dried in vacuum to afford 2-bromo-6-fluoro-3-hydroxybenzaldehyde (408 g, 1.86 mol, 87% yield) as a yellow solid. $^1$H NMR CDCl$_3$ 400 MHz, δ=ppm 10.32 (s, 1H), 7.28-7.22 (m, 1H), 7.15-7.05 (m, 1H), 5.90 (s, 1H).

Example 5:
2-bromo-3-(1,3-dioxolan-2-yl)-4-fluorophenol

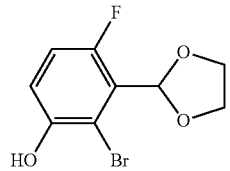

To a solution of 2-bromo-6-fluoro-3-hydroxybenzaldehyde (136 g, 621 mmol, 1.00 eq), ethylene glycol (193 g, 3.10 mol, 173 mL, 5.00 eq) in toluenetoluene (2000 mL) was added TsOH (10.7 g, 62.1 mmol, 0.100 eq) at 25° C. The mixture was stirred at 130° C. for 8 h under N$_2$. Three parallel reactions were set up. LC-MS showed no 2-bromo-6-fluoro-3-hydroxybenzaldehyde was remained. Several new peaks were shown on LC-MS and the desired mass was detected. Each batch of the reaction mixture was cooled to room temperature and concentrated to the third of the initial volume. The residual solution was then diluted with the saturated NaHCO$_3$ solution (1000 mL) and extracted with EtOAc (300 mL*3). The combined organic layers were washed with brine (200 mL), dried over Na$_2$SO$_4$, filtered and concentrated to provide the title compound as a solid. The three batches were combined and the residue was triturated with MTBE (100 mL) and filtered, the filter cake was 2-bromo-3-(1,3-dioxolan-2-yl)-4-fluorophenol. 2-bromo-3-(1,3-dioxolan-2-yl)-4-fluorophenol (355 g, 1.35 mol, 72% yield) was obtained as a white solid. $^1$H NMR CDCl$_3$ 400 MHz, δ=ppm 7.08-6.92 (m, 2H), 6.28 (s, 1H), 5.67 (s, 1H), 4.33-4.20 (m, 2H), 4.14-4.01 (m, 2H).

Example 6: (R)-2-(2-bromo-6-fluoro-3-(oxiran-2-ylmethoxy)phenyl)-1,3-dioxolane

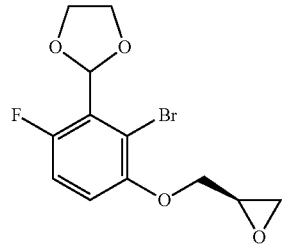 [SMILES: Fc1ccc(OC[C@H]2CO2)c(Br)c1C1OCCO1]

To a mixture of NaH (18.2 g, 456 mmol, 60% purity, 1.2 eq) in DMF (700 mL) was added dropwise 2-bromo-3-(1,3-dioxolan-2-yl)-4-fluorophenol (100 g, 380 mmol, 1.00 eq) in DMF (500 mL) at 0° C. The mixture was allowed to warm up to 25° C. and stirred for 0.5 hr. Then (R)-oxiran-2-ylmethyl 3-nitrobenzenesulfonate (98.6 g, 380 mmol, 1.00 eq) in DMF (500 mL) was added dropwise at 0° C. and the mixture was stirred at 25° C. for 12 h. HPLC showed that some 2-bromo-3-(1,3-dioxolan-2-yl)-4-fluorophenol remained. Additional (R)-oxiran-2-ylmethyl 3-nitrobenzenesulfonate (19.7 g, 76.0 mmol, 0.2 eq) in DMF (100 mL) was added dropwise at 25° C. and the mixture was stirred at 25° C. for 4 h. HPLC showed no 2-bromo-3-(1,3-dioxolan-2-yl)-4-fluorophenol remained. The mixture was quenched by the addition of water (2500 mL), filtered, and the filter cake was dried under reduced pressure. Then mother liquor was extracted with EtOAc (1000 mL*3). The combined organic layers were washed with brine (1000 mL), dried over Na₂SO₄, filtered, and concentrated to a solid. The solid and the filter cake were combined and triturated with MTBE (100 mL) and filtered to afford (R)-2-(2-bromo-6-fluoro-3-(oxiran-2-ylmethoxy)phenyl)-1,3-dioxolane (105 g, 329 mmol, 86% yield) as a white solid. ¹H NMR CDCl₃ 400 MHz, δ=ppm 7.06-6.99 (m, 1H), 6.99-6.94 (m, 1H), 6.42 (d, J=1.0 Hz, 1H), 4.34-4.21 (m, 3H), 4.13-3.98 (m, 3H), 3.40 (tdd, J=5.3, 4.1, 2.8 Hz, 1H), 2.99-2.90 (m, 1H), 2.85 (dd, J=4.9, 2.7 Hz, 1H).

Example 7: (S)-(4-(1,3-dioxolan-2-yl)-5-fluoro-2,3-dihydrobenzofuran-3-yl)methanol

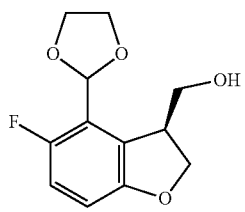 [SMILES: OC[C@H]1COc2ccc(F)c(C3OCCO3)c21]

To a mixture of (R)-2-(2-bromo-6-fluoro-3-(oxiran-2-ylmethoxy)phenyl)-1,3-dioxolane (113 g, 352 mmol, 1.00 eq) in THF (1200 mL) was added dropwise n-BuLi (2.5 M, 169 mL, 1.20 eq) at −78° C. The mixture was stirred at −78° C. for 2 h under N₂. TLC (Petroleum ether: Ethyl acetate=2:1, R_f=0.24) detected one major new spot with higher polarity. LC-MS showed no (R)-2-(2-bromo-6-fluoro-3-(oxiran-2-ylmethoxy)phenyl)-1,3-dioxolane remained. The reaction mixture was quenched by the addition of water (500 mL) at 0° C. and extracted with EtOAc (100 mL*3). The combined organic layers were washed with brine (100 mL), dried over Na₂SO₄, filtered, and concentrated under reduced pressure to obtain (S)-(4-(1,3-dioxolan-2-yl)-5-fluoro-2,3-dihydrobenzofuran-3-yl)methanol (85 g, crude) as a yellow oil. ¹H NMR DMSO-d₆ 400 MHz, δ=ppm 7.05-6.91 (m, 1H), 6.79 (dd, J=8.7, 3.9 Hz, 1H), 5.91 (s, 1H), 4.95 (t, J=5.3 Hz, 1H), 4.62 (dd, J=8.8, 1.8 Hz, 1H), 4.42 (t, J=8.7 Hz, 1H), 4.15-4.07 (m, 2H), 3.99-3.90 (m, 2H), 3.70-3.58 (m, 2H), 3.25-3.15 (m, 1H).

Example 8: (R)-3-((4-(1,3-dioxolan-2-yl)-5-fluoro-2,3-dihydrobenzofuran-3-yl)methoxy)-5-bromo-6-chloro-2-nitropyridine

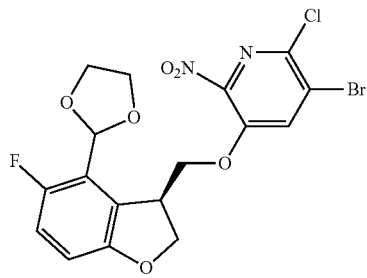 [SMILES: O=[N+]([O-])c1nc(Cl)c(Br)cc1OC[C@H]1COc2ccc(F)c(C3OCCO3)c21]

The reaction was set up in to parallel batches. To a solution of (S)-(4-(1,3-dioxolan-2-yl)-5-fluoro-2,3-dihydrobenzofuran-3-yl)methanol (45.0 g, 187 mmol, 1.00 eq) and 5-bromo-6-chloro-2-nitropyridin-3-ol (41.8 g, 165 mmol, 0.88 eq) in toluenetoluene (1800 mL) was added PPh₃ (73.7 g, 281 mmol, 1.50 eq). Then DIAD (45.5 g, 225 mmol, 43.7 mL, 1.20 eq) was added to the mixture at 20° C. The mixture was stirred at 20° C. for 12 h. LCMS indicated that the reaction was complete. The two batches were combined. The mixture was concentrated under reduced pressure. The residue was purified by column chromatography (SiO₂, Petroleum ether/Ethyl acetate=I/O to 0/1; Petroleum ether/Ethyl acetate=2/1, R_f=0.72). (R)-3-((4-(1,3-dioxolan-2-yl)-5-fluoro-2,3-dihydrobenzofuran-3-yl)methoxy)-5-bromo-6-chloro-2-nitropyridine (300 g, crude) was obtained as yellow oil. ¹H NMR CDCl₃ 400 MHz, δ=ppm 7.80 (s, 1H), 6.94 (dd, J=10.3, 8.8 Hz, 1H), 6.81 (dd, J=8.7, 4.0 Hz, 1H), 6.05 (s, 1H), 4.75-4.70 (m, 1H), 4.54-4.46 (m, 2H), 4.20-4.15 (m, 2H), 4.11-3.99 (m, 4H).

Example 9: (R)-3-((4-(1,3-dioxolan-2-yl)-5-fluoro-2,3-dihydrobenzofuran-3-yl)methoxy)-5-bromo-6-chloropyridin-2-amine

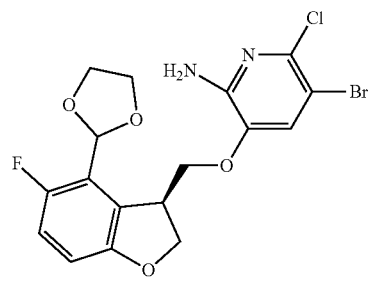 [SMILES: Nc1nc(Cl)c(Br)cc1OC[C@H]1COc2ccc(F)c(C3OCCO3)c21]

To a solution of (R)-3-((4-(1,3-dioxolan-2-yl)-5-fluoro-2,3-dihydrobenzofuran-3-yl)methoxy)-5-bromo-6-chloro-2-nitropyridine (150 g, 315 mmol, 1.00 eq) in AcOH (1250 mL) was added Fe (176 g, 3.15 mol, 10.0 eq) at 20° C. The mixture was stirred at 35° C. for 2 h. LCMS showed that the reaction was complete. The mixture was filtered and the filtrate was concentrated under reduced pressure to give (R)-3-((4-(1,3-dioxolan-2-yl)-5-fluoro-2,3-dihydrobenzofuran-3-yl)methoxy)-5-bromo-6-chloropyridin-2-amine (90.0 g, crude) as a black oil.

Example 10: (R)-3-(((2-amino-5-bromo-6-chloropyridin-3-yl)oxy)methyl)-5-fluoro-2,3-dihydrobenzofuran-4-carbaldehyde

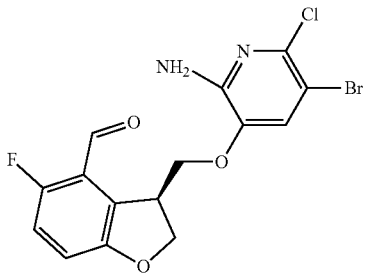

To a solution of (R)-3-((4-(1,3-dioxolan-2-yl)-5-fluoro-2,3-dihydrobenzofuran-3-yl)methoxy)-5-bromo-6-chloropyridin-2-amine (90.0 g, 202 mmol, 1.00 eq) in THF (1000 mL) was added HCl (1.5 M, 240 mL, 1.78 eq) at 20° C. The mixture was stirred at 20° C. for 10 h. The mixture was concentrated under reduced pressure. EtOAc (1000 mL) was added to the residue and the mixture was stirred at 20° C. for 10 mins. The mixture was filtered and the solid was washed with EtOAc (300 mL) and dried under reduced pressure. EtOAc (1000 mL) was added to the residue and the pH was adjusted to 8-9 with sat. aq. NaHCO$_3$. The organic layer was separated, washed with brine (300 mL), dried over Na$_2$SO$_4$, and filtered. The filtrate was concentrated under reduced pressure to give (R)-3-(((2-amino-S-bromo-6-chloropyridin-3-yl)oxy)methyl)-S-fluoro-2,3-dihydrobenzofuran-4-carbaldehyde (40.0 g, crude) as an off-white solid. $^1$H NMR DMSO-d$_6$ 400 MHz, δ=ppm 10.26 (s, 1H), 7.45-7.34 (m, 1H), 7.27-7.16 (m, 2H), 4.74 (br d, J=8.2 Hz, 1H), 4.61-4.50 (m, 1H), 4.23 (br s, 1H), 4.16 (br dd, J=9.5, 3.5 Hz, 1H), 3.89-3.80 (m, 1H).

Example 11: (R)-(3-(((2-amino-S-bromo-6-chloro-pyridin-3-yl)oxy)methyl)-S-fluoro-2,3-dihydrobenzofuran-4-yl)methanol

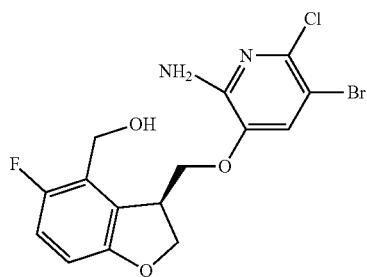 [SMILES: Nc1nc(Cl)c(Br)cc1OC[C@H]1COc2ccc(F)c(CO)c21]

To a solution of (R)-3-(((2-amino-S-bromo-6-chloropyridin-3-yl)oxy)methyl)-S-fluoro-2,3-dihydrobenzofuran-4-carbaldehyde (29.0 g, 72.2 mmol, 1.00 eq) in THF (300 mL) and MeOH (60 mL) was added NaBH$_4$ (4.10 g, 108 mmol, 1.50 eq) at 25° C. The mixture was stirred at 25° C. for 1 hr. LCMS showed the reaction was complete. The residue was poured into water (400 mL) and stirred for 5 mins. The aqueous phase was extracted with EtOAc (200 mL*2), dried with Na$_2$SO$_4$, filtered and concentrated in vacuum. (R)-(3-(((2-amino-S-bromo-6-chloropyridin-3-yl)oxy)methyl)-S-fluoro-2,3-dihydrobenzofuran-4-yl)methanol (32.0 g, crude) was obtained as a yellow solid. $^1$H NMR DMSO-d$_6$ 400 MHz, δ=ppm 7.42 (s, 1H), 7.02 (dd, J=10.2, 8.7 Hz, 1H), 6.78 (dd, J=8.6, 3.9 Hz, 1H), 6.47 (br s, 2H), 5.39 (t, J=5.4 Hz, 1H), 4.75-4.67 (m, 2H), 4.63-4.56 (m, 2H), 4.40 (dd, J=9.4, 4.2 Hz, 1H), 4.22-4.09 (m, 1H), 4.03-3.95 (m, 1H).

Example 12: (R)—S-bromo-6-chloro-3-((4-(chloromethyl)-S-fluoro-2,3-dihydrobenzofuran-3-yl)methoxy)pyridin-2-amine

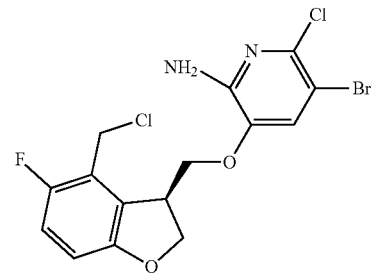 [SMILES: Nc1nc(Cl)c(Br)cc1OC[C@H]1COc2ccc(F)c(CCl)c21]

To a solution of (R)-(3-(((2-amino-S-bromo-6-chloropyridin-3-yl)oxy)methyl)-S-fluoro-2,3-dihydrobenzofuran-4-yl)methanol (30.0 g, 74.3 mmol, 1.00 eq) in THF (310 mL) was added SOCl$_2$ (13.3 g, 111 mmol, 8.09 mL, 1.5 eq) at 20° C. The mixture was stirred at 20° C. for 1 hr. LCMS showed the reaction was complete. The mixture was concentrated under reduced pressure. The residue was purified by column chromatography (SiO$_2$, Petroleum ether/Ethyl acetate=1/0 to 0/1, Petroleum ether/Ethyl acetate=2/1, R$_f$=0.56). (R)—S-bromo-6-chloro-3-((4-(chloromethyl)-S-fluoro-2,3-dihydrobenzofuran-3-yl)methoxy)pyridin-2-amine (30.0 g, crude) was obtained as a yellow solid. $^1$H NMR DMSO-d$_6$ 400 MHz, δ=ppm 7.48-7.53 (br. m, 2H), 7.32 (s, 1H), 7.06 (t, J=9.6 Hz, 1H), 6.82-6.85 (m, 1H), 4.82-4.84 (m, 2H), 4.62-4.64 (m, 2H), 4.28-4.31 (m, 1H), 3.98-4.07 (m, 2H).

Example 13: (R)-10-bromo-9-chloro-S-fluoro-6,7,13,13a-tetrahydro-1H-benzofuro[4,3-fg]pyrido[3,2-b][1,4]oxazonine

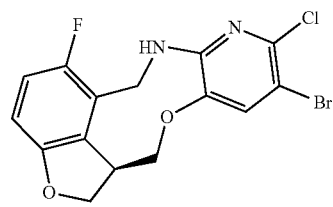 [SMILES: Fc1ccc2c3c1CNc1nc(Cl)c(Br)cc1OC[C@H]3CO2]

The reaction was set up in four parallel batches. To a solution of (R)—S-bromo-6-chloro-3-((4-(chloromethyl)-S-fluoro-2,3-dihydrobenzofuran-3-yl)methoxy)pyridin-2-amine (7.50 g, 17.8 mmol, 1.00 eq) in CH$_3$CN (1600 mL) was added Cs$_2$CO$_3$ (21.3 g, 65.4 mmol, 3.67 eq) and TBAI (1.21 g, 3.27 mmol, 0.18 eq) at 20° C. The mixture was stirred at 65° C. for 3.5 h. The four batches were combined and water (1000 mL) was added to the reaction mixture. The mixture was concentrated under reduced pressure to remove CH$_3$CN and the aqueous phase was extracted with EtOAc (500 mL*3). The combined organic layers were washed with brine (500 mL), dried over Na$_2$SO$_4$, filtered, and concentrated under reduced pressure. The residue was purified by column chromatography (SiO$_2$, Petroleum ether/Ethyl acetate=1/0 to 2/1, Petroleum ether/Ethyl acetate=2/1, R$_f$=0.76). (R)-10-bromo-9-chloro-S-fluoro-6,7,13,13a-tetrahydro-1H-benzofuro[4,3-fg]pyrido[3,2-b][1,4]oxazonine (12.0 g, 20.3 mmol, 47% yield) was obtained as a white solid. $^1$H NMR CDCl$_3$ 400 MHz, δ=ppm 7.25 (s, 1H), 6.88-6.80 (m, 1H), 6.62 (dd, J=8.7, 3.9 Hz, 1H), 5.36 (br t, J=7.8 Hz, 1H), 4.79 (dd, J=14.9, 9.2 Hz, 1H), 4.65-4.55 (m, 2H), 4.49 (dd, J=14.8, 6.8 Hz, 1H), 4.21 (dd, J=9.5, 2.9 Hz, 1H), 3.92-3.82 (m, 1H), 3.80-3.71 (m, 1H).

Example 14: tert-butyl (R)-10-bromo-9-chloro-S-fluoro-13,13a-dihydro-1H-benzofuro[4,3-fg]pyrido[3,2-b][1,4]oxazonine-7 (6H)-carboxylate

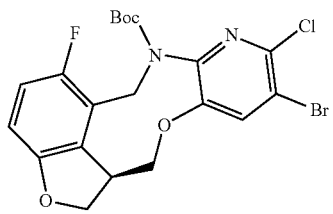 [SMILES: CC(C)(C)OC(=O)N1Cc2c(F)ccc3c2[C@@H](COc2cc(Br)c(Cl)nc21)CO3]

To a solution of (R)-10-bromo-9-chloro-S-fluoro-6,7,13,13a-tetrahydro-1H-benzofuro[4,3-fg]pyrido[3,2-b][1,4]oxazonine (5.80 g, 15.0 mmol, 1.00 eq) in THF (90 mL) was added DMAP (441 mg, 3.61 mmol, 0.24 eq), TEA (4.57 g, 45.1 mmol, 6.28 mL, 3.00 eq) and Boc$_2$O (19.70 g, 90.25 mmol, 20.73 mL, 6 eq) at 25° C. The mixture was stirred at 50° C. for 12 h. The reaction mixture was quenched by addition of water (50 mL) and extracted with EtOAc (30 mL*3). The combined organic layers were washed with sat. NaCl (30 mL), dried over Na$_2$SO$_4$, filtered, and concentrated under reduced pressure. The residue was purified by column chromatography (SiO$_2$, Petroleum ether/Ethyl acetate=1/0 to 0/1, Petroleum ether/Ethyl acetate=2:1, R$_f$=0.65). tert-butyl (R)-10-bromo-9-chloro-S-fluoro-13,13a-dihydro-1H-benzofuro[4,3-fg]pyrido[3,2-b][1,4]oxazonine-7 (6H)-carboxylate (6.60 g, 13.6 mmol, 90% yield) was obtained as a white solid. $^1$H NMR CDCl$_3$ 400 MHz, δ=ppm 7.60 (s, 1H), 6.83 (t, J=9.4 Hz, 1H), 6.65 (dd, J=8.6, 3.7 Hz, 1H), 5.00-4.87 (m, 2H), 4.46-4.38 (m, 1H), 4.31 (br dd, J=11.0, 5.1 Hz, 1H), 4.18-4.14 (m, 1H), 4.12-4.08 (m, 1H), 3.94-3.81 (m, 1H), 1.36 (s, 9H).

Example 15: tert-butyl (R)-10-bromo-S-fluoro-9-hydrazineyl-13,13a-dihydro-1H-benzofuro[4,3-fg]pyrido[3,2-b][1,4]oxazonine-7 (6H)-carboxylate

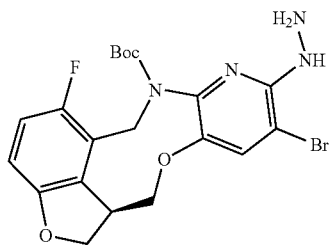 [SMILES: CC(C)(C)OC(=O)N1Cc2c(F)ccc3c2[C@@H](COc2cc(Br)c(NN)nc21)CO3]

The reaction was set up in four parallel batches. To a solution of tert-butyl (R)-10-bromo-9-chloro-S-fluoro-13,13a-dihydro-1H-benzofuro[4,3-fg]pyrido[3,2-b][1,4]oxazonine-7 (6H)-carboxylate (1.60 g, 3.29 mmol, 1.00 eq) in n-BuOH (60 mL) was added hydrazine hydrate (4.21 g, 82.4 mmol, 4.08 mL, 98% purity, 25 eq) at 25° C. The mixture was stirred at 100° C. for 12 h. The four batches were combined and the resulting mixture was concentrated under reduced pressure. The residue was purified by column chromatography (SiO$_2$, Petroleum ether/Ethyl acetate=1/0 to 0/1, Petroleum ether:Ethyl acetate=1:1, R$_f$=0.1). tert-butyl (R)-10-bromo-S-fluoro-9-hydrazineyl-13,13a-dihydro-1H-benzofuro[4,3-fg]pyrido[3,2-b][1,4]oxazonine-7 (6H)-carboxylate (4.20 g, 8.73 mmol, 66% yield) was obtained as a white solid. tert-butyl (R)-10-bromo-9-chloro-S-fluoro-13,13a-dihydro-1H-benzofuro[4,3-fg]pyrido[3,2-b][1,4]oxazonine-7 (6H)-carboxylate (0.7 g, crude) was recovered as a yellow oil. $^1$H NMR CDCl$_3$ 400 MHz, δ=ppm 7.47 (s, 1H), 6.88-6.82 (m, 1H), 6.65 (dd, J=8.7, 3.8 Hz, 1H), 6.06 (s, 1H), 5.11 (br d, J=15.7 Hz, 1H), 4.77 (br d, J=15.8 Hz, 1H), 4.39 (t, J=8.9 Hz, 1H), 4.18-4.12 (m, 1H), 4.10-4.05 (m, 2H), 3.96-3.87 (m, 2H), 1.33 (s, 9H).

Example 16: tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate

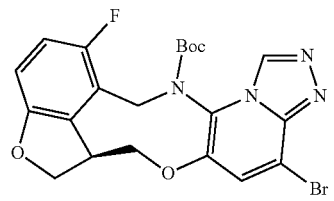 [SMILES: CC(C)(C)OC(=O)N1Cc2c(F)ccc3c2[C@H](CO3)COc2cc(Br)c3nncn3c21]

To a solution of tert-butyl (R)-10-bromo-S-fluoro-9-hydrazineyl-13,13a-dihydro-1H-benzofuro[4,3-fg]pyrido[3,2-b][1,4]oxazonine-7 (6H)-carboxylate (4.20 g, 8.73 mmol, 1.00 eq) in CH(OEt)$_3$ (40.1 g, 271 mmol, 45.0 mL, 31 eq) was added TFA (49.8 mg, 436 umol, 32.3 uL, 0.05 eq) at 25° C. The mixture was stirred at 100° C. for 3 h The reaction mixture was concentrated under reduced pressure. The residue was purified by column chromatography (SiO$_2$, Petroleum ether/Ethyl acetate=1/0 to 0/1, Petroleum ether/Ethyl acetate=1/2, R$_f$=0.28). tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (4.20 g, 8.55 mmol, 97% yield) was obtained as a yellow solid. $^1$H NMR CDCl$_3$ 400 MHz, δ=ppm 8.70 (br s, 1H), 7.30-7.27 (m, 1H), 6.70-6.55 (m, 2H), 5.31 (br s, 1H), 4.78-4.54 (m, 2H), 4.53-4.45 (m, 1H), 4.27 (d, J=9.8 Hz, 1H), 4.03-3.83 (m, 2H), 1.34 (br s, 9H).

Example 17: (S)-4-bromo-12-fluoro-7a,8,13,14-tetrahydro-7H-[1,2,4]triazolo[4',3':1,6]pyrido[3,2-b]benzofuro[4,3-fg][1,4]oxazonine

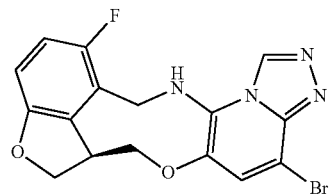 [SMILES: Fc1ccc2c3c1CNc1c(cc(Br)c4nncn14)OC[C@H]3CO2]

To tert-butyl (S)-4-bromo-12-fluoro-7a,13-dihydro-7H-[1,2,4]triazolo[4',3':1,6]pyrido[3,2-b]benzofuro[4,3-fg][1,4]

oxazonine-14 (8H)-carboxylate (2.50 g, 5.09 mmol, 1.00 eq) was added HFIP (25 mL) at 25° C. The mixture was stirred at 100° C. for 12 h The reaction mixture was concentrated under reduced pressure. The residue was purified by column chromatography (SiO$_2$, Petroleum ether/Ethyl acetate=1/0 to 0/1, Petroleum ether:Ethyl acetate=0:1, R$_f$=0.10). (S)-4-bromo-12-fluoro-7a,8,13,14-tetrahydro-7H-[1,2,4]triazolo [4',3':1,6]pyrido[3,2-b]benzofuro[4,3-fg][1,4]oxazonine (1.60 g, 4.09 mmol, 80% yield) was obtained as a white solid. $^1$H NMR DMSO-d$_6$ 400 MHz, δ=ppm 9.46 (s, 1H), 7.68 (s, 1H), 7.50 (br t, J=6.4 Hz, 1H), 6.97-6.89 (m, 1H), 6.67 (dd, J=8.6, 3.9 Hz, 1H), 4.88-4.69 (m, 2H), 4.57-4.38 (m, 2H), 4.19 (dd, J=9.5, 3.5 Hz, 1H), 4.01-3.94 (m, 1H), 3.89-3.78 (m, 1H).

Example 18: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)propan-2-ol Step 1: tert-butyl (S)-4-(6-acetylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

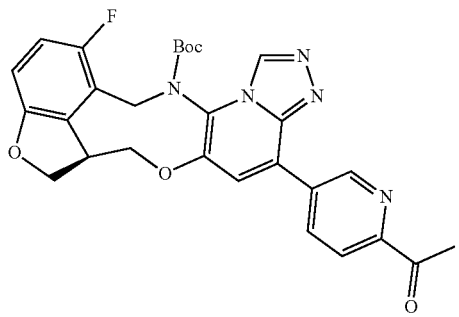 [SMILES: CC(=O)c1ccc(-c2cc3c(n4cnnc24)N(C(=O)OC(C)(C)C)Cc2c(F)ccc4c2[C@H](CO4)CO3)cn1]

To a solution of tert-butyl (S)-4-bromo-12-fluoro-7a,13-dihydro-7H-[1,2,4]triazolo[4',3':1,6]pyrido[3,2-b]benzofuro [4,3-fg][1,4]oxazonine-14 (8H)-carboxylate (100 mg, 204 umol, 1.00 eq) in dioxane (5 mL) and water (0.5 mL) was added 1-(5-(4,4,5,5-tetramethyl-1,3,2-dioxaborolan-2-yl)pyridin-2-yl)ethan-1-one (65.4 mg, 265 umol, 1.3 eq), NaHCO$_3$ (85.5 mg, 1.02 mmol, 39.6 uL, 5.00 eq) and Pd(dppf)Cl$_2$ (14.9 mg, 20.4 umol, 0.100 eq) at 20° C. under nitrogen atmosphere, the mixture was stirred at 80° C. for 12 h. The reaction was concentrated under the reduced pressure. The residue was purified by prep-TLC (SiO$_2$, Petroleum ether/Ethyl acetate=0/1). Tert-butyl (S)-4-(6-acetylpyridin-3-yl)-12-fluoro-7a,13-dihydro-7H-[1,2,4]triazolo[4',3':1,6]pyrido[3,2-b]benzofuro[4,3-fg][1,4] oxazonine-14 (8H)-carboxylate (80.0 mg, 151 umol, 73% yield) was obtained as a yellow oil.

Step 2: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)propan-2-ol formate salt

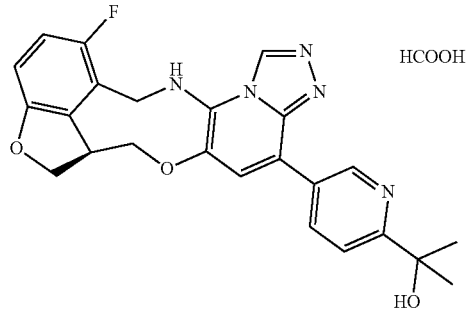 [SMILES: CC(C)(O)c1ccc(-c2cc3c(n4cnnc24)NCc2c(F)ccc4c2[C@H](CO4)CO3)cn1 ; "HCOOH"]

To a solution of tert-butyl (S)-4-(6-acetylpyridin-3-yl)-12-fluoro-7a,13-dihydro-7H-[1,2,4]triazolo[4',3':1,6]pyrido [3,2-b]benzofuro[4,3-fg][1,4]oxazonine-14 (8H)-carboxylate (70.0 mg, 132 umol, 1.00 eq) in toluene (4 mL) was added trimethylalumane (2 M, 217 uL, 3.3 eq) at 20° C., the mixture was stirred at 50° C. for 12 h. LC-MS showed tert-butyl (S)-4-(6-acetylpyridin-3-yl)-12-fluoro-7a,13-dihydro-7H-[1,2,4]triazolo[4',3':1,6]pyrido[3,2-b]benzofuro [4,3-fg][1,4]oxazonine-14 (8H)-carboxylate was consumed completely and the desired mass was detected. Water (3 mL) was added to the mixture, the mixture was the mixture was extracted with ethyl acetate (5 mL*3), the combined organic layers were dried over Na$_2$SO$_4$ and concentrated under reduced pressure. The residue was purified by prep-HPLC (column: Nano-micro Kromasil C18 100*30 mm 5 um; mobile phase: [water (0.225% FA)—ACN]; B %: 10% -45%, 12 min). (S)-2-(5-(12-fluoro-7a,8,13,14-tetrahydro-7H-[1,2,4]triazolo[4',3':1,6]pyrido[3,2-b]benzofuro[4,3-fg] [1,4]oxazonin-4-yl)pyridin-2-yl)propan-2-ol (25.0 mg, 50.6 umol, 38% yield, 99.9% purity, formate salt) was obtained as a yellow solid. $^1$H NMR DMSO-d$_6$ 400 MHz, δ=ppm 9.44 (s, 1H), 9.19 (s, 1H), 8.49 (dd, J=8.5, 1.9 Hz, 1H), 7.76-7.65 (m, 2H), 7.58 (br t, J=5.8 Hz, 1H), 6.94 (br t, J=9.6 Hz, 1H), 6.67 (dd, J=8.5, 3.6 Hz, 1H), 5.25 (s, 1H), 4.97-4.71 (m, 2H), 4.60-4.43 (m, 2H), 4.30-4.14 (m, 1H), 4.09-3.85 (m, 2H), 1.46 (s, 6H). LCMS (ESI+): m/z 448.2 (M+H)

Example 19: General Procedure D. Preparation of (S)-12-fluoro-4-(4-(methylsulfonyl)phenyl)-7a,8,13,14-tetrahydro-7H-[1,2,4]triazolo[4',3':1,6]pyrido[3,2-b]benzofuro[4,3-fg][1,4]oxazonine

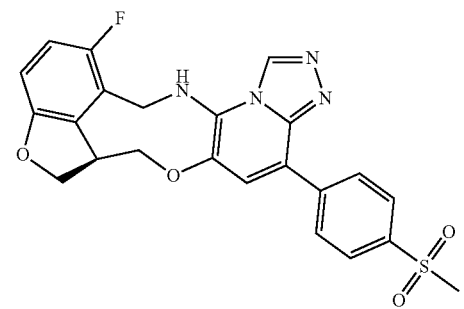 [SMILES: CS(=O)(=O)c1ccc(-c2cc3c(n4cnnc24)NCc2c(F)ccc4c2[C@H](CO4)CO3)cc1]

To a solution of (S)-4-bromo-12-fluoro-7a,8,13,14-tetrahydro-7H-[1,2,4]triazolo[4',3':1,6]pyrido[3,2-b]benzofuro

[4,3-fg][1,4]oxazonine (55.0 mg, 141 umol, 1.00 eq) and 4,4,5,5-tetramethyl-2-(4-(methylsulfonyl)phenyl)-1,3,2-dioxaborolane (51.6 mg, 183 umol, 1.3 eq) in dioxane (1 mL) and water (0.1 mL) were added Pd(dppf)Cl$_2$ (10.3 mg, 14.1 umol, 0.100 eq) and NaHCO$_3$ (59.1 mg, 703 umol, 27.3 uL, 5.00 eq) at 20° C. The mixture was degassed and purged with nitrogen 3 times, then stirred at 80° C. for 3 h under nitrogen atmosphere. Reaction progress was monitored by LC-MS. The reaction mixture was filtered and the filtrate was concentrated under reduced pressure to give a crude product. The crude product was purified by prep-HPLC (neutral condition). (S)-12-fluoro-4-(4-(methylsulfonyl)phenyl)-7a,8,13,14-tetrahydro-7H-[1,2,4]triazolo[4',3':1,6]pyrido[3,2-b]benzofuro[4,3-fg][1,4]oxazonine (12.7 mg, 26.3 umol, 18% yield, 96.7% purity) was obtained as a yellow solid. $^1$H NMR DMSO-d$_6$ 400 MHz, δ=ppm 9.48 (s, 1H), 8.52 (d, J=8.6 Hz, 2H), 7.97 (d, J=8.6 Hz, 2H), 7.89 (s, 1H), 7.77 (br s, 1H), 6.99-6.92 (m, 1H), 6.69 (dd, J=8.6, 3.7 Hz, 1H), 4.97-4.86 (m, 1H), 4.86-4.76 (m, 1H), 4.54 (br t, J=9.2 Hz, 2H), 4.21 (dd, J=9.6, 3.2 Hz, 1H), 4.11-4.01 (m, 1H), 3.97 (br d, J=10.8 Hz, 1H), 3.25 (s, 3H). LCMS (ESI+): m/z 467.1 (M+H).

Compounds 22 and 30 were prepared according to General Procedure D using the suitable starting materials, precursors, intermediates, and reagents.

Example 20: (S)-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine Step 1: 5-bromo-6-chloro-2-nitro-pyridin-3-ol

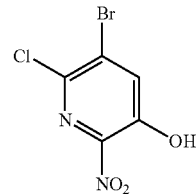

5-Bromo-6-chloro-pyridin-3-ol (5.00 g, 24.0 mmol) was added portion-wise to concentrated H$_2$SO$_4$ (15.0 mL) at 0° C. After 75 min, a mixture of conc. H$_2$SO$_4$ (98%) and fuming nitric acid (4.00 mL, 2.50/1.50 (v/v)) was added over 5 min with a dropping funnel under vigorous stirring. After stirring for 2 h at 0° C., the mixture was warmed to room temperature for 16 h. The mixture was slowly poured into 300 g of ice-water (2/1), and the mixture was stirred for 1 h.

| Cmpd No. | Compound Name | Structure | Spectral Data |
|---|---|---|---|
| 22 | (S)-4-(1,3-dimethyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine | 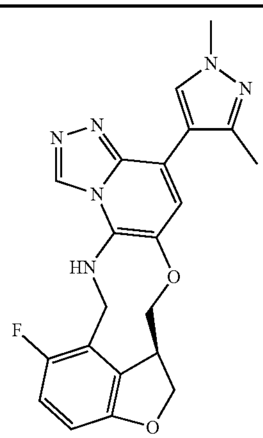 | $^1$H NMR CDCl$_3$ 400 MHz, δ = ppm 8.74 (s, 1H), 8.48 (s, 1H), 7.17 (s, 1H), 6.89-6.79 (m, 1H), 6.64 (dd, J = 8.7, 4.1 Hz, 1H), 5.04 (br dd, J = 14.8, 7.7 Hz, 1H), 4.80 (br dd, J = 14.6, 6.0 Hz, 1H), 4.65-4.58 (m, 2H), 4.47 (br s, 1H), 4.26 (dd, J = 9.8, 2.5 Hz, 1H), 3.89 (s, 3H), 3.88-3.81 (m, 1H), 2.49 (s, 3H). LCMS (ESI+): m/z 407.1 (M + H). |
| 30 | (S)-12-fluoro-4-(2-methoxypyrimidin-5-yl)-7a,8,13,14-tetrahydro-7H-[1,2,4]triazolo[4',3':1,6]pyrido[3,2-b]benzofuro[4,3-fg][1,4]oxazonine | 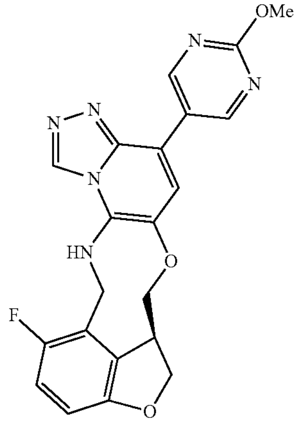 [SMILES: COc1ncc(-c2cc3c(n4cnnc24)NCc2c(F)ccc4c2[C@H](CO4)CO3)cn1] | $^1$H NMR DMSO-d$_6$ 400 MHz, δ = ppm 9.47 (s, 1H), 9.38 (s, 2H), 7.85 (s, 1H), 7.67-7.62 (m, 1H), 6.96 (t, J = 9.6 Hz, 1H), 6.69 (dd, J = 8.4, 3.6 Hz, 1H), 4.94-4.87 (m, 1H), 4.81 (br s, 1H), 4.58-4.50 (m, 2H), 4.22 (br d, J = 9.2 Hz, 1H), 4.04 (br s, 1H), 3.98 (s, 3H), 3.97-3.91 (m, 1H). LCMS (ESI+): m/z 421.2 (M + H). |

The mixture was filtered through a Buchner funnel, and the filter cake was washed with water (3×150 mL). The solid was dissolved in EtOAc (50 mL), and the organic phase was washed with brine (15 mL). The organic layer was dried (MgSO₄), filtered, and concentrated under reduced pressure to afford 5-bromo-6-chloro-2-nitro-pyridin-3-ol as a solid (3.98 g, 65%). ¹H NMR DMSO 500 MHz, δ 8.02 (s, 1H).

Step 2: 2-bromo-3-(1,3-dioxolan-2-yl) phenol

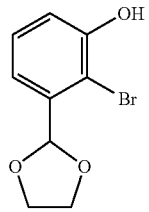 [SMILES: Oc1cccc(C2OCCO2)c1Br]

p-Toluenesulfonic acid (857 mg, 4.98 mmol) was added to a solution of 2-bromo-3-hydroxy-benzaldehyde (10.0 g, 49.8 mmol) and ethylene glycol (13.9 mL, 249 mmol) in toluene (225 mL). The mixture was stirred for 5 h at reflux. The mixture was cooled to room temperature and concentrated to a third of the initial volume. The residual solution was diluted with a saturated NaHCO₃ solution (150 mL), and the aqueous phase was extracted with EtOAc (3×75 mL). The combined organic layers were washed with brine (150 mL), dried (MgSO₄), filtered, and concentrated to provide 2-bromo-3-(1,3-dioxolan-2-yl) phenol as an oil (8.53 g, 70%). ¹H NMR CDCl₃ 500 MHz, δ 7.29-7.23 (m, 1H), 7.20-7.16 (m, 1H), 7.06 (dd, J=8.0, 1.7 Hz, 1H), 6.08 (s, 1H), 5.88 (s, 1H), 4.22-4.13 (m, 2H), 4.13-4.06 (m, 2H).

Step 3: 2-[2-bromo-3-[[(2R)-oxiran-2-yl] methoxy] phenyl]-1,3-dioxolane

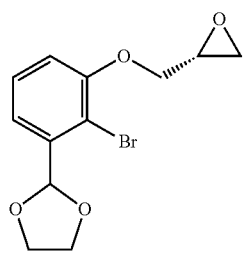 [SMILES: Brc1c(OC[C@H]2CO2)cccc1C1OCCO1]

CsF (10.6 g, 69.6 mmol) was added to a solution of 2-bromo-3-(1,3-dioxolan-2-yl) phenol (8.53 g, 34.8 mmol) in dry DMF (160 mL). The mixture was stirred for 1 hour at room temperature. [(2R)-Oxiran-2-yl] methyl 3-nitrobenzenesulfonate (9.02 g, 34.8 mmol) was added, and the mixture was stirred for 18 h. Water (250 mL) was added, and the aqueous phase was extracted with EtOAc (3×200 mL). The combined organic layers were washed with water (2×300 mL) and brine (250 mL), dried over MgSO₄, filtered, and concentrated under reduced pressure. The residue was purified by silica gel chromatography (120 g cartridge) eluting with EtOAc in hexanes (30-80%) to provide 2-[2-bromo-3-[[(2R)-oxiran-2-yl] methoxy]phenyl]-1,3-dioxolane as an oil (6.11 g, 58%). ¹H NMR CDCl₃ 400 MHz, δ 7.28 (t, J=7.7 Hz, 1H), 7.24 (dd, J=7.8, 1.9 Hz, 1H), 6.94 (dd, J=7.7, 1.9 Hz, 1H), 6.16 (s, 1H), 4.29 (dd, J=11.2, 3.1 Hz, 1H), 4.15-4.12 (m, 1H), 4.11-4.04 (m, 4H), 3.43-3.35 (m, 1H), 2.91 (dd, J=5.0, 4.2 Hz, 1H), 2.86 (dd, J=5.0, 2.6 Hz, 1H).

Step 4: [(3S)-4-(1,3-dioxolan-2-yl)-2,3-dihydrobenzofuran-3-yl] methanol

n-BuLi (8.93 mL, 22.3 mmol, 2.50 M in hexanes) was added drop wise to a solution of 2-[2-bromo-3-[[(2R)-oxiran-2-yl] methoxy] phenyl]-1,3-dioxolane (6.11 g, 20.3 mmol) in THF (100 mL) at −78° C. The mixture was warmed to room temperature over 3 h. A saturated NH₄Cl solution (100 mL) was added. The aqueous phase was extracted with EtOAc (3×100 mL), and the combined organic layers were washed with brine (100 mL), dried over MgSO₄, filtered, and concentrated under reduced pressure. The residue was purified by silica gel chromatography (120 g cartridge) eluting with EtOAc in hexanes (0-100%) to provide [(3S)-4-(1,3-dioxolan-2-yl)-2,3-dihydrobenzofuran-3-yl] methanol as a solid (1.93 g, 43%). ¹H NMR CDCl₃ 400 MHz, δ 7.19 (t, J=7.8 Hz, 1H), 7.05 (dd, J=7.7, 0.9 Hz, 1H), 6.84 (dd, J=8.0, 0.9 Hz, 1H), 5.87 (s, 1H), 4.62-4.49 (m, 2H), 4.24-4.11 (m, 2H), 4.10-4.01 (m, 2H), 3.85-3.68 (m, 3H), 2.33 (t, J=6.1 Hz, 1H). m/z (ES+) [M+H]⁺: 223.0; HPLC $t_R$ (B05)=1.39 min.

Step 5: 3-bromo-2-chloro-5—[[(3R)-4-(1,3-dioxolan-2-yl)-2,3-dihydrobenzofuran-3-yl] methoxy]-6-nitro-pyridine

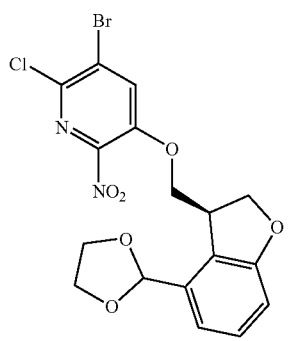 [SMILES: O=[N+]([O-])c1nc(Cl)c(Br)cc1OC[C@H]1COc2cccc(C3OCCO3)c21]

DIAD (1.92 mL, 9.77 mmol) was added drop wise to a solution of 5-bromo-6-chloro-2-nitro-pyridin-3-ol (2.19 g, 8.64 mmol), [(3S)-4-(1,3-dioxolan-2-yl)-2,3-dihydrobenzofuran-3-yl]methanol (1.81 g, 8.14 mmol), and PPh₃ (3.20 g, 12.2 mmol) in toluene (60.0 mL) at room temperature. The mixture was stirred at room temperature for 20 h and concentrated under reduced pressure. The residue was purified by silica gel chromatography (120 g cartridge) eluting with EtOAc in hexanes (0-60%) to afford the title compound, which was further purified by reverse phase column chromatography (C-18, 80 g cartridge) eluting with water (0.5% formic acid added)/ACN to provide 3-bromo-2-chloro-S—[[(3R)-4-(1,3-dioxolan-2-yl)-2,3-dihydrobenzofuran-3-yl] methoxy]-6-nitro-pyridine as a solid (3.38 g, 91%), ¹H NMR CDCl₃ 500 MHz, δ 7.85 (s, 1H), 7.23 (t, J=7.9 Hz, 1H), 7.06-7.02 (m, 1H), 6.87 (d, J=8.0 Hz, 1H), 5.85 (s, 1H), 4.71 (dd, J=9.4, 1.8 Hz, 1H), 4.55-4.48 (m, 2H), 4.19-4.12 (m, 2H), 4.12-4.06 (m, 2H), 4.06-3.96 (m, 2H). m/z (ES+) [M+H]⁺: 458.86; HPLC $t_R$ (B05)=2.11 min.

Step 6: 5-bromo-6-chloro-3-[[(3R)-4-(1,3-dioxolan-2-yl)-2,3-dihydrobenzofuran-3-yl] methoxy]pyridin-2-amine

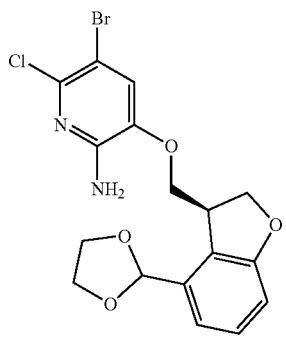 [SMILES: Nc1nc(Cl)c(Br)cc1OC[C@H]1COc2cccc(C3OCCO3)c21]

Fe (3.74 g, 67.0 mmol) was added in portions to a suspension of 3-bromo-2-chloro-S—[[(3R)-4-(1,3-dioxolan-2-yl)-2,3-dihydrobenzofuran-3-yl] methoxy]-6-nitro-pyridine (3.07 g, 6.70 mmol) in HOAc (60.0 mL) at room temperature. The mixture was stirred at room temperature for 2 h. The mixture was filtered through a pad of Celite. The Celite was washed with EtOAc (3×50 mL), and the filtrate was concentrated under reduced pressure. The residue was purified by silica gel chromatography (40.0 g cartridge) eluting with EtOAc in hexanes (0-70%) to afford 5-bromo-6-chloro-3-[[(3R)-4-(1,3-dioxolan-2-yl)-2,3-dihydrobenzofuran-3-yl]methoxy] pyridin-2-amine as a solid (2.39 g, 84%), ¹H NMR CDCl₃ 500 MHz, δ 7.23 (t, J=7.9 Hz, 1H), 7.14 (s, 1H), 7.05 (d, J=7.7 Hz, 1H), 6.87 (dd, J=8.0, 0.7 Hz, 1H), 5.88 (s, 1H), 4.81 (s, 2H), 4.66 (dd, J=9.2, 1.8 Hz, 1H), 4.58-4.49 (m, 1H), 4.34-4.23 (m, 1H), 4.19-4.12 (m, 2H), 4.11-4.04 (m, 2H), 4.04-3.97 (m, 2H); m/z (ES+) [M+H]⁺: 429.16; HPLC $t_R$ (B05)=2.02 min.

Step 7: N-[5-bromo-6-chloro-3-[[(3R)-4-(1,3-dioxolan-2-yl)-2,3-dihydrobenzofuran-3-yl]methoxy]-2-pyridyl]-2-nitro-benzenesulfonamide

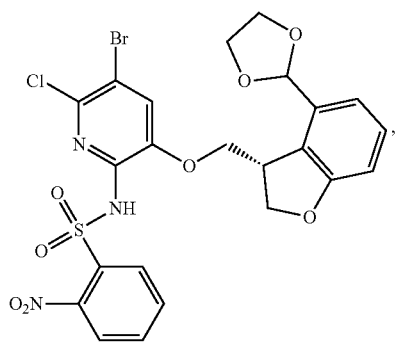

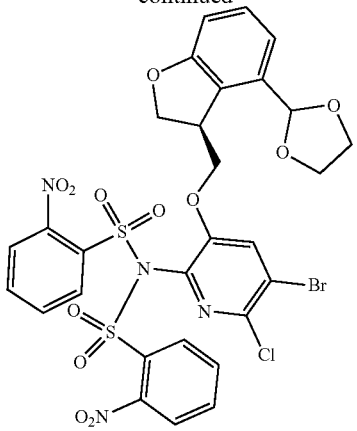

2-Nitrobenzenesulfonyl chloride (3.71 g, 16.7 mmol) was added to a stirred solution of 5-bromo-6-chloro-3-[[(3R)-4-(1,3-dioxolan-2-yl)-2,3-dihydrobenzofuran-3-yl] methoxy] pyridin-2-amine (1.59 g, 3.72 mmol) in pyridine (50.0 mL) at room temperature. The mixture was heated to 60° C. for 24 h. The mixture was concentrated, and water (30 mL) was added to the residue. The mixture was filtered through a Buchner funnel, and the solid was washed with water (100 mL). The solid was diluted in sat. NaHCO₃ (30 mL) and EtOAc (30 mL). The aqueous phase was extracted with EtOAc (3×50 mL). The combined organic layers were washed with brine (30 mL), dried over MgSO₄, filtered, and concentrated under reduced pressure. The residue was purified by silica gel chromatography (120 g cartridge) eluting with EtOAc in hexanes (0-60%) to afford the mono-Ns protected product as a solid (657 mg, 29%). m/z (ES+) [M+H]⁺: 613.93, HPLC $t_R$ (A05)=2.10 min (see step 8) and the bis-Ns protected product as a solid (1.04 g, 35%), ¹H NMR CDCl₃ 500 MHz, δ 8.64 (dd, J=7.9, 1.5 Hz, 1H), 8.62-8.58 (m, 1H), 7.89-7.80 (m, 4H), 7.73 (s, 1H), 7.72-7.65 (m, 2H), 7.19 (t, J=7.9 Hz, 1H), 6.98 (d, J=7.4 Hz, 1H), 6.81 (d, J=7.7 Hz, 1H), 5.74 (s, 1H), 4.31 (dd, J=9.2, 2.7 Hz, 1H), 4.19 (dd, J=9.4, 2.2 Hz, 1H), 4.17-4.09 (m, 3H), 4.08-4.02 (m, 2H), 3.73 (dd, J=11.0, 9.2 Hz, 1H), 3.57-3.48 (m, 1H); m/z (ES+) [M+H]⁺:798.64, HPLC $t_R$ (A05)=2.18 min.

Step 8: N-[5-bromo-6-chloro-3-[[(3R)-4-(1,3-dioxolan-2-yl)-2,3-dihydrobenzofuran-3-yl]methoxy]-2-pyridyl]-2-nitro-benzenesulfonamide

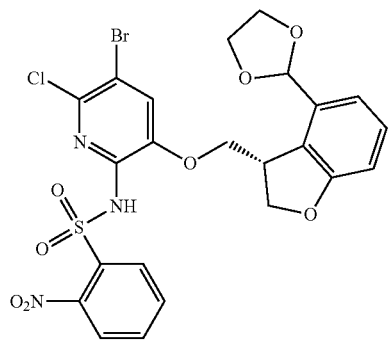 [SMILES: O=[N+]([O-])c1ccccc1S(=O)(=O)Nc1nc(Cl)c(Br)cc1OC[C@H]1COc2cccc(C3OCCO3)c21]

PhSH (27.9 μL, 0.263 mmol) and Cs$_2$CO$_3$ (85.7 mg, 0.263 mmol) were added to a solution of 3-bromo-2-chloro-S—[[(3R)-4-(1,3-dioxolan-2-yl)-2,3-dihydrobenzofuran-3-yl] methoxy]-6-nitro pyridine (210 mg, 0.263 mmol) in MeCN (15.0 mL) at room temperature. The mixture was stirred at room temperature for 3 h. The mixture was diluted with sat. aq. NaHCO$_3$ (10 mL) and EtOAc (30 mL). The aqueous phase was extracted with EtOAc (3×30 mL). The combined organic layers were washed with brine (25 mL), dried over MgSO$_4$, filtered, and concentrated. The residue was purified by silica gel chromatography (12 g, cartridge) eluting with EtOAc in hexanes (0-70%) to afford N-[5-bromo-6-chloro-3-[[(3R)-4-(1,3-dioxolan-2-yl)-2,3-dihydrobenzofuran-3-yl] methoxy]-2-pyridyl]-2-nitro-benzenesulfonamide as a solid (125 mg, 78%). $^1$H NMR CDCl$_3$ 500 MHz, δ 8.59 (dd, J=7.8, 1.1 Hz, 1H), 8.39 (s, 1H), 7.81-7.73 (m, 3H), 7.33 (s, 1H), 7.24 (t, J=8.0 Hz, 1H), 7.06 (d, J=7.5 Hz, 1H), 6.89 (d, J=7.9 Hz, 1H), 5.97 (s, 1H), 4.63-4.55 (m, 2H), 4.30 (dd, J=8.7, 5.1 Hz, 1H), 4.18-4.10 (m, 4H), 4.08-4.05 (m, 1H), 4.00 (t, J=8.7 Hz, 1H); m/z (ES+) [M+H]$^+$: 613.56, HPLC t$_R$ (B05)=1.78 min.

Step 9: N-[5-bromo-6-chloro-3-[[(3R)-4-formyl-2,3-dihydrobenzofuran-3-yl] methoxy]-2-pyridyl]-2-nitro-benzenesulfonamide

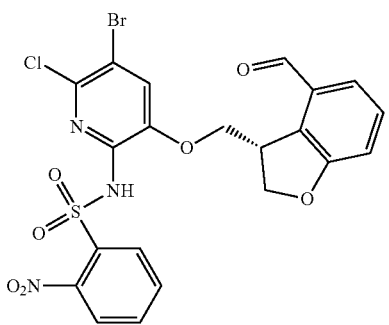 [SMILES: O=Cc1cccc2c1[C@@H](COc1cc(Br)c(Cl)nc1NS(=O)(=O)c1ccccc1[N+](=O)[O-])CO2]

Aqueous HCl (10.5 mL, 10.5 mmol, 1.00 M) was added to a solution of N-[5-bromo-6-chloro-3-[[(3R)-4-(1,3-dioxolan-2-yl)-2,3-dihydrobenzofuran-3-yl] methoxy]-2-pyridyl]-2-nitro-benzenesulfonamide (1.28 g, 2.09 mmol) in THF (25.0 mL) at room temperature. The mixture was stirred at room temperature for 18 h. A saturated NaHCO$_3$ solution (8 mL) was added, and the aqueous phase was extracted with EtOAc (3×25 mL). The combined organic extracts were washed with brine (15 mL), dried over MgSO$_4$, filtered, and concentrated to afford N-[5-bromo-6-chloro-3-[[(3R)-4-formyl-2,3-dihydrobenzofuran-3-yl] methoxy]-2-pyridyl]-2-nitro-benzenesulfonamide as a solid (1.18 g, 99%), which was used as such in next step without purification. m/z (ES+) [M+H]$^+$: 569.91, HPLC t$_R$ (A05)=2.16 min.

Step 10: N-[5-bromo-6-chloro-3-[[(3R)-4-(hydroxymethyl)-2,3-dihydrobenzofuran-3-yl] methoxy]-2-pyridyl]-2-nitro-benzenesulfonamide

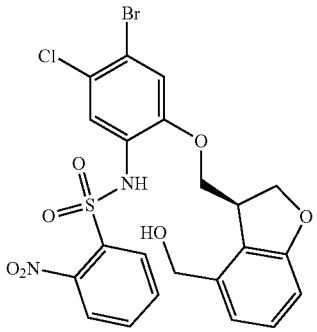 [SMILES: O=[N+]([O-])c1ccccc1S(=O)(=O)Nc1cc(Cl)c(Br)cc1OC[C@H]1COc2cccc(CO)c21]

NaBH$_4$ (0.118 g, 3.13 mmol) was added in portions to a mixture of 3-[(2-amino-S-bromo-6-chloro-3-pyridyl) oxymethyl]-2,3-dihydrobenzofuran-4-carbaldehyde (1.19 g, 2.08 mmol) in THF (15.0 mL) and MeOH (3.00 mL) at room temperature. The mixture was stirred at room temperature for 2 h. The mixture was diluted with sat. NH$_4$Cl (8.00 mL), water (10.0 mL), and EtOAc (30.0 mL). The aqueous phase was extracted with EtOAc (4×25.0 mL). The combined organic layers were washed with brine (30 mL), dried (MgSO$_4$), filtered, and concentrated. The residue was purified by silica gel chromatography (40 g, cartridge) with EtOAc in Hexanes (0-60%) to afford N-[5-bromo-6-chloro-3-[[(3R)-4-(hydroxymethyl)-2,3-dihydrobenzofuran-3-yl] methoxy]-2-pyridyl]-2-nitro-benzenesulfonamide as a solid (877 mg, 74%). $^1$H NMR CDCl$_3$ 500 MHz, δ 8.60 (d, J=7.8 Hz, 1H), 7.77 (d, J=7.6 Hz, 1H), 7.73 (s, 2H), 7.30 (s, 1H), 7.22 (t, J=7.8 Hz, 1H), 6.90 (d, J=7.6 Hz, 1H), 6.84 (d, J=7.9 Hz, 1H), 4.82 (dd, J=27.5, 12.3 Hz, 2H), 4.60 (dd, J=9.4, 7.5 Hz, 1H), 4.56-4.48 (m, 1H), 4.23 (t, J=7.1 Hz, 1H), 4.09-3.99 (m, 2H); m/z (ES+) [M+H]$^+$: 571.59, HPLC t$_R$ (B05)=1.71 min.

Step 11: (R)-10-bromo-9-chloro-7-((2-nitrophenyl) sulfonyl)-6,7,13,13a-tetrahydro-1H-benzofuro[4,3-fg]pyrido[3,2-b][1,4]oxazonine

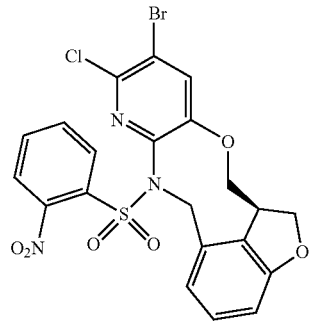 [SMILES: O=[N+]([O-])c1ccccc1S(=O)(=O)N1Cc2cccc3c2[C@@H](COc2cc(Br)c(Cl)nc21)CO3]

A solution of DIAD (0.398 mL, 2.02 mmol) in toluene (40.0 mL) was added drop wise over 1 h to a stirred solution of N-[5-bromo-6-chloro-3-[[4-(hydroxymethyl)-2,3-dihydrobenzofuran-3-yl] methoxy]-2-pyridyl]-2-nitro-benzenesulfonamide (770 mg, 1.35 mmol) and PPh$_3$ (637 mg, 2.43 mmol) in toluene (300 mL) at room temperature. The mixture was stirred at room temperature for 15 h and concentrated under reduced pressure. The residue was purified by silica gel chromatography (80 g, cartridge) with EtOAc in hexanes (0-50%) to provide (R)-10-bromo-9-chloro-7-((2-nitrophenyl)sulfonyl)-6,7,13,13a-tetrahydro-1H-benzofuro[4,3-fg]pyrido[3,2-b][1,4]oxazonine as a solid (600 mg, 81%). $^1$H NMR CDCl$_3$ 500 MHz, δ 8.42-8.35 (m, 1H), 7.79-7.73 (m, 3H), 7.42 (s, 1H), 7.04 (t, J=7.9 Hz, 1H), 6.86 (d, J=7.8 Hz, 1H), 6.68 (d, J=7.8 Hz, 1H), 5.28 (d, J=13.3 Hz, 1H), 5.08 (d, J=13.3 Hz, 1H), 4.69 (dd, J=10.6, 5.5 Hz, 1H), 4.50 (dd, J=9.6, 8.2 Hz, 1H), 4.23 (dd, J=9.7, 2.0 Hz, 1H), 4.07-3.98 (m, 1H), 3.90 (t, J=11.1 Hz, 1H); $^{13}$C NMR CDCl$_3$ 125 MHz, 159.71, 149.69, 148.38, 141.65, 141.11, 134.71, 134.60, 133.89, 133.76, 132.27, 131.64, 130.04, 127.65, 123.87, 122.62, 117.39, 109.80, 78.11, 72.09, 50.99, 40.87; m/z (ES+) [M+H]$^+$: 553.44, HPLC $t_R$ (B05)=2.42 min.

Step 12: (R)-10-bromo-9-chloro-6,7,13,13a-tetrahydro-1H-benzofuro[4,3-fg]pyrido[3,2-b][1,4]oxazonine

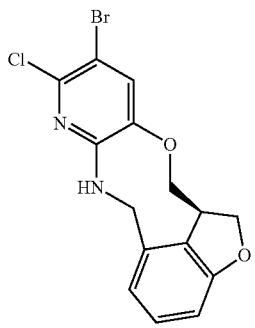 [SMILES: Clc1nc2c(cc1Br)OC[C@H]1COc3cccc(c31)CN2]

PhSH (0.0187 mL, 0.176 mmol) and Cs$_2$CO$_3$ (0.115 g, 0.353 mmol) were added to a solution of provide (R)-10-bromo-9-chloro-7-((2-nitrophenyl)sulfonyl)-6,7,13,13a-tetrahydro-1H-benzofuro[4,3-fg]pyrido[3,2-b][1,4]oxazonine (65.0 mg, 0.118 mmol) in MeCN (1.00 mL) at room temperature. The mixture was stirred at room temperature for 3 h. The mixture was diluted with sat. NaHCO$_3$ (10 mL) and EtOAc (10 mL). Water (10 mL) was added. The aqueous phase was extracted with EtOAc (3×30 mL). The combined organic layers were washed with brine (15 mL), dried over MgSO$_4$, filtered, and concentrated under reduced pressure. The residue was purified by silica gel chromatography (12 g, cartridge) eluting with EtOAc in hexanes (0-70%) to afford (R)-10-bromo-9-chloro-6,7,13,13a-tetrahydro-1H-benzofuro[4,3-fg]pyrido[3,2-b][1,4]oxazonine as a solid (43.0 mg, 99%). $^1$H NMR CDCl$_3$ 500 MHz, δ 7.29 (s, 1H), 7.14 (t, J=7.8 Hz, 1H), 6.76 (d, J=7.6 Hz, 1H), 6.71 (d, J=8.0 Hz, 1H), 5.35 (t, J=7.8 Hz, 1H), 4.70 (dd, J=15.1, 8.5 Hz, 1H), 4.54 (t, J=9.2 Hz, 2H), 4.46 (dd, J=9.5, 3.9 Hz, 1H), 4.17 (dd, J=9.6, 3.2 Hz, 1H), 3.95 (ddd, J=12.5, 8.4, 3.7 Hz, 1H), 3.90-3.79 (m, 1H). m/z (ES+) [M+H]$^+$: 368.97; HPLC $t_R$ (B05)=2.73 min.

Step 13

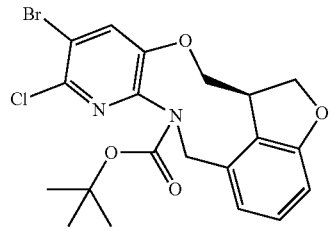 [SMILES: CC(C)(C)OC(=O)N1Cc2cccc3c2[C@@H](COc2cc(Br)c(Cl)nc21)CO3]

Boc anhydride (4.05 mL, 17.6 mmol) was added to a solution of (R)-10-bromo-9-chloro-6,7,13,13a-tetrahydro-1H-benzofuro[4,3-fg]pyrido[3,2-b][1,4]oxazonine (1.08 g, 2.94 mmol), TEA (1.23 mL, 8.82 mmol), and DMAP (90.0 mg, 0.735 mmol) in THF (50.0 mL). The mixture was stirred at 50° C. for 8 h. Water (40 mL) was added, and the aqueous phase was extracted with EtOAc (3×75 mL). The combined organic layers were washed with brine (30 mL), dried over MgSO$_4$, filtered, and concentrated under reduced pressure. The residue was purified by silica gel chromatography (40 g cartridge) eluting with EtOAc in hexanes (30-80%) to provide tert-butyl (R)-10-bromo-9-chloro-13,13a-dihydro-1H-benzofuro[4,3-fg]pyrido[3,2-b][1,4]oxazonine-7 (6H)-carboxylate as a solid (1.37 g, 99%). $^1$H NMR CDCl$_3$ 400 MHz, δ 7.52 (s, 1H), 7.06 (t, J=7.8 Hz, 1H), 6.78 (d, J=7.6 Hz, 1H), 6.68 (d, J=7.8 Hz, 1H), 4.92 (d, J=14.6 Hz, 1H), 4.74 (d, J=14.5 Hz, 1H), 4.42-4.33 (m, 2H), 4.15 (dd, J=9.5, 2.0 Hz, 1H), 4.01 (t, J=11.3 Hz, 1H), 3.81-3.72 (m, 1H), 1.35 (s, 9H). m/z (ES+) [M-Boc]$^+$: 367.6; HPLC $t_R$(B05)=2.87 min.

Step 14: tert-butyl (R)-10-bromo-9-hydrazineyl-13,13a-dihydro-1H-benzofuro[4,3-fg]pyrido[3,2-b][1,4]oxazonine-7 (6H)-carboxylate

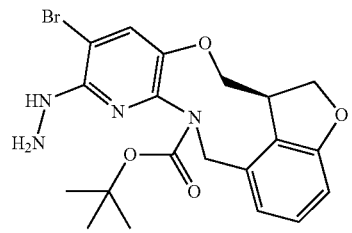 [SMILES: CC(C)(C)OC(=O)N1Cc2cccc3c2[C@@H](COc2cc(Br)c(NN)nc21)CO3]

Hydrazine monohydrate (0.519 mL, 10.7 mmol) was added to a solution of tert-butyl (R)-10-bromo-9-chloro-13,13a-dihydro-1H-benzofuro[4,3-fg]pyrido[3,2-b][1,4]oxazonine-7 (6H)-carboxylate (0.200 g, 0.428 mmol) in EtOH (10.0 mL). The mixture was heated to 100° C. for 72 h. After cooling to room temperature, the mixture was concentrated under reduced pressure, and the residue was purified by silica gel chromatography (24 g cartridge) with MeOH in DCM (0-10%) to afford tert-butyl (R)-10-bromo-9-hydrazineyl-13,13a-dihydro-1H-benzofuro[4,3-fg]pyrido[3,2-b][1,4]oxazonine-7 (6H)-carboxylate as a solid (178 mg, 90%). m/z (ES+) [M]$^+$: 463.77, HPLC $t_R$ (B05)=2.59 min.

Step 15: tert-butyl (S)-4-bromo-7a,13-dihydro-7H-[1,2,4]triazolo[4',3':1,6]pyrido[3,2-b]benzofuro[4,3-fg][1,4]oxazonine-14 (8H)-carboxylate

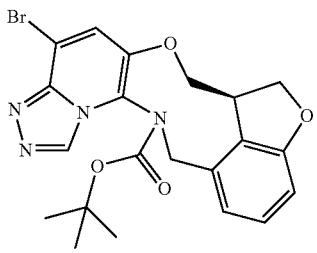 [SMILES: CC(C)(C)OC(=O)N1Cc2cccc3c2[C@H](CO3)COc2cc(Br)c3nncn3c21]

A mixture of tert-butyl (R)-10-bromo-9-hydrazineyl-13,13a-dihydro-1H-benzofuro[4,3-fg]pyrido[3,2-b][1,4]oxazonine-7 (6H)-carboxylate (330 mg, 0.712 mmol), triethyl orthoformate (21.3 mL, 128 mmol), and TFA (2.70 uL, 0.0356 mmol) was heated to 100° C. for 1 h. After cooling to room temperature, the mixture was concentrated, and the residue was purified by silica gel chromatography (24 g) with MeOH in DCM (0-10%) to afford tert-butyl (S)-4-bromo-7a,13-dihydro-7H-[1,2,4]triazolo[4',3':1,6]pyrido[3,2-b]benzofuro[4,3-fg][1,4]oxazonine-14 (8H)-carboxylate as a solid (315 mg, 93%). m/z (ES+) [M]$^+$: 473.74; HPLC $t_R$ (B05)=2.51 min.

Step 16: (S)-4-bromo-7a,8,13,14-tetrahydro-7H-[1,2,4]triazolo[4',3':1,6]pyrido[3,2-b]benzofuro[4,3-fg][1,4]oxazonine

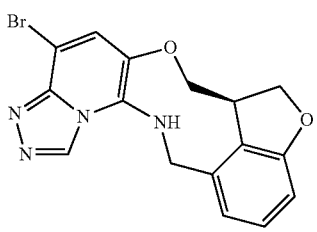 [SMILES: Brc1cc2c(n3cnnc13)NCc1cccc3c1[C@H](CO3)CO2]

A solution of tert-butyl tert-butyl (S)-4-bromo-7a,13-dihydro-7H-[1,2,4]triazolo[4',3':1,6]pyrido[3,2-b]benzofuro[4,3-fg][1,4]oxazonine-14 (8H)-carboxylate (0.110 g, 0.232 mmol) in HFIP (5.00 mL) was heated to 100° C. in an oil bath for 3 h. The mixture was concentrated under reduced pressure, and the residue was purified by silica gel chromatography (12 g) with MeOH in DCM (0-20%) to afford (S)-4-bromo-7a,8,13,14-tetrahydro-7H-[1,2,4]triazolo[4',3':1,6]pyrido[3,2-b]benzofuro[4,3-fg][1,4]oxazonine as a solid (44.0 mg, 51%). $^1$H NMR CD$_3$OD 400 MHz, δ 9.24 (s, J=15.5 Hz, 1H), 7.61 (s, 1H), 7.07 (t, J=7.8 Hz, 1H), 6.81 (d, J=7.5 Hz, 1H), 6.61 (d, J=7.9 Hz, 1H), 4.48 (t, J=9.4 Hz, 1H), 4.42 (dd, J=10.4, 4.4 Hz, 1H), 4.16 (dd, J=9.6, 3.6 Hz, 1H), 4.01-3.91 (m, J=13.1, 8.4, 4.0 Hz, 1H), 3.86-3.77 (m, 1H), 2.24 (t, J=7.4 Hz, 1H), 1.33-1.27 (m, 1H). m/z (ES+) [M]$^+$: 373.80; HPLC $t_R$ (B05)=2.35 min.

Step 17: (S)-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine

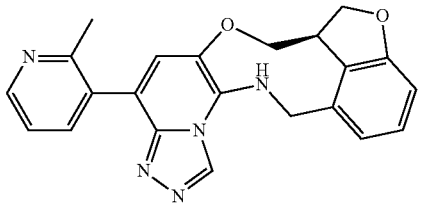 [SMILES: Cc1ncccc1-c1cc2c(n3cnnc13)NCc1cccc3c1[C@H](CO3)CO2]

Dioxane (3.00 mL) and water (0.600 mL) were sequentially added to a mixture of (S)-4-bromo-7a,8,13,14-tetrahydro-7H-[1,2,4]triazolo[4',3':1,6]pyrido[3,2-b]benzofuro[4,3-fg][1,4]oxazonine (44.0 mg, 0.118 mmol), 2-methyl-3-(4,4,5,5-tetramethyl-1,3,2-dioxaborolan-2-yl)pyridine (31.0 mg, 0.141 mmol), Pd(dppf)Cl$_2$ (8.63 mg, 0.0118 mmol), and NaHCO$_3$ (49.5 mg, 0.589 mmol) under N$_2$. The mixture was heated to 90° C. for 2 h. The mixture was concentrated under reduced pressure, and the residue was purified by silica gel chromatography (12 g cartridge) eluting with MeOH in DCM (0-30%) and further purified by HPLC (BEH 30×100 mm ACN/AmForm 31-51%) to afford (S)-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine as a solid (30.0 mg, 66%). $^1$H NMR DMSO 400 MHz, δ 9.38 (s, 1H), 8.47 (dd, J=4.8, 1.7 Hz, 1H), 7.76 (dd, J=7.7, 1.7 Hz, 1H), 7.52 (t, J=6.5 Hz, 1H), 7.31 (s, 1H), 7.29 (dd, J=7.7, 4.9 Hz, 1H), 7.13 (t, J=7.8 Hz, 1H), 6.91 (d, J=7.5 Hz, 1H), 6.68 (d, J=7.8 Hz, 1H), 4.87-4.74 (m, 2H), 4.51 (t, J=9.5 Hz, 1H), 4.47-4.39 (m, 1H), 4.16 (dd, J=9.6, 3.8 Hz, 1H), 4.07-3.96 (m, 1H), 3.83 (t, J=11.4 Hz, 1H), 2.36 (s, 3H). m/z (ES+) [M+H]$^+$: 386.91; HPLC $t_R$ (B05)=2.30 min.

Example 21: (S)-1-(4-(7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one Step 1: (S)-4-bromo-12-fluoro-7a,8,13,14-tetrahydro-7H-[1,2,4]triazolo[4',3':1,6]pyrido[3,2-b]benzofuro[4,3-fg][1,4]oxazonine [0812] (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was synthesized according to Example 20, step 15

Step 2: tert-butyl (S)-4-(1-acetyl-1,2,3,6-tetrahydropyridin-4-yl)-7a,13-dihydro-7H-[1,2,4]triazolo[4',3':1,6]pyrido[3,2-b]benzofuro[4,3-fg][1,4]oxazonine-14 (8H)-carboxylate

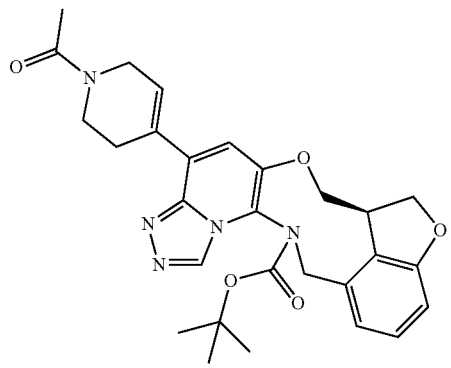 [SMILES: CC(=O)N1CC=C(c2cc3c(n4cnnc24)N(C(=O)OC(C)(C)C)Cc2cccc4c2[C@H](CO4)CO3)CC1]

Dioxane (2.00 mL), water (0.400 mL), and NaHCO₃ (0.634 mmol, 53.2 mg) were added to a mixture of tert-butyl (S)-4-(1-acetyl-1,2,3,6-tetrahydropyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (0.127 mmol, 60.0 mg), 1-[4-(4,4,5,5-tetramethyl-1,3,2-dioxaborolan-2-yl)-3,6-dihydro-2H-pyridin-1-yl]ethanone (0.133 mmol, 33.3 mg), and Pd(dppf)Cl₂ (0.0127 mmol, 9.28 mg) under N₂. The mixture was heated to 100° C. for 2 h. After cooling to room temperature, the mixture was concentrated under reduced pressure, and the residue was purified by silica gel chromatography (12 g cartridge) eluting with MeOH in DCM (0-30%) to tert-butyl (S)-4-(1-acetyl-1,2,3,6-tetrahydropyridin-4-yl)-7a,13-dihydro-7H-[1,2,4]triazolo[4',3':1,6]pyrido[3,2-b]benzofuro[4,3-fg][1,4]oxazonine-14 (8H)-carboxylate as a solid (63.0 mg, 96%). m/z (ES+) [M+H]⁺: 518.8; HPLC $t_R$ (B05)=2.42 min.

Step 3: tert-butyl (S)-4-(1-acetylpiperidin-4-yl)-7a,13-dihydro-7H-[1,2,4]triazolo[4',3':1,6]pyrido[3,2-b]benzofuro[4,3-fg][1,4]oxazonine-14 (8H)-carboxylate

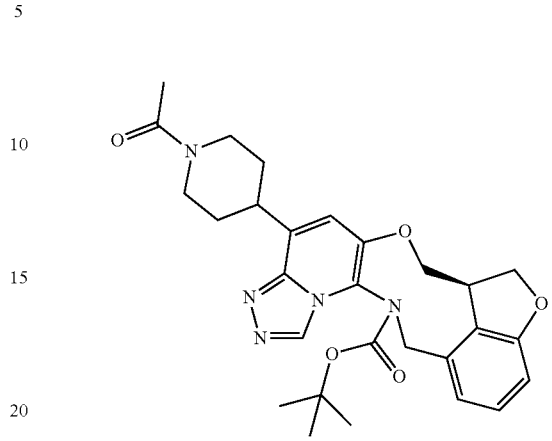

MeOH (10.00 mL) was added to a mixture of tert-butyl (S)-4-(1-acetyl-1,2,3,6-tetrahydropyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (0.122 mmol, 63.0 mg) and Pd/C (10.0%, 24.3 μmol, 25.9 mg) at room temperature. The reaction vessel was evacuated and purged with H₂. The solution was stirred at rt for 12 h. The mixture was filtered over Celite, and the Celite pad was washed with DCM (3×15 mL). The filtrate was concentrated under reduced pressure. The residue was used as such in the next step without further purification (63 mg, quant.). m/z (ES+) [M+H]⁺: 520.97. HPLC $t_R$ (B05)=2.36 min.

Step 4: (S)-1-(4-(7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one

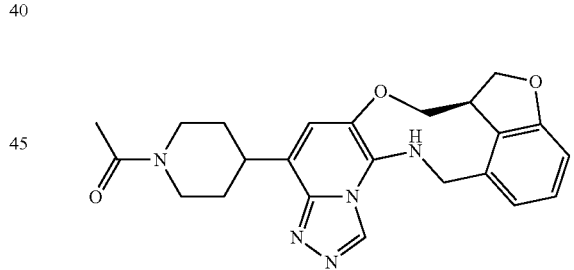

A solution of tert-butyl (S)-4-(1-acetylpiperidin-4-yl)-7a,13-dihydro-7H-[1,2,4]triazolo[4',3':1,6]pyrido[3,2-b]benzofuro[4,3-fg] [1,4]oxazonine-14 (8H)-carboxylate (0.121 mmol, 63.0 mg) in HFIP (2.00 mL) was heated to 100° C. for 3 h. The mixture was concentrated under reduced pressure, and the residue was purified by HPLC (BEH 30×100 mm ACN/AmBicarb, 27-47%) to afford (S)-1-(4-(7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one as a solid (32.0 mg, 63%). ¹H NMR DMSO 500 MHz, δ 9.29 (s, 1H), 7.18 (t, J=6.7 Hz, 1H), 7.08 (t, J=7.8 Hz, 1H), 7.06 (s, 1H), 6.86 (d, J=7.6 Hz, 1H), 6.64 (d, J=7.8 Hz, 1H), 4.75 (dd, J=14.7, 6.4 Hz, 1H), 4.69-4.59 (m, 1H), 4.57-4.50 (m, 1H), 4.48 (t, J=9.4 Hz, 1H), 4.45-4.38 (m, 1H), 4.16 (dd, J=9.6, 3.5 Hz, 1H), 4.00-3.87 (m, 2H), 3.74 (td, J=11.7, 3.7 Hz, 1H), 3.25-3.10 (m, 2H), 2.66-2.56 (m, 1H), 2.02 (d, J=3.8 Hz, 3H), 1.97-1.82 (m, 2H), 1.82-1.67 (m, 1H), 1.67-1.53 (m, 1H). m/z (ES+) [M+H]$^+$: 420.8; HPLC t$_R$ (B05)=2.22 min.

Example 22: 12-fluoro-4-(2-methylpyridin-3-yl)-7,8,13,14-tetrahydro-[1,2,4]triazolo[4',3':1,6]pyrido[3,2-b]benzo[f][1,4]oxazonine Hydrochloride Hydrochloride Step 1: methyl 2-bromo-6-fluoro-benzoate

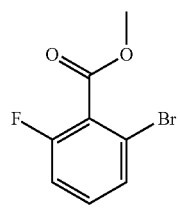

2-Bromo-6-fluorobenzoic acid (12.5 g, 57.1 mmol) was dissolved in a mixture of MeOH (60.0 mL) and concentrated sulfuric acid (60.0 mL). The solution was heated to 80° C. for 12 h. The mixture was slowly added to solution of aq. sodium carbonate solution (20%, 500 mL) at 0° C. The aqueous phase was extracted with DCM (3×175 mL), and the combined organic layers were dried (MgSO$_4$), filtered, and concentrated under reduced pressure to provide methyl 2-bromo-6-fluoro-benzoate as an oil (7.06 g, 53%). $^1$H NMR CDCl$_3$ 500 MHz, δ 7.40 (dt, J=8.1, 0.8 Hz, 1H), 7.27 (dd, J=14.1, 8.3 Hz, 1H), 7.09 (td, J=8.6, 1.0 Hz, 1H), 3.97 (s, 3H).

Step 2: methyl 2-allyl-6-fluoro-benzoate

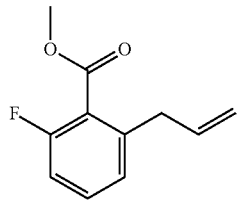

Dioxane (50.0 mL) and water (12.5 mL) were sequentially added to a mixture of methyl 2-bromo-6-fluoro-benzoate (5.00 g, 21.5 mmol), K$_2$CO$_3$ (9.00 g, 65.1 mmol), and Pd(dppf)Cl$_2$ (1.50 g, 2.05 mmol) under nitrogen. 2-Allyl-4,4,5,5-tetramethyl-1,3,2-dioxaborolane (6.04 mL, 32.2 mmol) was added, and the mixture was heated to 90° C. for 24 h. The mixture was diluted with DCM (150 mL), filtered (Celite), and the filtrated was concentrated under reduced pressure. The residue was purified by silica gel chromatography (40 g, cartridge) with a gradient of EtOAc in hexanes (0-100%) to afford methyl 2-allyl-6-fluoro-benzoate as an oil (2.12 g, 51%). $^1$H NMR CDCl$_3$ 500 MHz, δ 7.40-7.32 (m, 1H), 7.06 (d, J=7.7 Hz, 1H), 7.00 (t, J=8.9 Hz, 1H), 5.93 (ddt, J=16.8, 10.1, 6.6 Hz, 1H), 5.08 (tq, J=17.2, 1.6 Hz, 2H), 3.94 (s, 3H), 3.51 (d, J=6.6 Hz, 2H).

Step 3: (2-Allyl-6-fluoro-phenyl) methanol

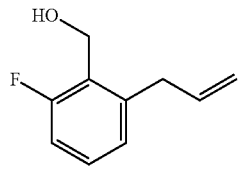

DIBAL-H (30.0 mL, 30.0 mmol) was added to a solution of methyl 2-allyl-6-fluoro-benzoate (2.10 g, 10.8 mmol) in THF (40.0 mL) at 0° C. The mixture was stirred at room temperature for 14 h. Water (1.60 mL) was added drop wise at 0° C., followed by NaOH (1.60 mL, 1.00 M) and additional water (1.60 mL). The mixture was stirred at room temperature for 1 h and filtered through Celite, washing with Et$_2$O (150 mL). The filtrate was concentrated under reduced pressure, and the residue was used as such without further purification (1.79 g, >99%). $^1$H NMR CDCl$_3$ 500 MHz, δ 7.23 (td, J=8.0, 5.9 Hz, 1H), 7.00 (d, J=7.6 Hz, 1H), 6.96 (t, J=9.0 Hz, 1H), 6.02 (ddt, J=16.3, 10.1, 6.2 Hz, 1H), 5.10 (dq, J=10.1, 1.6 Hz, 1H), 5.01 (dq, J=17.1, 1.7 Hz, 1H), 4.76 (dd, J=6.3, 1.8 Hz, 2H), 3.55 (dt, J=6.2, 1.5 Hz, 2H).

Step 4: (2-Allyl-6-fluoro-phenyl) methoxy-triisopropyl-silane

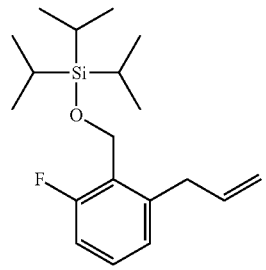 [SMILES: C=CCc1cccc(F)c1CO[Si](C(C)C)(C(C)C)C(C)C]

TIPS-C$_1$ (3.52 mL, 16.4 mmol) was added to a solution of (2-allyl-6-fluoro-phenyl) methanol (2.10 g, 12.6 mmol), imidazole (2.58 g, 37.9 mmol), and DMAP (30.0 mg, 0.246 mmol) in DCM (36.0 mL) at rt under nitrogen. The mixture was stirred at rt for 18. The solution was diluted with water (125 mL), and the aqueous phase was extracted with Et$_2$O (125 mL) and hexanes (2×50.0 mL). The combined organic layers were dried over MgSO$_4$, filtered, and concentrated under reduced pressure. The residue was purified by silica gel chromatography (40 g, cartridge) with a gradient of EtOAc in hexanes (0-100%) to afford (2-Allyl-6-fluoro-phenyl) methoxy-triisopropyl-silane as an oil (3.97 g, 97%). $^1$H NMR CDCl$_3$ 400 MHz, δ 7.19-7.13 (m, 1H), 6.96 (d, J=7.6 Hz, 1H), 6.87 (t, J=9.0 Hz, 1H), 5.97 (ddt, J=16.6, 10.1, 6.4 Hz, 1H), 5.01 (tq, J=17.0, 1.7 Hz, 2H), 4.81 (d, J=2.0 Hz, 2H), 3.57 (dt, J=6.4, 1.4 Hz, 2H), 1.20-1.07 (m, 3H), 1.06-1.00 (m, 18H).

Step 5: 2-[3-Fluoro-2-(triisopropylsilyloxymethyl) phenyl] acetaldehyde

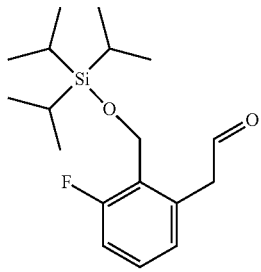 [SMILES: CC(C)[Si](OCc1c(F)cccc1CC=O)(C(C)C)C(C)C]

NaIO₄ (10.5 g, 49.2 mmol) was added to a stirred solution of OsO₄ (4.00%, 0.500 mL, 0.0787 mmol) and (2-allyl-6-fluoro-phenyl) methoxy-triisopropyl-silane (3.97 g, 12.3 mmol) in a mixture of 1,4-dioxane (50.0 mL) and water (16.0 mL) under N₂. The mixture was stirred at rt for 12 h. Sat. aq. Na₂SO₃ (100 mL) was added, and the aqueous phase was extracted with EtOAc (3×100 mL). The combined organic phases were washed with sat. aq. NaHCO₃ (100 mL), dried over MgSO₄, filtered, and concentrated under reduced pressure. The residue was used as such without further purification. ¹H NMR CDCl₃ 500 MHz, δ 9.74 (t, J=1.9 Hz, 1H), 7.30-7.20 (m, 1H), 7.03-6.96 (m, 2H), 4.84 (d, J=1.9 Hz, 2H), 3.90 (d, J=1.9 Hz, 2H), 1.17-1.11 (m, 3H), 1.05 (s, 18H).

Step 6: 2-[3-Fluoro-2-(triisopropylsilyloxymethyl) phenyl] ethanol

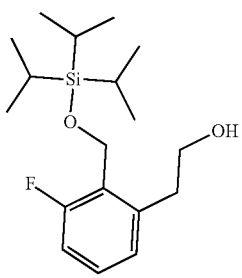 [SMILES: CC(C)[Si](OCc1c(F)cccc1CCO)(C(C)C)C(C)C]

NaBH₄ (700 mg, 18.5 mmol) was added to a solution of 2-[3-fluoro-2-(triisopropylsilyloxymethyl) phenyl] acetaldehyde (3.98 g, 12.3 mmol) in THF (60.0 mL) and MeOH (20.0 mL) at 0° C. The mixture was warmed to room temperature and stirred for 1 h. The mixture was diluted with sat. NH₄Cl (10 mL), water (100 mL), and EtOAc (200 mL). The mixture was stirred at room temperature for 30 min. The aqueous phase was extracted with EtOAc (2×200 mL). The combined organic layers were dried over MgSO₄, filtered, and concentrated under reduced pressure. The residue was purified by silica gel chromatography (24 g, cartridge) with a gradient of EtOAc in hexanes (0-40%) to afford 2-[3-Fluoro-2-(triisopropylsilyloxymethyl) phenyl] ethanol as an oil (2.44 g, 61% over 2 steps). ¹H NMR CDCl₃ 500 MHz, δ 7.30-7.24 (m, 1H), 7.08 (d, J=7.6 Hz, 1H), 6.96 (ddd, J=9.5, 8.3, 1.1 Hz, 1H), 4.89 (d, J=2.1 Hz, 2H), 3.92 (t, J=6.2 Hz, 2H), 3.06 (t, J=6.2 Hz, 2H), 1.27-1.18 (m, 3H), 1.12 (dd, J=7.1, 1.9 Hz, 18H).

Step 7: [2-[2-[(5-Bromo-6-chloro-2-nitro-3-pyridyl) oxy] ethyl]-3-fluoro-phenyl] methoxy-triisopropyl-silane

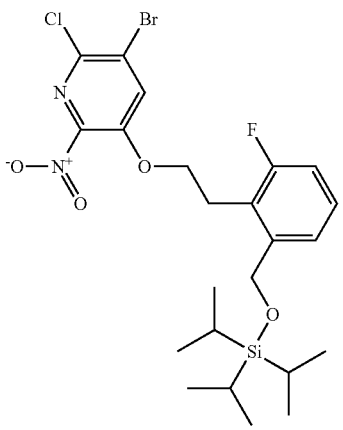

DIAD (1.00 mL, 5.08 mmol) was added drop wise to a solution of 2-[3-fluoro-2-(triisopropylsilyloxymethyl) phenyl] ethanol (1.20 g, 3.68 mmol), 5-bromo-6-chloro-2-nitro-pyridin-3-ol (1.02 g, 4.04 mmol), and triphenylphosphine (1.45 g, 5.51 mmol) in toluene (39.0 mL) at room temperature. The mixture was stirred at room temperature for 48 h. The mixture was concentrated under reduced pressure, and the residue was purified twice by silica gel chromatography with a gradient of MeOH in DCM (0-5%, 80 g, cartridge) and a gradient of ether in hexanes (0-10%, 40 g, cartridge) to afford [2-[2-[(5-Bromo-6-chloro-2-nitro-3-pyridyl) oxy] ethyl]-3-fluoro-phenyl] methoxy-triisopropyl-silane as an oil (480 mg, 23%). ¹H NMR CDCl₃ 500 MHz, δ 7.64 (s, 1H), 7.25-7.19 (m, 1H), 7.06 (d, J=7.4 Hz, 1H), 6.96 (t, J=9.0 Hz, 1H), 4.88 (d, J=2.0 Hz, 2H), 4.42 (t, J=6.6 Hz, 2H), 3.31 (t, J=6.6 Hz, 2H), 1.20-1.12 (m, 3H), 1.09-1.04 (m, 18H).

Step 8: 5-Bromo-6-chloro-3-[2-[2-fluoro-6-(triisopropylsilyloxymethyl) phenyl] ethoxy] pyridin-2-amine

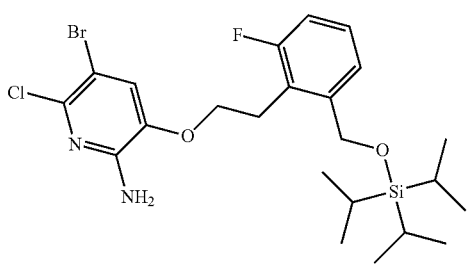 [SMILES: CC(C)[Si](OCc1cccc(F)c1CCOc1cc(Br)c(Cl)nc1N)(C(C)C)C(C)C]

Fe (1.00 g, 17.9 mmol) was added to a solution of [2-[2-[(5-bromo-6-chloro-2-nitro-3-pyridyl) oxy] ethyl]-3-fluoro-phenyl] methoxy-triisopropyl-silane (1.09 g, 1.94 mmol) in HOAc (18.0 mL) at 0° C. The mixture was slowly warmed to room temperature and stirred for 2 h. The mixture was filtered through a pad of Celite. The Celite was washed with EtOAc (3×100 mL), and the filtrate was concentrated under reduced pressure. The residue was purified by silica gel chromatography (12 g, cartridge) with a gradient of EtOAc in Hexanes (0-100%) to afford 5-Bromo-6-chloro-3-[2-[2-fluoro-6-(triisopropylsilyloxymethyl) phenyl] ethoxy] pyridin-2-amine as an oil (978 mg, 95%). $^1$H NMR CDCl$_3$ 500 MHz, δ 7.26-7.20 (m, 1H), 7.04 (d, J=7.2 Hz, 1H), 7.02 (s, 1H), 6.96 (ddd, J=9.5, 8.3, 1.0 Hz, 1H), 4.88 (d, J=2.0 Hz, 2H), 4.72 (s, 2H), 4.25 (t, J=7.0 Hz, 2H), 3.30 (t, J=7.0 Hz, 2H), 1.19-1.11 (m, 3H), 1.09-0.97 (m, 18H). m/z (ES+) [M-OTIPS]$^+$: 359.05; HPLC t$_R$ (A05)=3.07 min.

Step 9: [2-[2-[(2-amino-5-bromo-6-chloro-3-pyridyl) oxy] ethyl]-3-fluoro-phenyl] methanol

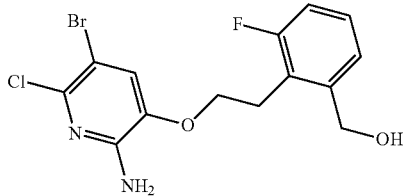 [SMILES: Nc1nc(Cl)c(Br)cc1OCCc1c(F)cccc1CO]

TBAF (1.04 mL, 1.04 mmol) was added to a stirred solution of 5-bromo-6-chloro-3-[2-[2-fluoro-6-(triisopropylsilyloxymethyl) phenyl] ethoxy] pyridin-2-amine (0.158 g, 0.297 mmol) in THF (2.00 mL) at room temperature. The mixture was stirred at room temperature for 2 h and concentrated under reduced pressure. The residue was purified by silica gel chromatography (12 g, cartridge) with MeOH in DCM (0-20%) to afford [2-[2-[(2-amino-5-bromo-6-chloro-3-pyridyl) oxy] ethyl]-3-fluoro-phenyl] methanol (0.105 mg, 94%) as a solid. $^1$H NMR CD$_3$OD 400 MHz, δ 7.31-7.24 (m, 1H), 7.23 (s, 1H), 7.17 (d, J=7.1 Hz, 1H), 6.99 (ddd, J=9.6, 8.2, 1.1 Hz, 1H), 4.76 (d, J=2.0 Hz, 2H), 4.27 (t, J=6.7 Hz, 2H), 3.30-3.26 (m, 2H). m/z (ES+) [M+H]$^+$: 377.0; HPLC t$_R$ (A05)=2.46 min.

Step 10: 5-Bromo-6-chloro-3-[2-[2-(chloromethyl)-6-fluoro-phenyl] ethoxy] pyridin-2-amine; Hydrochloride

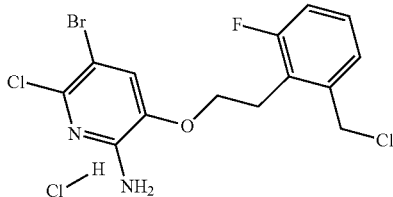

SOCl$_2$ (0.250 mL, 3.43 mmol) was added to a stirred solution of [2-[2-[(2-amino-5-bromo-6-chloro-3-pyridyl) oxy] ethyl]-3-fluoro-phenyl] methanol (0.670 g, 1.78 mmol) in THF (15.0 mL) at room temperature. The mixture was stirred at room temperature for 4 h. The mixture was concentrated under reduced pressure, and the residue was used as such in the next step without further purification (636 mg, 83%). $^1$H NMR CD$_3$OD 400 MHz, δ 7.34-7.28 (m, 2H), 7.18 (d, J=7.6 Hz, 1H), 7.01 (ddd, J=9.5, 8.4, 1.0 Hz, 1H), 4.79 (d, J=1.6 Hz, 1H), 4.31 (t, J=6.8 Hz, 1H), 3.29-3.27 (m, 2H). m/z (ES+) [M+H]$^+$: 395.09; HPLC t$_R$ (A05)=2.66 min.

Step 11: 3-Bromo-2-chloro-11-fluoro-6,7,12,13-tetrahydropyrido[2,3-c] [5,2] benzoxazonine

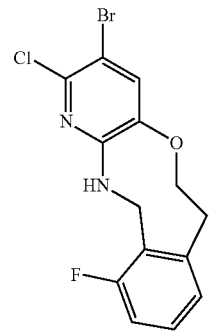 [SMILES: Fc1cccc2c1CNc1nc(Cl)c(Br)cc1OCC2]

Cs$_2$CO$_3$ (1.59 g, 0.153 mmol) and TBAI (0.636 g, 1.72 mmol) were added to a solution of 5-bromo-6-chloro-3-[2-[2-(chloromethyl)-6-fluoro-phenyl] ethoxy] pyridin-2-amine (636 mg, 1.61 mmol) in DMF (400 mL) at room temperature under nitrogen. The mixture was heated to 70° C. for 5 h. The mixture was concentrated under reduced pressure, and the residue was purified by silica gel chromatography (12 g, cartridge) with MeOH in DCM (0-20%) to afford 3-bromo-2-chloro-11-fluoro-6,7,12,13-tetrahydropyrido[2,3-c] [5,2] benzoxazonine as a solid (307 mg, 53%). $^1$H NMR CDCl$_3$ 500 MHz, δ 7.59 (s, 1H), 7.19 (td, J=8.0, 5.9 Hz, 1H), 7.10-6.95 (m, 3H), 4.58 (s, 2H), 4.33 (s, 2H), 3.01 (s, 2H). m/z (ES+) [M+H]$^+$: 359.0; HPLC t$_R$ (B05)=2.61 min.

Step 12: Tert-butyl 3-bromo-2-chloro-11-fluoro-7,12-dihydro-6H-pyrido[2,3-c] [5,2]benzoxazonine-13-carboxylate

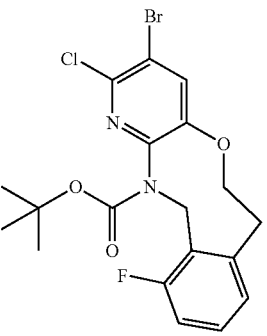 [SMILES: CC(C)(C)OC(=O)N1Cc2c(F)cccc2CCOc2cc(Br)c(Cl)nc21]

Boc$_2$O (3.85 mL, 16.8 mmol) was added to a mixture of tert-butyl 3-bromo-2-chloro-11-fluoro-7,12-dihydro-6H-pyrido[2,3-c][5,2]benzoxazonine-13-carboxylate (300 mg, 0.839 mmol), Et$_3$N (2.92 mL, 21.0 mol), and DMAP (0.0102 g, 0.0839 mmol) in THF (20.0 mL), and the mixture was stirred at room temperature for 12 h. DMAP (200 mg, 1.64 mmol) was added, and the mixture was stirred for 72 h. The mixture was concentrated under reduced pressure, and the residue was purified by silica gel chromatography (40 g, cartridge) with EtOAc and hexane (0-100%) to afford tert-butyl 3-bromo-2-chloro-11-fluoro-7,12-dihydro-6H-pyrido[2,3-c] [5,2]benzoxazonine-13-carboxylate as a solid (293 mg, 76%). $^1$H NMR CDCl$_3$ 500 MHz, δ 7.49 (s, 1H), 7.13

(td, J=7.9, 5.6 Hz, 1H), 6.91-6.78 (m, 2H), 4.99 (s, 2H), 4.37 (s, 2H), 2.92 (s, 2H), 1.40 (s, 9H). m/z (ES+) [M-tBu]+: 403.02; HPLC t_R (A05)=2.70 min.

Step 13: Tert-butyl 3-bromo-11-fluoro-2-hydrazino-7,12-dihydro-6H pyrido[2,3-c] [5,2]benzoxazonine-13-carboxylate

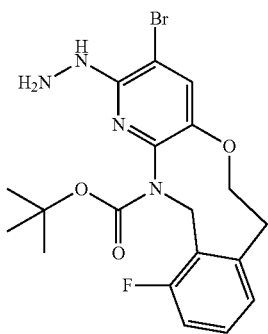 [SMILES: CC(C)(C)OC(=O)N1Cc2c(F)cccc2CCOc2cc(Br)c(NN)nc21]

Hydrazine monohydrate (0.776 mL, 0.0160 mmol) was added to a solution of tert-butyl 3-bromo-2-chloro-11-fluoro-7,12-dihydro-6H-pyrido [2,3-c] [5,2] benzoxazonine-13-carboxylate (293 mg, 0.64 mmol) in EtOH (15.0 mL). The mixture was stirred at 105° C. for 36 h. The mixture was concentrated under reduced pressure, and the residue was purified by silica gel chromatography (24 g, cartridge) with MeOH in DCM (0-15%) to afford tert-butyl 3-bromo-11-fluoro-2-hydrazino-7,12-dihydro-6H pyrido[2,3-c] [5,2] benzoxazonine-13-carboxylate as a solid (232 mg, 80%). m/z (ES+) [M+2H-tBu]+: 399.02; HPLC t_R (A05)=2.39 min.

Step 14: tert-butyl 4-bromo-12-fluoro-8,13-dihydro-[1,2,4]triazolo[4',3':1,6]pyrido[3,2-b]benzo[f][1,4]oxazonine-14 (7H)-carboxylate

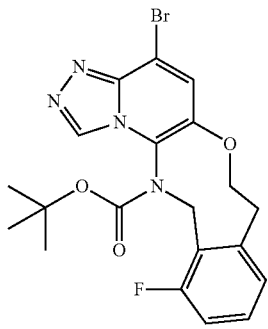 [SMILES: CC(C)(C)OC(=O)N1Cc2c(F)cccc2CCOc2cc(Br)c3nncn3c21]

TFA (1.90 µL, 0.0256 mmol) was added to a solution of tert-butyl 3-bromo-11-fluoro-2-hydrazino-7,12-dihydro-6H-pyrido[2,3-c] [5,2] benzoxazonine-13-carboxylate (232 mg, 0.512 mmol) in triethyl orthoformate (15.0 mL, 90.2 mmol). The mixture was heated to 100° C. for 1 h. The mixture was concentrated under reduced pressure, and the residue was purified by silica gel chromatography (24 g, cartridge) with MeOH in DCM (0-30%) to afford tert-butyl 4-bromo-12-fluoro-8,13-dihydro-[1,2,4]triazolo[4',3':1,6] pyrido[3,2-b]benzo[f][1,4]oxazonine-14 (7H)-carboxylateas a solid (218 mg, 92%). ¹H NMR (500 MHz, CDCl₃) δ 8.72 (s, 1H), 7.27 (s, 1H), 7.10 (dd, J=13.9, 7.8 Hz, 1H), 6.90 (d, J=7.6 Hz, 1H), 6.68 (t, J=8.7 Hz, 1H), 4.91 (d, J=11.6 Hz, 1H), 4.72 (dt, J=11.8, 3.2 Hz, 1H), 4.08 (t, J=11.6 Hz, 1H), 3.47 (t, J=13.2 Hz, 1H), 2.75 (d, J=14.7 Hz, 1H), 1.69 (s, 1H), 1.46-1.30 (m, 9H). m/z (ES+) [M-ᵗBu+2H]+: 409.01; HPLC t_R (A05)=2.37 min.

Step 15: tert-butyl 12-fluoro-4-(2-methylpyridin-3-yl)-8,13-dihydro-[1,2,4]triazolo[4',3':1,6]pyrido[3,2-b]benzo[f][1,4]oxazonine-14 (7H)-carboxylate

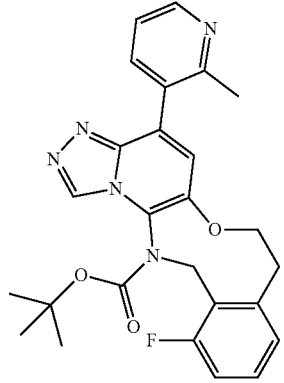 [SMILES: Cc1ncccc1-c1cc2c(n3cnnc13)N(C(=O)OC(C)(C)C)Cc1c(F)cccc1CCO2]

Dioxane (1.70 mL) and water (0.300 mL) were sequentially added to a mixture of tert-butyl 4-bromo-12-fluoro-8,13-dihydro-[1,2,4]triazolo[4',3':1,6]pyrido[3,2-b]benzo[f][1,4]oxazonine-14 (7H)-carboxylate (50.0 mg, 0.108 mmol), 2-methyl-3-(4,4,5,5-tetramethyl-1,3,2-dioxaborolan-2-yl) pyridine (28.4 mg, 0.130 mmol), Pd(dppf)Cl₂ (13.0 mg, 0.0178 mmol), and NaHCO₃ (50.0 mg, 0.595 mmol) under N₂. The mixture was heated to 90° C. for 3 h. The mixture was diluted with DCM (10 mL) and filtered though Celite. The filtrate was concentrated under reduced pressure, and the residue was purified by silica gel chromatography (12 g, cartridge) eluting with MeOH in DCM (0-30%) to afford tert-butyl 12-fluoro-4-(2-methylpyridin-3-yl)-8,13-dihydro-[1,2,4]triazolo[4',3':1,6]pyrido[3,2-b]benzo[f][1,4] oxazonine-14 (7H)-carboxylateas a solid (51.3 mg, >99%). m/z (ES+) [M-ᵗBu+2H]+:420.14, HPLC t_R (A05)=2.29 min.

Step 16: 12-fluoro-4-(2-methylpyridin-3-yl)-7,8,13,14-tetrahydro-[1,2,4]triazolo[4',3':1,6]pyrido[3,2-b]benzo[f][1,4]oxazonine Hydrochloride

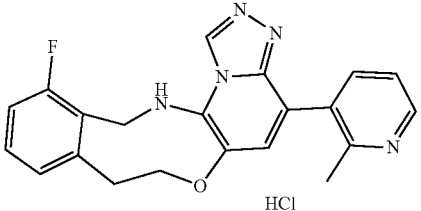 [SMILES: Cc1ncccc1-c1cc2c(n3cnnc13)NCc1c(F)cccc1CCO2 ; Cl]

A solution of tert-butyl tert-butyl 12-fluoro-4-(2-methylpyridin-3-yl)-8,13-dihydro-[1,2,4]triazolo[4',3':1,6]pyrido [3,2-b]benzo[f][1,4]oxazonine-14 (7H)-carboxylate (25.8 mg, 0.0543 mmol) in HFIP (2.50 mL) was heated at 100° C. in an oil bath for 6 h. The mixture was concentrated under reduced pressure, and the residue was purified by preparative HPLC (Gemini C18 30×100 mm AmBicarb/ACN 30-50%) to afford the free form of 12-fluoro-4-(2-methylpyridin-3-yl)-7,8,13,14-tetrahydro-[1,2,4]triazolo[4',3':1,6]pyrido[3,2-b]benzo[f][1,4]oxazonine hydrochloride as a solid (16.2 mg, 80%). $^1$H NMR (500 MHz, MeOD) δ 9.31 (s, 1H), 8.44 (dd, J=5.0, 1.7 Hz, 1H), 7.73 (dd, J=7.7, 1.7 Hz, 1H), 7.33 (dd, J=7.9, 4.8 Hz, 1H), 7.29 (s, 1H), 7.17 (td, J=7.9, 5.9 Hz, 1H), 7.00 (d, J=7.7 Hz, 1H), 6.95-6.90 (m, 1H), 5.01 (s, 2H), 4.41 (s, 2H), 3.13 (s, 2H), 2.32 (s, 3H). m/z (ES+)[M+H]$^+$: 376.1, HPLC $t_R$ (B05)=1.21 min.

HCl (0.0535 mmol, 13.4 μL, 4.0 M in 1, 4-dioxane) was added drop wise to a solution of 12-fluoro-4-(2-methylpyridin-3-yl)-7,8,13,14-tetrahydro-[1,2,4]triazolo[4',3':1,6]pyrido[3,2-b]benzo[f][1,4]oxazonine (16.2 mg, 0.0432 mmol) in DCM/MeOH (3.00 mL/0.300 mL). The mixture was stirred at room temperature for 1 h. The mixture was concentrated under reduced pressure to afford 12-fluoro-4-(2-methylpyridin-3-yl)-7,8,13,14-tetrahydro-[1,2,4]triazolo[4',3':1,6]pyrido[3,2-b]benzo[f][1,4]oxazonine hydrochloride as a solid (23.3 mg, 74%). $^1$H NMR MeOD 500 MHz, δ 9.34 (s, 1H), 8.53 (dd, J=5.0, 1.2 Hz, 1H), 7.96 (dd, J=7.8, 1.2 Hz, 1H), 7.51 (dd, J=7.7, 5.3 Hz, 1H), 7.39 (s, 1H), 7.18 (td, J=7.9, 5.9 Hz, 1H), 7.01 (d, J=7.7 Hz, 1H), 6.98-6.90 (m, 1H), 5.03 (s, 2H), 4.42 (s, 2H), 3.14 (s, 2H), 2.40 (s, 3H). ES+[M+H]$^+$: 376.1, HPLC $t_R$ (B05)=1.21 min.

Example 23: 1-(4-(12-fluoro-7,8,13,14-tetrahydro-[1,2,4]triazolo[4',3':1,6]pyrido[3,2-b]benzo[f][1,4]oxazonin-4-yl)piperidin-1-yl)ethan-1-one Bismesylate Step 1: tert-butyl 4-(1-acetyl-1,2,3,6-tetrahydropyridin-4-yl)-12-fluoro-8,13-dihydro-[1,2,4]triazolo[4',3':1,6]pyrido[3,2-b]benzo[f][1,4]oxazonine-14 (7H)-carboxylate 1, 4-Dioxane (1.80 mL) and water (0.350 mL) were sequentially added to a mixture of tert-butyl 4-bromo-12-fluoro-8,13-dihydro-[1,2,4]triazolo[4',3':1,6]pyrido[3,2-b]benzo[f][1,4]oxazonine-14 (7H)-carboxylate (from Example 22; 50.0 mg, 0.108 mmol), 1-[4-(4,4,5,5-tetramethyl-1,3,2-dioxaborolan-2-yl)-3,6-dihydro-2H-pyridin-1-yl] ethanone (28.4 mg, 0.113 mmol), Pd(dppf)Cl$_2$ (11.8 mg, 0.0162 mmol), and NaHCO$_3$ (30.0 mg, 0.357 mmol) under N$_2$. The mixture was stirred at 90° C. for 2.5 h. The mixture was filtered though a short silica pad, washing with DCM (3×5 mL). The filtrate was concentrated under reduced pressure, and the residue was purified by silica gel chromatography (12.0 g cartridge) eluting with MeOH in DCM (0-30%) to provide tert-butyl 4-(1-acetyl-1,2,3,6-tetrahydropyridin-4-yl)-12-fluoro-8,13-dihydro-[1,2,4]triazolo[4',3':1,6]pyrido[3,2-b]benzo[f][1,4]oxazonine-14 (7H)-carboxylateas a solid (66.1 mg, 97%, 80% purity). m/z (ES+) [M−$^t$Bu+2H]$^+$: 552.2; HPLC $t_R$ (B05)=2.28 min.

Step 2: tert-butyl 4-(1-acetylpiperidin-4-yl)-12-fluoro-8,13-dihydro-[1,2,4]triazolo[4',3':1,6]pyrido[3,2-b]benzo[f][1,4]oxazonine-14 (7H)-carboxylate

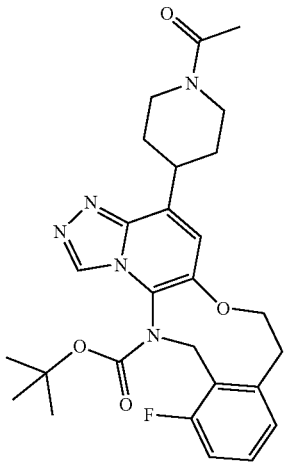

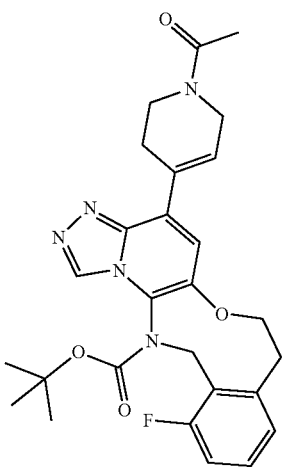 [SMILES: CC(=O)N1CC=C(c2cc3c(n4cnnc24)N(C(=O)OC(C)(C)C)Cc2c(F)cccc2CCO3)CC1]

A solution of tert-butyl 4-(1-acetyl-1,2,3,6-tetrahydropyridin-4-yl)-12-fluoro-8,13-dihydro-[1,2,4]triazolo[4',3':1,6]pyrido[3,2-b]benzo[f][1,4]oxazonine-14 (7H)-carboxylate (54.8 mg, 0.108 mmol) in MeOH (2.00 mL) was added to a flask charged with Pd/C (100 mg, 0.094 mmol) under nitrogen atmosphere at room temperature. The flask was evacuated and purged with H$_2$ 3 times. The mixture was stirred at 23° C. for 62 h and filtered through Celite, washing with MeOH (3×10.0 mL). The filtrated was concentrated under reduced pressure to provide tert-butyl 4-(1-acetylpiperidin-4-yl)-12-fluoro-8,13-dihydro-[1,2,4]triazolo[4',3':1,6]pyrido[3,2-b]benzo[f][1,4]oxazonine-14 (7H)-carboxylate as a solid (25.8 mg, 47%), which was used as such in the next step without further purification. m/z (ES+) [M+H]$^+$: 510.3; HPLC $t_R$ (A05)=2.26 min.

Step 3: 1-(4-(12-fluoro-7,8,13,14-tetrahydro-[1,2,4]triazolo[4',3':1,6]pyrido[3,2-b]benzo[f][1,4]oxazonin-4-yl)piperidin-1-yl)ethan-1-one

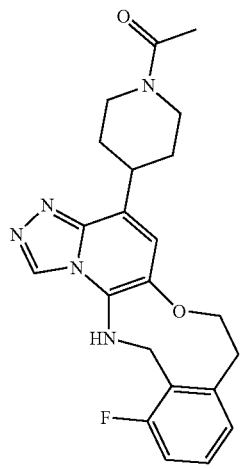 [SMILES: CC(=O)N1CCC(c2cc3c(n4cnnc24)NCc2c(F)cccc2CCO3)CC1]

A solution of tert-butyl 4-(1-acetylpiperidin-4-yl)-12-fluoro-8,13-dihydro-[1,2,4]triazolo[4',3':1,6]pyrido[3,2-b]benzo[f][1,4]oxazonine-14 (7H)-carboxylate (25.8 mg, 0.0506 mmol) in HFIP (2.50 mL) was heated at 100° C. for 3 h. The mixture was concentrated under reduced pressure, and the residue was purified by preparative HPLC (BEH C18 30×150 mm AmBicarb/ACN 25-45%) to 1-(4-(12-fluoro-7,8,13,14-tetrahydro-[1,2,4]triazolo[4',3':1,6]pyrido[3,2-b]benzo[f][1,4]oxazonin-4-yl)piperidin-1-yl)ethan-1-one as a solid (11.1 mg, 53%). $^1$H NMR MeOD 500 MHz, δ 9.23 (s, 1H), 7.13 (td, J=8.0, 5.9 Hz, 1H), 7.10 (s, 1H), 6.96 (d, J=7.2 Hz, 1H), 6.87 (ddd, J=9.9, 8.2, 0.9 Hz, 1H), 4.91 (s, 2H), 4.67 (ddt, J=13.2, 4.4, 2.2 Hz, 1H), 4.42-4.29 (m, 2H), 4.02 (ddt, J=13.5, 4.1, 1.9 Hz, 1H), 3.30-3.22 (m, 2H), 3.08 (s, 2H), 2.75 (td, J=13.0, 2.7 Hz, 1H), 2.13 (s, 3H), 2.05-1.98 (m, 1H), 1.97-1.91 (m, 1H), 1.75-1.57 (m, 2H). m/z (ES+) [M+H]$^+$:410.2; HPLC $t_R$ (B05)=1.12 min.

Step 5: 1-(4-(12-fluoro-7,8,13,14-tetrahydro-[1,2,4]triazolo[4',3':1,6]pyrido[3,2-b]benzo[f][1,4]oxazonin-4-yl)piperidin-1-yl)ethan-1-one Bismesylate

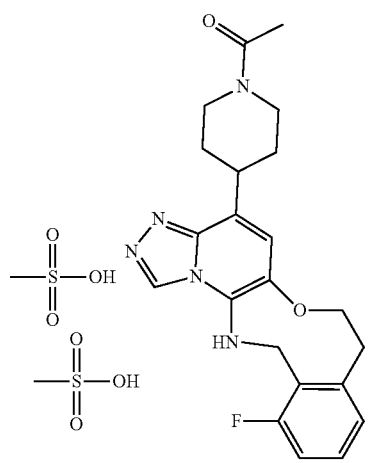

MsOH (3.52 μL, 0.0542 mmol) was added to a solution of 1-(4-(12-fluoro-7,8,13,14-tetrahydro-[1,2,4]triazolo[4',3':1,6]pyrido[3,2-b]benzo[f] [1,4]oxazonin-4-yl)piperidin-1-yl)ethan-1-one (11.1 mg, 0.0271 mmol) in MeCN (1.50 mL) and water (0.500 mL) at rt. The mixture was stirred for 14 h and concentrated under reduced pressure to provide the title compound as a solid (13.5 mg, 83%). $^1$H NMR MeOD 500 MHz, δ 9.42 (s, 1H), 7.77 (s, 1H), 7.19 (td, J=7.9, 5.9 Hz, 1H), 7.01 (d, J=7.6 Hz, 1H), 6.97-6.92 (m, 1H), 5.04 (s, 2H), 4.71 (ddt, J=8.1, 4.2, 2.1 Hz, 1H), 4.45 (s, 2H), 4.12-4.04 (m, 1H), 3.25 (td, J=13.4, 2.8 Hz, 1H), 3.19-3.05 (m, 3H), 2.76-2.71 (m, 1H), 2.71 (s, 6H), 2.14 (s, 3H), 1.97-1.86 (m, 2H), 1.76 (ddd, J=25.1, 12.6, 4.0 Hz, 1H), 1.63 (qd, J=12.4, 4.0 Hz, 1H). m/z (ES+) [M+H]$^+$: 410.2; HPLC $t_R$ (B05)=1.13 min.

Example 24: 12-fluoro-4-(2-methylpyridin-3-yl)-6,8,13,14-tetrahydro-[1,2,4]triazolo[4',3':1,6]pyrido[3,2-c]benzo[g][1,5]oxazonine Hydrochloride Salt

Step 1: 5-bromo-6-chloro-3-iodo-pyridin-2-amine

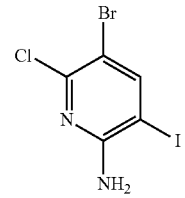

Acetic acid (100 mL) was added to a mixture of 5-bromo-6-chloro-pyridin-2-amine (10.4 g, 50.0 mmol) and N-iodosuccinimide (12.4 g, 55.0 mmol). TFA (1.00 mL) was added, and the mixture was stirred at 23° C. for 3 h. The mixture was poured into crushed ice, and the aq. phase was diluted to pH 10 with ammonium hydroxide (150 mL). The solid was filtered, washed with water and hexane, and dried under high vacuum to provide 5-bromo-6-chloro-3-iodo-pyridin-2-amine as a solid (16.4 g, 98%). $^1$H NMR CDCl$_3$ 400 MHz, δ 7.99 (d, J=0.8 Hz, 1H), 5.06 (br, 2H). m/z (ES+), [M+H]$^+$: 332.9. HPLC (A05) $t_R$=2.46 min.

Step 2: 5-bromo-6-chloro-3-vinyl-pyridin-2-amine

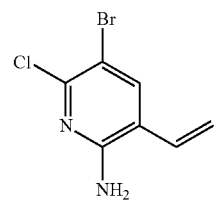

DME (60.0 mL) and water (20.0 mL) were added to a mixture of 5-bromo-6-chloro-3-iodo-pyridin-2-amine (6.67 g, 20.0 mmol), potassium vinyltrifluoroborate (2.68 g, 20.0 mmol), K$_2$CO$_3$ (2.76 g, 20.0 mmol), and Pd(dppf)Cl$_2$-DCM (1.63 g, 2.00 mmol). The mixture was heated to 85° C. for 18 h. After cooling down to 23° C., EtOAc (100 mL) was added, and the mixture was filtered through Celite. The filtrate was washed with brine (100 mL), and the organic phase was dried (MgSO$_4$), filtered, and concentrated under reduced pressure. The product was purified by silica gel chromatography (80 g cartridge) eluting with hexanes and EtOAc (0-20%), followed by trituration from hexanes (50.0 mL) to provide 5-bromo-6-chloro-3-vinyl-pyridin-2-amine as a solid (2.51 g; 54%). ¹H NMR CDCl₃ 500 MHz, δ 7.68 (s, 1H), 6.52 (ddd, J=17.3, 11.1, 0.6 Hz, 1H), 5.70 (dd, J=17.4, 0.8 Hz, 1H), 5.48 (dd, J=11.1, 0.8 Hz, 1H), 4.70 (br, 2H). m/z (ES+), [M+H]⁺: 232.9. HPLC (A05) $t_R$=2.38 min.

Step 3: 5-bromo-6-chloro-N,N-bis[(4-methoxyphenyl)methyl]-3-vinyl-pyridin-2-amine

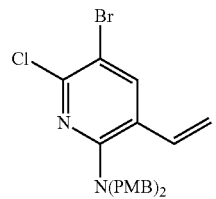

5-bromo-6-chloro-3-vinyl-pyridin-2-amine (0.500 g, 2.14 mmol) was dissolved in DMF (10.0 mL), and the mixture was cooled to 0° C. 60 wt. % NaH in mineral oil (0.343 g, 8.57 mmol) was added portion-wise, and the mixture was stirred at 0° C. for 10 min. 4-Methoxybenzyl chloride (0.639 mL, 4.71 mmol) was added, and the mixture was stirred at 0° C. for 1 h. Water (10.0 mL) was added drop-wise, and the mixture was stirred at 0° C. for 5 min. The aqueous phase was extracted with EtOAc (3×20.0 mL). The combined organic phases were washed with brine (20.0 mL), dried (MgSO₄), filtered, and concentrated under reduced pressure. The product was purified by silica gel chromatography (40 g cartridge) eluting with hexanes and EtOAc (0-10%) to provide 5-bromo-6-chloro-N,N-bis[(4-methoxyphenyl)methyl]-3-vinyl-pyridin-2-amine as an oil (0.859 g; 85%). ¹H NMR CDCl₃ 400 MHz, δ 7.78 (s, 1H), 7.16-7.08 (m, 4H), 6.87-6.81 (m, 4H), 6.77 (dd, J=17.5, 10.9 Hz, 1H), 5.64 (dd, J=17.5, 0.8 Hz, 1H), 5.35-5.28 (m, 1H), 4.35 (s, 4H), 3.80 (s, 6H). m/z (ES+), [M+H]⁺: 473.1. HPLC (A05) $t_R$=2.98 min.

Step 4: 2-[bis[(4-methoxyphenyl)methyl]amino]-5-bromo-6-chloro-pyridine-3-carbaldehyde

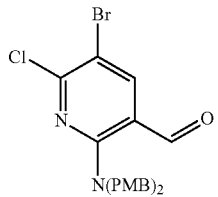

1,4-Dioxane (21.0 mL) and water (7.00 mL) were added to 5-bromo-6-chloro-N,N-bis[(4-methoxyphenyl)methyl]-3-vinyl-pyridin-2-amine (0.845 g, 1.78 mmol). After cooling down to 0° C., 2,6-lutidine (0.415 mL, 3.57 mmol), 4 wt. % OsO₄ in water (0.568 mL, 0.0892 mmol) and NaIO₄ (0.763 g, 3.57 mmol) were added. The mixture was warmed to 23° C. and stirred for 18 h. Water (20.0 mL) was added, and the aqueous phase was extracted with EtOAc (3×25.0 mL). The combined organic phases were washed with brine (25.0 mL), dried (MgSO₄), filtered, and concentrated under reduced pressure. The product was purified by silica gel chromatography (40 g cartridge) eluting with hexanes and EtOAc (0-15%) to provide 2-[bis[(4-methoxyphenyl)methyl]amino]-5-bromo-6-chloro-pyridine-3-carbaldehyde as an oil (0.675 g; 80%). ¹H NMR CDCl₃ 500 MHz, δ 9.80 (s, 1H), 8.09 (s, 1H), 7.13-7.06 (m, 4H), 6.89-6.79 (m, 4H), 4.62 (s, 4H), 3.80 (s, 6H). m/z (ES+), [M+H]⁺: 475.1. HPLC (A05) $t_R$=2.84 min.

Step 5: [2-[bis[(4-methoxyphenyl)methyl]amino]-5-bromo-6-chloro-3-pyridyl] methanol

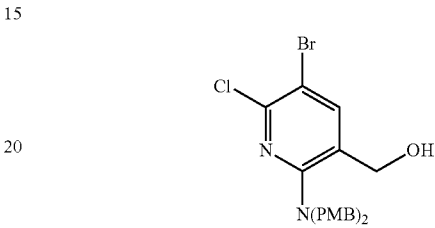

2-[Bis[(4-methoxyphenyl)methyl]amino]-5-bromo-6-chloro-pyridine-3-carbaldehyde (0.670 g, 1.41 mmol) was dissolved in a mixture of THF (8.00 mL) and MeOH (2.00 mL). NaBH₄ (6.51 mg, 0.172 mmol) was added portion-wise, and the mixture was stirred at 23° C. for 30 min. Sat. NH₄Cl (20.0 mL) was added drop-wise, and the aqueous phase was extracted with EtOAc (3×25.0 mL). The combined organic phases were washed with brine (25.0 mL), dried (MgSO₄), filtered and concentrated under reduced pressure. The product was purified by silica gel chromatography (25 g cartridge) eluting with hexanes and EtOAc (0-40%) to provide [2-[bis[(4-methoxyphenyl)methyl]amino]-5-bromo-6-chloro-3-pyridyl] as an oil (0.558 g; 83%). ¹H NMR CDCl₃ 500 MHz, δ 7.80 (s, 1H), 7.18-7.11 (m, 4H), 6.85-6.79 (m, 4H), 4.57 (d, J=5.4 Hz, 2H), 4.26 (s, 4H), 3.79 (s, 6H), 2.50 (t, J=5.6 Hz, 1H). m/z (ES+), [M+H]⁺: 477.3. HPLC (A05) $t_R$=2.72 min.

Step 6: methyl 2-(bromomethyl)-6-fluoro-benzoate

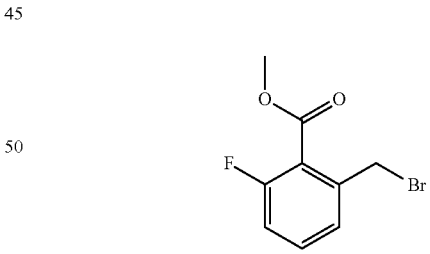

Benzoyl peroxide (75.0%, 1.15 g, 3.57 mmol) was added to a solution of methyl 2-fluoro-6-methyl-benzoate (6.00 g, 35.7 mmol) and NBS (6.99 g, 39.2 mmol) in CCl₄ (200 mL). The mixture was degassed by bubbling nitrogen through the solvent for 15 min. The mixture was heated to 80° C. for 12 h. Brine (100 mL) was added, and the aq. phase was extracted with DCM (3×150 mL). The combined organic layers were dried (MgSO₄), filtered, and concentrated under reduced pressure. The product was purified by silica gel chromatography (120 g cartridge) eluting with hexanes and EtOAc (0-10%) to provide methyl 2-(bromomethyl)-6-fluoro-benzoate as an oil (5.70 g, 65%). ¹H NMR CDCl₃ 500

MHz, δ 7.44-7.33 (m, 1H), 7.22 (dd, J=7.7, 0.4 Hz, 1H), 7.08 (ddd, J=9.5, 8.4, 1.0 Hz, 1H), 4.65 (s, 2H), 3.98 (s, 3H). m/z (ES+), No ionization. HPLC (A05) $t_R$=2.40 min.

Step 7: methyl 2-[[2-[bis[(4-methoxyphenyl)methyl] amino]-S-bromo-6-chloro-3-pyridyl]methoxymethyl]-6-fluoro-benzoate

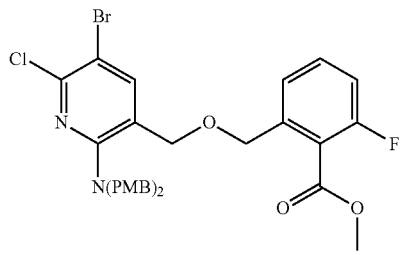

[2-[Bis[(4-methoxyphenyl)methyl]amino]-S-bromo-6-chloro-3-pyridyl]methanol (2.00 g, 4.19 mmol) was dissolved in THF (20.0 mL), and the mixture was cooled to 0° C. 60 wt. % NaH in mineral oil (335 mg, 8.37 mmol) was added portion-wise, and the mixture was warmed to 23° C. After stirring for 10 min, a solution of methyl 2-(bromomethyl)-6-fluoro-benzoate (1.55 g, 6.28 mmol) in THF (10.0 mL) was added drop-wise. The mixture was refluxed for 12 h. After cooling to 0° C., sat. NH$_4$Cl (10.0 mL) was added drop-wise, and the mixture was stirred at 0° C. for 5 min. The aqueous phase was extracted with EtOAc (2×100 mL), and the combined organic phases were washed with brine (50.0 mL), dried (MgSO$_4$), filtered, and concentrated under reduced pressure. The residue was purified by silica gel chromatography (80 g cartridge) eluting with hexanes and EtOAc (0-25%) to provide methyl 2-[[2-[bis[(4-methoxyphenyl)methyl]amino]-S-bromo-6-chloro-3-pyridyl] methoxymethyl]-6-fluoro-benzoateas an oil (2.10 g; 78%). $^1$H NMR CDCl$_3$ 400 MHz, δ 7.79 (s, 1H), 7.41-7.31 (m, 1H), 7.21-7.00 (m, 6H), 6.89-6.74 (m, 4H), 4.60 (s, 2H), 4.39 (s, 2H), 4.30 (s, 4H), 3.82 (s, 3H), 3.79 (s, 6H). m/z (ES+), [M+H]$^+$: 643.1. HPLC (A05) $t_R$=2.96 min.

Step 8: [2-[[2-[bis[(4-methoxyphenyl)methyl] amino]-S-bromo-6-chloro-3-pyridyl]methoxymethyl]-6-fluoro-phenyl]methanol

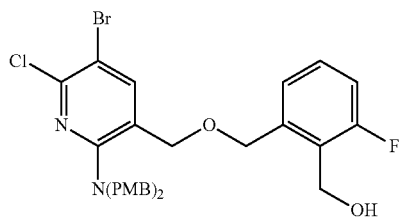

Methyl 2-[[2-[bis[(4-methoxyphenyl)methyl]amino]-S-bromo-6-chloro-3-pyridyl]methoxy methyl]-6-fluoro-benzoate (2.10 g, 3.26 mmol) was dissolved in THF (30.0 mL), and the mixture was cooled to -78° C. 1.0 M DIBAL-H in PhMe (13.0 mL, 13.0 mmol) was added drop-wise. The mixture was warmed to 0° C. and stirred for 1 h. Rochelle's salt was added (50.0 mL). The mixture was warmed to 23° C. and stirred until the solution became clear. The aq. phase was extracted with EtOAc (3×100 mL), and the combined organic phases were washed with brine (50.0 mL), dried (MgSO$_4$), filtered, and concentrated under reduced pressure. The residue was purified by silica gel chromatography (80 g cartridge) eluting with hexanes and EtOAc (0-40%) to provide [2-[[2-[bis[(4-methoxyphenyl)methyl]amino]-S-bromo-6-chloro-3-pyridyl] methoxymethyl]-6-fluoro-phenyl]methanol as an oil (1.90 g; 95%). $^1$H NMR CDCl$_3$ 400 MHz, δ 7.78 (s, 1H), 7.28-7.21 (m, 1H), 7.15-7.09 (m, 4H), 7.07 (t, J=8.8 Hz, 1H), 6.99 (d, J=7.5 Hz, 1H), 6.86-6.78 (m, 4H), 4.72 (dd, J=6.5, 1.5 Hz, 2H), 4.55 (s, 2H), 4.45 (s, 2H), 4.32 (s, 4H), 3.79 (s, 6H), 2.35 (t, J=6.5 Hz, 1H). m/z (ES+), [M+H]$^+$: 617.0. HPLC (A05) $t_R$=2.84 min.

Step 9: [2-[(2-amino-S-bromo-6-chloro-3-pyridyl) methoxymethyl]-6-fluoro-phenyl] methanol

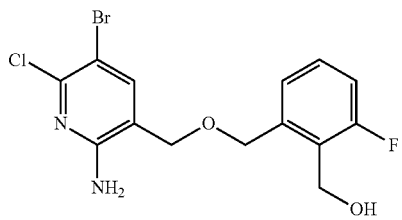 [SMILES: Nc1nc(Cl)c(Br)cc1COCc1cccc(F)c1CO]

[2-[[2-[Bis[(4-methoxyphenyl)methyl]amino]-S-bromo-6-chloro-3-pyridyl]methoxymethyl]-6-fluoro-phenyl] methanol (1.87 g, 3.04 mmol) was dissolved in DCM (15.0 mL). TFA (4.00 mL, 53.8 mmol) was added drop-wise, and the mixture was stirred at 23° C. for 3 h. The mixture was concentrated under reduced pressure. 2.0 N NaOH (50.0 ml) was added to the residue, and the aq. phase was extracted with EtOAc (3×100 mL). The combined organic phases were washed with brine (100 mL), dried (MgSO$_4$), filtered, and concentrated under reduced pressure. The product was purified by silica gel chromatography (80 g cartridge) eluting with EtOAc and hexane (0-50%) to provide [2-[(2-amino-S-bromo-6-chloro-3-pyridyl)methoxymethyl]-6-fluoro-phenyl] methanol as a solid (1.00 g; 87%). $^1$H NMR CDCl$_3$ 400 MHz, δ 7.50 (s, 1H), 7.34-7.27 (m, 1H), 7.15-7.07 (m, 2H), 5.09 (s, 2H), 4.78 (dd, J=6.4, 1.7 Hz, 2H), 4.63 (s, 2H), 4.47 (s, 2H), 2.26 (t, J=6.5 Hz, 1H). m/z (ES+), [M+H]$^+$: 377.0. HPLC (A05) $t_R$=2.39 min.

Step 10: 3-bromo-2-chloro-11-fluoro-5,7,12,13-tetrahydrobenzo[g]pyrido[3,2-c][1,5]oxazonine

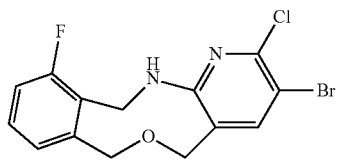 [SMILES: Fc1cccc2c1CNc1nc(Cl)c(Br)cc1COC2]

[2-[(2-Amino-S-bromo-6-chloro-3-pyridyl)methoxymethyl]-6-fluoro-phenyl]methanol (984 mg, 2.62 mmol) was dissolved in THF (15.0 mL). SOCl$_2$ (1.60 mL, 21.9 mmol) was added, and the mixture was heated to 50° C. for 40 min (gas evolution). The mixture was concentrated under reduced pressure, and the residue was repeatedly diluted with DCM and concentrated to remove any trace of SOCl$_2$.

The intermediate (m/z (ES+), [M−C]+: 394.9. HPLC (A05) $t_R$=2.60 m) was dried under high vacuum for 30 m. DMF (15.0 mL) was added to the solid followed by TBAI (968 mg, 2.62 mmol) and Cs$_2$CO$_3$ (2.56 g, 7.86 mmol). The mixture was stirred at 100° C. for 50 min. The mixture was concentrated under reduced pressure. Water (50.0 mL) was added, and the aq. phase was extracted with EtOAc (3×100 mL). The combined organic phases were washed with brine (50.0 mL), dried (MgSO$_4$), filtered, and concentrated under reduced pressure. The product was purified by silica gel chromatography (24 g cartridge) eluting with hexane and EtOAc (0-25%) to provide 3-bromo-2-chloro-11-fluoro-5,7,12,13-tetrahydrobenzo[g]pyrido[3,2-c][1,5]oxazonineas a solid (753 mg; 64%). $^1$H NMR CDCl$_3$ 500 MHz, δ 7.59 (s, 1H), 7.30-7.24 (m, 1H), 7.05 (t, J=8.8 Hz, 1H), 6.96 (d, J=7.6 Hz, 1H), 5.43 (t, J=7.2 Hz, 1H), 4.97 (s, 2H), 4.69 (dd, J=7.5, 2.0 Hz, 2H), 4.35 (s, 2H). m/z (ES+), [M+H]+: 357.0. HPLC (A05) $t_R$=2.63 min.

Step 11: tert-butyl 3-bromo-2-chloro-11-fluoro-7,12-dihydrobenzo[g]pyrido[3,2-c][1,5]oxazonine-13 (5H)-carboxylate

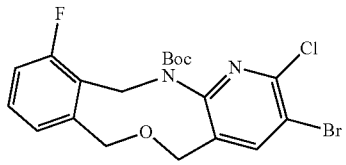 [SMILES: Fc1cccc2c1CNc1nc(Cl)c(Br)cc1COC2]

Di-tert-butyl dicarbonate (0.443 mL, 1.93 mmol) was added to a solution of 3-bromo-2-chloro-11-fluoro-5,7,12,13-tetrahydrobenzo[g]pyrido[3,2-c][1,5]oxazonine (115 mg, 0.322 mmol), NEt$_3$ (0.134 mL, 0.965 mmol), and DMAP (9.82 mg, 0.0804 mmol) in THF (2.00 mL). The mixture was heated to 50° C. for 15 h. Water (5.00 mL) was added, and the aq. phase was extracted with EtOAc (3×20.0 mL). The combined organic phases were washed with brine (20.0 mL), dried (MgSO$_4$), filtered, and concentrated under reduced pressure. The product was purified by silica gel chromatography (4 g cartridge) eluting with hexane and EtOAc (0-45%) to provide tert-butyl 3-bromo-2-chloro-11-fluoro-7,12-dihydrobenzo[g]pyrido[3,2-c][1,5]oxazonine-13 (5H)-carboxylate as a solid (91.0 mg; 62%). Complex NMR (rotamers). m/z (ES+), [M+H-tBu]+: 402.9. HPLC (A05) $t_R$=2.71 min.

Step 12: tert-butyl 3-bromo-11-fluoro-2-hydrazineyl-7,12-dihydrobenzo[g]pyrido[3,2-c][1,5]oxazonine-13 (5H)-carboxylate

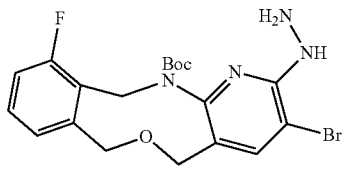 [SMILES: NNc1nc2c(cc1Br)COCc1cccc(F)c1CN2]

A solution of tert-butyl 3-bromo-2-chloro-11-fluoro-7,12-dihydrobenzo[g]pyrido[3,2-c][1,5]oxazonine-13 (5H)-carboxylate (91.0 mg, 0.199 mmol) and hydrazine monohydrate (0.500 mL, 10.3 mmol) in EtOH (2.00 mL) was heated at 100° C. for 18 h. After cooling to 23° C., the mixture was concentrated under reduced pressure. The product was purified by silica gel chromatography (4 g cartridge) eluting with DCM and MeOH (0-10%) to provide tert-butyl 3-bromo-11-fluoro-2-hydrazineyl-7,12-dihydrobenzo[g]pyrido[3,2-c][1,5]oxazonine-13 (5H)-carboxylateas a solid (82.0 mg; 91%). Complex NMR (rotamers). m/z (ES+), [M+H-tBu]+: 397.0. HPLC (A05) $t_R$=2.40 min.

Step 13: tert-butyl 4-bromo-12-fluoro-8,13-dihydro-[1,2,4]triazolo[4',3':1,6]pyrido[3,2-c]benzo[g][1,5]oxazonine-14 (6H)-carboxylate

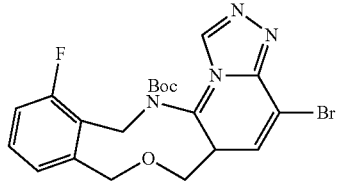

TFA (0.01 mL) was added to a solution of tert-butyl 3-bromo-11-fluoro-2-hydrazineyl-7,12-dihydrobenzo[g]pyrido[3,2-c][1,5]oxazonine-13 (5H)-carboxylate (82.0 mg, 0.181 mmol) in triethyl orthoformate (5.42 mL, 32.6 mmol). The mixture was heated to 100° C. for 1.5 h. After cooling to 23° C., the mixture was concentrated under reduced pressure. The product was purified by silica gel chromatography (4 g cartridge) eluting with DCM and MeOH (0-10%) to provide tert-butyl 4-bromo-12-fluoro-8,13-dihydro-[1,2,4]triazolo[4',3':1,6]pyrido[3,2-c]benzo[g][1,5]oxazonine-14 (6H)-carboxylate as a solid (66.0 mg; 78%). Complex NMR (rotamers). m/z (ES+), [M+H-tBu]+: 465.0. HPLC (A05) $t_R$=2.32 min.

Step 14: tert-butyl 12-fluoro-4-(2-methylpyridin-3-yl)-8,13-dihydro-[1,2,4]triazolo[4',3':1,6]pyrido[3,2-c]benzo[g][1,5]oxazonine-14 (6H)-carboxylate

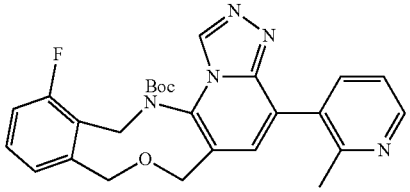 [SMILES: Cc1ncccc1-c1cc2c(n3cnnc13)NCc1c(F)cccc1COC2]

1,4-Dioxane (1.50 mL) and water (0.300 mL) were added to a mixture of tert-butyl 4-bromo-12-fluoro-8,13-dihydro-[1,2,4]triazolo[4',3':1,6]pyrido[3,2-c]benzo[g][1,5]oxazonine-14 (6H)-carboxylate (66.0 mg, 0.142 mmol), Pd(dppf)Cl$_2$ (10.4 mg, 0.0142 mmol), and NaHCO$_3$ (35.9 mg, 0.427 mmol) under nitrogen. The mixture was heated to 90° C. for 2 h. After cooling to 23° C., the mixture was filtered though a silica plug washing with EtOAc. The filtrate was concentrated under reduced pressure. The product was purified by silica gel chromatography (24 g cartridge) eluting with DCM and MeOH (0-10%) to provide tert-butyl 12-fluoro-4-(2-methylpyridin-3-yl)-8,13-dihydro-[1,2,4]triazolo[4',3':1,6]pyrido[3,2-c]benzo[g][1,5]oxazonine-14 (6H)-carboxylate as a solid (60.0 mg; 89%). Complex NMR (rotamers). m/z (ES+), [M+H]+: 476.2. HPLC (A05) $t_R$=2.24 min.

Step 15: tert-butyl 12-fluoro-4-(2-methylpyridin-3-yl)-8,13-dihydro-[1,2,4]triazolo[4',3':1,6]pyrido[3,2-c]benzo[g][1,5]oxazonine-14 (6H)-carboxylate Hydrochloride Salt

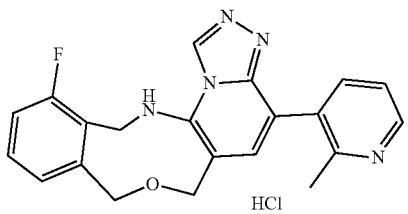 [SMILES: Cc1ncccc1-c1cc2c(n3cnnc13)NCc1c(F)cccc1COC2 ; Cl]

A solution of tert-butyl 12-fluoro-4-(2-methylpyridin-3-yl)-8,13-dihydro-[1,2,4]triazolo[4',3':1,6]pyrido[3,2-c]benzo[g][1,5]oxazonine-14 (6H)-carboxylate (53.0 mg, 0.111 mmol) in HFIP (1.50 mL) was heated to 100° C. for 15 h. After cooling to 23° C., the mixture was concentrated under reduced pressure. The product was purified by silica gel chromatography (24 g cartridge) eluting with DCM and MeOH (0-15%) to provide the free base of the title compound as a solid (28.0 mg; 67%). $^1$H NMR (500 MHz, MeOD) δ 9.50 (s, 1H), 8.48 (dd, J=5.0, 1.7 Hz, 1H), 7.76 (dd, J=7.7, 1.7 Hz, 1H), 7.36 (dd, J=7.7, 5.0 Hz, 1H), 7.33-7.28 (m, 2H), 7.16 (d, J=7.5 Hz, 1H), 7.05 (t, J=9.1 Hz, 1H), 4.90 (d, J=1.4 Hz, 2H), 4.84 (s, 2H), 4.63 (s, 2H), 2.33 (s, 3H). The compound was converted to the hydrochloride salt by adding 4.0 N HCl in dioxane (18.6 µL, 0.0746 mmol) to a solution of 5-fluoro-15-(2-methyl-3-pyridyl)-11-oxa-2,17,18,20-tetrazatetracyclo[11.7.0.04,9.016,20]icosa-1(13),4(9),5,7,14,16,18-heptaene (28.0 mg, 0.0746 mmol) in DCM (5.00 mL) and MeOH (0.500 mL). The mixture was stirred at 23° C. for 1 h. The mixture was concentrated under reduced pressure to afford the title compound as a solid (25.0 mg, 81%). $^1$H NMR MeOD 500 MHz, δ 9.62 (s, 1H), 8.74 (d, J=5.7 Hz, 1H), 8.45 (d, J=7.8 Hz, 1H), 7.93-7.89 (m, 1H), 7.53 (s, 1H), 7.38-7.29 (m, 1H), 7.15 (d, J=7.5 Hz, 1H), 7.09 (t, J=9.0 Hz, 1H), 4.98 (s, 2H), 4.94 (s, 2H), 4.67 (s, 2H), 2.58 (s, 3H). m/z (ES+), [M+H]$^+$: 376.5. HPLC (A05) $t_R$=2.03 min.

Example 25: 1-(4-(12-fluoro-6,8,13,14-tetrahydro-[1,2,4]triazolo[4',3':1,6]pyrido[3,2-c]benzo[g][1,5]oxazonin-4-yl)piperidin-1-yl)ethan-1-one Step 1: tert-butyl 4-(1-acetyl-1,2,3,6-tetrahydropyridin-4-yl)-12-fluoro-8,13-dihydro-[1,2,4]triazolo[4',3':1,6]pyrido[3,2-c]benzo[g][1,5]oxazonine-14 (6H)-carboxylate

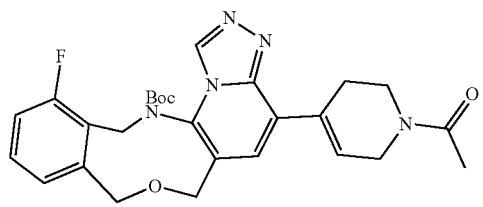 [SMILES: CC(=O)N1CC=C(c2cc3c(n4cnnc24)N(C(=O)OC(C)(C)C)Cc2c(F)cccc2COC3)CC1]

1,4-Dioxane (4.00 mL) and water (0.800 mL) were added to a mixture of tert-butyl 4-bromo-12-fluoro-8,13-dihydro-[1,2,4]triazolo[4',3':1,6]pyrido[3,2-c]benzo[g][1,5]oxazonine-14 (6H)-carboxylate (Example 24; 113 mg, 0.244 mmol), 1-[4-(4,4,5,5-tetramethyl-1,3,2-dioxaborolan-2-yl)-3,6-dihydro-2H-pyridin-1-yl]ethanone (67.4 mg, 0.268 mmol, Pd(dppf)Cl$_2$ (17.8 mg, 0.0244 mmol), and NaHCO$_3$ (61.5 mg, 0.732 mmol) under nitrogen. The mixture was heated at 90° C. for 2.5 h. The mixture was cooled to 23° C. and filtered though a silica plug, washing with EtOAc and 10% MeOH in DCM. The filtrate was concentrated under reduced pressure, and the residue was purified by silica gel chromatography (12 g cartridge) eluting with DCM and MeOH (0-10%) to provide tert-butyl 4-(1-acetyl-1,2,3,6-tetrahydropyridin-4-yl)-12-fluoro-8,13-dihydro-[1,2,4]triazolo[4',3':1,6]pyrido[3,2-c]benzo[g][1,5]oxazonine-14 (6H)-carboxylateas a solid (141 mg; 80% pure, 91%). Complex NMR (rotamers). m/z (ES+), [M+H]$^+$: 508.1. HPLC (A05) $t_R$=2.22 min.

Step 2: tert-butyl 4-(1-acetylpiperidin-4-yl)-12-fluoro-8,13-dihydro-[1,2,4]triazolo[4',3':1,6]pyrido[3,2-c]benzo[g][1,5]oxazonine-14 (6H)-carboxylate

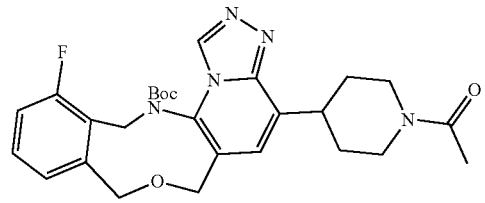 [SMILES: CC(=O)N1CCC(c2cc3c(n4cnnc24)N(C(=O)OC(C)(C)C)Cc2c(F)cccc2COC3)CC1]

A solution of tert-butyl 4-(1-acetyl-1,2,3,6-tetrahydropyridin-4-yl)-12-fluoro-8,13-dihydro-[1,2,4]triazolo[4',3':1,6]pyrido[3,2-c]benzo[g][1,5]oxazonine-14 (6H)-carboxylate (111 mg, 0.175 mmol) in MeOH (12.0 mL) was added at 23° C. to a flask charged with 10% Pd/C (74.0 mg, 0.0695 mmol) under nitrogen atmosphere. The flask was evacuated and purged with H$_2$ gas 3 times. The mixture was stirred at 23° C. for 1 h and filtered through Celite washing with MeOH. The filtrate was concentrated under reduced pressure, and the product was purified by silica gel chromatography (24 g) eluting with DCM and MeOH (0-10%) to provide tert-butyl 4-(1-acetylpiperidin-4-yl)-12-fluoro-8,13-dihydro-[1,2,4]triazolo[4',3':1,6]pyrido[3,2-c]benzo[g][1,5]oxazonine-14 (6H)-carboxylate as a solid (71.0 mg, 80%). Complex NMR (rotamers). m/z (ES+) [M+H]$^+$: 510.2. HPLC (A05) $t_R$=2.20 min.

Step 3: 1-(4-(12-fluoro-6,8,13,14-tetrahydro-[1,2,4]triazolo[4',3':1,6]pyrido[3,2-c]benzo[g][1,5]oxazonin-4-yl)piperidin-1-yl)ethan-1-one Methanesulfonyl Salt

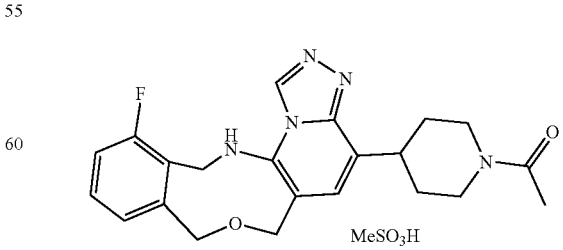

A solution of tert-butyl 4-(1-acetylpiperidin-4-yl)-12-fluoro-8,13-dihydro-[1,2,4]triazolo[4',3':1,6]pyrido[3,2-c]

benzo[g][1,5]oxazonine-14 (6H)-carboxylate (85.0 mg, 0.167 mmol) in HFIP (4.00 mL) was heated at 100° C. for 12 h. After cooling down to 23° C., the mixture was concentrated under reduced pressure. The product was purified by silica gel chromatography (12 g cartridge) eluting with DCM and MeOH (0-10%) to provide the free base of 1-(4-(12-fluoro-6,8,13,14-tetrahydro-[1,2,4]triazolo[4',3':1,6]pyrido[3,2-c]benzo[g][1,5]oxazonin-4-yl)piperidin-1-yl)ethan-1-one as a solid (40.0 mg; 59%). $^1$H NMR (500 MHz, MeOD) δ 9.44-9.33 (m, 1H), 7.33-7.23 (m, 1H), 7.16 (d, J=8.6 Hz, 1H), 7.14 (s, 1H), 7.03 (t, J=9.1 Hz, 1H), 4.73 (s, 2H), 4.72-4.68 (m, 1H), 4.69 (s, 2H), 4.52 (s, 2H), 4.06 (d, J=13.8 Hz, 1H), 3.39-3.33 (m, 1H), 3.30-3.24 (m, 1H), 2.79 (t, J=13.0 Hz, 1H), 2.14 (s, 3H), 2.07 (d, J=13.1 Hz, 1H), 2.00 (d, J=13.2 Hz, 1H), 1.82-1.63 (m, 2H). The compound was converted to the methanesulfonyl salt by adding MeSO$_3$H (3.01 μL, 0.0464 mmol) to a solution of 1-(4-(12-fluoro-6,8,13,14-tetrahydro-[1,2,4]triazolo[4',3':1,6]pyrido[3,2-c]benzo[g][1,5]oxazonin-4-yl)piperidin-1-yl)ethan-1-one (19.0 mg, 0.0464 mmol) in MeCN (2.00 mL). The mixture was stirred at 23° C. for 1 h. The mixture was concentrated under reduced pressure to provide the title compound as a solid (21.0 mg, 89%). $^1$H NMR MeOD 500 MHz, δ 9.75 (s, 1H), 7.85 (s, 1H), 7.37 (td, J=7.9, 5.7 Hz, 1H), 7.19-7.02 (m, 2H), 4.94 (s, 4H), 4.74 (d, J=13.5 Hz, 1H), 4.62 (s, 2H), 4.12 (d, J=13.9 Hz, 1H), 3.36-3.26 (m, 1H), 3.24-3.15 (m, 1H), 2.84-2.75 (m, 1H), 2.70 (s, 3H), 2.17 (s, 3H), 2.06-1.93 (m, 2H), 1.83 (qd, J=12.6, 3.8 Hz, 1H), 1.69 (qd, J=12.8, 4.2 Hz, 1H). m/z (ES+), [M+H]$^+$: 410.1. HPLC (A05) t$_R$=2.04 min.

Example 26: 12-fluoro-4-((1-methyl-1H-pyrazol-4-yl)methyl)-6,8,13,14-tetrahydro-[1,2,4]triazolo[4',3':1,6]pyrido[3,2-c]benzo[g][1,5]oxazonine Step 1 (12-fluoro-6,8,13,14-tetrahydro-[1,2,4]triazolo[4',3':1,6]pyrido[3,2-c]benzo[g][1,5]oxazonin-4-yl)(1-methyl-1H-pyrazol-4-yl)methanol

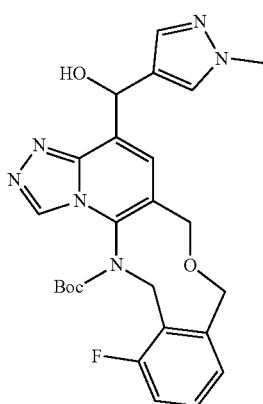

$^i$PrMgCl.LiCl (0.540 mL, 0.703 mmol) was drop wise added to a solution of tert-butyl 4-bromo-12-fluoro-8,13-dihydro-[1,2,4]triazolo[4',3':1,6]pyrido[3,2-c]benzo[g][1,5]oxazonine-14 (6H)-carboxylate (Example 24; 93.0 mg, 0.201 mmol) in THF (3.00 mL) at −78° C. under nitrogen. The mixture was stirred at −78° C. for 10 min and warmed to 0° C. for 30 min. A solution of 1-methylpyrazole-4-carbaldehyde (88.4 mg, 0.803 mmol) in THF (1.00 mL) was drop wise added at 0° C. The mixture was stirred at 0° C. for 30 min and warmed to room temperature for 2 h. The mixture was diluted with NH$_4$Cl (5 mL) and water (8 mL). The aqueous phase was extracted with ethyl acetate (5×20 mL). The combined organic layers were dried over MgSO$_4$, filtered, and concentrated. The residue was purified by silica gel chromatography (12 g cartridge) eluting with MeOH in DCM (0-15%) to provide (12-fluoro-6,8,13,14-tetrahydro-[1,2,4]triazolo[4',3':1,6]pyrido[3,2-c]benzo[g][1,5]oxazonin-4-yl)(1-methyl-1H-pyrazol-4-yl)methanol (31 mg, 31%) as a solid. m/z (ES+) [M+H]$^+$: 495.1; HPLC t$_R$ (A05)=2.13 min.

Step 2: 12-fluoro-4-((1-methyl-1H-pyrazol-4-yl)methyl)-6,8,13,14-tetrahydro-[1,2,4]triazolo[4',3':1,6]pyrido[3,2-c]benzo[g][1,5]oxazonine

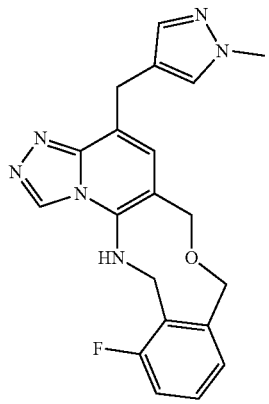 [SMILES: Cn1cc(Cc2cc3c(n4cnnc24)NCc2c(F)cccc2COC3)cn1]

Triethylsilane (0.400 mL, 2.51 mmol) and TFA (0.186 mL, 2.51 mmol) were added to a solution of (12-fluoro-6,8,13,14-tetrahydro-[1,2,4]triazolo[4',3':1,6]pyrido[3,2-c]benzo[g][1,5]oxazonin-4-yl)(1-methyl-1H-pyrazol-4-yl)methanol (31.0 mg, 0.0627 mmol) in MeCN (2.50 mL). The mixture was stirred at 60° C. for 3 h and concentrated under reduced pressure. The residue was purified by HPLC (Torus-2PIC 10×250 mm MeOH/CO$_2$ 5-55% of MeOH) to afford the title compound as a solid (7.47 mg, 31%). $^1$H NMR (500 MHz, MeOD) δ 9.39 (s, 1H), 7.45 (s, 1H), 7.32 (s, 1H), 7.28 (td, J=7.9, 5.6 Hz, 1H), 7.15 (d, J=7.3 Hz, 1H), 7.07 (s, 1H), 7.02 (t, J=8.6 Hz, 1H), 4.73 (d, J=1.6 Hz, 2H), 4.67 (s, 2H), 4.49 (s, 2H), 4.04 (s, 2H), 3.82 (s, 3H). m/z (ES+) [M+H]$^+$: 379.1; HPLC t$_R$ (A05)=2.05 min.

Example 27: (S)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine Step 1: (S)-4-bromo-12-fluoro-7a,8,13,14-tetrahydro-7H-[1,2,4]triazolo[4',3':1,6]pyrido[3,2-b]benzofuro[4,3-fg][1,4]oxazonine

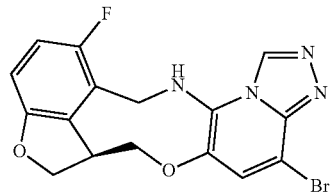 [SMILES: Fc1ccc2c3c1CNc1c(cc(Br)c4nncn14)OC[C@H]3CO2]

To a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (2.4 g, 4.88 mmol, 1.00 eq; as prepared in Example 17) in DCM (20 mL) was added TFA (9.24 g, 81.0 mmol, 6 mL, 16.6 eq) in one portion at 18° C. The mixture was stirred at 18° C. for 12 hrs. TLC (Petroleum ether:Ethyl acetate=0:1, $R_f$=0.2) detected one major new spot with larger polarity. The mixture was evaporated to obtain the product. To the residue was added EtOAc (20 mL), then basified to pH=8 by saturated aqueous NaHCO$_3$. The precipitate was generated. The mixture was filtered and the filter cake was washed with 10 mL of EtOAc, dried in vacuum to give (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (1.78 g, 4.55 mmol, 93% yield) as a gray solid.

Step 2: (S)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine

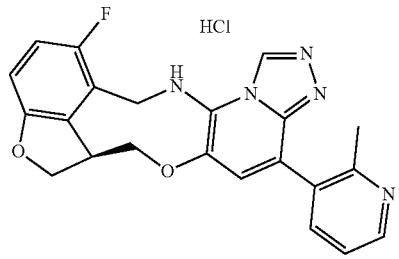 [SMILES: Cc1ncccc1-c1cc2c(n3cnnc13)NCc1c(F)ccc3c1[C@H](CO3)CO2 ; Cl]

Dioxane (181 mL) and water (39.0 mL) were sequentially added to a mixture of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (2.59 g, 6.62 mmol, 1.00 eq), 2-methyl-3-(4,4,5,5-tetramethyl-1,3,2-dioxaborolan-2-yl)pyridine (1.74 g, 7.94 mmol, 1.2 eq), Pd(dppf)Cl$_2$ (484 mg, 662 umol, 0.100 eq) and NaHCO$_3$ (2.78 g, 33.1 mmol, 1.29 mL, 5.00 eq) at 20° C. under N$_2$. The mixture was heated to 90° C. for 2 hrs. LC-MS showed no (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was remained. Several new peaks were shown on LC-MS and the desired mass was detected. The reaction mixture was concentrated under reduced pressure to remove solvent. The residue was combined with other two batches (from 1.82 of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine and 1.0 g of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine) and to the residue (18 g) was added MeOH (100 mL) and silica-thiol (700 mg, modified silicon gel for eliminating Pd, irregular silica gel, 100-200 mesh, chlorides (Cl), %≤0.004, Particle Size Distribution 45-75 um) at 20° C. and stirred at 20° C. for 12 hrs. The suspension was filtered and the filter cake was washed with 200 mL of MeOH and 20 mL of DMSO, the filtrate was concentrated under reduced pressure to remove MeOH and purified by prep-HPLC (HCl condition: column: Phenomenex luna c18 250 mm*100 mm*10 um; mobile phase: [water (0.05% HCl)—ACN]; B %: 1%-31%, 25 min). The fraction of prep-HPLC was concentrated under reduced pressure to remove MeCN at 30° C. and the residue was lyophilized. (S)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine (4.1 g, 9.29 mmol, 99.7% purity, 100% ee, HCl) was obtained as yellow solid. $^1$H NMR DMSO-d$_6$ 400 MHz, δ=ppm 9.89 (s, 1H), 8.86-8.75 (m, 1H), 8.64-8.57 (m, 1H), 8.54-8.49 (m, 1H), 7.98-7.89 (m, 1H), 7.82-7.75 (m, 1H), 7.03-6.92 (m, 1H), 6.71 (dd, J=8.6, 3.7 Hz, 1H), 5.00-4.91 (m, 1H), 4.84 (br dd, J=14.7, 5.6 Hz, 1H), 4.58-4.45 (m, 2H), 4.25-4.17 (m, 1H), 4.11-4.00 (m, 1H), 3.95-3.83 (m, 1H), 2.64 (s, 3H). LCMS (ESI+): m/z 404.1 (M+H).

Example 28: (S)-1-(4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one Step 1: tert-butyl (S)-4-(1-acetyl-1,2,3,6-tetrahydropyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

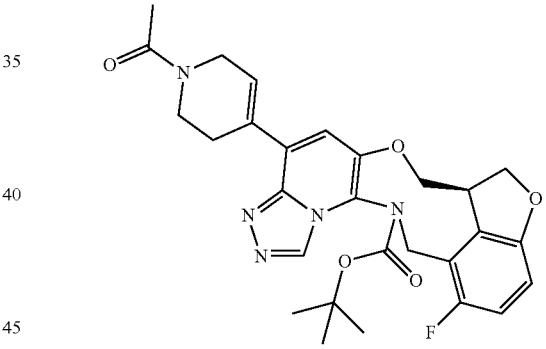

Dioxane (2.00 mL) and water (0.400 mL) were added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 0.122 mol, 60.0 mg), 1-[4-(4,4,5,5-tetramethyl-1,3,2-dioxaborolan-2-yl)-3,6-dihydro-2H-pyridin-1-yl]ethanone (0.128 mmol, 32.1 mg), Pd(dppf)Cl$_2$ (0.0122 mmol, 8.94 mg), and NaHCO$_3$ (0.366 mmol, 30.8 mg) under N$_2$. The mixture was stirred at 90° C. for 2.5 h. The mixture was filtered though a short silica pad. The filter cake was washed with EtOAc (3×5 mL). The filtrate was concentrated under reduced pressure, and the residue was purified by silica gel chromatography (4 g cartridge) eluting with MeOH in DCM (0-10%) to afford tert-butyl (S)-4-(1-acetyl-1,2,3,6-tetrahydropyridin-4-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate as a solid (53.6 mg, 82%). ES+ [M]$^+$:535.63; LC-MS (B05); $t_R$=2.23 min.

Step 2: tert-butyl (S)-4-(1-acetylpiperidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

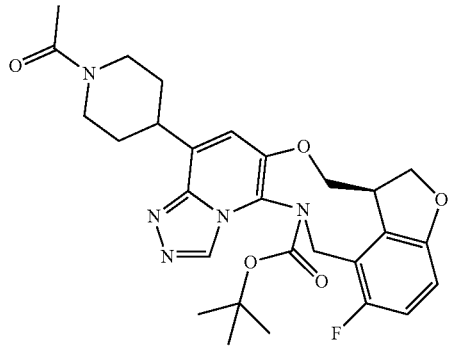 [SMILES: CC(=O)N1CCC(c2cc3c(n4cnnc24)N(C(=O)OC(C)(C)C)Cc2c(F)ccc4c2[C@H](CO4)CO3)CC1]

A solution of tert-butyl (S)-4-(1-acetyl-1,2,3,6-tetrahydropyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (99.0 µmol, 53.0 mg) in MeOH (10.0 mL) was added to a flask charged with Pd/C (19.8 µmol, 21.1 mg, 10.0%) under nitrogen atmosphere at room temperature. The flask was evacuated and purged with H₂ gas 3 times. The mixture was stirred at rt for 20 h and filtered through Celite. The filter cake was washed with MeOH (3×8 mL), and the filtrate was concentrated under reduced pressure. The residue (53 mg) was used as such in the next step without further purification. m/z (ES+) [M]⁺:537.75. HPLC (B05) $t_R$=2.09 min.

Step 3: (S)-1-(4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidin-1-yl)ethan-1-one

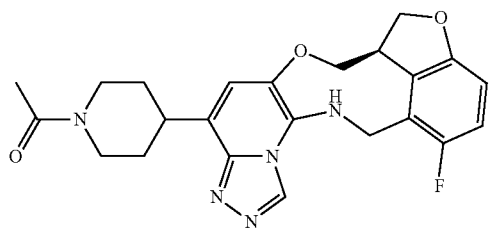 [SMILES: CC(=O)N1CCC(c2cc3c(n4cnnc24)NCc2c(F)ccc4c2[C@H](CO4)CO3)CC1]

A solution of tert-butyl (S)-4-(1-acetylpiperidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (98.6 µmol, 53.0 mg) in HFIP (2.00 mL) was heated to 100° C. for 3 h. The mixture was concentrated under reduced pressure, and the residue was purified by HPLC (BEH C18 30×150 mm AmBicarb/ACN 25-45%) to afford the title compound as a solid (22.7 mg, 53%). ¹H NMR DMSO 500 MHz, δ 9.33 (s, 1H), 7.15 (t, J=6.4 Hz, 1H), 7.07 (s, 1H), 6.97-6.84 (m, 1H), 6.66 (dd, J=8.6, 3.8 Hz, 1H), 4.82 (dd, J=14.9, 5.9 Hz, 1H), 4.68 (dd, J=14.9, 6.6 Hz, 1H), 4.51 (t, J=9.4 Hz, 2H), 4.48-4.38 (m, 1H), 4.20 (dd, J=9.6, 3.3 Hz, 1H), 4.02-3.86 (m, 2H), 3.77 (td, J=11.6, 4.2 Hz, 1H), 3.26-3.09 (m, 2H), 2.67-2.55 (m, 1H), 2.02 (d, J=3.9 Hz, 3H), 1.98-1.83 (m, 2H), 1.80-1.67 (m, 1H), 1.67-1.53 (m, 1H). m/z (ES+) [M+H]⁺: 438.61, HPLC (B05) $t_R$=1.91 min.

Example 29: (S)-12-fluoro-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine Step 1 tert-butyl (7aS)-12-fluoro-4-(hydroxy(1-methyl-1H-pyrazol-4-yl)methyl)-7a,13-dihydro-7H-[1,2,4]triazolo[4',3':1,6]pyrido[3,2-b]benzofuro[4,3-fg][1,4]oxazonine-14 (8H)-carboxylate

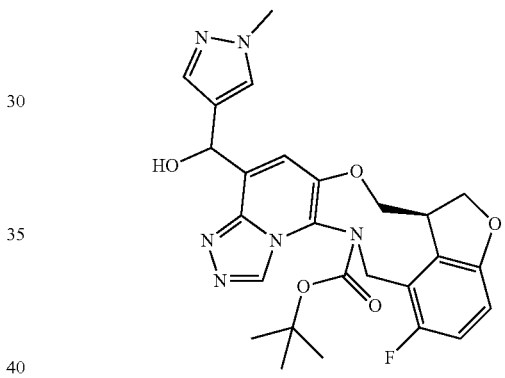

A solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 0.122 mmol, 60.0 mg) in THF (2.00 mL) was cooled to −78° C. ⁱPrMgCl.LiCl 0.427 mmol, 0.329 mL) was added dropwise. The mixture was stirred at −78° C. for 10 min and warmed to 0° C. for 30 min. A solution of 1-methylpyrazole-4-carbaldehyde (0.488 mmol, 53.8 mg) in THF (1.00 mL) was added drop-wise at 0° C. The mixture was stirred at 0° C. for 30 min and warmed to room temperature for 2 h. The mixture was diluted with NH₄Cl (5 mL) and water (8 mL). The aqueous phase was extracted with ethyl acetate (5×15 mL), and the combined organic layers were dried over MgSO₄, filtered, and concentrated under reduced pressure. The residue was purified by silica gel chromatography (4 g cartridge) eluting with MeOH in DCM (0-15%) to provide tert-butyl (7aS)-12-fluoro-4-(hydroxy(1-methyl-1H-pyrazol-4-yl)methyl)-7a,13-dihydro-7H-[1,2,4]triazolo[4',3':1,6]pyrido[3,2-b]benzofuro[4,3-fg][1,4]oxazonine-14 (8H)-carboxylate as a solid (10.5 mg, 17%). LC-MS m/z (ES+) [M+H]⁺:523.88; (A05) $t_R$=2.02 min.

169

Step 2: (S)-12-fluoro-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine

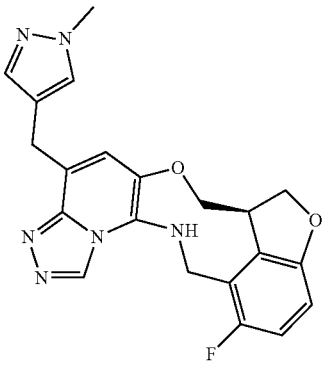 [SMILES: Cn1cc(Cc2cc3c(n4cnnc24)NCc2c(F)ccc4c2[C@H](CO4)CO3)cn1]

To a solution of tert-butyl 12-fluoro-4-(hydroxy(1-methyl-1H-pyrazol-4-yl)methyl)-8,13-dihydro-[1,2,4]triazolo[4',3':1,6]pyrido[3,2-c]benzo[g][1,5]oxazonine-14(6H)-carboxylate (0.0201 mmol, 10.5 mg) in MeCN (1.50 mL) was added Et$_3$SiH (0.804 mmol, 0.0597 mL) and TFA (0.804 mmol, 0.128 mL). The mixture was stirred at 60° C. for 3 h. The mixture was concentrated under reduced pressure, and the residue was purified by HPLC (BEH C18 30×50 mm AmBicarb/ACN 25-45%) to afford the title compound as a solid (5.2 mg, 64%). $^1$H NMR MeOD 400 MHz, δ 9.23 (s, 1H), 7.46 (s, 1H), 7.36 (s, 1H), 7.06 (s, 1H), 6.82 (dd, J=10.3, 8.7 Hz, 1H), 6.58 (dd, J=8.7, 3.8 Hz, 1H), 4.95 (d, J=14.8 Hz, 1H), 4.77 (d, J=14.7 Hz, 1H), 4.57-4.42 (m, 2H), 4.23 (dd, J=9.6, 3.0 Hz, 1H), 4.04-3.99 (m, 2H), 3.98-3.89 (m, 1H), 3.81 (s, 3H), 3.80-3.72 (m, 1H). m/z (ES+) [M+H]$^+$:407.62, HPLC (B05) tR=1.93 min.

Example 30: (S)-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine and (S)-7a,8,13,14-tetrahydro-7H-[1,2,4]triazolo[4',3':1,6]pyrido[3,2-b]benzofuro[4,3-fg][1,4]oxazonine

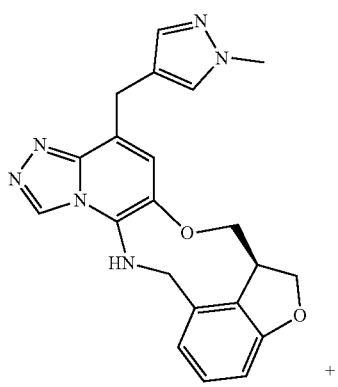

170

-continued

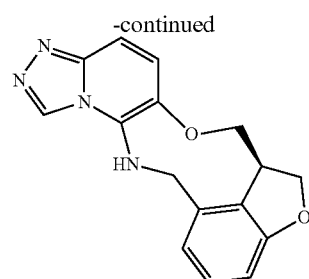

nitrogen (C$_2$H$_5$)$_3$SiH (7.93 mmol, 1.27 mL) and TFA (7.93 mmol, 0.589 mL) were added to a solution of (S)-12-fluoro-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine (Example 30; 0.198 mmol, 100 mg) in MeCN (2.00 mL). The mixture was heated to 60° C. for 3 h. The mixture was concentrated. The residue was purified by HPLC (BEH 30×50 mm ACN/AmBicarb 30-35%) to afford (S)-4-((1-methyl-1H-pyrazol-4-yl)methyl)-7a,8,13,14-tetrahydro-7H-[1,2,4]triazolo[4',3':1,6]pyrido[3,2-b]benzofuro[4,3-fg][1,4]oxazonine as a solid (8.00 mg, 10%). $^1$H NMR (500 MHz, MeOD) δ 9.18 (s, 1H), 7.46 (s, 1H), 7.36 (s, 1H), 7.11-7.04 (m, 2H), 6.84 (d, J=7.6 Hz, 1H), 6.62 (d, J=7.9 Hz, 1H), 4.89-4.84 (m, 1H), 4.75 (d, J=14.3 Hz, 1H), 4.49 (t, J=9.3 Hz, 1H), 4.41 (dd, J=10.5, 4.3 Hz, 1H), 4.17 (dd, J=9.6, 3.4 Hz, 1H), 4.02 (d, J=3.0 Hz, 2H), 3.99-3.92 (m, 1H), 3.81 (s, 3H), 3.78 (dd, J=11.9, 10.8 Hz, 1H). m/z (ES+) [M+H]$^+$: 389.95; HPLC t$_R$ (B05)=2.26 min.

From the preceding purification, (S)-7a,8,13,14-tetrahydro-7H-[1,2,4]triazolo[4',3':1,6]pyrido[3,2-b]benzofuro[4,3-fg][1,4]oxazonine was isolated as a solid (9.00 mg, 15%). $^1$H NMR (500 MHz, MeOD) δ 9.17 (d, J=0.8 Hz, 1H), 7.37 (d, J=9.5 Hz, 1H), 7.09 (t, J=7.8 Hz, 1H), 7.02 (dd, J=9.5, 0.9 Hz, 1H), 6.86 (d, J=7.7 Hz, 1H), 6.63 (d, J=7.9 Hz, 1H), 4.94-4.85 (m, 1H), 4.79 (s, 1H), 4.51 (t, J=9.4 Hz, 1H), 4.47 (dd, J=10.4, 4.4 Hz, 1H), 4.19 (dd, J=9.6, 3.5 Hz, 1H), 3.98 (ddd, J=13.1, 8.6, 4.0 Hz, 1H), 3.88-3.81 (m, 1H).

Example 31: (S)-4-(2,4-dimethylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine Step 1: tert-butyl (S)-4-(2,4-dimethylpyrimidin-5-yl)-12-fluoro-7a,13-dihydro-7H-[1,2,4]triazolo[4',3':1,6]pyrido[3,2-b]benzofuro[4,3-fg][1,4]oxazonine-14(8H)-carboxylate

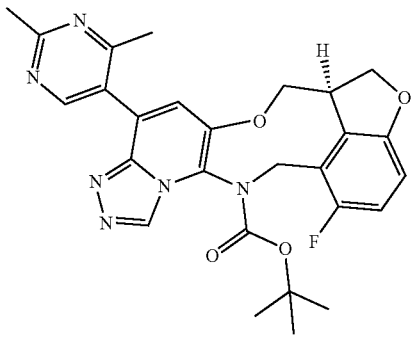 [SMILES: Cc1ncc(-c2cc3c(n4cnnc24)N(C(=O)OC(C)(C)C)Cc2c(F)ccc4c2[C@H](CO4)CO3)c(C)n1]

Dioxane (1.50 mL) and water (0.300 mL) were added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 0.122 mmol, 60.0 mg), 2,4-dimethyl-S-(4,4,5,5-tetramethyl-1,3,2-dioxaborolan-2-yl)pyrimidine (0.147 mmol, 34.3 mg), Pd(dppf)Cl$_2$ (0.0122 mmol, 8.94 mg), and NaHCO$_3$ (0.366 mmol, 30.8 mg) under N$_2$. The mixture was stirred at 90° C. for 4 h. The mixture was filtered though a silica pad, and the filter cake was washed with EtOAc (3×5 mL). The filtrate was concentrated under reduced pressure, and the residue was purified by silica gel chromatography (4 g cartridge) eluting with MeOH in DCM (0-15%) to afford tert-butyl (S)-4-(2,4-dimethylpyrimidin-S-yl)-12-fluoro-7a,13-dihydro-7H-[1,2,4]triazolo[4',3':1,6] pyrido[3,2-b]benzofuro[4,3-fg][1,4]oxazonine-14 (8H)-carboxylate as a solid (60 mg, 95%). ES+[M]$^+$:518.47; LC-MS (B05) $t_R$=2.10 min.

Step 3: (S)-4-(2,4-dimethylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

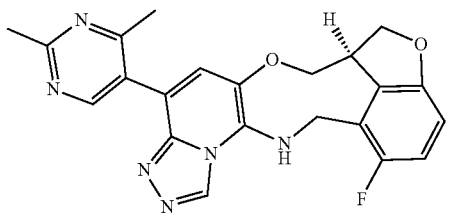 [SMILES: Cc1ncc(-c2cc3c(n4cnnc24)NCc2c(F)ccc4c2[C@H](CO4)CO3)c(C)n1]

A solution of tert-butyl (15R)-21-fluoro-10-(2,4-dimethylpyrimidyl)-13,17-dioxa-3,5,7,8-tetrazapentacyclo [13.6.1.04,12.05,9.018,22] docosa-1 (21),4 (12),6,8,10,18 (22),19-heptaene-3-carboxylate (0.116 mmol, 60.0 mg) in HFIP (1.50 mL) was heated to 100° C. for 4 h. The mixture was concentrated under reduced pressure, and the residue was purified by preparative HPLC (BEH C18 30×50 mm AmForm/ACN 35-45% 13 min) to afford (S)-4-(2,4-dimethylpyrimidin-S-yl)-12-fluoro-7a,8,13,14-tetrahydro-7H-[1,2,4]triazolo[4',3':1,6]pyrido[3,2-b]benzofuro[4,3-fg][1,4] oxazonine as a solid (11.2 mg, 23%). $^1$H NMR DMSO 400 MHz, δ 9.44 (s, 1H), 8.62 (s, 1H), 7.62 (t, J=6.3 Hz, 1H), 7.41 (s, 1H), 7.04-6.89 (m, 1H), 6.70 (dd, J=8.6, 3.8 Hz, 1H), 4.92 (dd, J=15.1, 5.7 Hz, 1H), 4.79 (dd, J=15.1, 6.7 Hz, 1H), 4.54 (t, J=9.4 Hz, 1H), 4.50-4.42 (m, 1H), 4.21 (dd, J=9.6, 3.5 Hz, 1H), 4.10-3.99 (m, 1H), 3.88 (t, J=11.4 Hz, 1H), 2.63 (s, 3H), 2.35 (s, 3H). ES+[M+H]$^+$:419.88; LC-MS (A05) $t_R$=1.91 min.

Example 32: 4-(2,4-dimethylpyrimidin-S-yl)-12-fluoro-7,8,13,14-tetrahydro-[1,2,4]triazolo[4',3':1,6]pyrido[3,2-b]benzo[f][1,4]oxazonine, 3MsOH Step 1: tert-butyl 4-(2,4-dimethylpyrimidin-S-yl)-12-fluoro-8,13-dihydro-[1,2,4]triazolo[4',3':1,6]pyrido[3,2-b]benzo[f][1,4]oxazonine-14 (7H)-carboxylate

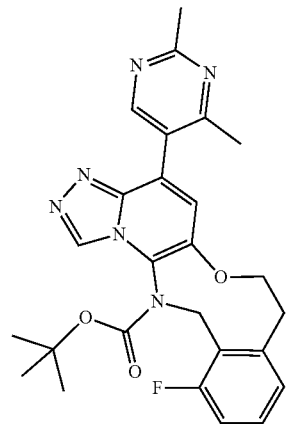 [SMILES: Cc1ncc(-c2cc3c(n4cnnc24)N(C(=O)OC(C)(C)C)Cc2c(F)cccc2CCO3)c(C)n1]

Dioxane (1.33 mL) and water (0.265 mL) were sequentially added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 50.0 mg, 0.108 mmol), 2, 4-dimethyl-S-(4,4,5,5-tetramethyl-1,3,2-dioxaborolan-2-yl)pyrimidine (35.4 mg, 0.151 mmol), Pd(dppf)Cl$_2$ (11.8 mg, 0.0162 mmol), and NaHCO$_3$ (27.2 mg, 0.324 mmol) under N$_2$. The mixture was stirred at 90° C. for 3 h. The mixture was filtered though a short silica pad, washing with DCM (3×5 mL). The filtrate was concentrated under reduced pressure, and the residue was purified by silica gel chromatography (12 g, cartridge) eluting with MeOH in DCM (0-15%) to afford tert-butyl 4-(2,4-dimethylpyrimidin-S-yl)-12-fluoro-8,13-dihydro-[1,2,4]triazolo[4',3':1,6]pyrido[3,2-b]benzo[f][1,4]oxazonine-14 (7H)-carboxylate as a solid (60.0 mg, 75% purity, 85%), which was used as such in the next step. ES+[M+H]$^+$: 491.21; HPLC $t_R$=2.25 min.

Step 2: 4-(2,4-dimethylpyrimidin-S-yl)-12-fluoro-7,8,13,14-tetrahydro-[1,2,4]triazolo[4',3':1,6]pyrido[3,2-b]benzo[f][1,4]oxazonine

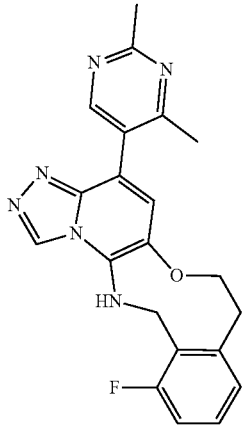 [SMILES: Cc1ncc(-c2cc3c(n4cnnc24)NCc2c(F)cccc2CCO3)c(C)n1]

A solution of tert-butyl 4-(2,4-dimethylpyrimidin-S-yl)-12-fluoro-8,13-dihydro-[1,2,4]triazolo[4',3':1,6]pyrido[3,2-b]benzo[f][1,4]oxazonine-14 (7H)-carboxylate (45.0 mg, 0.0917 mmol) in HFIP (3.00 mL) was heated to 100° C. for 4 h. The mixture was concentrated under reduced pressure, and the residue was purified by preparative HPLC (BEH C18 30×150 mm AmBicarb/ACN 25-45%) to afford 4-(2,4-dimethylpyrimidin-S-yl)-12-fluoro-7,8,13,14-tetrahydro-[1,2,4]triazolo[4',3':1,6]pyrido[3,2-b]benzo[f][1,4]oxazonine as a solid (14.7 mg, 41%). ES+[M+H]+: 391.2; HPLC $t_R$=2.08 min.

Step 3: 4-(2,4-dimethylpyrimidin-S-yl)-12-fluoro-7,8,13,14-tetrahydro-[1,2,4]triazolo[4',3':1,6]pyrido[3,2-b]benzo[f][1,4]oxazonine, 3MsOH

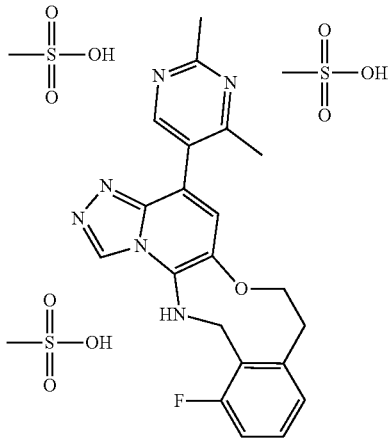

4-(2,4-dimethylpyrimidin-S-yl)-12-fluoro-7,8,13,14-tetrahydro-[1,2,4]triazolo[4',3':1,6]pyrido[3,2-b]benzo[f][1,4]oxazonine (14.7 mg, 0.0377 mmol) was dissolved in MeOH (4.00 mL). MsOH (7.34 uL, 0.113 mmol) was added, and the mixture was stirred for 2 h at rt. The mixture was concentrated under reduced pressure to afford the title compound as a solid (20.6 mg, 81%). 1H NMR MeOD 500 MHz, δ 9.54 (s, 1H), 8.84 (s, 1H), 8.00 (s, 1H), 7.24 (td, J=8.0, 5.9 Hz, 1H), 7.06 (d, J=6.9 Hz, 1H), 7.03-6.98 (m, 1H), 5.17 (s, 2H), 4.51 (s, 2H), 3.19 (s, 2H), 2.87 (s, 3H), 2.70 (s, 9H), 2.51 (s, 3H). ES+[M+H]+: 391.1; HPLC $t_R$=1.15 min.

Example 33: (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine Hydrochloride

Step 1: tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate

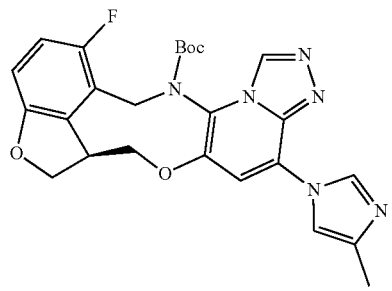

A flask was charged with tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 0.12 g, 244 umol, 1.00 eq), 4-methyl-1H-imidazole (30.1 mg, 366 umol, 1.5 eq) and $K_3PO_4$ (104 mg, 488 umol, 2.00 eq) at 15° C. and purged with $N_2$. Another flask was charged with $Pd_2(dba)_3$ (11.2 mg, 12.2 umol, 0.05 eq) and ditert-butyl-[2,3,4,5-tetramethyl-6-(2,4,6-triisopropylphenyl) phenyl] phosphane (11.7 mg, 24.4 umol, 0.100 eq), toluene (2 mL) and dioxane (0.4 mL) at 15° C., then purged with nitrogen and heated at 120° C. for 0.05 hr. Then it was cooled to 15° C. The obtained mixture (per-catalyst) was added to the first mixture via syringe. The resulting mixture was stirred at 120° C. for 10 h. LC-MS showed tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate was consumed completely and the desired mass was detected. The reaction mixture was concentrated under reduced pressure. The residue was purified by prep-TLC (SiO2, Ethyl acetate/Methanol=10/1) to afford tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate (40 mg) and (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine (15 mg). They were confirmed by LCMS, respectively. tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate (0.04 g, 81.22 umol, 33% yield) was obtained as a brown solid and used in the next step directly. (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine was further purified by prep-HPLC (formic acid conditions) (column: Luna C18 100*30 5 u; mobile phase: [water (0.2% FA)—ACN]; B %: 10%-25%, 12 min) to afford pure (S)-12-fluoro-4-(4-methyl-1H-imidazol-1-yl)-7a,8,13,14-tetrahydro-7H-[1,2,4]

triazolo[4',3':1,6]pyrido[3,2-b]benzofuro[4,3-fg] [1,4]oxazonine (3.20 mg, 7.15 umol, 2% yield, 97.974% purity, formate salt) as a yellow solid, which was combined with the other batch (de-Boc of tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate).

Step 2: (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine Hydrochloride

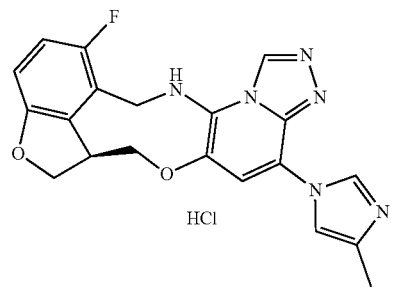

To a solution of tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate (0.030 g, 60.9 umol, 1.00 eq) in DCM (1 mL) was added TFA (1.54 g, 13.5 mmol, 1.00 mL, 222 eq) at 15° C. The mixture was stirred at 15° C. for 1 hr. LC-MS showed tert-butyl (S)-12-fluoro-4-(4-methyl-1H-imidazol-1-yl)-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. The reaction mixture was blown to dryness by nitrogen stream. The residue was purified by prep-HPLC (formic acid conditions) (column: Luna C18 100*30 5 u; mobile phase: [water (0.225% FA)—ACN]; B %: 1%-30%, 12 min). The fraction was combined with batch ((S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine from previous step, 3.2 mg as formate salt) and lyophilized together. Then one drop of 6 N of aqueous HCl solution was added and lyophilized again. (S)-12-fluoro-4-(4-methyl-1H-imidazol-1-yl)-7a,8,13,14-tetrahydro-7H-[1,2,4]triazolo[4',3':1,6]pyrido[3,2-b]benzofuro[4,3-fg][1,4]oxazonine (11.5 mg, 26.5 umol, 98.8% purity, HCl) was obtained as a yellow solid. $^1$H NMR CD$_3$OD 400 MHz, δ=ppm 9.82 (s, 1H), 9.33 (s, 1H), 8.40 (s, 1H), 7.71 (s, 1H), 6.93 (t, J=9.48 Hz, 1H), 6.69 (dd, J=8.68, 3.79 Hz, 1H), 5.20 (br d, J=14.79 Hz, 1H), 5.02 (br d, J=14.18 Hz, 1H), 4.80 (br s, 1H), 4.64 (t, J=9.41 Hz, 1H), 4.34 (br dd, J=9.66, 2.81 Hz, 1H), 4.11 (br s, 1H), 4.06-3.93 (m, 1H), 2.49 (s, 3H). LCMS (ESI+): m/z 393.2 (M+H).

Example 34: methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate Mesylate Salt Step 1: tert-butyl (S)-4-(1-(tert-butoxycarbonyl)-1,2,3,6-tetrahydropyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

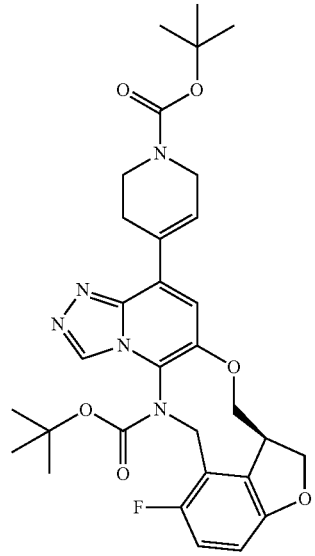 [SMILES: CC(C)(C)OC(=O)N1CC=C(c2cc3c(n4cnnc24)N(C(=O)OC(C)(C)C)Cc2c(F)ccc4c2[C@H](CO4)CO3)CC1]

Dioxane (2.00 mL) and water (0.400 mL) were added to a mixture of tert-butyl (R)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 0.204 mmol, 100 mg), tert-butyl 4-(4,4,5,5-tetramethyl-1,3,2-dioxaborolan-2-yl)-3,6-dihydro-2H-pyridine-1-carboxylate (0.305 mmol, 94.4 mg), Pd(dppf)Cl$_2$ (0.0204 mmol, 14.9 mg), and NaHCO$_3$ (0.611 mmol, 51.3 mg) under N$_2$. The mixture was stirred at 90° C. for 2 h. The mixture was filtered though a silica pad. The filter cake was washed with EtOAc (3×5 mL), and the filtrate was concentrated under reduced pressure. The residue was purified by silica gel chromatography (4 g cartridge) eluting with MeOH in DCM (0-10%) to afford tert-butyl (S)-4-(1-(tert-butoxycarbonyl)-1,2,3,6-tetrahydropyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (102 mg, 84%). ES+ [M]$^+$:593.48; LC-MS (A05); t$_R$=2.49 min.

Step 2: tert-butyl (S)-4-(1-(tert-butoxycarbonyl)piperidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

Step 3: (S)-12-fluoro-4-(piperidin-4-yl)-7a,8,13,14-tetrahydro-7H-[1,2,4]triazolo[4',3':1,6]pyrido[3,2-b]benzofuro[4,3-fg][1,4]oxazonine

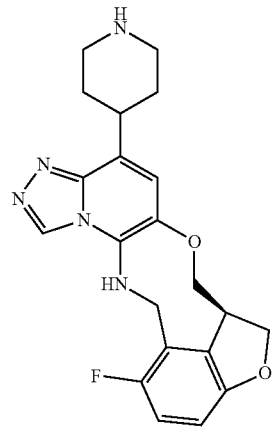

TFA (2.73 mmol, 0.209 mL) was added to a solution of tert-butyl (S)-4-(1-(tert-butoxycarbonyl)piperidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (136 μmol, 81.2 mg) in DCM (2.00 mL) at room temperature. The mixture was stirred at room temperature for 8.5 h. The mixture was concentrated under reduced pressure and used as such in the next step without further purification. m/z (ES+) [M]+: 395.54; LC-MS (A05), $t_R$=1.69 min.

Step 5: methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate

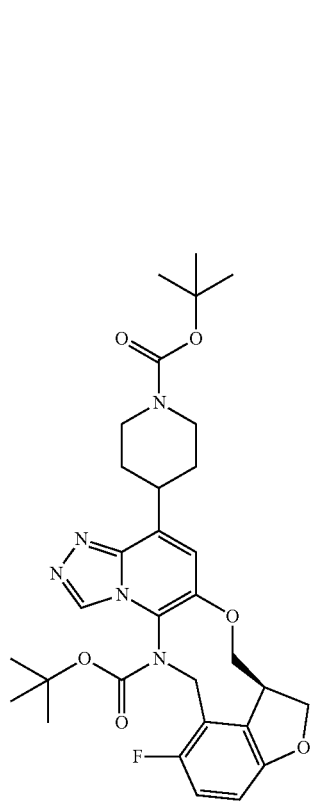 [SMILES: CC(C)(C)OC(=O)N1CCC(c2cc3c(n4cnnc24)N(C(=O)OC(C)(C)C)Cc2c(F)ccc4c2[C@H](CO4)CO3)CC1]

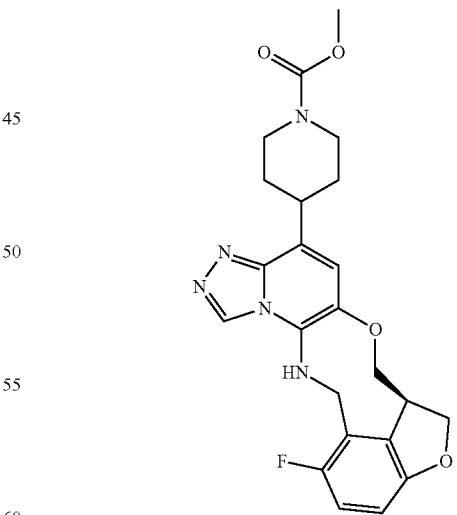

A solution of tert-butyl (S)-4-(1-(tert-butoxycarbonyl)-1,2,3,6-tetrahydropyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (172 μmol, 102 mg) in MeOH (10.0 mL) was added to a flask charged with Pd/C (34.4 μmol, 36.6 mg, 10.0%) under a nitrogen atmosphere at room temperature. The flask was evacuated and purged with H₂ gas 3 times. The mixture was stirred at rt for 20 h. The mixture was filtered through Celite, and the filter cake was washed with MeOH (3×8 mL). The filtrate was concentrated under reduced pressure, and the residue was purified by silica gel chromatography (4 g cartridge) eluting with MeOH in DCM (0-15%) to afford tert-butyl (S)-4-(1-(tert-butoxycarbonyl)piperidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate as a solid (81.2 mg, 79%). m/z (ES+) [M]+:596.32, LC-MS, (A05) $t_R$=2.52 min.

Methyl chloroformate (150 μmol, 14.2 mg, 11.6 μL) was added drop wise to a solution of (S)-12-fluoro-4-(piperidin-4-yl)-7a,8,13,14-tetrahydro-7H-[1,2,4]triazolo[4',3':1,6]pyrido[3,2-b]benzofuro[4,3-fg][1,4]oxazonine (136 μmol, 53.9 mg) and triethylamine (818 μmol, 82.8 mg, 114 μL) in DCM (2.00 mL) at 0° C. The mixture was stirred at 0° C. for Step 6: methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate mesylate Salt

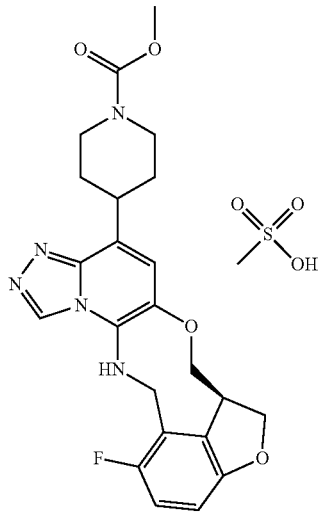

MeSO₃H (0.0529 mmol, 3.44 μL) was added to a stirred suspension of methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate (0.0529 mmol, 24.0 mg) in MeCN (1.00 mL) at room temperature. The mixture was stirred at room temperature for 1 h. The solution was concentrated under reduced pressure to afford the title compound as a solid (26.3 mg, 90%). ¹H NMR DMSO 500 MHz, δ 9.59 (s, 1H), 7.96 (s, 1H), 7.68 (s, 1H), 6.96 (dd, J=10.2, 8.8 Hz, 1H), 6.70 (dd, J=8.6, 3.8 Hz, 1H), 4.89 (dd, J=14.9, 5.3 Hz, 1H), 4.75 (dd, J=14.9, 6.8 Hz, 1H), 4.61-4.56 (m, 1H), 4.54 (t, J=9.5 Hz, 1H), 4.23 (dd, J=9.7, 3.5 Hz, 1H), 4.13 (s, 2H), 4.01 (ddd, J=13.6, 8.5, 3.9 Hz, 1H), 3.82 (t, J=11.4 Hz, 1H), 3.61 (s, 3H), 3.08 (tt, J=12.0, 3.2 Hz, 1H), 2.89 (s, 2H), 2.32 (s, 3H), 1.81 (t, J=13.4 Hz, 2H), 1.76-1.50 (m, 2H). m/z (ES+) [M−MsOH]⁺: 453.52; LC-MS (A05) tR=2.04 min.

2 h. The mixture was concentrated under reduced pressure, and the residue was purified by HPLC (Gemini C18 30×100 mm AmBiCarb/ACN 36-56%) to afford methyl (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)piperidine-1-carboxylate as a solid (30.5 mg, 49%). ¹H NMR DMSO 500 MHz, δ 9.32 (s, 1H), 7.14 (t, J=6.4 Hz, 1H), 7.07 (s, 1H), 6.92 (dd, J=10.2, 8.8 Hz, 1H), 6.66 (dd, J=8.6, 3.8 Hz, 1H), 4.82 (dd, J=14.9, 5.9 Hz, 1H), 4.68 (dd, J=15.0, 6.9 Hz, 1H), 4.51 (t, J=9.4 Hz, 1H), 4.44 (d, J=6.4 Hz, 1H), 4.20 (dd, J=9.6, 3.3 Hz, 1H), 4.15-4.03 (m, 2H), 4.02-3.91 (m, 1H), 3.78 (t, J=11.5 Hz, 1H), 3.61 (s, 3H), 3.22-3.09 (m, 1H), 2.91 (brs, 2H), 1.89 (t, J=13.7 Hz, 2H), 1.76-1.60 (m, 2H). m/z (ES+) [M]⁺:453.25; LC-MS (A05); tR=2.17 min.

Example 35: (S)-12-fluoro-4-(4-methylpyrimidin-5-yl)-7a,8,13,14-tetrahydro-7H-[1,2,4]triazolo[4',3':1,6]pyrido[3,2-b]benzofuro[4,3-fg][1,4]oxazonine Step 1: 4-methyl-5-(4,4,5,5-tetramethyl-1,3,2-dioxaborolan-2-yl)pyrimidine

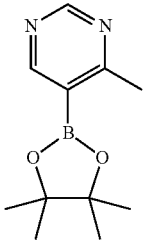

To a solution of 5-bromo-4-methylpyrimidine (700 mg, 4.05 mmol, 1.00 eq), 4,4,5,5-tetramethyl-2-(4,4,5,5-tetramethyl-1,3,2-dioxaborolan-2-yl)-1,3,2-dioxaborolane (1.34 g, 5.26 mmol, 1.3 eq) in dioxane (10 mL) was added KOAc (794 mg, 8.09 mmol, 2.00 eq) Pd(dppf)Cl₂ (296 mg, 405 umol, 0.100 eq) at 25° C., then the mixture was stirred at 80° C. under nitrogen for 12 h. LCMS showed the reaction was complete, starting material was consumed, desired target MS was detected. The mixture was concentrated, then dissolved with EtOAc (15 mL), filtered, the filtrate was concentrated. The residue was purified by column chromatography (SiO₂, Petroleum ether/Ethyl acetate=1/0 to 0/1 and then Ethyl acetate/MeOH=1/0 to 0/1). 4-methyl-5-(4,4,5,5-tetramethyl-1,3,2-dioxaborolan-2-yl)pyrimidine (0.800 g, 3.64 mmol, 89% yield) was obtained as a yellow oil. ¹H NMR CDCl₃ 400 MHz, δ=ppm 9.08 (s, 1H), 8.90 (s, 1H), 2.71 (s, 3H), 1.36 (s, 12H).

Step 2: (S)-12-fluoro-4-(4-methylpyrimidin-5-yl)-7a,8,13,14-tetrahydro-7H-[1,2,4]triazolo[4',3':1,6]pyrido[3,2-b]benzofuro[4,3-fg][1,4]oxazonine

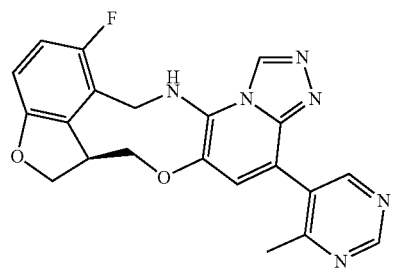 [SMILES: Cc1ncncc1-c1cc2c(n3cnnc13)NCc1c(F)ccc3c1[C@H](CO3)CO2]

To a solution of 4-methyl-5-(4,4,5,5-tetramethyl-1,3,2-dioxaborolan-2-yl)pyrimidine (56.3 mg, 256 umol, 2.00 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (50.0 mg, 128 umol, 1.00 eq) in dioxane (5 mL), water (0.5 mL) was added NaHCO₃ (53.7 mg, 639. umol, 24.9 uL, 5.00 eq), Pd(dppf)Cl₂ (9.35 mg, 12.8 umol, 0.100 eq) in 25° C., then the mixture was stirred at 80° C. for 6 h. LCMS showed the reaction was complete, starting material was consumed, desired target mass was detected. The mixture was concentrated under reduced pressure, dissolved in Ethyl acetate (20 mL), then filtered, the filtrate was concentrated under reduced pressure to afford crude product. The crude product was purified by prep-HPLC (column: Luna C18 100*30 5 u; mobile phase: [water (0.225% FA)—ACN]; B %: 20%-50%, 12 min). (S)-12-fluoro-4-(4-methylpyrimidin-S-yl)-7a,8,13,14-tetrahydro-7H-[1,2,4]triazolo[4',3':1,6]pyrido[3,2-b]benzofuro[4,3-fg][1,4]oxazonine (19.8 mg, 48.2 umol, 37% yield, 98.5% purity) was obtained as a white solid. $^1$H NMR DMSO-d$_6$ 400 MHz, δ=ppm 9.46 (s, 1H), 9.06 (s, 1H), 8.76 (s, 1H), 7.69-7.62 (m, 1H), 7.48 (s, 1H), 6.98 (br t, J=9.4 Hz, 1H), 6.71 (br dd, J=8.4, 3.5 Hz, 1H), 4.98-4.89 (m, 1H), 4.86-4.74 (m, 1H), 4.54 (br d, J=9.5 Hz, 1H), 4.52-4.45 (m, 1H), 4.22 (br dd, J=9.4, 3.4 Hz, 1H), 4.05 (br d, J=3.5 Hz, 1H), 3.95-3.83 (m, 1H), 2.41 (s, 3H). LCMS (ESI+): m/z 405.1 (M+H).

Example 36: (S)-12-fluoro-4-(2-methylpyrimidin-S-yl)-7a,8,13,14-tetrahydro-7H-[1,2,4]triazolo[4',3':1,6]pyrido[3,2-b]benzofuro[4,3-fg][1,4]oxazonine

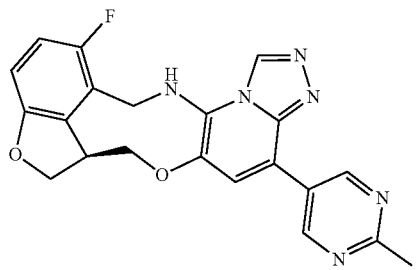 [SMILES: Cc1ncc(-c2cc3c(n4cnnc24)NCc2c(F)ccc4c2[C@H](CO4)CO3)cn1]

To a stirred solution of 2-methyl-S-(4,4,5,5-tetramethyl-1,3,2-dioxaborolan-2-yl)pyrimidine (45.0 mg, 205 umol, 2.00 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (40.0 mg, 102 umol, 1.00 eq) and NaHCO$_3$ (43.0 mg, 511 umol, 19.9 uL, 5.00 eq) in dioxane (3.00 mL) and water (0.60 mL) was added Pd(dppf)Cl$_2$ (7.48 mg, 10.2 umol, 0.100 eq) at 15° C. under N$_2$. The resulting mixture was stirred at 90° C. for 2 h. The mixture was concentrated under reduced pressure. The residue was purified by neutral prep-HPLC. (S)-12-fluoro-4-(2-methylpyrimidin-S-yl)-7a,8,13,14-tetrahydro-7H-[1,2,4]triazolo[4',3':1,6]pyrido[3,2-b]benzofuro[4,3-fg][1,4]oxazonine (8.20 mg, 19.5 umol, 19% yield, 96.0% purity) was obtained as a yellow solid. $^1$H NMR DMSO-d$_6$ 400 MHz, δ=ppm 9.48 (s, 3H), 7.93 (s, 1H), 7.73 (br s, 1H), 6.96 (t, J=9.3 Hz, 1H), 6.69 (dd, J=8.6, 3.9 Hz, 1H), 4.97-4.87 (m, 1H), 4.83 (br s, 1H), 4.54 (br t, J=9.2 Hz, 2H), 4.23 (dd, J=9.6, 3.2 Hz, 1H), 4.03 (br d, J=9.0 Hz, 1H), 3.99-3.90 (m, 1H), 2.66 (s, 3H). LCMS (ESI+): m/z 405.1 (M+H).

Example 37: (S)-4-(3-(difluoromethyl)-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 4-bromo-3-(difluoromethyl)-1-methyl-1H-pyrazole

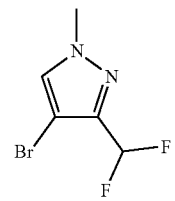

The reaction was set up as two separate batches. To a solution of 4-bromo-1-methyl-1H-pyrazole-3-carbaldehyde (450 mg, 2.38 mmol, 1.00 eq) in DCM (8 mL) was added DAST (2.30 g, 14.3 mmol, 1.89 mL, 6 eq) at 0° C., then the mixture was stirred at 20° C. for 5 h under nitrogen atmosphere. LCMS indicated that the complete conversion. The batches were combined, aq. NaHCO$_3$ (5%, 6 mL) was added dropwise to the reaction solution under ice bath cooling to adjust pH to 7-8, then the mixture was extracted with EtOAc (10 mL*3), the organic layers were dried over Na$_2$SO$_4$ and concentrated under reduced pressure. The residue was purified by column chromatography (SiO$_2$, Petroleum ether/Ethyl acetate=1/0 to 3/1; Petroleum ether/Ethyl acetate=3/1, R$_f$=0.4). 4-bromo-3-(difluoromethyl)-1-methyl-1H-pyrazole (830 mg, 3.93 mmol, 82% yield) was obtained as a light brown oil.

Step 2: (3-(difluoromethyl)-1-methyl-1H-pyrazol-4-yl)boronic Acid

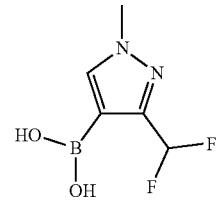

To a solution of 4-bromo-3-(difluoromethyl)-1-methyl-1H-pyrazole (400 mg, 1.90 mmol, 1.00 eq) in THF (10 mL) was added n-BuLi (2.5 M, 910 uL, 1.2 eq) at −78° C., the mixture was stirred at −78° C. for 0.5 hr, then triisopropyl borate (1.07 g, 5.69 mmol, 1.31 mL, 3.00 eq) was added to the mixture at −78° C., the mixture was stirred at −78° C. for 1.5 h. LCMS showed 4-bromo-3-(difluoromethyl)-1-methyl-1H-pyrazole was consumed completely and the desired mass was detected. Water (10 mL) was added to the mixture, then the mixture was concentrated. The residue was purified by prep-HPLC (column: Xbridge 150*30 mm*10 um; mobile phase: [water (0.1% TFA)—ACN]; B %: 1%-20%, 10 min). (3-(difluoromethyl)-1-methyl-1H-pyrazol-4-yl)boronic acid (110 mg, 625 umol, 32% yield) was obtained as a white solid.

Step 3: (S)-4-(3-(difluoromethyl)-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine

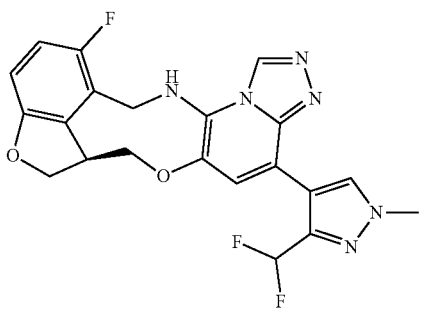 [SMILES: Cn1cc(-c2cc3c(n4cnnc24)NCc2c(F)ccc4c2[C@H](CO4)CO3)c(C(F)F)n1]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (60.0 mg, 153.4 umol, 1.00 eq) in dioxane (1 mL), water (0.1 mL) was added (3-(difluoromethyl)-1-methyl-1H-pyrazol-4-yl)boronic acid (67.5 mg, 383 umol, 2.5 eq), Pd(dppf)Cl$_2$ (11.2 mg, 15.3 umol, 0.100 eq) and NaHCO$_3$ (64.4 mg, 767 umol, 29.8 uL, 5.00 eq) at 20° C., the mixture was stirred at 80° C. for 12 h under N$_2$. LC-MS showed that (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was consumed completely and the desired mass was detected. The reaction was filtered, the filtrate was concentrated. The residue was purified by prep-HPLC (column: Luna C18 100*30 5 u; mobile phase: [water (0.2% FA)—ACN]; B %: 35%-45%, 12 min). (S)-4-(3-(difluoromethyl)-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine (25.0 mg, 56.0 umol, 36% yield, 99.1% purity) was obtained as a yellow solid. $^1$H NMR DMSO-d$_6$ 400 MHz, δ=ppm 9.43 (s, 1H), 8.61 (s, 1H), 7.47 (br t, J=6.4 Hz, 1H), 7.41 (s, 1H), 7.24 (t, J=54.0 Hz, 1H), 6.99-6.91 (m, 1H), 6.69 (dd, J=8.6, 3.9 Hz, 1H), 4.93-4.73 (m, 2H), 4.57-4.42 (m, 2H), 4.24 (dd, J=9.5, 3.3 Hz, 1H), 4.04 (br s, 1H), 3.96 (s, 3H), 3.89-3.80 (m, 1H). $^1$H NMR CDCl$_3$ 400 MHz, δ=ppm 8.77 (s, 1H), 8.73 (s, 1H), 7.47 (br t, J=6.4 Hz, 1H), 7.41 (s, 1H), 6.92-6.82 (m, 1H), 6.85 (t, J=54.0 Hz, 1H), 6.67 (dd, J=8.6, 3.9 Hz, 1H), 5.13-5.05 (m, 1H), 4.88-4.80 (m, 1H), 4.70-4.60 (m, 2H), 4.30 (dd, J=9.5, 3.3 Hz, 1H), 3.99 (s, 3H), 3.97-3.80 (m, 2H). LCMS (ESI+): m/z 443.1 (M+H).

Example 38: (S)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one and (R)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one

Step 1: 1-methyl-4-(4,4,5,5-tetramethyl-1,3,2-dioxaborolan-2-yl)pyridin-2 (1H)-one

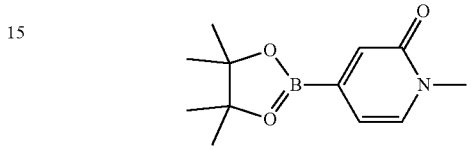

To a solution of 4-bromo-1-methylpyridin-2 (1H)-one (950 mg, 5.05 mmol, 1.00 eq) in dioxane (50 mL) was added KOAc (1.49 g, 15.2 mmol, 3.00 eq), 4,4,4',4',5,5,5',5'-octamethyl-2,2'-bi(1,3,2-dioxaborolane) (1.80 g, 7.07 mmol, 1.4 eq) and Pd(dppf)Cl$_2$.DCM (413 mg, 505 umol, 0.100 eq). The mixture was stirred at 110° C. for 2 hrs under nitrogen atmosphere. LCMS showed the starting material was consumed completely and the desired MS was detected. The reaction mixture was concentrated under reduced pressure to give a residue. The residue was purified by column chromatography (SiO$_2$, Ethyl acetate:Methanol=0:1 to 1:0). 1-methyl-4-(4,4,5,5-tetramethyl-1,3,2-dioxaborolan-2-yl)pyridin-2 (1H)-one (650 mg, crude) was obtained as yellow oil. $^1$H NMR CDCl$_3$ 400 MHz, δ=ppm 7.27-7.21 (m, 1H), 7.01 (s, 1H), 6.40 (d, J=6.6 Hz, 1H), 3.53 (s, 3H), 1.31 (s, 12H).

Step 2: (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2 (1H)-one

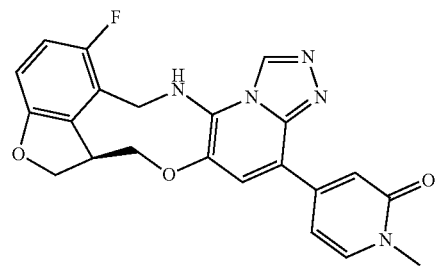 [SMILES: Cn1ccc(-c2cc3c(n4cnnc24)NCc2c(F)ccc4c2[C@H](CO4)CO3)cc1=O]

To a solution of 1-methyl-4-(4,4,5,5-tetramethyl-1,3,2-dioxaborolan-2-yl)pyridin-2 (1H)-one (397 mg, 1.69 mmol, 2.2 eq) in dioxane (10 mL) and water (2 mL) was added NaHCO$_3$ (193 mg, 2.30 mmol, 89.5 uL, 3.00 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (Example 17; 300 mg, 767 umol, 1.00 eq) and Pd(dppf)Cl$_2$ (56.1 mg, 76.7 umol, 0.100 eq) under nitrogen atmosphere. The mixture was stirred at 80° C. for 8 hrs. LCMS showed the starting material was consumed completely and the desired MS was detected. The reaction mixture was filtered and the filter cake was washed by MeOH (20 mL). The filter cake was dried under reduced pressure to give a crude product. The crude product was used to the next step without further purification. (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2 (1H)-one (280 mg, crude) was obtained as a green solid. $^1$H NMR DMSO-$d_6$ 400 MHz, δ=ppm 9.39 (s, 1H), 7.80 (s, 1H), 7.63 (s, 1H), 7.56 (s, 1H), 7.01 (s, 1H), 6.92 (s, 1H), 6.65 (s, 1H), 4.89 (s, 2H), 4.51 (s, 2H), 4.04-3.90 (m, 2H), 4.04-3.89 (m, 3H), 3.32 (s, 3H).

Step 3: (S)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one and (R)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one

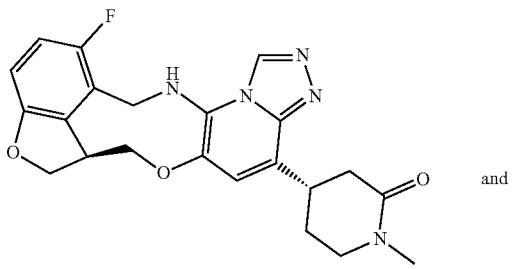

and

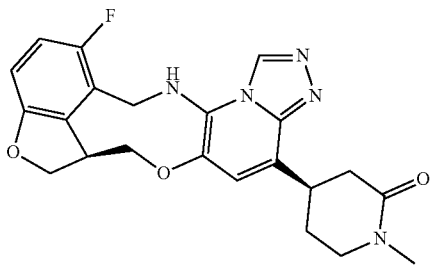

To a solution of (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2 (1H)-one (190 mg, 453 umol, 1.00 eq) in MeOH (20 mL) was added AcOH (10.5 g, 175 mmol, 10.0 mL, 386 eq) and 10% Pd/C (200 mg, 50% purity at 20° C. The mixture was stirred at 50° C. for 5 hrs under H$_2$ (15 Psi) atmosphere. LCMS showed most of the starting material was consumed and the desired MS was detected. The reaction mixture was filtered and the filtrate was concentrated under reduced pressure to give a residue. The residue was purified by prep-HPLC (formic acid conditions) to give 4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one (120 mg). The diastereomers were separated by chrial SFC. Column conditions:Waters Prep 80Q SFC; Chiralpak AD, 250*30 mm i.d. 10 u; Mobile phase A for CO$_2$; Mobile phase B for MeOH (0.1% NH$_3$H$_2$O)—CH$_3$CN (2:1); Gradient, B %=50%; Flow rate, 80 g/min; 40° C.; 100 bar. [0887]

(S)-4-((S)-12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpiperidin-2-one (54.4 mg, 126.6 umol, 27% yield, 98.6% purity) (Rt=1.71 min) was obtained as a yellow solid. $^1$H NMR DMSO-$d_6$ 400 MHz, δ=ppm 9.35 (s, 1H), 7.22 (t, J=6.2 Hz, 1H), 7.09 (s, 1H), 6.93 (t, J=9.5 Hz, 1H), 6.68 (dd, J=8.6, 3.7 Hz, 1H), 4.87-4.80 (m, 1H), 4.75-4.67 (m, 1H), 4.52 (t, J=9.4 Hz, 1H), 4.44 (d, J=6.4 Hz, 1H), 4.21 (dd, J=9.6, 3.1 Hz, 1H), 4.04-3.95 (m, 1H), 3.84-3.76 (m, 1H), 3.49-3.39 (m, 2H), 3.32-3.25 (m, 1H), 2.86 (s, 3H), 2.60 (d, J=8.3 Hz, 2H), 2.16-2.06 (m, 2H). LCMS (ESI+): m/z 424.2 (M+H). [0888] (R)-4-((S)-12-fluoro-7a,8,13,14-tetrahydro-7H-[1,2,4]triazolo[4',3':1,6]pyrido [3,2-b]benzofuro[4,3-fg][1,4]oxazonin-4-yl)-1-methylpiperidin-2-one (41.6 mg, 93.64 umol, 20% yield, 95.254% purity) (Rt=2.44 min) was obtained as a white solid. $^1$H NMR ET15715-773-P2B2 DMSO-$d_6$ 400 MHz, δ=ppm 9.36 (s, 1H), 7.23 (t, J=6.1 Hz, 1H), 7.08 (s, 1H), 6.93 (t, J=9.5 Hz, 1H), 6.67 (dd, J=8.6, 3.7 Hz, 1H), 4.84 (dd, J=15.0, 5.7 Hz, 1H), 4.73-4.65 (m, 1H), 4.52 (t, J=9.4 Hz, 1H), 4.46 (d, J=5.6 Hz, 1H), 4.23 (dd, J=9.5, 2.8 Hz, 1H), 3.98 (br s, 1H), 3.85-3.77 (m, 1H), 3.43 (dd, J=10.4, 5.5 Hz, 2H), 3.32-3.28 (m, 1H), 2.86 (s, 3H), 2.60-2.56 (m, 2H), 2.18-2.10 (m, 2H). LCMS (ESI+): m/z 424.2 (M+H).

Example 39: methyl 4-(12-fluoro-6,8,13,14-tetrahydro-[1,2,4]triazolo[4',3':1,6]pyrido[3,2-c]benzo[g][1,5]oxazonin-4-yl)piperidine-1-carboxylate Methanesulfonyl Salt Step 1: tert-butyl 12-fluoro-4-(1-(methoxycarbonyl)-1,2,3,6-tetrahydropyridin-4-yl)-8,13-dihydro-[1,2,4]triazolo[4',3':1,6]pyrido[3,2-c]benzo[g][,5]oxazonine-14 (6H)-carboxylate 1,4-Dioxane (3.00 mL) and water (0.600 mL) were added to a mixture of tert-butyl 4-bromo-12-fluoro-8,13-dihydro-[1,2,4]triazolo[4',3':1,6]pyrido[3,2-c]benzo[g][1,5]oxazonine-14 (6H)-carboxylate (from Example 24; 99.0 mg, 0.214 mmol), methyl 4-(4,4,5,5-tetramethyl-1,3,2-dioxaborolan-2-yl)-3,6-dihydro-2H-pyridine-1-carboxylate (68.5 mg, 0.256 mmol), Pd(dppf)Cl$_2$ (15.6 mg, 0.0214 mmol), and NaHCO$_3$ (53.9 mg, 0.641 mmol) under nitrogen. The mixture was heated to 90° C. for 2.5 h. After cooling to 23° C., the mixture was filtered though a silica plug which was then washed with EtOAc and 10% MeOH in DCM. The combined filtrates were concentrated under reduced pressure. The product was purified by silica gel chromatography (12 g cartridge) eluting with DCM and MeOH (0-10%) to provide tert-butyl 12-fluoro-4-(1-(methoxycarbonyl)-1,2,3,6-tetrahydropyridin-4-yl)-8,13-dihydro-[1,2,4]triazolo[4',3':1,6]pyrido[3,2-c]benzo[g][1,5]oxazonine-14 (6H)-carboxylate as a solid (107 mg, 77%). Complex NMR (rotamers). m/z (ES+), [M+H]$^+$: 524.2. HPLC (A05) $t_R$=2.37 min.

Step 2: tert-butyl 12-fluoro-4-(1-(methoxycarbonyl) piperidin-4-yl)-8,13-dihydro-[1,2,4]triazolo[4',3':1,6] pyrido[3,2-c]benzo[g][1,5]oxazonine-14 (6H)-carboxylate

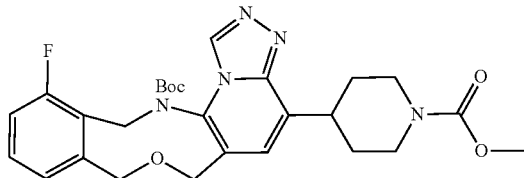

A solution of tert-butyl 12-fluoro-4-(1-(methoxycarbonyl)-1,2,3,6-tetrahydropyridin-4-yl)-8,13-dihydro-[1,2,4] triazolo[4',3':1,6]pyrido[3,2-c]benzo[g][1,5]oxazonine-14 (6H)-carboxylate (102 mg, 156 μmol) in MeOH (12.0 mL) was added at 23° C. to a flask charged with 10% Pd/C (65.9 mg, 0.0619 mmol) under nitrogen atmosphere. The flask was evacuated and purged with $H_2$ gas 3 times. The mixture was stirred at 23° C. for 1.5 h and filtered through Celite washing with MeOH. The filtrate was concentrated under reduced pressure. The product was purified by silica gel chromatography (12 g) eluting with DCM and MeOH (0-10%) to provide tert-butyl 12-fluoro-4-(1-(methoxycarbonyl)piperidin-4-yl)-8,13-dihydro-[1,2,4]triazolo[4',3':1,6]pyrido[3,2-c]benzo[g][1,5]oxazonine-14 (6H)-carboxylate as a solid (69.0 mg, 84%). Complex NMR (rotamers). m/z (ES+) [M+H]$^+$: 526.2. HPLC (A05) $t_R$=2.33 min.

Step 3: methyl 4-(12-fluoro-6,8,13,14-tetrahydro-[1,2,4]triazolo[4',3':1,6]pyrido[3,2-c]benzo[g][1,5]oxazonin-4-yl)piperidine-1-carboxylate Mesylate

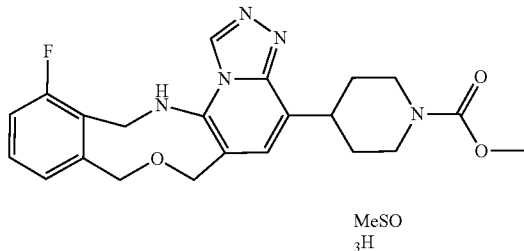 [SMILES: COC(=O)N1CCC(c2cc3c(n4cnnc24)NCc2c(F)cccc2COC3)CC1]

A solution of tert-butyl 12-fluoro-4-(1-(methoxycarbonyl)piperidin-4-yl)-8,13-dihydro-[1,2,4]triazolo[4',3':1,6] pyrido[3,2-c]benzo[g][1,5]oxazonine-14 (6H)-carboxylate (69.0 mg, 0.131 mmol) in HFIP (4.00 mL) was heated to 100° C. for 12 h. After cooling to 23° C., the mixture was concentrated under reduced pressure. The product was purified by silica gel chromatography (12 g cartridge) eluting with DCM and MeOH (0-10%) to provide the free base of the title compound as a solid (48.0 mg; 86%). $^1$H NMR (500 MHz, MeOD) δ 9.39 (s, 1H), 7.29 (td, J=7.9, 5.7 Hz, 1H), 7.16 (d, J=7.6 Hz, 1H), 7.14 (s, 1H), 7.03 (t, J=9.0 Hz, 1H), 4.73 (s, 2H), 4.68 (s, 2H), 4.52 (s, 2H), 4.26 (d, J=10.7 Hz, 2H), 3.71 (s, 3H), 3.29-3.24 (m, 1H), 3.08-2.92 (m, 2H), 1.99 (d, J=12.9 Hz, 2H), 1.70 (qd, J=12.6, 4.1 Hz, 2H). The compound was converted to the methanesulfonyl salt by addition of MeSO$_3$H (3.36 μL, 51.7 mmol) to a solution the free base (22.0 mg, 0.0517 mmol) in MeCN (2.00 mL). The mixture was stirred at 23° C. for 1 h. The mixture was concentrated under reduced pressure to provide the title compound as a solid (24.0 mg, 89%). $^1$H NMR MeOD 500 MHz, δ 9.74 (s, 1H), 7.85 (s, 1H), 7.37 (td, J=8.0, 5.7 Hz, 1H), 7.20-7.04 (m, 2H), 4.94 (s, 2H), 4.93 (s, 2H), 4.61 (s, 2H), 4.31 (d, J=12.2 Hz, 2H), 3.72 (s, 3H), 3.19-3.07 (m, 1H), 3.06-2.94 (m, 2H), 2.70 (s, 3H), 1.93 (d, J=13.1 Hz, 2H), 1.74 (qd, J=12.4, 4.1 Hz, 2H). m/z (ES+), [M+H]$^+$: 426.5. HPLC (A05) $t_R$=2.15 min.

Example 40: (S)-4-ethyl-12-fluoro-7a,8,13,14-tetrahydro-7H-[1,2,4]triazolo[4',3':1,6]pyrido[3,2-b]benzofuro[4,3-fg][1,4]oxazonine Step 1: (S)-12-fluoro-4-vinyl-7a,8,13,14-tetrahydro-7H-[1,2,4]triazolo[4',3':1,6]pyrido[3,2-b]benzofuro[4,3-fg][1,4]oxazonine

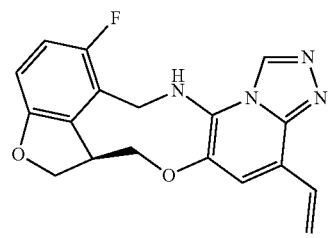 [SMILES: C=Cc1cc2c(n3cnnc13)NCc1c(F)ccc3c1[C@H](CO3)CO2]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 255.63 umol, 1.00 eq), 4,4,5,5-tetramethyl-2-vinyl-1,3,2-dioxaborolane (78.7 mg, 511 umol, 86.7 uL, 2.00 eq) and NaHCO$_3$ (107 mg, 1.28 mmol, 49.7 uL, 5.00 eq) in dioxane (2 mL) and water (0.2 mL) was added Pd(dppf)Cl$_2$ (18.70 mg, 25.56 umol, 0.100 eq) at 25° C. The resulting mixture was stirred at 80° C. under nitrogen for 2.5 h. The mixture was concentrated under reduced pressure. The residue was purified by prep-TLC (SiO$_2$, EtOAc:MeOH=20:1). (S)-12-fluoro-4-vinyl-7a,8,13,14-tetrahydro-7H-[1,2,4]triazolo[4',3':1,6]pyrido[3,2-b]benzofuro[4,3-fg][1,4]oxazonine (100 mg, crude) was obtained as yellow solid.

Step 2: (S)-4-ethyl-12-fluoro-7a,8,13,14-tetrahydro-7H-[1,2,4]triazolo[4',3':1,6]pyrido[3,2-b]benzofuro[4,3-fg][1,4]oxazonine

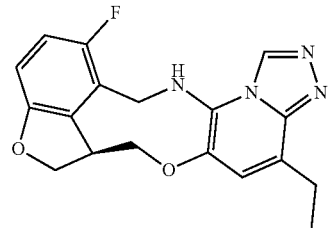 [SMILES: CCc1cc2c(n3cnnc13)NCc1c(F)ccc3c1[C@H](CO3)CO2]

To a solution of (S)-12-fluoro-4-vinyl-7a,8,13,14-tetrahydro-7H-[1,2,4]triazolo[4',3':1,6]pyrido[3,2-b]benzofuro[4,3-fg][1,4]oxazonine (90.0 mg, 266 umol, 1.00 eq) in MeOH (4 mL) was added 10% Pd/C (90.0 mg, 50% purity) at 25° C. The mixture was stirred at 40° C. under H$_2$ (15 psi) for 1 hr. The mixture was filtered and the filtrate was concentrated under reduced pressure. The residue was purified by acidic prep-HPLC (column: Luna C18 100*30 5 u; mobile phase: [water (0.225% FA)—ACN]; B %: 10%-50%, 12 min). (S)-4-ethyl-12-fluoro-7a,8,13,14-tetrahydro-7H-[1,2,4]triazolo[4',3':1,6]pyrido[3,2-b]benzofuro[4,3-fg] [1,4]oxazonine (11.7 mg, 32.9 umol, 12% yield, 95.6% purity) was obtained as a white solid. $^1$H NMR CDCl$_3$ 400 MHz, δ=ppm 8.68 (s, 1H), 6.80 (s, 1H), 6.80-6.72 (m, 1H), 6.56 (dd, J=8.6, 3.9 Hz, 1H), 4.92 (br dd, J=14.5, 7.4 Hz, 1H), 4.70 (br dd, J=14.5, 5.7 Hz, 1H), 4.58-4.45 (m, 3H), 4.17 (dd, J=9.6, 2.6 Hz, 1H), 3.86-3.71 (m, 2H), 2.97-2.82 (m, 2H), 1.27 (t, J=7.5 Hz, 3H). LCMS (ESI+): m/z 341.1 (M+H).

Example 41: (S)-12-fluoro-4-(1H-pyrazol-1-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(1H-pyrazol-1-yl)-7a,13-dihydro-7H-[1,2,4]triazolo[4',3':1,6]pyrido[3,2-b]benzofuro[4,3-fg][1,4]oxazonine-14 (8H)-carboxylate

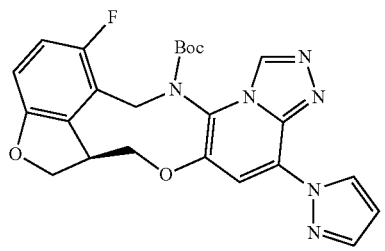 [SMILES: CC(C)(C)OC(=O)N1Cc2c(F)ccc3c2[C@H](CO3)COc2cc(-n3cccn3)c3nncn3c21]

A flask was charged with tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (0.120 g, 244 umol, 1.00 eq), 1H-pyrazole (24.9 mg, 366 umol, 1.5 eq) and K$_3$PO$_4$ (104 mg, 488 umol, 2.00 eq) at 15° C. and purged with N$_2$. Another flask was charged with Pd$_2$(dba)$_3$ (11.2 mg, 12.2 umol, 0.0500 eq) and ditert-butyl-[2,3,4,5-tetramethyl-6-(2,4,6-triisopropylphenyl)phenyl]phosphane (11.7 mg, 24.4 umol, 0.100 eq), toluene (2.00 mL) and dioxane (0.400 mL) were added at 15° C., then purged with nitrogen and heated at 120° C. for 0.05 hr, then it cooled to 15° C. The obtained mixture (per-catalyst) was added to the first mixture via syringe. The resulting mixture was stirred at 120° C. for 10 h. LC-MS indicated complete conversion. The reaction mixture was concentrated under reduced pressure. The residue was purified by prep-TLC (SiO$_2$, Petroleum ether/Ethyl acetate=1/1). tert-butyl (S)-12-fluoro-4-(1H-pyrazol-1-yl)-7a,13-dihydro-7H-[1,2,4]triazolo[4',3':1,6]pyrido[3,2-b]benzofuro[4,3-fg][1,4]oxazonine-14 (8H)-carboxylate (0.070 g, 146 umol, 59% yield) was obtained as a brown solid.

Step 2: (S)-12-fluoro-4-(1H-pyrazol-1-yl)-7a,8,13,14-tetrahydro-7H-[1,2,4]triazolo[4',3':1,6]pyrido[3,2-b]benzofuro[4,3-fg][1,4]oxazonine

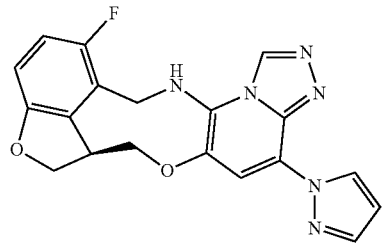 [SMILES: Fc1ccc2c3c1CNc1c(cc(-n4cccn4)c4nncn14)OC[C@H]3CO2]

A mixture of tert-butyl (S)-12-fluoro-4-(1H-pyrazol-1-yl)-7a,13-dihydro-7H-[1,2,4]triazolo[4',3':1,6]pyrido[3,2-b]benzofuro[4,3-fg][1,4]oxazonine-14 (8H)-carboxylate (0.0700 g, 146 umol, 1.00 eq) in HFIP (2 mL) was stirred at 80° C. for 12 h under nitrogen atmosphere. LC-MS indicated complete conversion. The reaction mixture was blown to dryness by nitrogen stream. The residue was purified by prep-HPLC (formic acid conditions). (S)-12-fluoro-4-(1H-pyrazol-1-yl)-7a,8,13,14-tetrahydro-7H-[1,2,4]triazolo[4',3':1,6]pyrido[3,2-b]benzofuro[4,3-fg][1,4]oxazonine (15.3 mg, 34.9 umol, 23% yield, 96.8% purity, formate salt) was obtained as a yellow solid. $^1$H NMR DMSO-d$_6$ 400 MHz, δ=ppm 9.52 (s, 1H), 9.05 (d, J=1.96 Hz, 1H), 7.80 (s, 1H), 7.78 (s, 1H), 7.50 (br t, J=6.11 Hz, 1H), 6.94 (br t, J=9.54 Hz, 1H), 6.67 (dd, J=8.56, 3.67 Hz, 1H), 6.56 (d, J=1.96 Hz, 1H), 4.95-4.83 (m, 1H), 4.82-4.71 (m, 1H), 4.58-4.45 (m, 2H), 4.23 (br dd, J=9.41, 3.06 Hz, 1H), 4.04 (br s, 1H), 3.92-3.81 (m, 1H). LCMS (ESI+): m/z 379.1 (M+H).

Example 42: (S)-4-(1,5-dimethyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine

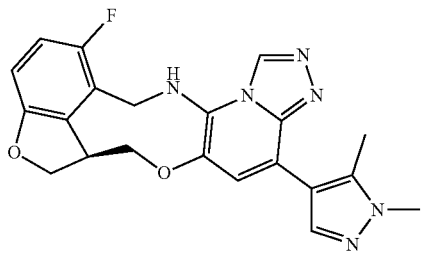 [SMILES: Cc1c(-c2cc3c(n4cnnc24)NCc2c(F)ccc4c2[C@H](CO4)CO3)cnn1C]

To a mixture of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq) and 1,5-dimethyl-4-(4,4,5,5-tetramethyl-1,3,2-dioxaborolan-2-yl)-1H-pyrazole (85.2 mg, 383 umol, 1.5 eq) in EtOH (3.5 mL) and water (0.5 mL) was added KOAc (50.2 mg, 511 umol, 2.00 eq), 4-ditert-butylphosphanyl-N,N-dimethyl-aniline; dichloropalladium (18.1 mg, 25.6 umol, 18.1 uL, 0.100 eq) in one portion at 25° C. under N$_2$. The mixture was stirred at 80° C. for 16 h under N$_2$. LC-MS showed no (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was remained. Several new peaks were shown on LC-MS and the desired MS was detected. The reaction mixture was filtered and the filtrate was concentrated under reduced pressure. The residue was purified by prep-HPLC (column: Waters Xbridge 150*25 5 u; mobile phase: [water (10 mM NH$_4$HCO$_3$)—ACN]; B %: 10%-40%, 10 min). (S)-4-(1,5-dimethyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine (13.21 mg, 32.13 umol, 12% yield, 98.9% purity) was obtained as a white solid. $^1$H NMR DMSO-d$_6$ 400 MHz, δ=ppm 9.37 (s, 1H), 7.83 (s, 1H), 7.27 (t, J=6.3 Hz, 1H), 7.16 (s, 1H), 7.01-6.89 (m, 1H), 6.68 (dd, J=8.7, 3.9 Hz, 1H), 4.92-4.82 (m, 1H), 4.79-4.69 (m, 1H), 4.58-4.41 (m, 2H), 4.21 (dd, J=9.6, 3.2 Hz, 1H), 4.11-3.96 (m, 1H), 3.92-3.83 (m, 1H), 3.80 (s, 3H), 2.37 (s, 3H). LCMS (ESI+): m/z 407.1 (M+H).

Example 43: (S)-4-(2,3-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 2,3-dimethyl-4-(4,4,5,5-tetramethyl-1,3,2-dioxaborolan-2-yl)pyridine

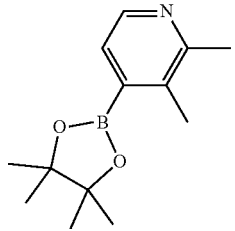

To a mixture of 4-bromo-2,3-dimethylpyridine (0.81 g, 4.35 mmol, 1.00 eq), KOAc (855 mg, 8.71 mmol, 2.00 eq) and 4,4,4',4',5,5,5',5'-octamethyl-2,2'-bi(1,3,2-dioxaborolane) (2.21 g, 8.71 mmol, 2.00 eq) in dioxane (20 mL) was added Pd(dppf)Cl$_2$ (320 mg, 437 umol, 0.100 eq) in one portion at 18° C. under N$_2$. The mixture was stirred at 110° C. for 15 h The mixture was evaporated to obtain the product. The residue was purified by column chromatography (SiO$_2$, Petroleum ether/Ethyl acetate=1/0 to 0/1, Petroleum ether/Ethyl acetate=0:1, R$_f$=0.06). 2,3-dimethyl-4-(4,4,5,5-tetramethyl-1,3,2-dioxaborolan-2-yl)pyridine (400 mg, 1.72 mmol, 39% yield) was obtained as a white solid.

Step 2: (S)-4-(2,3-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine

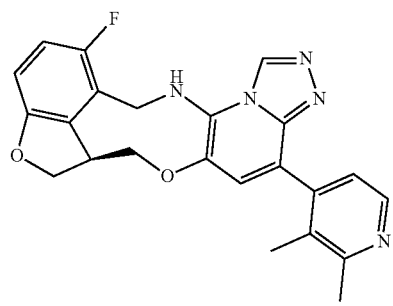 [SMILES: Cc1nccc(-c2cc3c(n4cnnc24)NCc2c(F)ccc4c2[C@H](CO4)CO3)c1C]

To a mixture of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (50 mg, 127.81 umol, 1.00 eq), NaHCO$_3$ (53.7 mg, 639 umol, 24.9 uL, 5.00 eq) and 2,3-dimethyl-4-(4,4,5,5-tetramethyl-1,3,2-dioxaborolan-2-yl)pyridine (89.4 mg, 383.4 umol, 3.00 eq) in dioxane (5 mL) and water (0.5 mL) was added Pd(dppf)Cl$_2$ (9.35 mg, 12.8 umol, 0.100 eq) in one portion at 15° C. under N$_2$. The mixture was stirred at 80° C. for 2 h. LCMS showed that the starting material was consumed completely. The mixture was evaporated to obtain the crude product. The residue was purified by prep-HPLC (neutral condition:column: Nano-micro Kromasil C18 100*30 mm 5 um; mobile phase: [water (10 mM NH$_4$HCO$_3$)—ACN]; B %: 35%-52%, 10 min). (S)-4-(2,3-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine (25.7 mg, 61.2 umol, 47% yield, 99.4% purity) was obtained as a yellow solid. $^1$H NMR DMSO-d$_6$ 400 MHz, δ=ppm 9.42 (s, 1H), 8.28 (d, J=5.1 Hz, 1H), 7.54 (br t, J=6.2 Hz, 1H), 7.28 (s, 1H), 7.20 (d, J=5.0 Hz, 1H), 7.00-6.92 (m, 1H), 6.70 (dd, J=8.6, 3.9 Hz, 1H), 4.96-4.87 (m, 1H), 4.84-4.74 (m, 1H), 4.54 (t, J=9.4 Hz, 1H), 4.46 (br d, J=5.9 Hz, 1H), 4.20 (dd, J=9.5, 3.5 Hz, 1H), 4.09-3.99 (m, 1H), 3.90-3.80 (m, 1H), 2.50 (s, 3H), 2.07 (s, 3H). $^1$H NMR CD$_3$OD 400 MHz, δ=ppm 9.71 (s, 1H), 8.65 (d, J=6.1 Hz, 1H), 8.17 (s, 1H), 7.96 (d, J=6.1 Hz, 1H), 6.99-6.88 (m, 1H), 6.69 (dd, J=8.7, 3.8 Hz, 1H), 5.23 (br d, J=14.8 Hz, 1H), 5.02 (br d, J=14.9 Hz, 1H), 4.78 (br s, 1H), 4.63 (t, J=9.5 Hz, 1H), 4.32 (dd, J=9.7, 3.2 Hz, 1H), 4.10 (br d, J=9.5 Hz, 1H), 4.02-3.92 (m, 1H), 2.87 (s, 3H), 2.36 (s, 3H). LCMS (ESI+): m/z 418.2 (M+H).

Example 44: (S)-12-fluoro-4-(6-methoxypyridin-3-yl)-7a,8,13,14-tetrahydro-7H-[1,2,4]triazolo[4',3':1,6]pyrido[3,2-b]benzofuro[4,3-fg][1,4]oxazonine

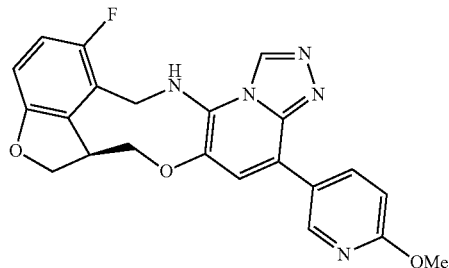 [SMILES: COc1ccc(-c2cc3c(n4cnnc24)NCc2c(F)ccc4c2[C@H](CO4)CO3)cn1]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (50.0 mg, 128 umol, 1.00 eq), 2-methoxy-S-(4,4,5,5-tetramethyl-1,3,2-dioxaborolan-2-yl)pyridine (90.1 mg, 383 umol, 3.00 eq) in dioxane (3 mL) and water (0.3 mL) were added Na$_2$CO$_3$ (27.1 mg, 256 umol, 2.00 eq) and Pd(PPh$_3$)$_4$ (14.77 mg, 12.78 umol, 0.100 eq) at 25° C. The mixture was stirred at 90° C. for 12 h. LC-MS showed no (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was remained. Several new peaks were shown on LC-MS and the desired MS was detected. The reaction mixture was filtered and the filtrate was concentrated under reduced pressure. The residue was purified by prep-HPLC (column: Waters Xbridge 150*25 5 u; mobile phase: [water (10 mM NH$_4$HCO$_3$)-ACN]; B %: 20%-50%, 10 min). (S)-12-fluoro-4-(6-methoxypyridin-3-yl)-7a,8,13, 14-tetrahydro-7H-[1,2,4]triazolo[4',3':1,6]pyrido[3,2-b]benzofuro[4,3-fg][1,4]oxazonine (19.10 mg, 44.33 umol, 34% yield, 97.4% purity) was obtained as a white solid. $^1$H NMR DMSO-$d_6$ 400 MHz, δ=ppm 9.44 (s, 1H), 8.98 (d, J=2.4 Hz, 1H), 8.48 (dd, J=8.7, 2.5 Hz, 1H), 7.67 (s, 1H), 7.50 (br t, J=6.3 Hz, 1H), 6.99-6.87 (m, 2H), 6.68 (dd, J=8.6, 3.7 Hz, 1H), 4.94-4.84 (m, 1H), 4.83-4.72 (m, 1H), 4.58-4.46 (m, 2H), 4.21 (dd, J=9.7, 3.3 Hz, 1H), 4.10-3.98 (m, 1H), 3.94 (br d, J=11.0 Hz, 1H), 3.90 (s, 3H). LCMS (ESI+): m/z 420.2 (M+H).

Example 45: (S)-4-(6-ethyl-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 5-bromo-2-ethyl-4-methylpyridine

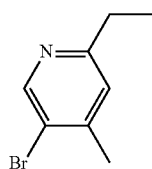

To a stirred solution of 2,5-dibromo-4-methylpyridine (2.00 g, 7.97 mmol, 1.00 eq.) and ZnEt$_2$ (1 M, 4.78 mL, 0.6 eq.) in THF (15.0 mL) was added Pd(PPh$_3$)$_4$ (92.1 mg, 79.7 umol, 0.01 eq.) at 0° C. under N$_2$. The resulting mixture was stirred at 70° C. for 1 hr. The mixture was added to saturated aqueous NaHCO$_3$ solution (30 mL) and then the mixture was extracted with EtOAc (20 mL*3) and the combined organic layers were dried over Na$_2$SO$_4$ and then concentrated under reduced pressure. The mixture was purified by MPLC (SiO$_2$, PE/EtOAc=1/0 to 5/1). 5-bromo-2-ethyl-4-methylpyridine (720 mg, 3.60 mmol, 45% yield) was obtained as colourless oil. $^1$H NMR CDCl$_3$ 400 MHz, δ=ppm 8.54 (s, 1H), 7.05 (s, 1H), 2.75 (q, J=7.5 Hz, 2H), 2.37 (s, 3H), 1.29 (t, J=7.6 Hz, 3H).

Step 2: 2-ethyl-4-methyl-S-(4,4,5,5-tetramethyl-1,3,2-dioxaborolan-2-yl)pyridine

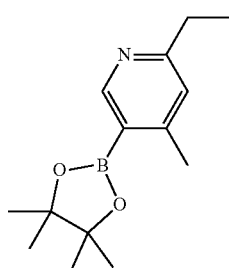

To a stirred solution of 5-bromo-2-ethyl-4-methylpyridine (290 mg, 1.45 mmol, 1.00 eq.), 4,4,5,5-tetramethyl-2-(4,4,5,5-tetramethyl-1,3,2-dioxaborolan-2-yl)-1,3,2-dioxaborolane (1.47 g, 5.80 mmol, 4.00 eq.) and KOAc (285 mg, 2.90 mmol, 2.00 eq) in dioxane (15.00 mL) was added Pd(dppf)Cl$_2$.DCM (237 mg, 290 umol, 0.20 eq) at 15° C. under N$_2$. The resulting mixture was stirred at 80° C. for 8 h. LCMS showed 5-bromo-2-ethyl-4-methylpyridine was consumed and the desired mass was detected. The mixture was concentrated under reduced pressure. The mixture was purified by MPLC (SiO$_2$, PE/EtOAc=1/1 to EtOAc/MeOH=1/1). 2-ethyl-4-methyl-S-(4,4,5,5-tetramethyl-1,3,2-dioxaborolan-2-yl)pyridine (200 mg, 809 umol, 55% yield) was obtained as brown oil. $^1$H NMR CDCl$_3$ 400 MHz, δ=ppm 8.76 (s, 1H), 6.96 (s, 1H), 2.78 (q, J=7.6 Hz, 2H), 2.50 (s, 3H), 1.27-1.25 (m, 15H).

Step 3: (S)-4-(6-ethyl-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

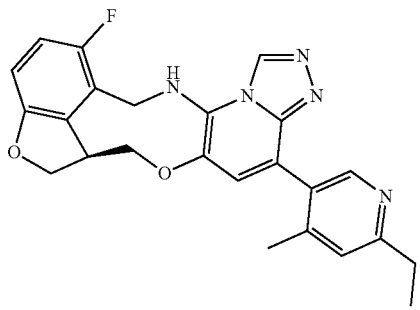 [SMILES: CCc1cc(C)c(-c2cc3c(n4cnnc24)NCc2c(F)ccc4c2[C@H](CO4)CO3)cn1]

To a stirred solution of 2-ethyl-4-methyl-S-(4,4,5,5-tetramethyl-1,3,2-dioxaborolan-2-yl)pyridine (126 mg, 511 umol, 4.00 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (50.0 mg, 128 umol, 1.00 eq) and NaHCO$_3$ (53.7 mg, 639 umol, 24.9 uL, 5.00 eq) in dioxane (4.00 mL) and water (0.80 mL) was added Pd(dppf)Cl$_2$ (9.35 mg, 12.8 umol, 0.100 eq) at 15° C. under N$_2$. The resulting mixture was stirred at 90° C. for 5 h. The mixture was concentrated under reduced pressure. The mixture was purified by neutral prep-HPLC. (S)-4-(6-ethyl-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (21.7 mg, 49.4 umol, 38% yield, 98.1% purity) was obtained as a white solid. $^1$H NMR DMSO-$d_6$ 400 MHz, δ=ppm 9.42 (s, 1H), 8.38 (s, 1H), 7.49 (br t, J=6.4 Hz, 1H), 7.30 (s, 1H), 7.22 (s, 1H), 7.02-6.92 (m, 1H), 6.71 (dd, J=8.6, 3.9 Hz, 1H), 4.96-4.86 (m, 1H), 4.83-4.75 (m, 1H), 4.55 (t, J=9.3 Hz, 1H), 4.47 (br d, J=6.6 Hz, 1H), 4.21 (dd, J=9.4, 3.3 Hz, 1H), 4.05 (br s, 1H), 3.91-3.82 (m, 1H), 2.76 (q, J=7.5 Hz, 2H), 2.17 (s, 3H), 1.26 (t, J=7.6 Hz, 3H). LCMS (ESI+): m/z 432.1 (M+H).

Example 46: (S)-4-(2-(difluoromethyl)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-bromo-2-(difluoromethyl)pyridine

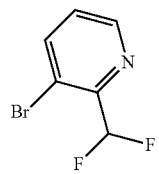

To a solution of 3-bromopicolinaldehyde (1.00 g, 5.38 mmol, 1.00 eq) in DCM (20 mL) was added DAST (1.73 g, 10.8 mmol, 1.42 mL, 2.00 eq) at 0° C. under nitrogen atmosphere. The mixture was stirred at 0° C. for 2 h. LC-MS showed 3-bromopicolinaldehyde was consumed completely and one main peak with desired mass was detected. The reaction mixture was quenched by addition of water (20 mL), and then diluted with EtOAc (20 mL) and extracted with EtOAc (20 mL*3). The combined organic layers were washed with sat. aq. NaCl (30 mL), dried over $Na_2SO_4$, filtered and concentrated under reduced pressure. The residue was purified by column chromatography ($SiO_2$, Petroleum ether:Ethyl acetate=1:0 to 0:1; Petroleum ether:Ethyl acetate=5:1, $R_f$=0.4). 3-bromo-2-(difluoromethyl)pyridine (480 mg, 2.31 mmol, 42% yield) was obtained as a yellow oil.

Step 2: 2-(difluoromethyl)-3-(4,4,5,5-tetramethyl-1,3,2-dioxaborolan-2-yl)pyridine

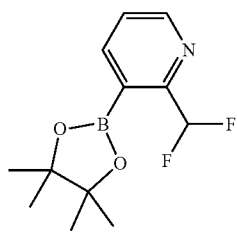 [SMILES: CC1(C)OB(c2cccnc2C(F)F)OC1(C)C]

To a solution of 3-bromo-2-(difluoromethyl)pyridine (480 mg, 2.31 mmol, 1.00 eq) in dioxane (6 mL) was added 4,4,4',4',5,5,5',5'-octamethyl-2,2'-bi(1,3,2-dioxaborolane) (762 mg, 3.00 mmol, 1.3 eq), KOAc (453 mg, 4.62 mmol, 2.00 eq) and Pd(dppf)Cl$_2$ (169 mg, 231 umol, 0.100 eq) at 25° C. under nitrogen atmosphere. The mixture was stirred at 80° C. for 12 h. LC-MS indicated presence of the remaining starting material. To the mixture was added 4,4,4',4',5,5,5',5'-octamethyl-2,2'-bi(1,3,2-dioxaborolane) (586.00 mg, 2.31 mmol, 1.00 eq), KOAc (452.96 mg, 4.62 mmol, 2.00 eq) and Pd(dppf)Cl$_2$ (169 mg, 231 umol, 0.100 eq) at 25° C. under nitrogen atmosphere. The mixture was stirred at 80° C. for 2 h. LC-MS indicated completed conversion. The mixture was concentrated in vacuum. The residue was purified by prep-TLC (SiO$_2$, Petroleum ether: Ethyl acetate=1:1, $R_f$=0.5). 2-(difluoromethyl)-3-(4,4,5,5-tetramethyl-1,3,2-dioxaborolan-2-yl)pyridine (500 mg, crude) was obtained as a yellow solid. $^1$H NMR CDCl$_3$ 400 MHz, δ=ppm 8.78 (br d, J=3.2 Hz, 1H), 8.17 (br d, J=7.6 Hz, 1H), 7.43-7.37 (m, 1H), 7.26 (t, J=53.2 Hz, 1H), 1.37 (s, 12H).

Step 3: (S)-4-(2-(difluoromethyl)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

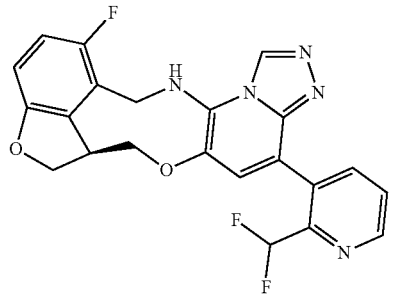 [SMILES: Fc1ccc2c3c1CNc1c(cc(-c4cccnc4C(F)F)c4nncn14)OC[C@H]3CO2]

To a solution of 2-(difluoromethyl)-3-(4,4,5,5-tetramethyl-1,3,2-dioxaborolan-2-yl)pyridine (156 mg, 614 umol, 4.00 eq) in dioxane (4.5 mL) and water (0.5 mL) were added (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (60.0 mg, 153 umol, 1.00 eq), NaHCO$_3$ (64.4 mg, 767 umol, 29.8 uL, 5.00 eq) and Pd(dppf)Cl$_2$ (11.2 mg, 15.3 umol, 0.100 eq) at 25° C. under nitrogen atmosphere. The mixture was stirred at 80° C. for 5 h. LC-MS showed 2-(difluoromethyl)-3-(4,4,5,5-tetramethyl-1,3,2-dioxaborolan-2-yl)pyridine was consumed completely and one main peak with desired mass was detected. The reaction mixture was filtered and the filtrate was dried under high vacuum. The residue was purified by prep-HPLC (neutral condition: column: Waters Xbridge 150*25 5 u; mobile phase: [water (10 mM NH$_4$HCO$_3$)—ACN]; B %: 25%-35%, 10 min). (S)-4-(2-(difluoromethyl)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (7.64 mg, 17.2 umol, 11% yield, 98.7% purity) was obtained as a yellow solid. $^1$H NMR DMSO-d$_6$ 400 MHz, δ=ppm 9.45 (s, 1H), 8.74 (dd, J=4.6, 1.3 Hz, 1H), 8.05 (d, J=7.9 Hz, 1H), 7.66 (dd, J=7.9, 4.4 Hz, 2H), 7.32 (s, 1H), 6.98 (t, J=10.0 Hz, 1H), 6.90 (t, J=53.6 Hz, 1H), 6.71 (dd, J=8.8, 4.0 Hz, 1H), 4.97-4.89 (m, 1H), 4.86-4.74 (m, 1H), 4.58-4.43 (m, 2H), 4.21 (dd, J=9.5, 3.5 Hz, 1H), 4.04 (br s, 1H), 3.93-3.83 (m, 1H). LCMS (ESI+): m/z 440.1 (M+H).

Example 47: (S)-4-(2,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Formate

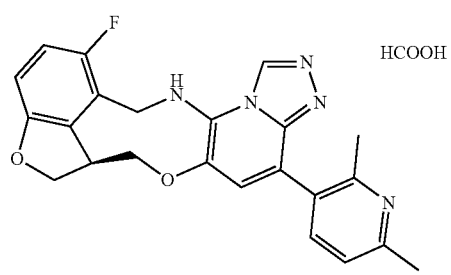 [SMILES: Cc1ccc(-c2cc3c(n4cnnc24)NCc2c(F)ccc4c2[C@H](CO4)CO3)c(C)n1 ; "HCOOH"]

To a solution of (S)-4-bromo-12-fluoro-7a,8,13,14-tetrahydro-7H-[1,2,4]triazolo[4',3':1,6]pyrido[3,2-b]benzofuro

[4,3-fg][1,4]oxazonine (100 mg, 256 umol, 1.00 eq) and 2,6-dimethyl-3-(4,4,5,5-tetramethyl-1,3,2-dioxaborolan-2-yl)pyridine (89.4 mg, 383 umol, 1.50 eq) in water (0.30 mL) and EtOH (2.10 mL) was added 4-ditert-butylphosphanyl-N,N-dimethyl-aniline dichloropalladium (18.1 mg, 25.6 umol, 18.1 uL, 0.100 eq) and KOAc (50.2 mg, 511 umol, 2.00 eq) at 20° C. The mixture was stirred at 80° C. for 12 h. The mixture was filtered and the filtrate was concentrated under reduced pressure. The residue was purified by prep-HPLC (formic acid conditions). (S)-4-(2,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (4.00 mg, 8.48 umol, 3% yield, 98.3% purity, formate salt) was obtained as a yellow solid. $^1$H NMR DMSO-$d_6$ 400 MHz, δ=ppm 9.33 (s, 1H), 7.70 (d, J=7.8 Hz, 1H), 7.34 (s, 1H), 7.24 (d, J=7.8 Hz, 1H), 6.95-6.82 (m, 1H), 6.65 (dd, J=8.6, 3.9 Hz, 1H), 5.08 (d, J=14.8 Hz, 1H), 4.86 (s, 1H), 4.59 (br t, J=9.4 Hz, 2H), 4.29 (dd, J=9.6, 3.1 Hz, 1H), 4.11-3.97 (m, 1H), 3.95-3.81 (m, 1H), 2.58 (s, 3H), 2.38 (s, 3H). LCMS (ESI+): m/z 418.2 (M+H).

Example 48: (S)-12-fluoro-4-(6-methylpyridin-2-yl)-7a,8,13,14-tetrahydro-7H-[1,2,4]triazolo[4',3':1,6]pyrido[3,2-b]benzofuro[4,3-fg][1,4]oxazonine Formate

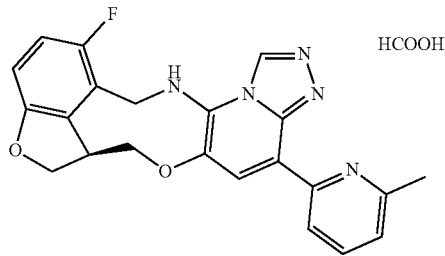 [SMILES: Cc1cccc(-c2cc3c(n4cnnc24)NCc2c(F)ccc4c2[C@H](CO4)CO3)n1 ; "HCOOH"]

Step 1: tert-butyl (S)-12-fluoro-4-(6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

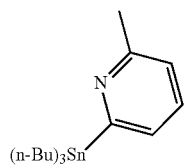

To a solution of 2-bromo-6-methylpyridine (500 mg, 2.91 mmol, 331 uL, 1.00 eq) in THF (20 mL) was added n-BuLi (2.5 M, 1.74 mL, 1.5 eq) at −70° C., the mixture was stirred at −70° C. for 0.5 hr, then tributyl(chloro)stannane (3.78 g, 11.6 mmol, 3.13 mL, 4.00 eq) was added to the mixture at −70° C., then the mixture was stirred at 20° C. for 12 h. TLC (Petroleum ether/Ethyl acetate=5/1 Rf=0.5) and LCMS showed the starting material was consumed completely. The residue was poured into water (10 mL) and stirred for 5 min. The aqueous phase was extracted with ethyl acetate (10 mL*2). The combined organic phase was washed with brine (10 mL), dried with anhydrous Na$_2$SO$_4$, filtered, and concentrated in vacuum. The residue was purified by column chromatography (SiO$_2$, Petroleum ether/Ethyl acetate=1/0 to 1/1). Tert-butyl (S)-12-fluoro-4-(6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (1.00 g, 2.62 mmol, 90% yield) was obtained as a yellow oil. 1H NMR CDCl3 400 MHz δ=ppm 7.36 (t, J=7.5 Hz, 1H), 7.21-7.15 (m, 1H), 6.96 (d, J=7.7 Hz, 1H), 2.54 (s, 3H), 1.70-1.51 (m, 12H), 1.43-1.22 (m, 6H), 0.95-0.87 (td, J=16.9, 7.4 Hz, 9H).

Step 2: tert-butyl (S)-12-fluoro-4-(6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

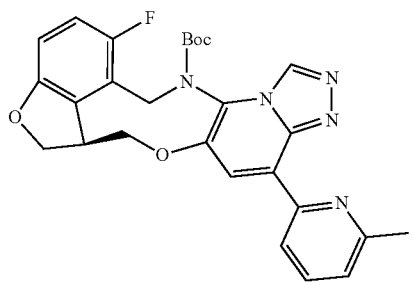 [SMILES: Cc1cccc(-c2cc3c(n4cnnc24)N(C(=O)OC(C)(C)C)Cc2c(F)ccc4c2[C@H](CO4)CO3)n1]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq) in dioxane (10 mL) was added tert-butyl (S)-12-fluoro-4-(6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (467 mg, 1.22 mmol, 4.00 eq), CuI (23.3 mg, 122 umol, 0.4 eq), LiCl (25.9 mg, 611 umol, 12.5 uL, 2.00 eq) and Pd(PPh$_3$)$_4$ (35.3 mg, 30.5 umol, 0.100 eq) at 20° C. under nitrogen atmosphere. The mixture was stirred at 80° C. for 12 h under nitrogen atmosphere. The mixture was evaporated to obtain the crude product. The residue was purified by prep-TLC (SiO$_2$, Petroleum ether:Ethyl acetate=1:2). S)-12-Fluoro-4-(6-methylpyridin-2-yl)-7a,8,13,14-tetrahydro-7H-[1,2,4]triazolo[4',3':1,6]pyrido[3,2-b]benzofuro[4,3-fg][1,4]oxazonine (120 mg, 238 umol, 78% yield) was obtained as a yellow solid.

Step 3: (S)-12-fluoro-4-(6-methylpyridin-2-yl)-7a,8,13,14-tetrahydro-7H-[1,2,4]triazolo[4',3':1,6]pyrido[3,2-b]benzofuro[4,3-fg][1,4]oxazonine

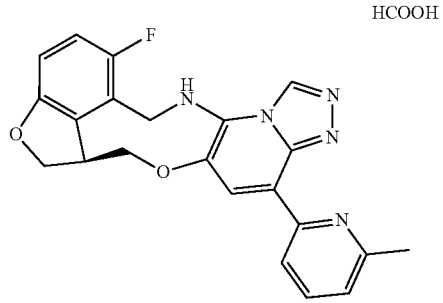 [SMILES: "HCOOH" ; Cc1cccc(-c2cc3c(n4cnnc24)NCc2c(F)ccc4c2[C@H](CO4)CO3)n1]

To a mixture of tert-butyl (S)-12-fluoro-4-(6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (110 mg, 218.46 umol, 1.00 eq) in DCM (10 mL) was added TFA (5.08 g, 44.6 mmol, 3.30 mL, 204 eq) in one portion at 18° C. The mixture was stirred at 18C for 1.5 h. The mixture was evaporated to obtain the crude product. The suspension was filtered, the filtrate was concentrated and purified by acidic prep-HPLC (formic acid conditions; column: Welch Xtimate C18 150*40 mm*10 um; mobile phase: [water (0.225% FA)—ACN]; B %: 10%-50%,12 min). The product-containing fraction was concentrated under reduced pressure to remove most of MeCN at 30° C. and the aqueous phase was lyophilized. (S)-12-fluoro-4-(6-methylpyridin-2-yl)-7a,8,13,14-tetrahydro-7H-[1,2,4]triazolo[4',3':1,6]pyrido[3,2-b]benzofuro[4,3-fg][1,4]oxazonine (54.7 mg, 120 umol, 54% yield, 98.3% purity, formate salt) was obtained as an orange solid. 1H NMR DMSO-d6 400 MHz δ=ppm 12.74 (br s, 1H), 9.48 (s, 1H), 8.82 (d, J=7.9 Hz, 1H), 8.29 (s, 1H), 8.13 (s, 1H), 7.82-7.72 (m, 2H), 7.16 (d, J=7.6 Hz, 1H), 6.99-6.91 (m, 1H), 6.68 (dd, J=8.6, 3.8 Hz, 1H), 4.97-4.88 (m, 1H), 4.86-4.77 (m, 1H), 4.52 (br t, J=9.4 Hz, 2H), 4.27 (br dd, J=9.4, 3.1 Hz, 1H), 4.05 (br s, 1H), 3.95-3.84 (m, 1H), 2.54 (s, 3H). LCMS (ESI+): m/z 404.2 (M+H).

Example 49: (S)-4-(4,6-dimethylpyridazin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 6,8-dimethyl-[1,2,4]triazolo[4,3-b]pyridazine

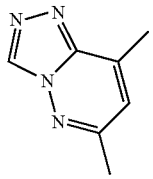

To a mixture of 6,8-dimethyl-[1,2,4]triazolo[4,3-b]pyridazine (5.95 g, 59.5 mmol, 6.11 mL, 1.00 eq) and 1,2,4-triazol-4-amine (5.00 g, 59.5 mmol, 1.00 eq) in toluene (30 mL) was added TsOH.water (56.6 mg, 297 umol, 0.005 eq) in one portion at 18° C. The mixture was stirred at 120° C. for 16 h. TLC (Ethyl acetate/Methanol=5/1 Rf=0.5) showed that the starting material was consumed completely. The mixture was evaporated under reduced pressure to obtain the crude product. The residue was purified by re-crystallization from EtOH/TBME (50 mL, v/v=1/5) to give the pure product. 6,8-Dimethyl-[1,2,4]triazolo[4,3-b]pyridazine (6.60 g, 44.5 mmol, 74% yield) was obtained as a white solid. 1H NMR DMSO-d6 400 MHz δ=ppm 9.52 (s, 1H), 7.11 (s, 1H), 2.59 (s, 3H), 2.53 (br s, 3H)

Step 2: 4,6-dimethylpyridazin-3-amine

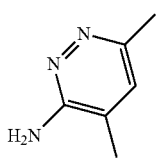

To a mixture of 6,8-dimethyl-[1,2,4]triazolo[4,3-b]pyridazine (6.60 g, 44.5 mmol, 1.00 eq) in MeCN (60 mL) was added 2-bromo-1-phenylethan-1-one (8.87 g, 44.5 mmol, 1.00 eq) in one portion at 18° C. The mixture was stirred at 85° C. for 6 h. Most of the solvent was removed by evaporation and water (27 mL) was added to the residue followed by addition of NaOH (3.00 g, 75.0 mmol, 1.68 eq) in one portion at 18° C. The mixture was stirred at 100° C. for 16 h. LCMS indicated formation of the desired product. The suspension was filtered through a pad of Celite and the filter cake was washed with water (40 mL*2) at 50° C. The filtrates were cooled to 18° C. and the obtained precipitate was filtered off. The filter cake was washed with 30 mL of water and dried in vacuum to give a afford product. 4,6-Dimethylpyridazin-3-amine (2.00 g, 16.2 mmol, 36% yield) was obtained as a yellow solid. 1H NMR DMSO-d6 400 MHz δ=ppm 6.99 (s, 1H), 5.91 (br s, 2H), 2.33 (s, 3H), 2.03 (s, 3H).

Step 3: 3-bromo-4,6-dimethylpyridazine

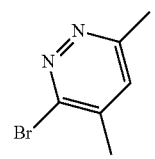

To a mixture of 4,6-dimethylpyridazin-3-amine (1.80 g, 14.6 mmol, 1.00 eq) in HBr (26.8 g, 159 mmol, 18.0 mL, 48% purity, 10.9 eq) was added NaNO₂ (1.02 g, 14.8 mmol, 1.01 eq) in water (8 mL) in one portion at 0° C. Then to the mixture was added CuBr (2.94 g, 20.5 mmol, 623 uL, 1.40 eq) in HBr (26.8 g, 159 mmol, 18.0 mL, 48% purity, 10.9 eq) in one portion at 0° C. The mixture was stirred at 100° C. for 5 h The aqueous phase layer was made alkaline with aqueous NaOH (10%) till pH=10. The aqueous phase was extracted with ethyl acetate (10 mL*2). The combined organic phases were washed with brine (10 mL*2), dried with anhydrous Na₂SO₄, filtered, and concentrated in vacuum. The residue was purified by column chromatography (SiO₂, Petroleum ether/Ethyl acetate=1/0 to 1/1). Tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (1.20 g, 6.40 mmol, 43% yield) was obtained as a white solid. 1H NMR DMSO-d6 400 MHz δ=ppm 7.57 (s, 1H), 2.54 (s, 3H), 2.32 (s, 3H).

Step 4: tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

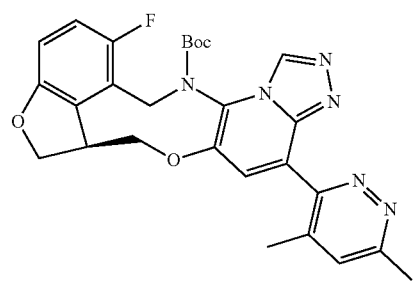 [SMILES: Cc1cc(C)c(-c2cc3c(n4cnnc24)N(C(=O)OC(C)(C)C)Cc2c(F)ccc4c2[C@H](CO4)CO3)nn1]

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (100 mg, 143 umol, 1.00 eq) in dioxane (5 mL) was added 3-bromo-4,6-dimethylpyridazine (66.7 mg, 356 umol, 1.06 uL, 2.50 eq), CuI (10.9 mg, 57.0 umol, 0.400 eq), LiCl (12.1 mg, 285 umol, 5.84 uL, 2.00 eq) and Pd(PPh₃)₄ (16.5 mg, 14.3 umol, 0.100 eq) at 20° C. under nitrogen atmosphere. The mixture was stirred at 80° C. for 12 h under nitrogen atmosphere. The mixture was evaporated under reduced pressure to obtain the product. The residue was purified by prep-TLC (SiO₂, EtOAc:MeOH=10:1). Tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (50 mg, 96.42 umol, 67% yield) was obtained as a yellow solid.

Step 5: (S)-4-(4,6-dimethylpyridazin-3-yl)-12-fluoro-7a,8,13,14-tetrahydro-7H-[1,2,4]triazolo[4',3':1,6]pyrido[3,2-b]benzofuro[4,3-fg][1,4]oxazonine Formate

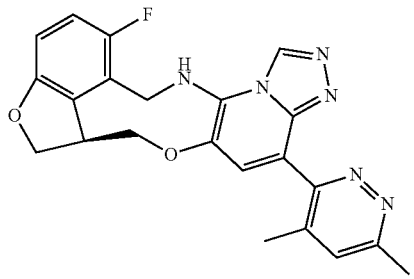

HCOOH

To a mixture of tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate (60.0 mg, 116 umol, 1.00 eq) in DCM (10 mL) was added TFA (2.69 g, 23.6 mmol, 1.75 mL, 204 eq) in one portion at 18° C. The mixture was stirred at 18° C. for 1.5 h. LCMS showed ~0% of tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate remained. Several new peaks were shown on LCMS and ~74% of a product with the desired mass was detected. The mixture was combined with another batch (from 50 mg of tert-butyl (S)-4-(4,6-dimethylpyridazin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate) and evaporated under reduced pressure. The crude product was dissolved in DMSO (2 mL) and filtered to remove the insoluble material. The filtrate was purified by acidic prep-HPLC (formic acid conditions; column: Welch Xtimate C18 150*40 mm*10 um; mobile phase: [water (0.225% FA)—ACN]; B %: 1%-40%, 12 min). The product-containing fraction was concentrated under reduced pressure to remove most of MeCN at 30° C. and the aqueous phase was lyophilized. (S)-4-(4,6-Dimethylpyridazin-3-yl)-12-fluoro-7a,8,13,14-tetrahydro-7H-[1,2,4]triazolo[4',3':1,6]pyrido [3,2-b]benzofuro[4,3-fg][1,4]oxazonine (19.5 mg, 40.7 umol, 96.96% purity, formate salt) was obtained as a yellow solid. 1H NMR DMSO-d6 400 MHz δ=ppm 9.46 (br s, 1H), 7.67 (br s, 1H), 7.52 (br s, 1H), 7.47 (s, 1H), 6.97 (t, J=9.5 Hz, 1H), 6.70 (dd, J=8.6, 3.8 Hz, 1H), 4.97-4.88 (m, 1H), 4.86-4.76 (m, 1H), 4.59-4.46 (m, 2H), 4.23 (dd, J=9.7, 3.3 Hz, 1H), 4.06 (br s, 1H), 3.92-3.80 (m, 1H), 2.63 (s, 3H), 2.18 (s, 3H). LCMS (ESI+): m/z 419.1 (M+H).

Example 50: (S)-12-fluoro-4-(3-methylpyrazin-2-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(3-methylpyrazin-2-yl)-7a,13-dihydro-7H-[1,2,4]triazolo[4',3':1,6]pyrido[3,2-b]benzofuro[4,3-fg][1,4]oxazonine-14 (8H)-carboxylate

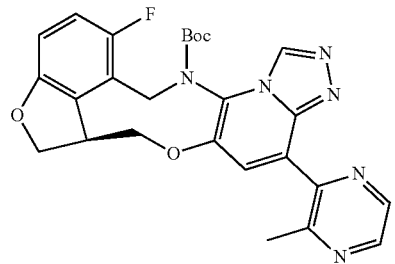 [SMILES: Cc1nccnc1-c1cc2c(n3cnnc13)N(C(=O)OC(C)(C)C)Cc1c(F)ccc3c1[C@H](CO3)CO2]

A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (150 mg, 214 umol, 1.00 eq), 2-bromo-3-methylpyrazine (44.4 mg, 257 umol, 1.20 eq), CuI (16.3 mg, 85.5 umol, 0.400 eq), LiCl (18.1 mg, 428 umol, 8.76 uL, 2.00 eq) and Pd(PPh₃)₄ (24.7 mg, 21.4 umol, 0.100 eq) in dioxane (4.00 mL) was degassed and purged with nitrogen 3 times at 20° C., and then the mixture was stirred at 80° C. for 2.5 h under nitrogen atmosphere. LCMS showed the reaction was complete and the desired mass was detected. The mixture was filtered and the filtrate was concentrated under reduced pressure. The residue was purified by prep-TLC (SiO₂, Petroleum ether:Ethyl acetate=0:1). Tert-butyl (S)-12-fluoro-4-(3-methylpyrazin-2-yl)-7a,13-dihydro-7H-[1,2,4]triazolo[4',3':1,6]pyrido[3,2-b]benzofuro[4,3-fg][1,4]oxazonine-14 (8H)-carboxylate (90.00 mg, crude) was obtained as a yellow solid.

Step 2: (S)-12-fluoro-4-(3-methylpyrazin-2-yl)-7a,8,13,14-tetrahydro-7H-[1,2,4]triazolo[4',3':1,6]pyrido[3,2-b]benzofuro[4,3-fg][1,4]oxazonine Formate


HCOOH

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (90.0 mg, 178 umol, 1.00 eq) in DCM (1.50 mL) was added TFA (770 mg, 6.75 mmol, 0.500 mL, 37.9 eq) at 20° C. The mixture was stirred at 20° C. for 1 hr. The mixture was concentrated under reduced pressure. The residue was combined with other batch (12 mg of final target with 96.3% purity). The mixture was dissolved in DMSO (3 mL). The suspension was filtered, the filtrate was concentrated and purified by acidic prep-HPLC (formic acid conditions). The product-containing fraction was concentrated under reduced pressure to remove most of MeCN at 30° C. and the aqueous phase was lyophilized. (S)-12-Fluoro-4-(3-methylpyrazin-2-yl)-7a,8,13,14-tetrahydro-7H-[1,2,4]triazolo[4',3':1,6]pyrido[3,2-b]benzofuro[4,3-fg][1,4]oxazonine (30.0 mg, 65.7 umol, 36% yield, 98.6% purity, formate salt) was obtained as a yellow solid. 1H NMR DMSO-d6 400 MHz δ=ppm 9.44 (s, 1H), 8.62-8.45 (m, 2H), 7.69 (br t, J=6.2 Hz, 1H), 7.48 (s, 1H), 7.04-6.87 (m, 1H), 6.68 (dd, J=8.6, 3.7 Hz, 1H), 4.96-4.86 (m, 1H), 4.84-4.73 (m, 1H), 4.57-4.40 (m, 2H), 4.20 (dd, J=9.5, 3.5 Hz, 1H), 4.03 (br s, 1H), 3.88-3.75 (m, 1H), 2.40 (s, 3H). LCMS (ESI+): m/z 405.1 (M+H).

Example 51: (S)-12-fluoro-4-(5-fluoro-3-methylpyridin-2-yl)-7a,8,13,14-tetrahydro-7H-[1,2,4]triazolo[4',3':1,6]pyrido[3,2-b]benzofuro[4,3-fg][1,4]oxazonine Step 1:
5-fluoro-3-methyl-2-(trimethylstannyl)pyridine

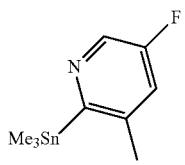

2-bromo-5-fluoro-3-methylpyridine (200 mg, 1.05 mmol, 1.00 eq), trimethyl(trimethylstannyl)stannane (690 mg, 2.11 mmol, 437 uL, 2.00 eq) and Pd(PPh3)4 (122 mg, 105 umol, 0.100 eq) were taken up into a microwave tube in dioxane (10 mL) at 18° C. under N2. The sealed tube was heated at 110° C. for 3 h under microwave. LCMS showed the reaction was complete. The suspension was filtered through a pad of Celite and the filter cake was washed with dioxane (1 mL). 5-Fluoro-3-methyl-2-(trimethylstannyl)pyridine (288 mg, 1.05 mmol, 99% yield) in dioxane (11 mL) was used for the next step without further purification.

Step 2: tert-butyl (S)-12-fluoro-4-(5-fluoro-3-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

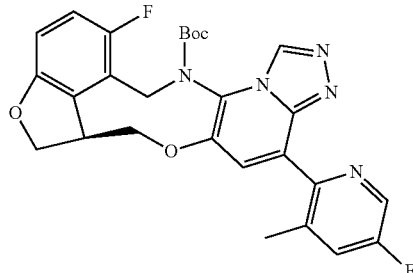

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407.08 umol, 1.00 eq) in dioxane (10 mL) was added 5-fluoro-3-methyl-2-(trimethylstannyl)pyridine (288 mg, 1.05 mmol, 2.59 eq) in dioxane (11 mL), CuI (31.0 mg, 163 umol, 0.400 eq), LiCl (34.5 mg, 814 umol, 16.7 uL, 2.00 eq) and Pd(PPh3)4 (47.0 mg, 40.7 umol, 0.100 eq) at 20° C. under nitrogen atmosphere. The mixture was stirred at 80° C. for 2 h under nitrogen atmosphere. LCMS showed tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate was consumed completely. Several new peaks were shown on LCMS and the desired mass was detected. The mixture was evaporated under reduced pressure to obtain the crude product. The residue was purified by prep-TLC (SiO2, Petroleum ether:Ethyl acetate=0:1). tert-butyl (S)-12-fluoro-4-(5-fluoro-3-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (200 mg, 384 umol, 94% yield) was obtained as a yellow solid.

Step 3: (S)-12-fluoro-4-(5-fluoro-3-methylpyridin-2-yl)-7a,8,13,14-tetrahydro-7H-[1,2,4]triazolo[4',3':1,6]pyrido[3,2-b]benzofuro[4,3-fg][1,4]oxazonine Formate

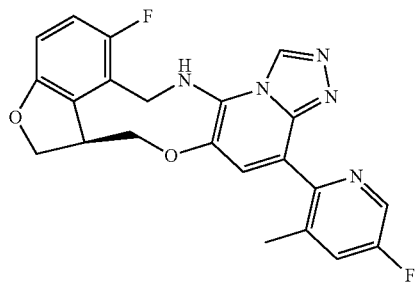

To a solution of tert-butyl (S)-12-fluoro-4-(5-fluoro-3-methylpyridin-2-yl)-7a,13-dihydro-7H-[1,2,4]triazolo[4',3':1,6]pyrido[3,2-b]benzofuro[4,3-fg][1,4]oxazonine-14 (8H)- carboxylate (150 mg, 288 umol, 1.00 eq) in DCM (3 mL) was added TFA (1.54 g, 13.5 mmol, 1.00 mL, 47.0 eq) at 20° C. The mixture was stirred at 20° C. for 2 hrTLC (SiO$_2$, PE:EtOAc=0:1) indicated tert-butyl (S)-12-fluoro-4-(5-fluoro-3-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate was consumed completely. The reaction mixture was concentrated under reduced pressure. The crude product was dissolved in MeCN (2 mL) and filtered to remove the insoluble material. The the filtrate was evaporated and purified by acidic prep-HPLC (formic acid conditions; column: Phenomenex Luna C18 200*40 mm*10 um; mobile phase: [water (0.225% FA)—ACN]; B %: 15%-45%, 12 min). The product-containing fraction was concentrated under reduced pressure to remove most of MeCN at 30° C. and the aqueous phase was lyophilized. (S)-12-Fluoro-4-(5-fluoro-3-methylpyridin-2-yl)-7a,8,13,14-tetrahydro-7H-[1,2,4]triazolo[4',3':1,6]pyrido[3,2-b]benzofuro[4,3-fg][1,4]oxazonine (33.4 mg, 78.7 umol, 27% yield, 99.3% purity, formate salt) was obtained as white solid. 1H NMR DMSO-d6 400 MHz δ=ppm 9.43 (s, 1H), 8.45 (d, J=2.4 Hz, 1H), 7.72 (dd, J=9.6, 2.3 Hz, 1H), 7.62-7.53 (m, 1H), 7.35 (s, 1H), 6.96 (t, J=9.4 Hz, 1H), 6.75-6.65 (m, 1H), 4.97-4.85 (m, 1H), 4.84-4.71 (m, 1H), 4.59-4.44 (m, 2H), 4.28-4.17 (m, 1H), 4.05 (br s, 1H), 3.89-3.75 (m, 1H), 2.20 (s, 3H). LCMS (ESI+): m/z 422.2 (M+H).

Example 52: General Procedure A. Preparation of (S)-4-(3,5-dimethylisoxazol-4-yl)-12-fluoro-7a,8,13,14-tetrahydro-7H-[1,2,4]triazolo[4',3':1,6]pyrido[3,2-b]benzofuro[4,3-fg][1,4]oxazonine

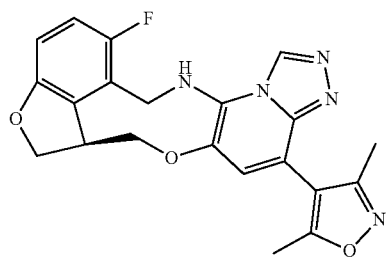 [SMILES: Cc1noc(C)c1-c1cc2c(n3cnnc13)NCc1c(F)ccc3c1[C@H](CO3)CO2]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (80.0 mg, 205 umol, 1.00 eq) in dioxane (2.00 mL) and water (0.200 mL) was added 3,5-dimethyl-4-(4,4,5,5-tetramethyl-1,3,2-dioxaborolan-2-yl) isoxazole (57.6 mg, 409 umol, 2.00 eq), Na$_2$CO$_3$ (43.4 mg, 409 umol, 2.00 eq) and Pd(dppf)Cl$_2$ (15.0 mg, 20.4 umol, 0.100 eq) at 20° C. The mixture was stirred at 80° C. for 2 h under nitrogen atmosphere. Reaction progress was monitored by LC-MS. The reaction mixture was filtered, the filtrate was concentrated. The residue was dissolved in MeOH (8 mL) and silica-thiol (500 mg, modified silicon gel for eliminating Pd, irregular silica gel, 100-200 mesh, Chlorides (Cl), %≤0.004, particle size distribution 45-75 um) was added at 20° C. and stirred at 20° C. for 2 h. The suspension was filtered and the filtrate was evaporated and purified by neutral prep-HPLC (column: Nano-micro Kromasil C18 80*25 mm 3 um; mobile phase: [water (10 mM NH4HCO3)—ACN]; B %: 30%-50%, 10 min). The product-containing fraction was concentrated under reduced pressure to remove most of MeCN at 30° C. and the residue was lyophilized. (S)-4-(3,5-dimethylisoxazol-4-yl)-12-fluoro-7a,8,13,14-tetrahydro-7H-[1,2,4]triazolo[4',3':1,6] pyrido[3,2-b]benzofuro[4,3-fg][1,4]oxazonine (58.0 mg, 140 umol, 68% yield, 98.4% purity) was obtained as a white solid. 1H NMR DMSO-d6 400 MHz δ=ppm 9.41 (s, 1H), 7.52 (br s, 1H), 7.35 (s, 1H), 6.98 (t, J=9.5 Hz, 1H), 6.71 (dd, J=8.6, 3.7 Hz, 1H), 4.95-4.87 (m, 1H), 4.83-4.74 (m, 1H), 4.56-4.49 (m, 1H), 4.45 (br d, J=6.5 Hz, 1H), 4.21 (dd, J=9.5, 3.5 Hz, 1H), 4.05 (br s, 1H), 3.92-3.77 (m, 1H), 2.36 (s, 3H), 2.19 (s, 3H). LCMS (ESI+): m/z 408.1 (M+H)

Compounds 49, 58, 72, 77-78, 91, 94, 96, 103, 105-106, 108-109, 111-112, 114-118, and 142 were prepared according to General Procedure A using the suitable starting materials, precursors, intermediates, and reagents.

| Cmpd No. | Compound Name | Compound Structure | Spectral Data |
|---|---|---|---|
| 72 | (S)-4-(1-ethyl-1H-pyrazol-5-yl)-12-fluoro-7a,8,13,14-tetrahydro-7H-[1,2,4]triazolo[4',3':1,6]pyrido[3,2-b]benzofuro[4,3-fg][1,4]oxazonine | 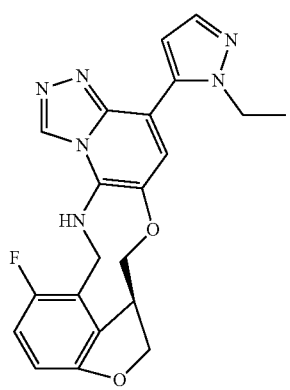 [SMILES: CCn1nccc1-c1cc2c(n3cnnc13)NCc1c(F)ccc3c1[C@H](CO3)CO2] | 1H NMR DMSO-d6 400 MHz δ = ppm 9.42 (s, 1H), 7.63 (br t, J = 6.4 Hz, 1H), 7.50 (d, J = 1.5 Hz, 1H), 7.34 (s, 1H), 6.99-6.90 (m, 1H), 6.68 (dd, J = 8.7, 3.9 Hz, 1H), 6.43 (d, J = 1.5 Hz, 1H), 4.93-4.84 (m, 1H), 4.82-4.72 (m, 1H), 4.56-4.41 (m, 2H), 4.19 (dd, J = 9.6, 3.6 Hz, 1H), 4.08 (q, J = 7.2 Hz, 2H), 4.02 (br s, 1H), 3.90-3.78 (m, 1H), 1.23 (t, J = 7.2 Hz, 3H). LCMS (ESI+): m/z 407.1 (M + H). |

| Cmpd No. | Compound Name | Compound Structure | Spectral Data |
|---|---|---|---|
| 49 | (S)-4-(12-fluoro-7a,8,13,14-tetrahydro-7H-[1,2,4]triazolo[4',3':1,6]pyrido[3,2-b]benzofuro[4,3-fg][1,4]oxazonin-4-yl)-3-methylbenzonitrile | 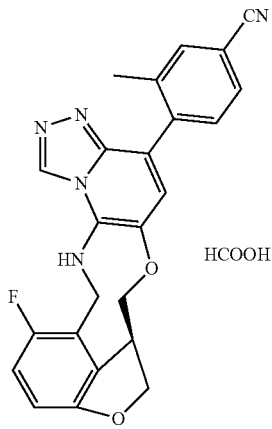 [SMILES: Cc1cc(C#N)ccc1-c1cc2c(n3cnnc13)NCc1c(F)ccc3c1[C@H](CO3)CO2 ; "HCOOH"] | 1H NMR DMSO-d6 400 MHz δ = ppm 9.43 (s, 1H), 7.81 (s, 1H), 7.75-7.69 (m, 1H), 7.63-7.55 (m, 2H), 7.34 (s, 1H), 6.98 (dd, J = 10.1, 8.9 Hz, 1H), 6.71 (dd, J = 8.6, 3.7 Hz, 1H), 4.98-4.87 (m, 1H), 4.84-4.75 (m, 1H), 4.59-4.43 (m, 2H), 4.21 (dd, J = 9.4, 3.5 Hz, 1H), 4.09-4.00 (m, 1H), 3.92-3.83 (m, 1H), 2.23 (s, 3H). LCMS (ESI+): m/z 428.1 (M + H) |
| 78 | (S)-4-(2-(difluoromethoxy)pyridin-3-yl)-12-fluoro-7a,8,13,14-tetrahydro-7H-[1,2,4]triazolo[4',3':1,6]pyrido[3,2-b]benzofuro[4,3-fg][1,4]oxazonine | 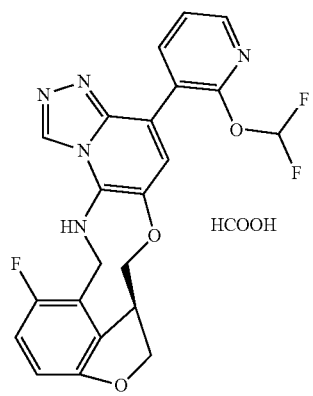 [SMILES: Fc1ccc2c3c1CNc1c(cc(-c4cccnc4OC(F)F)c4nncn14)OC[C@H]3CO2 ; "HCOOH"] | 1H NMR DMSO-d6 400 MHz δ = ppm 9.45 (s, 1H), 8.40 (dd, J = 7.5, 1.5 Hz, 1H), 8.26 (dd, J = 4.8, 1.7 Hz, 1H), 7.73 (t, J = 72.4 Hz, 1H), 7.66 (br t, J = 6.4 Hz, 1H), 7.56 (s, 1H), 7.40 (dd, J = 7.5, 5.0 Hz, 1H), 6.97 (t, J = 9.5 Hz, 1H), 6.70 (dd, J = 3.7, 8.6 Hz, 1H), 4.97-4.87 (m, 1H), 4.86-4.77 (m, 1H), 4.54 (t, J = 9.5 Hz, 1H), 4.46 (br s, 1H), 4.21 (dd, J = 9.5, 3.4 Hz, 1H), 4.06 (br s, 1H), 3.92-3.80 (m, 1H). LCMS (ESI+): m/z 456.1 (M + H). |
| 77 | (S)-12-fluoro-4-(2-methoxypyridin-3-yl)-7a,8,13,14-tetrahydro-7H-[1,2,4]triazolo[4',3':1,6]pyrido[3,2-b]benzofuro[4,3-fg][1,4]oxazonine | 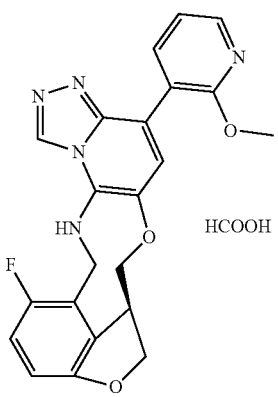 [SMILES: COc1ncccc1-c1cc2c(n3cnnc13)NCc1c(F)ccc3c1[C@H](CO3)CO2 ; "HCOOH"] | 1H NMR CDCl3 400 MHz δ = ppm 8.93 (s, 1H), 8.32 br d, J = 7.1 Hz, 1H), 8.15 (br d, J = 3.9 Hz, 1H), 7.57 (s, 1H), 6.99 (dd, J = 7.0, 5.2 Hz, 1H), 6.85 (br t, J = 9.4 Hz, 1H), 6.65 (dd, J = 8.6, 3.7 Hz, 1H), 5.36 (br s, 1H), 5.07 (br dd, J = 14.6, 6.4 Hz, 1H), 4.91-4.77 (m, 1H), 4.69-4.50 (m, 2H), 4.18-4.28 (m, 1H), 3.97 (s, 3H), 3.95-3.76 (m, 2H). LCMS (ESI+): m/z 420.1 (M + H). |

| Cmpd No. | Compound Name | Compound Structure | Spectral Data |
|---|---|---|---|
| 58 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,4-trimethylpyrimidine-2-carboxamide | 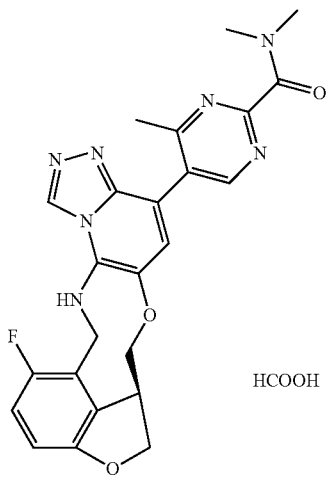 [SMILES: Cc1nc(C(=O)N(C)C)ncc1-c1cc2c(n3cnnc13)NCc1c(F)ccc3c1[C@H](CO3)CO2 ; "HCOOH"] HCOOH | 1H NMR DMSO-d6 400 MHz δ = ppm 9.58 (s, 1H), 8.82 (s, 1H), 7.98 (br s, 1H), 7.68 (s, 1H), 6.99 (t, J = 9.2 Hz, 1H), 6.72 (dd, J = 8.4, 3.6 Hz, 1H), 5.03-4.91 (m, 1H), 4.83 (br d, J = 8.4 Hz, 1H), 4.62-4.51 (m, 2H), 4.23 (br d, J = 6.4 Hz, 1H), 4.06 (br s, 1H), 3.93-3.84 (m, 1H), 3.04 (s, 3H), 2.86 (s, 3H), 2.44 (s, 3H). LCMS (ESI+): m/z 476.2 (M + H). |
| 96 | (S)-4-(2-ethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine | HCOOH 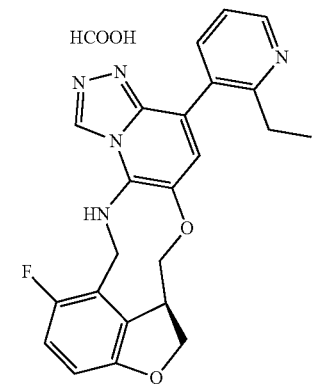 [SMILES: CCc1ncccc1-c1cc2c(n3cnnc13)NCc1c(F)ccc3c1[C@H](CO3)CO2 ; "HCOOH"] | 1H NMR DMSO-d$_6$ 400 MHz δ = ppm 9.41 (s, 1H), 8.53 (dd, J = 4.9, 1.5 Hz, 1H), 7.68 (dd, J = 7.6, 1.7 Hz, 1H), 7.55-7.47 (m, 1H), 7.33-7.22 (m, 2H), 7.00-6.90 (m, 1H), 6.73-6.64 (m, 1H), 4.95-4.84 (m, 1H), 4.81-4.72 (m, 1H), 4.57-4.42 (m, 2H), 4.25-4.16 (m, 1H), 4.07-3.97 (m, 1H), 3.89-3.78 (m, 1H), 2.60 (q, J = 7.4 Hz, 2H), 1.06 (t, J = 7.5 Hz, 3H). LCMS (ESI+): m/z 418.0 (M + H). |
| 105 | (S)-12-fluoro-4-(2-methoxy-6-methylpyridin-3-yl)-7a,8,13,14-tetrahydro-7H-[1,2,4]triazolo[4',3':1,6]pyrido[3,2-b]benzofuro[4,3-fg][1,4]oxazonine | HCOOH 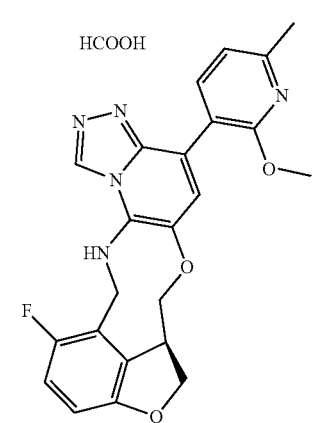 [SMILES: COc1nc(C)ccc1-c1cc2c(n3cnnc13)NCc1c(F)ccc3c1[C@H](CO3)CO2 ; "HCOOH"] | $^1$H NMR DMSO-d$_6$ 400 MHz δ = ppm 9.40 (d, J = 2.3 Hz, 1H), 8.17 (d, J = 7.6 Hz, 1H), 7.55 (s, 1H), 7.47 (br t, J = 6.2 Hz, 1H), 7.00-6.89 (m, 2H), 6.69 (dd, J = 8.7, 3.8 Hz, 1H), 4.95-4.86 (m, 1H), 4.83-4.74 (m, 1H), 4.58-4.42 (m, 2H), 4.22 (dd, J = 9.5, 3.5 Hz, 1H), 4.10-3.99 (m, 1H), 3.89 (s, 3H), 3.85-3.78 (m, 1H), 2.45 (s, 3H). LCMS (ESI+): m/z 434.1 (M + H). |

-continued

| Cmpd No. | Compound Name | Compound Structure | Spectral Data |
| --- | --- | --- | --- |
| 106 | (S)-12-fluoro-4-(6-methoxy-2-methylpyridin-3-yl)-7a,8,13,14-tetrahydro-7H-[1,2,4]triazolo[4',3':1,6]pyrido[3,2-b]benzofuro[4,3-fg][1,4]oxazonine | 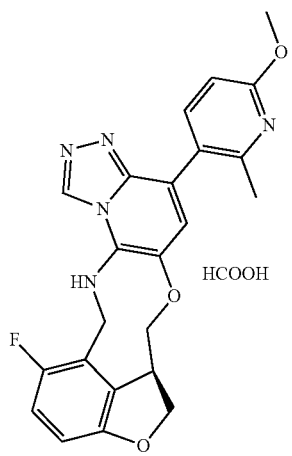 [SMILES: COc1ccc(-c2cc3c(n4cnnc24)NCc2c(F)ccc4c2[C@H](CO4)CO3)c(C)n1 ; "HCOOH"] | $^1$H NMR CDCl$_3$ 400 MHz δ = ppm 8.88 (s, 1H), 7.60 (d, J = 8.4 Hz, 1H), 7.03 (s, 1H), 6.87 (t, J = 9.5 Hz, 1H), 6.67 (dd, J = 8.7, 3.9 Hz, 1H), 6.61 (d, J = 8.4 Hz, 1H), 5.16-5.03 (m, 2H), 4.83 (br d, J = 9.3 Hz, 1H), 4.64 (t, J = 9.4 Hz, 1H), 4.58 (dd, J = 9.9, 4.2 Hz, 1H), 4.25 (dd, J = 9.7, 3.3 Hz, 1H), 4.00 9 是, 3H), 3.98-3.89 (m, 1H), 3.87-3.77 (m, 1H), 2.38 (s, 3H). LCMS (ESI+): m/z 434.2 (M + H) |
| 114 | (S)-12-fluoro-4-(2-(trifluoromethyl)pyrimidin-5-yl)-7a,8,13,14-tetrahydro-7H-[1,2,4]triazolo[4',3':1,6]pyrido[3,2-b]benzofuro[4,3-fg][1,4]oxazonine | 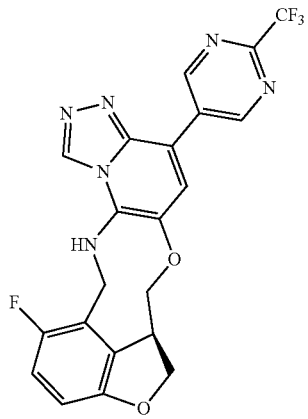 [SMILES: Fc1ccc2c3c1CNc1c(cc(-c4cnc(C(F)(F)F)nc4)c4nncn14)OC[C@H]3CO2] | $^1$H NMR DMSO-d$_6$ 400 MHz δ = ppm 9.86 (s, 2H), 9.45 (s, 1H), 8.22 (s, 1H), 7.95 (br s, 1H), 7.03-6.89 (m, 1H), 6.78-6.65 (m, 1H), 4.97-4.88 (m, 1H), 4.87-4.79 (m, 1H), 4.53 (br t, J = 9.3 Hz, 2H), 4.25-4.18 (m, 1H), 4.09-4.00 (m, 1H), 3.99-3.91 (m, 1H). LCMS (ESI+): m/z 459.2 (M + H). |
| 115 | (S)-12-fluoro-4-(1-methyl-3-(trifluoromethyl)-1H-pyrazol-5-yl)-7a,8,13,14-tetrahydro-7H-[1,2,4]triazolo[4',3':1,6]pyrido[3,2-b]benzofuro[4,3-fg][1,4]oxazonine | 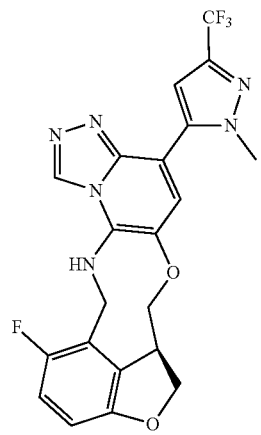 [SMILES: Cn1nc(C(F)(F)F)cc1-c1cc2c(n3cnnc13)NCc1c(F)ccc3c1[C@H](CO3)CO2] | $^1$H NMR DMSO-d$_6$ 400 MHz δ = ppm 9.47 (s, 1H), 7.81 (br t, J = 6.2 Hz, 1H), 7.57 (s, 1H), 7.02 (s, 1H), 7.00-6.91 (m, 1H), 6.70 (dd, J = 8.6, 3.9 Hz, 1H), 4.98-4.88 (m, 1H), 4.86-4.76 (m, 1H), 4.58-4.44 (m, 2H), 4.21 (dd, J = 9.6, 3.5 Hz, 1H), 4.10-3.99 (m, 1H), 3.92 (s, 3H), 3.91-3.84 (m, 1H). LCMS (ESI+): m/z 461.2 (M + H). |

| Cmpd No. | Compound Name | Compound Structure | Spectral Data |
|---|---|---|---|
| 116 | (S)-12-fluoro-4-(6-morpholinopyridin-3-yl)-7a,8,13,14-tetrahydro-7H-[1,2,4]triazolo[4',3':1,6]pyrido[3,2-b]benzofuro[4,3-fg][1,4]oxazonine | 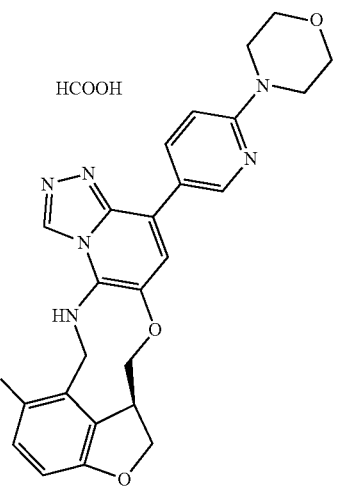 | $^1$H NMR DMSO-$d_6$ 400 MHz δ = ppm 9.41 (s, 1H), 8.96 (d, J = 2.3 Hz, 1H), 8.36 (dd, J = 9.0, 2.4 Hz, 1H), 7.60 (s, 1H), 7.41 (br t, J = 6.5 Hz, 1H), 6.97-6.89 (m, 2H), 6.67 (dd, J = 8.6, 3.9 Hz, 1H), 4.92-4.82 (m, 1H), 4.80-4.68 (m, 1H), 4.56-4.46 (m, 2H), 4.21 (dd, J = 9.5, 3.2 Hz, 1H), 4.07-3.86 (m, 2H), 3.76-3.67 (m, 4H), 3.53-3.46 (m, 4H). LCMS (ESI+): m/z 475.2 (M + H). |
| 117 | (S)-12-fluoro-4-(6-(4-methylpiperazin-1-yl)pyridin-3-yl)-7a,8,13,14-tetrahydro-7H-[1,2,4]triazolo[4',3':1,6]pyrido[3,2-b]benzofuro[4,3-fg][1,4]oxazonine | 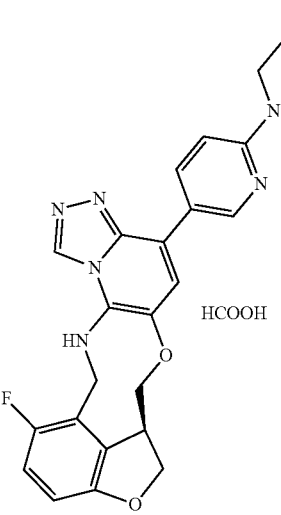 | $^1$H NMR DMSO-$d_6$ 400 MHz δ = ppm 9.41 (s, 1H), 8.93 (d, J = 2.4 Hz, 1H), 8.37-8.30 (m, 1H), 8.15 (s, 1H), 7.27 (s, 1H), 7.44-7.33 (m, 1H), 7.00-6.85 (m, 2H), 6.71-6.63 (m, 1H), 4.92-4.83 (m, 1H), 4.81-4.71 (m, 1H), 4.57-4.46 (m, 2H), 4.25-4.17 (m, 1H), 4.09-3.99 (m, 1H), 3.96-3.86 (m, 1H), 3.57-3.52 (m, 4H), 2.43 (br t, J = 4.9 Hz, 4H), 2.24 (s, 3H). LCMS (ESI+): m/z 488.2 (M + H). |
| 118 | (S)-12-fluoro-4-(2-(4-methylpiperazin-1-yl)pyrimidin-5-yl)-7a,8,13,14-tetrahydro-7H-[1,2,4]triazolo[4',3':1,6]pyrido[3,2-b]benzofuro[4,3-fg][1,4]oxazonine | 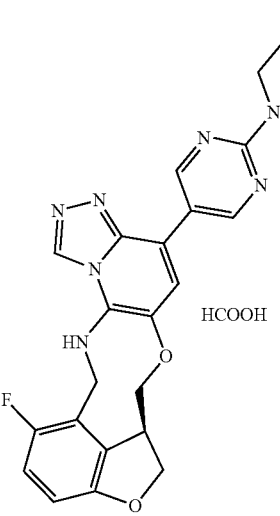 | $^1$H NMR DMSO-$d_6$ 400 MHz δ = ppm 9.42 (s, 1H), 9.13 (s, 2H), 8.15 (s, 1H), 7.66 (s, 1H), 7.48 (br t, J = 6.4 Hz, 1H), 6.99-6.90 (m, 1H), 6.73-6.63 (m, 1H), 4.91-4.83 (m, 1H), 4.80-4.71 (m, 1H), 4.56-4.42 (m, 2H), 4.25-4.16 (m, 1H), 4.08-3.97 (m, 1H), 3.95-3.86 (m, 1H), 3.82-3.75 (m, 4H), 2.42-2.37 (m, 4H), 2.23 (s, 3H). LCMS (ESI+): m/z 489.2 (M + H). |

| Cmpd No. | Compound Name | Compound Structure | Spectral Data |
|---|---|---|---|
| 112 | (S)-12-fluoro-4-(6-(trifluoromethyl)pyridin-3-yl)-7a,8,13,14-tetrahydro-7H-[1,2,4]triazolo[4',3':1,6]pyrido[3,2-b]benzofuro[4,3-fg][1,4]oxazonine | 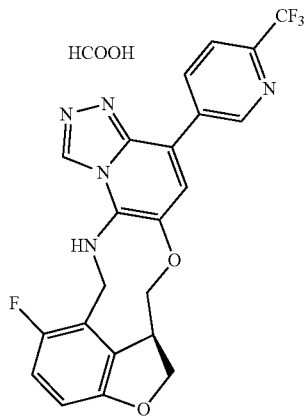 [SMILES: Fc1ccc2c3c1CNc1c(cc(-c4ccc(C(F)(F)F)nc4)c4nncn14)OC[C@H]3CO2 ; "HCOOH"] | ¹H NMR DMSO-d₆ 400 MHz δ = ppm 9.56 (s, 1H), 9.51 (s, 1H), 8.97 (d, J = 7.0 Hz, 1H), 8.51 (s, 1H), 8.03 (s, 1H), 7.99 (d, J = 8.3 Hz, 1H), 7.89 (s, 1H), 6.97 (t, J = 9.5 Hz, 1H), 6.70 (dd, J = 8.6, 3.7 Hz, 1H), 4.98-4.90 (m, 1H), 4.88-4.79 (m, 1H), 4.55 (t, J = 9.3 Hz, 2H), 4.23 (dd, J = 9.7, 3.0 Hz, 1H), 4.06 (s, 1H), 4.01-3.92 (m, 1H). LCMS (ESI+): m/z 458.1 (M + H). |
| 109 | (S)-4-(2-ethoxypyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine | 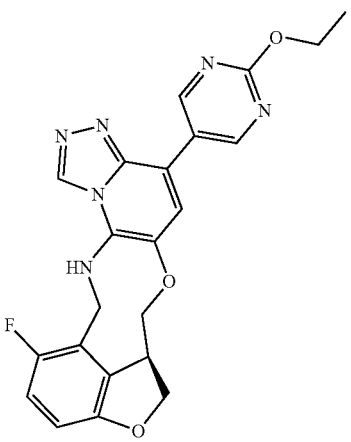 [SMILES: CCOc1ncc(-c2cc3c(n4cnnc24)NCc2c(F)ccc4c2[C@H](CO4)CO3)cn1] | ¹H NMR DMSO-d₆ 400 MHz δ = ppm 9.45 (s, 1H), 9.35 (s, 2H), 7.82 (s, 1H), 7.60 (br s, 1H), 6.98-6.89 (m, 1H), 6.72-6.63 (m, 1H), 4.94-4.85 (m, 1H), 4.82-4.72 (m, 1H), 4.60-4.48 (m, 2H), 4.40 (q, J = 7.1 Hz, 2H), 4.26-4.17 (m, 1H), 4.08-3.86 (m, 2H), 1.36 (t, J = 7.1 Hz, 3H). LCMS (ESI+): m/z 435.1 (M + H). |
| 94 | (S)-12-fluoro-4-(6-methylpyridin-3-yl)-7a,8,13,14-tetrahydro-7H-[1,2,4]triazolo[4',3':1,6]pyrido[3,2-b]benzofuro[4,3-fg][1,4]oxazonine | 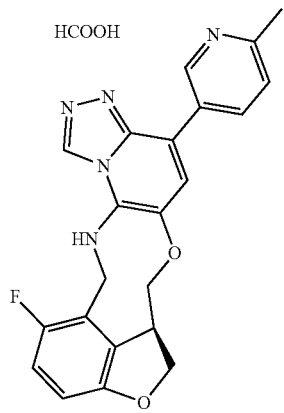 [SMILES: Cc1ccc(-c2cc3c(n4cnnc24)NCc2c(F)ccc4c2[C@H](CO4)CO3)cn1 ; "HCOOH"] | ¹H NMR DMSO-d₆ 400 MHz δ = ppm 9.45 (s, 1H), 9.22 (s, 1H), 8.46 (dd, J = 8.1, 2.3 Hz, 1H), 7.75 (s, 1H), 7.62-7.55 (m, 1H), 7.33 (d, J = 8.2 Hz, 1H), 6.95 (dd, J = 10.0, 8.9 Hz, 1H), 6.68 (dd, J = 8.6, 3.8 Hz, 1H), 4.95-4.85 (m, 1H), 4.83-4.74 (m, 1H), 4.58-4.49 (m, 2H), 4.24-4.18 (m, 1H), 4.08-3.99 (m, 1H), 3.97-3.90 (m, 1H), 2.52 (br s, 3H). LCMS (ESI+): m/z 404.1 (M + H). |

| Cmpd No. | Compound Name | Compound Structure | Spectral Data |
|---|---|---|---|
| 108 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpyrimidin-2-amine | 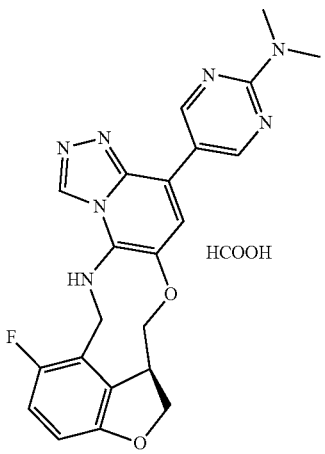 [SMILES: CN(C)c1ncc(-c2cc3c(n4cnnc24)NCc2c(F)ccc4c2[C@H](CO4)CO3)cn1 ; "HCOOH"] HCOOH | $^1$H NMR DMSO-$d_6$ 400 MHz δ = ppm 9.42 (s, 1H), 9.12 (s, 2H), 7.64 (s, 1H), 7.44 (br t, J = 6.5 Hz, 1H), 6.99-6.90 (m, 1H), 6.67 (dd, J = 8.5, 3.9 Hz, 1H), 4.92-4.83 (m, 1H), 4.81-4.72 (m, 1H), 4.57-4.45 (m, 2H), 4.21 (dd, J = 9.8, 3.2 Hz, 1H), 4.09-3.97 (m, 1H), 3.96-3.87 (m, 1H), 3.17 (s, 6H). LCMS (ESI+): m/z 434.1 (M + H). |
| 111 | (S)-12-fluoro-4-(5-fluoro-2-methoxypyridin-3-yl)-7a,8,13,14-tetrahydro-7H-[1,2,4]triazolo[4',3':1,6]pyrido[3,2-b]benzofuro[4,3-fg][1,4]oxazonine | 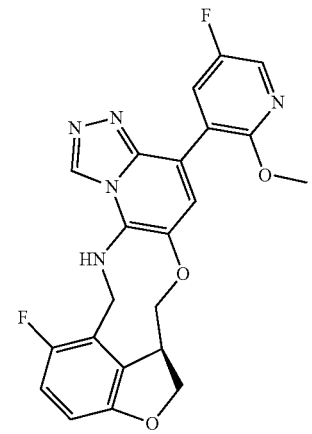 [SMILES: COc1ncc(F)cc1-c1cc2c(n3cnnc13)NCc1c(F)ccc3c1[C@H](CO3)CO2] | $^1$H NMR DMSO-$d_6$ 400 MHz δ = ppm 9.44 (s, 1H), 8.53-8.40 (m, 1H), 8.14 (s, 1H), 7.77 (s, 1H), 7.72-7.60 (m, 1H), 7.01-6.91 (m, 1H), 6.74-6.65 (m, 1H), 4.96-4.86 (m, 1H), 4.85-4.74 (m, 1H), 4.58-4.42 (m, 2H), 4.27-4.16 (m, 1H), 4.11-3.98 (m, 1H), 3.94 (s, 3H), 3.87-3.78 (m, 1H). LCMS (ESI+): m/z 438.1 (M + H). |
| 103 | (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpyridin-2-amine | 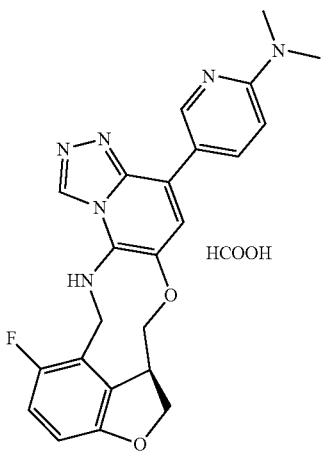 [SMILES: CN(C)c1ccc(-c2cc3c(n4cnnc24)NCc2c(F)ccc4c2[C@H](CO4)CO3)cn1 ; "HCOOH"] HCOOH | $^1$H NMR DMSO-$d_6$ 400 MHz δ = ppm 9.38 (s, 1H), 8.89 (d, J = 2.2 Hz, 1H), 8.28 (dd, J = 9.0, 2.4 Hz, 1H), 8.12 (s, 1H), 7.52 (s, 1H), 7.32 (t, J = 6.4 Hz, 1H), 6.95-6.86 (m, 1H), 6.70 (d, J = 9.0 Hz, 1H), 6.65 (dd, J = 8.6, 4.0 Hz, 1H), 4.89-4.81 (m, 1H), 4.79-4.68 (m, 1H), 4.55-4.43 (m, 2H), 4.19 (dd, J = 9.6, 3.2 Hz, 1H), 4.07-3.95 (m, 1H), 3.94-3.84 (m, 1H), 3.05 (s, 6H). LCMS (ESI+): m/z 433.1 (M + H). |

| Cmpd No. | Compound Name | Compound Structure | Spectral Data |
|---|---|---|---|
| 91 | (S)-12-fluoro-4-(pyrimidin-5-yl)-7a,8,13,14-tetrahydro-7H-[1,2,4]triazolo[4',3':1,6]pyrido[3,2-b]benzofuro[4,3-fg][1,4]oxazonine | 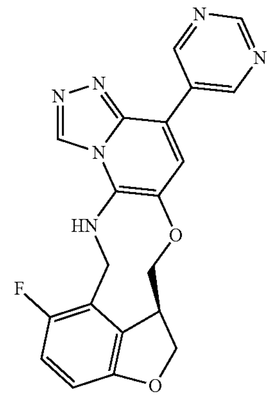 [SMILES: Fc1ccc2c3c1CNc1c(cc(-c4cncnc4)c4nncn14)OC[C@H]3CO2] | $^1$H NMR DMSO-$d_6$ 400 MHz δ = ppm 9.61 (s, 2H), 9.51 (s, 1H), 9.12 (s, 1H), 8.00 (s, 1H), 7.82 (t, J = 6.0 Hz, 1H), 6.97 (t, J = 9.6 Hz, 1H), 6.70 (dd, J = 8.6, 3.7 Hz, 1H), 5.02-4.88 (m, 1H), 4.84 (s, 1H), 4.55 (t, J = 9.3 Hz, 2H), 4.23 (dd, J = 9.6, 3.0 Hz, 1H), 4.05 (s, 1H), 4.01-3.91 (m, 1H), 2.88-2.64 (m, 1H). LCMS (ESI+): m/z 391.1 (M + H). |
| 142 | (S)-12-fluoro-4-(1H-pyrazol-5-yl)-7a,8,13,14-tetrahydro-7H-[1,2,4]triazolo[4',3':1,6]pyrido[3,2-b]benzofuro[4,3-fg][1,4]oxazonine | 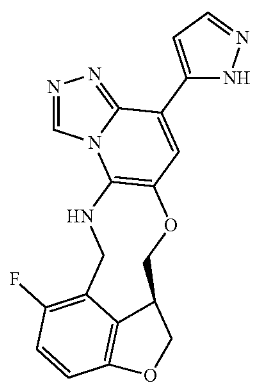 [SMILES: Fc1ccc2c3c1CNc1c(cc(-c4ccn[nH]4)c4nncn14)OC[C@H]3CO2] | $^1$H NMR ET20970-391-P1C12 DMSO-$d_6$ 400 MHz δ = ppm 9.39 (s, 1H), 7.81 (s, 1H), 7.67 (br s, 1H), 7.32 (br s, 1H), 7.20 (br s, 1H), 6.92 (dd, J = 10.4, 8.8 Hz, 1H), 6.66 (dd, J = 8.8, 4.0 Hz, 1H), 4.98-4.89 (m, 1H), 4.87-4.78 (m, 1H), 4.59-4.48 (m, 2H), 4.23 (dd, J = 9.6, 3.6 Hz, 1H), 4.13-4.00 (m, 1H), 3.97-3.87 (m, 1H). LCMS (ESI+): m/z 379.1 (M + H). |

Example 53: (S)-12-fluoro-4-(3-fluoropyridin-2-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(3-fluoropyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

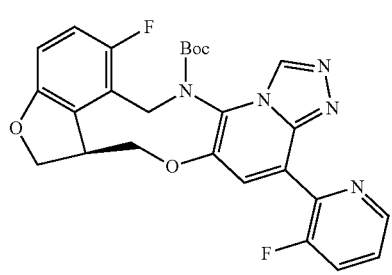 [SMILES: CC(C)(C)OC(=O)N1Cc2c(F)ccc3c2[C@H](CO3)COc2cc(-c3ncccc3F)c3nncn3c21]

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (150 mg, 214 umol, 1.00 eq) and 3-fluoro-2-iodo-pyridine (62.0 mg, 278 umol, 1.30 eq) in dioxane (6 mL) was added LiCl (18.1 mg, 428 umol, 8.76 uL, 2.00 eq), CuI (16.3 mg, 85.5 umol, 0.400 eq) and Pd(PPh$_3$)4 (24.7 mg, 21.4 umol, 0.100 eq) under nitrogen atmosphere. The mixture was stirred at 80° C. for 8 h under nitrogen atmosphere. The reaction mixture was filtered, the obtained solid was washed with MeOH (20 mL) and dried under reduced pressure to give 82 mg of the product. The filtrate was concentrated under reduced pressure and the residue was purified by prep-TLC (SiO$_2$, EtOAc:MeOH=10:1) to give additional 10 mg of the product which was combined with the first batch. tert-butyl (S)-12-fluoro-4-(3-fluoropyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (92.0 mg, 181 umol, 84% yield) was obtained as a yellow oil.

Step 2: (S)-12-fluoro-4-(3-fluoropyridin-2-yl)-7a,8,13,14-tetrahydro-7H-[1,2,4]triazolo[4',3':1,6]pyrido[3,2-b]benzofuro[4,3-fg][1,4]oxazonine Formate

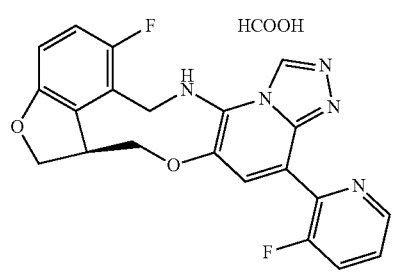 [SMILES: Fc1cccnc1-c1cc2c(n3cnnc13)NCc1c(F)ccc3c1[C@H](CO3)CO2 ; "HCOOH"]

A mixture of tert-butyl (S)-12-fluoro-4-(3-fluoropyridin-2-yl)-7a,13-dihydro-7H-[1,2,4]triazolo[4',3':1,6]pyrido[3,2- b]benzofuro[4,3-fg][1,4]oxazonine-14 (8H)-carboxylate (92.0 mg, 181 umol, 1.00 eq) and HFIP (5 mL) was stirred at 80° C. for 8 h. The reaction mixture was concentrated under reduced pressure. The residue was purified by prep-HPLC (formic acid conditions). The product-containing fraction was concentrated under reduced pressure to remove most of MeCN at 30° C. and the aqueous phase was lyophilized. (S)-12-Fluoro-4-(3-fluoropyridin-2-yl)-7a,8,13,14-tetrahydro-7H-[1,2,4]triazolo[4',3':1,6]pyrido[3,2-b]benzofuro[4,3-fg][1,4]oxazonine (23.0 mg, 50.3 umol, 27% yield, 99.2% purity, formate salt) was obtained as a yellow solid. 1H NMR DMSO-d6 400 MHz δ=ppm 9.45 (s, 1H), 8.49 (d, J=3.1 Hz, 1H), 7.85-7.70 (m, 2H), 7.56-7.45 (m, 2H), 6.93 (t, J=9.4 Hz, 1H), 6.66 (dd, J=8.5, 3.2 Hz, 1H), 4.93-4.85 (m, 1H), 4.79 (br s, 1H), 4.57-4.37 (m, 2H), 4.25-4.15 (m, 1H), 4.01 (br s, 1H), 3.88-3.75 (m, 1H). LCMS (ESI+): m/z 408.1 (M+H).

Example 54: (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine Mesylate Salt Step 1: Step 1: tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate

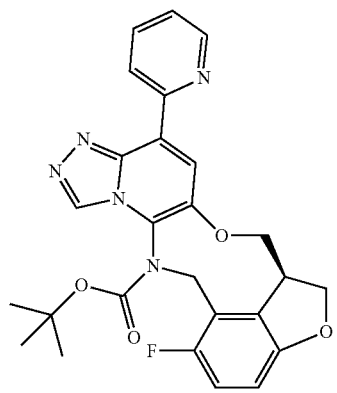 [SMILES: CC(C)(C)OC(=O)N1Cc2c(F)ccc3c2[C@H](CO3)COc2cc(-c3ccccn3)c3nncn3c21]

Tributyl (2-pyridyl) stannane (56.2 mg, 0.153 mmol) was added to a solution of tert-butyl (S)-4-bromo-12-fluoro-7a,13-dihydro-7H-[1,2,4]triazolo[4',3':1,6]pyrido[3,2-b]benzofuro[4,3-fg] [1,4]oxazonine-14 (8H)-carboxylate (Example 16; 50.0 mg, 0.102 mmol) and tetrakis(triphenylphosphine)palladium(0) (35.3 mg, 0.0306 mmol) in toluene (1.00 mL) under nitrogen. The mixture was stirred at 115° C. for 16 h and diluted with sat. aq. NaCl (15.0 mL). The aqueous phase was extracted with DCM (3×15 mL). The combined organic layers were dried over MgSO4, filtered, and concentrated under reduced pressure. The residue was purified by flash column chromatography on silica gel (12 g cartridge) eluting with EtOAc in hexanes (0-100%) to afford the tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate compound as an oil (31.3 mg, 63%). 1H NMR (500 MHz, CDCl3) δ 9.21 (d, J=8.0 Hz, 1H), 8.72 (s, 1H), 8.67 (d, J=3.8 Hz, 1H), 8.22 (s, 1H), 7.85 (td, J=7.8, 1.9 Hz, 1H), 7.35-7.27 (m, 1H), 6.60 (s, 1H), 6.53 (s, 1H), 5.37 (s, 1H), 4.74 (s, 1H), 4.62 (s, 1H), 4.48 (t, J=8.8 Hz, 1H), 4.26 (dd, J=9.7, 1.2 Hz, 1H), 4.18-4.11 (m, 1H), 3.97-3.86 (m, 1H), 1.35 (s, 9H). m/z (ES+) [M+H]+: 490.11. HPLC tR (A05)=2.44 min.

Step 2: (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine

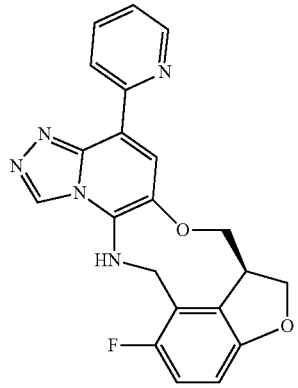 [SMILES: Fc1ccc2c3c1CNc1c(cc(-c4ccccn4)c4nncn14)OC[C@H]3CO2]

A solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (31.3 mg, 0.0639 mmol) in HFIP (2.00 mL) was stirred at 100° C. for 5 h. The solution was concentrated under reduced pressure, and the residue was purified by preparative HPLC (BEH C18 30×150 mm AmBicarb/ACN 35-55%) to afford (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine as a solid (13.0 mg, 52%). 1H NMR (400 MHz, DMSO-d6) δ 9.49 (s, 1H), 9.01 (d, J=8.2 Hz, 1H), 8.64 (d, J=5.0 Hz, 1H), 8.31 (d, J=1.7 Hz, 1H), 7.90 (t, J=7.8 Hz, 1H), 7.79 (t, J=6.6 Hz, 1H), 7.30 (dd, J=7.6, 4.7 Hz, 1H), 6.95 (t, J=9.8 Hz, 1H), 6.68 (dd, J=9.7, 3.6 Hz, 1H), 4.87 (tdd, J=16.6, 11.3, 5.2 Hz, 2H), 4.54 (dd, J=20.7, 10.4 Hz, 2H), 4.25 (d, J=11.4 Hz, 1H), 4.05 (s, 1H), 3.88 (t, J=10.9 Hz, 1H). m/z (ES+) [M+H]+: 390.2. HPLC tR (A05)=2.73 min.

Step 3: (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine Monomesylate

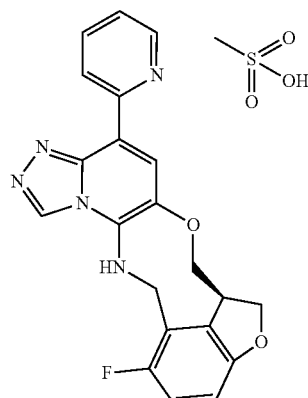

Methanesulfonic acid (0.00217 mL, 0.0334 mmol) was added to a suspension of (S)-12-fluoro-4-(pyridin-2-yl)-7a,8,13,14-tetrahydro-7H-[1,2,4]triazolo[4',3':1,6]pyrido[3,2-b]benzofuro[4,3-fg][1,4]oxazonine (13.0 mg, 0.0334 mmol) in MeCN (2.00 mL). The mixture was stirred at rt for 1 h. The mixture was concentrated under reduced pressure to provide the title compound as a solid (15.2 mg, 94%). 1H NMR (500 MHz, DMSO-d6) δ 9.67 (s, 1H), 8.74 (d, J=4.8 Hz, 1H), 8.66-8.47 (m, 3H), 8.08 (t, J=7.5 Hz, 1H), 7.49-7.42 (m, 1H), 6.99 (t, J=9.0 Hz, 1H), 6.73 (d, J=6.9 Hz, 1H), 4.98 (dd, J=25.9, 15.4 Hz, 2H), 4.65 (s, 1H), 4.56 (t, J=9.0 Hz, 1H), 4.25 (d, J=6.9 Hz, 1H), 4.11 (s, 1H), 3.99 (s, 1H), 2.30 (s, 3H). m/z (ES+) [M+H-MsOH]+: 393.2, HPLC tR (B05)=1.33 min.

Example 55: General Procedure E. Preparation of (S)-12-fluoro-N,N-dimethyl-7a,8,13,14-tetrahydro-7H-[1,2,4]triazolo[4',3':1,6]pyrido[3,2-b]benzofuro[4,3-fg][1,4]oxazonine-4-carboxamide Step 1: tert-butyl (S)-12-fluoro-4-vinyl-7a,13-dihydro-7H-[1,2,4]triazolo[4',3':1,6]pyrido[3,2-b]benzofuro[4,3-fg][1,4]oxazonine-14 (8H)-carboxylate

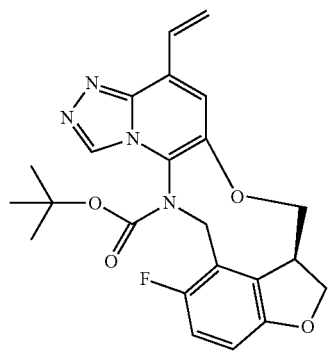 [SMILES: C=Cc1cc2c(n3cnnc13)N(C(=O)OC(C)(C)C)Cc1c(F)ccc3c1[C@H](CO3)CO2]

A mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 300 mg, 0.611 mmol), potassium vinyltrifluoroborate (164 mg, 1.22 mmol), Pd(dppf)Cl2 (44.7 mg, 0.0611 mmol), and NaHCO3 (256 mg, 3.05 mmol) in 1,4-dioxane/water (5.00/0.500 mL) deoxygenated by applying vacuum and refilling with nitrogen. Two additional deoxygenation cycles were applied. The mixture was stirred at 90° C. for 4 h. The mixture was diluted with water (15.0 mL) at room temperature, and the aqueous phase was extracted with EtOAc (4×25.0 mL). The combined organic layers were washed with sat. aq. NaCl (15.0 mL), dried over MgSO4, filtered, and concentrated under reduced pressure. The residue was purified by silica gel chromatography (24 g cartridge) eluting with MeOH in DCM (0-15%) to provide tert-butyl (S)-12-fluoro-4-vinyl-7a,13-dihydro-7H-[1,2,4]triazolo[4',3':1,6]pyrido[3,2-b]benzofuro[4,3-fg][1,4]oxazonine-14 (8H)-carboxylate as a solid (0.258 g, 96%). ES+[M]+: 438.37; HPLC tR (A05)=2.27 min.

Step 2: tert-butyl (S)-12-fluoro-4-formyl-7a,13-dihydro-7H-[1,2,4]triazolo[4',3':1,6]pyrido[3,2-b]benzofuro[4,3-fg][1,4]oxazonine-14 (8H)-carboxylate

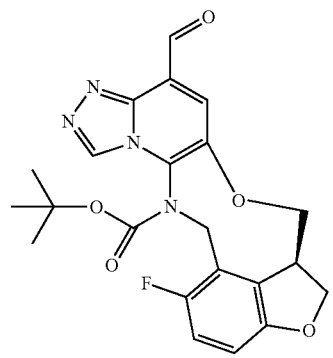 [SMILES: CC(C)(C)OC(=O)N1Cc2c(F)ccc3c2[C@H](CO3)COc2cc(C=O)c3nncn3c21]

NaIO4 (755 mg, 3.53 mmol) and 2,6-lutidine (0.137 mL, 1.18 mmol) were sequentially added to a stirred solution of aq. OsO4 (0.187 mL, 29.4 μmol, 4.00%) and tert-butyl (S)-12-fluoro-4-vinyl-7a,13-dihydro-7H-[1,2,4]triazolo[4',3':1,6]pyrido[3,2-b]benzofuro[4,3-fg][1,4]oxazonine-14 (8H)-carboxylate (258 mg, 0.588 mmol) in 1,4-dioxane/water (6.00 mL/2.00 mL) under N2. The mixture was stirred at room temperature for 4.5 h. Water (15.0 mL) and EtOAc (20.0 mL) were added. The aqueous phase was extracted with EtOAc (3×30 mL). The combined organic layers were washed with sat. aq. NaCl (15.0 mL), dried over MgSO4, filtered, and concentrated under reduced pressure. The residue was purified by silica gel chromatography (24 g cartridge) with EtOAc in hexanes (10-90%) to afford tert-butyl (S)-12-fluoro-4-formyl-7a,13-dihydro-7H-[1,2,4]triazolo[4',3':1,6]pyrido[3,2-b]benzofuro[4,3-fg][1,4]oxazonine-14 (8H)-carboxylate (159 mg, 61%) as a solid. 1H NMR (400 MHz, CDCl3) δ 10.63 (s, 1H), 8.72 (s, 1H), 7.66 (s, 1H), 6.72-6.47 (m, 2H), 5.34 (bs, 1H), 4.74 (bs, 1H), 4.63 (bs, 1H), 4.48 (dd, J=9.6, 7.8 Hz, 1H), 4.27 (dd, J=9.7, 1.4 Hz, 1H), 4.01 (t, J=11.5 Hz, 1H), 3.96-3.85 (m, 1H), 1.36 (s, 9H). m/z (ES+) [M+H]+: 441.62; HPLC tR (A05)=2.13 min.

Step 3: (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic Acid

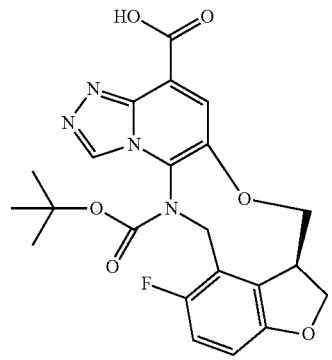 [SMILES: CC(C)(C)OC(=O)N1Cc2c(F)ccc3c2[C@H](CO3)COc2cc(C(=O)O)c3nncn3c21]

2-Methyl-2-butene (0.373 mL, 3.52 mmol) was added to a solution of tert-butyl (S)-12-fluoro-4-formyl-7a,13-dihydro-7H-[1,2,4]triazolo[4',3':1,6]pyrido[3,2-b]benzofuro[4,3-fg][1,4]oxazonine-14 (8H)-carboxylate (155 mg, 0.352 mmol) in tBuOH (4.50 mL). A solution of NaClO$_2$ (95.5 mg, 1.06 mmol) and NaH$_2$PO$_4$ (76.0 mg, 0.633 mmol) in water (3.00 mL) was added dropwise. The mixture was stirred at room temperature for 2 h. The mixture was concentrated under reduced pressure. Water (10.0 mL) was added, and the aqueous phase was extracted with EtOAc (4×20.0 mL). The combined organic layers were washed with sat. aq. NaCl (8.00 mL), dried over MgSO4, filtered, and concentrated under reduced pressure. The residue was purified by silica gel chromatography (12 g, cartridge) with MeOH in DCM (0-30%) to afford (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid as a solid (128 mg, 80%). m/z (ES+) [M]$^+$: 456.73; HPLC tR (A05)=1.98 min monitored by chromatography. The mixture was concentrated under reduced pressure. Water (10.0 mL) was added, and the aqueous phase was extracted with EtOAc (3×20.0 mL). The combined organic layers were washed with sat. aq. NaCl (8.00 mL), dried over MgSO$_4$, filtered, and concentrated under reduced pressure. The residue was purified by silica gel chromatography (4 g, cartridge) with MeOH in DCM (0-10%) to provide tert-butyl (S)-4-(dimethylcarbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate as a solid (25.0 mg, 79%). m/z (ES+) [M+H]$^+$: 484.78; HPLC tR (A05)=2.05 min.

Step 5: (S)-12-fluoro-N,N-dimethyl-7a,8,13,14-tetrahydro-7H-[1,2,4]triazolo[4',3':1,6]pyrido[3,2-b]benzofuro[4,3-fg][1,4]oxazonine-4-carboxamide Step 4: tert-butyl (S)-4-(dimethylcarbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

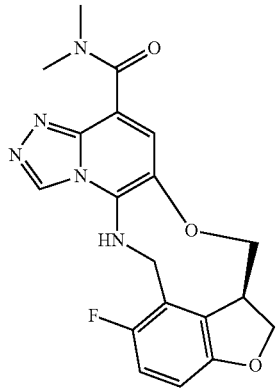

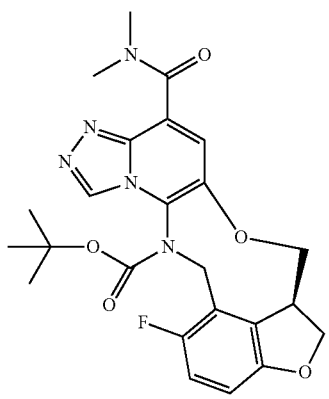 [SMILES: CN(C)C(=O)c1cc2c(n3cnnc13)N(C(=O)OC(C)(C)C)Cc1c(F)ccc3c1[C@H](CO3)CO2]

N,N-Diisopropylethylamine (22.9 µL, 0.131 mmol) was added to a solution of (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid (30.0 mg, 0.0657 mmol) and dimethylamine hydrochloride (8.04 mg, 0.0986 mmol) in DMF (1.00 mL). HATU (50.0 mg, 0.131 mmol) was added. The mixture was stirred at room temperature for 2 h. Reaction completion was A solution of tert-butyl (S)-4-(dimethylcarbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (25.0 mg, 0.0517 mmol) in HFIP (1.00 mL) was heated to 100° C. for 2 h. The mixture was concentrated under reduced pressure. The residue was purified by preparative HPLC (Gemini C18 30×100 mm AmBicarb/ACN 25-45%) to afford the title compound as a solid (4.50 mg, 23%). 1H NMR (400 MHz, CD3OD) δ 9.30 (s, 1H), 7.51 (s, 1H), 6.86 (dd, J=10.3, 8.7 Hz, 1H), 6.62 (dd, J=8.7, 3.9 Hz, 1H), 5.05 (d, J=14.8 Hz, 1H), 4.86 (d, J=14.6 Hz, 1H), 4.57 (t, J=9.3 Hz, 2H), 4.27 (dd, J=9.6, 3.3 Hz, 1H), 3.99 (ddd, J=12.9, 9.8, 4.8 Hz, 1H), 3.92-3.77 (m, 1H), 3.13 (s, 3H), 2.94 (s, 3H). m/z (ES+) [M]$^+$: 383.38; HPLC tR (A05)=1.83 min.

Compounds 38 and 64 were prepared according to General Procedure E using the suitable starting materials, precursors, intermediates, and reagents.

| Cmpd No. | Compound Name | Structure | Spectral Data |
|---|---|---|---|
| 64 | (S)-12-fluoro-N-methyl-N-(tetrahydro-2H-pyran-4-yl)-7a,8,13,14-tetrahydro-7H-[1,2,4]triazolo[4',3':1,6]pyrido[3,2-b]benzofuro[4,3-fg][1,4]oxazonine-4-carboxamide | 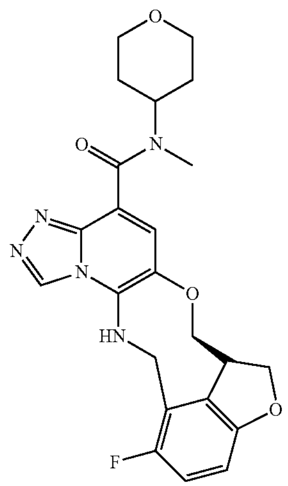 | 1H NMR (500 MHz, MeOD) δ 9.31 (s, 1H), 7.49 (s, 1H), 6.86 (dd, J = 10.3, 8.7 Hz, 1H), 6.62 (dd, J = 8.7, 3.8 Hz, 1H), 5.05 (d, J = 14.8 Hz, 1H), 4.86 (m, 2H), 4.56 (t, J = 9.3 Hz, 2H), 4.27 (dd, J = 9.6, 3.2 Hz, 1H), 4.09-3.93 (m, 2H), 3.85 (t, J = 11.2 Hz, 2H), 3.56 (bs, 1H), 3.11-2.72 (m, 3H), 2.20-2.10 (m, 1H), 1.98-1.85 (m, 2H), 1.79 (bs, 2H) (rotamers); m/z (ES+) [M]+: 453.35; LC-MS (A05) tR = 1.85 min. |
| 38 | (S)-12-fluoro-N-methyl-N-(2,2,2-trifluoroethyl)-7a,8,13,14-tetrahydro-7H-[1,2,4]triazolo[4',3':1,6]pyrido[3,2-b]benzofuro[4,3-fg][1,4]oxazonine-4-carboxamide | 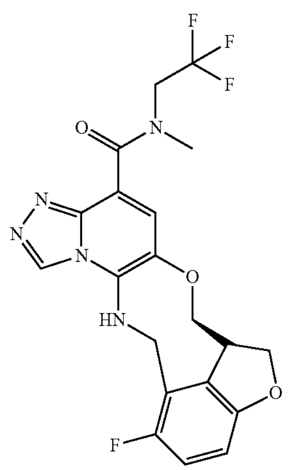 | 1H NMR (500 MHz, DMSO) δ 9.42 (s, 1H), 7.79 (s, 1H), 7.45 (s, 1H), 6.96 (dd, J = 10.2, 8.8 Hz, 1H), 6.69 (dd, J = 8.7, 3.8 Hz, 1H), 4.90 (d, J = 15.0 Hz, 1H), 4.80 (d, J = 15.4 Hz, 1H), 4.52 (t, J = 9.4 Hz, 1H), 4.46 (bs, 1H), 4.35 (bs, 2H), 4.21 (dd, J = 9.5, 3.7 Hz, 1H), 4.02 (t, J = 10.8 Hz, 1H), 3.80 (t, J = 11.4 Hz, 1H), 3.02 (s, 3H) (rotamers); m/z (ES+) [M]+: 451.21; LC-MS (A05) tR = 2.03 min. |

Example 56: (S)-12-fluoro-4-(1-methyl-1H-pyrazol-3-yl)-7a,8,13,14-tetrahydro-7H-[1,2,4]triazolo[4',3':1,6]pyrido[3,2-b]benzofuro[4,3-fg][1,4]oxazonine Mesylate Step 1: tributyl-(1-methylpyrazol-3-yl)stannane

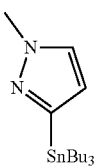

n-BuLi in THF (0.960 mL, 2.40 mmol, 2.50 M) was added dropwise to a solution of 5-bromo-1-methyl-1H-pyrazole (0.322 g, 2.00 mmol) in THF (10.0 mL) at −78° C. The mixture was stirred at −78° C. for 30 min. Tributyltin chloride (0.651 mL, 2.40 mmol) was added dropwise. The mixture was stirred at −78° C. for 1 h, warmed to room temperature, and stirred for 2 h. Sat. NH4Cl (10 mL) was added, and the aqueous phase was extracted with EtOAc (3×20 mL). The combined organic phases were washed with brine (20 mL), dried over MgSO4, filtered, and concentrated. The residue was purified by silica gel chromatography (40 g cartridge) eluting with hexanes and EtOAc (0-20%) to provide the title compound as an oil (0.142 g, 19%). 1H NMR (500 MHz, CDCl3) δ 7.42 (d, J=2.0 Hz, 1H), 6.32 (d, J=2.1 Hz, 1H), 3.96 (s, 3H), 1.60-1.52 (m, 6H), 1.38-1.28 (m, 6H), 1.10-1.04 (m, 6H), 0.88 (t, J=7.3 Hz, 9H); m/z (ES+) [M]+: 371.06 (multiple Sn isotopes), HPLC tR (A05)=3.03 min.

Step 2: tert-butyl (S)-12-fluoro-4-(1-methyl-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate

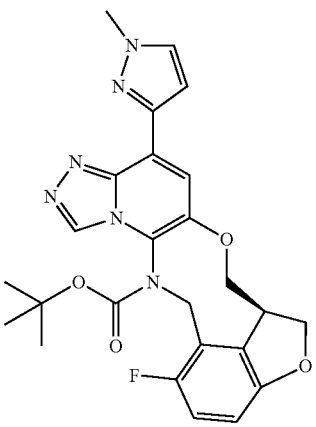 [SMILES: Cn1ccc(-c2cc3c(n4cnnc24)N(C(=O)OC(C)(C)C)Cc2c(F)ccc4c2[C@H](CO4)CO3)n1]

A solution of tributyl-(1-methylpyrazol-3-yl) stannane (51.0 mg, 0.137 mmol) in toluene (1.50 mL) was added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 50.0 mg, 0.102 mmol) and Pd(PPh$_3$)$_4$ (23.5 mg, 0.0204 mmol) under nitrogen. The mixture was heated at 110° C. for 20 h. The mixture was concentrated under reduced pressure, and the residue was purified by silica gel chromatography (4 g cartridge) eluting with MeOH in DCM (0-15%) to provide tert-butyl (S)-12-fluoro-4-(1-methyl-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylateas a solid (37.0 mg, 74%). m/z (ES+) [M+H]$^+$:493.49; HPLC tR (A05)=2.21 min.

Step 3: (S)-12-fluoro-4-(1-methyl-H-pyrazol-3-yl)-7a,8,13,14-tetrahydro-7H-[1,2,4]triazolo[4',3':1,6]pyrido[3,2-b]benzofuro[4,3-fg][1,4]oxazonine

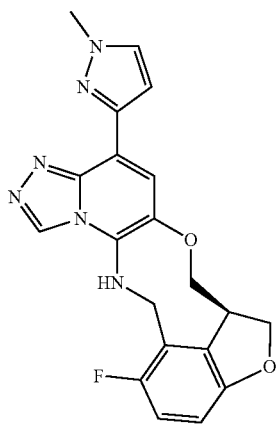 [SMILES: Cn1ccc(-c2cc3c(n4cnnc24)NCc2c(F)ccc4c2[C@H](CO4)CO3)n1]

A solution of tert-butyl (S)-12-fluoro-4-(1-methyl-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (37.0 mg, 75.1 μmol) in HFIP (2.00 mL) was heated at 100° C. for 16 h. The mixture was concentrated under reduced pressure, and the residue was purified by HPLC (Gemini C18 30×100 mm AmBicarb/ACN 27-47%) to afford the deprotected material as a solid (20.8 mg, 71%). 1H NMR (500 MHz, DMSO) δ 9.41 (s, 1H), 7.74 (d, J=2.1 Hz, 1H), 7.73 (s, 1H), 7.44 (t, J=5.3 Hz, 1H), 7.22 (d, J=2.2 Hz, 1H), 6.99-6.88 (m, 1H), 6.66 (dd, J=8.6, 3.8 Hz, 1H), 4.88 (d, J=11.4 Hz, 1H), 4.76 (d, J=11.6 Hz, 1H), 4.55-4.50 (m, 2H), 4.24 (dd, J=9.6, 3.4 Hz, 1H), 4.06-3.97 (m, 1H), 3.90 (s, 3H), 3.84 (t, J=11.5 Hz, 1H). m/z (ES+) [M+H]$^+$: 392.38; HPLC tR (A05)=1.97 min.

Step 4: (S)-12-fluoro-4-(1-methyl-H-pyrazol-3-yl)-7a,8,13,14-tetrahydro-7H-[1,2,4]triazolo[4',3':1,6]pyrido[3,2-b]benzofuro[4,3-fg][1,4]oxazonine Mesylate Salt

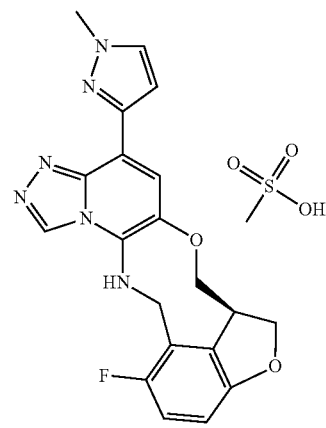

Methanesulfonic acid (1.90 μL, 29.3 μmol) was added to a suspension of (S)-12-fluoro-4-(1-methyl-1H-pyrazol-3-yl)-7a,8,13,14-tetrahydro-7H-[1,2,4]triazolo[4',3':1,6]pyrido[3,2-b]benzofuro[4,3-fg][1,4]oxazonine (11.5 mg, 29.3 μmol) in MeCN (1.50 mL). The mixture was stirred at room temperature for 1 h. The mixture was concentrated under reduced pressure to provide the title compound as a solid (13.5 mg, 94%). 1H NMR (400 MHz, CD3OD) δ 9.47 (s, 1H), 8.28 (s, 1H), 7.70 (d, J=2.4 Hz, 1H), 6.89 (dd, J=10.3, 8.7 Hz, 1H), 6.85 (d, J=2.4 Hz, 1H), 6.66 (dd, J=8.7, 3.9 Hz, 1H), 5.14 (d, J=14.8 Hz, 1H), 4.94 (d, J=14.9 Hz, 1H), 4.76 (dd, J=9.9, 4.1 Hz, 1H), 4.60 (t, J=9.3 Hz, 1H), 4.31 (dd, J=9.7, 3.3 Hz, 1H), 4.09-4.02 (m, 1H), 4.01 (s, 3H), 4.01-3.92 (m, 1H), 2.70 (s, 3H). m/z (ES+) [M-MeSO$_3$H]$^+$: 392.1; HPLC tR (B05)=1.53 min.

Example 57: General Procedure B. Preparation of (S)-4-(3,5-difluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1: tert-butyl (S)-4-(3,5-difluoropyridin-2-yl)-12-fluoro-7a,13-dihydro-7H-[1,2,4]triazolo[4',3':1,6]pyrido[3,2-b]benzofuro[4,3-fg][1,4]oxazonine-14(8H)-carboxylate

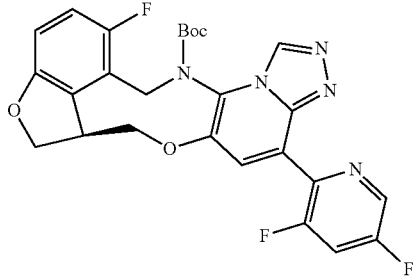 [SMILES: CC(C)(C)OC(=O)N1Cc2c(F)ccc3c2[C@H](CO3)COc2cc(-c3ncc(F)cc3F)c3nncn3c21]

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14(8H)-carboxylate (200 mg, 285 umol, 1.00 eq) in dioxane (5 mL) was added 2-bromo-3,5-difluoro-pyridine (55.3 mg, 285 umol, 1.00 eq), CuI (21.7 mg, 114 umol, 0.400 eq), Pd(PPh$_3$)$_4$ (33.0 mg, 28.5 umol, 0.100 eq) and LiCl (24.2 mg, 570 umol). Reaction completion was monitored by LC-MS. The reaction mixture was concentrated under reduced pressure. The residue was purified by prep-TLC (SiO$_2$, Petroleum ether/Ethyl acetate=1/4). tert-butyl (S)-4-(3,5-difluoropyridin-2-yl)-12-fluoro-7a,13-dihydro-7H-[1,2,4]triazolo[4',3':1,6]pyrido[3,2-b]benzofuro[4,3-fg][1,4]oxazonine-14(8H)-carboxylate (140 mg, crude) was obtained as a yellow solid.

Step 2: (S)-4-(3,5-difluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine

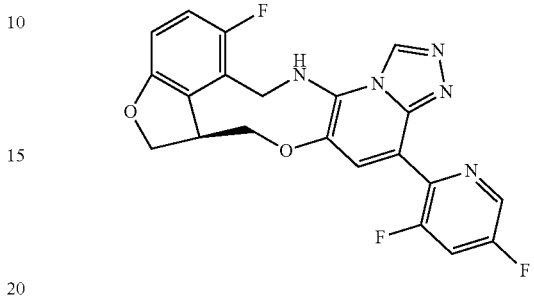

To a solution of tert-butyl (S)-4-(3,5-difluoropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 228 umol, 1.00 eq) in DCM (3 mL) was added TFA (1.5 mL) at 15° C. The mixture was stirred at 15° C. for 2 h. Reaction completion was monitored by LC-MS. The reaction mixture was concentrated under reduced pressure. The residue was purified by prep-HPLC (FA system). (S)-4-(3,5-difluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine (50 mg, 104.59 umol, 45% yield, 98.607% purity, formate salt) was obtained as a yellow solid. 1H NMR ET20970-310-P1C11 DMSO-d6 400 MHz δ=ppm 9.46 (s, 1H), 8.62 (s, 1H), 8.08 (br t, J=9.2 Hz, 1H), 7.75 (br t, J=5.6 Hz, 1H), 7.54 (s, 1H), 6.97 (t, J=9.6 Hz, 1H), 6.70 (dd, J=8.8, 3.6 Hz, 1H), 4.98-4.88 (m, 1H), 4.87-4.76 (m, 1H), 4.60-4.46 (m, 2H), 4.22 (br dd, J=9.4, 3.2 Hz, 1H), 4.05 (br s, 1H), 3.92-3.79 (m, 1H). LCMS (ESI+): m/z 426.1 (M+H).

Compounds 83, 93, 95, 101, 123, 135, 144, and 149 were prepared according to General Procedure B using the suitable starting materials, precursors, intermediates, and reagents.

| Cmpd No. | Compound Name | Structure | Spectral Data |
|---|---|---|---|
| 95 | (S)-12-fluoro-4-(3-methylpyridin-2-yl)-7a,8,13,14-tetrahydro-7H-[1,2,4]triazolo[4',3':1,6]pyrido[3,2-b]benzofuro[4,3-fg][1,4]oxazonine | 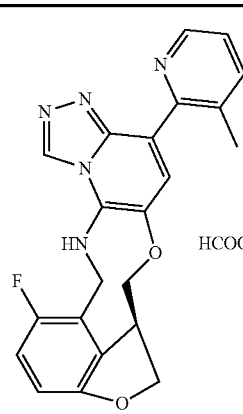 | 1H NMR DMSO-d6 400 MHz δ = ppm 9.48 (br s, 1H), 8.49 (br s, 1H), 7.80 (br s, 1H), 7.71 (br s, 1H), 7.48 (s, 1H), 7.41 (br s, 1H), 7.07-6.91 (m, 1H), 6.71 (dd, J = 8.7, 3.8 Hz, 1H), 4.98-4.88 (m, 1H), 4.88-4.75 (m, 1H), 4.60-4.47 (m, 2H), 4.24 (dd, J = 9.6, 3.5 Hz, 1H), 4.05 (br s, 1H), 3.91-3.79 (m, 1H), 2.24 (s, 3H). LCMS (ESI+): m/z 404.1 (M + H). |

| Cmpd No. | Compound Name | Structure | Spectral Data |
|---|---|---|---|
| 101 | (S)-4-(5-chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine | 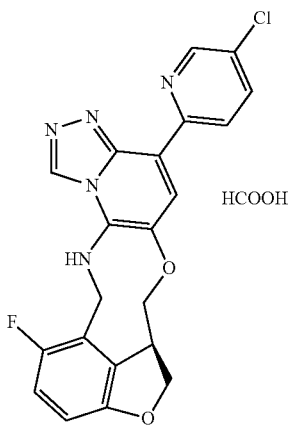 [SMILES: Fc1ccc2c3c1CNc1c(cc(-c4ccc(Cl)cn4)c4nncn14)OC[C@H]3CO2 ; "HCOOH"] | $^1$H NMR CD$_3$OD 400 MHz. δ = ppm 9.50 (br s, 1H), 8.71 (br s, 1H), 8.60 (s, 1H), 8.17 (br s, 1H), 7.99 (s, 1H), 6.90 (t, J = 9.6 Hz, 1H), 6.66 (dd, J = 8.6, 3.7 Hz, 1H), 5.19 (d, J = 14.8 Hz, 1H), 4.97 (br d, J = 15.0 Hz, 1H), 4.79 (br d, J = 6.2 Hz, 1H), 4.62 (t, J = 9.2 Hz, 1H), 4.32 (dd, J = 9.5, 2.9 Hz, 1H), 4.13-3.92 (m, 2H). LCMS (ESI+): m/z 424.0 (M + H). |
| 144 | (S)-4-(3-(difluoromethyl)-6-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine | 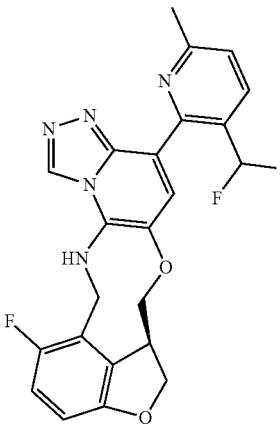 | $^1$H NMR DMSO-d$_6$ 400 MHz δ = ppm 9.43 (s, 1H), 8.01 (d, J = 8.2 Hz, 1H), 7.67 (br t, J = 6.3 Hz, 1H), 7.44 (d, J = 8.2 Hz, 1H), 7.41 (s, 1H), 7.05 (t, J = 52.8 Hz, 1H), 6.99-6.90 (m, 1H), 6.68 (dd, J = 8.6, 3.7 Hz, 1H), 4.96-4.87 (m, 1H), 4.83-4.74 (m, 1H), 4.56-4.46 (m, 2H), 4.22 (dd, J = 9.7, 3.5 Hz, 1H), 4.08-3.98 (m, 1H), 3.86-3.80 (m, 1H), 2.54 (s, 3H). LCMS (ESI+): m/z 454.1 (M + H). |
| 83 | (S)-12-fluoro-4-(2-(trifluoromethoxy)pyridin-3-yl)-7a,8,13,14-tetrahydro-7H-[1,2,4]triazolo[4',3':1,6]pyrido[3,2-b]benzofuro[4,3-fg][1,4]oxazonine | 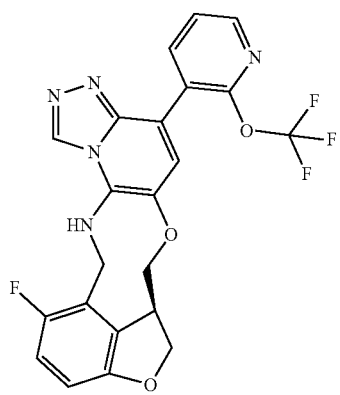 [SMILES: Fc1ccc2c3c1CNc1c(cc(-c4cccnc4OC(F)(F)F)c4nncn14)OC[C@H]3CO2] | $^1$H NMR DMSO-d$_6$ 400 MHz δ = ppm 9.40 (br d, J = 1.2 Hz, 1H), 8.36 (dd, J = 5.2, 3.2 Hz, 2H), 7.68 (br t, J = 6.2 Hz, 1H), 7.58-7.48 (m, 2H), 6.96 (t, J = 9.5 Hz, 1H), 6.70 (dd, J = 8.6, 3.7 Hz, 1H), 4.90 (br d, J = 5.6 Hz, 1H), 4.81 (br s, 1H), 4.61-4.41 (m, 2H), 4.24-4.15 (m, 1H), 4.04 (br s, 1H), 3.87 (br d, J = 11.5 Hz, 1H). LCMS (ESI+): m/z 474.2 (M + H). |

| Cmpd No. | Compound Name | Structure | Spectral Data |
|---|---|---|---|
| 93 | (S)-12-fluoro-4-(thiazol-5-yl)-7a,8,13,14-tetrahydro-7H-[1,2,4]triazolo[4',3':1,6]pyrido[3,2-b]benzofuro[4,3-fg][1,4]oxazonine | 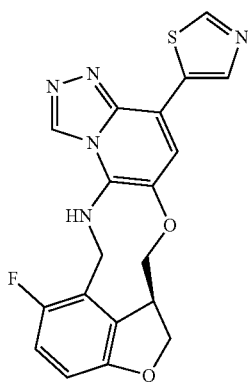 [SMILES: Fc1ccc2c3c1CNc1c(cc(-c4cncs4)c4nncn14)OC[C@H]3CO2] | $^1$H NMR DMSO-d$_6$ 400 MHz δ = ppm 9.49 (s, 1H), 9.08 (s, 1H), 8.70 (s, 1H), 7.87 (s, 1H), 7.75 (br t, J = 6.4 Hz, 1H), 6.95 (dd, J = 10.1, 8.8 Hz, 1H), 6.68 (dd, J = 8.7, 3.9 Hz, 1H), 4.95-4.86 (m, 1H), 4.85-4.76 (m, 1H), 4.59-4.47 (m, 2H), 4.22 (dd, J = 9.6, 3.4 Hz, 1H), 4.09-3.99 (m, 1H), 3.97-3.87 (m, 1H). LCMS (ESI+): m/z 396.1 (M + H). |
| 135 | (S)-4-(1,4-dimethyl-1H-imidazol-2-yl)-12-fluoro-7a,8,13,14-tetrahydro-7H-[1,2,4]triazolo[4',3':1,6]pyrido[3,2-b]benzofuro[4,3-fg][1,4]oxazonine | 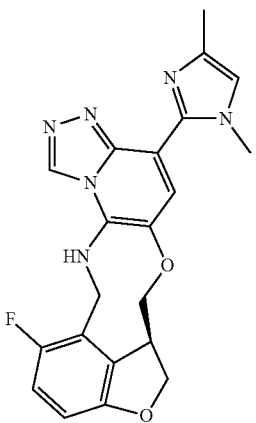 [SMILES: Cc1cn(C)c(-c2cc3c(n4cnnc24)NCc2c(F)ccc4c2[C@H](CO4)CO3)n1] | $^1$H NMR CD$_3$OD 400 MHz δ = ppm 9.54 (s, 1H), 8.04 (s, 1H), 7.45 (s, 1H), 6.95-6.87 (m, 1H), 6.68 (dd, J = 8.7, 3.9 Hz, 1H), 5.20 (d, J = 14.8 Hz, 1H), 4.96 (br d, J = 14.7 Hz, 1H), 4.74 (br d, J = 6.2 Hz, 1H), 4.62 (t, J = 9.4 Hz, 1H), 4.31 (dd, J = 9.7, 3.2 Hz, 1H), 4.06 (br d, J = 2.8 Hz, 1H), 3.93 (br d, J = 10.9 Hz, 1H), 3.83 (s, 3H), 2.42 (s, 3H). LCMS (ESI+): m/z 407.2 (M + H). |
| 149 | (S)-12-fluoro-4-(4-methylpyridin-2-yl)-7a,8,13,14-tetrahydro-7H-[1,2,4]triazolo[4',3':1,6]pyrido[3,2-b]benzofuro[4,3-fg][1,4]oxazonine | 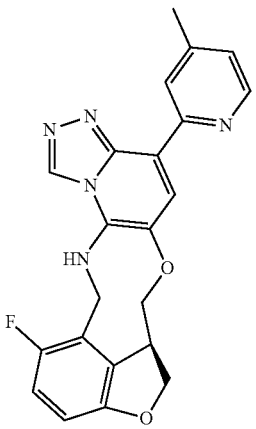 [SMILES: Cc1ccnc(-c2cc3c(n4cnnc24)NCc2c(F)ccc4c2[C@H](CO4)CO3)c1] | $^1$H NMR CD$_3$OD 400 MHz δ = ppm 9.86 (br s, 1H), 8.65 (br s, 2H), 8.34 (br s, 1H), 7.61 (br s, 1H), 6.90 (br t, J = 9.3 Hz, 1H), 6.71-6.61 (m, 1H), 5.28-5.08 (m, 1H), 5.04-4.96 (m, 1H), 4.81 (br s, 1H), 4.62 (br t, J = 7.8 Hz, 1H), 4.32 (br d, J = 8.9 Hz, 1H), 4.03 (hr s, 2H), 2.67 (s, 3H). VTNMR DMSO-d$_6$ 400 MHz δ = ppm 8.81 (br s, 1H), 8.63 (br s, 1H), 7.02-6.88 (m, 1H), 6.70 (br dd, J = 8.3, 3.3 Hz, 1H), 5.07-4.87 (m, 2H), 4.66-4.51 (m, 2H), 4.25-4.18 (m, 1H), 4.15-4.06 (m, 1H), 4.02 (br d, J = 10.8 Hz, 1H), 2.54 (s, 3H). LCMS (ESI+): m/z 404.1 (M + H). |

| Cmpd No. | Compound Name | Structure | Spectral Data |
|---|---|---|---|
| 123 | (S)-12-fluoro-4-(6-methylpyridazin-4-yl)-7a,8,13,14-tetrahydro-7H-[1,2,4]triazolo[4',3':1,6]pyrido[3,2-b]benzofuro[4,3-fg][1,4]oxazonine | 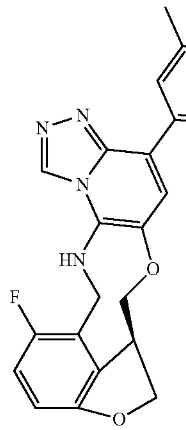 | 1H NMR DMSO-d6 400 MHz δ = ppm 9.92 (d, J = 1.8 Hz, 1H), 9.50 (s, 1H), 8.47 (d, J = 2.0 Hz, 1H), 8.18 (s, 1H), 8.06-7.96 (m, 1H), 6.99-6.90 (m, 1H), 6.68 (dd, J = 8.7, 3.9 Hz, 1H), 4.97-4.89 (m, 1H), 4.84 (br s, 1H), 4.53 (br t, J = 9.3 Hz, 2H), 4.20 (dd, J = 9.3, 3.3 Hz, 1H), 4.04 (br s, 1H), 3.99-3.88 (m, 1H), 2.65 (s, 3H). LCMS (ESI+): m/z 405.1 (M + H) |

Example 58: (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine Step 1: 2-iodo-5-methylpyrimidine

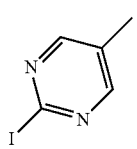

A mixture of 2-chloro-5-methylpyrimidine (1.00 g, 7.78 mmol, 1.00 eq) in HI (13.6 g, 50.0 mmol, 8.00 mL, 47% purity, 6.42 eq) was stirred at 0° C. for 1 hr under nitrogen atmosphere. LC-MS showed some of the starting material remained. The mixture was stirred at 15° C. for additional 2 h. The reaction mixture was adjusted pH to 8-9 by added sat. aq. NaHCO₃ and extracted with EtOAc (50 mL*3). The combined organic layers were dried over anhydrous Na₂SO₄, filtered and concentrated under reduced pressure. Then the residue was purified by flash silica gel (PE/MTBE=1/1) to give 2-iodo-5-methylpyrimidine (400 mg, crude) as a white solid.

Step 2: tert-butyl (S)-12-fluoro-4-(5-methylpyrimidin-2-yl)-7a,13-dihydro-7H-[1,2,4]triazolo[4',3':1,6]pyrido[3,2-b]benzofuro[4,3-fg][1,4]oxazonine-14(8H)-carboxylate

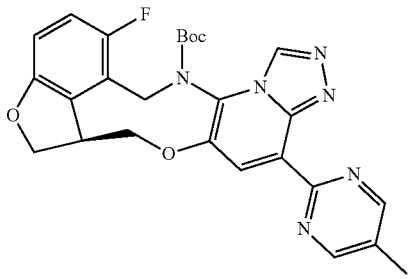 [SMILES: Cc1cnc(-c2cc3c(n4cnnc24)N(C(=O)OC(C)(C)C)Cc2c(F)ccc4c2[C@H](CO4)CO3)nc1]

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14(8H)-carboxylate (150 mg, 214 umol, 1.00 eq) in dioxane (4 mL) was added CuI (16.3 mg, 85.5 umol, 0.400 eq), 2-iodo-5-methylpyrimidine (56.5 mg, 257 umol, 1.20 eq), Pd(PPh₃)4 (24.7 mg, 21.4 umol, 0.100 eq) and LiCl (18.1 mg, 428 umol, 8.76 uL, 2.00 eq) at 15° C. The mixture was stirred at 80° C. for 12 h under nitrogen atmosphere. The reaction mixture was concentrated under reduced pressure. The residue was purified by prep-TLC (SiO₂, Petroleum ether/Ethyl acetate=0/1). (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine (55.0 mg, crude) was obtained as yellow solid.

Step 3: (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine Hydrochloride

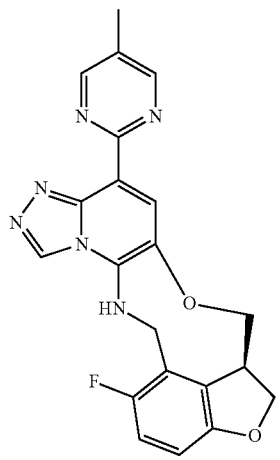 [SMILES: Cc1cnc(-c2cc3c(n4cnnc24)NCc2c(F)ccc4c2[C@H](CO4)CO3)nc1]

To a solution of tert-butyl (S)-12-fluoro-4-(5-methylpyrimidin-2-yl)-7a,13-dihydro-7H-[1,2,4]triazolo[4',3':1,6]pyrido[3,2-b]benzofuro[4,3-fg][1,4]oxazonine-14 (8H)-carboxylate (55.0 mg, 109 umol, 1.00 eq) in DCM (2 mL) was added TFA (1.54 g, 13.5 mmol, 1.00 mL, 124 eq) at 15° C. The mixture was stirred at 15° C. for 2 h The reaction mixture was concentrated under reduced pressure. The residue was purified by prep-HPLC (column: Welch Xtimate C18 150*40 mm*10 um; mobile phase: [water (0.225% FA)—ACN]; B %: 10%-50%, 12 min). (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine (29.5 mg, 46.1 umol, 42% yield, 99.1% purity, formate salt) was obtained as a yellow solid. The compound was additionally purified by prep-HPLC (column: Phenomenex Luna C18 150*30 mm*5 um; mobile phase: [water (0.04% HCl) —ACN]; B %: 15%-50%, 10 min). (S)-12-fluoro-4-(5-methylpyrimidin-2-yl)-7a,8,13,14-tetrahydro-7H-[1,2,4]triazolo[4',3':1,6]pyrido[3,2-b]benzofuro[4,3-fg][1,4]oxazonine (25.0 mg, 56.5 umol, 51% yield, 99.6% purity, HCl salt) was obtained as a yellow solid. 1H NMR CD3OD 400 MHz δ=ppm 9.55 (s, 1H), 8.88 (s, 1H), 8.79 (s, 2H), 6.93 (t, J=9.4 Hz, 1H), 6.69 (dd, J=8.5, 3.7 Hz, 1H), 5.24 (br d, J=14.8 Hz, 1H), 5.01 (br d, J=15.6 Hz, 1H), 4.85-4.80 (m, 1H), 4.70-4.61 (m, 1H), 4.35 (br d, J=6.8 Hz, 1H), 4.09 (br s, 1H), 4.04-3.94 (m, 1H), 2.41 (s, 3H). LCMS (ESI+): m/z 405.2 (M+H).

Example 59: (S)-4-(3,5-dimethylpyrazin-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3,5-dimethylpyrazin-2-yl trifluoromethanesulfonate

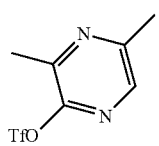

To a solution of 3,5-dimethylpyrazin-2-ol (200 mg, 1.61 mmol, 1.00 eq) and TEA (326 mg, 3.22 mmol, 448 uL, 2.00 eq) in DCM (5 mL) was added Tf$_2$O (682 mg, 2.42 mmol, 399 uL, 1.50 eq) at 0° C. under nitrogen atmosphere. The mixture was stirred at 0° C. for 0.5 hr and then at 25° C. for 12 h. LC-MS showed 3,5-dimethylpyrazin-2-ol was consumed completely and one main peak with desired mass was detected. The reaction mixture was quenched by addition of ice water (5 mL), and then diluted with DCM (5 mL) and extracted with DCM (5 mL*3). The combined organic layers were washed with sat. aq. NaCl (10 mL), dried over Na$_2$SO$_4$, filtered and blown to dryness by nitrogen stream. The residue was purified by prep-TLC (SiO$_2$, Petroleum ether: Ethyl acetate=3:1, Rf=0.5). 3,5-dimethylpyrazin-2-yl trifluoromethanesulfonate (200 mg, 781 umol, 48% yield) was obtained as a yellow oil.

Step 2: tert-butyl (S)-4-(3,5-dimethylpyrazin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

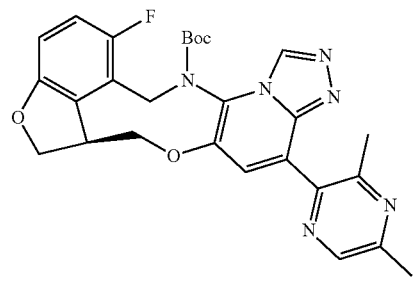 [SMILES: Cc1cnc(-c2cc3c(n4cnnc24)N(C(=O)OC(C)(C)C)Cc2c(F)ccc4c2[C@H](CO4)CO3)c(C)n1]

A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (200 mg, 285 umol, 1.00 eq), 3,5-dimethylpyrazin-2-yl trifluoromethanesulfonate (110 mg, 428 umol, 1.50 eq), LiCl (36.3 mg, 855 umol, 17.5 uL, 3.00 eq), Pd(PPh$_3$)4 (33.0 mg, 28.5 umol, 0.100 eq) in dioxane (5 mL) was degassed and purged with nitrogen for 3 times at 25° C., and then the mixture was stirred at 100° C. for 17 h under nitrogen atmosphere. LC-MS showed presence of the starting material. The mixture was stirred at 100° C. for 7 h The reaction was still incomplete by LC-MS. To the mixture was added 3,5-dimethylpyrazin-2-yl trifluoromethanesulfonate (110 mg, 428 umol, 1.500 eq), LiCl (36.3 mg, 855 umol, 17.5 uL, 3.00 eq), Pd(PPh$_3$)4 (33.0 mg, 28.5 umol, 0.100 eq) at 25° C. under nitrogen atmosphere. The mixture was stirred at 100° C. for 16 h. The reaction mixture was quenched by addition of water (5 mL), and then diluted with EtOAc (5 mL) and extracted with EtOAc (5 mL*3). The combined organic layers were washed with sat. aq. NaCl (10 mL), dried over Na$_2$SO$_4$, filtered and concentrated under reduced pressure. The residue was purified by prep-TLC (SiO$_2$, Ethyl acetate: Methanol=10:1, Rf=0.5). tert-butyl (S)-4-(3,5-dimethylpyrazin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (130 mg, 251 umol, 87% yield) was obtained as a yellow oil.

Step 3: (S)-4-(3,5-dimethylpyrazin-2-yl)-12-fluoro-7a,8,13,14-tetrahydro-7H-[1,2,4]triazolo[4',3':1,6]pyrido[3,2-b]benzofuro[4,3-fg][1,4]oxazonine Formate

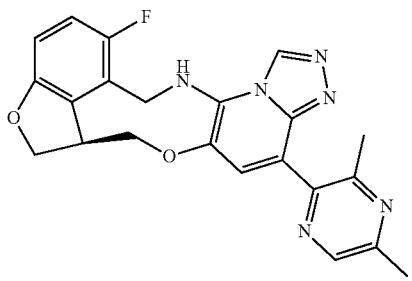

A mixture of tert-butyl (S)-4-(3,5-dimethylpyrazin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 231.42 umol, 1.00 eq) in HFIP (5 mL) was degassed by purging with nitrogen 3 times at 25° C., and then the mixture was stirred at 80° C. for 12 h under nitrogen atmosphere. The mixture was concentrated in vacuum. The residue was purified by prep-HPLC (formic acid conditions: column: Phenomenex Luna C18 200*40 mm*10 um; mobile phase: [water (0.225% FA)—ACN]; B %: 10%-40%, 12 min). (S)-4-(3,5-dimethylpyrazin-2-yl)-12-fluoro-7a,8,13,14-tetrahydro-7H-[1,2,4]triazolo[4',3':1,6]pyrido[3,2-b]benzofuro[4,3-fg][1,4]oxazonine (24.5 mg, 52.2 umol, 22% yield, 99.0% purity, formate) was obtained as a yellow solid. 1H NMR CDCl3 400 MHz δ=ppm 9.02 (s, 1H), 8.33 (s, 1H), 7.33 (s, 1H), 6.83 (t, J=9.4 Hz, 1H), 6.64 (dd, J=8.6, 3.9 Hz, 1H), 5.67 (br s, 1H), 5.06 (br dd, J=14.5, 7.0 Hz, 1H), 4.84 (br dd, J=14.6, 6.1 Hz, 1H), 4.65-4.54 (m, 2H), 4.22 (br d, J=7.8 Hz, 1H), 3.97-3.86 (m, 2H), 2.58 (s, 3H), 2.53 (s, 3H). LCMS (ESI+): m/z 419.2 (M+H) Example 60: (S)-12-fluoro-4-(1-(2-methoxyethyl)-1H-pyrazol-4-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(1-(2-methoxyethyl)-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate

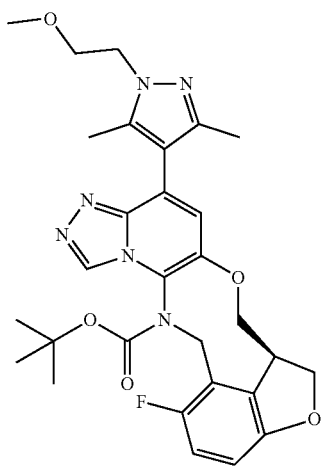 [SMILES: COCCn1nc(C)c(-c2cc3c(n4cnnc24)N(C(=O)OC(C)(C)C)Cc2c(F)ccc4c2[C@H](CO4)CO3)c1C]

Pd(PPh3)4 (25.9 mg, 0.0224 mmol) was added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 55.0 mg, 0.112 mmol), 1-(2-methoxyethyl)-3,5-dimethyl-4-(4,4,5,5-tetramethyl-1,3,2-dioxaborolan-2-yl) pyrazole (50.2 mg, 0.179 mmol), and NaHCO3 (47.0 mg, 0.560 mmol) in 1,4-dioxane (1.00 mL) and water (0.200 mL). Nitrogen was bubbled through the mixture for 5 minutes. The mixture was stirred at 110° C. for 3 h. The mixture was cooled to room temperature and concentrated under reduced pressure. The residue was purified by silica gel chromatography (40 g cartridge) eluting with MeOH in DCM (0-10%) to provide tert-butyl (S)-12-fluoro-4-(1-(2-methoxyethyl)-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate as a solid (56.0 mg, 87%). 1H NMR (400 MHz, cdcl3) (rotamers, partial characterization) δ 8.66 (s, 1H), 6.77 (s, 1H), 6.56 (s, 2H), 4.18 (t, J=5.6 Hz, 2H), 3.75 (t, J=5.6 Hz, 2H), 3.33 (s, 3H), 2.18 (s, 3H), 2.13 (s, 3H), 1.36 (s, 9H). m/z (ES+) [M+H]+: 565.5. HPLC tR (A05)=2.18 min.

243

Step 2: (S)-12-fluoro-4-(1-(2-methoxyethyl)-1H-pyrazol-4-yl)-7a,8,13,14-tetrahydro-7H-[1,2,4]triazolo[4',3':1,6]pyrido[3,2-b]benzofuro[4,3-fg][1,4]oxazonine

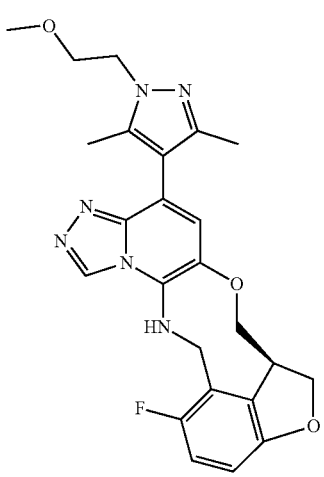 [SMILES: COCCn1nc(C)c(-c2cc3c(n4cnnc24)NCc2c(F)ccc4c2[C@H](CO4)CO3)c1C]

A solution of tert-butyl (S)-12-fluoro-4-(1-(2-methoxyethyl)-1H-pyrazol-4-yl)-7a,13-dihydro-7H-[1,2,4]triazolo[4',3':1,6]pyrido[3,2-b]benzofuro[4,3-fg][1,4]oxazonine-14(8H)-carboxylate (56.0 mg, 99.2 μmol) in HFIP (2.00 mL) was heated at 100° C. for 5 h. The mixture was concentrated under reduced pressure, and the residue was purified by silica gel chromatography (24 g cartridge) eluting with MeOH in DCM (0-10%) to afford the title compound 4 as a solid (37.0 mg, 80%). 1H NMR (400 MHz, CDCl3) δ 8.93 (s, 1H), 6.94 (s, 1H), 6.84 (dd, J=10.1, 8.8 Hz, 1H), 6.64 (dd, J=8.7, 3.9 Hz, 1H), 5.35 (s, 1H), 5.05 (dd, J=14.7, 7.0 Hz, 1H), 4.81 (dd, J=14.8, 5.8 Hz, 1H), 4.61 (t, J=9.4 Hz, 1H), 4.53 (dd, J=10.0, 4.3 Hz, 1H), 4.22 (dd, J=9.7, 3.2 Hz, 1H), 4.17 (t, J=5.7 Hz, 2H), 3.93 (dt, J=8.3, 6.2 Hz, 1H), 3.81 (dd, J=11.9, 10.1 Hz, 1H), 3.75 (t, J=5.7 Hz, 2H), 3.32 (s, 3H), 2.21 (s, 3H), 2.18 (s, 3H). m/z (ES+) [M+H]+: 466.1. HPLC tR (A05)=2.03 min.

244

Example 61: (S)-12-fluoro-4-(4-methyl-1H-pyrazol-1-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(4-methyl-1H-pyrazol-1-yl)-7a,13-dihydro-7H-[1,2,4]triazolo[4',3':1,6]pyrido[3,2-b]benzofuro[4,3-fg][1,4]oxazonine-14(8H)-carboxylate

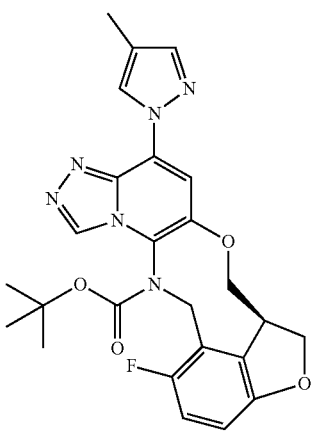 [SMILES: Cc1cnn(-c2cc3c(n4cnnc24)N(C(=O)OC(C)(C)C)Cc2c(F)ccc4c2[C@H](CO4)CO3)c1]

Toluene (2.00 mL) and dioxane (0.400 mL) were added to a mixture of Pd2(dba)3 (5.85 mg, 10.2 μmol) and di-tert-butyl-[2,3,4,5-tetramethyl-6-(2,4,6-triisopropylphenyl)phenyl]phosphane (9.79 mg, 20.4 μmol) in a sealed tube. Nitrogen was bubbled through the mixture. The mixture was heated at 120° C. for 4 min and added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (Example 16; 100 mg, 204 μmol), 4-methyl-1H-pyrazole (25.3 μL, 305 μmol), and K3PO4 (86.4 mg, 407 μmol) under N2. The mixture was stirred at 120° C. for 7 h. The mixture was concentrated under reduced pressure, and the residue was purified by silica gel chromatography (40 g cartridge) eluting with MeOH in DCM (0-10%) to afford tert-butyl (S)-12-fluoro-4-(4-methyl-1H-pyrazol-1-yl)-7a,13-dihydro-7H-[1,2,4]triazolo[4',3':1,6]pyrido[3,2-b]benzofuro[4,3-fg][1,4]oxazonine-14(8H)-carboxylate as a solid (56.0 mg, 56%). m/z (ES+) [M+H]+: 493.8, HPLC tR (A05)=2.39 min.

Step 2: (S)-12-fluoro-4-(4-methyl-H-pyrazol-1-yl)-7a,8,13,14-tetrahydro-7H-[1,2,4]triazolo[4',3':1,6]pyrido[3,2-b]benzofuro[4,3-fg][1,4]oxazonine

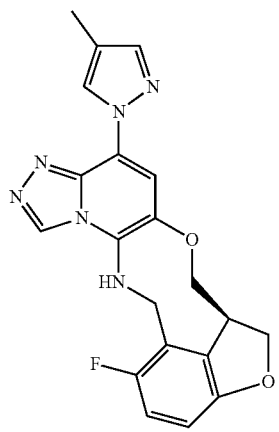 [SMILES: Cc1cnn(-c2cc3c(n4cnnc24)NCc2c(F)ccc4c2[C@H](CO4)CO3)c1]

A solution of tert-butyl (S)-12-fluoro-4-(4-methyl-1H-pyrazol-1-yl)-7a,13-dihydro-7H-[1,2,4]triazolo[4',3':1,6]pyrido[3,2-b]benzofuro[4,3-fg][1,4]oxazonine-14 (8H)-carboxylate (45.0 mg, 91.4 μmol) in HFIP (2.00 mL) was heated at 100° C. for 5 h. The mixture was concentrated under reduced pressure, and the residue was purified by silica gel chromatography (24 g cartridge) eluting with MeOH in DCM (0-10%) to afford the title compound as a solid (26.0 mg, 73%). 1H NMR (500 MHz, DMSO) δ 9.51 (s, 1H), 8.86 (s, 1H), 7.74 (s, 1H), 7.60 (s, 1H), 7.44 (t, J=6.4 Hz, 1H), 6.94 (dd, J=10.3, 8.7 Hz, 1H), 6.67 (dd, J=8.6, 3.8 Hz, 1H), 4.89-4.85 (m, 2H), 4.52 (t, J=9.4 Hz, 2H), 4.23 (dd, J=9.6, 3.5 Hz, 1H), 4.07-3.99 (m, 1H), 3.87 (t, J=11.4 Hz, 1H), 2.13 (s, 3H). m/z (ES+) [M+H]$^+$: 393.1. HPLC tR (A05)=2.16 min.

Example 62: (S)-4-(1,4-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine Hydrochloride

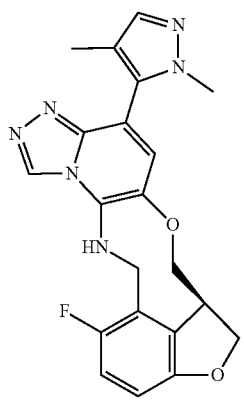 [SMILES: Cc1cnn(C)c1-c1cc2c(n3cnnc13)NCc1c(F)ccc3c1[C@H](CO3)CO2]

To a stirred solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (120 mg, 307 umol, 1.00 eq), 1,4-dimethyl-S-(4,4,5,5-tetramethyl-1,3,2-dioxaborolan-2-yl)-1H-pyrazole (136 mg, 614 umol, 2.00 eq) and NaHCO$_3$ (129 mg, 1.53 mmol, 5.00 eq) in dioxane (4.00 mL) and water (0.800 mL) was added Pd(dppf)Cl$_2$ (22.5 mg, 30.7 umol, 0.100 eq) at 15° C. under N$_2$. The resulting mixture was stirred at 80° C. of 12 h. LCMS showed (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was remained and the desired mass was detected. The mixture was stirred at 80° C. for 6 h. LCMS showed (S)-4-bromo-12-fluoro-7a,8,13,14-tetrahydro-7H-[1,2,4]triazolo[4',3':1,6]pyrido[3,2-b]benzofuro[4,3-fg][1,4]oxazonine remained. To the mixture was added Pd(dppf)Cl$_2$ (0.100 eq) at 15° C. under N$_2$. The resulting mixture was stirred at 80° C. for 12 h. To the mixture was added silica-thiol (400 mg, modified Silicon Gel for Eliminating Pd, Irregular Silica Gel, 100-200 mesh, Chlorides (Cl), %≤0.004, Particle Size Distribution 45-75 um) at 15° C. and stirred at 15° C. for 4 h. The suspension was filtered off and the filter cake was washed with MeOH (5 mL*3). The filtrate was concentrated under reduced pressure. The residue was purified by acidic prep-HPLC (HCl conditions). The product-containing fraction was concentrated under reduced pressure to remove most of MeCN at 30° C. and the aqueous phase was lyophilized. (S)-4-(1,4-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine (25.8 mg, 56.8 umol, 18% yield, 97.5% purity, HCl salt) was obtained as a yellow solid. 1H NMR DMSO-d6 400 MHz δ=ppm 10.19 (br s, 1H), 9.17 (br s, 1H), 7.98 (s, 1H), 7.44 (s, 1H), 7.02 (br t, J=9.4 Hz, 1H), 6.75 (br dd, J=8.5, 3.4 Hz, 1H), 5.09-4.97 (m, 1H), 4.92 (br s, 1H), 4.62-4.49 (m, 2H), 4.27-4.20 (m, 1H), 4.12 (br s, 1H), 3.91 (br s, 1H), 3.65 (s, 3H), 1.90 (s, 3H). LCMS (ESI+): m/z 407.2 (M+H).

Example 63: (S)-4-(4-(difluoromethyl)pyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

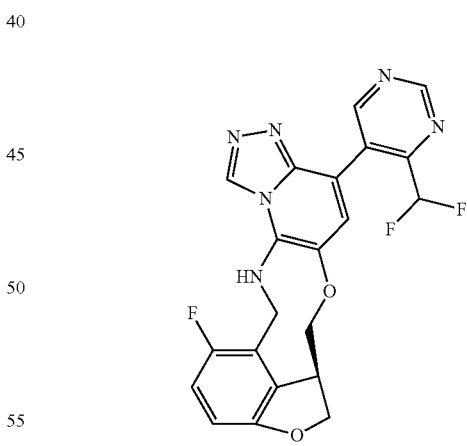

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (150 mg, 383 umol, 1.00 eq) in EtOH (10.0 mL), water (2.00 mL) were added 4-(difluoromethyl)-S-(4,4,5,5-tetramethyl-1,3,2-dioxaborolan-2-yl)pyrimidine (1.13 g, 4.39 mmol, 11.5 eq), Pd(Amphos)2C$_{12}$ (27.2 mg, 38.3 umol, 0.100 eq) and KOAc (75.3 mg, 767 umol, 2.00 eq) at 20° C. The mixture was stirred at 80° C. for 2 h. LCMS indicated complete conversion. The reaction moisture was filtered and the filtrate was concentrated. The residue was dissolved in MeOH (8.00 mL) and silica-thiol (600 mg, modified silicon gel for eliminating Pd, irregular silica gel, 100-200 mesh, Chlorides (Cl), %≤0.004, particle size distribution 45-75 um) was added at 20° C. and stirred at 20° C. for 12 h. The suspension was filtered and the filtrate was evaporated. The residue was purified by neutral prep-HPLC (column: Waters Xbridge Prep OBD C18 150*40 mm*10 um; mobile phase: [water (10 mM NH4HCO3)—ACN]; B %: 20%-50%, 8 min). The product-containing fraction was concentrated under reduced pressure to remove most of MeCN at 30° C. and the aqueous phase was lyophilized. (S)-4-(4-(difluoromethyl)pyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (40.0 mg, 87.9 umol, 22% yield, 96.7% purity) was obtained as a yellow solid. 1H NMR DMSO-d6 400 MHz δ=ppm 9.48 (s, 1H), 9.38 (s, 1H), 9.15 (s, 1H), 7.79 (br t, J=6.4 Hz, 1H), 7.51 (s, 1H), 7.06 (t, J=53.2 Hz, 1H), 7.99 (t, J=10.0 Hz, 1H), 6.72 (dd, J=8.7, 3.8 Hz, 1H), 5.01-4.89 (m, 1H), 4.87-4.72 (m, 1H), 4.61-4.46 (m, 2H), 4.23 (dd, J=9.6, 3.5 Hz, 1H), 4.05 (br s, 1H), 3.96-3.86 (m, 1H). LCMS (ESI+): m/z 441.1 (M+H).

Example 64: (S)-4-(2-(difluoromethyl)-4-methylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

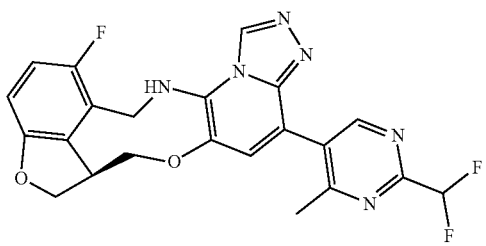 [SMILES: Cc1nc(C(F)F)ncc1-c1cc2c(n3cnnc13)NCc1c(F)ccc3c1[C@H](CO3)CO2]

To a solution of 2-(difluoromethyl)-4-methyl-S-(4,4,5,5-tetramethyl-1,3,2-dioxaborolan-2-yl)pyrimidine (104 mg, 383 umol, 2.50 eq) in EtOH (4.00 mL) and water (0.560 mL) was added 4-ditert-butylphosphanyl-N,N-dimethyl-aniline dichloropalladium (10.9 mg, 15.3 umol, 0.100 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (60.0 mg, 153 umol, 1.00 eq) and KOAc (45.2 mg, 460 umol, 3.00 eq) at 20° C. under nitrogen atmosphere. The mixture was stirred at 80° C. for 8 h under nitrogen atmosphere. LCMS showed the starting material was consumed completely and the desired MS was detected. The reaction mixture was concentrated under reduced pressure. The residue was dissolved in MeOH (10.0 mL) and silica-thiol (100 mg, modified silicon gel for eliminating Pd, irregular silica gel, 100-200 mesh, Chlorides (Cl), %≤0.004, particle size distribution 45-75 um) was added at 20° C. and stirred at 20° C. for 4 h. The suspension was filtered and the filtrate was concentrated and then purified by neutral prep-HPLC. The product-containing fraction was concentrated under reduced pressure to remove most of MeCN at 30° C. and the aqueous phase was lyophilized. (S)-4-(2-(difluoromethyl)-4-methylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (30.0 mg, 65.4 umol, 42% yield, 99.1% purity) was obtained as a yellow solid. 1H NMR CDCl3 400 MHz δ=ppm 8.95 (s, 1H), 8.76 (s, 1H), 7.11 (s, 1H), 6.91-6.84 (m, 1H), 6.68 (dd, J=8.8, 4.8 Hz, 1H), 6.67 (t, J=54.4 Hz, 1H), 5.37 (t, J=6.8 Hz, 1H), 5.11 (dd, J=14.7, 7.4 Hz, 1H), 4.85 (dd, J=14.4, 6.3 Hz, 1H), 4.70-4.57 (m, 2H), 4.26 (dd, J=9.7, 3.3 Hz, 1H), 4.01-3.88 (m, 1H), 3.86-3.76 (m, 1H), 2.57 (s, 3H). LCMS (ESI+): m/z 455.1 (M+H).

Example 65: (S)-12-fluoro-4-(1-(2,2,2-trifluoroethyl)-1H-pyrazol-3-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate

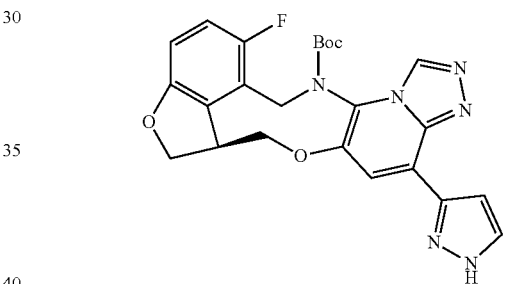

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (220 mg, 448 umol, 1.00 eq), 5-(4,4,5,5-tetramethyl-1,3,2-dioxaborolan-2-yl)-1H-pyrazole (130 mg, 672 umol, 1.50 eq) and Na2CO3 (94.9 mg, 896 umol, 2.00 eq) in dioxane (1.00 mL) and water (0.100 mL) was added Pd(dppf)Cl2 (32.8 mg, 44.8 umol, 0.100 eq) under nitrogen at 25° C. The resulting mixture was stirred at 80° C. under nitrogen for 10 h. LCMS indicated incomplete conversion. To the mixture was added 5-(4,4,5,5-tetramethyl-1,3,2-dioxaborolan-2-yl)-1H-pyrazole (130 mg, 672 umol, 1.50 eq) and Pd(dppf)Cl2 (32.8 mg, 44.8 umol, 0.100 eq) at 25° C. The resulting mixture was stirred at 80° C. under nitrogen for 3 h. The reaction mixture was concentrated under reduced pressure. The residue was purified by prep-TLC (SiO2, EtOAc:MeOH=5:1). tert-butyl (S)-12-fluoro-4-(1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (280 mg, crude) was obtained as yellow solid.

Step 2: tert-butyl (S)-12-fluoro-4-(1-(2,2,2-trifluoro-ethyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate

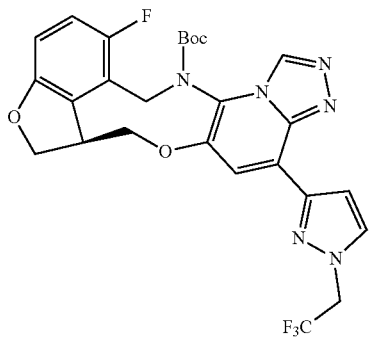 [SMILES: CC(C)(C)OC(=O)N1Cc2c(F)ccc3c2[C@H](CO3)COc2cc(-c3ccn(CC(F)(F)F)n3)c3nncn3c21]

A mixture of tert-butyl (S)-12-fluoro-4-(1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (80.0 mg, 167 umol, 1.00 eq) and Cs$_2$CO$_3$ (109 mg, 334 umol, 2.00 eq) in DMF (2.00 mL) was stirred at 25° C. for 0.5 hr. 2,2,2-trifluoroethyl trifluoromethanesulfonate (58.2 mg, 251 umol, 1.50 eq) was added and the mixture was stirred at 25° C. for 10 h The reaction mixture was concentrated under reduced pressure. The residue was purified by prep-TLC (SiO$_2$, PE:EtOAc=0:1). tert-butyl (S)-12-fluoro-4-(1-(2,2,2-trifluoroethyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (65.0 mg, crude) was obtained as yellow oil.

Step 3: (S)-12-fluoro-4-(1-(2,2,2-trifluoroethyl)-1H-pyrazol-3-yl)-7a,8,13,14-tetrahydro-7H-[1,2,4]triazolo[4',3':1,6]pyrido[3,2-b]benzofuro[4,3-fg][1,4]oxazonine

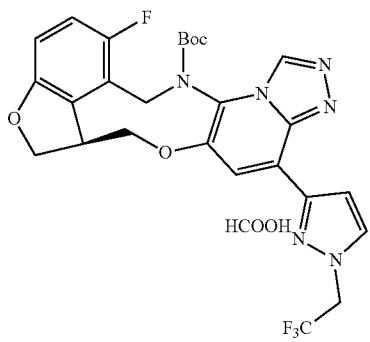 [SMILES: CC(C)(C)OC(=O)N1Cc2c(F)ccc3c2[C@H](CO3)COc2cc(-c3ccn(CC(F)(F)F)n3)c3nncn3c21 ; "HCOOH"]

To tert-butyl (S)-12-fluoro-4-(1-(2,2,2-trifluoroethyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (85.0 mg, 152 umol, 1.00 eq) in DCM (1.50 mL) was added TFA (0.500 mL) at 15° C. The mixture was stirred at 15° C. for 10 h. The reaction mixture was concentrated under reduced pressure. The suspension was filtered and the filtrate was concentrated and then purified by acidic prep-HPLC (column: Phenomenex Luna C18 100*30 mm*5 um; mobile phase: [water (0.2% FA)—ACN]; B %: 20%-45%, 12 min). (S)-12-fluoro-4-(1-(2,2,2-trifluoroethyl)-1H-pyrazol-3-yl)-7a,8,13,14-tetrahydro-7H-[1,2,4]triazolo[4',3':1,6]pyrido[3,2-b]benzofuro[4,3-fg][1,4]oxazonine (22.7 mg, 43.8 umol, 28% yield, 97.7% purity, formate) was obtained as a white solid. 1H NMR CD3OD 400 MHz δ=ppm 9.40 (s, 1H), 8.12 (s, 1H), 7.86 (d, J=2.0 Hz, 1H), 7.15-7.10 (m, 1H), 6.91-6.83 (m, 1H), 6.67-6.60 (m, 1H), 5.12-5.01 (m, 3H), 4.92 (s, 1H), 4.69 (br dd, J=9.9, 3.7 Hz, 1H), 4.58 (t, J=9.2 Hz, 1H), 4.29 (dd, J=9.7, 3.2 Hz, 1H), 4.07-3.99 (m, 1H), 3.99-3.90 (m, 1H). LCMS (ESI+): m/z 461.1 (M+H) Example 66: (S)-4-(4-(difluoromethyl)-2-methylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

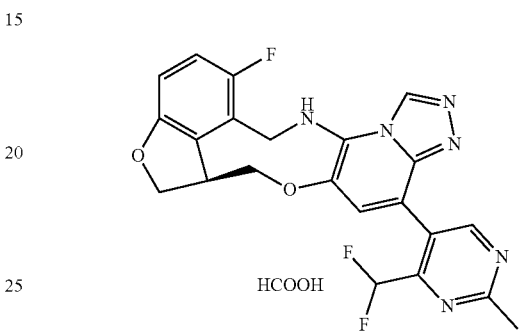

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq) in EtOH (5.00 mL) and water (1.00 mL) were added 4-(difluoromethyl)-2-methyl-S-(4,4,5,5-tetramethyl-1,3,2-dioxaborolan-2-yl)pyrimidine (690 mg, 2.56 mmol, 10.0 eq), KOAc (50.2 mg, 511 umol, 2.00 eq) and 4-ditert-butylphosphanyl-N,N-dimethyl-aniline dichloropalladium (18.1 mg, 25.6 umol, 0.100 eq) at 25° C. under nitrogen atmosphere. The mixture was stirred at 80° C. for 2 h under nitrogen atmosphere. The reaction mixture was filtered and the filtrate concentrated under high vacuum. The residue was dissolved in MeOH (5.00 mL) and silica-thiol (260 mg, modified silicon gel for eliminating Pd, irregular silica gel, 100-200 mesh, Chlorides (Cl), %≤0.00400, particle size distribution 45.0-75.0 um) was added at 25° C. and stirred at 25° C. for 3 h. The suspension was filtered and the filtrate was concentrated and purified by FA prep-HPLC (column: Phenomenex Luna C18 100*30.0 mm*5.00 um; mobile phase: [water (0.200% FA)—ACN]; B %: 20.0%-45.0%, 12.0 min). The fraction containing the product was concentrated under reduced pressure to remove most of MeCN at 30° C. and the aqueous phase was lyophilized. (S)-4-(4-(difluoromethyl)-2-methylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (29.6 mg, 58.6 umol, 22% yield, 99.0% purity, formate) was obtained as a yellow solid. 1H NMR DMSO-d6 400 MHz δ=ppm 9.46 (s, 1H), 9.00 (s, 1H), 7.73 (br t, J=6.2 Hz, 1H), 7.44 (s, 1H), 6.98 (t, J=9.6 Hz, 1H), 6.98 (t, J=53.0 Hz 1H), 6.71 (dd, J=8.6, 3.7 Hz, 1H), 4.99-4.89 (m, 1H), 4.86-4.75 (m, 1H), 4.59-4.52 (m, 1H), 4.49 (br d, J=6.1 Hz, 1H), 4.22 (dd, J=9.6, 3.4 Hz, 1H), 4.10-3.98 (m, 1H), 3.95-3.83 (m, 1H), 2.76 (s, 3H). LCMS (ESI+): m/z 455.1 (M+H) Example 67: (S)-4-(2-(difluoromethoxy)pyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 5-bromo-2-(difluoromethoxy)pyrimidine

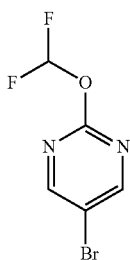

To 5-bromopyrimidin-2-ol (5.00 g, 28.6 mmol, 1.00 eq), sodium; 2-chloro-2,2-difluoro-acetate (8.71 g, 57.2 mmol, 2.00 eq), K₂CO₃ (8.29 g, 60.0 mmol, 2.10 eq) was added in DMF (33.3 mL) at 20° C. The mixture was degassed and purged with nitrogen 3 times, and then the mixture was stirred at 65° C. for 1.5 h under nitrogen atmosphere. LC-MS showed 5-bromopyrimidin-2-ol was consumed completely and one main peak with desired mass was detected. Water (150 mL) was added and the mixture was extracted with EtOAc (150 mL*4). The combined organic layers were dried over anhydrous Na₂SO₄, filtered and concentrated under reduced pressure. The residue was purified by column chromatography (SiO₂, Petroleum ether/Ethyl acetate=1/0 to 1/1). 5-bromo-2-(difluoromethoxy)pyrimidine (191 mg, crude) was obtained as yellow oil. $^1$H NMR CD₃OD 400 MHz δ=ppm 8.78 (s, 2H), 7.52 (t, J=71.6 Hz, 1H)

Step 2: 2-(difluoromethoxy)-5-(4,4,5,5-tetramethyl-1,3,2-dioxaborolan-2-yl)pyrimidine

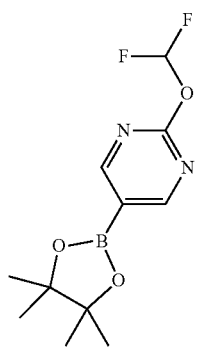 [SMILES: CC1(C)OB(c2cnc(OC(F)F)nc2)OC1(C)C]

To 5-bromo-2-(difluoromethoxy)pyrimidine (190 μmg, 844 umol, 1.00 eq), 4,4,4',4',5,5,5',5'-octamethyl-2,2'-bi(1,3,2-dioxaborolane) (429 mg, 1.69 mmol, 2.00 eq), Pd(dppf)Cl₂·DCM (69.0 mg, 84.5 umol, 0.100 eq), KOAc (166 mg, 1.69 mmol, 2.00 eq) was added dioxane (3.00 mL) at 20° C. The mixture was degassed and purged with nitrogen 3 times, and then the mixture was stirred at 80° C. for 4 h under nitrogen atmosphere. The reaction mixture was concentrated under reduced pressure to give 2-(difluoromethoxy)-5-(4,4,5,5-tetramethyl-1,3,2-dioxaborolan-2-yl)pyrimidine (200 mg, crude) as brown solid.

Step 3: (S)-4-(2-(difluoromethoxy)pyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

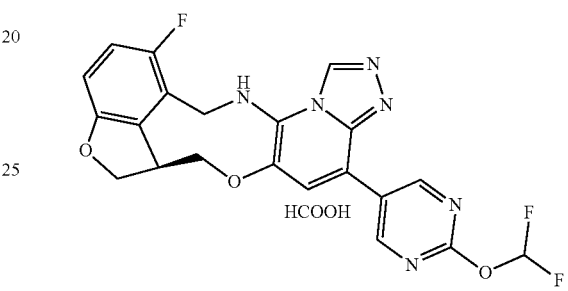

To (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (180 mg, 460 umol, 1.00 eq), 2-(difluoromethoxy)-S-(4,4,5,5-tetramethyl-1,3,2-dioxaborolan-2-yl)pyrimidine (200 mg, 736 umol, 1.60 eq), Na₂CO₃ (97.5 mg, 920 umol, 2.00 eq), Pd(dppf)Cl2 (33.7 mg, 46.0 umol, 0.100 eq) was added dioxane (3.00 mL) and water (0.300 mL) at 20° C. The mixture was degassed and purged with nitrogen 3 times, and then the mixture was stirred at 80° C. for 3 h under nitrogen atmosphere. The reaction mixture was filtered and the filtrate was concentrated under reduced pressure. The residue was dissolved in dioxane (10.0 mL) and silica-thiol (500 mg, modified silicon gel for eliminating Pd, irregular silica gel, 100-200 mesh, Chlorides (Cl), %≤0.004, particle size distribution 45-75 um) was added at 20° C. and stirred at 20° C. for 3 h. The suspension was filtered and the filtrate was concentrated under reduced pressure. The residue was purified by acidic prep-HPLC (formic acid conditions). The product-containing fraction was concentrated under reduced pressure to remove most of MeCN at 30° C. and the aqueous phase was lyophilized. (S)-4-(2-(difluoromethoxy)pyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (23.5 mg, 45.2 umol, 9% yield, 96.7% purity, formate) was obtained as yellow solid. $^1$H NMR DMSO-d₆ 400 MHz δ=ppm 9.49 (s, 2H), 9.46 (s, 1H), 7.99 (s, 1H), 7.72 (t, J=71.6 Hz, 1H), 7.71 (br s, 1H), 6.95 (t, J=9.5 Hz, 1H), 6.74-6.63 (m, 1H), 4.96-4.87 (m, 1H), 4.85-4.75 (m, 1H), 4.60-4.48 (m, 2H), 4.27-4.17 (m, 1H), 4.09-3.99 (m, 1H), 3.98-3.88 (m, 1H). LCMS (ESI+): m/z 457.1 (M+H).

Example 68: (S)-12-fluoro-4-(6-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine Example 69: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2(1H)-one

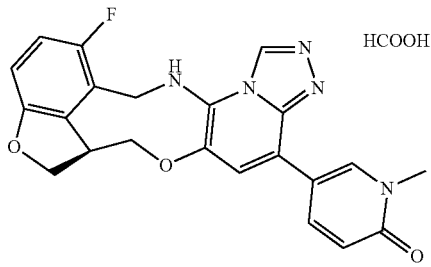

To a stirred solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq), 1-methyl-S-(4,4,5,5-tetramethyl-1,3,2-dioxaborolan-2-yl)pyridin-2-one (120 mg, 511 umol, 2.00 eq) and $Na_2CO_3$ (54.2 mg, 512 umol, 2.00 eq) in dioxane (2.50 mL) and water (0.500 mL) was added Pd(dppf)Cl$_2$ (18.7 mg, 25.6 umol, 0.100 eq) at 15° C. under N$_2$. The resulting mixture was stirred at 80° C. for 3 h. The mixture was concentrated under reduced pressure. The mixture was purified by prep-TLC (SiO$_2$, EtOAc/MeOH=4/1) to give the crude product and the crude product was purified by acidic prep-HPLC (FA). The product-containing fraction was concentrated under reduced pressure to remove most of MeCN at 30° C. and the aqueous phase was lyophilized. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methylpyridin-2(1H)-one (18.8 mg, 39.6 umol, 15% yield, 98.1% purity, formate salt) was obtained as a yellow solid. $^1$H NMR DMSO-d$_6$ 400 MHz δ=ppm 9.44 (s, 1H), 8.82 (d, J=2.4 Hz, 1H), 8.23 (dd, J=9.6, 2.6 Hz, 1H), 7.60 (s, 1H), 7.45 (br t, J=6.1 Hz, 1H), 6.94 (dd, J=10.1, 9.0 Hz, 1H), 6.68 (dd, J=8.6, 3.9 Hz, 1H), 6.50 (d, J=9.5 Hz, 1H), 4.92-4.83 (m, 1H), 4.81-4.72 (m, 1H), 4.57-4.48 (m, 2H), 4.22 (dd, J=9.4, 3.1 Hz, 1H), 4.07-3.98 (m, 1H), 3.97-3.88 (m, 1H), 3.53 (s, 3H). LCMS (ESI+): m/z 420.1 (M+H).

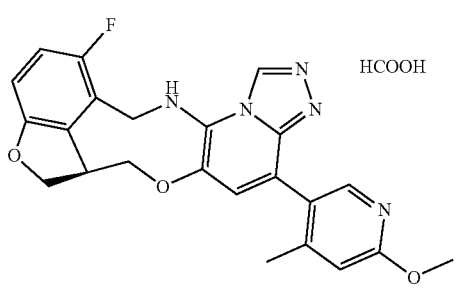 [SMILES: COc1cc(C)c(-c2cc3c(n4cnnc24)NCc2c(F)ccc4c2[C@H](CO4)CO3)cn1 ; "HCOOH"]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (90.0 mg, 230 umol, 1.00 eq) in dioxane (5.00 mL) and water (0.500 mL) was added (6-methoxy-4-methyl-3-pyridyl)boronic acid (76.8 mg, 460 umol, 2.00 eq), Pd(dppf)Cl$_2$ (16.8 mg, 23.0 umol, 0.100 eq) and Na$_2$CO$_3$ (48.8 mg, 460 umol, 2.00 eq) at 20° C. The mixture was stirred at 80° C. for 2 h under nitrogen atmosphere. LCMS showed (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was consumed completely and the desired mass was detected. The reaction was filtered, the filtrate was concentrated. The residue was dissolved in MeOH (5.00 mL) and silica-thiol (600 mg, modified silicon gel for eliminating Pd, irregular silica gel, 100-200 mesh, Chlorides (Cl), %≤0.004, particle size distribution 45-75 um) was added at 20° C. and stirred at 20° C. for 12 h. The suspension was filtered, the filtrate was concentrated and purified by acidic prep-HPLC (column: Phenomenex Luna C18 200*40 mm*10 um; mobilephase: [water (0.225% FA)—ACN]; B %: 25%-45%, 12 min). The product-containing fraction was concentrated under reduced pressure to remove most of MeCN at 30° C. and the aqueous phase was lyophilized. (S)-12-fluoro-4-(6-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine (65.0 mg, 136 umol, 58% yield, 100% purity, formate salt) was obtained as a white solid. $^1$H NMR DMSO-d$_6$ 400 MHz. δ=ppm 9.41 (s, 1H), 8.09 (s, 1H), 7.48 (br t, J=6.2 Hz, 1H), 7.26 (s, 1H), 7.03-6.92 (m, 1H), 6.79 (s, 1H), 6.75-6.66 (m, 1H), 6.71 (dd, J=8.6, 3.8 Hz, 1H), 4.97-4.86 (m, 1H), 4.82-4.74 (m, 1H), 4.58-4.40 (m, 2H), 4.22 (dd, J=9.5, 3.3 Hz, 1H), 4.04 (br s, 1H), 3.87 (s, 3H), 3.83-3.80 (m, 1H), 2.15 (s, 3H). LCMS (ESI+): m/z 434.1 (M+H).

Example 70: (S)-12-fluoro-4-(2-(trifluoromethyl)pyridin-3-yl)-7a,8,13,14-tetrahydro-7H-[1,2,4]triazolo[4',3':1,6]pyrido[3,2-b]benzofuro[4,3-fg][1,4]oxazonine

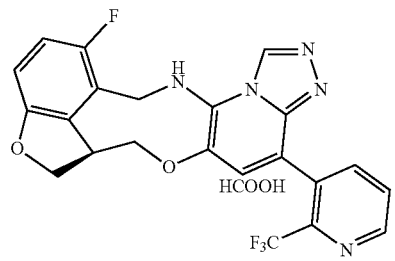 [SMILES: Fc1ccc2c3c1CNc1c(cc(-c4cccnc4C(F)(F)F)c4nncn14)OC[C@H]3CO2 ; "HCOOH"]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq) in dioxane (3.60 mL) and water (0.400 mL) were added [2-(trifluoromethyl)-3-pyridyl]boronic acid (195 mg, 1.02 mmol, 4.00 eq), $Na_2CO_3$ (67.7 mg, 639 umol, 2.50 eq) and $Pd(dppf)Cl_2$ (18.7 mg, 25.6 umol, 0.100 eq) at 25° C. under nitrogen atmosphere. The mixture was stirred at 80° C. for 12 h under nitrogen atmosphere. LC-MS showed (S)-4-bromo-12-fluoro-7a,8,13,14-tetrahydro-7H-[1,2,4]triazolo[4',3':1,6]pyrido[3,2-b]benzofuro[4,3-fg][1,4]oxazonine was remained and one main peak with desired mass was detected. To the mixture were added [2-(trifluoromethyl)-3-pyridyl]boronic acid (97.6 mg, 511 umol, 2.00 eq), $Na_2CO_3$ (67.7 mg, 639 umol, 2.50 eq) and Pd(dppf)Cl2 (18.7 mg, 25.7 umol, 0.100 eq) at 25° C. under nitrogen atmosphere. The mixture was stirred at 80° C. for 3 h under nitrogen atmosphere. The reaction mixture (combined with another batch from 50 μmg of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine) was filtered and the filtrate concentrated under high vacuum. The residue was dissolved in MeOH (5.00 mL) and silica-thiol (540 mg, modified silicon gel for eliminating Pd, irregular silica gel, 100-200 mesh, Chlorides (Cl), %≤0.004, particle size distribution 45-75 um) was added at 25° C. and stirred at 25° C. for 3 h. The suspension was filtered, the filtrate was concentrated and purified by prep-HPLC (column: Phenomenex Luna C18 200*40 mm*10 um; mobile phase: [water (0.225% FA)—ACN]; B %: 20.0%-50.0%, 12 min. The product-containing fraction was concentrated under reduced pressure to remove most of MeCN at 30° C. and the aqueous phase was lyophilized. (S)-12-fluoro-4-(2-(trifluoromethyl)pyridin-3-yl)-7a,8,13,14-tetrahydro-7H-[1,2,4]triazolo[4',3':1,6]pyrido[3,2-b]benzofuro[4,3-fg][1,4]oxazonine (24.2 mg, 46.6 umol, 18% yield, 96.9% purity, formate salt) was obtained as a yellow solid. $^1H$ NMR DMSO-$d_6$ 400 MHz δ=ppm 9.44 (s, 1H), 8.80 (br d, J=3.8 Hz, 1H), 8.09 (br d, J=7.5 Hz, 1H), 7.79 (dd, J=7.8, 4.7 Hz, 1H), 7.62 (br s, 1H), 7.30 (s, 1H), 6.97 (t, J=9.5 Hz, 1H), 6.71 (dd, J=8.6, 3.7 Hz, 1H), 4.99-4.86 (m, 1H), 4.83-4.69 (m, 1H), 4.59-4.40 (m, 2H), 4.21 (br dd, J=9.6, 3.2 Hz, 1H), 4.02 (br s, 1H), 3.88-3.70 (m, 1H). LCMS (ESI+): m/z 458.1 (M+H).

Example 71: (S)-12-fluoro-4-(2-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine

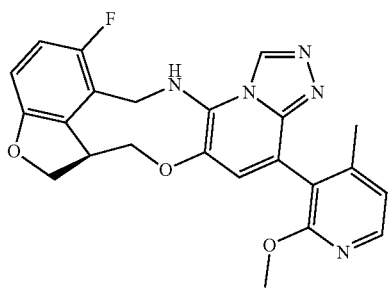 [SMILES: COc1nccc(C)c1-c1cc2c(n3cnnc13)NCc1c(F)ccc3c1[C@H](CO3)CO2]

Two parallel reactions were set up (each of 100 mg (S)-4-bromo-12-fluoro-7a,8,13,14-tetrahydro-7H-[1,2,4]triazolo[4',3':1,6]pyrido[3,2-b]benzofuro[4,3-fg][1,4]oxazonine. To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq), 2-methoxy-4-methyl-3-(4,4,5,5-tetramethyl-1,3,2-dioxaborolan-2-yl)pyridine (127 mg, 511 umol, 2.00 eq) in water (0.400 mL), EtOH (4.00 mL) was added 4-ditert-butylphosphanyl-N,N-dimethyl-aniline dichloropalladium (36.2 mg, 51.1 umol, 0.200 eq), KOAc (75.3 mg, 767 umol, 3.00 eq) at 25° C., then the mixture was stirred at 80° C. for 12 h under $N_2$. The batches were combined. The resulting mixture was concentrated, the residue was dissolved in MeOH (4.0 mL) and silica-thiol (40.0 mg, modified silicon gel for eliminating Pd, irregular silica gel, 100-200 mesh, Chlorides (Cl), %≤0.004, particle size distribution 45-75 um) was added at 20° C. and stirred at 20° C. for 2 h. The suspension was filtered, the filtrate was concentrated and purified by prep-HPLC (column: Waters Xbridge Prep OBD C18 150*40 mm*10 um; mobile phase: [water (10 mM $NH_4HCO_3$)—ACN]; B %: 30%-40%, 8 min). The fraction was then blown to dryness by nitrogen stream to remove most of MeCN and the aqueous phase was lyophilized. (S)-12-fluoro-4-(2-methoxy-4-methylpyridin-3-yl)-7a,8,13,14-tetrahydro-7H-[1,2,4]triazolo[4',3':1,6]pyrido[3,2-b]benzofuro[4,3-fg][1,4]oxazonine (25.0 mg, 56.7 umol, 11% yield, 98.3% purity) was obtained as a white solid. $^1H$ NMR DMSO-$d_6$ 400 MHz δ=ppm 9.38 (s, 1H), 8.08-8.04 (m, 1H), 7.46-7.35 (m, 1H), 7.17 (d, J=2.2 Hz, 1H), 7.00-6.90 (m, 2H), 6.73-6.63 (m, 1H), 4.94-4.85 (m, 1H), 4.80-4.68 (m, 1H), 4.57-4.48 (m, 1H), 4.43 (br dd, J=10.0, 4.1 Hz, 1H), 4.24-4.15 (m, 1H), 4.07-3.96 (m, 1H), 3.72 (br s, 1H), 3.65 (s, 1.5H), 3.71 (s, 1.5H), 2.03 (s, 1.5H), 1.92 (s, 1.5H). LCMS (ESI+): m/z 434.2 (M+H).

Example 72: (S)-12-fluoro-4-(1-(2,2,2-trifluoroethyl)-1H-pyrazol-S-yl)-7a,8,13,14-tetrahydro-7H-[1,2,4]triazolo[4',3':1,6]pyrido[3,2-b]benzofuro[4,3-fg][1,4]oxazonine Step 1: (1-(2,2,2-trifluoroethyl)-1H-pyrazol-S-yl)boronic Acid

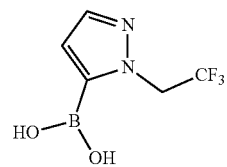 [SMILES: OB(O)c1ccnn1CC(F)(F)F]

To a solution of 5-(4,4,5,5-tetramethyl-1,3,2-dioxaborolan-2-yl)-1H-pyrazole (2.00 g, 10.3 mmol, 1.00 eq) in MeCN (50.0 mL) was added $Cs_2CO_3$ (6.72 g, 20.6 mmol, 2.00 eq) and 2,2,2-trifluoroethyl trifluoromethanesulfonate (3.59 g, 15.5 mmol, 1.50 eq) at 20° C. The mixture was stirred at 20° C. for 3 h. LC-MS showed no 5-(4,4,5,5-tetramethyl-1,3,2-dioxaborolan-2-yl)-1H-pyrazole was remained. Several new peaks were shown on LC-MS and desired m/s was detected. The reaction mixture was filtered, and the filtrate was diluted with water (50.0 mL) and extracted with DCM (40.0 mL*3). The combined organic layers were washed with water (90.0 mL*4), dried over $Na_2SO_4$, filtered and concentrated under reduced pressure. The residue was purified by prep-HPLC (column: Welch Xtimate C18 250*50 mm*10 um; mobile phase: [water (0.225% FA)—ACN]; B %: 0%-20%, 20 min). (1-(2,2,2-trifluoroethyl)-1H-pyrazol-S-yl)boronic acid (200 mg, crude) was obtained as a yellow oil. (1-(2,2,2-trifluoroethyl)-1H-pyrazol-3-yl)boronic acid (900 mg, crude) was Step 2: (S)-12-fluoro-4-(1-(2,2,2-trifluoroethyl)-1H-pyrazol-S-yl)-7a,8,13,14-tetrahydro-7H-[1,2,4]triazolo[4',3':1,6]pyrido[3,2-b]benzofuro[4,3-fg][1,4]oxazonine

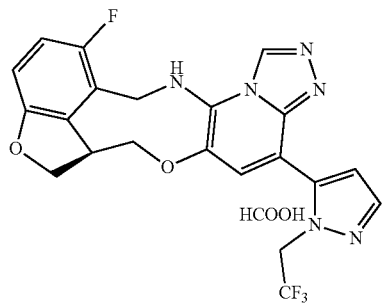 [SMILES: Fc1ccc2c3c1CNc1c(cc(-c4ccnn4CC(F)(F)F)c4nncn14)OC[C@H]3CO2 ; "HCOOH"]

To a solution (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (90.0 mg, 230 umol, 1.00 eq) in dioxane (5.00 mL) was added Pd(dppf)Cl₂.DCM (18.8 mg, 23.0 umol, 0.100 eq), Na₂CO₃ (73.2 mg, 690 umol, 3.00 eq), (1-(2,2,2-trifluoroethyl)-1H-pyrazol-S-yl)boronic acid (89.2 mg, 460 umol, 2.00 eq) and water (0.500 mL) at 20° C. under N₂. The mixture was stirred at 80° C. for 3 h. The reaction mixture was concentrated under reduced pressure. The residue was dissolved in MeOH (3.00 mL) and silicathiol (50.0 mg, modified silicon gel for eliminating Pd, irregular silica gel, 100-200 mesh, Chlorides (Cl), %≤0.004, particle size distribution 45-75 um) was added at 20° C. and stirred at 20° C. for 2 h. The suspension was filtered, the filtrate was concentrated and purified by prep-HPLC (column: Phenomenex Luna C18 100*30 mm*5 um; mobile phase: [water (0.2% FA)—ACN]; B %: 35%-65%, 10 min). The product-containing fraction was concentrated under reduced pressure to remove most of MeCN at 30° C. and the aqueous phase was lyophilized. (S)-12-fluoro-4-(1-(2,2,2-trifluoroethyl)-1H-pyrazol-S-yl)-7a,8,13,14-tetrahydro-7H-[1,2,4]triazolo[4',3':1,6]pyrido[3,2-b]benzofuro[4,3-fg][1,4]oxazonine (65.0 mg, 141 umol, 61% yield, 99.7% purity) was obtained as a white solid. ¹H NMR DMSO-d₆ 400 MHz δ=ppm 9.48 (s, 1H), 7.77 (br t, J=6.4 Hz, 1H), 7.68 (d, J=1.6 Hz, 1H), 7.47 (s, 1H), 6.97 (dd, J=10.0, 8.8 Hz, 1H), 6.71 (dd, J=8.7, 3.6 Hz, 1H), 6.61 (d, J=1.8 Hz, 1H), 5.37-5.24 (m, 2H), 4.97-4.88 (m, 1H), 4.85-4.75 (m, 1H), 4.59-4.46 (m, 2H), 4.23 (dd, J=9.6, 3.6 Hz, 1H), 4.04 (br s, 1H), 3.93-3.81 (m, 1H). LCMS (ESI+): m/z 461.1 (M+H).

Example 73: (S)-12-fluoro-4-(5-fluoro-6-methylpyridin-2-yl)-7a,8,13,14-tetrahydro-7H-[1,2,4]triazolo[4',3':1,6]pyrido[3,2-b]benzofuro[4,3-fg][1,4]oxazonine Step 1:
3-fluoro-2-methyl-6-(trimethylstannyl)pyridine To a solution of 6-bromo-3-fluoro-2-methylpyridine (1.00 g, 5.26 mmol, 1.00 eq) in dioxane (20.0 mL) were added trimethyl(trimethylstannyl)stannane (3.44 g, 10.5 mmol, 2.18 mL, 2.00 eq) and Pd(PPh₃)₄ (608 mg, 526 umol, 0.100 eq) at 20° C., the mixture was stirred at 100° C. for 4 h under nitrogen atmosphere. The obtained solution of 3-fluoro-2-methyl-6-(trimethylstannyl)pyridine (1.44 g, 5.26 mmol theoretical yield) in dioxane (20.0 mL) was used in the next step directly.

Step 2: tert-butyl (S)-12-fluoro-4-(5-fluoro-6-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

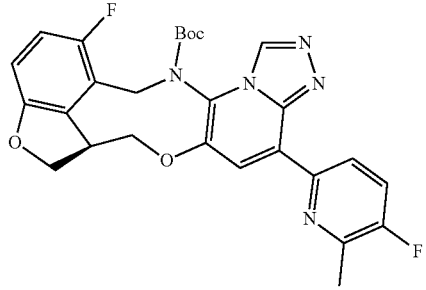 [SMILES: Cc1nc(-c2cc3c(n4cnnc24)N(C(=O)OC(C)(C)C)Cc2c(F)ccc4c2[C@H](CO4)CO3)ccc1F]

To a solution of 3-fluoro-2-methyl-6-(trimethylstannyl)pyridine (2.85 mmol, 7.00 eq. based on the theoretical yield in the previous step) in dioxane were added tert-butyl (S)-4-bromo-12-fluoro-7a,13-dihydro-7H-[1,2,4]triazolo[4',3':1,6]pyrido [3,2-b]benzofuro[4,3-fg][1,4]oxazonine-14 (8H)-carboxylate (200 mg, 407 umol, 1.00 eq), Pd(PPh₃)₄ (47.0 mg, 40.7 umol, 0.100 eq), CuI (31.0 mg, 163 umol, 0.400 eq) and LiCl (34.5 mg, 814 umol, 2.00 eq) at 20° C. The mixture was stirred at 80° C. for 12 h under nitrogen atmosphere. LC-MS showed tert-butyl (S)-4-bromo-12-fluoro-7a,13-dihydro-7H-[1,2,4]triazolo[4',3':1,6]pyrido[3,2-b]benzofuro[4,3-fg] [1,4]oxazonine-14 (8H)-carboxylate was consumed completely and the desired mass was detected. The reaction mixture was filtered, the filtrate was concentrated. The residue was purified by prep-TLC (SiO₂, Petroleum ether/Ethyl acetate=1/1). tert-butyl (S)-12-fluoro-4-(5-fluoro-6-methylpyridin-2-yl)-7a,13-dihydro-7H-[1,2,4]triazolo[4',3':1,6]pyrido [3,2-b]benzofuro[4,3-fg][1,4]oxazonine-14 (8H)-carboxylate (150 mg, 288 umol, 70% yield) was obtained as a yellow oil.

Step 3: (S)-12-fluoro-4-(5-fluoro-6-methylpyridin-2-yl)-7a,8,13,14-tetrahydro-7H-[1,2,4]triazolo[4',3':1,6]pyrido[3,2-b]benzofuro[4,3-fg][1,4]oxazonine

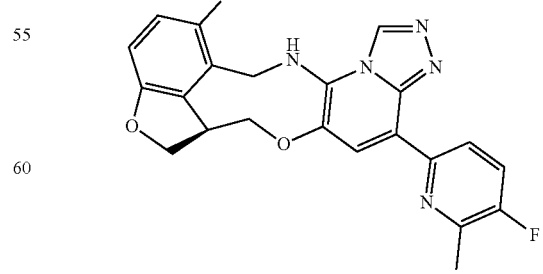

A mixture of tert-butyl (S)-12-fluoro-4-(5-fluoro-6-methylpyridin-2-yl)-7a,13-dihydro-7H-[1,2,4]triazolo[4',3':1,6]

pyrido[3,2-b]benzofuro[4,3-fg][1,4]oxazonine-14 (8H)-carboxylate (140 mg, 268 umol, 1.00 eq) in TFA (3.00 mL) and DCM (6.00 mL) was stirred at 20° C. for 2 h. The reaction mixture was concentrated. The residue was dissolved in DMSO (4.00 mL). The solution was purified by acidic prep-HPLC (column: Phenomenex Luna C18 100*30 mm*5 um; mobile phase: [water (0.2% FA)—ACN]; B %: 20%-50%, 12 min). The product-containing fraction was concentrated under reduced pressure to remove most of MeCN at 30° C. and the aqueous phase was lyophilized. (S)-12-fluoro-4-(5-fluoro-6-methylpyridin-2-yl)-7a,8,13,14-tetrahydro-7H-[1,2,4]triazolo[4',3':1,6]pyrido[3,2-b]benzofuro[4,3-fg][1,4]oxazonine (33.0 mg, 70.3 umol, 26% yield, 99.6% purity, formate salt) was obtained as a yellow solid. $^1$H NMR DMSO-$d_6$ 400 MHz δ =ppm 9.42 (br s, 1H), 8.77 (br d, J=5.1 Hz, 1H), 8.13 (s, 1H), 7.73 (br s, 1H), 7.65 (t, J=8.9 Hz, 1H), 6.86 (br t, J=9.5 Hz, 1H), 6.58 (dd, J=8.6, 3.7 Hz, 1H), 4.87-4.68 (m, 2H), 4.42 (br t, J=9.4 Hz, 2H), 4.20-4.10 (m, 1H), 3.95 (br s, 1H), 3.85-3.74 (m, 1H), 2.44 (s, 3H). LCMS (ESI+): m/z 422.1 (M+H).

Example 74: (S)-4-(4,5-dimethyl-4H-1,2,4-triazol-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: tert-butyl (S)-4-(4,5-dimethyl-4H-1,2,4-triazol-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

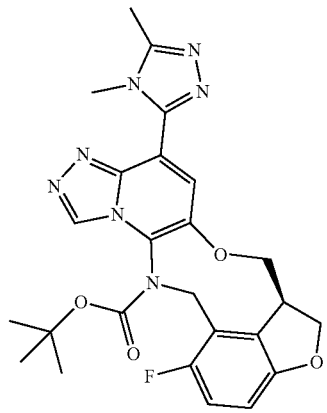 [SMILES: Cc1nnc(-c2cc3c(n4cnnc24)N(C(=O)OC(C)(C)C)Cc2c(F)ccc4c2[C@H](CO4)CO3)n1C]

Pd(OAc)2 (34.3 mg, 0.153 mmol) and di(1-adamantyl)-n-butylphosphine hydroiodide (149 mg, 0.305 mmol) were added to a solution of 3,4-dimethyl-1,2,4-triazole (74.1 mg, 0.763 mmol), (Example 16; 150.0 mg, 0.305 mmol), 2,2-dimethylpropanoic acid (31.2 mg, 0.305 mmol), and K2CO$_3$ (127 mg, 0.916 mmol) in toluene (2.50 mL). The mixture was stirred at 120° C. for 6 h. Water (0.5 mL) was added. The mixture was extracted with ethyl acetate (3×25 mL). The combined organic layers were dried over Na$_2$SO$_4$, filtered, and concentrated under reduced pressure. The residue was purified by silica gel chromatography (4 g cartridge) eluting with MeOH in DCM (0-10%) to provide tert-butyl (S)-4-(4,5-dimethyl-4H-1,2,4-triazol-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylateas a solid (66.0 mg, 30%, 70% purity). 1H NMR (400 MHz, MeOD) δ 9.19 (br, 1H), 7.73 (s, 1H), 6.74-6.62 (m, 1H), 6.59 (dd, J=8.5, 3.7 Hz, 1H), 5.35-5.20 (m, 1H), 4.72-4.63 (m, 1H), 4.47 (dd, J=9.6, 7.7 Hz, 1H), 4.34 (d, J=9.6 Hz, 1H), 4.18-4.08 (m, 1H), 4.08-4.01 (m, 2H), 3.77 (s, 3H), 2.37 (s, 3H), 1.56-1.33 (m, 9H). m/z (ES+) [M+H]$^+$: 508.6; HPLC tR (A05)=2.01 min.

Step 2: (S)-4-(4,5-dimethyl-4H-1,2,4-triazol-3-yl)-12-fluoro-7a,8,13,14-tetrahydro-7H-[1,2,4]triazolo[4',3':1,6]pyrido[3,2-b]benzofuro[4,3-fg][1,4]oxazonine

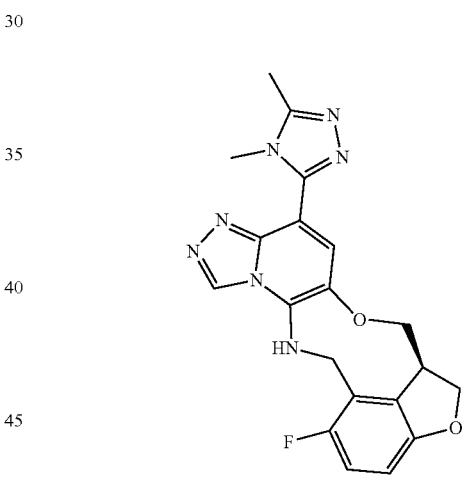

A solution of tert-butyl (S)-4-(4,5-dimethyl-4H-1,2,4-triazol-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (66.0 mg, 70% pure, 91.0 μmol) in HFIP (2.50 mL) was heated at 100° C. for 15 h. After evaporating the solvent under reduced pressure, the residue was purified by HPLC (Gemini C18 30×100 mm AmBicarb/ACN 23-43%) to afford the title compound as a solid (16.3 μmg, 44%). $^1$H NMR (500 MHz, DMSO) δ 9.48-9.39 (s, 1H), 7.83 (t, J=5.4 Hz, 1H), 7.54 (s, 1H), 7.02-6.91 (m, 1H), 6.70 (dd, J=8.6, 3.8 Hz, 1H), 4.93 (dd, J=15.0, 6.1 Hz, 1H), 4.85-4.75 (m, 1H), 4.54 (t, J=9.5 Hz, 1H), 4.51-4.41 (m, 1H), 4.22 (dd, J=9.6, 3.6 Hz, 1H), 4.05 (s, 1H), 3.91-3.78 (m, 1H), 3.49 (s, 3H), 2.42 (s, 3H). m/z (ES+) [M+H]$^+$: 408.6; HPLC $t_R$ (A05)=1.80 min.

Example 75: (S)-12-fluoro-4-(5-methyl-1,3,4-oxadiazol-2-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(5-methyl-1,3,4-oxadiazol-2-yl)-7a,13-dihydro-7H-[1,2,4]triazolo[4',3':1,6]pyrido[3,2-b]benzofuro[4,3-fg][1,4]oxazonine-14 (8H)-carboxylate

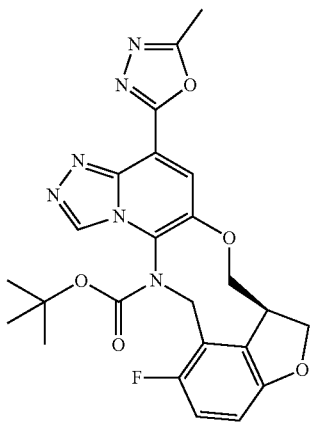 [SMILES: Cc1nnc(-c2cc3c(n4cnnc24)N(C(=O)OC(C)(C)C)Cc2c(F)ccc4c2[C@H](CO4)CO3)o1]

Pd(OAc)$_2$ (36.3 mg, 0.162 mmol) and di(1-adamantyl)-n-butylphosphine hydriodide (157 mg, 0.324 mmol) were added to a solution of 2-methyl-1,3,4-oxadiazole (68.0 mg, 0.809 mmol) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 16; 159 mg, 0.324 mmol), 2,2-dimethylpropanoic acid (33.1 mg, 0.324 mmol), K$_2$CO$_3$ (134 mg, 0.971 mmol) in toluene (2.50 mL). The mixture was stirred at 120° C. for 6 h. Water (0.5 mL) was added. The aqueous phase was extracted with ethyl acetate (3×15 mL). The combined organic layers were dried over Na$_2$SO$_4$, filtered, and concentrated under reduced pressure. The residue was purified by silica gel chromatography (4 g cartridge) eluting with MeOH in DCM (0-10%) to provide tert-butyl (S)-12-fluoro-4-(5-methyl-1,3,4-oxadiazol-2-yl)-7a,13-dihydro-7H-[1,2,4]triazolo[4',3':1,6]pyrido[3,2-b]benzofuro[4,3-fg][1,4]oxazonine-14 (8H)-carboxylate as a solid (99.0 mg, 43%, 70% purity). m/z (ES+) [M+H]$^+$: 495.4; (A05) t$_R$=2.09 min.

Step 2: (S)-12-fluoro-4-(5-methyl-1,3,4-oxadiazol-2-yl)-7a,8,13,14-tetrahydro-7H-[1,2,4]triazolo[4',3':1,6]pyrido[3,2-b]benzofuro[4,3-fg][1,4]oxazonine A solution of tert-butyl (S)-12-fluoro-4-(5-methyl-1,3,4-oxadiazol-2-yl)-7a,13-dihydro-7H-[1,2,4]triazolo[4',3':1,6]pyrido[3,2-b]benzofuro[4,3-fg][1,4]oxazonine-14 (8H)-carboxylate (99.0 mg, 70% pure, 140 μmol) in HFIP (2.50 mL) was heated at 100° C. for 15 h. After evaporating the solvent under reduced pressure, the residue was purified by HPLC (BEH C18 30×150 mm ACN/AmBic 25-45%) to afford the title compound as a solid (18.6 mg, 34%). $^1$H NMR (500 MHz, DMSO) δ 9.51 (s, 1H), 8.17 (s, 1H), 7.97 (s, 1H), 7.03-6.90 (m, 1H), 6.70 (dd, J=8.7, 3.8 Hz, 1H), 4.99-4.90 (m, 1H), 4.90-4.81 (m, 1H), 4.53 (t, J=9.4 Hz, 2H), 4.26-4.15 (m, 1H), 4.09-4.00 (m, 1H), 3.94-3.83 (m, 1H), 2.59 (s, 3H). m/z (ES+) [M+H]$^+$: 395.5; HPLC t$_R$ (A05)=1.88 min.

Example 76: (S)-4-(6-(difluoromethyl)-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-bromo-2-methyl-6-vinylpyridine

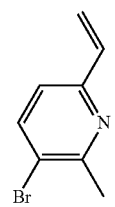

To a stirred solution of 3,6-dibromo-2-methylpyridine (8.60 g, 34.3 mmol, 1.00 eq), 4,4,5,5-tetramethyl-2-vinyl-1,3,2-dioxaborolane (5.28 g, 34.3 mmol, 1.00 eq) and Na$_2$CO$_3$ (7.27 g, 68.6 mmol, 2.00 eq) in dioxane (90.0 mL) and water (18.0 mL) was added Pd(dppf)Cl$_2$ (2.51 g, 3.43 mmol, 0.100 eq) at 15° C. under N$_2$. The resulting mixture was stirred at 80° C. for 12 h. The mixture was concentrated under reduced pressure. The mixture was purified by MPLC (SiO$_2$, PE/EtOAc=1/0 to 1/1). 3-bromo-2-methyl-6-vinylpyridine (5.70 g, 28.8 mmol, 84% yield) was obtained as colourless oil.

Step 2: 5-bromo-6-methylpicolinaldehyde

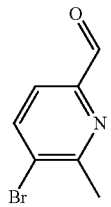

Ozone (15 psi) was bubbled into a solution of 3-bromo-2-methyl-6-vinylpyridine (5.70 g, 28.8 mmol, 1.00 eq) in DCM (100 mL) at −78° C. for 0.5 hr. After excess O3 was purged with $O_2$ for 0.5 hr, to the mixture was added $Me_2S$ (35.8 g, 576 mmol, 42.3 mL, 20.0 eq) at −78° C. The resulting mixture was stirred at 15° C. for 12 h. The mixture was concentrated under reduced pressure. The mixture was purified by MPLC ($SiO_2$, PE/EtOAc=1/0 to 10/1). 5-bromo-6-methylpicolinaldehyde (1.60 g, 8.00 mmol, 27% yield) was obtained as a yellow solid. $^1$H NMR DMSO-$d_6$ 400 MHz δ=ppm 9.92 (s, 1H), 8.27 (d, J=8.1 Hz, 1H), 7.67 (d, J=8.1 Hz, 1H), 2.68 (s, 3H).

Step 3: 3-bromo-6-(difluoromethyl)-2-methylpyridine

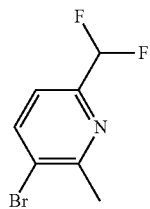

To a stirred solution of 5-bromo-6-methylpicolinaldehyde (1.60 g, 8.00 mmol, 1.00 eq) in DCM (50.0 mL) was added DAST (2.84 g, 17.6 mmol, 2.32 mL, 2.20 eq) at −78° C. under $N_2$. The resulting mixture was stirred at 15° C. for 12 h. The mixture was basified by saturated aqueous $NaHCO_3$ solution to pH=7-8 and then the mixture was extracted with EtOAc (20 mL*3). The combined organic layers were dried over $Na_2SO_4$ and then concentrated under reduced pressure. The mixture was purified by MPLC ($SiO_2$, PE/EtOAc=1/0 to 1/1). 3-bromo-6-(difluoromethyl)-2-methylpyridine (1.40 g, 6.31 mmol, 78% yield) was obtained as colourless oil.

Step 4: 6-(difluoromethyl)-2-methyl-3-(tributylstannyl)pyridine

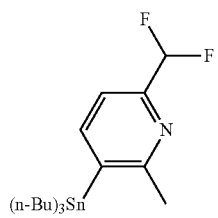

To a solution of 3-bromo-6-(difluoromethyl)-2-methylpyridine (1.30 g, 5.86 mmol, 1.00 eq) in THF (15.0 mL) was added n-BuLi (2.50 M, 2.58 mL, 1.10 eq) at −78° C. under nitrogen and the mixture was stirred at −78° C. for 0.5 hr under $N_2$. Then tributyl(chloro)stannane (5.72 g, 17.6 mmol, 4.73 mL, 3.00 eq) was added to the mixture under nitrogen atmosphere at −78° C. and the resulting mixture was stirred at −78° C. for 2 h under $N_2$. The mixture was quenched with saturated aqueous $NH_4Cl$ solution (20.0 mL) and the mixture was extracted with EtOAc (20.0 mL*3). The combined organic layers were dried over $Na_2SO_4$ and then concentrated under reduced pressure. The mixture was purified by MPLC ($SiO_2$, PE/EtOAc=1/0 to 1/1). 6-(difluoromethyl)-2-methyl-3-(tributylstannyl)pyridine (1.00 g, 2.31 mmol, 39% yield) was obtained as yellow oil.

Step 5: tert-butyl (S)-4-(6-(difluoromethyl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

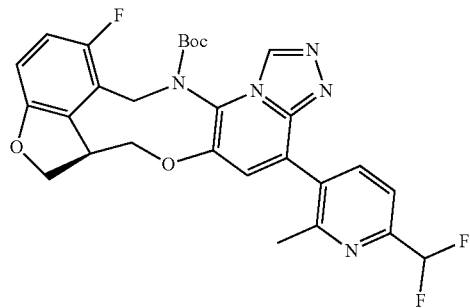

To a stirred solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (130 mg, 265 umol, 1.00 eq), 6-(difluoromethyl)-2-methyl-3-(tributylstannyl)pyridine (263 mg, 609 umol, 2.30 eq), CuI (20.2 mg, 106 umol, 0.400 eq) and LiCl (22.4 mg, 529 umol, 2.00 eq) in dioxane (4.00 mL) was added $Pd(PPh_3)_4$ (30.6 mg, 26.5 umol, 0.100 eq) at 15° C. under $N_2$. The resulting mixture was stirred at 80° C. for 12 h. The mixture was concentrated under reduced pressure. The mixture was purified by prep-TLC ($SiO_2$, PE/EtOAc=0/1). tert-butyl (S)-4-(6-(difluoromethyl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, crude) was obtained as yellow oil.

Step 6: (S)-4-(6-(difluoromethyl)-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

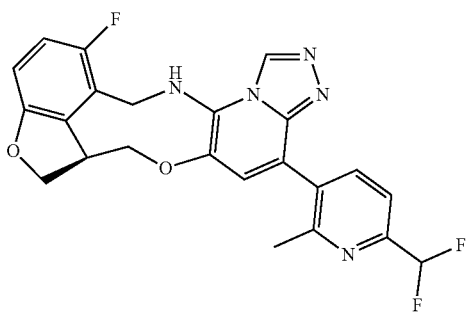 [SMILES: Cc1nc(C(F)F)ccc1-c1cc2c(n3cnnc13)NCc1c(F)ccc3c1[C@H](CO3)CO2]

To tert-butyl (S)-4-(6-(difluoromethyl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 361 umol, 1.00 eq) was added HFIP (3.00 mL) at 15° C. The resulting mixture was stirred at 80° C. for 12 h. LCMS showed the reactant was consumed and the desired mass was detected. The mixture was concentrated under reduced pressure. The mixture was purified by neutral prep-HPLC. The fraction was concentrated under reduced pressure to remove most of MeCN at 30° C. and the aqueous phase was lyophilized. (S)-4-(6-(difluoromethyl)-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (15.2 mg, 31.6 umol, 8% yield, 94.2% purity) was obtained as a yellow solid. $^1$H NMR DMSO-$d_6$ 400 MHz δ=ppm 9.42 (s, 1H), 7.97 (d, J=7.7 Hz, 1H), 7.63-7.53 (m, 2H), 7.39 (s, 1H), 6.96 (t, J=54.8 Hz, 1H), 6.96 (t, J=10.6 Hz, 1H), 6.68 (dd, J=8.6, 3.7 Hz, 1H), 4.95-4.87 (m, 1H), 4.84-4.73 (m, 1H), 4.57-4.41 (m, 2H), 4.19 (dd, J=9.7, 3.5 Hz, 1H), 4.09-3.97 (m, 1H), 3.91-3.81 (m, 1H), 2.41 (s, 3H). LCMS (ESI+): m/z 454.2 (M+H).

Example 77: (S)-4-(5-(difluoromethyl)-6-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 6-bromo-2-methylnicotinaldehyde

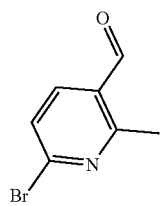

To a solution of 3,6-dibromo-2-methylpyridine (10.0 g, 39.9 mmol, 1.00 eq) in Et$_2$O (230 mL) was added n-BuLi (2.50 M, 18.3 mL, 1.15 eq) at −78° C. and the reaction mixture was stirred at −78° C. for 1 hr. TLC (SiO$_2$, PE/EtOAc=10/1) showed 3,6-dibromo-2-methylpyridine was consumed completely and new spots were formed. To the mixture was added DMF (5.15 g, 70.5 mmol, 5.42 mL, 1.77 eq) at −78° C. and the reaction mixture was stirred at −78° C. for 1 hr. Then the mixture was stirred at 15° C. for 1 hr. TLC (SiO$_2$, PE/EtOAc=10/1) showed the intermediate was consumed completely and new spots were formed. The mixture was quenched with saturated aqueous NH$_4$Cl solution (80.0 mL) and the mixture was extracted with EtOAc (50.0 mL*3). The combined organic layers were dried over Na$_2$SO$_4$ and then concentrated under reduced pressure. The mixture was purified by MPLC (SiO$_2$, PE/EtOAc=1/0 to 1/1). 6-bromo-2-methylnicotinaldehyde (5.20 g, 26.0 mmol, 65% yield) was obtained as a yellow solid. $^1$H NMR DMSO-$d_6$ 400 MHz δ=ppm 10.22 (s, 1H), 8.05 (d, J=8.2 Hz, 1H), 7.69 (d, J=8.2 Hz, 1H), 2.75 (s, 3H).

Step 2: 6-bromo-3-(difluoromethyl)-2-methylpyridine

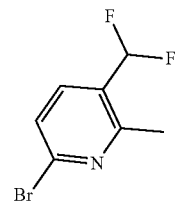

To a stirred solution of 6-bromo-2-methylnicotinaldehyde (2.00 g, 10.0 mmol, 1.00 eq) in DCM (80.0 mL) was added DAST (3.55 g, 22.0 mmol, 2.91 mL, 2.20 eq) at −78° C. under N$_2$. The resulting mixture was stirred at 15° C. for 12 h. LCMS showed 6-bromo-2-methylnicotinaldehyde was consumed and the desired mass was detected. The mixture was basified by saturated aqueous NaHCO$_3$ solution to pH=7-8 and then the mixture was extracted with EtOAc (50 mL*3). The combined organic layers were dried over Na$_2$SO$_4$ and then concentrated under reduced pressure. The mixture was purified by MPLC (SiO$_2$, PE/EtOAc=1/0 to 1/1). 6-bromo-3-(difluoromethyl)-2-methylpyridine (1.70 g, 7.66 mmol, 76% yield) was obtained as yellow oil.

Step 3: 3-(difluoromethyl)-2-methyl-6-(trimethylstannyl)pyridine

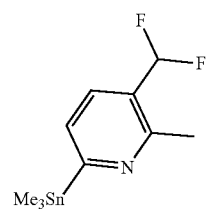

To a solution of 6-bromo-3-(difluoromethyl)-2-methylpyridine (500 mg, 2.25 mmol, 1.00 eq) in dioxane (15.0 mL) was added trimethyl(trimethylstannyl)stannane (1.49 g, 4.50 mmol, 943 uL, 2.00 eq), Pd(PPh$_3$)$_4$ (260 mg, 225 umol, 0.100 eq) at 25° C. under nitrogen atmosphere. The sealed tube was heated at 110° C. for 3 h under microwave irradiation. The suspension was filtered through a pad of Celite gel and the filter cake was washed with dioxane (1.00 mL). 3-(difluoromethyl)-2-methyl-6-(trimethylstannyl)pyridine (680 mg, 2.22 mmol, 98% yield) was obtained as yellow oil (in 16.0 mL of dioxane).

Step 4: tert-butyl (S)-4-(5-(difluoromethyl)-6-methylpyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

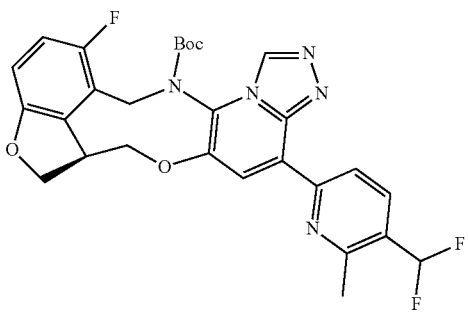

To a solution of 3-(difluoromethyl)-2-methyl-6-(trimethylstannyl)pyridine (340 mg, 1.11 mmol, 5.46 eq) in dioxane (8.00 mL) was added tert-butyl (S)-4-bromo-12-fluoro-7a,13-dihydro-7H-[1,2,4]triazolo[4',3':1,6]pyrido[3,2-b]benzofuro[4,3-fg] [1,4]oxazonine-14 (8H)-carboxylate (100 mg, 204 umol, 1.00 eq), LiCl (17.3 mg, 407 umol, 8.34 uL, 2.00 eq), CuI (15.5 mg, 81.4 umol, 0.400 eq) and Pd(PPh$_3$)4 (23.5 mg, 20.4 umol, 0.100 eq) at 15° C. under nitrogen atmosphere. The mixture was stirred at 80° C. for 3 h. The mixture was concentrated under reduced pressure. The residue was purified by prep-TLC (SiO$_2$, PE/EtOAc=1/1). tert-butyl (S)-4-(5-(difluoromethyl)-6-methylpyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, crude) was obtained as a yellow oil.

Step 5: (S)-4-(5-(difluoromethyl)-6-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine

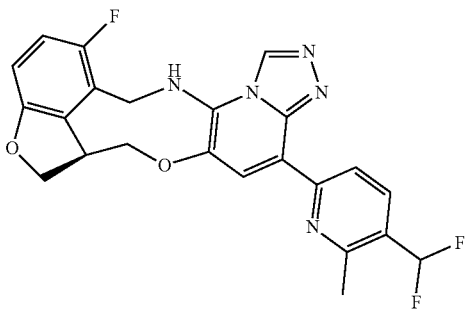 [SMILES: Cc1nc(-c2cc3c(n4cnnc24)NCc2c(F)ccc4c2[C@H](CO4)CO3)ccc1C(F)F]

To tert-butyl (S)-4-(5-(difluoromethyl)-6-methylpyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 271 umol, 1.00 eq) was added HFIP (4.00 mL) at 15° C. The resulting mixture was stirred at 80° C. for 12 h. The mixture was concentrated under reduced pressure. The mixture was purified by neutral prep-HPLC. The fraction was concentrated under reduced pressure to remove most of MeCN at 30° C. and the aqueous phase was lyophilized. (S)-4-(5-(difluoromethyl)-6-methylpyridin-2-yl)-12-fluoro-7a,8,13,14-tetrahydro-7H-[1,2,4]triazolo[4', 3':1,6]pyrido[3,2-b]benzofuro[4,3-fg][1,4]oxazonine (14.0 mg, 29.7 umol, 11% yield, 96.1% purity) was obtained as yellow solid. $^1$H NMR DMSO-d$_6$ 400 MHz δ=ppm 9.49 (s, 1H), 8.96 (d, J=8.4 Hz, 1H), 8.35 (s, 1H), 8.01 (d, J=8.4 Hz, 1H), 7.90 (br s, 1H), 7.24 (t, J=54.8 Hz, 1H), 6.94 (t, J=9.5 Hz, 1H), 6.67 (dd, J=8.7, 3.6 Hz, 1H), 4.98-4.75 (m, 2H), 4.50 (br t, J=9.4 Hz, 2H), 4.31-4.20 (m, 1H), 4.10-3.99 (m, 1H), 3.95-3.82 (m, 1H), 2.63 (s, 3H). LCMS (ESI+): m/z 454.2 (M+H).

Example 78: (S)-4-(3-(12-fluoro-7a,8,13,14-tetrahydro-7H-[1,2,4]triazolo[4',3':1,6]pyrido [3,2-b]benzofuro[4,3-fg][1,4]oxazonin-4-yl)pyridin-2-yl)-2-methylbutan-2-ol Step 1: 4-(3-bromopyridin-2-yl)-2-methylbut-3-yn-2-ol

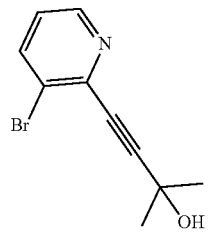

To a solution of 3-bromo-2-iodopyridine (2.00 g, 7.04 mmol, 1.00 eq) in THF (20.0 mL), Et$_3$N (20.0 mL) were added 2-methylbut-3-yn-2-ol (652 mg, 7.75 mmol, 757 uL, 1.10 eq), Pd(PPh$_3$)$_2$Cl$_2$ (494 mg, 704 umol, 0.100 eq) and CuI (134 mg, 704 umol, 0.100 eq) at 20° C. The mixture was stirred at 70° C. for 12 h under nitrogen atmosphere. The reaction was filtered, the filtrate was concentrated. The residue was purified by column chromatography (SiO$_2$, Petroleum ether/Ethyl acetate=1/0 to 0/1). 4-(3-bromopyridin-2-yl)-2-methylbut-3-yn-2-ol (1.51 g, 6.29 mmol, 89% yield) was obtained as a yellow oil.

Step 2: 3-bromo-2-(3-((tert-butyldimethylsilyl)oxy)-3-methylbut-1-yn-1-yl)pyridine

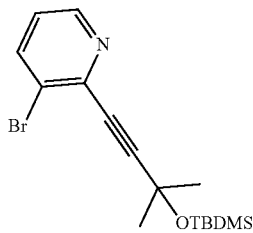 [SMILES: CC(C)(C#Cc1ncccc1Br)O[Si](C)(C)C(C)(C)C]

To a solution of 4-(3-bromopyridin-2-yl)-2-methylbut-3-yn-2-ol (600 mg, 2.50 mmol, 1.00 eq), 2,6-dimethylpyridine (535 mg, 4.99 mmol, 582 uL, 2.00 eq) in MeCN (10.0 mL) was added TBDMS-OTf (1.06 g, 4.00 mmol, 919 uL, 1.60 eq) at 0° C. Then the mixture was stirred at 60° C. for 12 h under nitrogen atmosphere. The reaction was concentrated. The residue was purified by prep-TLC (SiO$_2$, Petroleum ether/Ethyl acetate=3/1). 3-bromo-2-(3-((tert-butyldimethylsilyl)oxy)-3-methylbut-1-yn-1-yl)pyridine (800 mg, 2.26 mmol, 90% yield) was obtained as a yellow oil.

Step 3: 2-(3-((tert-butyldimethylsilyl)oxy)-3-methyl-but-1-yn-1-yl)-3-(tributylstannyl)pyridine

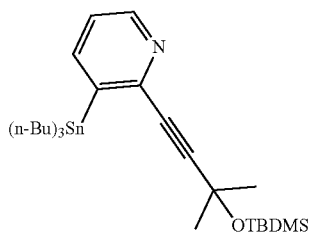

To a solution of 3-bromo-2-(3-((tert-butyldimethylsilyl)oxy)-3-methylbut-1-yn-1-yl)pyridine (1.00 g, 2.82 mmol, 1.00 eq) in THF (10.0 mL) was added n-BuLi (2.50 M, 1.24 mL, 1.10 eq) at −70° C. under nitrogen atmosphere. The reaction mixture was stirred at −70° C. for 0.5 hr under nitrogen atmosphere, then tributyl(chloro)stannane (2.76 g, 8.48 mmol, 2.28 mL, 3.00 eq) was added under nitrogen atmosphere and the resulting mixture was stirred at −70° C. for 2 h under nitrogen atmosphere. The reaction solution was poured into water (10.0 mL), the mixture was extracted with ethyl acetate (10 mL*3), the combined organic layers were dried over Na$_2$SO$_4$, and concentrated under reduced pressure. The residue was purified by prep-TLC (SiO$_2$, Petroleum ether/Ethyl acetate=10/1). 2-(3-((tert-butyldimethylsilyl)oxy)-3-methylbut-1-yn-1-yl)-3-(tributylstannyl)pyridine (1.30 g, 2.30 mmol, 81% yield) was obtained as a yellow oil.

Step 4: tert-butyl (S)-4-(2-(3-((tert-butyldimethylsilyl)oxy)-3-methylbut-1-yn-1-yl)pyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

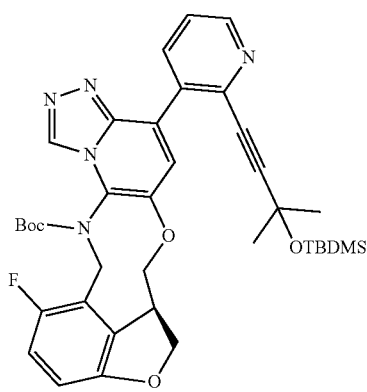 [SMILES: CC(C)(C)OC(=O)N1Cc2c(F)ccc3c2[C@H](CO3)COc2cc(-c3cccnc3C#CC(C)(C)O[Si](C)(C)C(C)(C)C)c3nncn3c21]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (240 mg, 488 umol, 1.00 eq) in dioxane (8.00 mL) was added 2-(3-((tert-butyldimethylsilyl)oxy)-3-methylbut-1-yn-1-yl)-3-(tributylstannyl)pyridine (551 mg, 976 umol, 2.00 eq), CuI (37.2 mg, 195 umol, 0.400 eq), LiCl (41.4 mg, 977 umol, 2.00 eq) and Pd(PPh$_3$)$_4$ (56.5 mg, 48.9 umol, 0.100 eq) at 20° C. under nitrogen atmosphere. The mixture was stirred at 80° C. for 12 h under nitrogen atmosphere. The reaction was concentrated. The residue was purified by prep-TLC (SiO$_2$, Petroleum ether/Ethyl acetate=1/2). tert-butyl (S)-4-(2-(3-((tert-butyldimethylsilyl)oxy)-3-methylbut-1-yn-1-yl)pyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (300 mg, 437 umol, 89% yield) was obtained as a yellow oil.

Step 5: tert-butyl (S)-12-fluoro-4-(2-(3-hydroxy-3-methylbut-1-yn-1-yl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

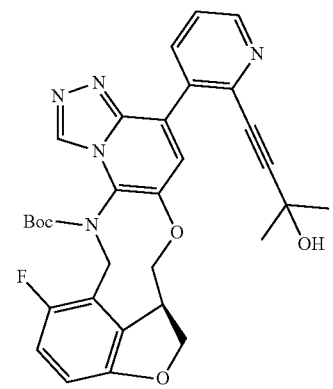 [SMILES: CC(C)(O)C#Cc1ncccc1-c1cc2c(n3cnnc13)N(C(=O)OC(C)(C)C)Cc1c(F)ccc3c1[C@H](CO3)CO2]

To a solution of tert-butyl (S)-4-(2-(3-((tert-butyldimethylsilyl)oxy)-3-methylbut-1-yn-1-yl)pyridin-3-yl)-12-fluoro-7a,13-dihydro-7H-[1,2,4]triazolo[4',3':1,6]pyrido [3,2-b]benzofuro[4,3-fg][1,4]oxazonine-14 (8H)-carboxylate (280 mg, 408 umol, 1.00 eq) in THF (8.00 mL) was added TBAF (1.00 M, 815 uL, 2.00 eq) at 20° C. The mixture was stirred at 40° C. for 12 h. LCMS showed tert-butyl (S)-4-(2-(3-((tert-butyldimethylsilyl)oxy)-3-methylbut-1-yn-1-yl)pyridin-3-yl)-12-fluoro-7a,13-dihydro-7H-[1,2,4]triazolo[4',3':1,6]pyrido [3,2-b]benzofuro[4,3-fg][1,4]oxazonine-14 (8H)-carboxylate was consumed completely and the desired mass was detected. Water (10.0 mL) was added to the reaction solution, the mixture was extracted with ethyl acetate (10.0 mL*3), the combined organic layers were dried over Na$_2$SO$_4$, and concentrated under reduced pressure. tert-butyl (S)-12-fluoro-4-(2-(3-hydroxy-3-methylbut-1-yn-1-yl)pyridin-3-yl)-7a,13-dihydro-7H-[1,2,4]triazolo[4',3':1,6]pyrido [3,2-b]benzofuro[4,3-fg][1,4]oxazonine-14 (8H)-carboxylate (230 mg, crude) was obtained as a brown oil.

Step 6: tert-butyl (S)-12-fluoro-4-(2-(3-hydroxy-3-methylbutyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

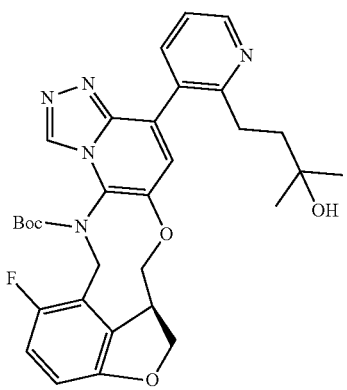 [SMILES: CC(C)(O)CCc1ncccc1-c1cc2c(n3cnnc13)N(C(=O)OC(C)(C)C)Cc1c(F)ccc3c1[C@H](CO3)CO2]

To a solution of tert-butyl (S)-12-fluoro-4-(2-(3-hydroxy-3-methylbut-1-yn-1-yl)pyridin-3-yl)-7a,13-dihydro-7H-[1,2,4]triazolo[4',3':1,6]pyrido [3,2-b]benzofuro[4,3-fg] [1,4]oxazonine-14 (8H)-carboxylate (200 mg, 350 umol, 1.00 eq) in MeOH (15.0 mL) was added 10% Pd/C (80.0 mg, 50% purity) at 20° C. under nitrogen atmosphere. The suspension was degassed and purged with H₂ three times. The mixture was stirred under H₂ (15 Psi) at 40° C. for 3 h. The reaction was filtered, the filtrate was concentrated. tert-butyl (S)-12-fluoro-4-(2-(3-hydroxy-3-methylbutyl)pyridin-3-yl)-7a,13-dihydro-7H-[1,2,4]triazolo[4',3':1,6]pyrido [3,2-b]benzofuro[4,3-fg][1,4]oxazonine-14 (8H)-carboxylate (200 mg, crude) was obtained as a yellow oil.

Step 7: (S)-4-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)-2-methylbutan-2-ol

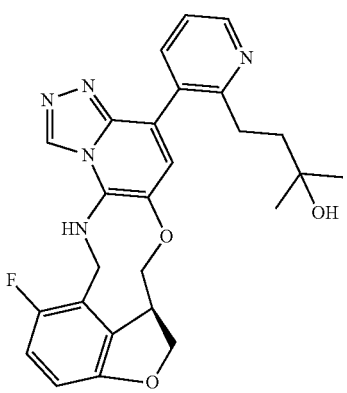 [SMILES: CC(C)(O)CCc1ncccc1-c1cc2c(n3cnnc13)NCc1c(F)ccc3c1[C@H](CO3)CO2]

A mixture of tert-butyl (S)-12-fluoro-4-(2-(3-hydroxy-3-methylbutyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (200 mg, 347 umol, 1.00 eq) in HFIP (20.0 mL) was stirred at 80° C. for 12 h. LCMS showed tert-butyl (S)-12-fluoro-4-(2-(3-hydroxy-3-methylbutyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate remained and the desired mass was detected. The mixture was stirred at 100° C. for 3.5 h at which time LCMS showed complete conversion. The reaction mixture was concentrated. The residue was dissolved in DMSO (8.00 mL). The solution was purified by neutral prep-HPLC. The fraction containing the product was concentrated under reduced pressure to remove most of MeCN at 30° C. and the aqueous phase was lyophilized. (S)-4-(3-(12-fluoro-7a,8,13,14-tetrahydro-7H-[1,2,4]triazolo[4',3':1,6]pyrido[3,2-b]benzofuro[4,3-fg] [1,4]oxazonin-4-yl)pyridin-2-yl)-2-methylbutan-2-ol (24.0 mg, 49.4 umol, 14% yield, 97.9% purity) was obtained as a white solid. ¹H NMR CDCl₃ 400 MHz δ=ppm 8.77 (s, 1H), 8.47 (br d, J=3.4 Hz, 1H), 7.61 (br d, J=7.8 Hz, 1H), 7.13 (dd, J=7.6, 5.0 Hz, 1H), 6.99 (s, 1H), 6.81 (t, J=9.4 Hz, 1H), 6.60 (dd, J=8.6, 3.9 Hz, 1H), 5.08-4.91 (m, 2H), 4.76 (br dd, J=14.1, 4.6 Hz, 1H), 4.59-4.47 (m, 2H), 4.17 (dd, J=9.8, 2.7 Hz, 1H), 3.91-3.63 (m, 3H), 2.79 (br t, J=7.2 Hz, 2H), 1.85 (br t, J=7.4 Hz, 2H), 1.07 (s, 6H). LCMS (ESI+): m/z 476.0 (M+H).

Example 79: (S)-12-fluoro-4-(1,3,5-trimethyl-1H-pyrazol-4-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-4-(2,4-dioxopentan-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

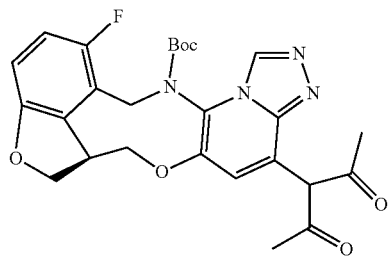 [SMILES: CC(=O)C(C(C)=O)c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (250 mg, 509 umol, 1.00 eq), pentane-2,4-dione (509 mg, 5.09 mmol, 523 uL, 10.0 eq) in toluene (5.00 mL) was added t-BuONa (2.00 M, 509 uL, 2.00 eq), t-BuXPhos Pd G₃ (40.4 mg, 50.9 umol, 0.100 eq) at 20° C. The mixture was degassed and purged with nitrogen for 3 times, and then the mixture was stirred at 100° C. for 12 h under nitrogen atmosphere. The reaction mixture was concentrated under reduced pressure. The residue was purified by prep-TLC (SiO₂, EtOAc:MeOH=10:1). tert-butyl (S)-4-(2,4-dioxopentan-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (59.7 mg, crude) was obtained as yellow solid.

Step 2: tert-butyl (S)-12-fluoro-4-(1,3,5-trimethyl-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate

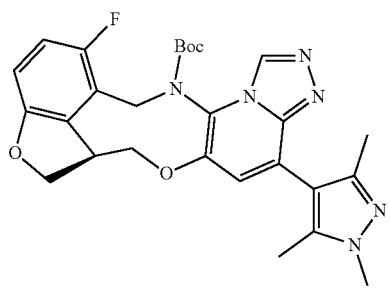 [SMILES: Cc1nn(C)c(C)c1-c1cc2c(n3cnnc13)N(C(=O)OC(C)(C)C)Cc1c(F)ccc3c1[C@H](CO3)CO2]

To a solution of tert-butyl (S)-4-(2,4-dioxopentan-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (59.7 mg, 117 umol, 1.00 eq) in EtOH (2.00 mL) was added methylhydrazine (269 mg, 2.34 mmol, 308 uL, 20.0 eq) at 20° C. Then the mixture was stirred at 80° C. for 4 h. The reaction mixture was filtered and the filtrate was concentrated under reduced pressure. The residue was purified by prep-TLC (SiO$_2$, EtOAc:MeOH=5:1). tert-butyl (S)-12-fluoro-4-(1,3,5-trimethyl-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate (15 mg, crude) was obtained as yellow oil.

Step 3: (S)-12-fluoro-4-(1,3,5-trimethyl-1H-pyrazol-4-yl)-7a,8,13,14-tetrahydro-7H-[1,2,4]triazolo[4',3':1,6]pyrido[3,2-b]benzofuro[4,3-fg][1,4]oxazonine Formate

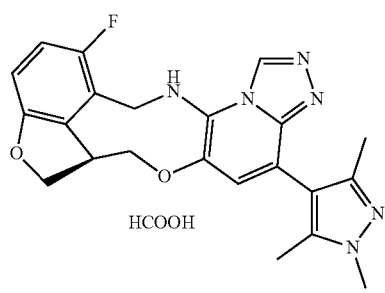 [SMILES: Cc1nn(C)c(C)c1-c1cc2c(n3cnnc13)NCc1c(F)ccc3c1[C@H](CO3)CO2 ; "HCOOH"]

To tert-butyl (S)-12-fluoro-4-(1,3,5-trimethyl-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate (15.0 mg, 28.8 umol, 1.00 eq) was added HFIP (2.00 mL) at 20° C. The mixture was stirred at 100° C. for 12 h. LC-MS showed tert-butyl (S)-12-fluoro-4-(1,3,5-trimethyl-1H-pyrazol-4-yl)-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. The reaction mixture was concentrated under reduced pressure. The crude product was purified by prep-HPLC (formic acid conditions). (S)-12-fluoro-4-(1,3,5-trimethyl-1H-pyrazol-4-yl)-7a,8,13,14-tetrahydro-7H-[1,2,4]triazolo[4',3':1,6]pyrido[3,2-b]benzofuro[4,3-fg][1,4]oxazonine (5.00 mg, 10.6 umol, 36% yield, 98.6% purity, formate salt) was obtained as yellow solid. $^1$H NMR CDCl$_3$ 400 MHz δ=ppm 8.81 (s, 1H), 7.27 (s, 1H), 6.91-6.84 (m, 1H), 6.70-6.64 (m, 1H), 5.19-5.00 (m, 1H), 4.89-4.78 (m, 2H), 4.72-4.50 (m, 2H), 4.32-4.20 (m, 1H), 3.98-3.89 (m, 1H), 3.86-3.79 (m, 1H), 3.77 (s, 3H), 2.21 (s, 3H), 2.20 (s, 3H). LCMS (ESI+): m/z 421.2 (M+H).

Example 80: (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol

Step 1: 1-(1H-pyrazol-1-yl)propan-2-one

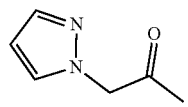

To a solution of 1H-pyrazole (10.0 g, 147 mmol, 1.00 eq) in 1-chloropropan-2-one (20.4 g, 220 mmol, 5.00 mL, 1.50 eq) was added Cs$_2$CO$_3$ (14.4 g, 44.2 mmol, 3.0le-1 eq) at 20° C. The mixture was stirred at 90° C. for 6 h. TLC (Petroleum ether:Ethyl acetate=1:1) indicated no 1H-pyrazole was remained, and one new spot with lower polarity was detected. The reaction mixture was concentrated under reduced pressure. The residue was purified by column chromatography (SiO$_2$, Petroleum ether/Ethyl acetate=1/0 to 1/1). 1-(1H-pyrazol-1-yl)propan-2-one (5.30 g, crude) was obtained as yellow oil.

Step 2: 2-methyl-1-(1H-pyrazol-1-yl)propan-2-ol

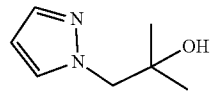

To a solution of 1-(1H-pyrazol-1-yl)propan-2-one (5.00 g, 40.3 mmol, 1.00 eq) in toluene (100 mL) was added Al(CH$_3$)$_3$ (2.00 M, 60.4 mL, 3.00 eq) at 0° C. under N$_2$. The mixture was stirred at 50° C. for 6 h. The reaction mixture was quenched by addition of MeOH (100 mL) at 0° C., and then the mixture was filtered. The filtrate was concentrated under reduced pressure. The residue was purified by column chromatography (SiO$_2$, Petroleum ether/Ethyl acetate=1/0 to 3/2). 2-methyl-1-(1H-pyrazol-1-yl)propan-2-ol (2.80 g, crude) was obtained as a white solid. $^1$H NMR DMSO-d$_6$ 400 MHz δ=ppm 7.63 (d, J=2.2 Hz, 1H), 7.39 (d, J=0.8 Hz, 1H), 6.21 (t, J=1.6 Hz, 1H), 4.65 (s, 1H), 3.99 (s, 2H), 1.01 (s, 6H).

Step 3: 2-methyl-1-(5-(tributylstannyl)-1H-pyrazol-1-yl)propan-2-ol

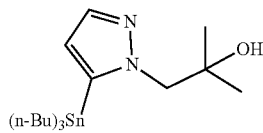

To a solution of 2-methyl-1-(1H-pyrazol-1-yl)propan-2-ol (200 mg, 1.43 mmol, 1.00 eq) in THF (5.00 mL) was added n-BuLi (2.50 M, 1.14 mL, 2.00 eq) and TMEDA (332 mg, 2.86 mmol, 431 uL, 2.00 eq) at −70° C. under $N_2$. The mixture was stirred at −70° C. for 30 mins. Then tributyl (chloro)stannane (697 mg, 2.14 mmol, 576 uL, 1.50 eq) was added to the mixture at −70° C. and the mixture was stirred at 0° C. for 1 hr. The reaction mixture was quenched by addition of MeOH (3.00 mL) at 0° C. And the reaction mixture was concentrated under reduced pressure. The residue was purified by column chromatography ($SiO_2$, Petroleum ether/Ethyl acetate=1/0 to 10/1). 2-methyl-1-(5-(tributylstannyl)-1H-pyrazol-1-yl)propan-2-ol (350 mg, crude) was obtained as a yellow liquid.

Step 4: (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol

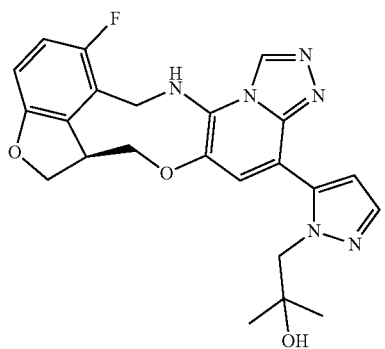 [SMILES: CC(C)(O)Cn1nccc1-c1cc2c(n3cnnc13)NCc1c(F)ccc3c1[C@H](CO3)CO2]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (90.0 mg, 230 umol, 1.00 eq) in DMF (4.00 mL) was added LiCl (19.5 mg, 460 umol, 2.00 eq), $Pd(PPh_3)_4$ (26.6 mg, 23.0 umol, 0.100 eq), CuI (18.4 mg, 96.6 umol, 0.420 eq) and 2-methyl-1-(5-(tributylstannyl)-1H-pyrazol-1-yl)propan-2-ol (148 mg, 345 umol, 1.50 eq) at 20° C. under $N_2$. The mixture was stirred at 80° C. for 6 h. The reaction mixture was concentrated under reduced pressure. The residue was purified by prep-HPLC (column: Phenomenex Luna C18 100*30 mm*5 um; mobile phase: [water (0.2% FA)—ACN]; B %: 15%-45%, 12 min). (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol (28.0 mg, 55.4 umol, 24% yield, 98.3% purity, formate salt) was obtained as a yellow solid. $^1$H NMR DMSO-$d_6$ 400 MHz δ=ppm 9.45 (s, 1H), 7.64 (br t, J=6.4 Hz, 1H), 7.56 (s, 1H), 7.50 (s, 1H), 6.96 (dd, J=10.2, 8.8 Hz, 1H), 6.70 (dd, J=8.6, 4.0 Hz, 1H), 6.48 (s, 1H), 4.96-4.87 (m, 1H), 4.84-4.74 (m, 1H), 4.58-4.50 (m, 2H), 4.22 (dd, J=9.5, 3.6 Hz, 1H), 4.10-3.99 (m, 3H), 3.90-3.79 (m, 1H), 0.93 (s, 6H).

Example 81: (S)-12-fluoro-4-(5-(trifluoromethyl)pyridin-2-yl)-7a,8,13,14-tetrahydro-7H-[1,2,4]triazolo[4',3':1,6]pyrido[3,2-b]benzofuro[4,3-fg][1,4]oxazonine Step 1: 5-(trifluoromethyl)-2-(trimethylstannyl)pyridine

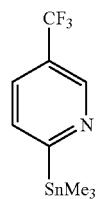

To a solution of 2-bromo-S-(trifluoromethyl)pyridine (240 mg, 1.06 mmol, 1.00 eq) and trimethyl (trimethylstannyl) stannane (696 mg, 2.12 mmol, 440 uL, 2.00 eq) in dioxane (8.00 mL) was added $Pd(PPh_3)_4$ (61.4 mg, 53.1 umol, 0.0500 eq) under nitrogen atmosphere. The mixture was stirred at 100° C. for 2 h under nitrogen atmosphere. LCMS showed the 2-bromo-S-(trifluoromethyl)pyridine was consumed completely and the desired MS was detected. 5-(trifluoromethyl)-2-(trimethylstannyl)pyridine (329 mg, crude) was obtained as yellow liquid (in 8.00 mL of dioxane), which was used to the next step directly.

Step 2: tert-butyl (S)-12-fluoro-4-(5-(trifluoromethyl)pyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

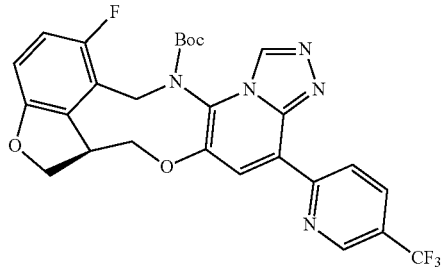 [SMILES: CC(C)(C)OC(=O)N1Cc2c(F)ccc3c2[C@H](CO3)COc2cc(-c3ccc(C(F)(F)F)cn3)c3nncn3c21]

A mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (158 mg, 322 umol, 1.00 eq), 5-(trifluoromethyl)-2-(trimethylstannyl) pyridine (329 mg, 1.06 mmol, 3.30 eq), LiCl (27.3 mg, 643 umol, 2.00 eq), CuI (24.5 mg, 129 umol, 0.400 eq) and $Pd(PPh_3)_4$ (37.2 mg, 32.2 umol, 0.100 eq) in dioxane (8.00 mL) was degassed and purged with nitrogen 3 times, and the mixture was stirred at 80° C. for 8 h under nitrogen atmosphere. LCMS indicated incomplete conversion. $Pd(PPh_3)_4$ (37.2 mg, 32.2 umol, 0.100 eq) was added to the mixture under nitrogen atmosphere. The mixture was stirred at 100° C. for 2 h under nitrogen atmosphere. The reaction mixture was diluted with water (5.00 mL) and extracted with EtOAc (3.00 mL*3). The combined organic layers were washed with brine (5.00 mL), dried over $Na_2SO_4$, filtered and concentrated under reduced pressure. The residue was purified by prep-TLC (SiO$_2$, PE:EtOAc=1:1). tert-butyl (S)-12-fluoro-4-(5-(trifluoromethyl)pyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (50.0 mg, crude) was obtained as yellow oil.

Step 3: (S)-12-fluoro-4-(5-(trifluoromethyl)pyridin-2-yl)-7a,8,13,14-tetrahydro-7H-[1,2,4]triazolo[4',3':1,6]pyrido[3,2-b]benzofuro[4,3-fg][1,4]oxazonine

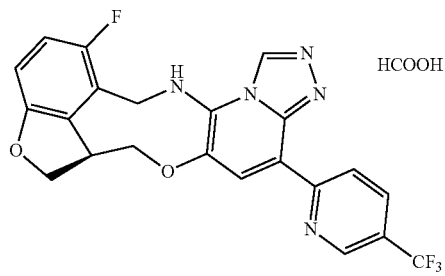 [SMILES: Fc1ccc2c3c1CNc1c(cc(-c4ccc(C(F)(F)F)cn4)c4nncn14)OC[C@H]3CO2 ; "HCOOH"]

A mixture of tert-butyl (S)-12-fluoro-4-(5-(trifluoromethyl)pyridin-2-yl)-7a,13-dihydro-7H-[1,2,4]triazolo[4',3':1,6]pyrido[3,2-b]benzofuro[4,3-fg] [1,4]oxazonine-14 (8H)-carboxylate (50.0 mg, 89.7 umol, 1.00 eq) and HFIP (2.00 mL) was stirred at 80° C. for 8 h. LCMS indicated small amount of the starting material remaining. The mixture was stirred at 100° C. for 2 h. LCMS indicated complete conversion. The reaction mixture was concentrated under reduced pressure. The residue was purified by prep-HPLC (neutral conditions). The product-containing fraction was concentrated under reduced pressure to remove most of MeCN at 30° C. and the aqueous phase was lyophilized. QC indicated insufficient purity. The material was re-purified by prep-HPLC (formic acid conditions). The product-containing fraction was concentrated under reduced pressure to remove most of MeCN at 30° C. and the aqueous phase was lyophilized. (S)-12-fluoro-4-(5-(trifluoromethyl)pyridin-2-yl)-7a,8,13,14-tetrahydro-7H-[1,2,4]triazolo[4',3':1,6]pyrido[3,2-b]benzofuro[4,3-fg][1,4]oxazonine (22.3 mg, 43.5 umol, 48% yield, 98.2% purity, formate salt) was obtained as a yellow solid. $^1$HNMR DMSO-d$_6$ 400 MHz δ=ppm 9.56 (s, 1H), 9.26 (d, J=8.4 Hz, 1H), 9.00 (s, 1H), 8.43 (s, 1H), 8.36-8.30 (m, 1H), 8.11 (br s, 1H), 6.98 (t, J=9.5 Hz, 1H), 6.71 (dd, J=8.7, 3.9 Hz, 1H), 5.03-4.94 (m, 1H), 4.89 (s, 1H), 4.60 (br s, 1H), 4.55 (t, J=9.5 Hz, 1H), 4.30-4.25 (m, 1H), 4.08 (br s, 1H), 3.98-3.84 (m, 1H). LCMS (ESI+): m/z 458.1 (M+H).

Example 82: (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol Step 1: 1-(3-iodo-1H-pyrazol-1-yl)propan-2-one

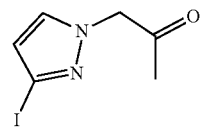

To a solution of 3-iodo-1H-pyrazole (2.00 g, 10.3 mmol, 1.00 eq) in MeCN (20.0 mL) was added Cs$_2$CO$_3$ (6.72 g, 20.6 mmol, 2.00 eq) and 1-chloropropan-2-one (1.43 g, 15.5 mmol, 1.50 eq) at 20° C. The mixture was stirred at 60° C. for 2 h. The reaction mixture was concentrated under reduced pressure. The residue was purified by prep-HPLC (column: Phenomenex luna C18 250*50 mm*15 um; mobile phase: [water (0.225% FA)—ACN]; B %: 5%-35%, 20 min). 1-(3-iodo-1H-pyrazol-1-yl)propan-2-one (385 mg, crude) was obtained as a white solid. 1-(5-iodo-1H-pyrazol-1-yl)propan-2-one (310 mg, crude) was obtained as a white solid. $^1$H NMR CDCl$_3$ 400 MHz δ=ppm 7.20 (d, J=2.8 Hz, 1H), 6.44 (d, J=2.0 Hz, 1H), 4.85 (s, 2H), 2.08 (s, 3H).

Step 2: 1-(3-iodo-1H-pyrazol-1-yl)-2-methylpropan-2-ol

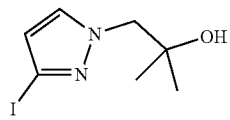

To a solution of 1-(3-iodo-1H-pyrazol-1-yl)propan-2-one (380 mg, 1.52 mmol, 1.00 eq) in toluene (10.0 mL) was added AlMe$_3$ (2.00 M, 3.80 mL, 5.00 eq) at 20° C. under N$_2$. The mixture was stirred at 60° C. for 12 h. LC-MS showed some of 1-(3-iodo-1H-pyrazol-1-yl)propan-2-one remained. The reaction mixture was quenched by addition of MeOH (5.00 mL) at 0° C. Then the mixture was filtered and the filtrate was concentrated under reduced pressure. The residue was purified by column chromatography (SiO$_2$, Petroleum ether/Ethyl acetate=1/0 to 4/1). 1-(3-iodo-1H-pyrazol-1-yl)-2-methylpropan-2-ol (127 mg, crude) was obtained as yellow oil.

Step 3: tert-butyl (S)-12-fluoro-4-(1-(2-hydroxy-2-methylpropyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate

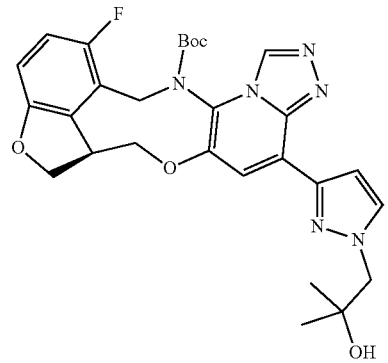 [SMILES: CC(C)(O)Cn1ccc(-c2cc3c(n4cnnc24)N(C(=O)OC(C)(C)C)Cc2c(F)ccc4c2[C@H](CO4)CO3)n1]

To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (110 mg, 157 umol, 1.00 eq) in dioxane (5.00 mL) was added 1-(3-iodo-1H-pyrazol-1-yl)-2-methylpropan-2-ol (83.5 mg, 314 umol, 2.00 eq), LiCl (13.3 mg, 314 umol, 2.00 eq), Pd(PPh$_3$)$_4$ (18.1 mg, 15.7 umol, 9.99e-2 eq) and CuI (11.9 mg, 62.5 umol, 3.98e-1 eq) at 20° C. under N$_2$. The mixture was stirred at 80° C. for 3 h. The reaction mixture was concentrated under reduced pressure. The residue was purified by column chromatography (SiO$_2$, Petroleum ether/Ethyl acetate=1/0 to 1/1). tert-butyl (S)-12-fluoro-4-(1-(2-hydroxy-2-methylpropyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (80.0 mg, crude) was obtained as a yellow solid.

Step 4: (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)-1H-pyrazol-1-yl)-2-methylpropan-2-ol

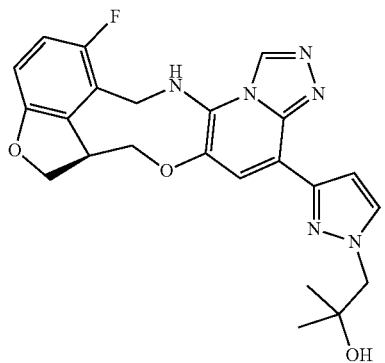 [SMILES: CC(C)(O)Cn1ccc(-c2cc3c(n4cnnc24)NCc2c(F)ccc4c2[C@H](CO4)CO3)n1]

A mixture of tert-butyl (S)-12-fluoro-4-(1-(2-hydroxy-2-methylpropyl)-1H-pyrazol-3-yl)-7a,13-dihydro-7H-[1,2,4]triazolo[4',3':1,6]pyrido[3,2-b]benzofuro[4,3-fg][1,4]oxazonine-14 (8H)-carboxylate (80.0 mg, 145 umol, 1.00 eq) in HFIP (2.00 mL) was stirred at 100° C. for 2 h. The reaction mixture was concentrated under reduced pressure. The residue was purified by prep-HPLC (column: Phenomenex Luna C18 200*40 mm*10 um; mobile phase: [water (0.2% FA)—ACN]; B %: 10%-50%, 10 min). The product-containing fraction was concentrated under reduced pressure to remove most of MeCN at 30° C. and the aqueous phase was lyophilized to give a yellow solid. The material was additionally purified by prep-HPLC (column: Phenomenex Luna C18 200*40 mm*10 um; mobile phase: [water (0.2% FA)—ACN]; B %: 20%-40%, 10 min). (S)-1-(3-(12-fluoro-7a,8,13,14-tetrahydro-7H-[1,2,4]triazolo[4',3':1,6] pyrido[3,2-b]benzofuro[4,3-fg][1,4]oxazonin-4-yl)-1H-pyrazol-1-yl)-2-methylpropan-2-ol (4.00 mg, 7.80 umol, 5% yield, 96.8% purity, formate salt) was obtained as a yellow solid. $^1$H NMR DMSO-d$_6$ 400 MHz δ=ppm 9.42 (s, 1H), 7.81-7.68 (m, 2H), 7.46 (br s, 1H), 7.25 (s, 1H), 6.99-6.88 (m, 1H), 6.67 (dd, J=8.8, 3.6 Hz, 1H), 4.93-4.84 (m, 1H), 4.82-4.70 (m, 2H), 4.59-4.48 (m, 2H), 4.26 (dd, J=9.5, 3.2 Hz, 1H), 4.09 (s, 2H), 4.03 (br s, 1H), 3.91-3.80 (m, 1H), 1.10 (s, 6H) LCMS (ESI+): m/z 451.1 (M+H).

Example 83: (S)-12-fluoro-4-(1-methyl-1H-imidazol-2-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(1-methyl-1H-imidazol-2-yl)-7a,13-dihydro-7H-[1,2,4]triazolo[4',3':1,6]pyrido[3,2-b]benzofuro[4,3-fg][1,4]oxazonine-14 (8H)-carboxylate

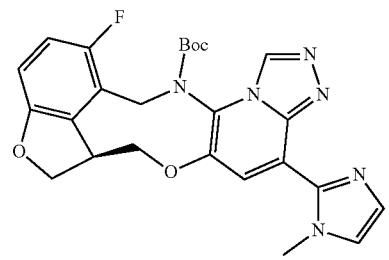 [SMILES: Cn1ccnc1-c1cc2c(n3cnnc13)N(C(=O)OC(C)(C)C)Cc1c(F)ccc3c1[C@H](CO3)CO2]

To tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (200 mg, 285 umol, 1.00 eq) in dioxane (3.00 mL) was added 2-bromo-1-methyl-imidazole (91.8 mg, 570 umol, 2.00 eq), Pd(PPh$_3$)$_4$ (33.0 mg, 28.5 umol, 0.100 eq), CuI (21.7 mg, 114 umol, 0.400 eq), LiCl (24.2 mg, 570 umol, 2.00 eq) at 20° C. The mixture was degassed and purged with nitrogen 3 times, then the mixture was stirred at 100° C. for 12 h under nitrogen atmosphere. The reaction mixture was filtered and the filtrate was concentrated under reduced pressure. The residue was purified by prep-TLC (SiO$_2$, EtOAc:MeOH=10:1). tert-butyl (S)-12-fluoro-4-(1-methyl-1H-imidazol-2-yl)-7a,13-dihydro-7H-[1,2,4]triazolo[4',3':1,6]pyrido[3,2-b]benzofuro[4,3-fg][1,4]oxazonine-14 (8H)-carboxylate (140 mg, crude) was obtained as a yellow solid.

Step 2: (S)-12-fluoro-4-(1-methyl-1H-imidazol-2-yl)-7a,8,13,14-tetrahydro-7H-[1,2,4]triazolo[4',3':1,6]pyrido[3,2-b]benzofuro[4,3-fg][1,4]oxazonine

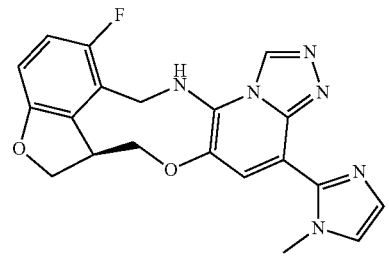 [SMILES: Cn1ccnc1-c1cc2c(n3cnnc13)NCc1c(F)ccc3c1[C@H](CO3)CO2]

To tert-butyl (S)-12-fluoro-4-(1-methyl-1H-imidazol-2-yl)-7a,13-dihydro-7H-[1,2,4]triazolo[4',3':1,6]pyrido[3,2-b]benzofuro[4,3-fg][1,4]oxazonine-14 (8H)-carboxylate (140 mg, 284 umol, 1.00 eq) was added HFIP (2.00 mL) at 20° C. The mixture was stirred at 100° C. for 12 h. The reaction mixture was concentrated under reduced pressure. The crude product was purified by prep-HPLC (formic acid conditions). The product-containing fraction was concentrated under reduced pressure to remove most of MeCN at 30° C. and the aqueous phase was lyophilized. (S)-12-fluoro-4-(1- methyl-1H-imidazol-2-yl)-7a,8,13,14-tetrahydro-7H-[1,2,4]triazolo[4',3':1,6]pyrido[3,2-b]benzofuro[4,3-fg][1,4]oxazonine (26.2 mg, 59.8 umol, 21% yield, 100% purity, formate salt) was obtained as yellow solid. $^1$H NMR CD$_3$OD 400 MHz δ=ppm 9.84 (s, 1H), 8.38 (s, 1H), 7.83 (s, 1H), 7.79 (s, 1H), 6.93 (t, J=9.6 Hz, 1H), 6.69 (dd, J=8.6, 3.9 Hz, 1H), 5.26 (br d, J=14.7 Hz, 1H), 5.07 (br s, 1H), 4.78 (br s, 1H), 4.63 (br t, J=9.5 Hz, 1H), 4.31 (br d, J=6.1 Hz, 1H), 4.20-4.06 (m, 1H), 4.04-3.92 (m, 1H), 3.89 (s, 3H). LCMS (ESI+): m/z 393.1 (M+H).

Example 84: (S)-12-fluoro-4-(5-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine Step 1: 5-fluoro-2-methyl-4-(trimethylstannyl)pyridine

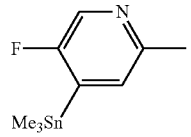

To a mixture of 4-bromo-S-fluoro-2-methylpyridine (150 mg, 789 umol, 1.00 eq), trimethyl(trimethylstannyl)stannane (517 mg, 1.58 mmol, 327 uL, 2.00 eq) and Pd(PPh$_3$)$_4$ (91.2 mg, 78.9 umol, 0.100 eq) was added dioxane (3.00 mL) at 20° C. under N$_2$. Then the mixture was stirred at 100° C. for 12 h under nitrogen atmosphere. LC-MS showed 4-bromo-S-fluoro-2-methylpyridine was consumed completely and one main peak with desired mass was detected. The obtained solution of 5-fluoro-2-methyl-4-(trimethylstannyl)pyridine was used in the next step directly.

Step 2: tert-butyl (S)-12-fluoro-4-(5-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate

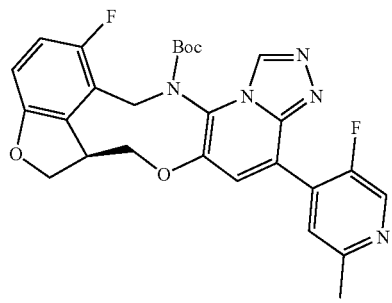 [SMILES: Cc1cc(-c2cc3c(n4cnnc24)N(C(=O)OC(C)(C)C)Cc2c(F)ccc4c2[C@H](CO4)CO3)c(F)cn1]

To a solution of 5-fluoro-2-methyl-4-(trimethylstannyl)pyridine (216 mg, 789 umol, 3.23 eq) in dioxane (3.00 mL) was added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 244 umol, 1.00 eq), Pd(PPh$_3$)$_4$ (28.2 mg, 24.4 umol, 0.100 eq), LiCl (20.7 mg, 488 umol, 2.00 eq) and CuI (18.6 mg, 97.7 umol, 0.400 eq) at 20° C. The mixture was degassed and purged with nitrogen 3 times, and then the mixture was stirred at 100° C. for 3 h under nitrogen atmosphere. The reaction mixture was filtered and the filtrate was concentrated under reduced pressure. The residue was purified by prep-TLC (SiO$_2$, EtOAc). tert-butyl (S)-12-fluoro-4-(5-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (130 mg, crude) was obtained as a yellow solid.

Step 3: (S)-12-fluoro-4-(5-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine

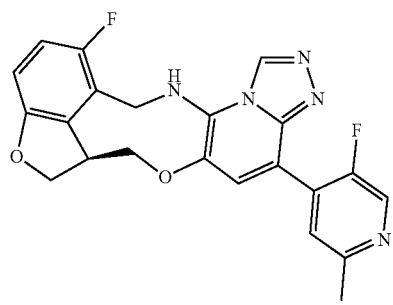 [SMILES: Cc1cc(-c2cc3c(n4cnnc24)NCc2c(F)ccc4c2[C@H](CO4)CO3)c(F)cn1]

To tert-butyl (S)-12-fluoro-4-(5-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (130 mg, 249 umol, 1.00 eq) was added HFIP (2.00 mL) at 20° C. The mixture was stirred at 100° C. for 12 h. The reaction mixture was concentrated under reduced pressure. The crude product was purified by prep-HPLC (formic acid conditions). (S)-12-fluoro-4-(5-fluoro-2-methylpyridin-4-yl)-7a,8,13,14-tetrahydro-7H-[1,2,4]triazolo[4',3':1,6]pyrido[3,2-b]benzofuro[4,3-fg] [1,4]oxazonine (57.3 mg, 122 umol, 49% yield, 99.6% purity, formate salt) was obtained as yellow solid. $^1$H NMR CD$_3$OD 400 MHz δ=ppm 9.79 (s, 1H), 9.04 (d, J=4.0 Hz, 1H), 8.42 (s, 1H), 8.33 (d, J=6.5 Hz, 1H), 6.93 (dd, J=10.1, 8.9 Hz, 1H), 6.70 (dd, J=8.7, 3.9 Hz, 1H), 5.27-5.21 (m, 1H), 5.13-4.97 (m, 1H), 4.92-4.75 (m, 1H), 4.68-4.56 (m, 1H), 4.38-4.27 (m, 1H), 4.19-3.94 (m, 2H), 2.89 (s, 3H). LCMS (ESI+): m/z 422.2 (M+H).

Example 85: (S)-4-(6-(difluoromethyl)-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 5-bromo-2-(difluoromethyl)-4-methylpyridine

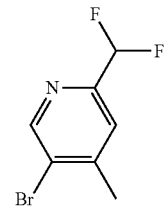

To a solution of 5-bromo-4-methylpicolinaldehyde (1.00 g, 5.00 mmol, 1.00 eq) in DCM (10.0 mL) was added DAST (3.22 g, 20.0 mmol, 2.64 mL, 4.00 eq) at −78° C. The mixture was stirred at −78° C. for 30 min. The reaction mixture was quenched by addition of sat. aq. Na$_2$CO$_3$ (80.0 mL) at 0° C., diluted with water (30.0 mL) and extracted with DCM (30.0 mL*3). The combined organic layers were washed with brine (30.0 mL), dried over Na$_2$SO$_4$, filtered and concentrated under reduced pressure. The residue was purified by column chromatography (SiO$_2$, Petroleum ether/Ethyl acetate=1/0 to 15/1). 5-bromo-2-(difluoromethyl)-4-methylpyridine (812 mg, crude) was obtained as a yellow oil.

Step 2: 2-(difluoromethyl)-4-methyl-S-(4,4,5,5-tetramethyl-1,3,2-dioxaborolan-2-yl)pyridine

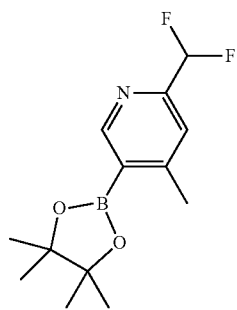 [SMILES: Cc1cc(C(F)F)ncc1B1OC(C)(C)C(C)(C)O1]

A mixture of 5-bromo-2-(difluoromethyl)-4-methylpyridine (200 mg, 901 umol, 1.00 eq), 4,4,5,5-tetramethyl-2-(4,4,5,5-tetramethyl-1,3,2-dioxaborolan-2-yl)-1,3,2-dioxaborolane (343 mg, 1.35 mmol, 1.50 eq), KOAc (265 mg, 2.70 mmol, 3.00 eq), Pd(dppf)Cl$_2$ (65.9 mg, 90.1 umol, 0.100 eq) in dioxane (2.00 mL) was degassed and purged with nitrogen 3 times at 20° C., and then the mixture was stirred at 80° C. for 2 h under nitrogen atmosphere. The reaction mixture was concentrated under reduced pressure. The residue was purified by column chromatography (SiO$_2$, Petroleum ether/Ethyl acetate=1/0 to 10/1). 2-(difluoromethyl)-4-methyl-S-(4,4,5,5-tetramethyl-1,3,2-dioxaborolan-2-yl)pyridine (180 mg, 669 umol, 74% yield) was obtained as yellow oil.

Step 3: (S)-4-(6-(difluoromethyl)-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

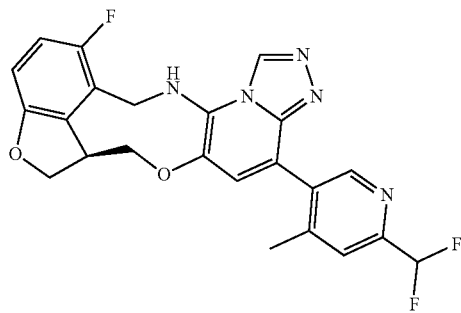 [SMILES: Cc1cc(C(F)F)ncc1-c1cc2c(n3cnnc13)NCc1c(F)ccc3c1[C@H](CO3)CO2]

To a solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (Example 17; 80.0 mg, 205 umol, 1.00 eq) and 2-(difluoromethyl)-4-methyl-S-(4,4,5,5-tetramethyl-1,3,2-dioxaborolan-2-yl)pyridine (165 mg, 614 umol, 3.00 eq) in dioxane (2.00 mL) and water (0.400 mL) was added Na$_2$CO$_3$ (65.0 mg, 614 umol, 3.00 eq) and Pd(dppf)Cl$_2$ (15.0 mg, 20.5 umol, 0.100 eq). The mixture was stirred at 80° C. for 2 h under nitrogen atmosphere. The reaction mixture was concentrated under reduced pressure. The residue was dissolved in MeOH (10.0 mL) and silica-thiol (20.0 mg, modified silicon gel for eliminating Pd, irregular silica gel, 100-200 mesh, Chlorides (Cl), %≤0.004, particle size distribution 45-75 um) was added at 20° C. and stirred at 20° C. for 4 h. The suspension was filtered, the filtrate was concentrated and purified by prep-HPLC (formic acid conditions). The product-containing fraction was concentrated under reduced pressure to remove most of MeCN at 30° C. and the aqueous phase was lyophilized. (S)-4-(6-(difluoromethyl)-4-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (32.8 mg, 62.7 umol, 30% yield, 95.4% purity, formate salt) was obtained as a yellow solid. $^1$HNMR DMSO-d$_6$ 400 MHz δ=ppm 9.45 (s, 1H), 8.62 (s, 1H), 7.68 (s, 1H), 7.62 (t, J=6.4 Hz, 1H), 7.43 (s, 1H), 6.99 (t, J=60.8 Hz, 1H), 7.03-6.94 (m, 1H), 6.71 (dd, J=8.7, 3.5 Hz, 1H), 4.98-4.89 (m, 1H), 4.86-4.74 (m, 1H), 4.59-4.52 (m, 1H), 4.48 (d, J=8.1 Hz, 1H), 4.22 (dd, J=9.5, 3.5 Hz, 1H), 4.05 (s, 1H), 3.94-3.83 (m, 1H), 2.30 (s, 3H). LCMS (ESI+): m/z 454.2 (M+H).

Example 86: (S)-12-fluoro-4-(3-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine Step 1: 3-fluoro-2-methyl-4-(trimethylstannyl)pyridine

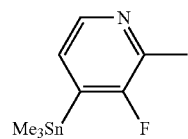

To a stirred solution of 4-bromo-3-fluoro-2-methylpyridine (70.0 mg, 368 umol, 1.00 eq) and trimethyl(trimethylstannyl)stannane (241 mg, 737 umol, 153 uL, 2.00 eq) in dioxane (3.00 mL) was added Pd(PPh$_3$)$_4$ (42.6 mg, 36.8 umol, 0.100 eq) at 15° C. under N$_2$. The resulting mixture was stirred at 100° C. for 12 h. 3-fluoro-2-methyl-4-(trimethylstannyl)pyridine (100 mg, crude) was obtained as brown liquid (in 3.00 mL dioxane), which was used to the next step directly.

Step 2: tert-butyl (S)-12-fluoro-4-(3-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate

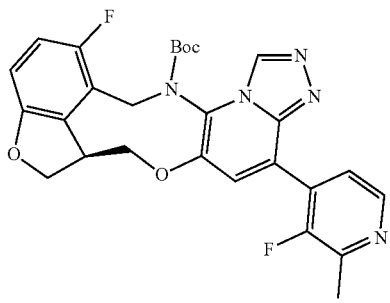 [SMILES: Cc1nccc(-c2cc3c(n4cnnc24)N(C(=O)OC(C)(C)C)Cc2c(F)ccc4c2[C@H](CO4)CO3)c1F]

To a solution of 3-fluoro-2-methyl-4-(trimethylstannyl)pyridine (100 mg, 365 umol, 2.00 eq) in dioxane (3.00 mL) was added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (89.7 mg, 183 umol, 1.00 eq), LiCl (15.5 mg, 365 umol, 2.00 eq), CuI (13.9 mg, 73.0 umol, 0.400 eq) and Pd(PPh$_3$)$_4$ (21.1 mg, 18.3 umol, 0.100 eq) at 15° C. under nitrogen atmosphere. The mixture was stirred at 100° C. for 12 h. The mixture was concentrated under reduced pressure. The residue was purified by prep-TLC (SiO$_2$, PE/EtOAc=0/1). tert-butyl (S)-12-fluoro-4-(3-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (60.0 mg, crude) was obtained as a brown solid.

Step 3: (S)-12-fluoro-4-(3-fluoro-2-methylpyridin-4-yl)-7a,8,13,14-tetrahydro-7H-[1,2,4]triazolo[4',3':1,6]pyrido[3,2-b]benzofuro[4,3-fg][1,4]oxazonine

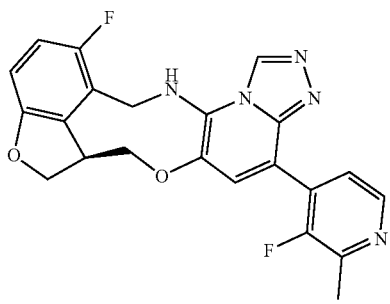 [SMILES: Cc1nccc(-c2cc3c(n4cnnc24)NCc2c(F)ccc4c2[C@H](CO4)CO3)c1F]

To tert-butyl (S)-12-fluoro-4-(3-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate (60.0 mg, 115 umol, 1.00 eq) was added HFIP (2.00 mL) at 15° C. The resulting mixture was stirred at 80° C. for 12 h. LCMS showed tert-butyl (S)-12-fluoro-4-(3-fluoro-2-methylpyridin-4-yl)-7a,13-dihydro-7H-[1,2,4]triazolo[4',3':1,6]pyrido[3,2-b]benzofuro[4,3-fg][1,4]oxazonine-14 (8H)-carboxylate was consumed and the desired mass was detected. The mixture was concentrated under reduced pressure. The mixture was purified by acidic prep-HPLC (FA). The fraction was concentrated under reduced pressure to remove most of MeCN at 30° C. and the aqueous phase was lyophilized. The title compound (7.10 mg, 14.9 umol, 13% yield, 98.1% purity, formate salt) was obtained as a yellow solid. $^1$H NMR DMSO-d$_6$ 400 MHz δ=ppm 9.45 (s, 1H), 8.32 (d, J=5.1 Hz, 1H), 7.94 (t, J=5.2 Hz, 1H), 7.84-7.76 (m, 1H), 7.64 (s, 1H), 7.00-6.89 (m, 1H), 6.68 (dd, J=8.8, 3.7 Hz, 1H), 4.95-4.86 (m, 1H), 4.85-4.75 (m, 1H), 4.55-4.42 (m, 2H), 4.22-4.16 (m, 1H), 4.09-3.96 (m, 1H), 3.90-3.79 (m, 1H), 2.50 (s, 3H). $^1$H NMR CDCl$_3$ 400 MHz δ=ppm 8.84-8.77 (m, 1H), 8.41-8.33 (m, 1H), 8.07-7.99 (m, 1H), 7.58-7.52 (m, 1H), 6.92-6.82 (m, 1H), 6.72-6.63 (m, 1H), 5.19-5.08 (m, 1H), 4.98-4.81 (m, 2H), 4.69-4.61 (m, 2H), 4.31-4.21 (m, 1H), 3.95-3.80 (m, 2H), 2.59 (d, J=3.3 Hz, 3H). LCMS (ESI+): m/z 422.1 (M+H).

Example 87: (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)-2-methylpropan-2-ol Step 1: 1-(3-bromopyridin-2-yl)-2-methylpropan-2-ol

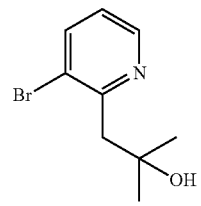

To a solution of N-isopropylpropan-2-amine (765 mg, 7.56 mmol, 1.07 mL, 1.30 eq) in THF (15.0 mL) was added n-BuLi (2.50 M, 2.79 mL, 1.20 eq) at −70° C. under N$_2$, and stirred at −70° C. for 0.5 hr. 3-Bromo-2-methylpyridine (1.00 g, 5.81 mmol, 1.00 eq) was added to the mixture at −70° C. and stirred at −70° C. for 0.5 hr. Acetone (675 mg, 11.6 mmol, 854 uL, 2.00 eq) was added to the mixture at −70° C., and stirred at 0° C. for 1 hr. The reaction mixture was quenched by addition of MeOH (7.00 mL) at 0° C. Then the mixture was concentrated under reduced pressure. The residue was purified by column chromatography (SiO$_2$, Petroleum ether/Ethyl acetate=1/0 to 5/1). 1-(3-bromopyridin-2-yl)-2-methylpropan-2-ol (1.00 g, crude) was obtained as yellow oil. $^1$H NMR CDCl$_3$ 400 MHz δ=ppm 8.38 (d, J=4.4 Hz, 1H), 7.81 (d, J=8.0 Hz, 1H), 7.00 (dd, J=8.0, 4.8 Hz, 1H), 5.70 (s, 1H), 3.06 (s, 2H), 1.20 (s, 6H).

Step 2: 2-methyl-1-(3-(tributylstannyl)pyridin-2-yl)propan-2-ol

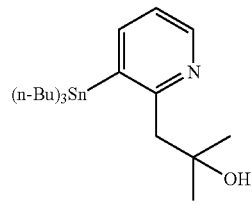

To a solution of 1-(3-bromopyridin-2-yl)-2-methylpropan-2-ol (500 mg, 2.17 mmol, 1.00 eq) in THF (9.00 mL) was added n-BuLi (2.50 M, 1.74 mL, 2.00 eq) and TMEDA (504 mg, 4.34 mmol, 654 uL, 2.00 eq) at −70° C. under N₂. The mixture was stirred at −70° C. for 30 min. Sn(n-Bu)₃Cl (1.06 g, 3.26 mmol, 877 uL, 1.50 eq) was added at −70° C. and the reaction mixture was stirred at 0° C. for 1 hr. The reaction mixture was quenched by addition of MeOH (2.00 mL) at 0° C., and then mixture was concentrated under reduced pressure. The residue was purified by column chromatography (SiO₂, Petroleum ether/Ethyl acetate=1/0 to 10/1). 2-methyl-1-(3-(tributylstannyl)pyridin-2-yl)propan-2-ol (190 mg, crude) was obtained as a yellow liquid.

Step 3: tert-butyl (S)-12-fluoro-4-(2-(2-hydroxy-2-methylpropyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

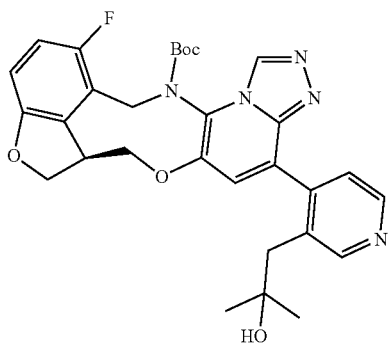 [SMILES: CC(C)(O)Cc1cnccc1-c1cc2c(n3cnnc13)N(C(=O)OC(C)(C)C)Cc1c(F)ccc3c1[C@H](CO3)CO2]

To a solution of (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (140 mg, 285 umol, 1.00 eq) in dioxane (3.00 mL) was added 2-methyl-1-(3-(tributylstannyl)pyridin-2-yl)propan-2-ol (188 mg, 427 umol, 1.50 eq), LiCl (24.2 mg, 571 umol, 2.00 eq), Pd(PPh₃)₄ (36.2 mg, 31.3 umol, 0.110 eq) and CuI (21.7 mg, 114 umol, 0.400 eq) at 20° C. under N₂. The mixture was stirred at 80° C. for 3 h. The reaction mixture was concentrated under reduced pressure. The residue was purified by prep-TLC (SiO₂, Petroleum ether/Ethyl acetate=1/2). tert-butyl (S)-12-fluoro-4-(2-(2-hydroxy-2-methylpropyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (80.0 mg, crude) was obtained as a brown solid.

Step 4: (S)-1-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)-2-methylpropan-2-ol

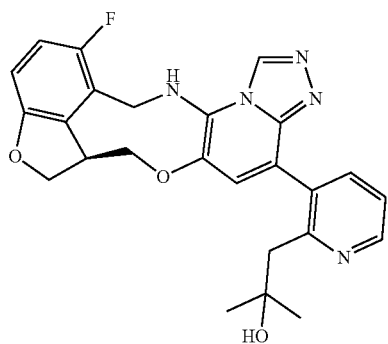 [SMILES: CC(C)(O)Cc1ncccc1-c1cc2c(n3cnnc13)NCc1c(F)ccc3c1[C@H](CO3)CO2]

A mixture of tert-butyl (S)-12-fluoro-4-(2-(2-hydroxy-2-methylpropyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (60.0 mg, 107 umol, 1.00 eq) in HFIP (2.00 mL) was stirred at 100° C. for 2 h. The reaction mixture was concentrated under reduced pressure. The residue was purified by prep-HPLC (column: Phenomenex Luna C18 100*30 mm*5 um; mobile phase: [water (0.2% FA)—ACN]; B %: 1%-25%, 12 min). The title compound (23.0 mg, 45.3 umol, 42% yield, 99.9% purity, formate salt) was obtained as a yellow solid. ¹H NMR DMSO-d₆ 400 MHz δ=ppm 9.43 (s, 1H), 8.56 (dd, J=4.6, 1.2 Hz, 1H), 7.78 (dd, J=7.6, 1.6 Hz, 1H), 7.52 (br t, J=6.4 Hz, 1H), 7.37-7.34 (m, 1H), 7.33 (s, 1H), 7.00-6.93 (m, 1H), 6.70 (dd, J=8.6, 4.0 Hz, 1H), 5.43 (br s, 1H), 4.97-4.87 (m, 1H), 4.85-4.74 (m, 1H), 4.59-4.51 (m, 1H), 4.48 (br d, J=6.4 Hz, 1H), 4.21 (dd, J=9.6, 3.6 Hz, 1H), 4.08-3.99 (m, 1H), 3.90-3.81 (m, 1H), 2.76 (s, 2H), 0.95 (s, 6H). LCMS (ESI+): m/z 462.2 (M+H).

Example 88: (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine Mesylate Step 1: (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine

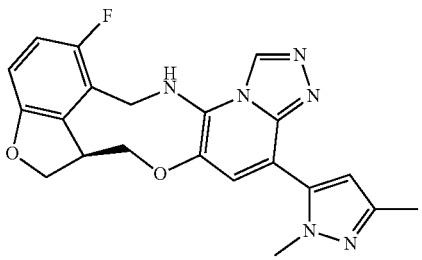 [SMILES: Cc1cc(-c2cc3c(n4cnnc24)NCc2c(F)ccc4c2[C@H](CO4)CO3)n(C)n1]

To a stirred solution of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (852 mg, 3.83 mmol, 1.50 eq) and Na₂CO₃ (542 mg, 5.11 mmol, 2.00 eq) in dioxane (20.0 mL) and water (4.00 mL) was added Pd(dppf)Cl₂ (187 mg, 256 umol, 0.100 eq) at 15° C. under N₂. The resulting mixture was stirred at 80° C. for 3 h. The mixture was concentrated under reduced pressure. The residue was dissolved in DMSO (10.0 mL), MeOH (20.0 mL) and silica-thiol (1.20 g, modified Silicon Gel for Eliminating Pd, Irregular Silica Gel, 100-200 mesh, Chlorides (Cl), %≤0.004, Particle Size Distribution 45-75 um) was added to the mixture at 15° C. and stirred at 15° C. for 12 h. The suspension was filtered and the filter cake was washed with MeOH (20.0 mL). The filtrate was concentrated under reduced pressure to remove MeOH and purified by acidic prep-HPLC (FA). The product-containing fraction was concentrated under reduced pressure to remove most of MeCN at 30° C. and the aqueous phase was lyophilized. (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine (480 mg, 1.18 mmol, 46% yield) was obtained as a white solid.

Step 2: (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine Mesylate

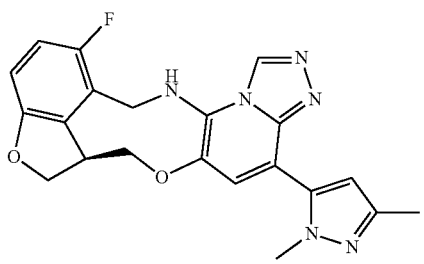 [SMILES: Cc1cc(-c2cc3c(n4cnnc24)NCc2c(F)ccc4c2[C@H](CO4)CO3)n(C)n1]

To (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine (480 mg, 1.18 mmol, 1.00 eq) in MeCN (20.0 mL) was added $CH_3SO_3H$ (114 mg, 1.18 mmol, 84.1 uL, 1.00 eq) at 15° C. Water (50.0 mL) was added to the mixture at 15° C. The solution was concentrated under reduced pressure to remove most of MeCN and the aqueous phase was lyophilized. (S)-4-(1,3-dimethyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine (525 mg, 1.17 mmol, 99% yield, 99.1% purity, 0.4 eq. $CH_3SO_3H$) was obtained as a yellow solid. $^1$H NMR DMSO-$d_6$ 400 MHz δ=ppm 9.51 (s, 1H), 7.96 (br s, 1H), 7.59 (s, 1H), 6.96 (t, J=9.5 Hz, 1H), 6.69 (dd, J=8.6, 3.7 Hz, 1H), 6.31 (s, 1H), 4.99-4.87 (m, 1H), 4.86-4.75 (m, 1H), 4.58-4.45 (m, 2H), 4.19 (br dd, J=9.6, 3.4 Hz, 1H), 4.04 (br d, J=9.9 Hz, 2H), 3.89-3.82 (m, 1H), 3.69 (s, 3H), 2.28 (s, 1.2H), 2.17 (s, 3H). LCMS (ESI+): m/z 407.1 (M+H).

Example 89: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,1-dimethyl-1H-pyrazol-3-amine Step 1: tert-butyl (5-bromo-1-methyl-1H-pyrazol-3-yl)carbamate

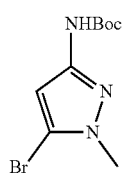

To a solution of 5-bromo-1-methyl-1H-pyrazol-3-amine (300 mg, 1.70 mmol, 1.00 eq) in THF (8.00 mL) was added TEA (345 mg, 3.41 mmol, 475 uL, 2.00 eq) and $Boc_2O$ (893 mg, 4.09 mmol, 940 uL, 2.40 eq) at 20° C. The mixture was stirred at 80° C. for 6 h. The reaction was concentrated. The residue was purified by prep-TLC ($SiO_2$, Petroleum ether/Ethyl acetate=3/1). tert-butyl (5-bromo-1-methyl-1H-pyrazol-3-yl)carbamate (270 mg, 978 umol, 57% yield) was obtained as a white solid.

Step 2: tert-butyl (5-bromo-1-methyl-1H-pyrazol-3-yl)(methyl)carbamate

To a mixture of tert-butyl (5-bromo-1-methyl-1H-pyrazol-3-yl)carbamate (270 mg, 978 umol, 1.00 eq) in THF (6.00 mL) was added NaH (78.2 mg, 1.96 mmol, 60.0% purity, 2.00 eq) at 0° C. The mixture was stirred at 0° C. for 0.5 hr. Then MeI (278 mg, 1.96 mmol, 122 uL, 2.00 eq) was added to the mixture at 0° C., the mixture was stirred at 20° C. for 12 h. Water (5.00 mL) was added to the reaction solution, the mixture was extracted with ethyl acetate (5.00 mL*3), the combined organic layers were dried over $Na_2SO_4$, and concentrated under reduced pressure. The residue was purified by prep-TLC ($SiO_2$, Petroleum ether/Ethyl acetate=3/1). tert-butyl (5-bromo-1-methyl-1H-pyrazol-3-yl)(methyl)carbamate (150 mg, 517 umol, 52% yield) was obtained as a yellow oil.

Step 3: tert-butyl methyl(I-methyl-S-(tributylstannyl)-1H-pyrazol-3-yl)carbamate

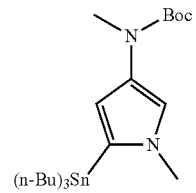

To a solution of tert-butyl (5-bromo-1-methyl-1H-pyrazol-3-yl)(methyl)carbamate (150 mg, 517 umol, 1.00 eq) in THF (5.00 mL) was added n-BuLi (2.50 M, 620 uL, 3.00 eq) at −70° C. The mixture was stirred at −70° C. for 0.5 hr. Then tributyl(chloro)stannane (673 mg, 2.07 mmol, 556 uL, 4.00 eq) was added to the mixture at −70° C. under nitrogen atmosphere and the mixture was stirred at 20° C. for 12 h. Water (5.00 mL) was added to the reaction solution, the mixture was extracted with ethyl acetate (5.00 mL*3), the combined organic layers were dried over $MgSO_4$, and concentrated under reduced pressure. The residue was purified by column chromatography ($SiO_2$, Petroleum ether/Ethyl acetate=3/1). tert-butyl methyl(1-methyl-S-(tributylstannyl)-1H-pyrazol-3-yl)carbamate (200 mg, 400 umol, 77% yield) was obtained as a yellow oil.

Step 4: tert-butyl (S)-4-(3-((tert-butoxycarbonyl)
(methyl)amino)-1-methyl-1H-pyrazol-S-yl)-12-
fluoro-7a,13-dihydro-7H-[1,2,4]triazolo[4',3':1,6]
pyrido[3,2-b]benzofuro[4,3-fg][1,4]oxazonine-14
(8H)-carboxylate

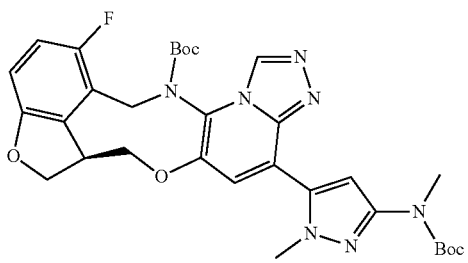 [SMILES: CN(C(=O)OC(C)(C)C)c1cc(-c2cc3c(n4cnnc24)N(C(=O)OC(C)(C)C)Cc2c(F)ccc4c2[C@H](CO4)CO3)n(C)n1]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (100 mg, 204 umol, 1.00 eq) in dioxane (6.00 mL) were added tert-butyl methyl(1-methyl-S-(tributylstannyl)-1H-pyrazol-3-yl)carbamate (175 mg, 350 umol, 1.72 eq), CuI (15.5 mg, 81.4 umol, 0.400 eq) and LiCl (17.3 mg, 407 umol, 2.00 eq) Pd(PPh$_3$)$_4$ (23.5 mg, 20.4 umol, 0.100 eq) at 20° C. under nitrogen atmosphere. The mixture was stirred at 90° C. for 12 h under nitrogen atmosphere. The reaction was filtered, the filtrate was concentrated. The residue was purified by prep-TLC (SiO$_2$, Petroleum ether/Ethyl acetate=0/1). tert-butyl (S)-4-(3-((tert-butoxycarbonyl)(methyl)amino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 193 umol, 94% yield) was obtained as a yellow solid. In addition, 60 mg of crude product and 30 mg of crude deprotected material were obtained.

Step 5: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,1-dimethyl-1H-pyrazol-3-amine

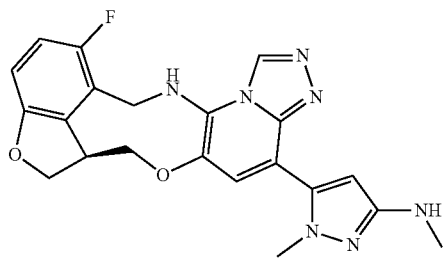 [SMILES: CNc1cc(-c2cc3c(n4cnnc24)NCc2c(F)ccc4c2[C@H](CO4)CO3)n(C)n1]

A mixture of tert-butyl (S)-4-(3-((tert-butoxycarbonyl)(methyl)amino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 193 umol, 1.00 eq) in DCM (4.00 mL) and TFA (2.00 mL) was stirred at 20° C. for 12 h. The reaction was concentrated. The residue was dissolved in DMSO (3.00 mL). The suspension was purified by acidic prep-HPLC (column: Phenomenex Luna C18 100*30 mm*5 um; mobile phase: [water (0.04% HCl)-ACN]; B %: 15%-40%, 10 min). The product-containing fraction was concentrated under reduced pressure to remove most of MeCN at 30° C. and the aqueous phase was lyophilized. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,1-dimethyl-1H-pyrazol-3-amine (37.0 mg, 76.6 umol, 39% yield, 94.8% purity, HCl salt) was obtained as a yellow solid. $^1$H NMR CD$_3$OD 400 MHz δ=ppm 9.55 (s, 1H), 8.05 (s, 1H), 7.02-6.89 (m, 1H), 6.70 (dd, J=8.7, 3.9 Hz, 1H), 6.44 (s, 1H), 5.22 (d, J=14.5 Hz, 1H), 4.98 (br d, J=14.8 Hz, 1H), 4.78 (br s, 1H), 4.64 (t, J=9.5 Hz, 1H), 4.33 (dd, J=9.7, 3.3 Hz, 1H), 4.06 (br d, J=8.8 Hz, 1H), 3.97-3.86 (m, 1H), 3.77 (s, 3H), 3.07 (s, 3H). LCMS (ESI+): m/z 422.2 (M+H).

Example 90: (R)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine

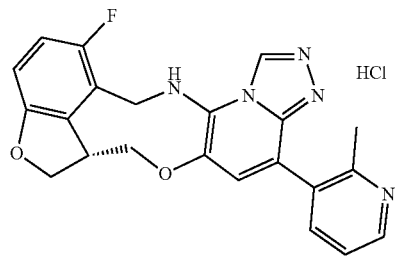 [SMILES: Cc1ncccc1-c1cc2c(n3cnnc13)NCc1c(F)ccc3c1[C@@H](CO3)CO2 ; Cl]

A mixture of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (enantiomer of Example 17; obtained via the same sequence using (R)-oxiran-2-ylmethyl 3-nitrobenzenesulfonate in the Example 6 procedure) (200 mg, 511 umol, 1.00 eq), 2-methyl-3-(4,4,5,5-tetramethyl-1,3,2-dioxaborolan-2-yl)pyridine (224 mg, 1.02 mmol, 2.00 eq), Pd(dppf)Cl$_2$ (37.4 mg, 51.1 umol, 0.100 eq) and NaHCO$_3$ (85.9 mg, 1.02 mmol, 39.8 uL, 2.00 eq) in dioxane (4.00 mL) and water (0.400 mL) was degassed and purged with nitrogen 3 times at 20° C., and then the mixture was stirred at 80° C. for 12 h under nitrogen atmosphere. Silica-thiol (100 mg, modified silicon gel for eliminating Pd, irregular silica gel, 100-200 mesh, Chlorides (Cl), %≤0.004, particle size distribution 45-75 um) was added to the reaction mixture at 20° C. and stirred at 20° C. for 2 h. The mixture was concentrated under reduced pressure. The residue was dissolved in DMSO (4.00 mL), the suspension was filtered, the filtrate was concentrated and purified by acidic prep-HPLC (HCl conditions, column: Phenomenex Luna C18 150*30 mm*5 um; mobile phase: [water (0.04% HCl)—ACN]; B %: 20%-40%, 10 min. The fraction was lyophilized. (R)-12-fluoro-4-(2-methylpyridin-3-yl)-7a,8,13,14-tetrahydro-7H-[1,2,4]triazolo[4',3':1,6]pyrido[3,2-b]benzofuro[4,3-fg][1,4]oxazonine (68.5 mg, 155 umol, 30% yield, 99.8% purity, HCl salt) was obtained as a yellow solid. $^1$H NMR DMSO-d$_6$ 400 MHz δ=ppm 9.70 (d, J=2.4 Hz, 1H), 8.81 (d, J=5.5 Hz, 1H), 8.52 (br d, J=7.3 Hz, 1H), 8.32-8.23 (m, 1H), 7.92 (br t, J=6.8 Hz, 1H), 7.72 (s, 1H), 7.06-6.93 (m, 1H), 6.71 (dd, J=8.7, 3.9 Hz, 1H), 5.02-4.91 (m, 1H), 4.89-4.77 (m, 1H), 4.60-4.47 (m, 2H), 4.22 (dd, J=9.7, 3.3 Hz, 1H), 4.12-4.00 (m, 1H), 3.92-3.85 (m, 1H), 2.64 (s, 3H).

Example 91: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,1-trimethyl-1H-pyrazol-3-amine Step 1: 5-bromo-N,N,1-trimethyl-1H-pyrazol-3-amine

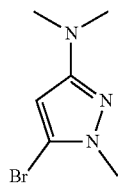

To a solution of 5-bromo-1-methyl-1H-pyrazol-3-amine (200 mg, 1.14 mmol, 1.00 eq) and 37% aqueous HCHO (369 mg, 4.55 mmol, 338 uL, 4.00 eq) in MeOH (5.00 mL) was added AcOH (6.82 mg, 114 umol, 6.50 uL, 0.100 eq) at 20° C. The mixture was stirred at 20° C. for 1 hr. Then NaBH$_3$CN (179 mg, 2.84 mmol, 2.50 eq) was added to the mixture, and the mixture was stirred at 20° C. for 10 h. The reaction mixture was concentrated under reduced pressure. The residue was dissolved with DCM (8.00 mL), washed with saturated aqueous sodium bicarbonate (3.00 mL). The organic layer was dried over Na$_2$SO$_4$ and then concentrated under reduced pressure. The residue was purified by prep-TLC (SiO$_2$, Petroleum ether:Ethyl acetate=2:1). 5-bromo-N,N,1-trimethyl-1H-pyrazol-3-amine (180 mg, 882 umol, 77% yield) was obtained as a light yellow oil.

Step 2: N,N,1-trimethyl-S-(tributylstannyl)-1H-pyrazol-3-amine

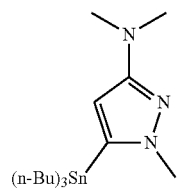

To a solution of 5-bromo-N,N,1-trimethyl-1H-pyrazol-3-amine (180 mg, 882 umol, 1.00 eq) in THF (6.00 mL) was added dropwised n-BuLi (2.50 M, 529 uL, 1.50 eq) at −78° C. The mixture was stirred at −78° C. for 0.5 hr. Then tributyl(chloro)stannane (861 mg, 2.65 mmol, 712 uL, 3.00 eq) was added to the mixture at −78° C., and the mixture was stirred at −78° C. for 1 hr. The reaction mixture was quenched by saturated aqueous NH$_4$Cl solution (2.00 mL) at 0° C., then diluted with water (5.00 mL), extracted with ethyl acetate (4.00 mL*3). The combined organic layers were dried over anhydrous sodium sulfate, filtered, and the filtrate was concentrated under reduced pressure. The residue was purified by prep-TLC (SiO$_2$, Petroleum ether:Ethyl acetate=4:1). N,N-1-trimethyl-S-(tributylstannyl)-1H-pyrazol-3-amine (200 mg, 483 umol, 54% yield) was obtained as a colourless oil.

Step 3: tert-butyl (S)-4-(3-(dimethylamino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

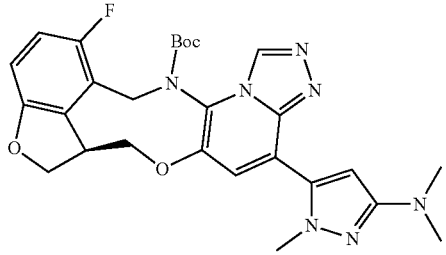 [SMILES: CN(C)c1cc(-c2cc3c(n4cnnc24)N(C(=O)OC(C)(C)C)Cc2c(F)ccc4c2[C@H](CO4)CO3)n(C)n1]

A mixture of N,N,1-trimethyl-S-(tributylstannyl)-1H-pyrazol-3-amine (194 mg, 468 umol, 1.15 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq), LiCl (25.9 mg, 611 umol, 1.50 eq), CuI (38.8 mg, 204 umol, 0.500 eq) and Pd(PPh$_3$)$_4$ (23.5 mg, 20.4 umol, 0.0500 eq) in dioxane (5.00 mL) was degassed and purged with nitrogen 3 times at 20° C., and then the mixture was stirred at 80° C. for 10 h under nitrogen atmosphere. The reaction mixture was filtered and the filtrate was concentrated under reduced pressure. The residue was purified by prep-TLC (SiO$_2$, Ethyl acetate:Methanol=8:1). tert-butyl (S)-4-(3-(dimethylamino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 373 umol, 91% yield) was obtained as a yellow solid.

Step 4: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,1-trimethyl-1H-pyrazol-3-amine

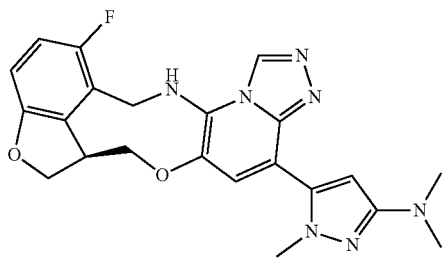 [SMILES: CN(C)c1cc(-c2cc3c(n4cnnc24)NCc2c(F)ccc4c2[C@H](CO4)CO3)n(C)n1]

To a solution of tert-butyl (S)-4-(3-(dimethylamino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 373 umol, 1.00 eq) in DCM (4.00 mL) was added TFA (4.62 g, 40.5 mmol, 3.00 mL, 109 eq) at 20° C. The mixture was stirred at 20° C. for 3 h. LC-MS showed tert-butyl (S)-4-(3-(dimethylamino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. The reaction mixture was concentrated under reduced pressure. The residue was purified by prep-HPLC (formic acid conditions)

(column: Phenomenex Synergi C18 150*25 mm*10 um; mobile phase: [water (0.225% FA)—ACN]; B %: 20%-50%, 12 min). (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N,1-trimethyl-1H-pyrazol-3-amine (102 mg, 210 umol, 56% yield, 99.6% purity, formate salt) was obtained as a white solid. ¹H NMR DMSO-d₆ 400 MHz δ=ppm 9.43 (s, 1H), 8.13 (s, 1H), 7.67-7.58 (m, 1H), 7.37 (s, 1H), 6.96 (t, J=9.6 Hz, 1H), 6.69 (dd, J=8.5, 3.6 Hz, 1H), 5.94 (s, 1H), 4.94-4.85 (m, 1H), 4.83-4.71 (m, 1H), 4.58-4.39 (m, 2H), 4.20 (br d, J=9.7 Hz, 1H), 4.03 (br s, 1H), 3.92-3.79 (m, 1H), 3.62 (s, 3H), 2.75 (s, 6H). LCMS (ESI+): m/z 436.2 (M+H).

Example 92: (S)-12-fluoro-4-(6-methoxypyridin-2-yl)-7a,8,13,14-tetrahydro-7H-[1,2,4]triazolo[4',3':1,6]pyrido[3,2-b]benzofuro[4,3-fg][1,4]oxazonine Step 1: 2-methoxy-6-(tributylstannyl)pyridine

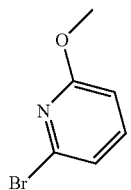

To a solution of 2-bromo-6-methoxypyridine (300 mg, 1.60 mmol, 196 uL, 1.00 eq) in THF (6.00 mL) was added n-BuLi (2.50 M, 1.28 mL, 2.00 eq) at −78° C. Then the mixture was stirred at −78° C. for 0.5 hr. Tributyl(chloro)stannane (779 mg, 2.39 mmol, 644 uL, 1.50 eq) was added to the mixture, and the mixture was stirred at −78° C. for 2 h. The reaction mixture was quenched by saturated aqueous NH₄Cl solution (2.00 mL) at 0° C. then diluted with water (6.00 mL) and extracted with ethyl acetate (5.00 mL*3). The combined organic layers were dried over anhydrous sodium sulfate, filtered, and concentrated under reduced pressure. The residue was purified by prep-TLC (SiO₂, Petroleum ether:Ethyl acetate=10:1). 2-methoxy-6-(tributylstannyl)pyridine (300 mg, 753 umol, 47% yield) was obtained as a colourless oil.

Step 2: tert-butyl (S)-12-fluoro-4-(6-methoxypyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

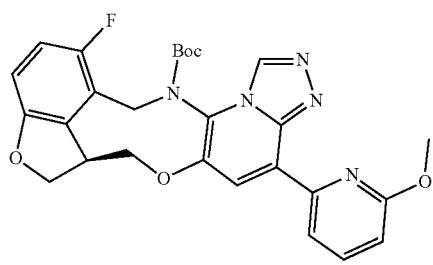 [SMILES: COc1cccc(-c2cc3c(n4cnnc24)N(C(=O)OC(C)(C)C)Cc2c(F)ccc4c2[C@H](CO4)CO3)n1]

A mixture of 2-methoxy-6-(tributylstannyl)pyridine (146 mg, 366 umol, 1.20 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq), LiCl (19.4 mg, 458 umol, 9.38 uL, 1.50 eq), CuI (29.1 mg, 153 umol, 0.500 eq) and Pd(PPh₃)₄ (17.6 mg, 15.3 umol, 0.0500 eq) in dioxane (4.00 mL) was degassed and purged with nitrogen for 3 times at 20° C., and then the mixture was stirred at 80° C. for 10 h under nitrogen atmosphere. The reaction mixture was concentrated under reduced pressure. The residue was purified by prep-TLC (SiO₂, Petroleum ether:Ethyl acetate=1:1). tert-butyl (S)-12-fluoro-4-(6-methoxypyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (130 mg, 250 umol, 82% yield) was obtained as a yellow solid.

Step 3: (S)-12-fluoro-4-(6-methoxypyridin-2-yl)-7a,8,13,14-tetrahydro-7H-[1,2,4]triazolo[4',3':1,6]pyrido[3,2-b]benzofuro[4,3-fg][1,4]oxazonine

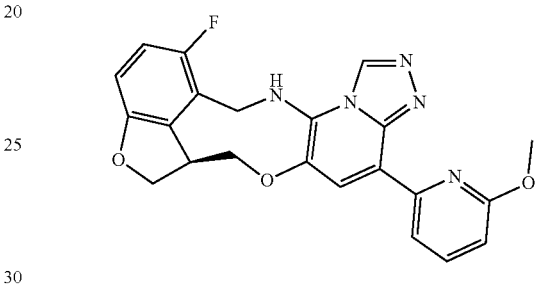

A mixture of tert-butyl (S)-12-fluoro-4-(6-methoxypyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, 192 umol, 1.00 eq) in HFIP (3.00 mL) was stirred at 80° C. for 3 h under nitrogen atmosphere. The reaction mixture was concentrated under reduced pressure. The residue was purified by prep-HPLC (formic acid conditions) (column: Phenomenex Luna C18 200*40 mm*10 um; mobile phase: [water (0.2% FA)—ACN]; B %: 30%-60%, 10 min). (S)-12-fluoro-4-(6-methoxypyridin-2-yl)-7a,8,13,14-tetrahydro-7H-[1,2,4]triazolo[4',3':1,6]pyrido[3,2-b]benzofuro[4,3-fg][1,4]oxazonine (34.9 mg, 74.5 umol, 38% yield, 99.3% purity, formate salt) was obtained as a yellow solid. ¹H NMR DMSO-d₆ 400 MHz δ=ppm 9.50 (s, 1H), 8.66 (d, J=7.5 Hz, 1H), 8.32 (s, 1H), 7.85-7.75 (m, 2H), 7.01-6.94 (m, 1H), 6.74 (d, J=8.2 Hz, 1H), 6.70 (dd, J=8.7, 3.6 Hz, 1H), 4.98-4.80 (m, 2H), 4.53 (br t, J=9.4 Hz, 2H), 4.26 (br d, J=6.2 Hz, 1H), 4.08 (br s, 1H), 4.00 (s, 3H), 3.98-3.90 (m, 1H). LCMS (ESI+): m/z 420.1 (M+H).

Example 93: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-amine Step 1: tert-butyl (5-bromo-1-methyl-1H-pyrazol-3-yl)carbamate

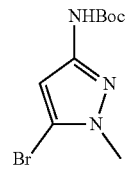

Two parallel reactions were set up. To a solution of 5-bromo-1-methyl-1H-pyrazol-3-amine (350 mg, 1.99 mmol, 1.00 eq) in THF (6.00 mL) was added TEA (403 mg, 3.98 mmol, 554 uL, 2.00 eq) and Boc₂O (1.04 g, 4.77 mmol, 1.10 mL, 2.40 eq) at 20° C. The mixture was stirred at 80° C. for 12 h. The batches were combined and the obtained mixture was concentrated. The residue was purified by column chromatography (SiO₂, Petroleum ether/Ethyl acetate=1/0 to 3/1). tert-butyl (5-bromo-1-methyl-1H-pyrazol-3-yl)carbamate (760 mg, 2.75 mmol, 69% yield) was obtained as a white solid.

Step 2: tert-butyl (1-methyl-S-(trimethylstannyl)-1H-pyrazol-3-yl)carbamate

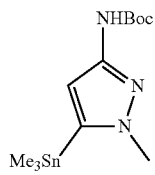

To a solution of tert-butyl (5-bromo-1-methyl-1H-pyrazol-3-yl)carbamate (240 mg, 869 umol, 1.00 eq) in dioxane (15.0 mL) was added trimethyl(trimethylstannyl)stannane (570 mg, 1.74 mmol, 361 uL, 2.00 eq) and Pd(PPh₃)₄ (100 mg, 86.9 umol, 0.100 eq) at 20° C. The mixture was stirred at 100° C. for 12 h under nitrogen atmosphere. LCMS showed tert-butyl (5-bromo-1-methyl-1H-pyrazol-3-yl)carbamate was remained and the desired mass was detected. tert-butyl (1-methyl-S-(trimethylstannyl)-1H-pyrazol-3-yl)carbamate (310 mg, crude) in dioxane (15.0 mL) as a brown liquid used for next step directly.

Step 3: tert-butyl (S)-4-(3-((tert-butoxycarbonyl)amino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

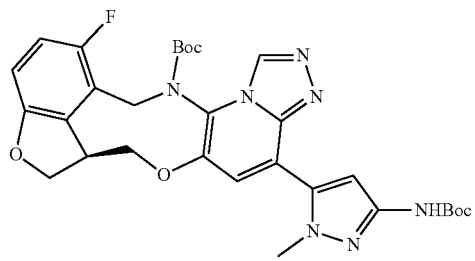 [SMILES: Cn1nc(NC(=O)OC(C)(C)C)cc1-c1cc2c(n3cnnc13)N(C(=O)OC(C)(C)C)Cc1c(F)ccc3c1[C@H](CO3)CO2]

To a solution of tert-butyl (1-methyl-S-(trimethylstannyl)-1H-pyrazol-3-yl)carbamate (300 mg, 833 umol, 2.00 eq) in dioxane (14.5 mL) was added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (205 mg, 417 umol, 1.00 eq), Pd(PPh₃)₄ (48.1 mg, 41.7 umol, 0.100 eq), CuI (31.7 mg, 167 umol, 0.400 eq) and LiCl (35.3 mg, 833 umol, 17.1 uL, 2.00 eq) at 20° C. The mixture was stirred at 100° C. for 12 h under nitrogen atmosphere. The reaction was filtered, the filtrate was concentrated. The residue was purified by prep-TLC (SiO₂, Petroleum ether/Ethyl acetate=1/1). tert-butyl (S)-4-(3-((tert-butoxycarbonyl)amino)-1-methyl-1H-pyrazol-5-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (270 mg, crude) was obtained as a yellow oil.

Step 4: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-amine

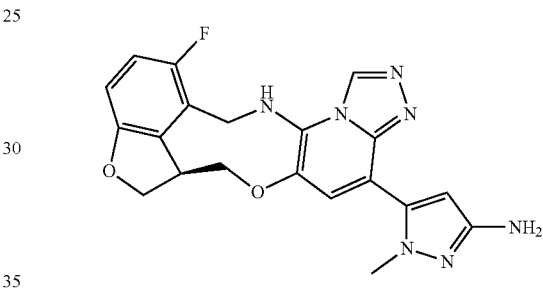

A mixture of tert-butyl (S)-4-(3-((tert-butoxycarbonyl)amino)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (270 mg, 444 umol, 1.00 eq) in TFA (2.50 mL) and DCM (5.00 mL) was stirred at 20° C. for 6 h. The reaction was concentrated. The residue was dissolved in MeOH (5.00 mL), the suspension was filtered, the filtrate was concentrated and purified by neutral prep-HPLC (column: Waters Xbridge Prep OBD C18 150*40 mm*10 um; mobile phase: [water (0.04% NH₃H₂O+10 mM NH₄HCO₃)—ACN]; B %: 5%-35%, 10 min). The product-containing fraction was concentrated under reduced pressure to remove most of MeCN at 30° C. and the aqueous phase was lyophilized. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-amine (20.3 mg, 49.7 umol, 11% yield, 99.7% purity) was obtained as a white solid. $^1$H NMR DMSO-d₆ 400 MHz δ=ppm 9.42 (s, 1H), 7.59 (br t, J=6.4 Hz, 1H), 7.34 (s, 1H), 6.97 (t, J=9.5 Hz, 1H), 6.70 (dd, J=8.6, 3.8 Hz, 1H), 5.76 (s, 1H), 4.97-4.86 (m, 1H), 4.84-4.73 (m, 1H), 4.59 (s, 2H), 4.54 (br t, J=9.4 Hz, 1H), 4.49 (br s, 1H), 4.21 (br dd, J=9.7, 3.4 Hz, 1H), 4.04 (br s, 1H), 3.91-3.82 (m, 1H), 3.56 (s, 3H). LCMS (ESI+): m/z 408.1 (M+H).

Example 94: (S)-12-fluoro-4-(1-methyl-1H-imidazol-4-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(1-methyl-1H-imidazol-4-yl)-7a,13-dihydro-7H-[1,2,4]triazolo[4',3':1,6]pyrido[3,2-b]benzofuro[4,3-fg][1,4]oxazonine-14 (8H)-carboxylate

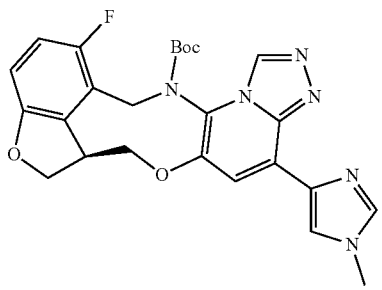 [SMILES: Cn1cnc(-c2cc3c(n4cnnc24)N(C(=O)OC(C)(C)C)Cc2c(F)ccc4c2[C@H](CO4)CO3)c1]

Two parallel reactions were set up. A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg] [1,4]oxazonine-14 (8H)-carboxylate (120 mg, 171 umol, 1.00 eq), 4-bromo-1-methyl-imidazole (82.6 mg, 513 umol, 3.00 eq), palladium tritert-butylphosphane (8.74 mg, 17.1 umol, 0.100 eq) in dioxane (2.00 mL) was degassed and purged with nitrogen for 3 times at 20° C., and then the mixture was stirred at 100° C. for 4 h under nitrogen atmosphere. The batches were combined. The reaction mixture was diluted with water (5.00 mL) and extracted with EtOAc (5.00 mL*3). The combined organic layers were washed with brine (3.00 mL), dried over Na$_2$SO$_4$, filtered and concentrated under reduced pressure. The residue was purified by prep-TLC (SiO$_2$, EtOAc:MeOH=5:1). tert-butyl (S)-12-fluoro-4-(1-methyl-1H-imidazol-4-yl)-7a,13-dihydro-7H-[1,2,4]triazolo[4',3':1,6]pyrido[3,2-b]benzofuro[4,3-fg][1,4]oxazonine-14 (8H)-carboxylate (50 mg, crude) was obtained as a yellow oil.

Step 2: (S)-12-fluoro-4-(1-methyl-1H-imidazol-4-yl)-7a,8,13,14-tetrahydro-7H-[1,2,4]triazolo[4',3':1,6]pyrido[3,2-b]benzofuro[4,3-fg][1,4]oxazonine

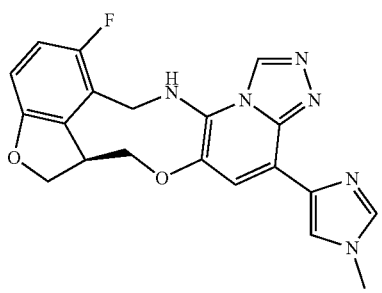 [SMILES: Cn1cnc(-c2cc3c(n4cnnc24)NCc2c(F)ccc4c2[C@H](CO4)CO3)c1]

A mixture of tert-butyl (S)-12-fluoro-4-(1-methyl-1H-imidazol-4-yl)-7a,13-dihydro-7H-[1,2,4]triazolo[4',3':1,6]pyrido[3,2-b]benzofuro[4,3-fg][1,4]oxazonine-14 (8H)-carboxylate (50.0 mg, 102 umol, 1.00 eq) and HFIP (2.00 mL) was stirred at 80° C. for 8 h under nitrogen atmosphere. The reaction mixture was concentrated under reduced pressure. The residue was purified by prep-HPLC (HCl condition). The product-containing fraction was concentrated under reduced pressure to remove most of MeCN at 30° C. and the aqueous phase was lyophilized. (S)-12-fluoro-4-(1-methyl-1H-imidazol-4-yl)-7a,8,13,14-tetrahydro-7H-[1,2,4]triazolo[4',3':1,6]pyrido[3,2-b]benzofuro[4,3-fg][1,4]oxazonine (16.0 mg, 37.1 umol, 36% yield, 99.3% purity, HCl) was obtained as a yellow solid. $^1$HNMR DMSO-d6 400 MHz δ=ppm 9.61 (s, 1H), 9.17 (s, 1H), 8.36 (s, 1H), 8.18 (s, 1H), 8.10-8.00 (m, 1H), 6.93 (t, J=9.5 Hz, 1H), 6.67 (dd, J=8.5, 3.9 Hz, 1H), 4.93-4.85 (m, 1H), 4.80 (s, 1H), 4.56-4.45 (m, 2H), 4.21 (d, J=9.7 Hz, 1H), 4.03 (s, 1H), 3.92 (s, 3H), 3.88-3.80 (m, 1H). $^1$HNMR CD$_3$OD 400 MHz δ=ppm 9.60 (s, 1H), 9.07 (s, 1H), 8.11 (s, 1H), 8.06 (s, 1H), 6.88 (t, J=9.5 Hz, 1H), 6.65 (dd, J=8.6, 3.7 Hz, 1H), 5.14 (d, J=15.0 Hz, 1H), 4.93 (d, J=15.0 Hz, 1H), 4.76 (d, J=5.3 Hz, 1H), 4.61 (t, J=9.3 Hz, 1H), 4.31 (dd, J=9.6, 2.8 Hz, 1H), 4.10-4.04 (m, 1H), 4.03 (s, 3H), 3.98-3.90 (m, 1H). LCMS (ESI+): m/z 393.2 (M+H).

Example 95: (S)-4-(1,2-dimethyl-1H-imidazol-5-yl)-12-fluoro-7a,8,13,14-tetrahydro-7H-[1,2,4]triazolo[4',3':1,6]pyrido[3,2-b]benzofuro[4,3-fg][1,4] oxazonine Step 1: 1,2-dimethyl-S-(tributylstannyl)-1H-imidazole

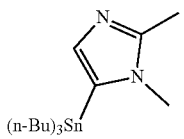

To a solution of 5-bromo-1,2-dimethyl-1H-imidazole (250 mg, 1.43 mmol, 1.00 eq) in THF (2.00 mL) was added n-BuLi (2.50 M, 1.14 mL, 2.00 eq) at −78° C. under nitrogen atmosphere. The mixture was stirred at −78° C. for 0.5 hr. Then tributyl(chloro)stannane (1.86 g, 5.71 mmol, 1.54 mL, 4.00 eq) was added to the mixture under nitrogen atmosphere at −78° C., and the mixture was stirred at −78° C. for 1 hr under nitrogen atmosphere. Then the mixture was warmed slowly to 20° C. The mixture was stirred at 20° C. for 10 h under nitrogen atmosphere. The reaction mixture was quenched by saturated aqueous NH$_4$Cl solution (4.00 mL) at 0° C., then diluted with water (5.00 mL), and extracted with ethyl acetate (5.00 mL*3). The combined organic layers were dried over anhydrous sodium sulfate, filtered, and concentrated under reduced pressure to afford a crude product. 1,2-dimethyl-S-(tributylstannyl)-1H-imidazole (500 mg, crude) was obtained as a yellow gum.

Step 2: tert-butyl (S)-4-(1,2-dimethyl-1H-imidazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

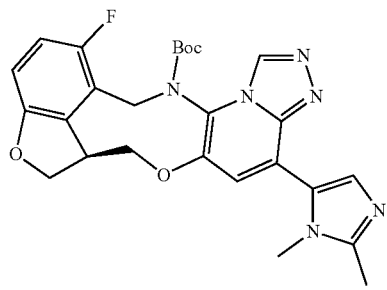 [SMILES: Cc1ncc(-c2cc3c(n4cnnc24)N(C(=O)OC(C)(C)C)Cc2c(F)ccc4c2[C@H](CO4)CO3)n1C]

A mixture of 1,2-dimethyl-S-(tributylstannyl)-1H-imidazole (470 mg, 1.22 mmol, 4.00 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq), LiCl (19.4 mg, 458 umol, 1.50 eq), CuI (29.1 mg, 153 umol, 0.500 eq) and Pd(PPh₃)₄ (17.6 mg, 15.3 umol, 0.0500 eq) in dioxane (6.00 mL) was degassed and purged with nitrogen 3 times at 20° C., and then the mixture was stirred at 80° C. for 10 h under nitrogen atmosphere. The reaction mixture was concentrated under reduced pressure. The residue was purified by column chromatography (SiO₂, Ethyl acetate/Methanol=1/0 to 3/1). tert-butyl (S)-4-(1,2-dimethyl-1H-imidazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 296 umol, 97% yield) was obtained as a yellow solid.

Step 3: (S)-4-(1,2-dimethyl-1H-imidazol-S-yl)-12-fluoro-7a,8,13,14-tetrahydro-7H-[1,2,4]triazolo[4',3':1,6]pyrido[3,2-b]benzofuro[4,3-fg][1,4]oxazonine

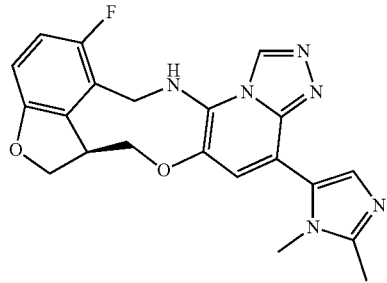 [SMILES: Cc1ncc(-c2cc3c(n4cnnc24)NCc2c(F)ccc4c2[C@H](CO4)CO3)n1C]

To a solution of tert-butyl (S)-4-(1,2-dimethyl-1H-imidazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate3 (130 mg, 257 umol, 1.00 eq) in DCM (3.00 mL) was added TFA (2.31 g, 20.3 mmol, 1.50 mL, 78.9 eq) at 20° C. The mixture was stirred at 20° C. for 3 h The reaction mixture was concentrated under reduced pressure. The residue was purified by prep-HPLC (formic acid conditions). (S)-4-(1,2-dimethyl-1H-imidazol-S-yl)-12-fluoro-7a,8,13,14-tetrahydro-7H-[1,2,4]triazolo[4',3':1,6]pyrido[3,2-b]benzofuro[4,3-fg][1,4]oxazonine (79.5 mg, 174 umol, 67% yield, 99.2% purity, formate salt) was obtained as a light yellow solid. ¹H NMR DMSO-d₆ 400 MHz δ=ppm 9.49 (s, 1H), 7.89 (br t, J=6.1 Hz, 1H), 7.75 (s, 1H), 7.51 (s, 1H), 7.02-6.90 (m, 1H), 6.71 (dd, J=8.7, 3.8 Hz, 1H) 4.99-4.89 (m, 1H), 4.87-4.74 (m, 1H), 4.60-4.43 (m, 2H), 4.22 (br dd, J=9.5, 3.3 Hz, 1H), 4.04 (br s, 1H), 3.87 (br t, J=10.9 Hz, 1H), 3.65 (s, 3H), 2.66 (s, 3H). LCMS (ESI+): m/z 407.1 (M+H).

Example 96: (S)-4-(4,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: (4,6-dimethylpyridin-3-yl)boronic Acid

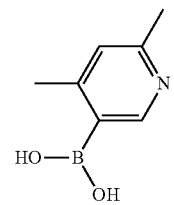

To a solution of 5-bromo-2,4-dimethylpyridine (400 mg, 2.15 mmol, 1.00 eq) in THF (10.0 mL) was added n-BuLi (2.50 M, 1.12 mL, 1.30 eq) at −65° C. and stirred at −65° C. for 0.5 hr. Triisopropyl borate (809 mg, 4.30 mmol, 989 uL, 2.00 eq) was added to the solution and the reaction mixture was stirred at −65° C. for 1 hr. MeOH (2.00 mL) was added to the solution and the mixture was concentrated. (4,6-dimethylpyridin-3-yl)boronic acid (400 mg, crude) was obtained as a white solid.

Step 2: (S)-4-(4,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

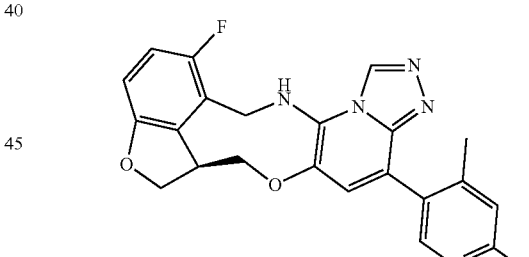

To a solution of (4,6-dimethylpyridin-3-yl)boronic acid (116 mg, 767 umol, 3.00 eq) in EtOH (5.00 mL) and water (1.00 mL) was added (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (100 mg, 256 umol, 1.00 eq), KOAc (75.3 mg, 767 umol, 3.00 eq) and 4-ditert-butylphosphanyl-N,N-dimethyl-aniline dichloropalladium (18.1 mg, 25.6 umol, 18.1 uL, 0.100 eq) at 20° C. under nitrogen atmosphere. The mixture was stirred at 80° C. for 2 h under nitrogen atmosphere. The reaction mixture was concentrated under reduced pressure. The residue was dissolved in MeOH (10.0 mL) and silica-thiol (20.0 mg, modified silicon gel for eliminating Pd, irregular silica gel, 100-200 mesh, Chlorides (Cl), %≤0.004, particle size distribution 45-75 um) was added at 20° C. and stirred at 20° C. for 4 h. The suspension was filtered, the filtrate was concentrated and purified by prep-HPLC (formic acid conditions). The product-containing fraction was concentrated under reduced pressure to remove most of MeCN at 30° C. and the aqueous phase was lyophilized. (S)-4-(4,6-dimethylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (26.0 mg, 56.1 umol, 22% yield, 100% purity, formate salt) was obtained as a yellow solid. $^1$HNMR DMSO-d$_6$ 400 MHz δ=ppm 9.39 (s, 1H), 8.33 (s, 1H), 7.48 (t, J=6.3 Hz, 1H), 7.26 (s, 1H), 7.18 (s, 1H), 6.95 (dd, J=10.3, 8.9 Hz, 1H), 6.68 (dd, J=8.6, 3.7 Hz, 1H), 4.95-4.83 (m, 1H), 4.82-4.71 (m, 1H), 4.57-4.49 (m, 1H), 4.45 (d, J=5.7 Hz, 1H), 4.19 (dd, J=9.5, 3.5 Hz, 1H), 4.00 (d, J=9.3 Hz, 1H), 3.90-3.76 (m, 1H), 2.45 (s, 3H), 2.14 (s, 3H). LCMS (ESI+): m/z 418.1 (M+H).

Example 97: (S)-4-(4-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 5-bromo-4-iodo-2-methylpyridine

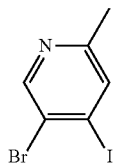

To a stirred solution of 5-bromo-2-methylpyridin-4-amine (2.05 g, 11.0 mmol, 1.00 eq) and diiodomethane (5.87 g, 21.9 mmol, 1.77 mL, 2.00 eq) in MeCN (20.0 mL) was added isopentyl nitrite (2.82 g, 24.1 mmol, 3.25 mL, 2.20 eq) in MeCN (10.0 mL) at 0° C. The resulting mixture was stirred at 0° C. for 1 hr and then stirred at 60° C. for 12 h. The mixture was concentrated under reduced pressure. The mixture was purified by MPLC (SiO$_2$, PE/EtOAc=1/0 to 3/1). 5-bromo-4-iodo-2-methylpyridine (1.50 g, 5.03 mmol, 45% yield) was obtained as a yellow solid.

Step 2: 5-bromo-2-methyl-4-vinylpyridine

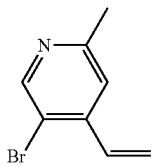

To a stirred solution of 5-bromo-4-iodo-2-methylpyridine (1.50 g, 5.03 mmol, 1.00 eq), 4,4,5,5-tetramethyl-2-vinyl-1,3,2-dioxaborolane (620 mg, 4.03 mmol, 683 uL, 0.800 eq) and Na$_2$CO$_3$ (1.07 g, 10.1 mmol, 2.00 eq) in dioxane (20.0 mL) and water (4.00 mL) was added Pd(dppf)Cl$_2$ (369 mg, 504 umol, 0.100 eq) at 15° C. under N$_2$. The resulting mixture was stirred at 80° C. for 12 h. LCMS indicated incomplete conversion. To the mixture was added 4,4,5,5-tetramethyl-2-vinyl-1,3,2-dioxaborolane (0.200 eq) and Pd(dppf)Cl$_2$ (0.100 eq) at 15° C. under N$_2$. The resulting mixture was stirred at 80° C. for 2 h. LCMS showed that 5-bromo-4-iodo-2-methylpyridine was consumed completely. The mixture was concentrated under reduced pressure. The mixture was purified by MPLC (SiO$_2$, PE/EtOAc=1/0 to 3/1). 5-bromo-2-methyl-4-vinylpyridine (900 mg, 4.54 mmol, 90% yield) was obtained as yellow oil.

Step 3: 5-bromo-2-methylisonicotinaldehyde

Ozone (15 psi) was bubbled into a solution of 5-bromo-2-methyl-4-vinylpyridine (900 mg, 4.54 mmol, 1.00 eq) in DCM (30.0 mL) at −78° C. for 0.5 hr. After excess O3 was purged by O$_2$ (15 psi) for 0.5 hr, to the mixture was added Me$_2$S (5.65 g, 90.9 mmol, 6.67 mL, 20.0 eq) at −78° C. The resulting mixture was stirred at 15° C. for 2 h. The mixture was concentrated under reduced pressure. The mixture was purified by MPLC (SiO$_2$, PE/EtOAc=1/0 to 1/1). 5-bromo-2-methylisonicotinaldehyde (450 mg, 2.25 mmol, 49% yield) was obtained as a white solid.

Step 4: 5-bromo-4-(difluoromethyl)-2-methylpyridine

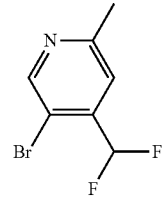

To a stirred solution of 5-bromo-2-methylisonicotinaldehyde (450 mg, 2.25 mmol, 1.00 eq) in DCM (5.00 mL) was added DAST (798 mg, 4.95 mmol, 654 uL, 2.20 eq) at −78° C. under N$_2$. The resulting mixture was stirred at 15° C. for 12 h. The mixture was basified by saturated aqueous NaHCO$_3$ solution to pH=7-8 and the mixture was extracted with EtOAc (10.0 mL*3). The combined organic layers were dried over Na$_2$SO$_4$ and concentrated under reduced pressure. The mixture was purified by MPLC (SiO$_2$, PE/EtOAc=1/0 to 3/1). 5-bromo-4-(difluoromethyl)-2-methylpyridine (210 mg, 946 umol, 42% yield) was obtained as yellow oil. $^1$H NMR CDCl$_3$ 400 MHz δ=ppm 8.66 (s, 1H), 7.40 (s, 1H), 6.79 (t, J=54.4 Hz, 1H), 2.58 (s, 3H).

Step 5: 4-(difluoromethyl)-2-methyl-S-(tributylstannyl)pyridine

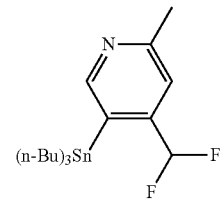

To a solution of 5-bromo-4-(difluoromethyl)-2-methylpyridine (190 mg, 856 umol, 1.00 eq) in THF (5.00 mL) was added n-BuLi (2.50 M, 377 uL, 1.10 eq) at −78° C. under nitrogen and the mixture was stirred at −78° C. for 0.5 hr under N$_2$. Tributyl(chloro)stannane (836 mg, 2.57 mmol, 691 uL, 3.00 eq) was added to the mixture under nitrogen atmosphere at −78° C. and the resulting mixture was stirred at −78° C. for 2 h under N$_2$. The mixture was quenched with saturated aqueous NH$_4$Cl solution (5.00 mL) and the mixture was extracted with EtOAc (5.00 mL*3). The combined organic layers were dried over Na$_2$SO$_4$ and then concentrated under reduced pressure. The mixture was purified by MPLC (SiO$_2$, PE/EtOAc=1/0 to 1/1). 4-(difluoromethyl)-2-methyl-S-(tributylstannyl)pyridine (120 mg, 278 umol, 32% yield) was obtained as yellow oil.

Step 6: tert-butyl (S)-4-(4-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

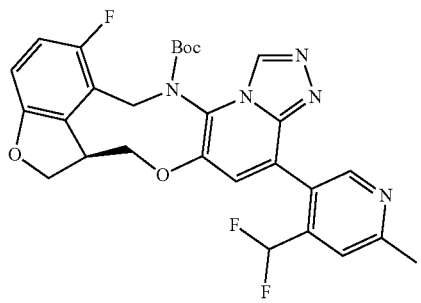 [SMILES: Cc1cc(C(F)F)c(-c2cc3c(n4cnnc24)N(C(=O)OC(C)(C)C)Cc2c(F)ccc4c2[C@H](CO4)CO3)cn1]

To a stirred solution of 4-(difluoromethyl)-2-methyl-S-(tributylstannyl)pyridine (120 mg, 278 umol, 1.00 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (136 mg, 278 umol, 1.00 eq) in dioxane (4.00 mL) was added CuI (21.2 mg, 111 umol, 0.400 eq), LiCl (23.5 mg, 555 umol, 11.4 uL, 2.00 eq) and Pd(PPh$_3$)$_4$ (32.1 mg, 27.8 umol, 0.100 eq) at 20° C. under N$_2$. The resulting mixture was stirred at 100° C. for 12 h. The mixture was concentrated under reduced pressure. The mixture was purified by prep-TLC (SiO$_2$, PE/EtOAc=0/1). tert-butyl (S)-4-(4-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, crude) was obtained as a yellow solid.

Step 7: (S)-4-(4-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

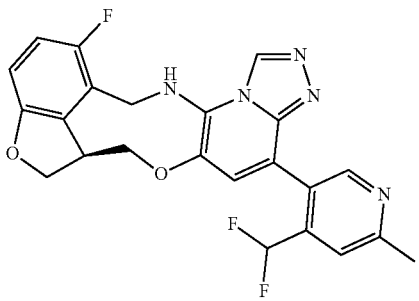 [SMILES: Cc1cc(C(F)F)c(-c2cc3c(n4cnnc24)NCc2c(F)ccc4c2[C@H](CO4)CO3)cn1]

To tert-butyl (S)-4-(4-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 271 umol, 1.00 eq) was added HFIP (3.00 mL) at 20° C. The mixture was concentrated under reduced pressure. The mixture was purified by acidic prep-HPLC (HCl conditions). HPLC analysis indicated insufficient purity. The material was additionally purified by acidic prep-HPLC (FA). The product-containing fraction was concentrated under reduced pressure to remove most of MeCN at 30° C. and the aqueous phase was lyophilized. (S)-4-(4-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (20.9 mg, 45.5 umol, 16% yield, 98.6% purity) was obtained as a yellow solid. $^1$H NMR DMSO-d$_6$ 400 MHz δ=ppm 9.42 (s, 1H), 8.63 (s, 1H), 7.61 (br t, J=6.4 Hz, 1H), 7.56 (s, 1H), 7.34 (s, 1H), 7.05 (t, J=54.4 Hz, 1H), 6.96 (dd, J=10.0, 8.8 Hz, 1H), 6.69 (dd, J=8.7, 3.9 Hz, 1H), 4.96-4.87 (m, 1H), 4.85-4.72 (m, 1H), 4.58-4.42 (m, 2H), 4.20 (dd, J=9.6, 3.4 Hz, 1H), 4.07-3.96 (m, 1H), 3.93-3.84 (m, 1H), 2.59 (s, 3H). LCMS (ESI+): m/z 454.2 (M+H).

Example 98: (S)-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)methanamine Step 1: (5-bromo-1-methyl-1H-pyrazol-3-yl)methanol

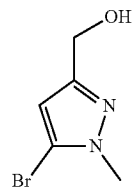

To a solution of methyl 5-bromo-1-methyl-1H-pyrazole-3-carboxylate (5.20 g, 23.7 mmol, 1.00 eq) in DCM (200 mL) was added DIBAL-H (1.00 M, 47.5 mL, 2.00 eq) at −65° C. under N$_2$ and stirred at −65° C. for 1 hr. TLC (Petroleum ether/Ethyl acetate=3/1) showed that the reaction was complete. The mixture was added dropwise to sat.

aq. potassium sodium tartrate (200 mL), stirred for 0.5 hr at 20° C., then extracted with DCM (200 mL*3). The combined organic layers were dried over Na₂SO₄ and concentrated. (5-bromo-1-methyl-1H-pyrazol-3-yl)methanol (4.50 g, crude) was obtained as yellow oil.

Step 2:
5-bromo-1-methyl-1H-pyrazole-3-carbaldehyde

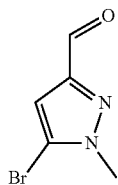

To a solution of (5-bromo-1-methyl-1H-pyrazol-3-yl) methanol (4.50 g, 23.6 mmol, 1.00 eq) in DCM (100 mL) was added DMP (20.0 g, 47.1 mmol, 14.6 mL, 2.00 eq) at 0° C., stirred at 20° C. for 12 h. The mixture was filtered, the filtrate was concentrated. The residue was purified by MPLC (SiO₂, Petroleum ether/Ethyl acetate=1/0 to 0/1). 5-Bromo-1-methyl-1H-pyrazole-3-carbaldehyde (2.70 g, 14.3 mmol, 60% yield) was obtained as a white solid.

Step 3:
5-bromo-1-methyl-1H-pyrazole-3-carbaldehyde oxime

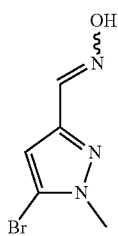

To a solution of 5-bromo-1-methyl-1H-pyrazole-3-carbaldehyde (1.00 g, 5.29 mmol, 1.00 eq) in DCM (10.0 mL) was added hydroxylamine hydrochloride (735 mg, 10.6 mmol, 2.00 eq), TEA (2.14 g, 21.2 mmol, 2.95 mL, 4.00 eq) at 20° C., and the mixture was stirred at 20° C. for 1 hr. TLC (Petroleum ether/Ethyl acetate=3/1) showed that the reaction was complete. Water (5.00 mL) was added to the solution and the mixture was extracted with DCM (10.0 mL*3). The combined organic layers were dried over Na₂SO₄ and concentrated. 5-bromo-1-methyl-1H-pyrazole-3-carbaldehyde oxime (1.15 g, crude) was obtained as a yellow oil.

Step 4:
(5-bromo-1-methyl-1H-pyrazol-3-yl)methanamine

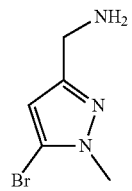

To a solution of 5-bromo-1-methyl-1H-pyrazole-3-carbaldehyde oxime (1.00 g, 4.90 mmol, 1.00 eq) in AcOH (10.0 mL) was added to Zn (3.21 g, 49.0 mmol, 10.0 eq) at 20° C. and the mixture was stirred at 20° C. for 12 h. MeOH (10.0 mL) was added to the solution which was then filtered and the filtrate was concentrated. 1.20 g of crude (5-bromo-1-methyl-1H-pyrazol-3-yl)methanamine (AcOH salt) including (1-methyl-1H-pyrazol-3-yl)methanamine was obtained as a yellow oil.

Step 5: tert-butyl ((5-bromo-1-methyl-1H-pyrazol-3-yl)methyl)carbamate

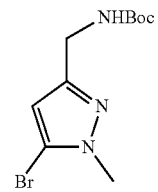 [SMILES: Cn1nc(CNC(=O)OC(C)(C)C)cc1Br]

To a solution of (5-bromo-1-methyl-1H-pyrazol-3-yl) methanamine (1.20 g, 4.80 mmol, 1.00 eq, HOAc) in DCM (20.0 mL) was added TEA (3.88 g, 38.4 mmol, 5.34 mL, 8.00 eq), (Boc)₂O (1.57 g, 7.20 mmol, 1.65 mL, 1.50 eq) at 20° C., then the mixture was stirred at 20° C. for 2 h. The mixture was concentrated. The residue was purified by MPLC (SiO₂, Petroleum ether/Ethyl acetate=1/0 to 0/1). tert-butyl ((5-bromo-1-methyl-1H-pyrazol-3-yl)methyl)carbamate (300 mg, 1.03 mmol, 21% yield) was obtained as a yellow oil.

Step 6: tert-butyl ((1-methyl-S-(tributylstannyl)-1H-pyrazol-3-yl)methyl)carbamate

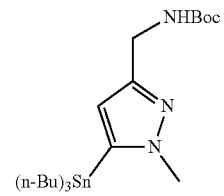

To a solution of tert-butyl ((5-bromo-1-methyl-1H-pyrazol-3-yl)methyl)carbamate (250 mg, 862 umol, 1.00 eq) in THF (6.00 mL) was added n-BuLi (2.50 M, 689 uL, 2.00 eq) at −65° C. under N₂ and the reaction mixture was stirred at −65° C. for 0.5 hr. Sn(n-Bu)₃Cl (1.12 g, 3.45 mmol, 927 uL, 4.00 eq) was added to the solution at −65° C. and the mixture was stirred at −65° C. for 1 hr under N₂. LCMS showed the reaction was complete. Sat. aq. NH₄Cl (4.00 mL) was added to the solution, then the mixture was extracted with EtOAc (4.00 mL*3), the combined organic layers was dried over Na₂SO₄, then concentrated. tert-butyl ((1-methyl-S-(tributylstannyl)-1H-pyrazol-3-yl)methyl)carbamate (430 mg, crude) was obtained as a yellow oil.

Step 7: tert-butyl (S)-4-(3-(((tert-butoxycarbonyl) amino)methyl)-1-methyl-1H-pyrazol-S-yl)-12-fluoro-7a,13-dihydro-7H-[1,2,4]triazolo[4',3':1,6] pyrido[3,2-b]benzofuro[4,3-fg][1,4]oxazonine-14 (8H)-carboxylate

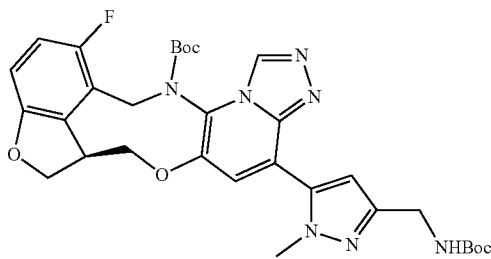 [SMILES: Cn1nc(CNC(=O)OC(C)(C)C)cc1-c1cc2c(n3cnnc13)N(C(=O)OC(C)(C)C)Cc1c(F)ccc3c1[C@H](CO3)CO2]

To a solution of tert-butyl ((1-methyl-S-(tributylstannyl)-1H-pyrazol-3-yl)methyl)carbamate (430 mg, 859 umol, 1.92 eq), tert-butyl (S)-4-bromo-12-fluoro-7a,13-dihydro-7H-[1,2,4]triazolo[4',3':1,6]pyrido[3,2-b]benzofuro[4,3-fg][1,4] oxazonine-14 (8H)-carboxylate (220 mg, 448 umol, 1.00 eq) in dioxane (4.00 mL) was added LiCl (1.90 mg, 44.8 umol, 0.100 eq), CuI (8.53 mg, 44.8 umol, 0.100 eq) and Pd(PPh₃)₄ (51.7 mg, 44.8 umol, 0.100 eq) at 20° C. and the mixture was stirred at 80° C. for 12 h under N₂. LCMS showed the reaction was complete. The mixture was concentrated. The residue was purified by prep-TLC (SiO₂, Petroleum ether/Ethyl acetate=0/1). tert-butyl (S)-4-(3-(((tert-butoxycarbonyl)amino)methyl)-1-methyl-1H-pyrazol-S-yl)-12-fluoro-7a,13-dihydro-7H-[1,2,4]triazolo[4',3':1,6]pyrido [3,2-b]benzofuro[4,3-fg][1,4]oxazonine-14 (8H)-carboxylate (260 mg, crude) was obtained as a yellow oil.

Step 8: (S)-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)methanamine

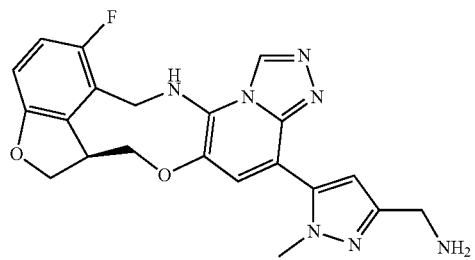 [SMILES: Cn1nc(CN)cc1-c1cc2c(n3cnnc13)NCc1c(F)ccc3c1[C@H](CO3)CO2]

A solution of tert-butyl (S)-4-(3-(((tert-butoxycarbonyl) amino)methyl)-1-methyl-1H-pyrazol-S-yl)-12-fluoro-7a, 13-dihydro-7H-[1,2,4]triazolo[4',3':1,6]pyrido [3,2-b]benzofuro[4,3-fg][1,4]oxazonine-14 (8H)-carboxylate (100 mg, 161 umol, 1.00 eq) in TFA (1.50 mL) and DCM (3.00 mL) was stirred at 20° C. for 1 hr. The mixture was concentrated. The mixture was purified by prep-HPLC (column: Phenomenex Luna C18 150*30 mm*5 um; mobile phase: [water (0.04% HCl)-ACN]; B %: 10%-45%, 10 min). The fraction was blown to dryness by a nitrogen stream to remove most of MeCN and the aqueous phase was lyophilized. (S)-(5-(12-fluoro-7a,8,13,14-tetrahydro-7H-[1,2,4]triazolo[4',3':1, 6]pyrido [3,2-b]benzofuro[4,3-fg][1,4]oxazonin-4-yl)-1-methyl-1H-pyrazol-3-yl)methanamine (45.0 mg, 98.0 umol, 60% yield, 99.7% purity, HCl salt) was obtained as a yellow solid. ¹H NMR CD₃OD 400 MHz δ=ppm 9.51 (s, 1H), 7.98-7.89 (m, 1H), 6.93 (t, J=9.4 Hz, 1H), 6.70 (dd, J=8.6, 3.7 Hz, 1H), 6.61 (s, 1H), 5.19 (br d, J=14.7 Hz, 1H), 4.99-4.93 (m, 1H), 4.80-4.71 (m, 1H), 4.63 (t, J=9.4 Hz, 1H), 4.32 (br dd, J=9.6, 3.0 Hz, 1H), 4.19 (s, 2H), 4.13-4.02 (m, 1H), 3.97-3.86 (m, 1H), 3.83 (s, 3H). LCMS (ESI+): m/z 422.2 (M+H).

Example 99: (S)-1-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylmethanamine

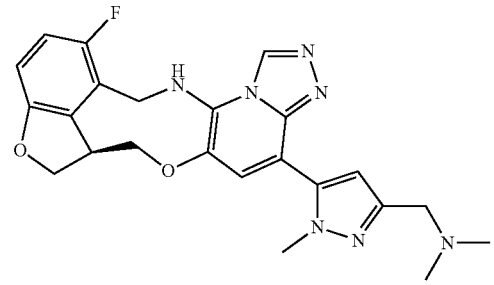 [SMILES: CN(C)Cc1cc(-c2cc3c(n4cnnc24)NCc2c(F)ccc4c2[C@H](CO4)CO3)n(C)n1]

To a solution of (S)-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)methanamine (86.1 mg, 161 umol, 1.00 eq, TFA) in MeOH (3.00 mL) was added AcOH (96.6 ug, 1.61 umol, 0.0920 mL, 0.0100 eq), formaldehyde (26.1 mg, 322 umol, 23.9 uL, 2.00 eq) at 20° C. and stirred at 20° C. for 0.5 hr. NaBH₃CN (20.2 mg, 321 umol, 2.00 eq) was added to the solution at 20° C. and stirred at 20° C. for 1 hr. LCMS showed that the reaction was complete. The mixture was concentrated. The mixture was purified by prep-HPLC (column: Phenomenex Luna C18 100*30 mm*5 um; mobile phase: [water (0.04% HCl) —ACN]; B %: 5%-35%, 10 min), the fraction was blown to dryness by a nitrogen stream to remove most of MeCN and the aqueous phase was lyophilized. (S)-1-(5-(12-fluoro-7a, 8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylmethanamine (35.0 mg, 69.7 umol, 43% yield, 96.7% purity, HCl salt) was obtained as a yellow solid. ¹H NMR CD₃OD 400 MHz δ=ppm 9.56 (s, 1H), 8.06 (s, 1H), 6.94 (t, J=9.5 Hz, 1H), 6.74 (s, 1H), 6.70 (dd, J=8.7. 3.9 Hz, 1H), 5.22 (d, J=14.9 Hz, 1H), 4.98 (br d, J=15.0 Hz, 1H), 4.81-4.75 (m, 1H), 4.68-4.59 (m, 1H), 4.39 (s, 2H), 4.33 (br dd, J=9.7, 3.2 Hz, 1H), 4.12-4.03 (m, 1H), 3.98-3.89 (m, 1H), 3.85 (s, 3H), 2.96 (s, 6H). LCMS (ESI+): m/z 450.2 (M+H).

Example 100: (S)-4-(4-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 4-cyclopropyl-S-(trimethylstannyl)pyrimidine

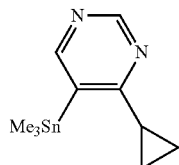

A mixture of 5-bromo-4-cyclopropylpyrimidine (200 mg, 1.00 mmol, 1.00 eq), trimethyl(trimethylstannyl)stannane (658 mg, 2.01 mmol, 417 uL, 2.00 eq), Pd(PPh$_3$)$_4$ (116 mg, 100 umol, 0.100 eq) in dioxane (8.00 mL) was degassed and purged with nitrogen 3 times at 20° C., and the mixture was stirred at 100° C. for 2 h under nitrogen atmosphere. 4-cyclopropyl-S-(trimethylstannyl)pyrimidine (284 mg, 1.00 mmol, 99% yield) was obtained as yellow liquid in dioxane (8.00 mL), which was used to the next step directly.

Step 2: tert-butyl (S)-4-(4-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

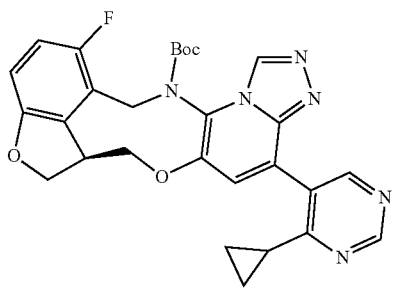 [SMILES: CC(C)(C)OC(=O)N1Cc2c(F)ccc3c2[C@H](CO3)COc2cc(-c3cncnc3C3CC3)c3nncn3c21]

A mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (164 mg, 335 umol, 1.00 eq), 4-cyclopropyl-S-(trimethylstannyl)pyrimidine (284 mg, 1.00 mmol, 3.00 eq), LiCl (28.4 mg, 669 umol, 13.7 uL, 2.00 eq), CuI (25.5 mg, 134 umol, 0.400 eq) and Pd(PPh$_3$)$_4$ (38.7 mg, 33.5 umol, 0.100 eq) in dioxane (8.00 mL) was degassed and purged with nitrogen 3 times at 20° C., and then the mixture was stirred at 80° C. for 2 h under nitrogen atmosphere. The reaction mixture was diluted with water (3.00 mL) and extracted with EtOAc (3.00 mL*3). The combined organic layers were washed with brine (3.00 mL), dried over Na$_2$SO$_4$, filtered, and concentrated under reduced pressure. The residue was purified by prep-TLC (SiO$_2$, PE:EtOAc=3:1). tert-butyl (S)-4-(4-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 283 umol, 84% yield) was obtained as a yellow oil.

Step 3: (S)-4-(4-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

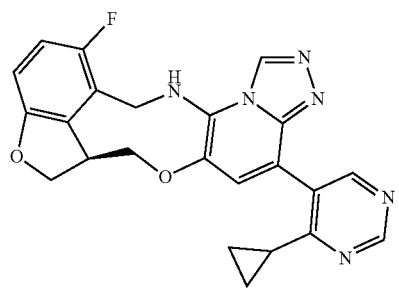 [SMILES: Fc1ccc2c3c1CNc1c(cc(-c4cncnc4C4CC4)c4nncn14)OC[C@H]3CO2]

To HFIP (4.00 mL) was added tert-butyl (S)-4-(4-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 283 umol, 1.00 eq) at 20° C., then the mixture was stirred at 80° C. for 12 h. The mixture was concentrated. The mixture was purified by prep-HPLC (column: Waters Xbridge BEH C18 100*30 mm*10 um; mobile phase: [water (10 mM NH$_4$HCO$_3$)—ACN]; B %: 28%-48%, 10 min). 50.0 mg of the product was obtained, which was then purified by prep-HPLC (column: Phenomenex Luna C18 200*40 mm*10 um; mobile phase: [water (0.2% FA)—ACN]; B %: 10%-45%, 10 min). (S)-4-(4-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (33.6 mg, 77.4 umol, 27% yield, 99.2% purity) was obtained as a white solid. $^1$H NMR DMSO-d$_6$ 400 MHz δ=ppm 9.44 (s, 1H), 8.97 (s, 1H), 8.65 (s, 1H), 7.61 (br t, J=6.4 Hz, 1H), 7.45 (s, 1H), 7.02-6.92 (m, 1H), 6.70 (dd, J=8.7, 3.9 Hz, 1H), 4.98-4.89 (m, 1H), 4.86-4.74 (m, 1H), 4.59-4.43 (m, 2H), 4.21 (br dd, J=9.1, 3.4 Hz, 1H), 4.11-3.99 (m, 1H), 3.93-3.81 (m, 1H), 2.00-1.87 (m, 1H), 1.10 (br d, J=3.5 Hz, 2H), 0.95 (br dd, J=7.6, 2.8 Hz, 2H). LCMS (ESI+): m/z 431.1 (M+H).

Example 101: (S)-12-fluoro-4-(5-fluoro-6-methylpyridin-3-yl)-7a,8,13,14-tetrahydro-7H-[1,2,4]triazolo[4',3':1,6]pyrido[3,2-b]benzofuro[4,3-fg][1,4]oxazonine Step 1: 3-fluoro-2-methyl-S-(4,4,5,5-tetramethyl-1,3,2-dioxaborolan-2-yl)pyridine

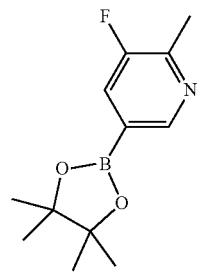

To a solution of 5-bromo-3-fluoro-2-methylpyridine (100 mg, 526 umol, 1.00 eq), 4,4,5,5-tetramethyl-2-(4,4,5,5-tetramethyl-1,3,2-dioxaborolan-2-yl)-1,3,2-dioxaborolane (200 mg, 789 umol, 1.50 eq) in dioxane (4.00 mL) was added KOAc (103 mg, 1.05 mmol, 2.00 eq), Pd(dppf)Cl₂ (38.5 mg, 52.6 umol, 0.100 eq) at 20° C., stirred at 100° C. for 2 h under N₂. The mixture was concentrated. 3-fluoro-2-methyl-S-(4,4,5,5-tetramethyl-1,3,2-dioxaborolan-2-yl)pyridine (124 mg, crude) as obtained as black oil.

Step 2: (S)-12-fluoro-4-(5-fluoro-6-methylpyridin-3-yl)-7a,8,13,14-tetrahydro-7H-[1,2,4]triazolo[4',3':1,6]pyrido[3,2-b]benzofuro[4,3-fg][1,4]oxazonine

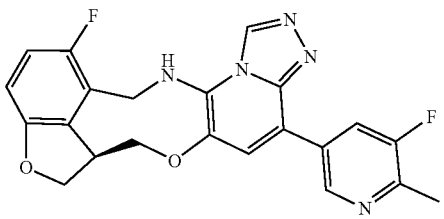 [SMILES: Cc1ncc(-c2cc3c(n4cnnc24)NCc2c(F)ccc4c2[C@H](CO4)CO3)cc1F]

To a solution of 3-fluoro-2-methyl-S-(4,4,5,5-tetramethyl-1,3,2-dioxaborolan-2-yl)pyridine (96.9 mg, 409 umol, 2.00 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (80.0 mg, 205 umol, 1.00 eq), 4-ditert-butylphosphanyl-N,N-dimethyl-aniline dichloropalladium (14.5 mg, 20.5 umol, 14.5 uL, 0.100 eq) in EtOH (4.00 mL) and water (0.400 mL) was added KOAc (40.1 mg, 409 umol, 2.00 eq) at 20° C. and the reaction mixture was stirred at 100° C. for 12 h. The residue was dissolved in MeOH (3.00 mL) and silica-thiol (100 mg, modified silicon gel for eliminating Pd, irregular silica gel, 100-200 mesh, Chlorides (Cl), %≤0.004, particle size distribution 45-75 um) was added at 20° C. and stirred at 20° C. for 3 h. The mixture was filtered, the filtrate was concentrated under reduced pressure. The residue was purified by prep-HPLC (column: Waters Xbridge BEH C18 100*25 mm*5 um; mobile phase: [water (10 mM NH₄HCO₃)—ACN]; B %: 20%-50%, 8 min). The fraction was blown to dryness by a nitrogen stream to remove most of MeCN and the aqueous phase was lyophilized, then the product dissolved in MeOH (10.0 mL) and water (3.00 mL). Aq. HCl (2.00 mL, 1.00 M) was added to the solution which was then lyophilized. (S)-12-fluoro-4-(5-fluoro-6-methylpyridin-3-yl)-7a,8,13,14-tetrahydro-7H-[1,2,4]triazolo[4',3':1,6]pyrido[3,2-b]benzofuro[4,3-fg][1,4]oxazonine (23.8 mg, 50.1 umol, 24% yield, 96.3% purity, HCl salt) was obtained as a yellow solid. ¹H NMR CD₃OD 400 MHz δ=ppm 9.63 (s, 1H), 8.96 (d, J=1.5 Hz, 1H), 8.51 (dd, J=9.7, 1.2 Hz, 1H), 8.23 (s, 1H), 6.92 (dd, J=10.1, 8.8 Hz, 1H), 6.69 (dd, J=8.6, 3.9 Hz, 1H), 5.20 (d, J=14.7 Hz, 1H), 5.01-4.96 (m, 1H), 4.87-4.78 (m, 1H), 4.68-4.59 (m, 1H), 4.35 (dd, J=9.7, 2.9 Hz, 1H), 4.12-3.95 (m, 2H), 2.76 (d, J=2.4 Hz, 3H). LCMS (ESI+): m/z 422.0 (M+H).

Example 102: (S)-4-(3-(difluoromethyl)-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1:
5-bromo-3-(difluoromethyl)-1-methyl-1H-pyrazole

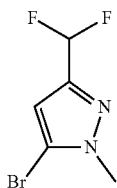

To a solution of 5-bromo-1-methyl-1H-pyrazole-3-carbaldehyde (300 mg, 1.59 mmol, 1.00 eq) in DCM (3.00 mL) was added DAST (512 mg, 3.17 mmol, 419 uL, 2.00 eq) at −78° C. The mixture was stirred at 20° C. for 12 h. The reaction mixture was quenched by addition of saturated aqueous NaHCO₃ (3.00 mL), concentrated under reduced pressure to remove DCM, and extracted with EtOAc (2.00 mL*3). The combined organic layers were washed with brine (3.00 mL), dried over Na₂SO₄, filtered, and concentrated under reduced pressure to give 5-bromo-3-(difluoromethyl)-1-methyl-1H-pyrazole (300 mg, crude) as a yellow oil.

Step 2: 3-(difluoromethyl)-1-methyl-S-(tributylstannyl)-1H-pyrazole

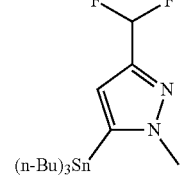

To a solution of 5-bromo-3-(difluoromethyl)-1-methyl-1H-pyrazole (290 mg, 1.37 mmol, 1.00 eq) in THF (10.0 mL) was added n-BuLi (2.50 M, 715 uL, 1.30 eq) at −78° C. under N₂. The mixture was stirred at −78° C. for 0.5 hr. To the mixture was added tributyl(chloro)stannane (1.79 g, 5.50 mmol, 1.48 mL, 4.00 eq) at −78° C. under N₂. The mixture was stirred at −78° C. for 2 h. LC-MS showed that 5-bromo-3-(difluoromethyl)-1-methyl-1H-pyrazole was consumed completely and the desired mass was detected. The reaction mixture was quenched by addition of saturated aqueous NH₄Cl (5.00 mL). THF layer was separated and the aqueous layer was extracted with EtOAc (3.00 mL*3). The combined organic layers were washed with brine (5.00 mL), dried over Na₂SO₄, filtered, and concentrated under reduced pressure to afford 3-(difluoromethyl)-1-methyl-S-(tributylstannyl)-1H-pyrazole (570 mg, crude) as a yellow oil.

Step 3: tert-butyl (S)-4-(3-(difluoromethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

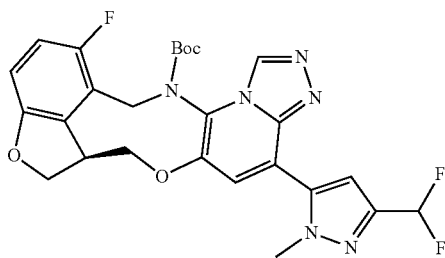 [SMILES: Cn1nc(C(F)F)cc1-c1cc2c(n3cnnc13)N(C(=O)OC(C)(C)C)Cc1c(F)ccc3c1[C@H](CO3)CO2]

A mixture of 3-(difluoromethyl)-1-methyl-S-(tributylstannyl)-1H-pyrazole (560 mg, 1.33 μmmol, 2.50 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (261 mg, 532 umol, 1.00 eq), Pd(PPh$_3$)$_4$ (61.5 mg, 53.2 umol, 0.100 eq), CuI (40.5 mg, 213 umol, 0.400 eq) and LiCl (45.1 mg, 1.06 mmol, 21.8 uL, 2.00 eq) in dioxane (10.0 mL) was degassed and purged with nitrogen 3 times at 20° C. The reaction mixture was stirred at 80° C. for 12 h under nitrogen atmosphere. The mixture was concentrated under reduced pressure. The residue was purified by column chromatography (SiO$_2$, Petroleum ether/Ethyl acetate=1/0 to 0/1). tert-butyl (S)-4-(3-(difluoromethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (230 mg, crude) was obtained as a brown solid.

Step 4: (S)-4-(3-(difluoromethyl)-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine

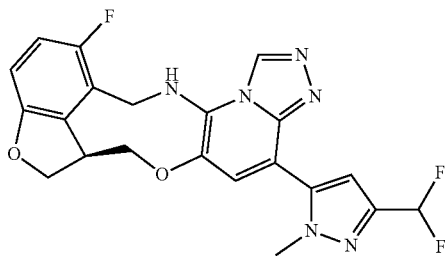 [SMILES: Cn1nc(C(F)F)cc1-c1cc2c(n3cnnc13)NCc1c(F)ccc3c1[C@H](CO3)CO2]

To the HFIP (5.00 mL) was added tert-butyl (S)-4-(3-(difluoromethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 369 umol, 1.00 eq) at 20° C., the mixture was stirred at 100° C. for 12 h The reaction mixture was concentrated under reduced pressure. The mixture was dissolved in DMSO (5.00 mL). The mixture was purified by neutral prep-HPLC (column: Welch Xtimate C18 150*25 mm*5 um; mobile phase: [water (10 mM NH$_4$HCO$_3$)—ACN]; B %: 35%-60%, 10 min). The fraction was lyophilized. 70 mg of crude product was obtained and dissolved in DMSO (5.00 mL). The obtained sample was purified by acidic prep-HPLC. (column: Phenomenex Luna C18 200*40 mm*10 um; mobile phase: [water (0.2% FA)—ACN]; B %: 20%-60%, 10 min). (S)-4-(3-(difluoromethyl)-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg] [1,4]oxazonine (58.3 mg, 126 umol, 34% yield, 95.9% purity) was obtained by lyophilization as a white solid. $^1$H NMR DMSO-d$_6$ 400 MHz δ=ppm 9.46 (s, 1H), 7.75 (br t, J=6.2 Hz, 1H), 7.53 (s, 1H), 7.00 (t, J=54.8 Hz, 1H), 6.99-6.93 (m, 1H), 6.82 (s, 1H), 6.70 (dd, J=8.7, 3.8 Hz, 1H), 4.96-4.88 (m, 1H), 4.86-4.76 (m, 1H), 4.60-4.45 (m, 2H), 4.24-4.17 (m, 1H), 4.10-3.98 (m, 1H), 3.93-3.88 (m, 1H), 3.87 (s, 3H). LCMS (ESI+): m/z 443.1 (M+H).

Example 103: (S)-4-(1,5-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine

Step 1: (1,5-dimethyl-1H-imidazol-4-yl)boronic Acid

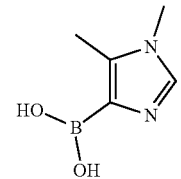

To a solution of 4-bromo-1,5-dimethyl-1H-imidazole (800 mg, 4.57 mmol, 1.00 eq) in THF (6.00 mL) was added n-BuLi (2.50 M, 3.66 mL, 2.00 eq) at 0° C. under N$_2$. The mixture was stirred at 20° C. for 1 hr. Then triisopropyl borate (2.58 g, 13.7 mmol, 3.15 mL, 3.00 eq) was added to the mixture at 0° C. and stirred at 0° C. for 1 hr. The reaction mixture was quenched by addition of MeOH (5.00 mL) at 0° C. The mixture was concentrated under reduced pressure. The residue was purified by prep-HPLC (column: Phenomenex Luna C18 200*40 mm*10 um; mobile phase: [water (0.2% FA)—ACN]; B %: 1%-20%, 10 min). (1,5-dimethyl-1H-imidazol-4-yl)boronic acid (450 mg, crude) was obtained as yellow oil.

Step 2: tert-butyl (S)-4-(1,5-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

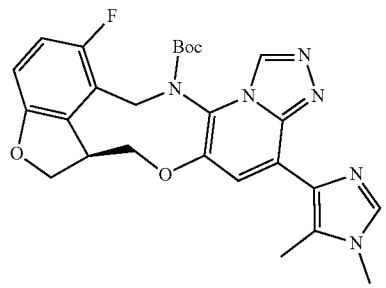 [SMILES: Cc1c(-c2cc3c(n4cnnc24)N(C(=O)OC(C)(C)C)Cc2c(F)ccc4c2[C@H](CO4)CO3)ncn1C]

To a solution of tert-butyl (S)-4-bromo-12-fluoro-7a,13-dihydro-7H-[1,2,4]triazolo[4',3':1,6]pyrido[3,2-b]benzofuro

[4,3-fg][1,4]oxazonine-14 (8H)-carboxylate (197 mg, 401 umol, 1.00 eq) in dioxane (5.00 mL) was added (1,5-dimethyl-1H-imidazol-4-yl)boronic acid (280 mg, 2.00 mmol, 5.00 eq), Pd(dppf)Cl$_2$ DCM complex (65.3 mg, 80.0 umol, 0.200 eq), water (0.500 mL) and Na$_2$CO$_3$ (106 mg, 1.00 mmol, 2.98 uL, 2.50 eq) at 20° C. under N$_2$. The mixture was stirred at 80° C. for 12 h. The reaction mixture was concentrated under reduced pressure. The residue was purified by prep-TLC (SiO$_2$, Ethyl acetate/MeOH=10/1). tert-butyl (S)-4-(1,5-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, crude) was obtained as a brown solid.

Step 3: (S)-4-(1,5-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine

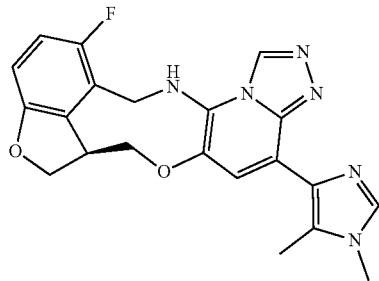 [SMILES: Cc1c(-c2cc3c(n4cnnc24)NCc2c(F)ccc4c2[C@H](CO4)CO3)ncn1C]

A mixture of tert-butyl (S)-4-(1,5-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, 158 umol, 1.00 eq) in HFIP (2.00 mL) was stirred at 100° C. for 3 h. The reaction mixture was concentrated under reduced pressure. The residue was purified by prep-HPLC (column: Phenomenex Luna C18 100*30 mm*5 um; mobile phase: [water (0.2% FA)—ACN]; B %: 10%-35%, 10 min). (S)-4-(1,5-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine (9.50 mg, 20.8 umol, 13% yield, 99.1% purity, formate salt) was obtained as a white solid. $^1$H NMR DMSO-d6 400 MHz δ=ppm 9.38 (br s, 1H), 7.63 (br s, 1H), 7.41-7.26 (m, 2H), 6.94 (t, J=9.6 Hz, 1H), 6.67 (dd, J=3.6, 8.8 Hz, 1H), 4.88 (br dd, J=5.6, 15.1 Hz, 1H), 4.75 (br dd, J=6.8, 14.8 Hz, 1H), 4.56-4.47 (m, 2H), 4.28-4.21 (m, 2H), 4.02 (br s, 1H), 3.90-3.78 (m, 1H), 3.59 (s, 3H), 2.35 (s, 3H). LCMS (ESI+): m/z 407.16 (M+H).

Example 104: (S)-4-(1,2-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 4-bromo-1,2-dimethyl-1H-imidazole

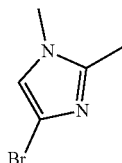

To a solution of 5-bromo-2-methyl-1H-imidazole (2.00 g, 12.4 mmol, 1.00 eq) and MeI (2.12 g, 14.9 mmol, 928 uL, 1.20 eq) in DMF (10.0 mL) was added K$_2$CO$_3$ (3.78 g, 27.3 mmol, 2.20 eq) at 20° C. The mixture was stirred at 20° C. for 12 h. The reaction mixture was diluted with water (30.0 mL), extracted with ethyl acetate (15.0 mL*3). The combined organic layers were dried over anhydrous sodium sulfate, filtered and the filtrate was concentrated under reduced pressure. The residue was purified by prep-TLC (SiO$_2$, Ethyl acetate:Methanol=20:1). 4-bromo-1,2-dimethyl-1H-imidazole (500 mg, 2.86 mmol, 23% yield) was obtained as a white solid. $^1$H NMR CD$_3$OD 400 MHz δ=ppm 6.97 (s, 1H), 3.58 (s, 3H), 2.31 (s, 3H).

Step 2: tert-butyl (S)-4-(1,2-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

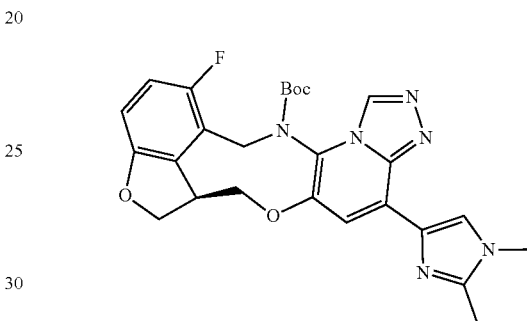

A mixture of 4-bromo-1,2-dimethyl-1H-imidazole (60.0 mg, 343 umol, 1.00 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Ex. 16; 241 mg, 344 umol, 1.00 eq), Pd(t-Bu$_3$P)$_2$ (17.6 mg, 34.4 umol, 0.100 eq) in dioxane (1.00 mL) was degassed and purged with nitrogen 3 times at 20° C., and the mixture was stirred at 100° C. for 2 h under nitrogen atmosphere. The reaction mixture was concentrated under reduced pressure. The residue was purified by prep-TLC (SiO$_2$, Ethyl acetate/Methanol=5/1). tert-butyl (S)-4-(1,2-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (90.0 mg, 178 umol, 51% yield) was obtained as a yellow solid.

Step 3: (S)-4-(1,2-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine

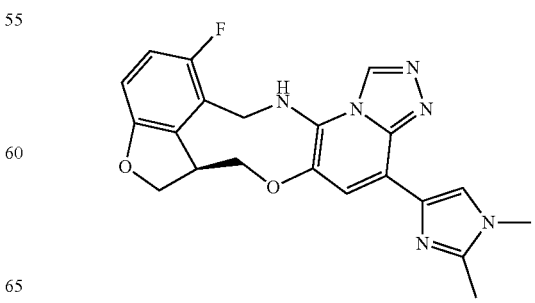

A solution of tert-butyl (S)-4-(1,2-dimethyl-1H-imidazol-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (90.0 mg, 178 umol, 1.00 eq) in HFIP (3.00 mL) was stirred at 80° C. for 1 hr. The reaction mixture was concentrated under reduced pressure. The residue was purified by prep-HPLC (HCl conditions). The product-containing fraction was concentrated under reduced pressure to remove most of MeCN at 30° C. and the aqueous phase was lyophilized. (S)-4-(1,2-dimethyl-1H-imidazol-4-yl)-12-fluoro-7a,8,13,14-tetrahydro-7H-[1,2,4]triazolo[4',3':1,6]pyrido[3,2-b]benzofuro[4,3-fg][1,4]oxazonine (15.5 mg, 34.1 umol, 19% yield, 97.5% purity, HCl salt) was obtained as a yellow solid. $^1$H NMR CD$_3$OD 400 MHz δ=ppm 9.54 (s, 1H), 8.01 (s, 1H), 7.99 (s, 1H), 6.88 (dd, J=10.1, 8.9 Hz, 1H), 6.64 (dd, J=8.7, 3.8 Hz, 1H), 5.11 (d, J=14.7 Hz, 1H), 4.93 (br s, 1H), 4.74 (br d, J=6.0 Hz, 1H), 4.60 (t, J=9.3 Hz, 1H), 4.31 (dd, J=9.7, 3.0 Hz, 1H), 4.09-3.99 (m, 1H), 3.95 (br d, J=10.3 Hz, 1H), 3.89 (s, 3H), 2.73 (s, 3H). LCMS (ESI+): m/z 407.1 (M+H).

Example 105: (S)-4-(2-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-bromo-2-iodo-6-methylpyridine

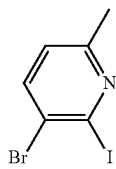

To a solution of I$_2$ (5.43 g, 21.4 mmol, 4.31 mL, 2.00 eq), CuI (2.65 g, 13.9 mmol, 1.30 eq), isopentyl nitrite (1.88 g, 16.0 mmol, 2.16 mL, 1.50 eq) in MeCN (30.0 mL) was added 3-bromo-6-methylpyridin-2-amine (2.00 g, 10.7 mmol, 1.00 eq) at 0° C. The mixture was stirred at 60° C. for 2 h The reaction mixture was quenched by Na$_2$SO$_3$-30.0 g at 20° C., and then filtered and the filtrate was concentrated under reduced pressure. The residue was purified by column chromatography (SiO$_2$, Petroleum ether/Ethyl acetate=1/0 to 10/1). 3-bromo-2-iodo-6-methylpyridine (1.60 g, 5.37 mmol, 50% yield) was obtained as a yellow solid.

Step 2: 3-bromo-6-methyl-2-vinylpyridine

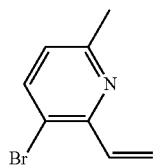

A mixture of 3-bromo-2-iodo-6-methylpyridine (1.60 g, 5.37 mmol, 1.00 eq), 4,4,5,5-tetramethyl-2-vinyl-1,3,2-dioxaborolane (744 mg, 4.83 mmol, 820 uL, 0.900 eq), Na$_2$CO$_3$ (1.14 g, 10.7 mmol, 2.00 eq) and Pd(dppf)Cl$_2$ (196 mg, 269 umol, 0.0500 eq) in dioxane (20.0 mL) and water (2.00 mL) was degassed and purged with nitrogen 3 times at 20° C., and the mixture was stirred at 80° C. for 2 h under nitrogen atmosphere. The reaction mixture was concentrated under reduced pressure. The residue was purified by column chromatography (SiO$_2$, Petroleum ether/Ethyl acetate=1/0 to 10/1). 3-bromo-6-methyl-2-vinylpyridine (600 mg, 3.03 mmol, 56% yield) was obtained as a yellow oil.

Step 3: 3-bromo-6-methylpicolinaldehyde

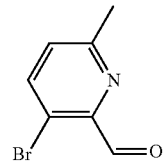

Ozone was bubbled into a solution of 3-bromo-6-methyl-2-vinylpyridine (600 mg, 3.03 mmol, 1.00 eq) in DCM (35.0 mL) at −78° C. for 0.5 hr. After excess O3 was purged by O$_2$, Me$_2$S (2.82 g, 45.5 mmol, 3.34 mL, 15.0 eq) was added to the mixture at 20° C. The mixture was stirred at 20° C. for 8 h. LC-MS showed 3-bromo-6-methyl-2-vinylpyridine was consumed completely and one main peak with desired mass was detected. The mixture was concentrated and water (10.0 mL) was added to the solution. The mixture was extracted with EtOAc (10.0 mL*3), the combined organic layers were dried over Na$_2$SO$_4$ and concentrated. The residue was purified by flash silica gel chromatography (ISCO®; 12 g SepaFlash® Silica Flash Column, Eluent of 0-11% Ethyl acetate/Petroleum ether gradient @ 40 mL/min). 3-bromo-6-methylpicolinaldehyde (250 mg, 1.25 mmol, 41% yield) was obtained as a white solid.

Step 4: 3-bromo-2-(difluoromethyl)-6-methylpyridine

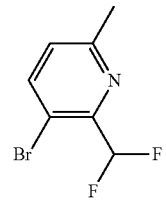

To a solution of 3-bromo-6-methylpicolinaldehyde (250 mg, 1.25 mmol, 1.00 eq) in DCM (4.00 mL) was added DAST (403 mg, 2.50 mmol, 330 uL, 2.00 eq) at 0° C. The mixture was stirred at 20° C. for 10 h. Cold water (2.00 mL) was added to the solution, then the mixture was extracted with EtOAc (3.00 mL*3), the combined organic layers were dried over Na$_2$SO$_4$ and concentrated. The residue was purified by prep-TLC (SiO$_2$, Petroleum ether/Ethyl acetate=5/1). 3-bromo-2-(difluoromethyl)-6-methylpyridine (100 mg, 450 umol, 36% yield) was obtained as a yellow gum.

Step 5: tert-butyl (S)-4-(2-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

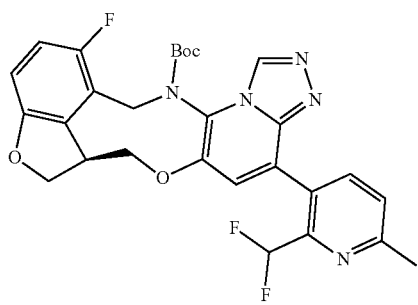 [SMILES: Cc1ccc(-c2cc3c(n4cnnc24)N(C(=O)OC(C)(C)C)Cc2c(F)ccc4c2[C@H](CO4)CO3)c(C(F)F)n1]

A mixture of 3-bromo-2-(difluoromethyl)-6-methylpyridine (70.0 mg, 315 umol, 1.00 eq), tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (221 mg, 315 umol, 1.00 eq) and Pd(t-Bu$_3$P)$_2$ (16.1 mg, 31.5 umol, 0.100 eq) in dioxane (1.00 mL) was degassed and purged with nitrogen 3 times at 20° C., and the mixture was stirred at 100° C. for 10 h under nitrogen atmosphere. The reaction mixture was concentrated under reduced pressure. The residue was purified by prep-TLC (SiO$_2$, Petroleum ether/Ethyl acetate=1/3). tert-butyl (S)-4-(2-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, 145 umol, 45% yield) was obtained as a yellow solid.

Step 6: (S)-4-(2-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

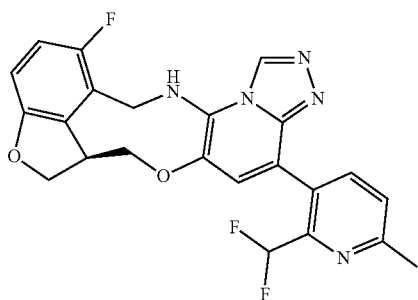 [SMILES: Cc1ccc(-c2cc3c(n4cnnc24)NCc2c(F)ccc4c2[C@H](CO4)CO3)c(C(F)F)n1]

A mixture of tert-butyl (S)-4-(2-(difluoromethyl)-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, 145 umol, 1.00 eq) in HFIP (2.00 mL) was stirred at 80° C. for 5 h under nitrogen atmosphere. The reaction mixture was concentrated under reduced pressure. The residue was purified by prep-HPLC (HCl conditions). $^1$H NMR indicated insufficient purity. The product was further purified by prep-HPLC (formic acid conditions). The product-containing fraction was concentrated under reduced pressure to remove most of MeCN at 30° C. and the aqueous phase was lyophilized. (S)-4-(2-(difluoromethyl)-6-methylpyridin-3-yl)-12-fluoro-7a,8,13,14-tetrahydro-7H-[1,2,4]triazolo[4',3':1,6]pyrido[3,2-b]benzofuro[4,3-fg] [1,4]oxazonine (18.0 mg, 38.0 umol, 26% yield, 95.6% purity) was obtained as a yellow solid. $^1$H NMR DMSO-d6 400 MHz δ=ppm 9.42 (s, 1H), 7.90 (d, J=7.9 Hz, 1H), 7.59 (br t, J=6.3 Hz, 1H), 7.49 (d, J=7.9 Hz, 1H), 7.24 (s, 1H), 6.96 (br t, J=9.6 Hz, 1H), 6.83 (t, J=54.8 Hz, 1H), 6.72-6.65 (m, 1H), 4.96-4.86 (m, 1H), 4.82-4.71 (m, 1H), 4.52 (br t, J=9.4 Hz, 1H), 4.44 (br s, 1H), 4.19 (br dd, J=9.5, 3.5 Hz, 1H), 4.02 (br s, 1H), 3.91-3.79 (m, 1H), 2.57 (s, 3H). LCMS (ESI+): m/z 454.1 (M+H).

Example 106: (S)-12-fluoro-4-(5-methylpyridin-2-yl)-7a,8,13,14-tetrahydro-7H-[1,2,4]triazolo[4',3':1,6]pyrido[3,2-b]benzofuro[4,3-fg][1,4]oxazonine Step 1: 5-methyl-2-(tributylstannyl)pyridine

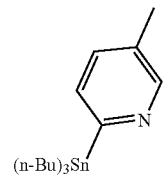

To a solution of 2-bromo-S-methylpyridine (1.00 g, 5.81 mmol, 1.00 eq) in THF (10.0 mL) was added n-BuLi (2.50 M, 2.81 mL, 1.21 eq) at −70° C. under N$_2$. The mixture was stirred at −70° C. for 0.5 hr. Tributyl(chloro)stannane (2.84 g, 8.72 mmol, 2.35 mL, 1.50 eq) was added to the mixture at −70° C. and the mixture was stirred at 0° C. for 1 hr The reaction mixture was quenched by addition of water (10.0 mL) at 20° C., and extracted with PE (15.0 mL*3). The combined organic layers were dried over Na$_2$SO$_4$, filtered, and concentrated under reduced pressure. The residue was purified by column chromatography (SiO$_2$, Petroleum ether/Ethyl acetate=1/0 to 20/1). 5-methyl-2-(tributylstannyl)pyridine (500 mg, crude) was obtained as a yellow liquid.

Step 2: tert-butyl (S)-12-fluoro-4-(5-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate

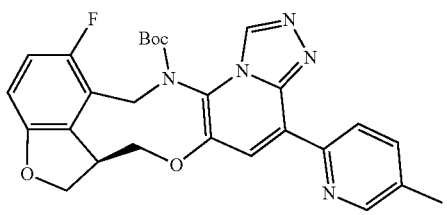 [SMILES: Cc1ccc(-c2cc3c(n4cnnc24)N(C(=O)OC(C)(C)C)Cc2c(F)ccc4c2[C@H](CO4)CO3)nc1]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq) in dioxane (6.00 mL) was added 5-methyl-2-(tributylstannyl)pyridine (311 mg, 814 umol, 2.00 eq), Pd(PPh$_3$)$_4$ (47.0 mg, 40.7 umol, 9.99e-2 eq) and LiCl (40.0 mg, 944 umol, 19.3 uL, 2.32 eq), CuI (30.0 mg, 158 umol, 3.87e-1 eq) at 20° C. under N$_2$. The mixture was stirred at 100° C. for 12 h. The reaction mixture was concentrated under reduced pressure. The residue was purified by prep-TLC (SiO₂, Petroleum ether/Ethyl acetate=1/3). tert-butyl (S)-12-fluoro-4-(5-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, crude) was obtained as a yellow solid.

Step 3: (S)-12-fluoro-4-(5-methylpyridin-2-yl)-7a,8,13,14-tetrahydro-7H-[[1,2,4]triazolo[4',3':1,6]pyrido[3,2-b]benzofuro[4,3-fg][1,4]oxazonine

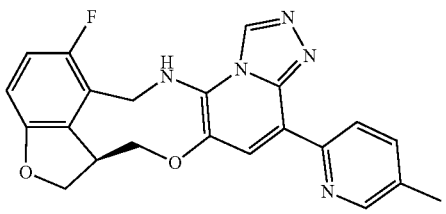 [SMILES: Cc1ccc(-c2cc3c(n4cnnc24)NCc2c(F)ccc4c2[C@H](CO4)CO3)nc1]

A mixture of tert-butyl (S)-12-fluoro-4-(5-methylpyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, 199 umol, 1.00 eq) in HFIP (2.00 mL) was stirred at 100° C. for 2 h. The reaction mixture was concentrated under reduced pressure. The residue was purified by prep-HPLC (column: Phenomenex Synergi C18 150*25 * 10 um; mobile phase: [water (0.04% HCl)—ACN]; B %: 10%-35%, 10 μmin). (S)-12-fluoro-4-(5-methylpyridin-2-yl)-7a,8,13, 14-tetrahydro-7H-[1,2,4]triazolo[4',3':1,6]pyrido[3,2-b]benzofuro[4,3-fg][1,4]oxazonine (38.0 mg, 84.1 umol, 42% yield, 97.3% purity, HCl) was obtained as a brown solid. ¹H NMR CD₃OD 400 MHz δ=ppm 9.65 (br s, 1H), 8.67 (s, 1H), 8.58 (s, 1H), 8.26 (br s, 1H), 8.10 (br s, 1H), 6.91 (br t, J=9.4 Hz, 1H), 6.67 (br dd, J=8.4, 3.0 Hz, 1H), 5.18 (br s, 1H), 5.07-4.99 (m, 1H), 4.81 (br s, 1H), 4.64 (br t, J=8.9 Hz, 1H), 4.33 (br d, J=9.2 Hz, 1H), 4.07 (br s, 2H), 2.51 (br s, 3H). ¹H NMR DMSO-d₆ 400 MHz δ=ppm 9.93 (br s, 1H), 8.96 (br s, 1H), 8.66 (br s, 2H), 8.44 (br s, 1H), 8.02 (br s, 1H), 7.09-6.94 (m, 1H), 6.74 (br d, J=6.0 Hz, 1H), 4.95 (br s, 2H), 4.57 (br d, J=9.2 Hz, 2H), 4.24 (br d, J=7.2 Hz, 1H), 4.11 (br s, 1H), 4.00-3.95 (m, 1H), 2.40 (s, 3H). LCMS (ESI+): m/z 404.0 (M+H).

Example 107: (S)-4-(5-chloro-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-chloro-2-methyl-S-(4,4,5,5-tetramethyl-1,3,2-dioxaborolan-2-yl)pyridine

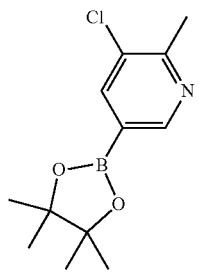

To 5-bromo-3-chloro-2-methylpyridine (150 mg, 727 umol, 1.00 eq) in dioxane (5.00 mL) were added 4,4,5,5-tetramethyl-2-(4,4,5,5-tetramethyl-1,3,2-dioxaborolan-2-yl)-1,3,2-dioxaborolane (369 mg, 1.45 mmol, 2.00 eq), Pd(dppf)Cl₂ (53.2 mg, 72.7 umol, 0.100 eq), KOAc (143 mg, 1.45 mmol, 2.00 eq) at 20° C. Then the mixture was stirred at 100° C. for 2 h under nitrogen atmosphere. The reaction mixture was concentrated under reduced pressure to give 3-chloro-2-methyl-S-(4,4,5,5-tetramethyl-1,3,2-dioxaborolan-2-yl)pyridine (200 mg, crude) as brown solid.

Step 2: tert-butyl (S)-4-(5-chloro-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

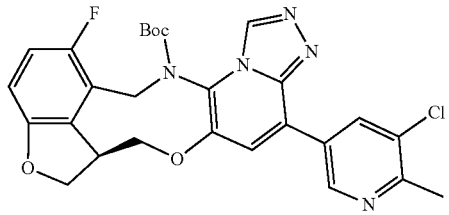 [SMILES: Cc1ncc(-c2cc3c(n4cnnc24)N(C(=O)OC(C)(C)C)Cc2c(F)ccc4c2[C@H](CO4)CO3)cc1Cl]

To 3-chloro-2-methyl-S-(4,4,5,5-tetramethyl-1,3,2-dioxaborolan-2-yl)pyridine (155 mg, 611 umol, 2.00 eq) in EtOH (3.00 mL) and water (0.600 mL) was added KOAc (89.9 mg, 916 umol, 3.00 eq), 4-ditert-butylphosphanyl-N,N-dimethyl-aniline dichloropalladium (21.6 mg, 30.5 umol, 21.6 uL, 0.100 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq) at 20° C. The mixture was stirred at 80° C. for 2 h under nitrogen atmosphere. The reaction mixture was concentrated under reduced pressure. The residue was purified by prep-TLC (SiO₂, PE:EtOAc=0:1). tert-butyl (S)-4-(5-chloro-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, crude) was obtained as yellow solid.

Step 3: (S)-4-(5-chloro-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

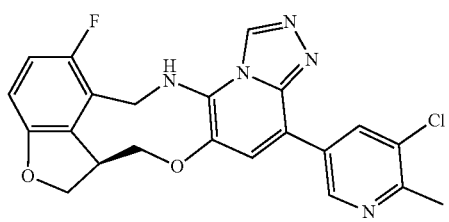 [SMILES: Cc1ncc(-c2cc3c(n4cnnc24)NCc2c(F)ccc4c2[C@H](CO4)CO3)cc1Cl]

To tert-butyl (S)-4-(5-chloro-6-methylpyridin-3-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate (120 mg, 223 umol, 1.00 eq) was added HFIP (2.00 mL) at 20° C. The mixture was stirred at 100° C. for 12 h. LC-MS showed tert-butyl (S)-4-(5-chloro-6-methylpyridin-3-yl)-12-fluoro-7a,13-dihydro-7H-[1,2,4]triazolo[4',3':1,6]pyrido

[3,2-b]benzofuro[4,3-fg][1,4]oxazonine-14 (8H)-carboxylate was consumed completely and one main peak with desired mass was detected. The reaction mixture was concentrated under reduced pressure. The crude product was purified by prep-HPLC (HCl conditions). (S)-4-(5-chloro-6-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (30.4 mg, 68.8 umol, 30% yield, 99.1% purity) was obtained as yellow solid. $^1$H NMR CD$_3$OD 400 MHz δ =ppm 9.81 (s, 1H), 9.09 (s, 1H), 8.97 (s, 1H), 8.33 (s, 1H), 6.90 (t, J=9.4 Hz, 1H), 6.66 (dd, J=8.5, 3.6 Hz, 1H), 5.19 (d, J=14.8 Hz, 1H), 5.09-4.93 (m, 1H), 4.89-4.76 (m, 1H), 4.62 (t, J=9.2 Hz, 1H), 4.42-4.28 (m, 1H), 4.19-3.90 (m, 2H), 2.93 (s, 3H). LCMS (ESI+): m/z 438.1/440.0 (M+H)/(M+3).

Example 108: (S)-12-fluoro-4-(2-methylpyridin-4-yl)-7a,8,13,14-tetrahydro-7H-[1,2,4]triazolo[4',3':1,6]pyrido[3,2-b]benzofuro[4,3-fg][1,4]oxazonine

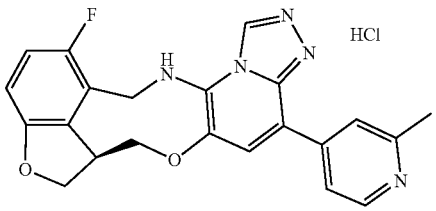 [SMILES: Cc1cc(-c2cc3c(n4cnnc24)NCc2c(F)ccc4c2[C@H](CO4)CO3)ccn1 ; Cl]

A mixture of (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (90.0 mg, 230 umol, 1.00 eq), (2-methyl-4-pyridyl)boronic acid (47.3 mg, 345 umol, 1.50 eq), 4-ditert-butylphosphanyl-N,N-dimethyl-aniline dichloropalladium (16.3 mg, 23.0 umol, 16.3 uL, 0.100 eq), KOAc (45.0 mg, 459 umol, 1.99 eq) in EtOH (5.00 mL) and water (0.500 mL) was degassed and purged with nitrogen 3 times and the mixture was stirred at 80° C. for 8 hr under nitrogen atmosphere. The residue was dissolved in MeOH (5.00 mL) and silica-thiol (200 mg, modified silicon gel for eliminating Pd, irregular silica gel, 100-200 mesh, Chlorides (Cl), %≤0.004, particle size distribution 45-75 um) was added at 20° C. and stirred at 20° C. for 3 h. The suspension was filtered, the filtrate was concentrated and purified by acidic prep-HPLC (column: Phenomenex Luna C18 150*30 mm*5 um; mobile phase: [water (0.04% HCl)-ACN]; B %: 15%-40%, 10 min). The product-containing fraction was concentrated under reduced pressure to remove most of MeCN at 30° C. and the aqueous phase was lyophilized. (S)-12-fluoro-4-(2-methylpyridin-4-yl)-7a,8,13,14-tetrahydro-7H-[1,2,4]triazolo[4',3':1,6]pyrido[3,2-b]benzofuro[4,3-fg][1,4]oxazonine (54.3 mg, 123 umol, 53% yield, 99.4% purity, HCl salt) was obtained as an orange solid. $^1$H NMR CD$_3$OD 400 MHz δ=ppm 9.61 (s, 1H), 8.68 (d, J=6.4 Hz, 1H), 8.49 (s, 1H), 8.44 (br d, J=6.2 Hz, 1H), 8.40 (s, 1H), 6.90 (t, J=9.4 Hz, 1H), 6.66 (dd, J=8.7, 3.9 Hz, 1H), 5.21 (br d, J=14.8 Hz, 1H), 4.98 (br d, J=14.6 Hz, 1H), 4.80 (br s, 1H), 4.62 (br t, J=9.2 Hz, 1H), 4.32 (br d, J=7.7 Hz, 1H), 4.14-3.91 (m, 2H), 2.83 (s, 3H). LCMS (ESI+): m/z 404.2 (M+H).

Example 109: (S)-12-fluoro-4-(3-methoxypyridin-2-yl)-7a,8,13,14-tetrahydro-7H-[1,2,4]triazolo[4',3':1,6]pyrido[3,2-b]benzofuro[4,3-fg][1,4]oxazonine Step 1: 3-methoxy-2-(trimethylstannyl)pyridine

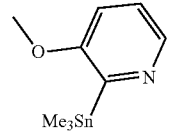

To a solution of 2-bromo-3-methoxypyridine (400 mg, 2.13 mmol, 1.00 eq) in dioxane (6.00 μmL) was added Pd(PPh$_3$)$_4$ (246 μmg, 213 umol, 0.100 eq) and trimethyl(trimethylstannyl)stannane (1.39 g, 4.25 mmol, 882 uL, 2.00 eq) at 20° C. under N$_2$. The mixture was stirred at 100° C. for 2 h. LC-MS showed no 2-bromo-3-methoxypyridine was remained. Several new peaks were shown on LC-MS and desired m/s was detected. The reaction mixture was filtered and the filtrate was collected. 3-methoxy-2-(trimethylstannyl)pyridine (578 mg, crude) was dissolved in dioxane (6.00 mL) and used into next step directly.

Step 2: tert-butyl (S)-12-fluoro-4-(3-methoxypyridin-2-yl)-7a,13-dihydro-7H-[1,2,4]triazolo[4',3':1,6]pyrido[3,2-b]benzofuro[4,3-fg][1,4]oxazonine-14(8H)-carboxylate

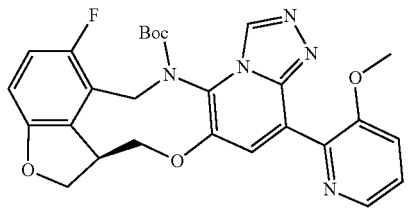 [SMILES: COc1cccnc1-c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq) in dioxane (2.00 mL) was added 3-methoxy-2-(trimethylstannyl)pyridine (578 mg, 2.13 mmol, 5.22 eq) in dioxane (6.00 mL), Pd(PPh$_3$)$_4$ (47.0 mg, 40.7 umol, 0.100 eq), CuI (38.8 mg, 204 umol, 0.500 eq) and LiCl (34.5 mg, 814 umol, 16.7 uL, 2.00 eq) at 20° C. under N$_2$. The mixture was stirred at 100° C. for 2 h. The reaction mixture was concentrated under reduced pressure. The residue was purified by prep-TLC (SiO$_2$, Petroleum ether/Ethyl acetate=0/1). tert-butyl (S)-12-fluoro-4-(3-methoxypyridin-2-yl)-7a,13-dihydro-7H-[1,2,4]triazolo[4',3':1,6]pyrido[3,2-b]benzofuro[4,3-fg][1,4]oxazonine-14 (8H)-carboxylate (85.0 mg, crude) was obtained as a yellow solid.

327

Step 3: (S)-12-fluoro-4-(3-methoxypyridin-2-yl)-7a,
8,13,14-tetrahydro-7H-[1,2,4]triazolo[4',3':1,6]
pyrido[3,2-b]benzofuro[4,3-fg][1,4]oxazonine

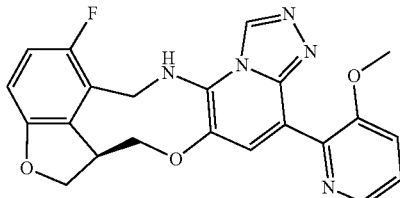

A mixture of tert-butyl (S)-12-fluoro-4-(3-methoxypyridin-2-yl)-7a,13-dihydro-7H-[1,2,4]triazolo[4',3':1,6]pyrido[3,2-b]benzofuro[4,3-fg] [1,4]oxazonine-14 (8H)-carboxylate (85.0 mg, 164 umol, 1.00 eq) in HFIP (2.00 mL) was stirred at 100° C. for 2 h. The reaction mixture was concentrated under reduced pressure. The residue was purified by prep-HPLC (column: Phenomenex Luna C18 150*30 mm*5 um; mobile phase: [water (0.04% HCl)—ACN]; B %: 20%-50%, 10 min). (S)-12-fluoro-4-(3-methoxypyridin-2-yl)-7a,8,13,14-tetrahydro-7H-[1,2,4]triazolo[4',3':1,6]pyrido[3,2-b]benzofuro[4,3-fg][1,4]oxazonine (23.0 mg, 48.9 umol, 29% yield, 97.0% purity, HCl salt) was obtained as a yellow solid. $^1$H NMR DMSO-d6 400 MHz δ=ppm 10.13 (s, 1H), 9.18 (br t, J=6.0 Hz, 1H), 8.66 (s, 1H), 8.42-8.34 (m, 1H), 7.80-7.71 (m, 1H), 7.50 (dd, J=8.4, 4.8 Hz, 1H), 7.02 (t, J=9.6 Hz, 1H), 6.75 (dd, J=8.4, 4.0 Hz, 1H), 5.06-4.92 (m, 2H), 4.54 (br t, J=9.2 Hz, 2H), 4.29-4.22 (m, 1H), 4.16 (br s, 1H), 4.00 (br s, 1H), 3.99 (s, 3H). LCMS (ESI+): m/z 420.0 (M+H).

Example 110: (S)-12-fluoro-4-(pyrimidin-4-yl)-7a,8,
13,14-tetrahydro-7H-[1,2,4]triazolo[4',3':1,6]pyrido
[3,2-b]benzofuro[4,3-fg][1,4]oxazonine Step 1: tert-butyl (S)-12-fluoro-4-(pyrimidin-4-yl)-
7a,13-dihydro-7H-[1,2,4]triazolo[4',3':1,6]pyrido[3,
2-b]benzofuro[4,3-fg][1,4]oxazonine-14 (8H)-carboxylate

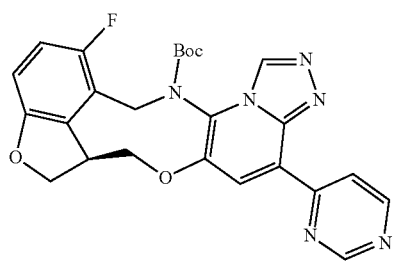

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (140 mg, 285 umol, 1.00 eq) in dioxane (6.00 mL) was added 4-(tributylstannyl)pyrimidine (210 mg, 569 umol, 2.00 eq), Pd(PPh$_3$)$_4$ (32.9 mg, 28.5 umol, 0.100 eq), LiCl (24.2 mg, 571 umol, 11.7 uL, 2.00 eq) and CuI (21.7 mg, 114 umol, 0.400 eq) at 20° C. The mixture was stirred at 100° C. for 12 h under nitrogen atmosphere. The reaction was concentrated. The residue was purified by prep-TLC (SiO$_2$, Petroleum ether/

328

Ethyl acetate=0/1). tert-butyl (S)-12-fluoro-4-(pyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (140 mg, crude) was obtained as a green solid.

Step 2: Example 151: (S)-12-fluoro-4-(pyrimidin-4-
yl)-7a,8,13,14-tetrahydro-7H-[1,2,4]triazolo[4',3':1,
6]pyrido[3,2-b]benzofuro[4,3-fg][1,4]oxazonine

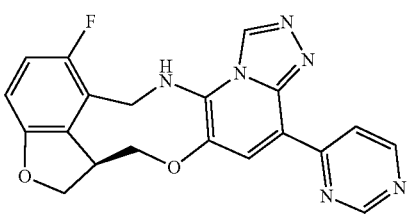 [SMILES: Fc1ccc2c3c1CNc1c(cc(-c4ccncn4)c4nncn14)OC[C@H]3CO2]

A mixture of tert-butyl (S)-12-fluoro-4-(pyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (140 mg, 285 umol, 1.00 eq) in HFIP (5.00 mL) was stirred at 100° C. for 12 h The reaction was concentrated. The residue was dissolved in DMSO (4.00 mL), the mixture was purified by acidic prep-HPLC (column: Phenomenex Luna C18 150*30 mm*5 um; mobile phase: [water (0.04% HCl)-ACN]; B %: 25%-40%, 10 min). The product-containing fraction was concentrated under reduced pressure to remove most of MeCN at 30° C. and the aqueous phase was lyophilized. (S)-12-fluoro-4-(pyrimidin-4-yl)-7a,8,13,14-tetrahydro-7H-[1,2,4]triazolo[4',3':1,6]pyrido[3,2-b]benzofuro[4,3-fg][1,4]oxazonine (36.2 mg, 84.8 umol, 29% yield, 100% purity, HCl salt) was obtained as an orange solid. $^1$H NMR DMSO-d$_6$ 400 MHz δ=ppm 9.95 (s, 1H), 9.22 (s, 1H), 9.01 (br s, 1H), 8.88 (br d, J=5.3 Hz, 1H), 8.67 (s, 2H), 6.98 (br t, J=9.5 Hz, 1H), 6.71 (dd, J=8.6, 3.5 Hz, 1H), 5.17-4.91 (m, 2H), 4.69-4.51 (m, 2H), 4.24 (dd, J=9.2, 4.1 Hz, 1H), 4.17-4.09 (m, 1H), 4.05-3.96 (m, 1H). LCMS (ESI+): m/z 391.1 (M+H).

Example 111: (S)-12-fluoro-4-(6-methylpyrimidin-
4-yl)-7a,8,13,14-tetrahydro-7H-[1,2,4]triazolo[4',3':
1,6]pyrido[3,2-b]benzofuro[4,3-fg][1,4]oxazonine Step 1: 4-methyl-6-(trimethylstannyl)pyrimidine

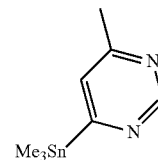

To 4-bromo-6-methylpyrimidine (200 mg, 1.16 mmol, 1.00 eq) in dioxane (4.00 mL) was added trimethyl(trimethylstannyl)stannane (757 mg, 2.31 mmol, 479 uL, 2.00 eq) and Pd(PPh$_3$)$_4$ (134 mg, 116 umol, 0.100 eq) at 20° C. The mixture was stirred at 100° C. for 12 h under nitrogen atmosphere. LC-MS showed 4-bromo-6-methylpyrimidine was consumed completely and one main peak with desired mass was detected. The obtained solution of 4-methyl-6-(trimethylstannyl)pyrimidine (297 mg, crude) was used in next step directly.

Step 2: tert-butyl (S)-12-fluoro-4-(6-methylpyrimidin-4-yl)-7a,13-dihydro-7H-[1,2,4]triazolo[4',3':1,6]pyrido[3,2-b]benzofuro[4,3-fg][1,4]oxazonine-14(8H)-carboxylate

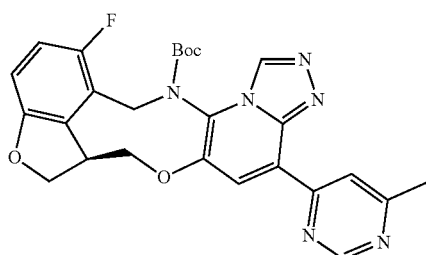

To 4-methyl-6-(trimethylstannyl)pyrimidine (297 mg, 1.16 mmol, 2.84 eq) in dioxane (4.00 μmL) was added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq), CuI (31.0 mg, 163 umol, 0.400 eq), LiCl (34.5 mg, 814 umol, 16.7 uL, 2.00 eq) and Pd(PPh$_3$)$_4$ (47.0 mg, 40.7 umol, 0.100 eq) at 20° C. The mixture was stirred at 80° C. for 2 h under nitrogen atmosphere. The reaction mixture was filtered and the filtrate was concentrated under reduced pressure. The residue was purified by prep-TLC (SiO$_2$, PE:EtOAc=1:1). tert-butyl (S)-12-fluoro-4-(6-methylpyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (180 mg, crude) was obtained as brown oil.

Step 3: (S)-12-fluoro-4-(6-methylpyrimidin-4-yl)-7a,8,13,14-tetrahydro-7H-[1,2,4]triazolo[4',3':1,6]pyrido[3,2-b]benzofuro[4,3-fg][1,4]oxazonine

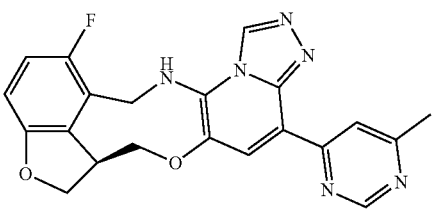 [SMILES: Cc1cc(-c2cc3c(n4cnnc24)NCc2c(F)ccc4c2[C@H](CO4)CO3)ncn1]

To tert-butyl (S)-12-fluoro-4-(6-methylpyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (180 mg, 357 umol, 1.00 eq) was added HFIP (2.00 mL) at 20° C. The mixture was stirred at 100° C. for 12 h. The reaction mixture was concentrated under reduced pressure. The crude product was purified by prep-HPLC (HCl conditions). (S)-12-fluoro-4-(6-methylpyrimidin-4-yl)-7a,8,13,14-tetrahydro-7H-[1,2,4]triazolo[4',3':1,6]pyrido[3,2-b]benzofuro[4,3-fg][1,4]oxazonine (24.9 mg, 55.9 umol, 15% yield, 98.9% purity, HCl salt) was obtained as yellow solid. $^1$H NMR CD$_3$OD 400 MHz. δ=ppm 9.60 (s, 1H), 9.26 (s, 1H), 8.89 (s, 1H), 8.41 (s, 1H), 6.94 (t, J=9.2 Hz, 1H), 6.76-6.66 (m, 1H), 5.35-5.27 (m, 1H), 5.03 (br s, 2H), 4.70-4.60 (m, 1H), 4.42-4.28 (m, 1H), 4.19-3.95 (m, 2H), 2.74 (s, 3H). LCMS (ESI+): m/z 405.1 (M+H).

Example 112: (S)-4-(3-ethyl-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine

Step 1: 3-ethyl-1-methyl-1H-pyrazol-S-ol

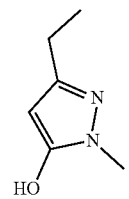

A mixture of methyl 3-oxopentanoate (5.00 g, 38.4 mmol, 4.76 mL, 1.00 eq), methylhydrazine (1.86 g, 16.2 mmol, 2.13 mL, 0.420 eq), HCl (12.0 M, 160 uL, 0.0500 eq) in EtOH (100 mL) was degassed and purged with nitrogen 3 times at 20° C., and the mixture was stirred at 80° C. for 10 h under nitrogen atmosphere. The reaction mixture was concentrated under reduced pressure. The residue was purified by flash silica gel chromatography (ISCO®; 40 g SepaFlash® Silica Flash Column, Eluent of 0-20% Ethylacetate/Petroleum ethergradient @ 50 mL/min). 3-Ethyl-1-methyl-1H-pyrazol-S-ol (1.90 g, 15.1 mmol, 39% yield) was obtained as a light red solid. $^1$H NMR DMSO-d$_6$ 400 MHz δ=ppm 10.67 (br s, 1H), 5.11 (s, 1H), 3.37 (br s, 3H), 2.34 (q, J=7.6 Hz, 2H), 1.06 (t, J=7.6 Hz, 3H).

Step 2: 3-ethyl-1-methyl-1H-pyrazol-S-yl trifluoromethanesulfonate

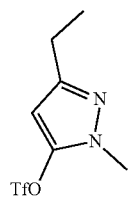 [SMILES: CCc1cc(OS(=O)(=O)C(F)(F)F)n(C)n1]

To a solution of 3-ethyl-1-methyl-1H-pyrazol-S-ol (500 mg, 3.96 mmol, 1.00 eq), 1,1,1-trifluoro-N-phenyl-N-(trifluoromethylsulfonyl)methanesulfonamide (1.70 g, 4.76 mmol, 1.20 eq) in DCM (10.0 mL) was added DIPEA (1.02 g, 7.93 mmol, 1.38 mL, 2.00 eq) at 0° C. The mixture was stirred at 20° C. for 10 h. The reaction mixture was concentrated under reduced pressure. The residue was purified by flash silica gel chromatography (ISCO®; 12 g SepaFlash® Silica Flash Column, Eluent of 0-20% Ethyl acetate/Petroleum ethergradient @ 30 mL/min). 3-ethyl-1-methyl-1H-pyrazol-S-yl trifluoromethanesulfonate (700 mg, 2.71 mmol, 68% yield) was obtained as a colourless oil.

331

Step 3: 3-ethyl-1-methyl-S-(4,4,5,5-tetramethyl-1,3,2-dioxaborolan-2-yl)-1H-pyrazole

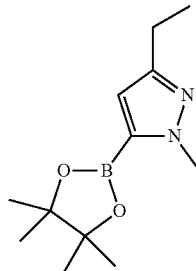

A mixture of 3-ethyl-1-methyl-1H-pyrazol-S-yl trifluoromethanesulfonate (500 mg, 1.94 mmol, 1.00 eq), 4,4,5,5-tetramethyl-2-(4,4,5,5-tetramethyl-1,3,2-dioxaborolan-2-yl)-1,3,2-dioxaborolane (740 mg, 2.91 mmol, 1.50 eq), KOAc (570 mg, 5.81 mmol, 3.00 eq), Pd(dppf)Cl₂ (142 mg, 194 umol, 0.100 eq) in dioxane (15.0 mL) was degassed and purged with nitrogen 3 times at 20° C., and the mixture was stirred at 90° C. for 10 h under nitrogen atmosphere. The reaction mixture was concentrated under reduced pressure. The residue was purified by prep-TLC (SiO₂, Petroleum ether/Ethyl acetate=1/1). 3-ethyl-1-methyl-S-(4,4,5,5-tetramethyl-1,3,2-dioxaborolan-2-yl)-1H-pyrazole (260 mg, 1.10 mmol, 56% yield) was obtained as a light yellow solid.

Step 4: tert-butyl (S)-4-(3-ethyl-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

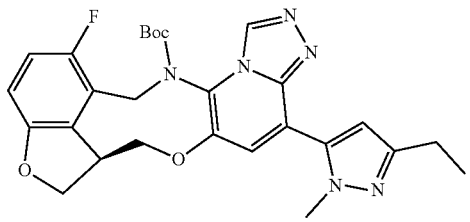 [SMILES: CCc1cc(-c2cc3c(n4cnnc24)N(C(=O)OC(C)(C)C)Cc2c(F)ccc4c2[C@H](CO4)CO3)n(C)n1]

A mixture of 3-ethyl-1-methyl-S-(4,4,5,5-tetramethyl-1,3,2-dioxaborolan-2-yl)-1H-pyrazole (127 mg, 538 umol, 1.20 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (220 mg, 448 umol, 1.00 eq), Na₂CO₃ (94.9 mg, 895 umol, 2.00 eq), Pd(dppf)Cl2 (32.8 mg, 44.8 umol, 0.100 eq) in dioxane (5.00 mL) and water (0.500 mL) was degassed and purged with nitrogen 3 times at 20° C., and the mixture was stirred at 80° C. for 10 h under nitrogen atmosphere. The reaction mixture was concentrated under reduced pressure. The residue was purified by prep-TLC (SiO₂, Petroleum ether/Ethyl acetate=0/1). tert-butyl (S)-4-(3-ethyl-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (110 mg, 211 umol, 47% yield) was obtained as a brown solid.

332

Step 5: (S)-4-(3-ethyl-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine

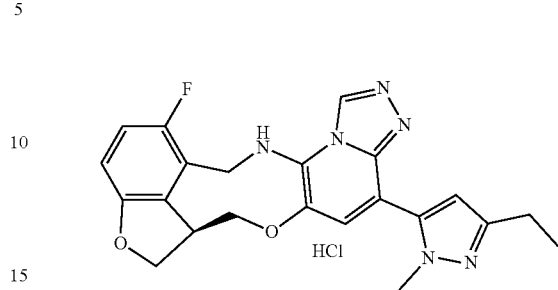

To a solution of tert-butyl (S)-4-(3-ethyl-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (110 mg, 211 umol, 1.00 eq) in DCM (2.50 mL) was added TFA (1.00 mL) at 20° C. The mixture was stirred at 20° C. for 1 hr. The reaction mixture concentrated under reduced pressure. The residue was purified by prep-HPLC (HCl condition). The product-containing fraction was concentrated under reduced pressure to remove most of MeCN at 30° C. and the aqueous phase was lyophilized. (S)-4-(3-ethyl-1-methyl-1H-pyrazol-S-yl)-12-fluoro-7a,8,13,14-tetrahydro-7H-[1,2,4]triazolo[4',3':1,6]pyrido[3,2-b]benzofuro[4,3-fg][1,4]oxazonine (36.6 mg, 79.9 umol, 37% yield, 99.8% purity, HCl) was obtained as a yellow solid. ¹H NMR CD₃OD 400 MHz δ=ppm 9.56 (s, 1H), 8.07 (s, 1H), 6.93 (dd, J=10.0, 8.8 Hz, 1H), 6.69 (dd, J=8.7, 3.9 Hz, 1H), 6.54 (s, 1H), 5.22 (d, J=14.8 Hz, 1H), 4.97 (br d, J=14.7 Hz, 1H), 4.83-4.72 (m, 1H), 4.63 (t, J=9.5 Hz, 1H), 4.32 (dd, J=9.7, 3.4 Hz, 1H), 4.12-4.00 (m, 1H), 3.97-3.86 (m, 1H), 3.81 (s, 3H), 2.76 (q, J=7.6 Hz, 2H), 1.33 (t, J=7.6 Hz, 3H). LCMS (ESI+): m/z 421.1 (M+H).

Example 113: (S)-4-(5-chloropyrimidin-4-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 5-chloro-4-iodopyrimidine

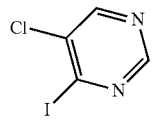

To a solution of 5-chloropyrimidin-4-amine (760 mg, 5.87 mmol, 1.00 eq) and CH₂I₂ (3.14 g, 11.7 mmol, 946 uL, 2.00 eq) in MeCN (15.0 mL) was added isopentyl nitrite (1.51 g, 12.9 mmol, 1.74 mL, 2.20 eq) in MeCN (3.00 mL) under nitrogen atmosphere at 0° C. The mixture was stirred at 0° C. for 3 h. Then the mixture was stirred at 60° C. for 36 h under nitrogen atmosphere. The reaction mixture was concentrated under reduced pressure. The residue was purified by column chromatography (SiO₂, Petroleum ether/Ethyl acetate=9/1). 5-Chloro-4-iodopyrimidine (570 mg, 2.37 mmol, 40% yield) was obtained as a light yellow solid.

Step 2: tert-butyl (S)-4-(5-chloropyrimidin-4-yl)-12-fluoro-7a,13-dihydro-7H-[1,2,4]triazolo[4',3':1,6]pyrido[3,2-b]benzofuro[4,3-fg][1,4]oxazonine-14(8H)-carboxylate

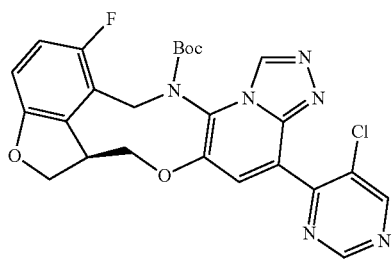 [SMILES: CC(C)(C)OC(=O)N1Cc2c(F)ccc3c2[C@H](CO3)COc2cc(-c3ncncc3Cl)c3nncn3c21]

A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14(8H)-carboxylate (200 mg, 285 umol, 1.00 eq), 5-chloro-4-iodopyrimidine (137 mg, 570 umol, 2.00 eq), Pd(t-Bu$_3$P)$_2$ (14.6 mg, 28.6 umol, 0.100 eq) in dioxane (5.00 mL) was degassed and purged with nitrogen 3 times, and the mixture was stirred at 100° C. for 16 h under nitrogen atmosphere. The reaction mixture was concentrated under reduced pressure. The residue was purified by prep-TLC (SiO$_2$, Petroleum ether/Ethyl acetate=1/3). tert-butyl (S)-4-(5-chloropyrimidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (125 mg, crude) was obtained as a yellow oil.

Step 3: (S)-4-(5-chloropyrimidin-4-yl)-12-fluoro-7a,8,13,14-tetrahydro-7H-[1,2,4]triazolo[4',3':1,6]pyrido[3,2-b]benzofuro[4,3-fg][1,4]oxazonine

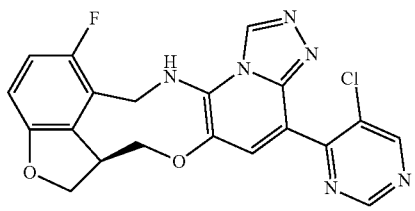

A mixture of tert-butyl (S)-4-(5-chloropyrimidin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (125 mg, 238 umol, 1.00 eq) in HFIP (5.00 mL) was stirred at 100° C. for 12 hr under nitrogen atmosphere. LC-MS indicated low conversion. The mixture was concentrated under reduced pressure. The residue was dissolved in DCM (5.00 mL) and TFA (2.00 mL) at 25° C. under nitrogen atmosphere, and the mixture was stirred at 25° C. for 1 hr. LC-MS showed that the reaction was complete. The mixture was concentrated under reduced pressure. The residue was purified by prep-HPLC (column: Phenomenex Synergi C18 150*25*10 um; mobile phase: [water (0.04% HCl)-ACN]; B %: 10%-30%, 10 min). The product-containing fraction was concentrated under reduced pressure to remove most of MeCN at 30° C. and the aqueous phase was lyophilized. (S)-4-(5-chloropyrimidin-4-yl)-12-fluoro-7a,8,13,14-tetrahydro-7H-[1,2,4]triazolo[4',3':1,6]pyrido[3,2-b]benzofuro[4,3-fg][1,4]oxazonine (22.0 mg, 46.9 umol, 19% yield, 98.3% purity, HCl) was obtained as a yellow solid. $^1$H NMR CD$_3$OD 400 MHz δ=ppm 9.65 (s, 1H), 9.20 (s, 1H), 8.98 (s, 1H), 8.95 (s, 1H), 6.95 (br t, J=9.5 Hz, 1H), 6.71 (dd, J=8.6, 3.8 Hz, 1H), 5.28 (br d, J=14.7 Hz, 1H), 5.05 (br d, J=14.7 Hz, 2H), 4.65 (br t, J=9.4 Hz, 1H), 4.35 (br d, J=7.2 Hz, 1H), 4.12 (br s, 1H), 3.98 (br s, 1H). LCMS (ESI+): m/z 425.0/427.0 (M+H)/(M+3).

Example 114: (S)-12-fluoro-4-(5-fluoropyrimidin-4-yl)-7a,8,13,14-tetrahydro-7H-[1,2,4]triazolo[4',3':1,6]pyrido[3,2-b]benzofuro[4,3-fg][1,4]oxazonine

Step 1: 5-fluoro-4-iodopyrimidine

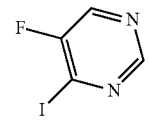

To a solution of 5-fluoropyrimidin-4-amine (250 mg, 2.21 mmol, 1.00 eq) and CH$_2$I$_2$ (1.18 g, 4.42 mmol, 357 uL, 2.00 eq) in MeCN (2.00 mL) was added isopentyl nitrite (570 mg, 4.87 mmol, 655 uL, 2.20 eq) in MeCN (0.500 mL) at 0° C. The mixture was stirred at 0° C. for 1 hr. Then the mixture was warmed to 60° C. The mixture was stirred at 60° C. for 1 hr. The residue was purified by prep-TLC (SiO$_2$, Petroleum ether/Ethyl acetate=10/1). 5-fluoro-4-iodopyrimidine (80.0 mg, 357 umol, 16% yield) was obtained as a yellow solid.

Step 2: 5-fluoro-4-(trimethylstannyl)pyrimidine

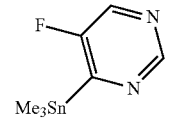

A mixture of 5-fluoro-4-iodopyrimidine (80.0 mg, 357 umol, 1.00 eq), trimethyl(trimethylstannyl)stannane (234 mg, 715 umol, 148 uL, 2.00 eq) and Pd(PPh$_3$)$_4$ (41.3 mg, 35.7 umol, 0.100 eq) in dioxane (3.00 mL) was degassed and purged with nitrogen 3 times at 20° C., and the mixture was stirred at 100° C. for 1 hr under nitrogen atmosphere. LC-MS showed 5-fluoro-4-iodopyrimidine was consumed completely and one main peak with desired mass was detected. 5-fluoro-4-(trimethylstannyl)pyrimidine (93.2 mg, crude) in 3.00 mL of dioxane was used in the next step directly.

Step 3: tert-butyl (S)-12-fluoro-4-(5-fluoropyrimidin-4-yl)-7a,13-dihydro-7H-[1,2,4]triazolo[4',3':1,6]pyrido[3,2-b]benzofuro[4,3-fg][1,4]oxazonine-14(8H)-carboxylate

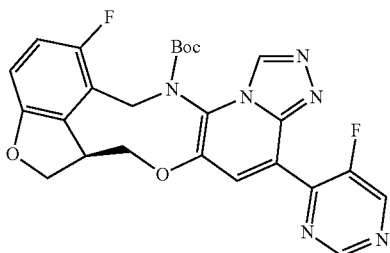

A mixture of 5-fluoro-4-(trimethylstannyl)pyrimidine (93.2 mg, 357 umol, 1.00 eq) in dioxane (3.00 μmL), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (176 mg, 358 umol, 1.00 eq), LiCl (22.7 mg, 535 umol, 11.0 uL, 1.50 eq), CuI (34.0 mg, 179 umol, 0.500 eq) and Pd(PPh$_3$)$_4$ (41.3 mg, 35.7 umol, 0.100 eq) in dioxane (1.00 mL) was degassed and purged with nitrogen for 3 times at 20° C., and the mixture was stirred at 100° C. for 12 h under nitrogen atmosphere. The reaction mixture was concentrated under reduced pressure. The residue was purified by prep-TLC (SiO$_2$, Ethyl acetate/Methanol=10/1). tert-butyl (S)-12-fluoro-4-(5-fluoropyrimidin-4-yl)-7a,13-dihydro-7H-[1,2,4]triazolo[4',3':1,6]pyrido[3,2-b]benzofuro[4,3-fg][1,4]oxazonine-14(8H)-carboxylate (80.0 mg, crude) was obtained as a yellow solid.

Step 4: (S)-12-fluoro-4-(5-fluoropyrimidin-4-yl)-7a,8,13,14-tetrahydro-7H-[1,2,4]triazolo[4',3':1,6]pyrido[3,2-b]benzofuro[4,3-fg][1,4]oxazonine

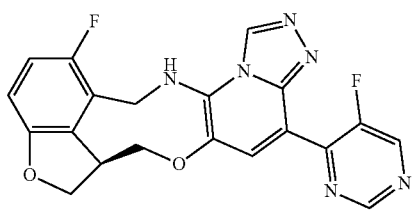 [SMILES: Fc1cncnc1-c1cc2c(n3cnnc13)NCc1c(F)ccc3c1[C@H](CO3)CO2]

A mixture of tert-butyl (S)-12-fluoro-4-(5-fluoropyrimidin-4-yl)-7a,13-dihydro-7H-[1,2,4]triazolo[4',3':1,6]pyrido[3,2-b]benzofuro[4,3-fg][1,4]oxazonine-14(8H)-carboxylate (75.0 mg, 148 umol, 1.00 eq) in HFIP (2.00 mL) was stirred at 80° C. for 10 h under nitrogen atmosphere. The reaction mixture was concentrated under reduced pressure. The residue was purified by prep-HPLC (HCl condition). The product-containing fraction was concentrated under reduced pressure to remove most of MeCN at 30° C. and the aqueous phase was lyophilized. (S)-12-fluoro-4-(5-fluoropyrimidin-4-yl)-7a,8,13,14-tetrahydro-7H-[1,2,4]triazolo[4',3':1,6]pyrido[3,2-b]benzofuro[4,3-fg][1,4]oxazonine (19.6 mg, 43.7 umol, 29% yield, 99.2% purity, HCl) was obtained as a yellow solid. $^1$H NMR CD$_3$OD 400 MHz δ=ppm 9.62 (s, 1H), 9.14 (d, J=2.9 Hz, 1H), 8.88 (d, J=4.4 Hz, 1H), 8.68 (d, J=1.5 Hz, 1H), 6.95 (dd, J=10.3, 8.8 Hz, 1H), 6.71 (dd, J=8.8, 3.9 Hz, 1H), 5.36-5.24 (m, 1H), 5.13-4.94 (m, 2H), 4.70-4.58 (m, 1H), 4.43-4.30 (m, 1H), 4.17-4.09 (m, 1H), 4.06-3.89 (m, 1H). LCMS (ESI+): m/z 409.0 (M+H).

Example 115: (S)-4-(1,4-dimethyl-1H-imidazol-5-yl)-12-fluoro-7a,8,13,14-tetrahydro-7H-[1,2,4]triazolo[4',3':1,6]pyrido[3,2-b]benzofuro[4,3-fg][1,4]oxazonine

Step 1: 5-bromo-1,4-dimethyl-1H-imidazole

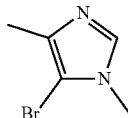

To a solution of NaH (745 mg, 18.6 mmol, 60% purity, 1.20 eq) in THF (12.5 mL) was added 5-bromo-4-methyl-1H-imidazole (2.50 g, 15.5 mmol, 1.00 eq) in THF (12.5 mL) at 0° C., and the mixture was stirred at 20° C. for 0.5 hr. To the reaction mixture was added MeI (3.31 g, 23.3 mmol, 1.45 mL, 1.50 eq) dropwise at 20° C. The mixture was stirred at 20° C. for 16 hr. The reaction mixture was quenched by addition of water (10.0 mL) and extracted with EtOAc (20.0 mL*5). The combined organic layers were dried over Na$_2$SO$_4$, filtered, and concentrated under reduced pressure. The residue was purified by prep-TLC (SiO$_2$, Petroleum ether:Ethyl acetate=0:1). 5-Bromo-1,4-dimethyl-1H-imidazole (540 mg, 3.09 mmol, 19% yield) was obtained as a light-yellow oil. $^1$H NMR CDCl$_3$ 400 MHz δ=ppm 7.47 (s, 1H), 3.57 (s, 3H), 2.19 (s, 3H).

Step 2: tert-butyl (S)-4-(1,4-dimethyl-1H-imidazol-5-yl)-12-fluoro-7a,13-dihydro-7H-[1,2,4]triazolo[4',3':1,6]pyrido[3,2-b]benzofuro[4,3-fg][1,4]oxazonine-14(8H)-carboxylate

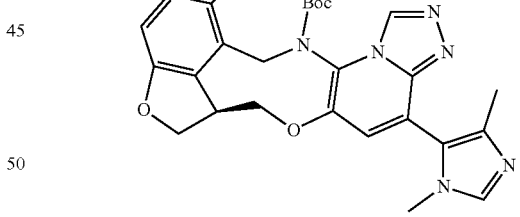

The reaction was set up in two batches. A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14(8H)-carboxylate (100 mg, 143 umol, 1.10 eq), 5-bromo-1,4-dimethyl-1H-imidazole (68.0 mg, 389 umol, 3.00 eq), Pd(t-Bu$_3$P)$_2$ (13.3 mg, 26.0 umol, 0.201 eq) in dioxane (5.00 mL) was degassed and purged with nitrogen 3 times, and the mixture was stirred at 100° C. for 16 h under nitrogen atmosphere. The batches we combined and concentrated under reduced pressure. The residue was dissolved in MeOH (5.00 mL) and silica-thiol (300 mg, modified silicon gel for eliminating Pd, irregular silica gel, 100-200 mesh, Chlorides (Cl), %≤0.004, particle size distribution 45-75 um) was added at 20° C. and stirred at 20°

C. for 3 h. The suspension was filtered, the filtrate was concentrated and purified by prep-HPLC (column: Welch Xtimate C18 150*25 mm*5 um; mobile phase: [water (10 mM NH₄HCO₃)—ACN]; B %: 40%-65%, 10 min). The product-containing fraction was concentrated under reduced pressure to remove most of MeCN at 30° C. and the aqueous phase was lyophilized. tert-butyl (S)-4-(1,4-dimethyl-1H-imidazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (13 mg, 25.7 umol, 9% yield) was obtained as a colorless oil.

Step 3: (S)-4-(1,4-dimethyl-1H-imidazol-S-yl)-12-fluoro-7a,8,13,14-tetrahydro-7H-[1,2,4]triazolo[4',3':1,6]pyrido[3,2-b]benzofuro[4,3-fg][1,4]oxazonine

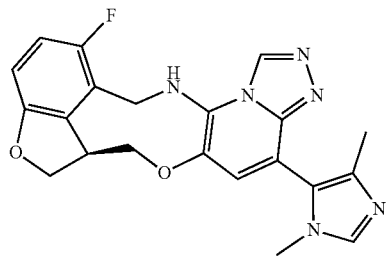 [SMILES: Cc1ncn(C)c1-c1cc2c(n3cnnc13)NCc1c(F)ccc3c1[C@H](CO3)CO2]

A mixture of tert-butyl (S)-4-(1,4-dimethyl-1H-imidazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (13.0 mg, 25.7 umol, 1.00 eq) in 1,1,1,3,3,3-hexafluoropropan-2-ol (1.00 mL) was degassed and purged with nitrogen 3 times, and the mixture was stirred at 100° C. for 36 hr under nitrogen atmosphere. The mixture was concentrated under reduced pressure. The residue was dissolved in DCM (2.00 mL) and TFA (1.54 g, 13.5 mmol, 1.00 mL, 526 eq) was added dropwise at 20° C. The mixture was stirred at 20° C. for 1 hr. The reaction mixture was concentrated under reduced pressure. The residue was purified by prep-HPLC (column: Phenomenex Synergi C18 150*25*10 um; mobile phase: [water (0.04% HCl)-ACN]; B %: 1%-20%, 10 min). The product-containing fraction was concentrated under reduced pressure to remove most of MeCN at 30° C. and the aqueous phase was lyophilized. The obtained product was combined with another batch of 5 mg. ¹H NMR indicated insufficient purity. The product was purified by prep-HPLC (column: Phenomenex Luna C18 150*30 mm*5 um; mobile phase: [water (0.04% HCl)-ACN]; B %: 15%-45%, 10 min). The product-containing fraction was concentrated under reduced pressure to remove most of MeCN at 30° C. and the aqueous phase was lyophilized. (S)-4-(1,4-dimethyl-1H-imidazol-S-yl)-12-fluoro-7a,8,13,14-tetrahydro-7H-[1,2,4]triazolo[4',3':1,6]pyrido[3,2-b]benzofuro[4,3-fg][1,4]oxazonine (10.1 mg, 22.7 umol, 88% yield, 99.6% purity, HCl salt) was obtained as a white solid. ¹H NMR CD₃OD 400 MHz δ=ppm 9.57 (s, 1H), 9.05 (s, 1H), 8.10 (s, 1H), 6.93 (t, J=9.4 Hz, 1H), 6.69 (dd, J=8.4, 3.7 Hz, 1H), 5.23 (br d, J=14.6 Hz, 1H), 4.97 (br d, J=15.0 Hz, 1H), 4.79 (br s, 1H), 4.63 (br t, J=9.3 Hz, 1H), 4.31 (br d, J=6.8 Hz, 1H), 4.07 (br s, 1H), 3.92 (br d, J=10.6 Hz, 1H), 3.70 (br s, 3H), 2.24 (br s, 3H). LCMS (ESI+): m/z 407.0 (M+H).

Example 116: (S)-4-(1,5-dimethyl-1H-imidazol-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 2-bromo-1,5-dimethyl-1H-imidazole

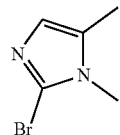

Two parallel reactions were set up. To a solution of 2-bromo-S-methyl-1H-imidazole (600 mg, 3.73 mmol, 1.00 eq) in THF (8.00 mL) was added NaH (298 mg, 7.45 mmol, 60% purity, 2.00 eq) at 0° C. The mixture was stirred at 0° C. for 0.5 hr under nitrogen atmosphere. MeI (1.06 g, 7.45 mmol, 464 uL, 2.00 eq) was added to the mixture at 0° C. and the mixture was stirred at 20° C. for 12 h under nitrogen atmosphere. LCMS showed 2-bromo-S-methyl-1H-imidazole was consumed completely and the desired mass was detected. TLC (SiO₂, Petroleum ether/Ethyl acetate=1/1) showed two new spots formed. The batches were combined, water (10.0 mL) was added, and the mixture was extracted with ethyl acetate (10.0 mL*3). The combined organic layers were dried over MgSO₄ and concentrated under reduced pressure. The residue was purified by column chromatography (SiO₂, Petroleum ether/Ethyl acetate=1/0 to 0/1). 2-Bromo-1,5-dimethyl-1H-imidazole (450 mg, 2.57 mmol, 34% yield) was obtained as a yellow oil.

Step 2: tert-butyl (S)-4-(1,5-dimethyl-1H-imidazol-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

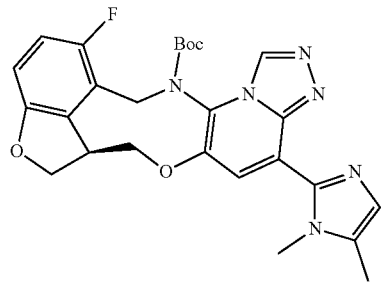 [SMILES: Cc1cnc(-c2cc3c(n4cnnc24)N(C(=O)OC(C)(C)C)Cc2c(F)ccc4c2[C@H](CO4)CO3)n1C]

To a mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (200 mg, 285 umol, 1.00 eq) in dioxane (8.00 mL) was added 2-bromo-1,5-dimethyl-1H-imidazole (99.8 mg, 570 umol, 2.00 eq), CuI (21.7 mg, 114 umol, 0.400 eq), LiCl (24.2 mg, 570 umol, 11.7 uL, 2.00 eq) and Pd(PPh₃)₄ (33.0 mg, 28.5 umol, 0.100 eq) at 20° C. The mixture was stirred at 100° C. for 12 h under nitrogen atmosphere. The reaction mixture was concentrated. The residue was dissolved in DMSO (7.00 mL) and purified by prep-HPLC (column: Phenomenex Luna C18 200*40 mm*10 um; mobile phase: [water (0.2% FA)—ACN]; B %: 25%-45%, 10 min). The product-containing fraction was concentrated under reduced pressure to remove most of MeCN at 30° C. and the aqueous phase was lyophilized. tert-Butyl (S)-4-(1,5-dimethyl-1H-imidazol-2-yl)-12-fluoro-7a,13-dihydro-7H-[1,2,4]triazolo [4',3':1,6]pyrido[3,2-b]benzofuro[4,3-fg][1,4]oxazonine-14 (8H)-carboxylate (140 mg, 253 umol, 88% yield, formate salt) was obtained as a green solid.

Step 3: (S)-4-(1,5-dimethyl-1H-imidazol-2-yl)-12-fluoro-7a,8,13,14-tetrahydro-7H-[1,2,4]triazolo[4',3':1,6]pyrido[3,2-b]benzofuro[4,3-fg][1,4]oxazonine

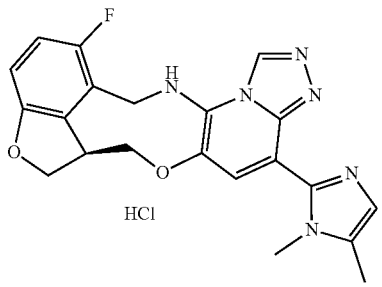 [SMILES: Cc1cnc(-c2cc3c(n4cnnc24)NCc2c(F)ccc4c2[C@H](CO4)CO3)n1C ; Cl]

A mixture of tert-butyl (S)-4-(1,5-dimethyl-1H-imidazol-2-yl)-12-fluoro-7a,13-dihydro-7H-[1,2,4]triazolo[4',3':1,6] pyrido[3,2-b]benzofuro[4,3-fg][1,4]oxazonine-14 (8H)-carboxylate (140 mg, 253 umol, 1.00 eq, FA) in HFIP (8.00 mL) was stirred at 100° C. for 6 h. The reaction was concentrated. The residue was dissolved in DMSO (5.00 mL). The suspension was filtered, the filtrate was concentrated and purified by acidic prep-HPLC (column: Waters Xbridge Prep OBD C18 150*40 mm*10 um; mobile phase: [water (0.04% NH$_3$H$_2$O+10 mM NH$_4$HCO$_3$)—ACN]; B %: 15%-55%, 10 min). The product-containing fraction was concentrated under reduced pressure to remove most of MeCN at 30° C. and the aqueous phase was lyophilized. The obtained product was dissolved in water (2.00 mL), then HCl (12.0 M, 0.0100 mL) was added to the mixture, and the solution was re-lyophilized. (S)-4-(1,5-dimethyl-1H-imidazol-2-yl)-12-fluoro-7a,8,13,14-tetrahydro-7H-[1,2,4]triazolo[4',3':1,6] pyrido[3,2-b]benzofuro[4,3-fg] [1,4]oxazonine (17.1 mg, 38.4 umol, 15% yield, 99.4% purity, HCl salt) was obtained as a green solid. $^1$H NMR CD$_3$OD+1 drop HCl in D$_2$O 400 MHz δ=ppm 9.80 (s, 1H), 8.36 (s, 1H), 7.57 (s, 1H), 7.05-6.86 (m, 1H), 6.71 (dd, J=8.7, 3.9 Hz, 1H), 5.27 (br d, J=14.8 Hz, 1H), 5.09 (br s, 1H), 4.81 (br s, 1H), 4.65 (t, J=9.5 Hz, 1H), 4.33 (br d, J=6.7 Hz, 1H), 4.15 (br s, 1H), 3.99 (br s, 1H), 3.74 (s, 3H), 2.49 (s, 3H). LCMS (ESI+): m/z 407.1 (M+H).

Example 117: (S)-12-fluoro-4-(2-methylpyrimidin-4-yl)-7a,8,13,14-tetrahydro-7H-[1,2,4]triazolo[4',3': 1,6]pyrido[3,2-b]benzofuro[4,3-fg][1,4]oxazonine Step 1: 2-methyl-4-(trimethylstannyl)pyrimidine

To a solution of 4-bromo-2-methylpyrimidine (250 mg, 1.44 mmol, 1.00 eq) in dioxane (8.00 mL) was added trimethyl(trimethylstannyl)stannane (946 mg, 2.89 mmol, 599 uL, 2.00 eq) and Pd(PPh$_3$)$_4$ (167 mg, 145 umol, 0.100 eq) at 20° C. under N$_2$. The mixture was stirred at 100° C. for 3 h. LC-MS showed the 4-bromo-2-methylpyrimidine was consumed completely and the desired mass was detected. The obtained solution of 2-methyl-4-(trimethylstannyl)pyrimidine was used in the next step directly.

Step 2: tert-butyl (S)-12-fluoro-4-(2-methylpyrimidin-4-yl)-7a,13-dihydro-7H-[1,2,4]triazolo[4',3':1,6] pyrido[3,2-b]benzofuro[4,3-fg][1,4]oxazonine-14 (8H)-carboxylate

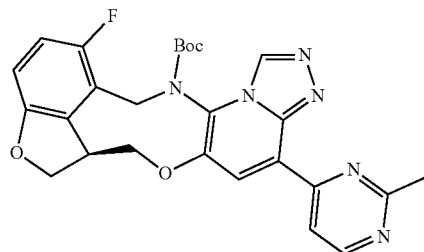

To a solution of 2-methyl-4-(trimethylstannyl)pyrimidine (157 mg, 611 umol, 2.00 eq) in dioxane (8.00 mL) was added tert-butyl (S)-4-bromo-12-fluoro-7a,13-dihydro-7H-[1,2,4]triazolo[4',3':1,6]pyrido[3,2-b]benzofuro[4,3-fg][1,4] oxazonine-14 (8H)-carboxylate (150 mg, 305 umol, 1.00 eq), Pd(PPh$_3$)$_4$ (35.3 mg, 30.6 umol, 0.100 eq), CuI (23.3 mg, 122 umol, 0.400 eq) and LiCl (25.9 mg, 611 umol, 12.5 uL, 2.00 eq) at 20° C. under N$_2$. The mixture was stirred at 100° C. for 12 h. The reaction mixture was concentrated under reduced pressure. The residue was purified by prep-TLC (SiO$_2$, Petroleum ether:Ethyl acetate=0:1). tert-Butyl (S)-12-fluoro-4-(2-methylpyrimidin-4-yl)-7a,13-dihydro-7H-[1,2,4]triazolo[4',3':1,6]pyrido[3,2-b]benzofuro[4,3-fg] [1,4]oxazonine-14 (8H)-carboxylate (154 mg, crude) was obtained as a brown oil.

Step 3: (S)-12-fluoro-4-(2-methylpyrimidin-4-yl)-7a,8,13,14-tetrahydro-7H-[1,2,4]triazolo[4',3':1,6] pyrido[3,2-b]benzofuro[4,3-fg][1,4]oxazonine

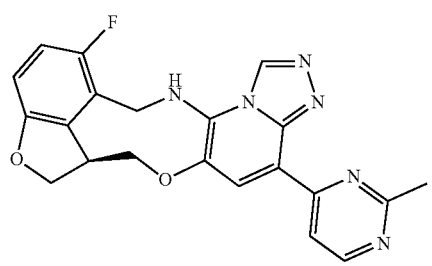 [SMILES: Cc1nccc(-c2cc3c(n4cnnc24)NCc2c(F)ccc4c2[C@H](CO4)CO3)n1]

To the HFIP (2.00 mL) was added tert-butyl (S)-12-fluoro-4-(2-methylpyrimidin-4-yl)-7a,13-dihydro-7H-[1,2,4]triazolo[4',3':1,6]pyrido[3,2-b]benzofuro[4,3-fg] [1,4] oxazonine-14 (8H)-carboxylate (154 mg, 305 umol, 1.00 eq) at 20° C. The mixture was stirred at 100° C. for 12 h. The reaction mixture was concentrated under reduced pressure.

The residue was dissolved in DMSO (5.00 mL). The suspension was purified by neutral prep-HPLC (column: Waters Xbridge BEH C18 100*25 mm*5 um; mobile phase: [water (10 mM NH$_4$HCO$_3$)—ACN]; B %: 20%-50%, 8 min). The product was isolated by lyophilization. The product (30.0 mg) was obtained as a yellow solid with insufficient purity. The material was dissolved in DMSO (5.00 mL). The suspension was purified twice by acidic prep-HPLC (column: Phenomenex Luna C18 150*30 mm*5 um; mobile phase: [water (0.04% HCl)-ACN]; B %: 25%-37%, 10 min). The product-containing fraction was lyophilized. (S)-12-fluoro-4-(2-methylpyrimidin-4-yl)-7a,8,13,14-tetrahydro-7H-[1,2,4]triazolo[4',3':1,6]pyrido[3,2-b]benzofuro[4,3-fg][1,4]oxazonine (21.1 mg, 46.9 umol, 15% yield, 97.9% purity, HCl alt) was obtained as a yellow solid. $^1$H NMR CD$_3$OD 400 MHz δ=ppm 9.63 (s, 1H), 8.92 (s, 1H), 8.87 (d, J=6.6 Hz, 1H), 8.45 (d, J=6.6 Hz, 1H), 6.94 (t, J=9.5 Hz, 1H), 6.71 (dd, J=8.7, 3.8 Hz, 1H), 5.33 (br d, J=14.4 Hz, 1H), 5.04 (br s, 2H), 4.66 (br t, J=9.2 Hz, 1H), 4.36 (br s, 1H), 4.11 (br s, 1H), 4.06-3.91 (m, 1H), 2.99 (s, 3H). LCMS (ESI+): m/z 405.0 (M+H).

Example 118: (S)-4-(3-chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-chloro-2-(tributylstannyl)pyridine

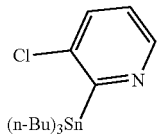

To a solution of 2-bromo-3-chloropyridine (6.00 g, 31.2 mmol, 1.00 eq) in THF (50.0 mL) was added n-BuLi (2.50 M, 13.7 mL, 1.10 eq) at −78° C. under nitrogen and the mixture was stirred at −78° C. for 0.5 hr. Tributyl(chloro)stannane (20.3 g, 62.4 mmol, 16.8 mL, 2.00 eq) was added to the mixture under nitrogen atmosphere at −78° C. and the resulting mixture was stirred at −78° C. for 1.5 h under N$_2$. The mixture was quenched with saturated aqueous NH$_4$Cl solution (30.0 mL) and the mixture was extracted with EtOAc (30.0 mL*3). The combined organic layers were dried over Na$_2$SO$_4$ and concentrated under reduced pressure. The mixture was purified by MPLC (SiO$_2$, PE/EtOAc=1/0 to 3/1) to give the crude product. The crude product was purified by neutral prep-HPLC. 3-Chloro-2-(tributylstannyl)pyridine (80.0 mg, 199 umol, 6.37e-1% yield) was obtained as yellow oil.

Step 2: tert-butyl (S)-4-(3-chloropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

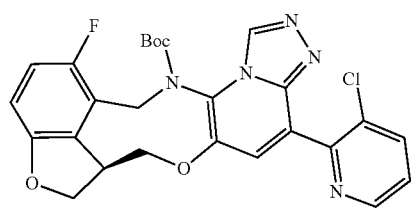 [SMILES: CC(C)(C)OC(=O)N1Cc2c(F)ccc3c2[C@H](CO3)COc2cc(-c3ncccc3Cl)c3nncn3c21]

To a stirred solution of 3-chloro-2-(tributylstannyl)pyridine (73.8 mg, 183 umol, 1.00 eq) in dioxane (2.00 mL) was added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (90.0 mg, 183 umol, 1.00 eq), CuI (14.0 mg, 73.3 umol, 0.400 eq), LiCl (15.5 mg, 366 umol, 7.50 uL, 2.00 eq) and Pd(PPh$_3$)$_4$ (21.2 mg, 18.3 umol, 0.100 eq) at 25° C. under N$_2$. The resulting mixture was stirred at 80° C. for 12 h. The mixture was concentrated under reduced pressure. The mixture was purified by prep-TLC (SiO$_2$, PE/EtOAc=0/1). tert-butyl (S)-4-(3-chloropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (90.0 mg, 172 umol, 93% yield) was obtained as yellow oil.

Step 3: (S)-4-(3-chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine

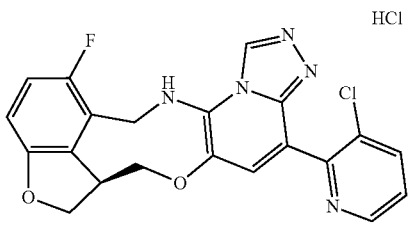 [SMILES: Cl ; Fc1ccc2c3c1CNc1c(cc(-c4ncccc4Cl)c4nncn14)OC[C@H]3CO2]

To tert-butyl (S)-4-(3-chloropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (90.0 mg, 172 umol, 1.00 eq) was added HFIP (2.00 mL) at 25° C. and the mixture was stirred at 80° C. for 12 h. The mixture was concentrated under reduced pressure. The mixture was purified by acidic prep-HPLC (HCl). (S)-4-(3-Chloropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine (25.3 mg, 53.7 umol, 31% yield, 97.7% purity, HCl salt) was obtained as an orange solid. $^1$H NMR CD$_3$OD 400 MHz δ=ppm 9.57 (s, 1H), 8.53 (d, J=5.3 Hz, 1H), 8.21 (s, 1H), 7.83 (s, 1H), 7.68 (d, J=5.3 Hz, 1H), 6.98-6.86 (m, 1H), 6.69 (dd, J=8.6, 3.9 Hz, 1H), 5.21 (d, J=14.8 Hz, 1H), 4.97 (br d, J=14.3 Hz, 1H), 4.84-4.78 (m, 1H), 4.64 (t, J=9.3 Hz, 1H), 4.34 (dd, J=9.8, 3.1 Hz, 1H), 4.13-3.91 (m, 2H). LCMS (ESI+): m/z 424.0 (M+H).

Example 119: (S)-4-(5-chloro-3-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine Step 1:
5-chloro-3-methyl-2-(trimethylstannyl)pyridine

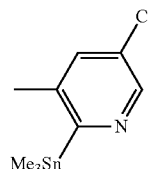

A mixture of 2-bromo-S-chloro-3-methylpyridine (150 mg, 727 umol, 1.00 eq), trimethyl(trimethylstannyl)stannane (476 mg, 1.45 mmol, 301 uL, 2.00 eq), Pd(PPh$_3$)$_4$ (84.0 mg, 72.7 umol, 0.100 eq) in dioxane (5.00 mL) was degassed and purged with nitrogen 3 times, and the mixture was stirred at 100° C. for 12 hr under nitrogen atmosphere. The obtained solution of 5-chloro-3-methyl-2-(trimethylstannyl)pyridine was used in the next step without further purification.

Step 2: tert-butyl (S)-4-(5-chloro-3-methylpyridin-2-yl)-12-fluoro-7a,13-dihydro-7H-[1,2,4]triazolo[4',3':1,6]pyrido[3,2-b]benzofuro[4,3-fg][1,4]oxazo-nine-14 (8H)-carboxylate

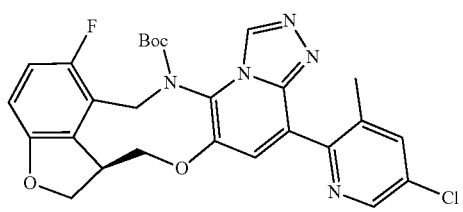 [SMILES: Cc1cc(Cl)cnc1-c1cc2c(n3cnnc13)N(C(=O)OC(C)(C)C)Cc1c(F)ccc3c1[C@H](CO3)CO2]

A mixture of 5-chloro-3-methyl-2-(trimethylstannyl)pyridine (211 mg, 727 umol, 2.38 eq) in dioxane (5.00 μmL), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq), Pd(PPh$_3$)$_4$ (35.3 mg, 30.5 umol, 0.100 eq), LiCl (19.4 mg, 458 umol, 9.37 uL, 1.50 eq) and CuI (29.1 mg, 153 umol, 0.500 eq) was degassed and purged with nitrogen 3 times, and then the mixture was stirred at 100° C. for 16 h under nitrogen atmosphere. The reaction mixture was concentrated under reduced pressure. The residue was purified by prep-TLC (SiO$_2$, Petroleum ether/Ethyl acetate=1/1). tert-butyl (S)-4-(5-chloro-3-methylpyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (127 mg, crude) was obtained as a yellow oil.

Step 3: (S)-4-(5-chloro-3-methylpyridin-2-yl)-12-fluoro-7a,8,13,14-tetrahydro-7H-[1,2,4]triazolo[4',3':1,6]pyrido[3,2-b]benzofuro[4,3-fg][1,4]oxazonine

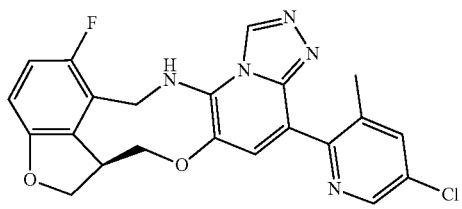 [SMILES: Cc1cc(Cl)cnc1-c1cc2c(n3cnnc13)NCc1c(F)ccc3c1[C@H](CO3)CO2]

A mixture of tert-butyl (S)-4-(5-chloro-3-methylpyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 223 umol, 1.00 eq) in TFA (2.00 mL) and DCM (4.00 mL) was stirred at 25° C. for 1 hr under nitrogen atmosphere. The mixture was concentrated under reduced pressure. The residue was purified by prep-HPLC (column: Phenomenex Luna C18 150*30 mm*5 um; mobile phase: [water (0.04% HCl)-ACN]; B %: 20%-45%, 10 min). The product-containing fraction was concentrated under reduced pressure to remove most of MeCN at 30° C. and the aqueous phase was lyophilized. (S)-4-(5-chloro-3-methylpyridin-2-yl)-12-fluoro-7a,8,13,14-tetrahydro-7H-[1,2,4]triazolo[4',3':1,6]pyrido[3,2-b]benzofuro[4,3-fg] [1,4]oxazonine (17.1 mg, 36.0 umol, 16% yield, 99.9% purity, HCl salt) was obtained as a light yellow solid. $^1$H NMR CD$_3$OD 400 MHz δ=ppm 9.54 (s, 1H), 8.58 (d, J=1.8 Hz, 1H), 8.21 (s, 1H), 7.96 (d, J=1.7 Hz, 1H), 6.94 (t, J=9.5 Hz, 1H), 6.70 (dd, J=8.7, 3.9 Hz, 1H), 5.21 (d, J=14.8 Hz, 1H), 5.00 (br d, J=14.8 Hz, 1H), 4.77 (br d, J=5.0 Hz, 1H), 4.63 (t, J=9.4 Hz, 1H), 4.33 (dd, J=9.7, 3.3 Hz, 1H), 4.17-4.03 (m, 1H), 4.02-3.89 (m, 1H), 2.50 (s, 3H). LCMS (ESI+): m/z 438.0 (M+H).

Example 120: (S)-4-(3-chloro-S-fluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazo-nine Step 1: 3-chloro-S-fluoro-2-iodopyridine

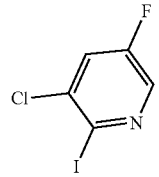

To a solution of 3-chloro-S-fluoropyridin-2-amine (450 mg, 3.07 mmol, 1.00 eq) and CuI (1.17 g, 6.14 mmol, 2.00 eq) in MeCN (8.00 mL) was added isopentyl nitrite (791 mg, 6.76 mmol, 910 uL, 2.20 eq) in MeCN (2.00 mL) at 0° C. under nitrogen atmosphere. The mixture was stirred at 0° C. for 1 hr and then the mixture was stirred at 60° C. for 12 h under nitrogen atmosphere. The reaction was filtered, water (10.0 mL) was added to the filtrate. The obtained solution was extracted with ethyl acetate (10.0 mL*3), the combined organic layers were dried over MgSO$_4$, and concentrated under reduced pressure. The residue was purified by prep-TLC (SiO$_2$, Petroleum ether/Ethyl acetate=10/1). 3-Chloro-S-fluoro-2-iodopyridine (230 mg, 893 umol, 29% yield) was obtained as a white solid.

Step 2: tert-butyl (S)-4-(3-chloro-S-fluoropyridin-2-yl)-12-fluoro-7a,13-dihydro-7H-[1,2,4]triazolo[4',3':1,6]pyrido[3,2-b benzofuro[4,3-fg][1,4]oxazonine-14 (8H)-carboxylate

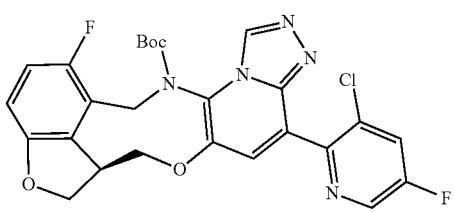 [SMILES: CC(C)(C)OC(=O)N1Cc2c(F)ccc3c2[C@H](CO3)COc2cc(-c3ncc(F)cc3Cl)c3nncn3c21]

To a mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (200 mg, 285 umol, 1.00 eq) in dioxane (6.00 mL) were added 3-chloro-S-fluoro-2-iodopyridine (147 mg, 570 umol, 2.00 eq), Pd(PPh₃)₄ (33.0 mg, 28.5 umol, 0.100 eq), CuI (21.7 mg, 114 umol, 0.400 eq) and LiCl (24.2 mg, 570 umol, 11.7 uL, 2.00 eq) at 20° C. The mixture was stirred at 100° C. for 12 h under nitrogen atmosphere. The reaction mixture was filtered, the filtrate was concentrated. The residue was purified by prep-TLC (SiO₂, Petroleum ether/Ethyl acetate=0/1). tert-butyl (S)-4-(3-chloro-S-fluoropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, crude) was obtained as a yellow oil.

Step 3: (S)-4-(3-chloro-S-fluoropyridin-2-yl)-12-fluoro-7a,8,13,14-tetrahydro-7H-[1,2,4]triazolo[4',3':1,6]pyrido[3,2-b]benzo furo[4,3-fg][1,4]oxazonine

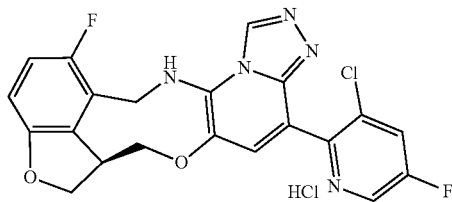 [SMILES: Fc1cnc(-c2cc3c(n4cnnc24)NCc2c(F)ccc4c2[C@H](CO4)CO3)c(Cl)c1 ; Cl]

A mixture of tert-butyl (S)-4-(3-chloro-S-fluoropyridin-2-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (80.0 mg, 148 umol, 1.00 eq) in HFIP (5.00 mL) was stirred at 100° C. for 3 h. The reaction was concentrated. The residue was dissolved in DMSO (4.00 mL). The suspension was purified by acidic prep-HPLC (column: Phenomenex Luna C18 150*30 mm*5 um; mobile phase: [water (0.04% HCl)-ACN]; B %: 20%-45%, 10 min). The product-containing fraction was concentrated under reduced pressure to remove most of MeCN at 30° C. and the aqueous phase was lyophilized. (S)-4-(3-chloro-S-fluoropyridin-2-yl)-12-fluoro-7a,8,13,14-tetrahydro-7H-[1,2,4]triazolo[4',3':1,6]pyrido[3,2-b]benzofuro[4,3-fg][1,4]oxazonine (12.5 mg, 26.1 umol, 17% yield, 99.8% purity, HCl) was obtained as a green solid. ¹H NMR CD₃OD 400 MHz δ=ppm 9.52 (s, 1H), 8.63 (d, J=2.4 Hz, 1H), 8.51 (s, 1H), 8.05 (dd, J=8.0, 2.3 Hz, 1H), 6.92 (t, J=9.6 Hz, 1H), 6.68 (dd, J=8.7, 3.6 Hz, 1H), 5.20 (d, J=15.0 Hz, 1H), 4.98 (br d, J=15.0 Hz, 1H), 4.76 (br s, 1H), 4.61 (t, J=9.5 Hz, 1H), 4.31 (dd, J=9.7, 3.1 Hz, 1H), 4.06 (br d, J=9.7 Hz, 1H), 3.97-3.89 (m, 1H). LCMS (ESI+): m/z 442.0 (M+H).

Example 121: (S)-12-fluoro-4-(1,4,5-trimethyl-1H-imidazol-2-yl)-7a,8,13,14-tetrahydro-7H-[1,2,4]triazolo[4',3':1,6]pyrido[3,2-b]benzofuro[4,3-fg][1,4]oxazonine Step 1: 1,4,5-trimethyl-1H-imidazole

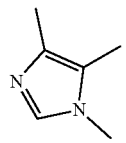

To a solution of 4,5-dimethyl-1H-imidazole (500 mg, 3.77 mmol, 1.00 eq, HCl) in THF (8.00 mL) was added NaH (377 mg, 9.43 mmol, 60% purity, 2.50 eq) at 20° C. under N₂. The mixture was stirred at 20° C. for 0.5 hr. MeI (500 mg, 3.52 mmol, 219 uL, 0.934 eq) was added to the mixture at 20° C. The mixture was stirred at 20° C. for 1 hr. The reaction mixture was quenched by addition of MeOH (2.00 mL) at 0° C. and the mixture was concentrated under reduced pressure. The residue was purified by prep-HPLC (column: Waters Xbridge Prep OBD C18 150*40 mm*10 um; mobile phase: [water (0.04% NH3 water+10 mM NH₄HCO₃)—ACN]; B %: 1%-15%, 10 min). 1,4,5-Trimethyl-1H-imidazole (300 mg, crude) was obtained as a yellow liquid.

Step 2: tert-butyl (S)-12-fluoro-4-(1,4,5-trimethyl-1H-imidazol-2-yl)-7a,13-dihydro-7H-[1,2,4]triazolo[4',3':1,6]pyrido[3,2-b]benzofuro[4,3-fg][1,4]oxazonine-14 (8H)-carboxylate

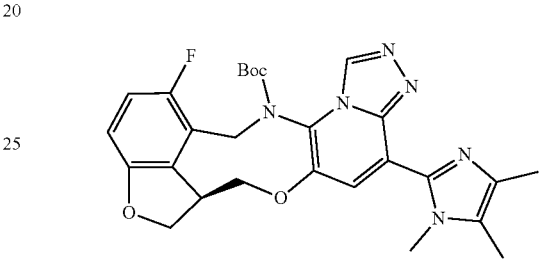

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq) in dioxane (2.00 mL) and EtOH (1.00 mL) in a microwave tube with a stir bar were added 1,4,5-trimethyl-1H-imidazole (100 mg, 908 umol, 2.23 eq), Pd(OAc)₂ (24.0 mg, 107 umol, 0.263 eq), PPh₃ (56.0 mg, 214 umol, 0.524 eq) and Na₂CO₃ (129 mg, 1.22 mmol, 3.00 eq) under argon. The tube was sealed with a silicon septum and subjected to microwave irradiation at 150° C. with stirring for 2 h The reaction mixture was concentrated under reduced pressure. The residue was purified by prep-TLC (SiO₂, Petroleum ether/Ethyl acetate=0/1). tert-butyl (S)-12-fluoro-4-(1,4,5-trimethyl-1H-imidazol-2-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, crude) was obtained as a yellow solid.

Step 3: (S)-12-fluoro-4-(1,4,5-trimethyl-1H-imidazol-2-yl)-7a,8,13,14-tetrahydro-7H-[1,2,4]triazolo[4',3':1,6]pyrido[3,2-b]benzofuro[4,3-fg][1,4]oxazonine

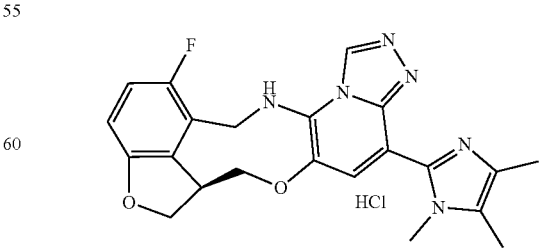

To a solution of tert-butyl (S)-12-fluoro-4-(1,4,5-trimethyl-1H-imidazol-2-yl)-7a,13-dihydro-7H-[1,2,4]triazolo

[4',3':1,6]pyrido[3,2-b]benzofuro[4,3-fg][1,4]oxazonine-14 (8H)-carboxylate (100 mg, 192 umol, 1.00 eq) in DCM (1.00 mL) was added TFA (1.00 mL) at 20° C. The mixture was stirred at 20° C. for 2 h. The reaction mixture was concentrated under reduced pressure. The residue was purified by prep-HPLC (column: Phenomenex Luna C18 150*30 mm*5 um; mobile phase: [water (0.04% HCl)—ACN]; B %: 20%-40%, 10 min). (S)-12-fluoro-4-(1,4,5-trimethyl-1H-imidazol-2-yl)-7a,8,13,14-tetrahydro-7H-[1,2,4]triazolo[4',3':1,6]pyrido[3,2-b]benzofuro[4,3-fg][1,4]oxazonine (65.0 mg, 141 umol, 73% yield, 99.4% purity, HCl salt) was obtained as a yellow solid. $^1$H NMR CD$_3$OD 400 MHz δ=ppm 9.58 (s, 1H), 8.08 (s, 1H), 7.00-6.89 (m, 1H), 6.70 (dd, J=8.7, 4.8 Hz, 1H), 5.23 (d, J=14.8 Hz, 1H), 5.00 (br d, J=14.8 Hz, 1H), 4.78 (br s, 1H), 4.65 (t, J=9.6 Hz, 1H), 4.33 (dd, J=9.8, 3.2 Hz, 1H), 4.14-4.04 (m, 1H), 4.01-3.90 (m, 1H), 3.71 (s, 3H), 2.39 (s, 6H). LCMS (ESI+): m/z 421.0 (M+H).

Example 122: (S)-12-fluoro-4-(5-methylpyrimidin-4-yl)-7a,8,13,14-tetrahydro-7H-[1,2,4]triazolo[4',3':1,6]pyrido[3,2-b]benzofuro[4,3-fg][1,4]oxazonine Step 1: 5-methylpyrimidin-4-yl trifluoromethanesulfonate

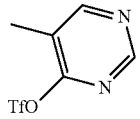

To a stirred solution of 5-methylpyrimidin-4-ol (300 mg, 2.72 mmol, 1.00 eq) and DIPEA (704 mg, 5.45 mmol, 949 uL, 2.00 eq) in DCM (5.00 mL) was added 1,1,1-trifluoro-N-phenyl-N-(trifluoromethylsulfonyl)methanesulfonamide (1.17 g, 3.27 mmol, 1.20 eq) at 25° C. The resulting mixture was stirred at 25° C. for 12 h. To the mixture was added water (10.0 mL) and the mixture was extracted with EtOAc (10.0 mL*3). The combined organic layers were dried over Na$_2$SO$_4$ and concentrated under reduced pressure. The residue was purified by prep-TLC (SiO$_2$, PE/EtOAc=10/1). 5-Methylpyrimidin-4-yl trifluoromethanesulfonate (240 mg, 991 umol, 36% yield) was obtained as yellow oil.

Step 2: tert-butyl (S)-12-fluoro-4-(5-methylpyrimidin-4-yl)-7a,13-dihydro-7H-[1,2,4]triazolo[4',3':1,6]pyrido[3,2-b]benzofuro[4,3-f][1,4]oxazonine-14 (8H)-carboxylate

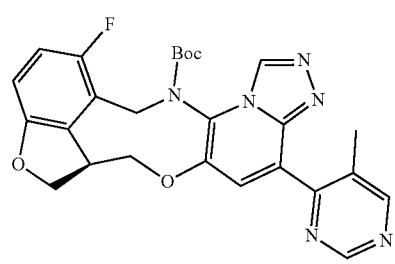 [SMILES: Cc1cncnc1-c1cc2c(n3cnnc13)N(C(=O)OC(C)(C)C)Cc1c(F)ccc3c1[C@H](CO3)CO2]

To 5-methylpyrimidin-4-yl trifluoromethanesulfonate (240 mg, 992 umol, 3.48 eq) and tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (200 mg, 285 umol, 1.00 eq) in dioxane (5.00 mL) were added CuI (21.7 mg, 114 umol, 0.400 eq), LiCl (24.2 mg, 570 umol, 11.7 uL, 2.00 eq) and Pd(PPh$_3$)$_4$ (33.0 mg, 28.5 umol, 0.100 eq) at 25° C. under N$_2$. The resulting mixture was stirred at 80° C. for 12 h. The mixture was concentrated under reduced pressure. The residue was purified by prep-TLC (SiO$_2$, PE/EtOAc=0/1). tert-butyl (S)-12-fluoro-4-(5-methylpyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, 238 umol, 83% yield) was obtained as a yellow solid.

Step 3: (S)-12-fluoro-4-(5-methylpyrimidin-4-yl)-7a,8,13,14-tetrahydro-7H-[1,2,4]triazolo[4',3':1,6]pyrido[3,2-b]benzofuro[4,3-fg][1,4]oxazonine

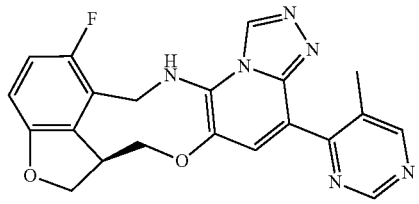 [SMILES: Cc1cncnc1-c1cc2c(n3cnnc13)NCc1c(F)ccc3c1[C@H](CO3)CO2]

To tert-butyl (S)-12-fluoro-4-(5-methylpyrimidin-4-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, 238 umol, 1.00 eq) was added HFIP (4.00 mL) at 25° C. The mixture was stirred at 80° C. for 12 h. The mixture was concentrated under reduced pressure. The mixture was purified by acidic prep-HPLC (HCl conditions). (S)-12-fluoro-4-(5-methylpyrimidin-4-yl)-7a,8,13,14-tetrahydro-7H-[1,2,4]triazolo[4',3':1,6]pyrido[3,2-b]benzofuro[4,3-fg][1,4]oxazonine (34.4 mg, 76.2 umol, 32% yield, 97.6% purity, HCl salt) was obtained as an orange solid. $^1$H NMR CD$_3$OD 400 MHz δ =ppm 9.57 (s, 1H), 9.18 (s, 1H), 8.84 (s, 1H), 8.45 (s, 1H), 7.03-6.89 (m, 1H), 6.72 (dd, J=8.6, 4.0 Hz, 1H), 5.27 (d, J=15.0 Hz, 1H), 5.04 (br d, J=15.6 Hz, 1H), 4.85-4.78 (m, 1H), 4.65 (t, J=9.4 Hz, 1H), 4.35 (dd, J=9.7, 3.5 Hz, 1H), 4.17-4.06 (m, 1H), 4.05-3.95 (m, 1H), 2.65 (s, 3H). LCMS (ESI+): m/z 405.0 (M+H).

Example 123: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-ol Step 1: methyl 2-(5-hydroxy-1-methyl-1H-pyrazol-3-yl)acetate

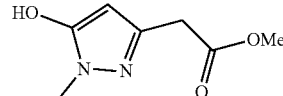

Methylhydrazine (6.61 g, 57.4 mmol, 7.56 mL, 40.0% in water, 1.00 eq) were added to dimethyl 3-oxopentanedioate (10.0 g, 57.4 mmol, 8.26 mL, 1.00 eq) in MeOH (100 mL) at 20° C., during which the reaction temperature rose to 65°

C. After completion of the addition, the mixture was stirred for a further 2 h and NaOMe (10.3 g, 57.4 mmol, 30.0% in MeOH, 1.00 eq) was then added at 65° C. The reaction was slightly exothermic. The reaction mixture was stirred for a further 4 h TLC (Petroleum ether:Ethyl acetate=0:1) indicated no dimethyl 3-oxopentanedioate was remained, and one major new spot with larger polarity was detected. The reaction mixture was concentrated under reduced pressure to remove solvent, and the residue was dissolved in water (40.0 mL). After acidification with glacial acetic acid to pH=5 the mixture was extracted with EtOAc (50.0 mL*3). The combined organic layers were dried over Na₂SO₄, filtered, and concentrated under reduced pressure. The residue was suspended in EtOAc (30.0 mL) and filtered, the filter cake was dried and collected. Methyl 2-(5-hydroxy-1-methyl-1H-pyrazol-3-yl)acetate (4.50 g, crude) was obtained as a white solid.

Step 2: methyl 2-(5-bromo-1-methyl-1H-pyrazol-3-yl)acetate

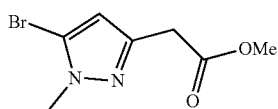

Twenty parallel reactions were set up. To a solution of methyl 2-(5-hydroxy-1-methyl-1H-pyrazol-3-yl)acetate (100 mg, 588 umol, 1.00 eq) in MeCN (4.00 mL) was added POBr₃ (842 mg, 2.94 mmol, 299 uL, 5.00 eq) at 20° C. The mixture was stirred at 80° C. for 12 h. All batches were combined and quenched by addition of sat. aq. NaHCO₃ (50.0 mL) at 0° C. Then the mixture was extracted with EtOAc (70.0 mL*3). The combined organic layers were dried over Na₂SO₄, filtered, and concentrated under reduced pressure. The residue was purified by column chromatography (SiO₂, Petroleum ether/Ethyl acetate=1/0 to 0/1). Methyl 2-(5-bromo-1-methyl-1H-pyrazol-3-yl)acetate (1.20 g, crude) was obtained as a yellow liquid.

Step 3: 2-(5-bromo-1-methyl-1H-pyrazol-3-yl)ethan-1-ol

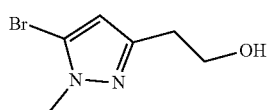

To a solution of methyl 2-(5-bromo-1-methyl-1H-pyrazol-3-yl)acetate (600 mg, 2.57 mmol, 1.00 eq) in DCM (10.0 mL) was added DIBAL-H (1.00 M, 9.01 mL, 3.50 eq) at 0° C. under N₂. The mixture was stirred at 25° C. for 12 h The reaction mixture was quenched by addition of MeOH (5.00 mL) at 0° C., and the mixture was concentrated under reduced pressure. The residue was purified by column chromatography (SiO₂, Petroleum ether/EtOH=1/0 to 20/1). 2-(5-bromo-1-methyl-1H-pyrazol-3-yl)ethan-1-ol (200 mg, crude) was obtained as a yellow liquid.

Step 4: 2-(1-methyl-S-(tributylstannyl)-1H-pyrazol-3-yl)ethan-1-ol

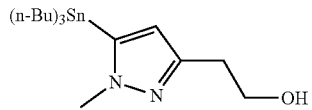

To a solution of 2-(5-bromo-1-methyl-1H-pyrazol-3-yl)ethan-1-ol (200 mg, 975 umol, 1.00 eq) in THF (5.00 mL) was added n-BuLi (2.50 M, 819 uL, 2.10 eq) at −70° C. under N₂. The mixture was stirred at −70° C. for 0.5 hr. Tributyl(chloro)stannane (476 mg, 1.46 mmol, 393 uL, 1.50 eq) was added to the mixture at −70° C. which was then stirred at −70° C. for 1 hr. The reaction mixture was quenched by addition of sat. aq. KF (1.00 mL) at 0° C. The mixture was extracted with MTBE (10.0 mL*3). The combined organic layers were dried over Na₂SO₄, filtered and concentrated under reduced pressure. 2-(1-Methyl-S-(tributylstannyl)-1H-pyrazol-3-yl)ethan-1-ol (350 mg, crude) was obtained as a yellow liquid.

Step 5: tert-butyl (S)-12-fluoro-4-(3-(2-hydroxyethyl)-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate

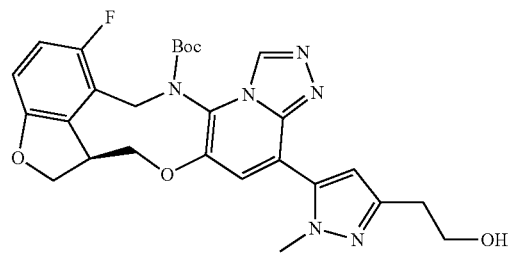 [SMILES: Cn1nc(CCO)cc1-c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq) in dioxane (5.00 mL) were added 2-(1-methyl-S-(tributylstannyl)-1H-pyrazol-3-yl)ethan-1-ol (338 mg, 814 umol, 2.00 eq), Pd(PPh₃)₄ (47.0 mg, 40.7 umol, 0.100 eq), CuI (31.0 mg, 162 umol, 0.400 eq) and LiCl (34.5 mg, 814 umol, 16.7 uL, 2.00 eq) at 20° C. under N₂. The mixture was stirred at 90° C. for 12 h. The reaction mixture was concentrated under reduced pressure. The residue was purified by prep-TLC (SiO₂, Petroleum ether/Ethyl acetate=0/1). tert-butyl (S)-12-fluoro-4-(3-(2-hydroxyethyl)-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, crude) was obtained as a brown solid.

Step 6: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-ol

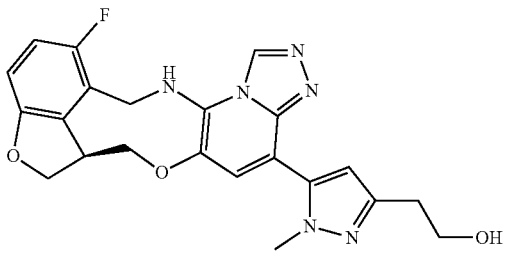 [SMILES: Cn1nc(CCO)cc1-c1cc2c(n3cnnc13)NCc1c(F)ccc3c1[C@H](CO3)CO2]

A mixture of tert-butyl (S)-12-fluoro-4-(3-(2-hydroxyethyl)-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, 224 umol, 1.00 eq) in HFIP (2.00 mL) was stirred at 100° C. for 2 h The reaction mixture was concentrated under reduced pressure. The residue was purified by prep-HPLC (column: Waters Xbridge BEH C18 100*30 mm*10 um; mobile phase: [water (10 mM NH$_4$HCO$_3$)—ACN]; B %: 20%-45%, 10 min). (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-ol (53.0 mg, 120 umol, 53% yield, 99.1% purity) was obtained as a white solid. $^1$H NMR DMSO-d$_6$ 400 MHz δ=ppm 9.44 (s, 1H), 7.64 (br t, J=6.4 Hz, 1H), 7.39 (s, 1H), 6.96 (dd, J=10.1, 8.8 Hz, 1H), 6.69 (dd, J=8.6, 4.0 Hz, 1H), 6.39 (s, 1H), 4.96-4.87 (m, 1H), 4.84-4.72 (m, 1H), 4.66 (t, J=5.2 Hz, 1H), 4.59-4.45 (m, 2H), 4.21 (dd, J=9.6, 3.6 Hz, 1H), 4.09-3.98 (m, 1H), 3.93-3.82 (m, 1H), 3.74 (s, 3H), 3.65 (dt, J=7.2, 5.4 Hz, 2H), 2.70 (t, J=7.2 Hz, 2H). LCMS (ESI+): m/z 437.0 (M+H).

Example 124: (S)-4-(2,5-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine

Step 1: 4-iodo-2,5-dimethylpyridine

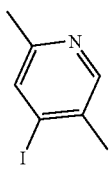

To a solution of 2,5-dimethylpyridin-4-amine (500 mg, 4.09 mmol, 1.00 eq), CuI (1.01 g, 5.32 mmol, 1.30 eq) in MeCN (10.0 mL) was added isopentyl nitrite (719 mg, 6.14 mmol, 826 uL, 1.50 eq) in MeCN (5.00 mL) at 0° C. The mixture was stirred at 60° C. for 12 h The reaction mixture was concentrated under reduced pressure. The residue was purified by column chromatography (SiO$_2$, Petroleum ether/Ethyl acetate=1/0 to 10/1). 4-Iodo-2,5-dimethylpyridine (320 mg, 1.37 mmol, 33% yield) was obtained as a yellow solid.

Step 2: tert-butyl (S)-4-(2,5-dimethylpyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

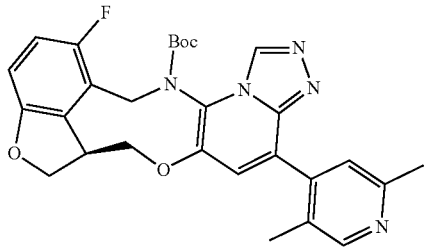 [SMILES: Cc1cc(-c2cc3c(n4cnnc24)N(C(=O)OC(C)(C)C)Cc2c(F)ccc4c2[C@H](CO4)CO3)c(C)cn1]

To a solution of 4-iodo-2,5-dimethylpyridine (73.1 mg, 314 umol, 1.10 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Ex. 16; 200 mg, 285 umol, 1.00 eq) in dioxane (2.00 mL) were added CuI (21.7 mg, 114 umol, 0.400 eq), LiCl (24.2 mg, 571 umol, 11.7 uL, 2.00 eq) and Pd(PPh$_3$)$_4$ (33.0 mg, 28.6 umol, 0.100 eq) at 20° C., then the mixture stirred at 80° C. for 12 h under N$_2$. The reaction mixture was concentrated under reduced pressure. The residue was purified by prep-TLC (SiO$_2$, PE:EtOAc=0:1). tert-butyl (S)-4-(2,5-dimethylpyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (70.0 mg, 135 umol, 47% yield) was obtained as a yellow solid.

Step 3: (S)-4-(2,5-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine

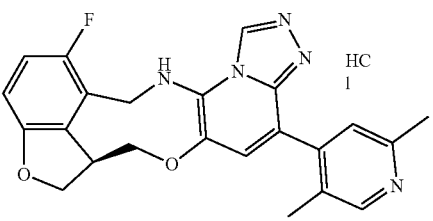 [SMILES: Cc1cc(-c2cc3c(n4cnnc24)NCc2c(F)ccc4c2[C@H](CO4)CO3)c(C)cn1]

To tert-butyl (S)-4-(2,5-dimethylpyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (70.0 mg, 135 umol, 1.00 eq) was added HFIP (2.00 mL) at 20° C., the mixture was stirred at 100° C. for 2 h under N$_2$. The reaction mixture was concentrated under reduced pressure. The residue was purified by prep-HPLC (HCl conditions). (S)-4-(2,5-dimethylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine (24.7 mg, 54.3 umol, 40% yield, 99.7% purity, HCl salt) was obtained as a yellow solid. $^1$H NMR CD$_3$OD 400 MHz δ=ppm 9.59 (s, 1H), 8.77 (s, 1H), 8.09 (s, 1H), 7.99 (s, 1H), 6.95 (br t, J=9.5 Hz, 1H), 6.71 (br dd, J=8.6, 3.9 Hz, 1H), 5.24 (br d, J=14.8 Hz, 1H), 5.04-4.94 (m, 1H), 4.85 (br s, 1H), 4.65 (br t, J=9.5 Hz, 1H), 4.33 (br dd, J=9.6, 3.2 Hz, 1H), 4.08 (br d, J=8.6 Hz, 1H), 3.94 (br t, J=10.8 Hz, 1H), 2.82 (s, 3H), 2.43 (s, 3H). LCMS (ESI+): m/z 418.0 (M+H).

Example 125: (S)-4-(3-chloro-2-methylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-chloro-2-methylpyridin-4-amine

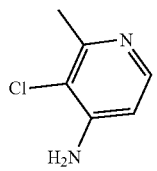

To a solution of 2-methylpyridin-4-amine (3.00 g, 27.7 mmol, 1.00 eq) in MeCN (20.0 mL) was added NCS (4.07 g, 30.5 mmol, 1.10 eq) in MeCN (10.0 mL) at 0° C. The mixture was stirred at 0° C. for 2 h. The reaction mixture was concentrated under reduced pressure. The residue was purified by column chromatography (SiO$_2$, Petroleum ether/Ethyl acetate=1/0 to 0/1). 3-chloro-2-methylpyridin-4-amine (2.01 g, 14.1 mmol, 50% yield) was obtained as a gray solid.

Step 2: 3-chloro-4-iodo-2-methylpyridine

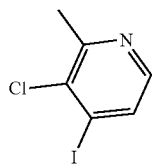

To a solution of 3-chloro-2-methylpyridin-4-amine (2.01 g, 14.1 mmol, 1.00 eq), CuI (3.49 g, 18.3 mmol, 1.30 eq) in MeCN (20.0 mL) was added isopentyl nitrite (2.48 g, 21.2 mmol, 2.85 mL, 1.50 eq) in MeCN (10.0 mL) at 0° C. The mixture was stirred at 60° C. for 2 h under N$_2$. The reaction mixture concentrated under reduced pressure. The residue was purified by column chromatography (SiO$_2$, Petroleum ether/Ethyl acetate=1/0 to 10/1). 3-chloro-4-iodo-2-methylpyridine (350 mg, 1.38 mmol, 9% yield) was obtained as a yellow solid.

Step 3: (3-chloro-2-methylpyridin-4-yl)boronic Acid

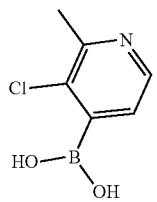

To a solution of 3-chloro-4-iodo-2-methylpyridine (350 mg, 1.38 mmol, 1.00 eq) in THF (5.00 mL) at −78° C. was added n-BuLi (2.50 M, 829 uL, 1.50 eq). The mixture was stirred at −78° C. for 0.5 hr. And to the mixture was added triisopropyl borate (779 mg, 4.14 mmol, 952 uL, 3.00 eq) at −78° C. The mixture was stirred at −78° C. for 1 hr under N$_2$. The reaction mixture was quenched by addition of MeOH (2.00 mL) at −78° C., the reaction mixture was concentrated under reduced pressure. (3-Chloro-2-methylpyridin-4-yl)boronic acid (235 mg, crude) was obtained as a yellow solid.

Step 4: tert-butyl (S)-4-(3-chloro-2-methylpyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

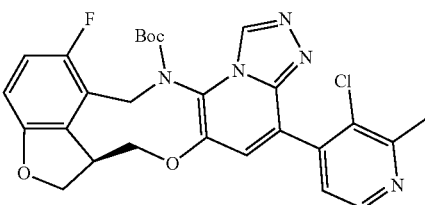

To a solution of (3-chloro-2-methylpyridin-4-yl)boronic acid (235 mg, 1.37 mmol, 1.00 eq) in dioxane (5.00 mL) and water (0.500 mL) were added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (222 mg, 452 umol, 0.330 eq), Pd(dppf)Cl$_2$ (10.0 mg, 13.7 umol, 0.0100 eq) and NaHCO$_3$ (230 mg, 2.74 mmol, 2.00 eq) at 20° C. The mixture was stirred at 80° C. for 12 h under N$_2$. The reaction mixture was concentrated under reduced pressure. The residue was purified by prep-TLC (SiO$_2$, PE:EtOAc=1:3). tert-butyl (S)-4-(3-chloro-2-methylpyridin-4-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (72.0 mg, 134 umol, 9% yield) was obtained as a yellow solid.

Step 5: (S)-4-(3-chloro-2-methylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine

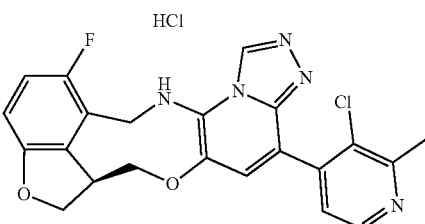

To tert-butyl (S)-4-(3-chloro-2-methylpyridin-4-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate (70.0 mg, 130 umol, 1.00 eq) was added HFIP (2.00 mL) at 20° C., the mixture was stirred at 80° C. for 12 h under N$_2$. The reaction mixture concentrated under reduced pressure. The residue was purified by prep-HPLC (HCl conditions). (S)-4-(3-chloro-2-methylpyridin-4-yl)-12-fluoro-7a,8,13,14-tetrahydro-7H-[1,2,4]triazolo[4',3':1,6]pyrido[3,2-b]benzofuro[4,3-fg][1,4]oxazonine (15.9 mg, 32.9 umol, 25% yield, 98.0% purity, HCl salt) was obtained as a yellow solid. $^1$H NMR CD$_3$OD 400 MHz δ=ppm 9.56 (br s, 1H), 8.67 (br d, J=5.5 Hz, 1H), 8.14 (br s, 1H), 7.79 (br d, J=5.5 Hz, 1H), 6.95 (br t, J=9.5 Hz, 1H), 6.71 (br dd, J=8.7, 3.9 Hz, 1H), 5.24 (br d, J=14.8 Hz, 1H), 4.99 (br d, J=14.5 Hz, 1H), 4.80 (br s, 1H), 4.65 (br t, J=9.5 Hz, 1H), 4.34 (br dd, J=9.8, 3.2 Hz, 1H), 4.13-4.04 (m, 1H), 4.01-3.90 (m, 1H), 2.85 (br s, 3H). LCMS (ESI+): m/z 438.1 (M+H).

Example 126: (S)-4-(5-chloro-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 3-bromo-S-chloro-2-methylpyridine

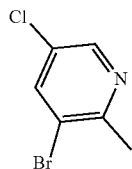

To a solution of 5-bromo-6-methylpyridin-3-amine (2.00 g, 10.7 mmol, 1.00 eq) and CuCl (2.12 g, 21.4 mmol, 511 uL, 2.00 eq) in MeCN (20.0 mL) was added isopentyl nitrite (3.13 g, 26.7 mmol, 3.60 mL, 2.50 eq) at 0° C. The mixture was stirred at 0° C. for 1 hr. The mixture was stirred at 80° C. for 12 h under $N_2$. LCMS showed the reaction was complete. The mixture was filtered, and the filtrate was concentrated under reduced pressure. The residue was purified by column chromatography (SiO$_2$, Petroleum ether/Ethyl acetate=1/0 to 10/1) to give 3-bromo-5-chloro-2-methylpyridine (850 mg, crude) as yellow oil.

Step 2: 5-chloro-2-methyl-3-(4,4,5,5-tetramethyl-1,3,2-dioxaborolan-2-yl)pyridine

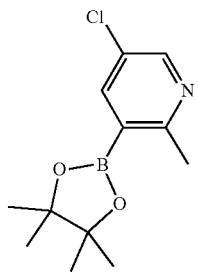

To a solution of 3-bromo-S-chloro-2-methylpyridine (600 mg, 2.91 mmol, 1.00 eq) and Pin$_2$B$_2$ (886 mg, 3.49 mmol, 1.20 eq) in dioxane (7.00 mL) were added Pd(dppf)Cl$_2$ (213 mg, 291 umol, 0.100 eq) and KOAc (570 mg, 5.81 mmol, 2.00 eq) at 25° C. The mixture was stirred at 80° C. for 2 h under $N_2$. The mixture was concentrated under reduced pressure to give 5-chloro-2-methyl-3-(4,4,5,5-tetramethyl-1,3,2-dioxaborolan-2-yl)pyridine (2.00 g, crude) as a black solid.

Step 3: tert-butyl (S)-4-(5-chloro-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

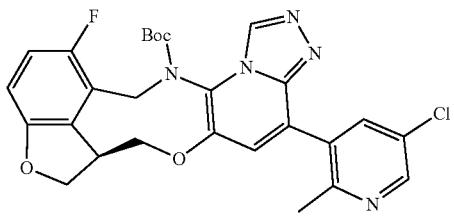 [SMILES: Cc1ncc(Cl)cc1-c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (100 mg, 204 umol, 1.00 eq) and 5-chloro-2-methyl-3-(4,4,5,5-tetramethyl-1,3,2-dioxaborolan-2-yl)pyridine (310 mg, 1.22 mmol, 6.00 eq) in dioxane (4.00 mL) and water (0.800 mL) were added Na$_2$CO$_3$ (43.2 mg, 407 umol, 2.00 eq) and Pd(dppf)Cl$_2$ (14.9 mg, 20.4 umol, 0.100 eq) at 25° C. The mixture was stirred at 80° C. for 12 h under $N_2$. The mixture was combined with the other batches (from 100 μmg of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate). The mixture was filtered and the filtrate was concentrated under reduced pressure. The residue was purified by prep-TLC (SiO$_2$, Petroleum ether:Ethyl acetate=1:1) to give tert-butyl (S)-4-(5-chloro-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, crude) was obtained as yellow oil.

Step 4: (S)-4-(5-chloro-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine

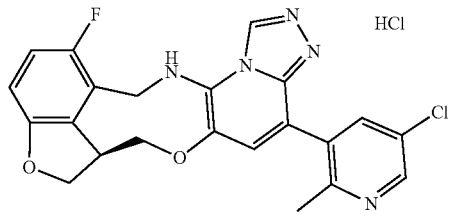 [SMILES: Cc1ncc(Cl)cc1-c1cc2c(n3cnnc13)NCc1c(F)ccc3c1[C@H](CO3)CO2 ; Cl]

To a solution of tert-butyl (S)-4-(5-chloro-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 279 umol, 1.00 eq) in DCM (2.00 mL) was added TFA (1.54 g, 13.5 mmol, 1.00 mL, 48.4 eq) at 25° C. The mixture was stirred at 25° C. for 1 hr. LCMS showed that the reaction was complete. The mixture was concentrated under reduced pressure. The residue was purified by prep-HPLC (HCl condition). (S)-4-(5-chloro-2-methylpyridin-3-yl)-12-fluoro-7a,8,13,14-tetrahydro-7H-[1,2,4]triazolo[4',3':1,6]pyrido[3,2-b]benzofuro[4,3-fg][1,4]oxazonine (43.6 mg, 90.5 umol, 32% yield, 98.4% purity, HCl) was obtained as a yellow solid. $^1$H NMR DMSO-d$_6$ 400 MHz δ=ppm 10.03 (s, 1H), 8.85 (br s, 1H), 8.65 (d, J=2.4 Hz, 1H), 7.99 (d, J=2.4 Hz, 1H), 7.94 (s, 1H), 7.07-6.96 (m, 1H), 6.74 (dd, J=8.6, 3.9 Hz, 1H), 5.09-4.95 (m, 1H), 4.89-4.85 (m, 1H), 4.57 (br t, J=9.4 Hz, 2H), 4.24 (dd, J=9.7, 3.6 Hz, 1H), 4.07-4.03 (m, 1H), 3.97-3.86 (m, 1H), 2.38 (s, 3H). LCMS (ESI+): m/z 438.1 (M+H).

Example 127: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylethan-1-amine Step 1: (5-bromo-1-methyl-1H-pyrazol-3-yl)methyl methanesulfonate

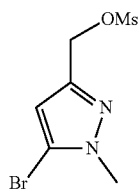

To a solution of (5-bromo-1-methyl-1H-pyrazol-3-yl)methanol (1.80 g, 9.42 mmol, 1.00 eq) in DCM (20.0 mL) was added TEA (1.43 g, 14.1 mmol, 1.97 mL, 1.50 eq) and MsCl (2.16 g, 18.9 mmol, 1.46 mL, 2.00 eq) at 0° C. Then the mixture was stirred at 0° C. for 30 mins. Saturated NaHCO$_3$ solution was added to the mixture to adjust pH to neutral. Then the mixture was extracted with EtOAc (10.0 mL*4). The combined organic layers were washed with brine (5.00 mL), dried over anhydrous Na$_2$SO$_4$, filtered, and the filtrate was concentrated under reduced pressure. 5-Bromo-1-methyl-1H-pyrazol-3-yl)methyl methanesulfonate (2.20 g, crude) was obtained as yellow oil.

Step 2: 2-(5-bromo-1-methyl-1H-pyrazol-3-yl)acetonitrile

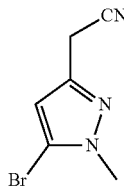

The reaction was set up in 10 parallel batches. To 5-bromo-1-methyl-1H-pyrazol-3-yl)methyl methanesulfonate (220 mg, 817 umol, 1.00 eq) in MeCN (2.00 mL) was added TMSCN (122 mg, 1.23 mmol, 154 uL, 1.51 eq) and TBAF (1.00 M, 1.23 mL, 1.50 eq) at 20° C. The mixture was stirred at 20° C. for 12 h. The 10 batches were combined. The reaction mixture was concentrated under reduced pressure followed by addition of water (20.0 mL). The mixture was extracted with EtOAc (20.0 mL*5). The combined organic layers were dried over anhydrous Na$_2$SO$_4$, filtered, and concentrated under reduced pressure. The residue was purified by prep-TLC (SiO$_2$, PE:EtOAc=1: 1). 2-(5-Bromo-1-methyl-1H-pyrazol-3-yl)acetonitrile (740 mg, crude) was obtained as yellow oil.

Step 3: 2-(5-bromo-1-methyl-1H-pyrazol-3-yl)ethan-1-amine

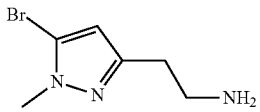

To 2-(5-bromo-1-methyl-1H-pyrazol-3-yl)acetonitrile (800 mg, 4.00 mmol, 1.00 eq) in THF (10.0 mL) was added BH$_3$.THF (1.00 M, 24.0 mL, 6.00 eq) dropwise at 0° C. The mixture was stirred at 60° C. for 12 h under nitrogen atmosphere. MeOH (10.0 mL) was added to the mixture. The mixture was concentrated under reduced. 2-(5Bbromo-1-methyl-1H-pyrazol-3-yl)ethan-1-amine (800 mg, crude) was obtained as colourless oil.

Step 4: tert-butyl (2-(5-bromo-1-methyl-1H-pyrazol-3-yl)ethyl)carbamate

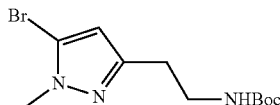

To 2-(5-bromo-1-methyl-1H-pyrazol-3-yl)ethan-1-amine (800 mg, 3.92 mmol, 1.00 eq) and Boc$_2$O (1.71 g, 7.84 mmol, 1.80 mL, 2.00 eq) in DCM (5.00 mL) was added TEA (792 mg, 7.83 mmol, 1.09 mL, 2.00 eq) at 20° C. The mixture was stirred at 20° C. for 3 hr. The reaction mixture was filtered and the filtrate was concentrated under reduced pressure. The residue was purified by prep-TLC (SiO$_2$, PE:EtOAc=1:1). tert-Butyl (2-(5-bromo-1-methyl-1H-pyrazol-3-yl)ethyl)carbamate (430 mg, crude) was obtained as yellow oil.

Step 5: tert-butyl (S)-4-(3-(2-((tert-butoxycarbonyl)amino)ethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

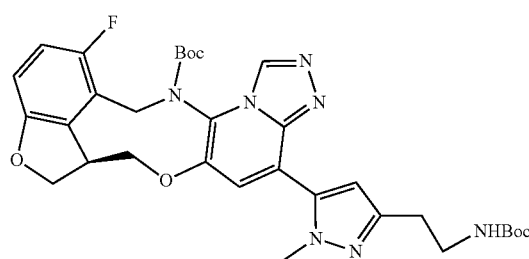

To tert-butyl (2-(5-bromo-1-methyl-1H-pyrazol-3-yl)ethyl)carbamate (182 mg, 599 umol, 1.50 eq) and tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (280 mg, 399 umol, 1.00 eq) in dioxane (4.00 mL) was added palladium tritert-butylphosphane (20.4 mg, 39.9 umol, 0.100 eq) at 20° C. The mixture was stirred at 80° C. for 2 hr under nitrogen atmosphere. LC-MS indicated partial conversion. The mixture stirred at 80° C. for additional 2 h. LC-MS showed incompleted reaction. tert-Butyl (2-(5-bromo-1-methyl-1H-pyrazol-3-yl)ethyl)carbamate (50.0 mg, 164 umol, 4.12e-1 eq) and palladium tritert-butylphosphane (20.4 mg, 39.9 umol, 0.100 eq) were added to the mixture. The mixture was stirred at 100° C. for 1 hr. LC-MS showed complete conversion. The reaction mixture was filtered and the filtrate was concentrated under reduced pressure. The residue was purified by prep-TLC (SiO$_2$, EtOAc). tert-Butyl (S)-4-(3-(2-((tert-butoxycarbonyl)amino)ethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, crude) was obtained as yellow oil.

Step 6: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-amine

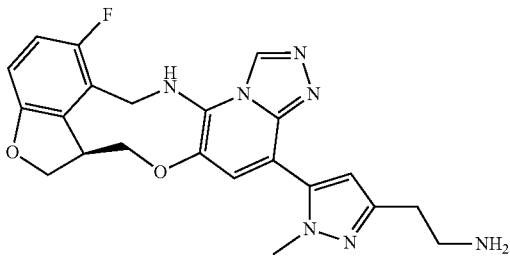 [SMILES: Cn1nc(CCN)cc1-c1cc2c(n3cnnc13)NCc1c(F)ccc3c1[C@H](CO3)CO2]

To tert-butyl (S)-4-(3-(2-((tert-butoxycarbonyl)amino)ethyl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 189 umol, 1.00 eq) in DCM (1.00 mL) was added TFA (462 mg, 4.05 mmol, 0.300 mL, 21.5 eq) at 20° C. The mixture was stirred at 20° C. for 1 hr. DIPEA was added to the mixture to adjust pH to 7-8. The reaction mixture was concentrated under reduced pressure. The product (90.0 mg, crude) was obtained as yellow oil.

Step 7: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylethan-1-amine

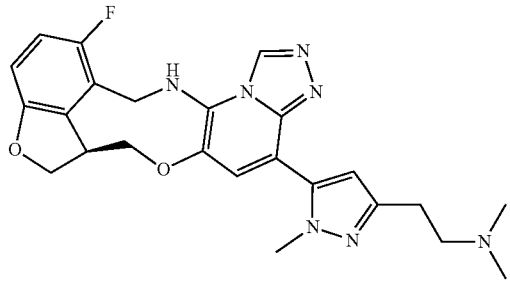 [SMILES: CN(C)CCc1cc(-c2cc3c(n4cnnc24)NCc2c(F)ccc4c2[C@H](CO4)CO3)n(C)n1]

The reaction was set up in 7 parallel batches. To (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)ethan-1-amine (20.0 mg, 45.9 umol, 1.00 eq) and formaldehyde (18.6 mg, 230 umol, 17.1 uL, 5.00 eq) in MeOH (2.00 mL) was added AcOH (2.76 mg, 45.9 umol, 2.63 uL, 1.00 eq) at 20° C. NaBH$_3$CN (5.77 mg, 91.9 umol, 2.00 eq) was added to each mixture and it was stirred at 20° C. for 2 h. The batches were combined. The mixture was concentrated. The crude product was purified by prep-HPLC (basic conditions) to afford the product as a free base. To the product was added aqueous HCl (0.05 mL, 37%) and the obtained salt was lyophilized. (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-N,N-dimethylethan-1-amine (13.6 mg, HCl salt) was obtained as yellow solid. $^1$H NMR CD$_3$OD 400 MHz δ=ppm 9.58 (s, 1H), 8.04 (s, 1H), 6.91 (dd, J=10.0, 8.9 Hz, 1H), 6.68 (dd, J=8.7, 3.9 Hz, 1H), 6.52 (s, 1H), 5.19 (d, J=14.8 Hz, 1H), 5.01-5.00 (m, 1H), 4.99 (br s, 1H), 4.76 (br d, J=6.2 Hz, 1H), 4.62 (t, J=9.5 Hz, 1H), 4.31 (dd, J=9.7, 3.1 Hz, 1H), 4.15-4.01 (m, 1H), 3.97-3.87 (m, 1H), 3.77 (s, 3H), 3.53 (t, J=7.3 Hz, 2H), 3.16 (t, J=7.2 Hz, 2H), 2.97 (s, 6H). LCMS (ESI+): m/z 464.3 (M+H).

Example 128: (S)-4-(1,3-dimethyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 14-(tert-butyl) 4-methyl (S)-12-fluoro-7a,13-dihydro-7H-[1,2,4]triazolo[4',3':1,6]pyrido[3,2-b]benzofuro[4,3-fg][1,4]oxazonine-4,14 (8H)-dicarboxylate

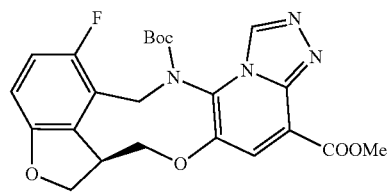 [SMILES: COC(=O)c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (4.50 g, 9.16 mmol, 1.00 eq) in MeOH (200 mL) was added TEA (9.27 g, 91.6 mmol, 12.8 mL, 10.0 eq) and Pd(dppf)Cl$_2$ (670 mg, 916 umol, 0.100 eq) at 20° C., stirred at 60° C. for 12 h under CO (50 psi). TLC (Petroleum ether/Ethyl acetate=0/1) showed the reaction was complete. The mixture was concentrated and water (50.0 mL) and EtOAc (50.0 mL) were added to the solution. Brown precipitate was filtered off and dried to give 14-(tert-butyl) 4-methyl (S)-12-fluoro-7a,13-dihydro-7H-[1,2,4]triazolo[4',3':1,6]pyrido[3,2-b]benzofuro[4,3-fg][1,4]oxazonine-4,14 (8H)-dicarboxylate (3.8 g, crude) as a brown solid.

Step 2: (S)-14-(tert-butoxycarbonyl)-12-fluoro-7a,8, 13,14-tetrahydro-7H-[1,2,4]triazolo[4',3':1,6]pyrido [3,2-b]benzofuro[4,3-fg][1,4]oxazonine-4-carboxylic Acid

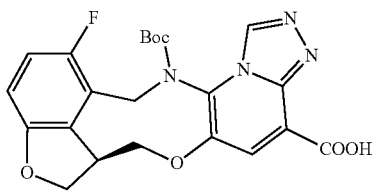 [SMILES: CC(C)(C)OC(=O)N1Cc2c(F)ccc3c2[C@H](CO3)COc2cc(C(=O)O)c3nncn3c21]

To a solution of 14-(tert-butyl) 4-methyl (S)-12-fluoro-7a,13-dihydro-7H-[1,2,4]triazolo[4',3':1,6]pyrido[3,2-b] benzofuro[4,3-fg] [1,4]oxazonine-4,14 (8H)-dicarboxylate (4.10 g, 8.72 mmol, 1.00 eq) in MeOH (60.0 mL), water (20.0 mL) and THF (60.0 mL) was added NaOH (697 mg, 17.4 mmol, 2.00 eq) at 20° C. and stirred at 20° C. for 1 hr. The mixture was concentrated, water (50.0 mL) was added to the solution. The mixture was extracted with EtOAc (100 mL*3), the aqueous phase was adjusted to pH of 2 with HCl (1 M), and extracted with EtOAc (50.0 mL*3). All organic layers were combined, dried over Na₂SO₄, then concentrated. (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid (3.20 g, 7.01 mmol, 80% yield) was obtained as a yellow solid.

Step 3: tert-butyl (S)-4-carbamoyl-12-fluoro-7a,13-dihydro-7H-[1,2,4]triazolo[4',3':1,6]pyrido[3,2-b] benzofuro[4,3-fg][1,4]oxazonine-14 (8H)-carboxylate

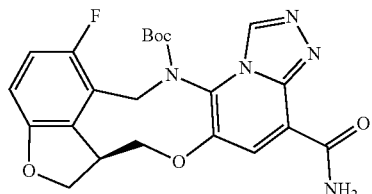

To (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid (2.00 g, 4.39 mmol, 1.00 eq) in DMF (20.0 mL) were added DIPEA (2.27 g, 17.6 mmol, 3.06 mL, 4.00 eq), HOBt (1.19 g, 8.78 mmol, 2.00 eq) and EDCI (1.68 g, 8.78 mmol, 2.00 eq) at 20° C. The mixture was stirred at 20° C. for 5 min. NH₄Cl (470 mg, 8.79 mmol, 2.00 eq) was added to the mixture at 20° C. The mixture was stirred at 20° C. for 12 h. LC-MS showed (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid was consumed completely and one main peak with desired mass was detected. The mixture was combined with the pilot batch (same reaction, from 200 mg of (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid) for the workup. Water (10.0 mL) was added to the mixture and it was extracted with ethyl acetate (20.0 mL*5). The combined organic layers were dried over anhydrous Na₂SO₄, filtered, and concentrated under reduced pressure. The residue was purified by column chromatography (SiO₂, Petroleum ether/Ethyl acetate=1/0 to 1/1). tert-butyl (S)-4-carbamoyl-12-fluoro-7a,13-dihydro-7H-[1,2,4]triazolo[4',3':1,6]pyrido[3,2-b]benzofuro[4,3-fg] [1,4]oxazonine-14 (8H)-carboxylate (1.86 g, crude) was obtained as yellow oil.

Step 4: tert-butyl (S,Z)-4-((1-(dimethylamino)ethylidene)carbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

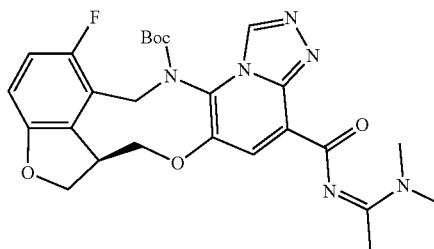

To tert-butyl (S)-4-carbamoyl-12-fluoro-7a,13-dihydro-7H-[1,2,4]triazolo[4',3':1,6]pyrido[3,2-b]benzofuro[4,3-fg] [1,4]oxazonine-14 (8H)-carboxylate (1.86 g, 4.08 mmol, 1.00 eq) was added 1,1-dimethoxy-N,N-dimethyl-ethanamine (21.2 g, 159 mmol, 23.3 mL, 39.0 eq) at 20° C. Then the mixture was stirred at 90° C. for 2 h The reaction mixture was concentrated under reduced pressure. tert-Butyl (S,Z)-4-((1-(dimethylamino)ethylidene)carbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (2.00 g, crude) was obtained as brown oil.

Step 5: tert-butyl (S)-4-(1,3-dimethyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

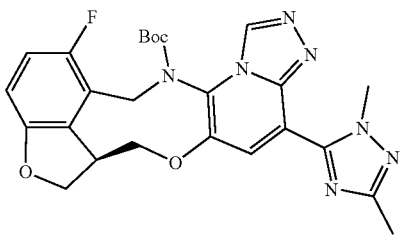 [SMILES: Cc1nc(-c2cc3c(n4cnnc24)N(C(=O)OC(C)(C)C)Cc2c(F)ccc4c2[C@H](CO4)CO3)n(C)n1]

To tert-butyl (S,Z)-4-((1-(dimethylamino)ethylidene)carbamoyl)-12-fluoro-7a,13-dihydro-7H-[1,2,4]triazolo[4',3':1, 6]pyrido[3,2-b]benzofuro[4,3-fg][1,4]oxazonine-14 (8H)-carboxylate (2.00 g, 3.81 mmol, 1.00 eq) in AcOH (21.0 g, 350 mmol, 20.0 mL, 91.7 eq) was added methylhydrazine (1.32 g, 11.4 mmol, 1.51 mL, 3.00 eq) at 20° C. The mixture was stirred at 60° C. for 2 h. LC-MS showed tert-butyl (S,Z)-4-((1-(dimethylamino)ethylidene)carbamoyl)-12-fluoro-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired desired mass was detected. Water (10.0 mL) was added to the mixture which was then extracted with ethyl acetate (50.0 mL*4). The combined organic layers were dried over anhydrous $Na_2SO_4$, filtered, and concentrated under reduced pressure. The residue was purified by column chromatography ($SiO_2$, Petroleum ether/Ethyl acetate=1/0 to 0/1). tert-butyl (S)-4-(1,3-dimethyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (1.20 g, crude) was obtained as yellow oil.

Step 6: (S)-4-(1,3-dimethyl-1H-1,2,4-triazol-S-yl)-12-fluoro-7a,8,13,14-tetrahydro-7H-[1,2,4]triazolo[4',3'0.1,6]pyrido[3,2-b]benzofuro[4,3-fg][1,4]oxazonine

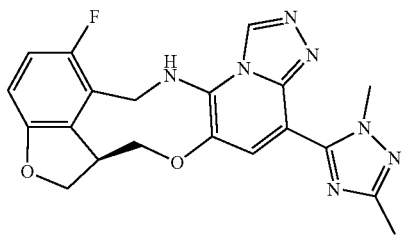 [SMILES: Cc1nc(-c2cc3c(n4cnnc24)NCc2c(F)ccc4c2[C@H](CO4)CO3)n(C)n1]

To tert-butyl (S)-4-(1,3-dimethyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (1.20 g, 2.36 mmol, 1.00 eq) in DCM (10.0 mL) was added TFA (5.10 g, 44.7 mmol, 3.31 mL, 18.9 eq) at 20° C. Then the mixture was stirred at 20° C. for 1 hr. The reaction mixture was concentrated under reduced pressure. The crude product was purified by prep-HPLC (formic acid conditions). (S)-4-(1,3-dimethyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine (280 mg, 687 umol, 29% yield, N/A purity) was obtained as white solid. $^1$H NMR DMSO-$d_6$ 400 MHz δ=ppm 9.48 (s, 1H), 7.87 (br t, J=6.3 Hz, 1H), 7.59 (s, 1H), 6.96 (dd, J=10.1, 9.0 Hz, 1H), 6.70 (dd, J=8.7, 3.8 Hz, 1H), 4.99-4.88 (m, 1H), 4.88-4.76 (m, 1H), 4.59-4.45 (m, 2H), 4.21 (dd, J=9.5, 3.7 Hz, 1H), 4.10-3.98 (m, 1H), 3.85 (br d, J=10.4 Hz, 1H), 3.78 (s, 3H), 2.27 (s, 3H).

Step 7: (S)-4-(1,3-dimethyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine Mesylate

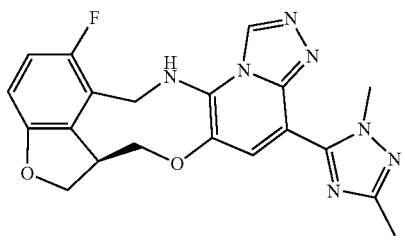 [SMILES: Cc1nc(-c2cc3c(n4cnnc24)NCc2c(F)ccc4c2[C@H](CO4)CO3)n(C)n1]

To free base (S)-4-(1,3-dimethyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine (257 mg, 631 umol, 1.00 eq) in MeCN (1.84 mL) was added MsOH (61.2 mg, 637 umol, 45.4 uL, 1.01 eq) in MeCN (0.276 mL) dropwise at 50° C. Then the mixture was stirred at 50° C. for 1 hr, then the mixture was cooled to 30° C. in the span of 1 hr, and the mixture was stirred at 30° C. for 2 h. The mixture was cooled to 25° C. and concentrated under reduced pressure to remove most of MeCN at 30° C. Water (10.0 mL) was added to the mixture followed by lyophilization. (S)-4-(1,3-dimethyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine (312 mg, 599 umol, 95% yield, 96.7% purity, $CH_3SO_3H$ salt) was obtained as a yellow crystalline solid. $^1$H NMR DMSO-$d_6$ 400 MHz δ=ppm 9.62 (s, 1H), 8.57-8.30 (m, 1H), 7.97 (br s, 1H), 7.00 (t, J=9.5 Hz, 1H), 6.73 (dd, J=8.6, 3.7 Hz, 1H), 5.09-4.78 (m, 2H), 4.56 (br t, J=9.5 Hz, 2H), 4.23 (br dd, J=9.5, 3.7 Hz, 1H), 4.14-4.02 (m, 1H), 3.95 (br s, 1H), 3.88 (s, 3H), 2.34 (s, 3H), 2.32 (s, 3H). LCMS (ESI+): m/z 408.2 (M+H).

Example 129: (S)-4-(3-ethyl-1-methyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-((1-iminopropyl)carbamoyl)-7a,13-dihydro-7H-[1,2,4]triazolo[4',3':1,6]pyrido[3,2-b]benzofuro[4,3-fg][,4]oxazonine-14 (8H)-carboxylate

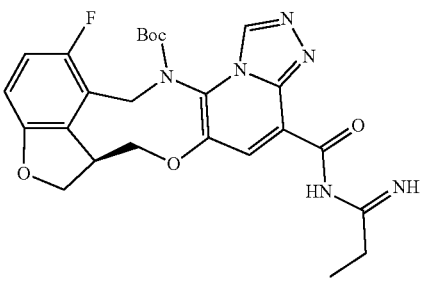 [SMILES: CCC(=N)NC(=O)c1cc2c(n3cnnc13)N(C(=O)OC(C)(C)C)Cc1c(F)ccc3c1[C@H](CO3)CO2]

To (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid (300 mg, 657 umol, 1.00 eq) in DMF (5.00 mL) was added DIPEA (340 mg, 2.63 mmol, 458 uL, 4.00 eq), the mixture was stirred at 20° C. for 5 mins. Then EDCI (252 mg, 1.31 mmol, 2.00 eq) and HOBt (178 mg, 1.31 mmol, 2.00 eq) were added to the mixture at 20° C. The mixture was stirred at 20° C. for 5 min followed by addition of propanamidine (143 mg, 1.31 mmol, 2.00 eq, HCl salt) at 20° C. The mixture was stirred at 20° C. for 12 hr. LC-MS showed that (S)-14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonine-4-carboxylic acid was consumed completely and one main peak with the desired mass was detected. The obtained material was used directly in the next step.

Step 2: tert-butyl (S)-4-(3-ethyl-1-methyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

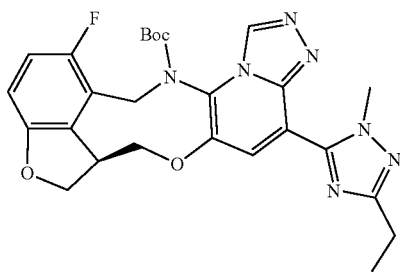 [SMILES: CCc1nc(-c2cc3c(n4cnnc24)N(C(=O)OC(C)(C)C)Cc2c(F)ccc4c2[C@H](CO4)CO3)n(C)n1]

To tert-butyl (S)-12-fluoro-4-((1-iminopropyl)carbamoyl)-7a,13-dihydro-7H-[1,2,4]triazolo[4',3':1,6]pyrido[3,2-b]benzofuro[4,3-fg][1,4]oxazonine-14 (8H)-carboxylate (656 umol theoretical yield, 1.00 eq) in DMF (5.00 mL) was added AcOH (315 mg, 5.25 mmol, 300 uL, 7.99 eq) and methylhydrazine (113 mg, 981 umol, 129 uL, 1.50 eq) at 20° C. The mixture was stirred at 60° C. for 2 hr. LC-MS showed tert-butyl (S)-12-fluoro-4-((1-iminopropyl)carbamoyl)-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with the desired mass was detected. Water (5.00 mL) was added to the mixture. The reaction mixture was extracted with ethyl acetate (5.00 mL*5). The combined organic layers were dried over anhydrous Na₂SO₄, filtered, and concentrated under reduced pressure. The residue was purified by prep-TLC (SiO₂, ethyl acetate). tert-Butyl (S)-4-(3-ethyl-1-methyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, crude) was obtained as yellow oil.

Step 3: (S)-4-(3-ethyl-1-methyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine

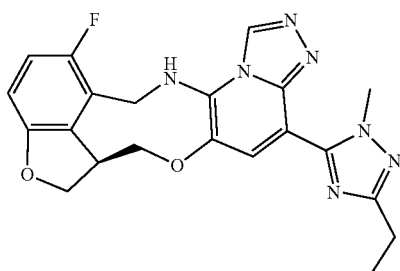 [SMILES: CCc1nc(-c2cc3c(n4cnnc24)NCc2c(F)ccc4c2[C@H](CO4)CO3)n(C)n1]

To tert-butyl (S)-4-(3-ethyl-1-methyl-1H-1,2,4-triazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 230 umol, 1.00 eq) in DCM (1.00 mL) was added TFA (462 mg, 4.05 mmol, 0.300 mL, 17.6 eq) at 20° C. The mixture was stirred at 20° C. for 1 hr. The reaction mixture was concentrated under reduced pressure. The crude product was purified by prep-HPLC (HCl conditions). (S)-4-(3-ethyl-1-methyl-1H-1,2,4-triazol-S-yl)-12-fluoro-7a,8,13,14-tetrahydro-7H-[1,2,4]triazolo[4',3':1,6]pyrido[3,2-b]benzofuro[4,3-fg][1,4]oxazonine (13.7 mg, 29.2 umol, 12% yield, 97.6% purity, HCl salt) was obtained as yellow solid. ¹H NMR CD₃OD 400 MHz δ=ppm 9.54 (s, 1H), 8.18 (s, 1H), 6.92 (dd, J=10.1, 8.8 Hz, 1H), 6.68 (dd, J=8.7, 3.9 Hz, 1H), 5.21 (d, J=14.8 Hz, 1H), 5.01-4.95 (m, 1H), 4.80-4.74 (m, 1H), 4.68-4.58 (m, 1H), 4.31 (dd, J=9.7, 3.4 Hz, 1H), 4.11-4.04 (m, 1H), 4.01 (s, 3H), 3.99-3.91 (m, 1H), 2.84 (q, J=7.6 Hz, 2H), 1.36 (br t, J=7.5 Hz, 3H). LCMS (ESI+): m/z 422.2 (M+H).

Example 130: (S)-12-fluoro-4-(2-methylpyridin-3-yl)-7a,8,13,14-tetrahydro-7H-[1,2,4]triazolo[1',5':1,6]pyrido[3,2-b]benzofuro[4,3-fg][1,4]oxazonine Step 1: tert-butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate

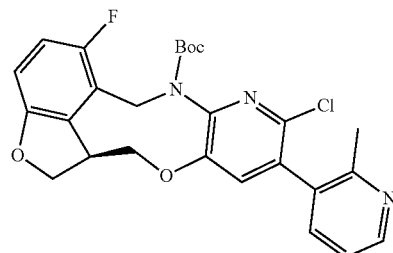

Two parallel reactions were set up. To a solution of tert-butyl (R)-10-bromo-9-chloro-S-fluoro-13,13a-dihydro-1H-benzofuro[4,3-fg]pyrido[3,2-b][1,4]oxazonine-7 (6H)-carboxylate (Example 16; 500 mg, 1.03 mmol, 1.00 eq) in dioxane (8.00 mL) and water (0.800 mL) was added 2-methyl-3-(4,4,5,5-tetramethyl-1,3,2-dioxaborolan-2-yl)pyridine (395 mg, 1.55 mmol, 1.50 eq, HCl), Pd(dppf)Cl₂ (75.3 mg, 103 umol, 0.100 eq) and NaHCO₃ (432 mg, 5.14 mmol, 5.00 eq) at 20° C. The mixture was stirred at 80° C. for 12 h under nitrogen atmosphere. The batches were combined, the mixture was filtered, the filtrate was concentrated. The residue was purified by column chromatography (SiO₂, Petroleum ether/Ethyl acetate=1/0 to 0/1). tert-butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate (720 mg, 1.45 mmol, 70% yield) was obtained as a yellow solid.

Step 2: tert-butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate

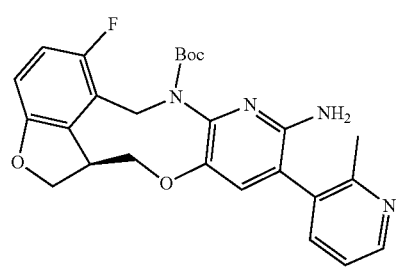 [SMILES: Cc1ncccc1-c1cc2c(nc1N)N(C(=O)OC(C)(C)C)Cc1c(F)ccc3c1[C@@H](CO2)CO3]

To a mixture of tert-butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate (450 mg, 904 umol, 1.00 eq), NaN₃ (823 mg, 12.7 mmol, 14.0 eq) and sodium ascorbate (215 mg, 1.09 mmol, 1.20 eq) in dioxane (15.0 mL) and water (3.00 mL) were added CuI (241 mg, 1.27 mmol, 1.40 eq) and (1S,2S)—N₁,N₂-dimethylcyclohexane-1,2-diamine (257 mg, 1.81 mmol, 2.00 eq) at 20° C. The mixture was stirred at 110° C. for 16 h under nitrogen atmosphere. Water (15.0 mL) was added to the reaction solution, the mixture was extracted with ethyl acetate (15.0 mL*3), the combined organic layers were dried over MgSO₄ and concentrated under reduced pressure. The residue was purified by prep-TLC (SiO₂, Petroleum ether/Ethyl acetate=0/1). tert-Butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate (400 mg, 836 umol, 92% yield) was obtained as a yellow oil.

Step 3: tert-butyl (R,Z)—S-fluoro-9-(((hydroxyamino)methylene)amino)-10-(2-methylpyridin-3-yl)-13,13a-dihydro-1H-benzofuro[4,3-fg]pyrido[3,2-b][1,4]oxazonine-7 (6H)-carboxylate

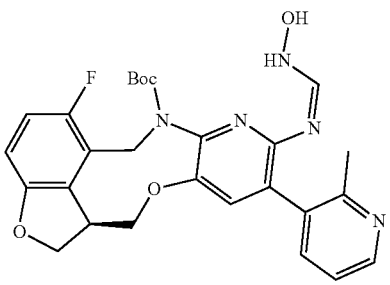 [SMILES: Cc1ncccc1-c1cc2c(nc1/N=C\NO)N(C(=O)OC(C)(C)C)Cc1c(F)ccc3c1[C@@H](CO2)CO3]

To a solution of tert-butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate (400 mg, 836 umol, 1.00 eq) in i-PrOH (6.00 mL) was added DMF-DMA (249 mg, 2.09 mmol, 278 uL, 2.50 eq) at 20° C., the mixture was stirred at 90° C. for 5 h under nitrogen atmosphere. Then NH₂OH.HCl (145 mg, 2.09 mmol, 2.50 eq) was added to the mixture at 20° C., and the mixture was stirred at 50° C. for 12 h. The reaction mixture was concentrated and the residue was purified by prep-TLC (SiO₂, Petroleum ether/Ethyl acetate=0/1). tert-Butyl (R,Z)—S-fluoro-9-(((hydroxyamino)methylene)amino)-10-(2-methylpyridin-3-yl)-13,13a-dihydro-1H-benzofuro[4,3-fg]pyrido[3,2-b][1,4]oxazonine-7 (6H)-carboxylate (390 mg, 748 umol, 89% yield) was obtained as a yellow oil.

Step 4: tert-butyl (S)-12-fluoro-4-(2-methylpyridin-3-yl)-7a,13-dihydro-7H-[1,2,4]triazolo[1',5':1,6]pyrido[3,2-b]benzofuro[4,3-fg][1,4]oxazonine-14 (8H)-carboxylate

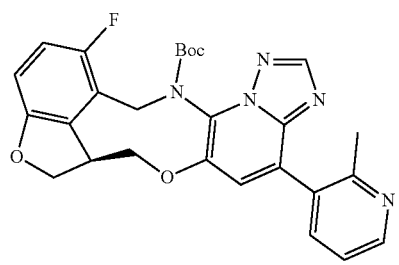 [SMILES: Cc1ncccc1-c1cc2c(n3ncnc13)N(C(=O)OC(C)(C)C)Cc1c(F)ccc3c1[C@H](CO3)CO2]

To a solution of tert-butyl (R,Z)—S-fluoro-9-(((hydroxyamino)methylene)amino)-10-(2-methylpyridin-3-yl)-13,13a-dihydro-1H-benzofuro[4,3-fg]pyrido[3,2-b][1,4]oxazonine-7 (6H)-carboxylate (460 mg, 882 umol, 1.00 eq) in THF (10.0 mL) was added TFAA (926 mg, 4.41 mmol, 613 uL, 5.00 eq) at 0° C., the mixture was stirred at 50° C. for 16 hr under nitrogen atmosphere. Water (10.0 mL) was added to the reaction solution, the mixture was extracted with ethyl acetate (10.0 mL*3), the combined organic layers were dried over MgSO₄ and concentrated under reduced pressure. tert-Butyl (S)-12-fluoro-4-(2-methylpyridin-3-yl)-7a,13-dihydro-7H-[1,2,4]triazolo[1',5':1,6]pyrido[3,2-b]benzofuro[4,3-fg][1,4]oxazonine-14 (8H)-carboxylate (1.00 g, crude) was obtained as a yellow oil.

Step 5: (S)-12-fluoro-4-(2-methylpyridin-3-yl)-7a,8,13,14-tetrahydro-7H-[1,2,4]triazolo[1',5':1,6]pyrido[3,2-b]benzofuro[4,3-fg][1,4]oxazonine

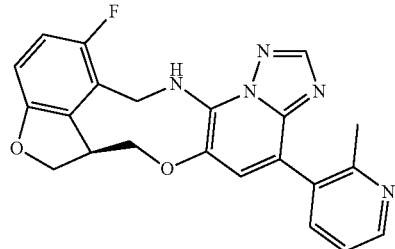

Two parallel reactions were set up. A mixture of tert-butyl (S)-12-fluoro-4-(2-methylpyridin-3-yl)-7a,13-dihydro-7H-[1,2,4]triazolo[1',5':1,6]pyrido[3,2-b]benzofuro[4,3-fg][1,4]oxazonine-14 (8H)-carboxylate (500 mg, 993 umol, 1.00 eq) in HFIP (10.0 mL) was stirred at 100° C. for 12 h. The batches were combined and concentrated under reduced pressure. The residue was dissolved in MeOH (5.00 mL). The mixture was purified by acidic prep-HPLC (column: Phenomenex luna C18 250*50 mm*10 um; mobile phase: [water (0.05% HCl)-ACN]; B %: 10%-40%, 10 min). The product-containing fraction was concentrated under reduced pressure to remove most of MeCN at 30° C. and the aqueous phase was lyophilized. (S)-12-fluoro-4-(2-methylpyridin-3-yl)-7a,8,13,14-tetrahydro-7H-[1,2,4]triazolo[1',5':1,6]pyrido[3,2-b]benzofuro[4,3-fg][1,4]oxazonine (100 mg, 227 umol, 11% yield, 100% purity, HCl salt) was obtained as a white solid. ¹H NMR CD₃OD 400 MHz δ=ppm 8.81 (dd, J=6.0, 1.5 Hz, 1H), 8.79 (s, 1H), 8.57 (dd, J=8.2, 1.3 Hz, 1H), 8.02 (dd, J=7.8, 6.1 Hz, 1H), 7.91 (s, 1H), 6.94-6.84 (m, 1H), 6.66 (dd, J=8.7, 3.9 Hz, 1H), 5.16 (d, J=14.8 Hz, 1H), 4.97 (br d, J=14.8 Hz, 1H), 4.82-4.76 (m, 1H), 4.61 (t, J=9.4 Hz, 1H), 4.31 (dd, J=9.8, 3.0 Hz, 1H), 4.10-3.88 (m, 2H), 2.66 (s, 3H). LCMS (ESI+): m/z 404.1 (M+H).

Example 131: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-2-methylpropanenitrile Step 1: (5-bromo-1-methyl-1H-pyrazol-3-yl)methyl Methanesulfonate

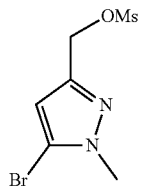

To (5-bromo-1-methyl-1H-pyrazol-3-yl)methanol (1.60 g, 8.38 mmol, 1.00 eq) in DCM (15.0 mL) was added TEA (1.70 g, 16.8 mmol, 2.33 mL, 2.00 eq) and MsCl (1.92 g, 16.8 mmol, 1.30 mL, 2.00 eq) at 0° C. The mixture was stirred at 0° C. for 1 hr. Saturated NaHCO$_3$ was added to the mixture to adjust pH to 7.0. The mixture was extracted with EtOAc (10.0 mL*4). The combined organic layers were washed with brine (5.00 mL), dried over anhydrous Na$_2$SO$_4$, filtered, and concentrated under reduced pressure to give (5-bromo-1-methyl-1H-pyrazol-3-yl)methyl methanesulfonate (2.00 g, crude) as a yellow oil.

Step 2: 2-(5-bromo-1-methyl-1H-pyrazol-3-yl)acetonitrile

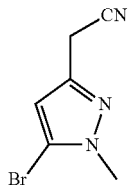

The reaction was set up in 20 parallel batches. To (5-bromo-1-methyl-1H-pyrazol-3-yl)methyl methanesulfonate (100 mg, 372 umol, 1.00 eq) in MeCN (1.00 mL) was added TMSCN (55.3 mg, 557 umol, 69.7 uL, 1.50 eq) and TBAF (1.00 M, 557 uL, 1.50 eq) at 25° C. The mixture was stirred at 25° C. for 12 h. LC-MS showed (5-bromo-1-methyl-1H-pyrazol-3-yl)methyl methanesulfonate was consumed completely and one main peak with desired mass was detected. The batches were combined and concentrated under reduced pressure. Water (30.0 mL) was added to the mixture. The mixture was extracted with EtOAc (50.0 mL*4). The combined organic layers were concentrated under reduced pressure. The residue was purified by column chromatography (SiO$_2$, Petroleum ether/Ethyl acetate=1/0 to 1/1). 2-(5-bromo-1-methyl-1H-pyrazol-3-yl)acetonitrile (800 mg, crude) was obtained as a yellow solid.

Step 3: 2-(5-bromo-1-methyl-1H-pyrazol-3-yl)-2-methylpropanenitrile

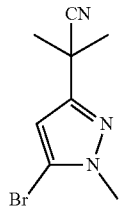

To NaH (390 mg, 9.75 mmol, 60% purity, 3.00 eq) was added THF (4.00 mL) at 25° C. The mixture was degassed and purged with nitrogen 3 times, the mixture was stirred at 0° C. for 10 mins. Then 2-(5-bromo-1-methyl-1H-pyrazol-3-yl)acetonitrile (650 mg, 3.25 mmol, 1.00 eq) in THF (1.00 mL) was added to the mixture at 0° C. The mixture was stirred at 0° C. for 0.5 hr under nitrogen atmosphere. MeI (1.84 g, 13.0 mmol, 809 uL, 4.00 eq) was added at 0° C. The mixture was stirred at 0° C. for 1 hr under nitrogen atmosphere. Water (5.00 mL) was added to the mixture. The mixture was extracted with EtOAc (20.0 mL*3). The combined organic layers were dried over anhydrous Na$_2$SO$_4$, filtered, and concentrated under reduced pressure. The residue was purified by prep-TLC (SiO$_2$, PE:EtOAc=2:1). 2-(5-bromo-1-methyl-1H-pyrazol-3-yl)-2-methylpropanenitrile (550 mg, crude) was obtained as a yellow oil.

Step 4: 2-methyl-2-(1-methyl-S-(tributylstannyl)-1H-pyrazol-3-yl)propanenitrile

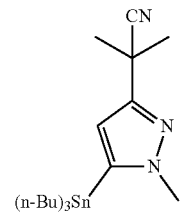

To 2-(5-bromo-1-methyl-1H-pyrazol-3-yl)-2-methylpropanenitrile (220 mg, 965 umol, 1.00 eq) in THF (3.00 mL) was added i-PrMgCl—LiCl (1.30 M, 1.48 mL, 2.00 eq) at −78° C. under N$_2$. Then the mixture was stirred at 0° C. for 0.5 hr under N$_2$. Then tributyl(chloro)stannane (628 mg, 1.93 mmol, 519 uL, 2.00 eq) was added into the mixture at 0° C. under N$_2$. The mixture was stirred at 0° C. for 1 hr under N$_2$. Water (5.00 mL) was added to the mixture. Then the mixture was extracted with ethyl acetate (10.0 mL*3), the combined organic layers were dried over anhydrous Na$_2$SO$_4$, filtered and the filtrate was concentrated under reduced pressure. 2-methyl-2-(1-methyl-S-(tributylstannyl)-1H-pyrazol-3-yl)propanenitrile (450 mg, crude) was obtained as a yellow oil.

Step 5: tert-butyl (S)-4-(3-(2-cyanopropan-2-yl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

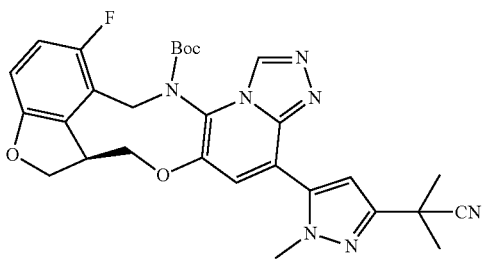 [SMILES: Cn1nc(C(C)(C)C#N)cc1-c1cc2c(n3cnnc13)N(C(=O)OC(C)(C)C)Cc1c(F)ccc3c1[C@H](CO3)CO2]

To 2-methyl-2-(1-methyl-S-(tributylstannyl)-1H-pyrazol-3-yl)propanenitrile (268 mg, 611 umol, 1.50 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 407 umol, 1.00 eq) in dioxane (3.00 mL) was added Pd(PPh$_3$)$_4$ (47.0 mg, 40.7 umol, 0.100 eq), LiCl (34.5 mg, 814 umol, 16.7 uL, 2.00 eq) and CuI (31.0 mg, 163 umol, 0.400 eq) at 25° C. The mixture was stirred at 80° C. for 12 hr under N$_2$. The mixture was filtered and the filtrate was concentrated under reduced pressure. The residue was purified by prep-TLC (SiO$_2$, Petroleum ether/Ethyl acetate=0/1). tert-Butyl (S)-4-(3-(2-cyanopropan-2-yl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, crude) was obtained as a yellow oil.

Step 6: (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-2-methylpropanenitrile

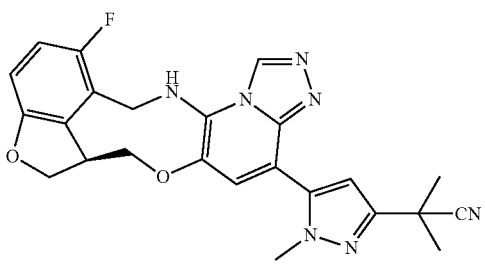 [SMILES: Cn1nc(C(C)(C)C#N)cc1-c1cc2c(n3cnnc13)NCc1c(F)ccc3c1[C@H](CO3)CO2]

To tert-butyl (S)-4-(3-(2-cyanopropan-2-yl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (180 mg, 322 umol, 1.00 eq) was added HFIP (2.00 mL) at 25° C., the mixture was stirred at 100° C. for 12 h. The mixture was combined with another batch from 20 mg of tert-butyl (S)-4-(3-(2-cyanopropan-2-yl)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate. The mixture was concentrated under reduced pressure. The crude product was purified by prep-HPLC (formic acid conditions). (S)-2-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-yl)-2-methylpropanenitrile (74.3 mg, 143 umol, 97.5% purity, formate salt) was obtained as a light-yellow solid. $^1$H NMR DMSO-d$_6$ 400 MHz δ=ppm 9.45 (s, 1H), 7.70 (br t, J=6.2 Hz, 1H), 7.47 (s, 1H), 6.96 (t, J=9.5 Hz, 1H), 6.70 (dd, J=8.6, 3.7 Hz, 1H), 6.64 (s, 1H), 4.97-4.87 (m, 1H), 4.85-4.74 (m, 1H), 4.60-4.45 (m, 2H), 4.20 (dd, J=9.6, 3.4 Hz, 1H), 4.10-3.96 (m, 1H), 3.94-3.84 (m, 1H), 3.81 (s, 3H), 1.68 (s, 6H). LCMS (ESI+): m/z 460.1 (M+H).

Example 132: (S)-12-fluoro-4-(3-fluoro-1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine Step 1: 3-fluoro-1-methyl-1H-pyrazole

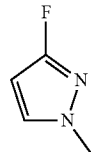

To NaH (488 mg, 12.2 mmol, 60% purity, 3.00 eq) in THF (1.00 mL) was added 3-fluoro-1H-pyrazole (350 mg, 4.07 mmol, 1.00 eq) at 0° C. under nitrogen atmosphere. The mixture was stirred at 0° C. for 0.5 hr under N$_2$. MeI (2.31 g, 16.3 mmol, 1.01 mL, 4.00 eq) in THF (2.00 mL) was added to the mixture at 0° C., and the mixture was stirred at 0° C. for 1 hr under nitrogen atmosphere. Water (5.00 mL) was added to the mixture, the mixture was extracted with EtOAc (5.00 mL*3). The combined organic layers were dried over anhydrous Na$_2$SO$_4$, filtered and the filtrate was concentrated under reduced pressure. 3-Fluoro-1-methyl-1H-pyrazole (300 mg, crude) was obtained as yellow oil. $^1$H NMR CDCl$_3$ 400 MHz δ=ppm 7.15 (t, J=2.2 Hz, 1H), 5.74 (dd, J=6.0, 2.4 Hz, 1H), 3.77 (s, 3H).

Step 2: 3-fluoro-1-methyl-S-(tributylstannyl)-1H-pyrazole

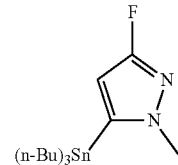

To 3-fluoro-1-methyl-1H-pyrazole (450 mg, 4.50 mmol, 1.00 eq) in THF (1.00 mL) was added n-BuLi (2.50 M, 3.60 mL, 2.00 eq) at −78° C. under N$_2$. The mixture was stirred at −78° C. for 30 min. Tributyl(chloro)stannane (2.93 g, 8.99 mmol, 2.42 mL, 2.00 eq) was added to the mixture at −78° C. under N$_2$. The mixture was stirred at −78° C. for 1 hr under N$_2$. The mixture was extracted with ethyl acetate (5.00 mL*3), the combined organic layers were dried over anhydrous Na$_2$SO$_4$, filtered, and concentrated under reduced pressure. The residue was purified by prep-TLC (SiO$_2$, Petroleum ether:ethyl acetate=10:1). 3-Fluoro-1-methyl-S-(tributylstannyl)-1H-pyrazole (350 mg, 899 umol, 20% yield) was obtained as a colorless oil.

Step 3: tert-butyl (S)-12-fluoro-4-(3-fluoro-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate

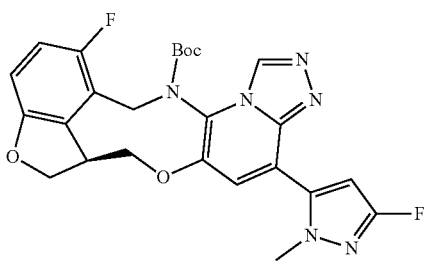 [SMILES: Cn1nc(F)cc1-c1cc2c(n3cnnc13)N(C(=O)OC(C)(C)C)Cc1c(F)ccc3c1[C@H](CO3)CO2]

To 3-fluoro-1-methyl-S-(tributylstannyl)-1H-pyrazole (178 mg, 458 umol, 1.50 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq) in dioxane (1.00 mL) was added Pd(PPh$_3$)$_4$ (35.3 mg, 30.5 umol, 0.100 eq), LiCl (25.9 mg, 611 umol, 12.5 uL, 2.00 eq) and CuI (23.3 mg, 122 umol, 0.400 eq) at 25° C. The mixture was stirred at 100° C. for 12 h under N$_2$. The mixture was filtered and the filtrate was concentrated under reduced pressure. The residue was purified by prep-TLC (SiO$_2$, Petroleum ether/Ethyl acetate=1/2). tert-butyl (S)-12-fluoro-4-(3-fluoro-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, crude) was obtained as a yellow oil.

Step 4: (S)-12-fluoro-4-(3-fluoro-1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine

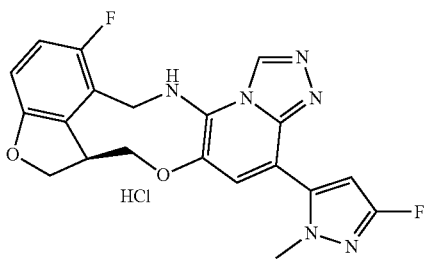 [SMILES: Cn1nc(F)cc1-c1cc2c(n3cnnc13)NCc1c(F)ccc3c1[C@H](CO3)CO2 ; Cl]

To tert-butyl (S)-12-fluoro-4-(3-fluoro-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (120 mg, 235 umol, 1.00 eq) was added HFIP (2.00 mL) at 25° C. The mixture was stirred at 100° C. for 3 h The mixture was concentrated under reduced pressure. The crude product was purified by prep-HPLC (HCl conditions). (S)-12-fluoro-4-(3-fluoro-1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine (39.6 mg, 88.62 umol, 37% yield, 100% purity, HCl salt) was obtained as a light-yellow solid. $^1$H NMR CD$_3$OD 400 MHz δ=ppm 9.44 (s, 1H), 7.85 (s, 1H), 6.90 (dd, J=10.0, 8.9 Hz, 1H), 6.67 (dd, J=8.6, 3.7 Hz, 1H), 6.12 (d, J=5.7 Hz, 1H), 5.16 (d, J=14.8 Hz, 1H), 4.94 (s, 1H), 4.76-4.67 (m, 1H), 4.60 (t, J=9.4 Hz, 1H), 4.30 (dd, J=9.6, 3.2 Hz, 1H), 4.09-3.98 (m, 1H), 3.93-3.84 (m, 1H), 3.66 (s, 3H). LCMS (ESI+): m/z 411.0 (M+H).

Example 133: (S)-12-fluoro-4-(1,2,4-trimethyl-1H-imidazol-S-yl)-7a,8,13,14-tetrahydro-7H-[1,2,4]triazolo[4',3':1,6]pyrido[3,2-b]benzofuro[4,3-fg][1,4]oxazonine

Step 1: tert-butyl (7aS)-12-fluoro-4-(1-hydroxypropyl)-7a,13-dihydro-7H-[1,2,4]triazolo[4',3':1,6]pyrido[3,2-b]benzofuro[4,3-fg][1,4]oxazonine-14 (8H)-carboxylate

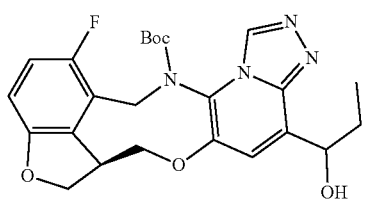 [SMILES: CCC(O)c1cc2c(n3cnnc13)N(C(=O)OC(C)(C)C)Cc1c(F)ccc3c1[C@H](CO3)CO2]

The reaction was set up in two parallel batches. To a stirred solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (500 mg, 1.02 mmol, 1.00 eq) in THF (7.00 mL) was added i-PrMgCl—LiCl (1.30 M, 1.57 mL, 2.00 eq) at −78° C. under nitrogen, and the mixture was stirred at 0° C. for 0.5 hr. To the mixture was added propanal (236 mg, 4.07 mmol, 296 uL, 4.00 eq) at −78° C. under N$_2$. The resulting mixture was stirred at 25° C. for 12 h. The batches were combined. To the resulting mixture was added water (20.0 mL) and it was extracted with EtOAc (10.0 mL*3). The combined organic layers were dried over Na$_2$SO$_4$ and concentrated under reduced pressure. The mixture was purified by MPLC (SiO$_2$, PE/EtOAc=10/1 to 1/2). tert-Butyl (7aS)-12-fluoro-4-(1-hydroxypropyl)-7a,13-dihydro-7H-[1,2,4]triazolo[4',3':1,6]pyrido[3,2-b]benzofuro[4,3-fg][1,4]oxazonine-14 (8H)-carboxylate (1.20 g, crude) was obtained as a brown solid.

Step 2: tert-butyl (S)-12-fluoro-4-propionyl-7a,13-dihydro-7H-[1,2,4]triazolo[4',3':1,6]pyrido[3,2-b]benzofuro[4,3-fg][1,4]oxazonine-14 (8H)-carboxylate

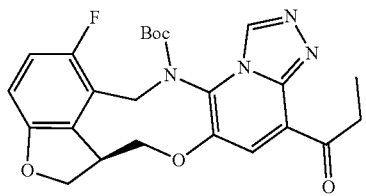 [SMILES: CCC(=O)c1cc2c(n3cnnc13)N(C(=O)OC(C)(C)C)Cc1c(F)ccc3c1[C@H](CO3)CO2]

To a stirred solution of tert-butyl (7aS)-12-fluoro-4-(1-hydroxypropyl)-7a,13-dihydro-7H-[1,2,4]triazolo[4',3':1,6]pyrido[3,2-b]benzofuro[4,3-fg][1,4]oxazonine-14 (8H)-carboxylate (1.20 g, 2.55 mmol, 1.00 eq) in DCM (30.0 mL) was added DMP (2.16 g, 5.10 mmol, 1.58 mL, 2.00 eq) at 25° C. The mixture was stirred at 25° C. for 12 h. The reaction mixture was diluted with water (30.0 mL) and extracted with EtOAc (30.0 mL*3). The combined organic layers were dried over MgSO$_4$, filtered, and concentrated under reduced pressure. The residue was purified by prep-TLC (SiO$_2$, PE/EtOAc=1/2). tert-butyl (S)-12-fluoro-4-propionyl-7a,13-dihydro-7H-[1,2,4]triazolo[4',3':1,6]pyrido[3,2-b]benzofuro[4,3-fg][1,4]oxazonine-14 (8H)-carboxylate (240 mg, crude) was obtained as a yellow solid.

Step 3: tert-butyl (S,Z)-12-fluoro-4-(2-(hydroxyimino)propanoyl)-7a,13-dihydro-7H-[1,2,4]triazolo[4',3':1,6]pyrido[3,2-b]benzofuro[4,3-fg][1,4]oxazonine-14 (8H)-carboxylate and (S,Z)-1-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-(hydroxyimino)propan-1-one

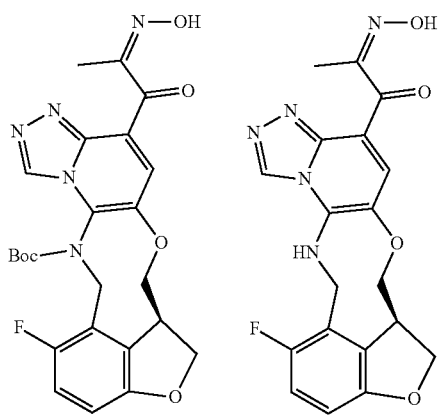 [SMILES: C/C(=N/O)C(=O)c1cc2c(n3cnnc13)N(C(=O)OC(C)(C)C)Cc1c(F)ccc3c1[C@H](CO3)CO2 ; C/C(=N/O)C(=O)c1cc2c(n3cnnc13)NCc1c(F)ccc3c1[C@H](CO3)CO2]

To a solution of tert-butyl (S)-12-fluoro-4-propionyl-7a,13-dihydro-7H-[1,2,4]triazolo[4',3':1,6]pyrido[3,2-b]benzofuro[4,3-fg][1,4]oxazonine-14 (8H)-carboxylate (240 mg, 512 umol, 1.00 eq) in DCM (3.00 mL) was added TMSCl (55.7 mg, 512 umol, 65.0 uL, 1.00 eq) at −20° C. To the cooled solution was added dropwise isoamyl nitrite (60.0 mg, 512 umol, 68.9 uL, 1.00 eq). The mixture was stirred at 25° C. for 12 h. The reaction mixture was concentrated under reduced pressure. The residue was purified by prep-TLC (SiO$_2$, EtOAc/MeOH=20/1). tert-butyl (S,Z)-12-fluoro-4-(2-(hydroxyimino)propanoyl)-7a,13-dihydro-7H-[1,2,4]triazolo[4',3':1,6]pyrido[3,2-b]benzofuro[4,3-fg][1,4]oxazonine-14 (8H)-carboxylate (30.0 mg, crude) was obtained as a yellow solid. (S,Z)-1-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-(hydroxyimino)propan-1-one (50.0 mg, crude) was obtained as a white solid.

Step 4: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1,2,4-trimethyl-1H-imidazole 3-oxide

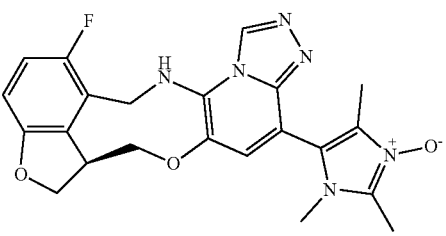

To a stirred solution of (S,Z)-1-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-(hydroxyimino)propan-1-one (50.0 mg, 126 umol, 1.00 eq) in AcOH (2.00 mL) was added MeCHO (5.54 mg, 126 umol, 7.06 uL, 1.00 eq) and MeNH$_2$ (9.77 mg, 126 umol, 30.2 uL, 40% aqueous solution, 1.00 eq) at 25° C. The resulting mixture was stirred at 100° C. for 12 h The mixture was concentrated under reduced pressure. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1,2,4-trimethyl-1H-imidazole 3-oxide (55.0 mg, crude) was obtained as yellow liquid, which was used to the next step directly.

Step 5: (S)-12-fluoro-4-(1,2,4-trimethyl-1H-imidazol-S-yl)-7a,8,13,14-tetrahydro-7H-[1,2,4]triazolo[4',3':1,6]pyrido[3,2-b]benzofuro[4,3-fg][1,4]oxazonine

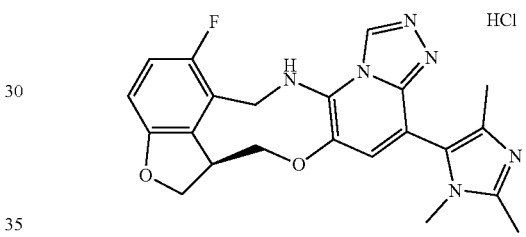

To a stirred solution of (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1,2,4-trimethyl-1H-imidazole 3-oxide (55.0 mg, 126 umol, 1.00 eq) in MeOH (10.0 mL) was added Raney-Ni (30.0 mg) at 25° C. under N$_2$. The resulting mixture was stirred at 50° C. for 12 h under H$_2$ (15 psi). The mixture was concentrated under reduced pressure. The mixture was purified by acidic prep-HPLC (HCl conditions) to give the crude product. The crude product was purified by acidic prep-HPLC (HCl) again. (S)-12-fluoro-4-(1,2,4-trimethyl-1H-imidazol-S-yl)-7a,8,13,14-tetrahydro-7H-[1,2,4]triazolo[4',3':1,6]pyrido[3,2-b]benzofuro[4,3-fg][1,4]oxazonine (2.00 mg, 4.26 umol, 3% yield, 97.4% purity, HCl salt) was obtained as a yellow solid. $^1$H NMR CD$_3$OD 400 MHz δ=ppm 9.53 (s, 1H), 7.98 (s, 1H), 6.93 (t, J=9.4 Hz, 1H), 6.69 (dd, J=8.6, 3.9 Hz, 1H), 5.22 (br d, J=14.7 Hz, 1H), 4.96 (br d, J=14.9 Hz, 1H), 4.84-4.69 (m, 1H), 4.68-4.59 (m, 1H), 4.31 (dd, J=9.6, 3.1 Hz, 1H), 4.14-4.00 (m, 1H), 3.95-3.84 (m, 1H), 3.35 (s, 3H), 2.69 (s, 3H), 2.20 (br s, 3H). $^1$H NMR DMSO-d$_6$ 400 MHz δ=ppm 14.47 (br s, 1H), 9.63 (s, 1H), 8.21 (br d, J=6.2 Hz, 1H), 7.59 (s, 1H), 7.04-6.94 (m, 1H), 6.71 (dd, J=8.7, 3.9 Hz, 1H), 5.01-4.92 (m, 1H), 4.88-4.78 (m, 1H), 4.59-4.51 (m, 1H), 4.49-4.42 (m, 1H), 4.20 (dd, J=9.6, 3.6 Hz, 1H), 4.12-4.01 (m, 1H), 3.86 (br t, J=11.1 Hz, 1H), 3.50 (br s, 3H), 2.63 (s, 3H), 2.16 (s, 3H). LCMS (ESI+): m/z 421.2 (M+H).

Example 134: (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxamide

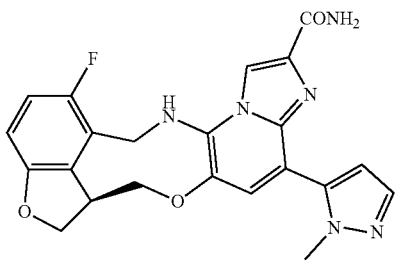 [SMILES: Cn1nccc1-c1cc2c(n3cc(C(N)=O)nc13)NCc1c(F)ccc3c1[C@H](CO3)CO2]

To a solution of (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylic acid (55.0 mg, 126 umol, 1.00 eq) in DMF (3.00 mL) was added NH$_4$Cl (20.3 mg, 379 umol, 3.00 eq), DIPEA (147 mg, 1.14 mmol, 198 uL, 9.00 eq) and HATU (72.1 mg, 190 umol, 1.50 eq) at 20° C. The mixture was stirred at 20° C. for 12 hr. The reaction mixture was filtered and the filtrate was concentrated under reduced pressure. The residue was purified by prep-HPLC (column: Welch Xtimate C18 150*25 mm*5 um; mobile phase: [water (0.04% HCl)-ACN]; B %: 40%-60%, 10 min). The product-containing fraction was concentrated under reduced pressure to remove most of MeCN at 30° C. and the aqueous phase was lyophilized. (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxamide (8.70 mg, 18.4 umol, 14% yield, 99.3% purity, HCl salt) was obtained as a yellow solid. $^1$H NMR CD$_3$OD 400 MHz δ=ppm 8.58 (s, 1H), 7.79 (s, 1H), 7.63 (d, J=2.1 Hz, 1H), 6.80 (dd, J=10.1, 8.9 Hz, 1H), 6.57 (dd, J=8.7, 3.9 Hz, 1H), 6.49 (d, J=2.1 Hz, 1H), 5.08 (d, J=14.7 Hz, 1H), 4.86 (br d, J=14.8 Hz, 1H), 4.66-4.58 (m, 1H), 4.50 (t, J=9.4 Hz, 1H), 4.19 (dd, J=9.7, 3.2 Hz, 1H), 4.02-3.90 (m, 1H), 3.88-3.76 (m, 1H), 3.69 (s, 3H). LCMS (ESI+): m/z 435.1 (M+H).

Example 135: (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylic Acid Step 1: tert-butyl (R)-9-chloro-S-fluoro-10-(1-methyl-1H-pyrazol-S-yl)-13,13a-dihydro-1H-benzofuro[4,3-fg]pyrido[3,2-b][1,4]oxazonine-7 (6H)-carboxylate

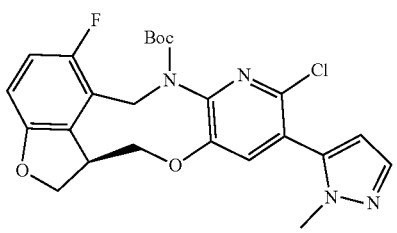 [SMILES: Cn1nccc1-c1cc2c(nc1Cl)N(C(=O)OC(C)(C)C)Cc1c(F)ccc3c1[C@@H](CO2)CO3]

To a solution of tert-butyl (R)-10-bromo-9-chloro-S-fluoro-13,13a-dihydro-1H-benzofuro[4,3-fg]pyrido[3,2-b][1,4]oxazonine-7 (6H)-carboxylate (2.00 g, 4.12 mmol, 1.00 eq) in dioxane (20.0 mL) and water (2.00 mL) was added (2-methylpyrazol-3-yl)boronic acid (780 mg 6.19 mmol, 1.50 eq), Cs$_2$CO$_3$ (4.02 g, 12.4 mmol, 3.00 eq) and Pd(dppf)Cl$_2$ (302 mg 413 umol, 0.100 eq) at 20° C. under nitrogen atmosphere. The mixture was stirred at 90° C. for 12 h under nitrogen atmosphere. LC-MS showed tert-butyl (R)-10-bromo-9-chloro-S-fluoro-13,13a-dihydro-1H-benzofuro[4,3-fg]pyrido[3,2-b][1,4]oxazonine-7 (6H)-carboxylate was remained and one peak with the desired mass was detected. Pd(dppf)Cl$_2$ (302 mg, 413 umol, 0.100 eq) and Cs$_2$CO$_3$ (2.68 g, 8.24 mmol, 2.00 eq) was added to the mixture at 20° C. under nitrogen atmosphere. The mixture was stirred at 90° C. for 18 h under nitrogen atmosphere. LC-MS showed tert-butyl (R)-10-bromo-9-chloro-S-fluoro-13,13a-dihydro-1H-benzofuro[4,3-fg]pyrido[3,2-b][1,4]oxazonine-7 (6H)-carboxylate was consumed completely and one main peak with the desired mass was detected. Water (15.0 mL) and ethyl acetate (15.0 mL) was added to the mixture and filtered, and the filtrate was extracted with ethyl acetate (10.0 mL*3). The organic layers were combined, washed by brine (20.0 mL), dried over Na$_2$SO$_4$, filtered, and concentrated under reduced pressure. The residue was purified by column chromatography (SiO$_2$, Petroleum ether/Ethyl acetate=1/0 to 1/1). tert-Butyl (R)-9-chloro-S-fluoro-10-(1-methyl-1H-pyrazol-S-yl)-13,13a-dihydro-1H-benzofuro[4,3-fg]pyrido[3,2-b][1,4]oxazonine-7 (6H)-carboxylate (1.00 g, 2.05 mmol, 49% yield) was obtained as a yellow oil.

Step 2: tert-butyl (R)-9-amino-S-fluoro-10-(1-methyl-1H-pyrazol-S-yl)-13,13a-dihydro-1H-benzofuro[4,3-fg]pyrido[3,2-b] 1,4 oxazonine-7 (6H)-carboxylate

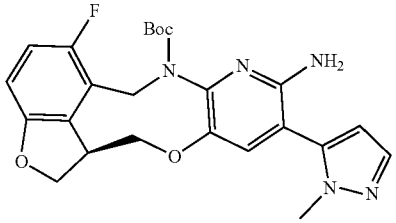 [SMILES: Cn1nccc1-c1cc2c(nc1N)N(C(=O)OC(C)(C)C)Cc1c(F)ccc3c1[C@@H](CO2)CO3]

To a solution of tert-butyl (R)-9-chloro-S-fluoro-10-(1-methyl-1H-pyrazol-S-yl)-13,13a-dihydro-1H-benzofuro[4,3-fg]pyrido[3,2-b][1,4]oxazonine-7 (6H)-carboxylate (950 mg, 1.95 mmol, 1.00 eq), NaN$_3$ (2.66 g, 41.0 mmol, 21.0 eq), sodium ascorbate (696 mg, 3.51 mmol, 1.80 eq) in dioxane (12.0 mL) and water (4.00 mL) was added CuI (780 mg, 4.09 mmol, 2.10 eq) and (1S,2S)—N$_1$,N$_2$-dimethylcyclohexane-1,2-diamine (832 mg, 5.85 mmol, 3.00 eq) at 20° C. under nitrogen atmosphere. The mixture was stirred at 110° C. for 12 h under nitrogen atmosphere. LC-MS indicated incomplete conversion. NaN$_3$ (1.01 g, 15.6 mmol, 8.00 eq), sodium ascorbate (387 mg, 1.95 mmol, 1.00 eq), CuI (372 mg, 1.95 mmol, 1.00 eq) and (1S,2S)—N$_1$,N$_2$-dimethylcyclohexane-1,2-diamine (278 mg, 1.95 mmol, 1.00 eq) in dioxane (18.0 mL) and water (6.00 mL) were added to the mixture at 20° C. under nitrogen atmosphere. The mixture was stirred at 110° C. for 18 h under nitrogen atmosphere. Saturated aqueous NaHCO$_3$ (20.0 mL) solution was added to mixture to adjust pH to ~10, the mixture was extracted with ethyl acetate (20.0 mL*3), the combined organic layers were dried over $Na_2SO_4$, filtered and concentrated under reduced pressure. NaClO (20.0 mL, 14%) was added dropwise to the aqueous phase to quench $NaN_3$ with stirring, and NaOH (2 M) was added to mixture to adjust to pH=10. The mixture was allowed to stand overnight. The residue from the evaporated organic phase was purified by column chromatography ($SiO_2$, Petroleum ether/Ethyl acetate=1/0 to 0/1). tert-Butyl (R)-9-amino-S-fluoro-10-(1-methyl-1H-pyrazol-S-yl)-13,13a-dihydro-1H-benzofuro[4,3-fg]pyrido[3,2-b][1,4]oxazonine-7 (6H)-carboxylate (740 mg, 1.58 mmol, 81% yield) was obtained as a brown oil.

Step 3: ethyl (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylate

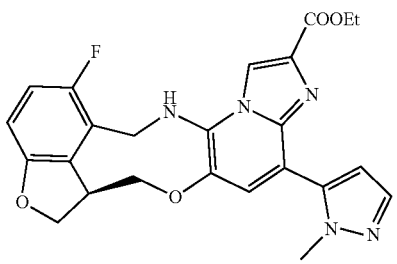

To a solution of tert-butyl (R)-9-amino-S-fluoro-10-(1-methyl-1H-pyrazol-S-yl)-13,13a-dihydro-1H-benzofuro[4,3-fg]pyrido[3,2-b][1,4]oxazonine-7 (6H)-carboxylate (740 mg, 1.58 mmol, 1.00 eq) in AcOH (10.0 mL) was added ethyl 3-bromo-2-oxo-propanoate (772 mg, 3.96 mmol, 495 uL, 2.50 eq) at 20° C. The mixture was stirred at 120° C. for 6 hr. The reaction mixture was concentrated, ethyl acetate (5.00 mL) and water (2.00 mL) were added to the mixture, followed by saturated $NaHCO_3$ solution (20.0 mL) to adjust pH to 9. The mixture was extracted with ethyl acetate (10.0 mL*3), the combined organic layers were dried over $Na_2SO_4$, filtered and concentrated under reduced pressure. The residue was purified by prep-TLC ($SiO_2$, Ethyl acetate/MeOH=20/1). ethyl (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylate (220 mg, 475 umol, 30% yield) was obtained as a pink solid.

Step 4: (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylic Acid

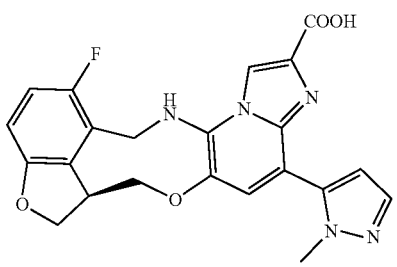 [SMILES: Cn1nccc1-c1cc2c(n3cc(C(=O)O)nc13)NCc1c(F)ccc3c1[C@H](CO3)CO2]

To a solution of ethyl (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylate (220 mg, 475 umol, 1.00 eq) in MeOH (8.00 mL) and water (8.00 mL) was added NaOH (57.0 mg, 1.42 mmol, 3.00 eq) at 20° C. The mixture was stirred at 20° C. for 5 h. 1 M HCl (5.00 mL) was added dropwise to the reaction mixture to adjust pH to 3-4. The mixture was concentrated under reduced pressure to afford 470 mg of crude product. 20.0 mg of the crude product was purified by prep-HPLC (column: Welch Xtimate C18 150*25 mm*5 um; mobile phase: [water (0.04% HCl)-ACN]; B %: 25%-55%, 10 min). The product-containing fraction was concentrated under reduced pressure to remove most of MeCN at 30° C. and the aqueous phase was lyophilized to give (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxylic acid (12.0 mg, 25.4 umol, 99.8% purity, HCl) as a yellow gum. The remaining batch of the crude product was used in the next step directly. $^1H$ NMR $CD_3OD$ 400 MHz δ=ppm 8.95 (s, 1H), 7.93 (s, 1H), 7.78 (d, J=2.0 Hz, 1H), 6.92 (dd, J=10.1, 8.8 Hz, 1H), 6.68 (dd, J=8.7, 3.9 Hz, 1H), 6.61 (d, J=2.0 Hz, 1H), 5.20 (d, J=14.5 Hz, 1H), 4.98 (br s, 1H), 4.78 (br d, J=6.1 Hz, 1H), 4.63 (t, J=9.4 Hz, 1H), 4.33 (dd, J=9.7, 2.9 Hz, 1H), 4.12-4.02 (m, 1H), 3.97-3.88 (m, 1H), 3.79 (s, 3H). LCMS (ESI+): m/z 436.1 (M+H).

Example 136: (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carbonitrile

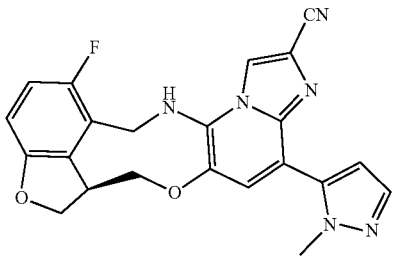 [SMILES: Cn1nccc1-c1cc2c(n3cc(C#N)nc13)NCc1c(F)ccc3c1[C@H](CO3)CO2]

To a solution of (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxamide (180 mg, 414 umol, 1.00 eq) and DIPEA (161 mg, 1.24 mmol, 217 uL, 3.00 eq) in DCM (5.00 mL) was added TFAA (174 mg, 829 umol, 115 uL, 2.00 eq) at 0° C. The mixture was stirred at 0° C. for 1 hr under nitrogen atmosphere. The reaction mixture was concentrated. MeOH (2.00 mL) was added to the mixture and $Na_2CO_3$ (8.00 mg) was added to the mixture adjust pH to 8. LC-MS showed the intermediate was consumed completely and one peak with the desired mass was detected. The residue was dissolved in MeOH (3.00 mL). The suspension was filtered, the filtrate was concentrated and purified by prep-HPLC (column: Phenomenex Luna C18 200*40 mm*10 um; mobile phase: [water (0.2% FA)—ACN]; B %: 30%-60%, 8 min). The product-containing fraction was concentrated under reduced pressure to remove most of MeCN at 30° C. and the aqueous phase was lyophilized. (S)—S-fluoro-12-(1-methyl-1H-pyrazol-S-yl)-6,7,15,15a-tetrahydro-1H-benzofuro[4,3-fg]imidazo[1',2':1,6]pyrido[3,2-b][1,4]oxazonine-10-carboxamide (13.1 mg, 28.16 umol, 6% yield, 99.4% purity, formate salt) was obtained as a yellow solid. ¹H NMR DMSO-d₆ 400 MHz δ=ppm 8.88 (s, 1H), 7.52 (s, 1H), 7.48 (d, J=1.6 Hz, 1H), 6.97 (t, J=9.5 Hz, 1H), 6.70 (dd, J=8.6, 3.7 Hz, 1H), 6.48 (d, J=1.7 Hz, 1H), 4.99-4.90 (m, 1H), 4.85-4.76 (m, 1H), 4.59-4.49 (m, 2H), 4.22 (dd, J=9.7, 3.2 Hz, 1H), 4.04 (br s, 1H), 3.95-3.84 (m, 1H), 3.76 (s, 3H). LCMS (ESI+): m/z 417.1 (M+H).

Example 137: (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylic Acid Step 1: tert-butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate

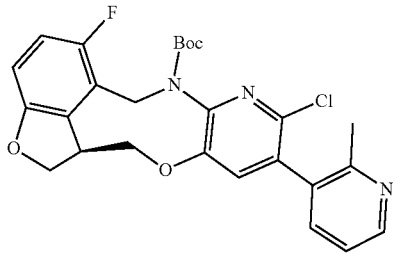 [SMILES: Cc1ncccc1-c1cc2c(nc1Cl)N(C(=O)OC(C)(C)C)Cc1c(F)ccc3c1[C@@H](CO2)CO3]

To a solution of tert-butyl (R)-10-bromo-9-chloro-S-fluoro-13,13a-dihydro-1H-benzofuro[4,3-fg]pyrido[3,2-b][1,4]oxazonine-7 (6H)-carboxylate (1.00 g, 2.06 mmol, 1.00 eq) in dioxane (10.0 mL) and water (1.00 mL) were added 2-methyl-3-(4,4,5,5-tetramethyl-1,3,2-dioxaborolan-2-yl) pyridine (586 mg, 2.68 mmol, 1.30 eq), Pd(dppf)Cl₂ (151 mg, 206 umol, 0.100 eq) and NaHCO₃ (865 mg, 10.3 mmol, 400 uL, 5.00 eq) at 20° C. under nitrogen atmosphere, and the mixture was stirred at 80° C. for 12 h under nitrogen atmosphere. Water (15.0 mL) was added to the reaction solution, the mixture was extracted with ethyl acetate (15.0 mL*3), the combined organic layers were dried over MgSO₄, and concentrated under reduced pressure. The residue was purified by column chromatography (SiO₂, Petroleum ether/Ethyl acetate=1/0 to 0/1). tert-Butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate (830 mg, 1.67 mmol, 81% yield) was obtained as a yellow oil.

Step 2: tert-butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate

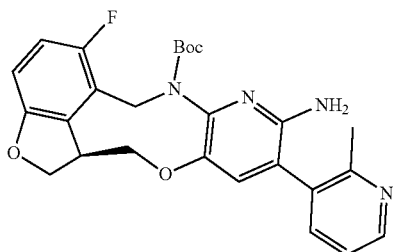

To a mixture of tert-butyl (R)-9-chloro-S-fluoro-10-(2-methylpyridin-3-yl)-13,13a-dihydro-1H-benzofuro[4,3-fg]pyrido[3,2-b][1,4]oxazonine-7 (6H)-carboxylate (415 mg, 833 umol, 1.00 eq), NaN₃ (759 mg, 11.7 mmol, 14.0 eq) and sodium ascorbate (198 mg, 1.00 mmol, 1.20 eq) in dioxane (6.00 mL) and water (1.20 mL) were added CuI (222 mg, 1.17 mmol, 1.40 eq) and (1S,2S)—N₁,N₂-dimethylcyclohexane-1,2-diamine (237 mg, 1.67 mmol, 2.00 eq) at 20° C., then the mixture was stirred at 110° C. for 12 h under nitrogen atmosphere. Saturated NaHCO₃ (25.0 mL) was added to the mixture to adjust pH to ~9, then the mixture was extracted with ethyl acetate (10.0 mL*3), the combined organic layers were dried over MgSO₄ and concentrated under reduced pressure. NaClO (20 mL, 14%) was added dropwise to the aqueous phase to quenched NaN₃ under stirring, and the mixture was allowed to stand overnight. The organic residue was purified by prep-TLC (SiO₂, Petroleum ether/Ethyl acetate=0/1). tert-butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate (260 mg, 543 umol, 65% yield) was obtained as a yellow oil.

Step 3: ethyl (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylate

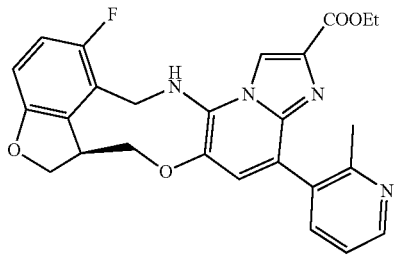 [SMILES: Cc1ncccc1-c1cc2c(n3cc(C(=O)O)nc13)NCc1c(F)ccc3c1[C@H](CO3)CO2]

To a solution of tert-butyl (R)-9-amino-S-fluoro-10-(2-methylpyridin-3-yl)-13,13a-dihydro-1H-benzofuro[4,3-fg]pyrido[3,2-b][1,4]oxazonine-7 (6H)-carboxylate (100 mg, 209 umol, 1.00 eq) in AcOH (3.00 mL) was added ethyl 3-bromo-2-oxo-propanoate (102 mg, 522 umol, 65.3 uL, 2.50 eq) at 20° C. The mixture was stirred at 120° C. for 2 h. NaHCO₃ (5%, 8.00 mL) was added to the mixture to adjust pH to 7-8, then the mixture was extracted with ethyl acetate (5.00 mL*3), the combined organic layers were dried over Na₂SO₄, and concentrated under reduced pressure. The residue was purified by prep-TLC (SiO₂, Ethyl acetate/Methanol=20/1). ethyl (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylate (40.0 mg, 84.3 umol, 40% yield) was obtained as a yellow oil.

Step 4: (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylic Acid

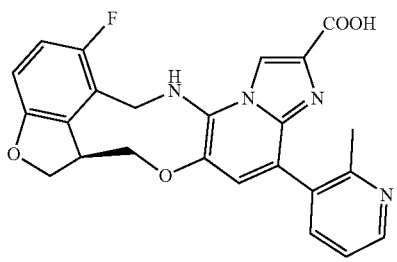

To a solution of ethyl (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylate (40.0 mg, 84.3 umol, 1.00 eq) in water (2.00 mL) and MeOH (2.00 mL) was added NaOH (10.1 mg, 253 umol, 3.00 eq) at 20° C. The mixture was stirred at 20° C. for 12 h. The reaction was concentrated. Aqueous HCl (1.00 M, 1.50 mL) was added to the mixture to adjust pH to 3-4, and the reaction was concentrated under reduced pressure to afford a crude product (40.0 mg). 20.0 mg of the crude product was purified by prep-HPLC (column: Luna Omega 5 u Polar C18 100A; mobile phase: [water (0.04% HCl)-ACN]; B %: 16%-34%, 7 min). (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylic acid (7.00 mg, 14.3 umol, 98.4% purity, HCl salt) was obtained as a yellow solid. $^1$H NMR DMSO-$d_6$ 400 MHz δ=ppm 9.03 (s, 1H), 8.83 (d, J=6.0 Hz, 1H), 8.48 (br d, J=7.7 Hz, 1H), 8.18 (br s, 1H), 8.01-7.91 (m, 1H), 7.73 (s, 1H), 6.97 (t, J=9.5 Hz, 1H), 6.70 (dd, J=8.7, 3.9 Hz, 1H), 4.97 (br dd, J=14.7, 5.2 Hz, 1H), 4.80 (br dd, J=14.0, 5.8 Hz, 1H), 4.55 (br t, J=9.4 Hz, 2H), 4.23 (br dd, J=9.8, 3.2 Hz, 1H), 4.03 (br d, J=9.5 Hz, 1H), 3.92-3.83 (m, 1H), 2.59 (s, 3H). LCMS (ESI+): m/z 447.2 (M+H).

Example 138: (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxamide

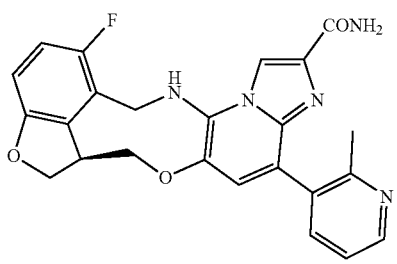 [SMILES: Cc1ncccc1-c1cc2c(n3cc(C(N)=O)nc13)NCc1c(F)ccc3c1[C@H](CO3)CO2]

To a solution of (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxylic acid (20.0 mg, 44.8 umol, 1.00 eq) in DMF (2.00 mL) was added NH$_4$Cl (7.19 mg, 134 umol, 3.00 eq), DIPEA (52.1 mg, 403 umol, 70.2 uL, 9.00 eq) and HATU (25.6 mg, 67.2 umol, 1.50 eq) at 20° C. The mixture was stirred at 20° C. for 12 h. The reaction was concentrated. The residue was purified by prep-HPLC (column: Luna Omega 5 u Polar C18 100A; mobile phase: [water (0.04% HCl)-ACN]; B %: 17%-35%, 7 min). (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxamide (6.1 mg, 12.6 umol, 28% yield, 99.6% purity, HCl salt) was obtained as a yellow solid. $^1$H NMR DMSO-$d_6$ 400 MHz δ=ppm 8.82 (br d, J=6.0 Hz, 1H), 8.68 (br s, 1H), 8.56 (br d, J=7.7 Hz, 1H), 8.02 (t, J=6.8 Hz, 1H), 7.82 (s, 1H), 6.89 (t, J=9.5 Hz, 1H), 6.65 (dd, J=3.7, 8.6 Hz, 1H), 5.17 (br d, J=14.8 Hz, 1H), 4.95 (br d, J=14.8 Hz, 1H), 4.72 (d, J=6.0 Hz, 1H), 4.60 (t, J=9.2 Hz, 1H), 4.30 (br d, J=8.0 Hz, 1H), 4.06 (br s, 1H), 3.98-3.88 (m, 1H), 2.65 (s, 3H). LCMS (ESI+): m/z 446.2 (M+H).

Example 139: General Procedure C for the preparation of (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine

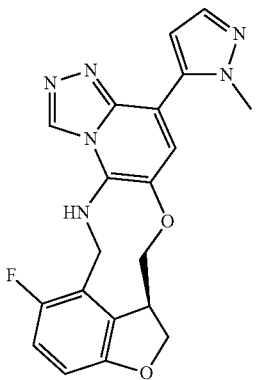 [SMILES: Cn1nccc1-c1cc2c(n3cnnc13)NCc1c(F)ccc3c1[C@H](CO3)CO2]

Step 1: tert-butyl (S)-12-fluoro-4-(1-methyl-1H-pyrazol-S-yl)-7a,13-dihydro-7H-[1,2,4]triazolo[4',3':1,6]pyrido[3,2-b]benzofuro[4,3-fg][1,4]oxazonine-14(8H)-carboxylate

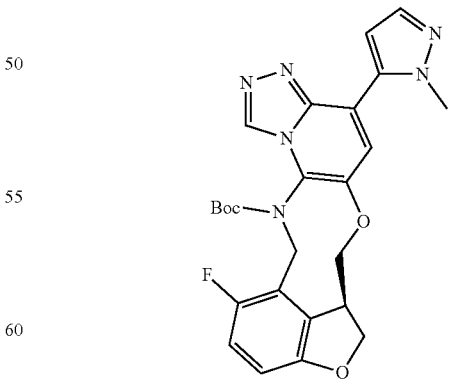

Two batches were set up. To tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (21.5 g, 43.8 mmol, 1.00 eq) and (2-methylpyrazol-3-yl)

boronic acid (7.16 g, 56.9 mmol, 1.30 eq) in dioxane (50.0 mL) and H₂O (5.00 mL) was added Pd(dppf)Cl₂ (3.20 g, 4.38 mmol, 0.100 eq) and Na₂CO₃ (9.28 g, 87.5 mmol, 2.00 eq) at 25° C. The mixture was stirred at 80° C. for 12 hrs under N₂. LC-MS showed tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. Two batches were combined together to work up. The mixture was filtered and the filtrate was concentrated under reduce pressure to give a residue. The residue was purified by column chromatography (SiO₂, Petroleum ether/Ethyl acetate=1/0 to 0/1). tert-butyl (S)-12-fluoro-4-(1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (36.4 g, crude) was obtained as brown solid.

Step 2: (S)-12-fluoro-4-(1-methyl-H-pyrazol-S-yl)-7a,8,13,14-tetrahydro-7H-[1,2,4]triazolo[4',3':1,6]pyrido[3,2-b]benzofuro[4,3-fg][1,4]oxazonine

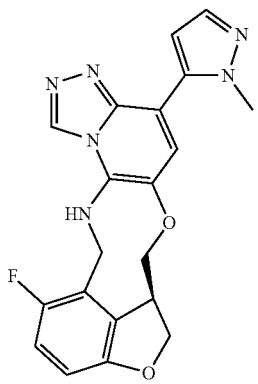 [SMILES: Cn1nccc1-c1cc2c(n3cnnc13)NCc1c(F)ccc3c1[C@H](CO3)CO2]

Three batches were set up. To tert-butyl (S)-12-fluoro-4-(1-methyl-1H-pyrazol-5-yl)-7a,13-dihydro-7H-[1,2,4]triazolo[4',3':1,6]pyrido[3,2-b]benzofuro[4,3-fg][1,4]oxazonine-14 (8H)-carboxylate (13.0 g, 26.4 mmol, 1.00 eq) in DCM (108 mL) was added TFA (60.1 g, 527 mmol, 39.0 mL, 20.0 eq) at 25° C. The mixture was stirred at 25° C. for 12 hrs. LC-MS showed tert-butyl (S)-12-fluoro-4-(1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. Three batches were combined together to work up. The mixture was concentrated under reduce pressure to give a residue. Then the residue was dissolved with EtOAc/H₂O (10.0 mL:10.0 mL). The NH₃.H₂O (25%) was added into the mixture to adjust pH=7.00-8.00, the mixture was filtered and the filter cake was dried under reduce pressure. (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine (30.0 μg, 76.5 mmol, 96.6% yield) was obtained as white solid.

Step 3: (S)-12-fluoro-4-(1-methyl-H-pyrazol-S-yl)-7a,8,13,14-tetrahydro-7H-[1,2,4]triazolo[4',3':1,6]pyrido[3,2-b]benzofuro[4,3-fg][1,4]oxazonine

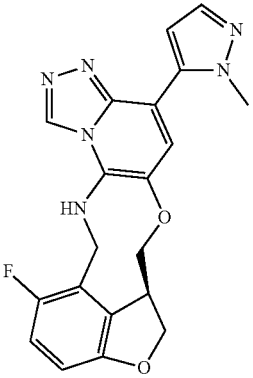 [SMILES: Cn1nccc1-c1cc2c(n3cnnc13)NCc1c(F)ccc3c1[C@H](CO3)CO2]

To (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine (27.0 g, 68.8 mmol, 1.00 eq) was added i-PrOH (80.0 mL) and H₂O (10.0 mL) at 25° C., the mixture was stirred at 80° C. for 1 hr. The mixture was cooled to 25° C. slowly and stood at 25° C. for 12 hrs. The mixture was filtered and the filter cake was dried by vacuum to afford 16.0 g of pure product. The filtrate was concentrated under reduce pressure to give a residue. The residue was purified by reversed-MPLC (neutral condition). The fraction was concentrated under reduced pressure to remove most of MeCN at 30° C. and the precipitate was filtered and the filter cake was dried by vacuum to give 2.00 g of the pure product. Totally 18.0 g of (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine was obtained as white solid.

Step 4: (S)-12-fluoro-4-(1-methyl-H-pyrazol-S-yl)-7a,8,13,14-tetrahydro-7H-[1,2,4]triazolo[4',3':1,6]pyrido[3,2-b]benzofuro[4,3-fg][1,4]oxazonine

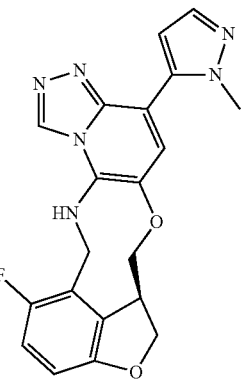

To (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine (3.50 g, 8.92 mmol, 1.00 eq) in MeCN (60.0 mL) was added MsOH (857 mg, 8.92 mmol, 635 uL, 1.00 eq) in MeCN (3.00 mL) dropwise at 50° C., the mixture was stirred at 50° C. for 1 hr. The mixture was cooled to 30° C. among 1 hr, the mixture was stirred at 30° C. for 2 hrs. The mixture was cooled to 25° C. The mixture was concentrated under reduced pressure to remove most of MeCN at 30° C., the another batch product (25.0 g, 50.66 mmol, 69.02% yield, 99.1% purity, MsOH salt) was combined together and then H$_2$O (600 mL) was added into the mixture, the aqueous phase was lyophilized. (S)-12-fluoro-4-(1-methyl-1H-pyrazol-S-yl)-7a,8,13,14-tetrahydro-7H-[1,2,4]triazolo[4',3':1,6]pyrido[3,2-b]benzofuro[4,3-fg][1,4]oxazonine (29.1 g, 59.2 mmol, 99.4% purity, MsOH) was obtained as yellow crystal. $^1$H NMR ET20857-653-P1D CD$_3$OD 400 MHz δ =ppm 9.51 (s, 1H), 8.03 (s, 1H), 7.68 (d, J=1.8 Hz, 1H), 6.92 (t, J=9.5 Hz, 1H), 6.68 (dd, J=8.8, 3.7 Hz, 1H), 6.58 (d, J=1.8 Hz, 1H), 5.20 (d, J=14.8 Hz, 1H), 4.96 (br d, J=14.8 Hz, 1H), 4.76 (br dd, J=9.8, 3.9 Hz, 1H), 4.62 (t, J=9.5 Hz, 1H), 4.31 (dd, J=9.7, 3.3 Hz, 1H), 4.16-3.99 (m, 1H), 3.98-3.87 (m, 1H), 3.81 (s, 3H), 2.70 (s, 4H). LCMS (ESI+): m/z 393.1 (M+H).

Compounds 17, 75, 100, and 171 were prepared according to General Procedure C using the suitable starting materials, precursors, intermediates, and reagents.

| Cmpd No. | Compound Name | Structure | Spectral Data |
|---|---|---|---|
| 75 | (S)-12-fluoro-4-(1-isopropyl-1H-pyrazol-5-yl)-7a,8,13,14-tetrahydro-7H-[1,2,4]triazolo[4',3':1,6]pyrido[3,2-b]benzofuro[4,3-fg][1,4]oxazonine | 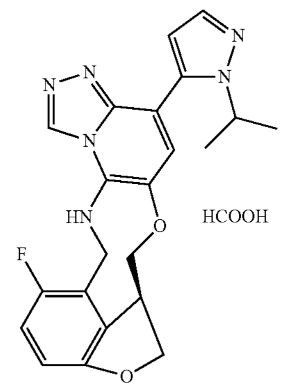 [SMILES: CC(C)n1nccc1-c1cc2c(n3cnnc13)NCc1c(F)ccc3c1[C@H](CO3)CO2 ; "HCOOH"] | 1H NMR DMSO-d6 400 MHz δ = ppm 9.44 (s, 1H), 7.65 (br t, J = 6.4 Hz, 1H), 7.54 (d, J = 1.3 Hz, 1H), 7.32 (s, 1H), 7.03-6.93 (m, 1H), 6.71 (dd, J = 8.6, 3.9 Hz, 1H), 6.37 (d, J = 1.6 Hz, 1H), 4.96-4.88 (m, 1H), 4.83-4.75 (m, 1H), 4.58-4.40 (m, 3H), 4.22 (dd, J = 9.5, 3.5 Hz, 1H), 4.10-4.00 (m, 1H), 3.91-3.81 (m, 1H), 1.34 (dd, J = 8.9, 6.6 Hz, 6H). LCMS (ESI+): m/z 421.2 (M + H) |
| 100 | (S)-4-(3-ethyl-1-methyl-1H-pyrazol-4-yl)-12-fluoro-7a,8,13,14-tetrahydro-7H-[1,2,4]triazolo[4',3':1,6]pyrido[3,2-b]benzofuro[4,3-fg][1,4]oxazonine | 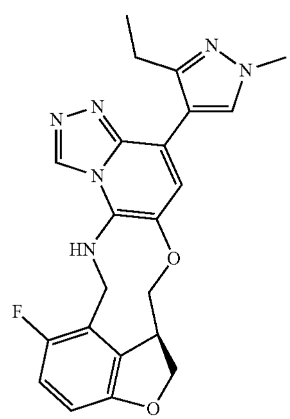 [SMILES: CCc1nn(C)cc1-c1cc2c(n3cnnc13)NCc1c(F)ccc3c1[C@H](CO3)CO2] | $^1$H NMR DMSO-d$_6$ 400 MHz δ = ppm 9.37 (s, 1H), 8.33 (s, 1H), 7.33-7.23 (m, 1H), 7.19 (s, 1H), 6.92 (dd, J = 10.1, 8.8 Hz, 1H), 6.66 (dd, J = 8.5, 3.9 Hz, 1H), 4.88-4.81 (m, 1H), 4.77-4.69 (m, 1H), 4.53-4.42 (m, 2H), 4.21 (dd, J = 9.7, 3.3 Hz, 1H), 4.06-3.96 (m, 3H), 3.89-3.83 (m, 1H), 3.82 (s, 3H), 2.77 (q, J = 7.5 Hz, 2H), 1.17 (t, J = 7.4 Hz, 3H). LCMS (ESI+): m/z 421.0 (M + H). |
| 171 | (S)-4-(5,6-dihydro-4H-pyrrolo[1,2-b]pyrazol-3-yl)-12-fluoro-7a,8,13,14-tetrahydro-7H-[1,2,4]triazolo[4',3':1,6]pyrido[3,2-b]benzofuro[4,3-fg][1,4]oxazonine | 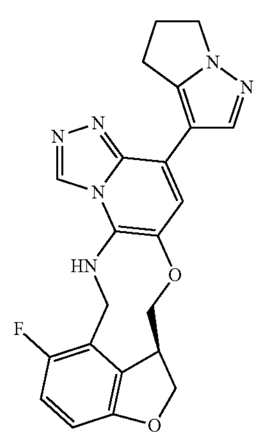 [SMILES: Fc1ccc2c3c1CNc1c(cc(-c4cnn5c4CCC5)c4nncn14)OC[C@H]3CO2] | $^1$H NMR DMSO-d$_6$ 400 MHz δ = ppm 9.37 (s, 1H), 8.27 (s, 1H), 7.27-7.23 (m, 1H), 7.22 (s, 1H), 6.93 (dd, J = 10.1, 8.8 Hz, 1H), 6.66 (dd, J = 8.6, 3.7 Hz, 1H), 4.90-4.79 (m, 1H), 4.78-4.67 (m, 1H), 4.57-4.42 (m, 2H), 4.22 (dd, J = 9.6, 3.2 Hz, 1H), 4.11 (t, J = 7.4 Hz, 2H), 4.01 (br dd, J = 8.7, 3.6 Hz, 1H), 3.94-3.83 (m, 1H), 3.17 (t, J = 7.3 Hz, 2H), 2.60 (quin, J = 7.2 Hz, 2H). LCMS (ESI+): m/z 419.1 (M + H). |

Example 140: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazole-4-carbonitrile Step 1: tert-butyl (S)-4-(4-cyano-1-methyl-1H-pyrazol-S-yl)-12-fluoro-7a,13-dihydro-7H-[1,2,4]triazolo[4',3':1,6]pyrido[3,2-b]benzofuro[4,3 fg][1,4]oxazonine-14 (8H)-carboxylate

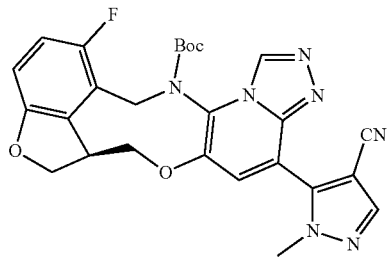 [SMILES: Cn1ncc(C#N)c1-c1cc2c(n3cnnc13)N(C(=O)OC(C)(C)C)Cc1c(F)ccc3c1[C@H](CO3)CO2]

The reaction was set up as 10 parallel batches. The solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (20.0 mg, 28.5 umol, 1.00 eq) and 5-bromo-1-methyl-1H-pyrazole-4-carbonitrile (5.30 mg, 28.5 umol, 1.00 eq) in dioxane (1.00 mL) was degassed with nitrogen three times. Xphos-Pd-G2 (3.00 mg, 3.81 umol, 1.34e-1 eq) was added at 25° C. and the resulting solution was stirred at 110° C. under nitrogen for 12 h. The batches were combined. The obtained mixture was concentrated under vacuum to give a crude product which was purified by prep-TLC (PE:EtOAc=1:2). tert-Butyl (S)-4-(4-cyano-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (40.0 mg, 77.3 umol) was obtained as a yellow oil.

Step 2: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazole-4-carbonitrile

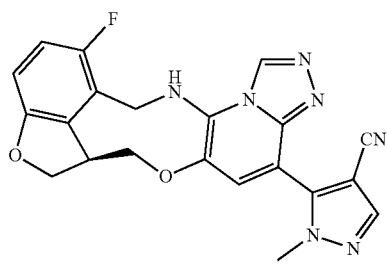 [SMILES: Cn1ncc(C#N)c1-c1cc2c(n3cnnc13)NCc1c(F)ccc3c1[C@H](CO3)CO2]

To a stirred solution of tert-butyl (S)-4-(4-cyano-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (20.0 mg, 38.7 umol, 1.00 eq) in MeOH (1.00 mL) was added HCl/MeOH (4.00 M, 1.00 mL) at 15° C. The resulting mixture was stirred at 15° C. for 12 h. The mixture was concentrated under reduced pressure and purified by acidic prep-HPLC (FA conditions). (S)—S—(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazole-4-carbonitrile (1.10 mg, 2.25 umol, 5% yield, 94.9% purity, formate salt) was obtained as a yellow solid. $^1$H NMR DMSO-d$_6$ 400 MHz δ=ppm 9.49 (s, 1H), 8.15 (s, 1H), 8.06-7.94 (m, 1H), 7.67 (s, 1H), 6.98 (t, J=9.5 Hz, 1H), 6.71 (dd, J=8.8, 3.6 Hz, 1H), 4.99-4.76 (m, 2H), 4.63-4.40 (m, 2H), 4.20 (br dd, J=9.8, 3.2 Hz, 1H), 4.13-3.99 (m, 1H), 3.91-3.73 (m, 1H), 3.81 (s, 3H). LCMS (ESI+): m/z 418.1 (M+H).

Example 141: (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carbonitrile

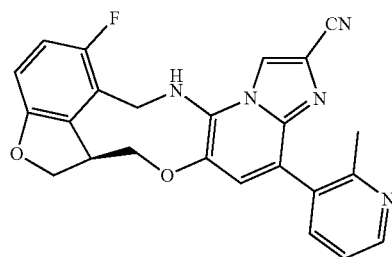

Two parallel reactions were set up. To a mixture of (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxamide (55.0 mg, 123 umol, 1.00 eq) in DCM (10.0 mL) was added methoxycarbonyl-(triethylammonio)sulfonyl-azanide (44.1 mg, 185 umol, 1.50 eq) at 0° C., the mixture was stirred at 20° C. for 2 h. LC-MS showed (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxamide was remained and the desired mass was detected. The mixture was stirred at 20° C. for 12 h, LCMS showed (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carboxamide was remained and the desired mass was detected. Combined the two batches. Water (2.00 mL) was added to the mixture, then the reaction was concentrated. The residue was dissolved in DMSO (3.00 mL). The solution was purified by acidic prep-HPLC (column: Phenomenex Luna C18 200*40 mm*10 um; mobile phase: [water (0.2% FA)—ACN]; B %: 20%-60%, 8 min). The product-containing fraction was concentrated under reduced pressure to remove most of MeCN at 30° C. and the aqueous phase was lyophilized. $^1$H NMR showed that the product was not pure, so the product was purified by prep-HPLC (column: Waters Xbridge BEH C18 100*25 mm*5 um; mobile phase: [water (10 mM NH$_4$HCO$_3$)—ACN]; B %: 25%-60%, 10 min)-ACN]; B %: 20%-60%, 8 min). The product-containing fraction was concentrated under reduced pressure to remove most of MeCN at 30° C. and the aqueous phase was lyophilized. (S)—S-fluoro-12-(2-methylpyridin-3-yl)-6,7,15,15a-tetrahydro-1H-benzofuro[4,3-fg]imidazo[1',2':1,6]pyrido[3,2-b][1,4]oxazonine-10-carbonitrile (14.0 mg, 32.1 umol, 13% yield, 97.9% purity) was obtained as a yellow solid. $^1$H NMR CDCl$_3$ 400 MHz δ=ppm 8.57 (br d, J=4.6 Hz, 1H), 8.02 (s, 1H), 7.66 (br d, J=7.7 Hz, 1H), 7.22 (dd, J=7.4, 5.0 Hz, 1H), 7.13 (s, 1H), 6.90 (t, J=9.4 Hz, 1H), 6.69 (dd, J=8.6, 3.9 Hz, 1H), 5.22-5.06 (m, 1H), 4.85 (br d, J=14.7 Hz, 1H), 4.76 (br s, 1H), 4.70-4.60 (m, 2H), 4.27 (dd, J=9.7, 2.8 Hz, 1H), 4.00-3.90 (m, 1H), 3.88-3.80 (m, 1H), 2.46 (s, 3H). LCMS (ESI+): m/z 428.1 (M+H).

Example 142: (S)-12-fluoro-4-(3-methylisoxazol-4-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(3-methylisoxazol-4-yl)-7a,13-dihydro-7H-[1,2,4]triazolo[4',3':1,6]pyrido[3,2-b]benzofuro[4,3-fg][1,4]oxazonine-14(8H)-carboxylate

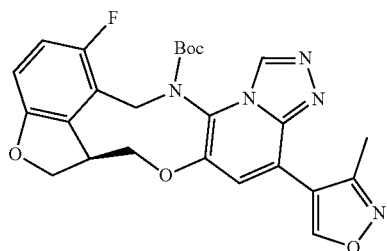

To a stirred solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (150 mg, 305 umol, 1.00 eq), 3-methyl-4-(4,4,5,5-tetramethyl-1,3,2-dioxaborolan-2-yl)isoxazole (95.7 mg, 457 umol, 1.50 eq) and Na$_2$CO$_3$ (64.7 mg, 610 umol, 2.00 eq) in dioxane (3.00 mL) and water (0.600 mL) was added Pd(dppf)Cl$_2$ (22.3 mg, 30.5 umol, 0.100 eq) at 15° C. under N$_2$. The resulting mixture was stirred at 80° C. for 2 h. The mixture was concentrated under reduced pressure. The residue was purified by prep-TLC (SiO$_2$, PE:EtOAc=1:1) to give tert-butyl (S)-12-fluoro-4-(3-methylisoxazol-4-yl)-7a,13-dihydro-7H-[1,2,4]triazolo[4',3':1,6]pyrido[3,2-b]benzofuro[4,3-fg][1,4]oxazonine-14(8H)-carboxylate (80 mg, 162 umol, 53% yield) as a yellow solid.

Step 2: (S)-12-fluoro-4-(3-methylisoxazol-4-yl)-7a,8,13,14-tetrahydro-7H-[1,2,4]triazolo[4',3':1,6]pyrido[3,2-b]benzofuro[4,3-fg][1,4]oxazonine

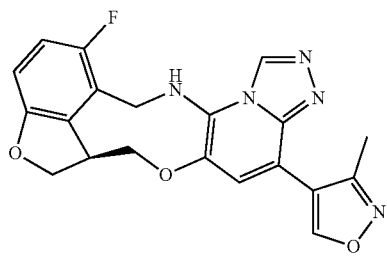 [SMILES: Cc1nocc1-c1cc2c(n3cnnc13)NCc1c(F)ccc3c1[C@H](CO3)CO2]

To tert-butyl (S)-12-fluoro-4-(3-methylisoxazol-4-yl)-7a,13-dihydro-7H-[1,2,4]triazolo[4',3':1,6]pyrido[3,2-b]benzofuro[4,3-fg][1,4]oxazonine-14(8H)-carboxylate (70.0 mg, 141.8 umol, 1.00 eq) was added HFIP (2.00 mL) at 15° C. The solution was stirred at 80° C. for 12 hr. The reaction mixture was concentrated under reduced pressure. The residue was purified by prep-HPLC (column: Phenomenex Luna C18 200*40 mm*10 um; mobile phase: [water (0.2% FA)—ACN]; B %: 30%-70%, 8 min). (S)-12-fluoro-4-(3-methyl-isoxazol-4-yl)-7a,8,13,14-tetrahydro-7H-[1,2,4]triazolo[4',3':1,6]pyrido[3,2-b]benzofuro[4,3-fg][1,4]oxazonine (23.0 mg, 51.9 umol, 36% yield, 99.1% purity, formate salt) was obtained as a white solid. $^1$H NMR DMSO-d$_6$ 400 MHz δ=ppm 9.42 (d, J=7.5 Hz, 1H), 7.54 (br t, J=6.2 Hz, 1H), 7.46 (s, 1H), 6.98-6.89 (m, 1H), 6.67 (dd, J=8.7, 3.9 Hz, 1H), 4.93-4.84 (m, 1H), 4.77 (br dd, J=14.8, 6.4 Hz, 1H), 4.57-4.44 (m, 2H), 4.21 (br dd, J=9.8, 3.2 Hz, 1H), 4.02-3.97 (m, 1H), 3.95-3.85 (m, 1H), 2.50 (s, 3H). $^1$H NMR CD$_3$OD+1 drop HCl (12 M) 400 MHz δ=ppm 9.83 (s, 1H), 8.98 (s, 1H), 8.01 (s, 1H), 6.96-6.86 (m, 1H), 6.72-6.65 (m, 1H), 5.15 (d, J=14.9 Hz, 1H), 4.98 (d, J=14.9 Hz, 1H), 4.82-4.70 (m, 1H), 4.61 (t, J=9.4 Hz, 1H), 4.32 (dd, J=9.6, 3.1 Hz, 1H), 4.17-4.07 (m, 1H), 3.99-3.86 (m, 1H), 2.32 (s, 3H). LCMS (ESI+): m/z 394.1 (M+H).

Example 143: (S)-12-fluoro-4-(5-fluoro-6-methoxypyridin-3-yl)-7a,8,13,14-tetrahydro-7H-[1,2,4]triazolo[4',3':1,6]pyrido[3,2-b]benzofuro[4,3-fg][1,4]oxazonine Step 1: tert-butyl (S)-12-fluoro-4-(5-fluoro-6-methoxypyridin-3-yl)-7a,13-dihydro-7H-[1,2,4]triazolo[4',3':1,6]pyrido[3,2-b]benzofuro[4,3-fg][1,4]oxazonine-14(8H)-carboxylate

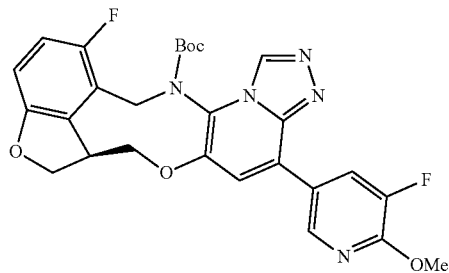 [SMILES: COc1ncc(-c2cc3c(n4cnnc24)N(C(=O)OC(C)(C)C)Cc2c(F)ccc4c2[C@H](CO4)CO3)cc1F]

To a stirred solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (150 mg, 305 umol, 1.00 eq), (5-fluoro-6-methoxy-3-pyridyl)boronic acid (78.3 mg, 457 umol, 1.50 eq) and KOAc (59.9 mg, 610 umol, 2.00 eq) in EtOH (2.10 mL) and water (0.300 mL) was added 4-ditert-butylphosphanyl-N,N-dimethylaniline dichloropalladium (21.6 mg, 30.5 umol, 21.6 uL, 0.100 eq) at 15° C. under N$_2$. The resulting mixture was stirred at 80° C. for 2 hr. The mixture was concentrated under reduced pressure. The mixture was purified by prep-TLC (SiO$_2$, PE:EtOAc=1:2). tert-Butyl (S)-12-fluoro-4-(5-fluoro-6-methoxypyridin-3-yl)-7a,13-dihydro-7H-[1,2,4]triazolo[4',3':1,6]pyrido[3,2-b]benzofuro[4,3-fg][1,4]oxazonine-14(8H)-carboxylate (100 mg, 186 umol, 61% yield) was obtained as a yellow solid.

Step 2: (S)-12-fluoro-4-(5-fluoro-6-methoxypyridin-3-yl)-7a,8,13,14-tetrahydro-7H-[1,2,4]triazolo[4',3':1,6]pyrido[3,2-b]benzofuro[4,3-fg][1,4]oxazonine

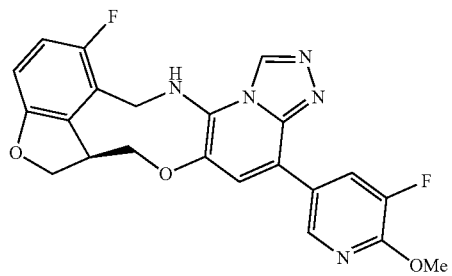 [SMILES: COc1ncc(-c2cc3c(n4cnnc24)NCc2c(F)ccc4c2[C@H](CO4)CO3)cc1F]

To tert-butyl (S)-12-fluoro-4-(5-fluoro-6-methoxypyridin-3-yl)-7a,13-dihydro-7H-[1,2,4]triazolo[4',3':1,6]pyrido[3,2-b]benzofuro[4,3-fg] [1,4]oxazonine-14 (8H)-carboxylate (90.0 mg, 167 umol, 1.00 eq) was added HFIP (2.00 mL) at 25° C. The solution was stirred at 80° C. for 12 h. The reaction mixture was concentrated under reduced pressure. The residue was purified by prep-HPLC (column: Phenomenex Luna C18 200*40 mm*10 um; mobile phase: [water (0.2% FA)—ACN]; B %: 45%-65%, 8 min). (S)-12-fluoro-4-(5-fluoro-6-methoxypyridin-3-yl)-7a,8,13,14-tetrahydro-7H-[1,2,4]triazolo[4',3':1,6]pyrido[3,2-b]benzofuro[4,3-fg][1,4]oxazonine (36.1 mg, 72.4 umol, 43% yield, 97.0% purity, formate salt) was obtained as a yellow solid. $^1$H NMR DMSO-$d_6$ 400 MHz δ=ppm 9.44 (s, 1H), 8.90 (d, J=2.0 Hz, 1H), 8.51 (dd, J=12.6, 2.0 Hz, 1H), 7.79 (s, 1H), 7.59 (br t, J=6.4 Hz, 1H), 6.93 (dd, J=10.1, 9.0 Hz, 1H), 6.67 (dd, J=8.7, 3.9 Hz, 1H), 4.93-4.84 (m, 1H), 4.83-4.73 (m, 1H), 4.58-4.46 (m, 2H), 4.20 (dd, J=9.5, 3.1 Hz, 1H), 4.07-3.99 (m, 1H), 3.98 (s, 3H), 3.97-3.88 (m, 1H). LCMS (ESI+): m/z 438.1 (M+H).

Example 144: (S)-4-(2-cyclopropyl-4-methylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: 2-cyclopropyl-6-methylpyrimidin-4-ol

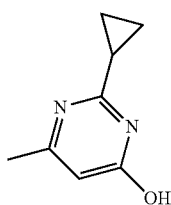

The reaction was set up in two parallel batches. A mixture of methyl 3-oxobutanoate (4.81 g, 41.5 mmol, 4.46 mL, 1.00 eq), cyclopropanecarboximidamide hydrochloride (5.00 g, 41.5 mmol, 1.00 eq) and Mona (14.9 g, 82.9 mmol, 54.4 mL, 30% purity, 2.00 eq) in MeOH (250 mL) was stirred at 25° C. for 18 h. The batches were combined. The mixture was diluted with saturated aqueous $Na_2SO_3$ (250 mL), then concentrated under reduced pressure. The residue was dissolved in water (50.0 mL) and adjusted to pH=4 with HCl (2.00 M). The precipitate was filtered off and dried under reduced pressure. 2-Cyclopropyl-6-methylpyrimidin-4-ol (11.4 g, crude) was obtained as white solid.

Step 2: 5-bromo-2-cyclopropyl-6-methylpyrimidin-4-ol

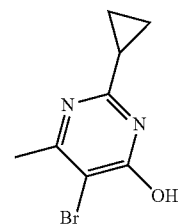

The reaction was set up in two parallel batches. To a solution of 2-cyclopropyl-6-methylpyrimidin-4-ol (5.20 g, 34.6 mmol, 1.00 eq) and KOH (1.94 g, 34.6 mmol, 1.00 eq) in water (60.0 mL) was added $Br_2$ (5.53 g, 34.6 mmol, 1.78 mL, 1.00 eq) at 0° C. The mixture was stirred at 30° C. for 18 h. The batches were combined. The precipitate was filtered off and dried under reduced pressure. 5-Bromo-2-cyclopropyl-6-methylpyrimidin-4-ol (11.2 g, 48.9 mmol, 70% yield) was obtained as a white solid.

Step 3: 5-bromo-4-chloro-2-cyclopropyl-6-methylpyrimidine

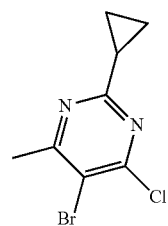

The reaction was set up in two parallel batches. To a mixture of 5-bromo-2-cyclopropyl-6-methylpyrimidin-4-ol (2.50 g, 10.9 mmol, 1.00 eq) and DMF (1.99 g, 27.3 mmol, 2.10 mL, 2.50 eq) in toluene (100 mL) was added dropwise $POCl_3$ (2.51 g, 16.4 mmol, 1.52 mL, 1.50 eq) in toluene (25.0 mL) at 0° C., and the mixture was stirred at 30° C. for 3 h The batches were combined. The mixture was added to aqueous $Na_2CO_3$ (1.00 M, 150 mL) which was then extracted with EtOAc (50.0 mL*3). The combined organic phases were concentrated under reduced pressure. 5-Bromo-4-chloro-2-cyclopropyl-6-methylpyrimidine (5.60 g crude) was obtained as a yellow oil.

Step 4: N'-(5-bromo-2-cyclopropyl-6-methylpyrimidin-4-yl)-4-methylbenzenesulfonohydrazide

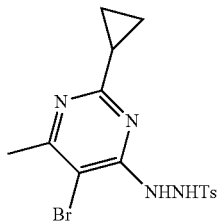

The reaction was set up in two parallel batches. A mixture of 5-bromo-4-chloro-2-cyclopropyl-6-methylpyrimidine (3.40 μg, 13.7 μmmol, 1.00 eq) and 4-methylbenzenesulfonohydrazide (7.67 g, 41.2 mmol, 3.00 eq) in CHCl₃ (300 mL) was stirred at 90° C. for 10 h. The batches were combined. The precipitate was filtered off, washed with DCM (50.0 mL), and dried under reduced pressure. N'-(5-bromo-2-cyclopropyl-6-methylpyrimidin-4-yl)-4-methylbenzenesulfonohydrazide (6.61 g, crude) was obtained as a white solid.

Step 5: 5-bromo-2-cyclopropyl-4-methylpyrimidine

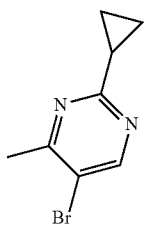

A mixture of N'-(5-bromo-2-cyclopropyl-6-methylpyrimidin-4-yl)-4-methylbenzenesulfonohydrazide (6.61 g, 16.6 mmol, 1.00 eq) in aq. Na₂CO₃ (0.56 M, 89.1 mL, 3.00 eq) was stirred at 90° C. for 2 hr. The mixture was extracted with ethyl acetate (50.0 mL*3), the combined organic layers were dried over Na₂SO₄, and concentrated under reduced pressure. The residue was purified by column chromatography (SiO₂, Petroleum ether/Ethyl acetate=1/0 to 0/1). 5-bromo-2-cyclopropyl-4-methylpyrimidine (2.47 g, 11.6 mmol, 69% yield) was obtained as a brown oil.

Step 6: (2-cyclopropyl-4-methylpyrimidin-5-yl)boronic Acid

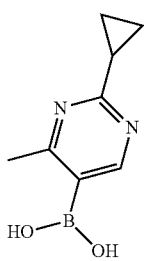

To a solution of 5-bromo-2-cyclopropyl-4-methylpyrimidine (500 mg, 2.35 mmol, 1.00 eq) in THF (5.00 mL) was added n-BuLi (2.50 M, 1.03 mL, 1.10 eq) at −78° C. under N₂, and the mixture was stirred at −78° C. for 30 min. B(OMe)₃ (732 mg, 7.04 mmol, 795 uL, 3.00 eq) was added to the mixture at −78° C., and the mixture was stirred at 25° C. under nitrogen for 5 hr. MeOH (5.00 mL) was added and the mixture was concentrated under reduced pressure. The residue was purified by reversed phase MPLC (TFA conditions). (2-cyclopropyl-4-methylpyrimidin-5-yl)boronic acid (300 mg, 1.69 mmol, 71% yield) was obtained as a yellow oil.

Step 7: (S)-4-(2-cyclopropyl-4-methylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine

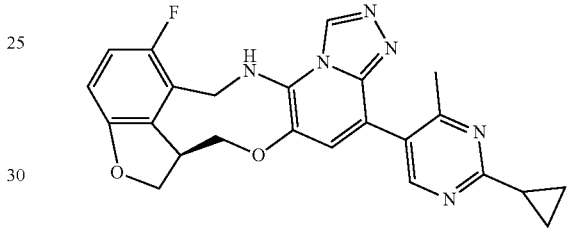

To a mixture of (2-cyclopropyl-4-methylpyrimidin-5-yl)boronic acid (150 mg, 843 umol, 2.00 eq) and (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (165 mg, 421 umol, 1.00 eq) in dioxane (3.00 mL) and water (0.300 mL) were added Pd(dppf)Cl₂ (30.8 mg, 42.1 umol, 0.100 eq) and Na₂CO₃ (89.3 mg, 843 umol, 2.00 eq) at 25° C., the mixture was stirred at 90° C. under nitrogen for 12 hr. The mixture was filtered and the filtrate was concentrated under reduced pressure. The residue was dissolved in MeOH (30.0 mL) and silica-thiol (3.00 g, modified silicone gel for eliminating Pd, irregular silica gel, 100-200 mesh, Chlorides (Cl), %≤0.004, particle size distribution 45-75 um) was added at 20° C. and stirred at 20° C. for 6 h. The suspension was filtered and the filtrate was concentrated under reduced pressure. The residue was purified by acidic prep-HPLC (FA conditions), the fraction was concentrated under reduced pressure to remove most of MeCN at 30° C. and the aqueous phase was lyophilized. (S)-4-(2-cyclopropyl-4-methylpyrimidin-5-yl)-12-fluoro-7a,8,13,14-tetrahydro-7H-[1,2,4]triazolo[4',3':1,6]pyrido[3,2-b]benzofuro[4,3-fg][1,4]oxazonine (12.4 mg, 25.3 umol, 6% yield, 100% purity, formate salt) was obtained as white solid. ¹H NMR CD₃OD 400 MHz δ=ppm 9.31 (s, 1H), 8.46 (s, 1H), 7.38 (s, 1H), 6.90-6.83 (m, 1H), 6.63 (dd, J=8.5, 3.9 Hz, 1H), 5.06 (d, J=15.7 Hz, 1H), 4.87 (d, J=15.7 Hz, 1H), 4.57 (t, J=9.3 Hz, 2H), 4.30-4.22 (m, 1H), 4.00 (br s, 1H), 3.92-3.83 (m, 1H), 2.34 (s, 3H), 2.25-2.18 (m, 1H), 1.15-1.08 (m, 4H). LCMS (ESI+): m/z 445.1 (M+H).

Example 145: (S)-12-fluoro-4-(3-methylpyridazin-4-yl)-7a,8,13,14-tetrahydro-7H-[1,2,4]triazolo[4',3':1,6]pyrido[3,2-b]benzofuro[4,3-fg][1,4]oxazonine Step 1: 6-methylpyridazine 1-oxide and 3-methylpyridazine 1-oxide

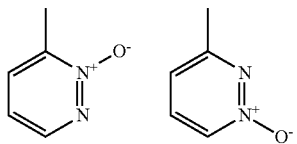

To a solution of 3-methylpyridazine (5.00 g, 53.1 mmol, 4.85 mL, 1.00 eq) in DCM (100 mL) was added m-CPBA (11.5 g, 53.1 mmol, 80.0% purity, 1.00 eq) at 0° C. The mixture was stirred at 20° C. for 2 h. The reaction mixture was filtered and the filtrate was concentrated under reduced pressure. The residue was purified by flash silica gel chromatography (ISCO®; 80 g SepaFlash® Silica Flash Column, Eluent of 5-18% EtOH/Petroleum ether gradient @ 40 mL/min). 3-Methylpyridazine 1-oxide (1.50 g, 13.6 mmol, 25% yield) with Rf=0.38 was obtained as a light yellow gum. 6-Methylpyridazine 1-oxide (2.00 g, 18.2 mmol, 34% yield) with Rf=0.43 was obtained as a light yellow solid. A mixture of 3-nethylpyridazine 1-oxide and 6-methylpyridazine 1-oxide (2.50 g crude) was obtained as a brown gum.

Step 2: 3-methyl-4-nitropyridazine 1-oxide

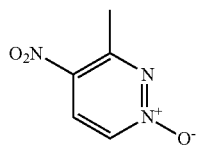

To a solution of 3-methylpyridazine 1-oxide (4.00 g, 36.3 mmol, 1.00 eq) in H$_2$SO$_4$ (45.0 mL) was added HNO$_3$ (15.9 g, 242 mmol, 11.4 mL, 96.0% purity, 6.67 eq) at 20° C. The mixture was stirred at 90° C. for 5 h. The reaction mixture was poured into ice water (150 mL) at 0° C. and extracted with DCM (50.0 mL*5). The combined organic layers were dried over anhydrous sodium sulfate, filtered, and the filtrate was concentrated under reduced pressure. The residue (~2.50 g) was purified by flash silica gel chromatography (ISCO®; 40 g SepaFlash® Silica Flash Column, Eluent of 50-80% Dichloromethane/Petroleum ethergradient @ 40 mL/min). 3-Methyl-4-nitropyridazine 1-oxide (900 mg, 5.80 mmol, 16% yield) was obtained as a yellow gum.

Step 3: 3-methylpyridazin-4-amine

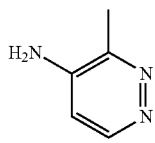

To a solution of 3-methyl-4-nitropyridazine 1-oxide (900 mg, 5.80 mmol, 1.00 eq) in MeOH (20.0 mL) was added Raney-Ni (1.00 g) and AcOH (3.15 g, 52.5 mmol, 3.00 mL, 9.04 eq) under N$_2$. The suspension was degassed under vacuum and purged with H$_2$ several times. The mixture was stirred under H$_2$ (15 psi) at 20° C. for 12 h. The reaction mixture was filtered and the filtrate was concentrated under reduced pressure to give a crude product. 3-methylpyridazin-4-amine (1.00 g, crude, HOAc) was obtained as a green solid.

Step 4: 4-iodo-3-methylpyridazine

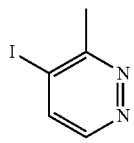

To a solution of 3-methylpyridazin-4-amine (1.00 g, 5.91 mmol, 1.00 eq, HOAc) and CH$_2$I$_2$ (7.92 g, 29.6 mmol, 2.38 mL, 5.00 eq) in MeCN (30.0 mL) was added isopentyl nitrite (1.52 g, 13.0 mmol, 1.75 mL, 2.20 eq) in MeCN (20.0 mL) at 0° C. under N$_2$. The reaction mixture was concentrated under reduced pressure. The residue was purified by flash silica gel chromatography (ISCO®; 12 g SepaFlash® Silica Flash Column, Eluent of 0-50% Ethyl acetate/Petroleum ethergradient @ 40 mL/min). 10.0 mL of dioxane was added to the fraction containing the product. Then the mixture was concentrated under reduced pressure until the residual volume of ~3 mL (mostly dioxane). 3-metbylpyridazin-4-amine (200 mg, 1.83 mmol, 31% yield) was recovered as a brown solid. Note: After chromatography on silica gel, if the fraction was concentrated completely, the product decomposed. The yield was estimated, and the material was used a solution in dioxane.

Step 5: tert-butyl (S)-12-fluoro-4-(3-methylpyridazin-4-yl)-7a,13-dihydro-7H-[1,2,4]triazolo[4',3':1,6]pyrido[3,2-b]benzofuro[4,3-fg][1,4]oxazonine-14 (8H)-carboxylate

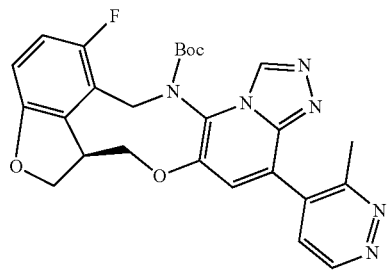 [SMILES: Cc1nnccc1-c1cc2c(n3cnnc13)N(C(=O)OC(C)(C)C)Cc1c(F)ccc3c1[C@H](CO3)CO2]

The reaction was set up in 7 parallel batches. A mixture of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (30.0 mg, 42.8 umol, 1.00 eq), 4-iodo-3-methylpyridazine (18.8 mg, 85.5 umol, 2.00 eq), LiCl (2.72 mg, 64.2 umol, 1.31 uL, 1.50 eq), Pd(PPh$_3$)$_4$ (4.94 mg, 4.28 umol, 0.100 eq) and CuI (4.07 mg, 21.4 umol, 0.500 eq) in dioxane (1.50 mL) was degassed and purged with nitrogen 3 times at 25° C., and the mixture was stirred at 80° C. for 2 h under nitrogen atmosphere. The batches were combined. LC-MS showed that tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate was consumed completely and one main peak with desired mass was detected. The reaction mixture was concentrated under reduced pressure. The residue was purified by prep-TLC (SiO$_2$, Ethyl acetate/MeOH=6/1). tert-butyl (S)-12-fluoro-4-(3-methylpyridazin-4-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, crude) was obtained as a brown solid.

Step 6: (S)-12-fluoro-4-(3-methylpyridazin-4-yl)-7a,8,13,14-tetrahydro-7H-[1,2,4]triazolo[4',3':1,6]pyrido[3,2-b]benzofuro[4,3-fg][1,4]oxazonine

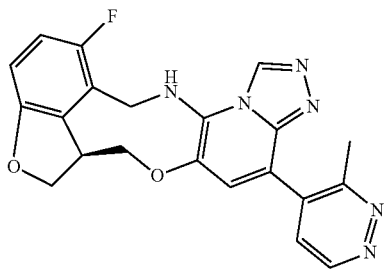 [SMILES: Cc1nnccc1-c1cc2c(n3cnnc13)NCc1c(F)ccc3c1[C@H](CO3)CO2]

A mixture of tert-butyl (S)-12-fluoro-4-(3-methylpyridazin-4-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, 198 umol, 1.00 eq) in HFIP (3.00 mL) was stirred at 80° C. for 12 h. The reaction mixture was concentrated under reduced pressure. The residue was purified by prep-HPLC (formic acid conditions). (S)-12-fluoro-4-(3-methylpyridazin-4-yl)-7a,8,13,14-tetrahydro-7H-[1,2,4]triazolo[4',3':1,6]pyrido[3,2-b]benzofuro[4,3-fg][1,4]oxazonine (21.1 mg, 51.6 umol, 26% yield, 98.9% purity) was obtained as a brown solid. $^1$H NMR DMSO-d6 400 MHz δ=ppm 9.47 (s, 1H), 9.15 (d, J=5.2 Hz, 1H), 7.81-7.71 (m, 2H), 7.55 (s, 1H), 7.02-6.93 (m, 1H), 6.72 (dd, J=8.6, 3.8 Hz, 1H), 4.99-4.89 (m, 1H), 4.87-4.75 (m, 1H), 4.54 (q, J=9.7 Hz, 2H), 4.22 (dd, J=9.6, 3.5 Hz, 1H), 4.05 (br s, 1H), 3.94-3.82 (m, 1H), 2.60 (s, 3H). LCMS (ESI+): m/z 405.1 (M+H).

Example 146: (S)-12-fluoro-4-(oxazol-S-yl)-7a,8,13,14-tetrahydro-7H-[1,2,4]triazolo[4',3':1,6]pyrido[3,2-b]benzofuro[4,3-fg][1,4]oxazonine Step 1: 2-(triisopropylsilyl)oxazole

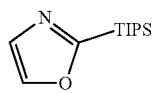

The reaction was set up in two parallel batches. To a stirred solution of oxazole (1.00 g, 14.5 mmol, 926 uL, 1.00 eq) in THF (10.0 mL) was added n-BuLi (2.50 M, 6.37 mL, 1.10 eq) at −30° C. under N$_2$. The resulting mixture was stirred at −30° C. for 0.5 hr. To the mixture was added TIPS-OTf (4.88 g, 15.9 mmol, 4.28 mL, 1.10 eq) at −10° C. under N$_2$. The resulting mixture was stirred at 15° C. for 12 h. The batches were combined. The resulting mixture was quenched by addition of saturated aqueous NH$_4$Cl solution (10.0 mL) and extracted with EtOAc (10.0 mL*3). The combined organic layers were dried over Na$_2$SO$_4$ and concentrated under reduced pressure. The mixture was purified by MPLC (SiO$_2$, PE/EtOAc=1/0 to 1/1) to give 2-(triisopropylsilyl)oxazole (3.00 g, 13.3 mmol, 46% yield) as a yellow oil.

Step 2: (2-(triisopropylsilyl)oxazol-S-yl)boronic Acid

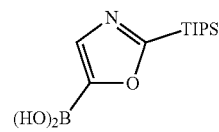

To the solution of 2-(triisopropylsilyl)oxazole (400 mg, 1.77 mmol, 1.00 eq) in THF (10.0 mL) was added n-BuLi (2.50 M, 781 uL, 1.10 eq) dropwise at −78° C. under N$_2$. The reaction mixture was stirred at −78° C. for 1 hr. Triisopropyl borate (668 mg, 3.55 mmol, 816 uL, 2.00 eq) was added at −78° C. The mixture was stirred at −78° C. for 1 hr then at 15° C. for 0.5 hr. LCMS indicated complete conversion. MeOH (2.00 mL) was added, and the mixture was concentrated under vacuum to give (2-(triisopropylsilyl)oxazol-S-yl)boronic acid (477 mg, crude) as a yellow oil which was used directly in the next step without further purification.

Step 3: tert-butyl (S)-12-fluoro-4-(2-(triisopropylsilyl)oxazol-S-yl)-7a,13-dihydro-7H-[1,2,4]triazolo[4',3':1,6]pyrido[3,2-b]benzofuro[4,3-fg][1,4]oxazonine-14 (8H)-carboxylate

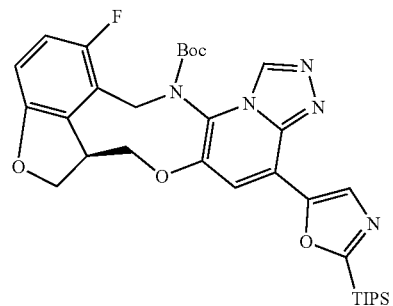

To the solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq) and (2-triisopropylsilyloxazol-S-yl)boronic acid (205 mg, 763 umol, 2.50 eq) in dioxane (6.00 mL) and water (1.00 mL) were added KOAc (59.9 mg, 611 umol, 2.00 eq) and Pd(dppf)Cl$_2$ (22.3 mg, 30.5 umol, 0.100 eq). The resulting solution was stirred at 90° C. under nitrogen for 12 h. The mixture was concentrated under vacuum. The crude product was purified by prep-TLC (SiO$_2$, PE:EtOAc=3:2) to obtain tert-butyl (S)-12-fluoro-4-(2-(triisopropylsilyl)oxazol-S-yl)-7a,13-dihydro-7H-[1,2,4]triazolo[4',3':1,6]pyrido[3,2-b]benzofuro[4,3-fg][1,4]oxazonine-14 (8H)-carboxylate (110 mg, 173 umol, 56% yield) as a yellow oil.

401

Step 4: (S)-12-fluoro-4-(oxazol-5-yl)-7a,8,13,14-tetrahydro-7H-[1,2,4]triazolo[4',3':1,6]pyrido[3,2-b]benzofuro[4,3-fg][1,4]oxazonine

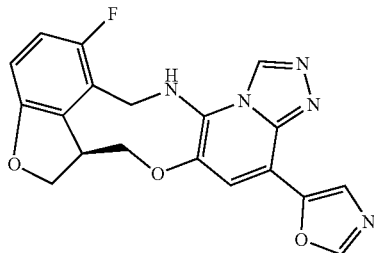 [SMILES: Fc1ccc2c3c1CNc1c(cc(-c4cnco4)c4nncn14)OC[C@H]3CO2]

To a solution of tert-butyl (S)-12-fluoro-4-(2-(triisopropylsilyl)oxazol-5-yl)-7a,13-dihydro-7H-[1,2,4]triazolo[4',3':1,6]pyrido[3,2-b]benzofuro[4,3-fg][1,4]oxazonine-14(8H)-carboxylate (110 mg, 173 umol, 1.00 eq) in DCM (2.00 mL) was added TFA (2.00 mL) at 15° C., and the resulting solution was stirred at 15° C. for 2 h. LCMS indicated incomplete conversion. Additional TFA (2.00 mL) was added and the resulting solution was stirred at 15° C. for 3 h. LCMS showed that the reaction was complete. The mixture was concentrated under a nitrogen stream to dryness. The crude product was purified by prep-HPLC (FA) to obtain (S)-12-fluoro-4-(oxazol-5-yl)-7a,8,13,14-tetrahydro-7H-[1,2,4]triazolo[4',3':1,6]pyrido[3,2-b]benzofuro[4,3-fg][1,4]oxazonine (28.5 mg, 67.0 umol, 38% yield, 100% purity, formate salt) as light yellow solid. $^1$H NMR CDCl$_3$ 400 MHz δ=ppm 8.92 (s, 1H), 8.12 (s, 1H), 7.93 (s, 1H), 7.51 (s, 1H), 6.83 (t, J=9.2 Hz, 1H), 6.65-6.62 (m, 1H), 5.24-5.22 (m, 1H), 5.12-5.08 (m, 1H), 4.90-4.85 (m, 1H), 4.67-4.60 (m, 2H), 4.28-4.25 (m, 1H), 3.91-3.87 (m, 2H). LCMS (ESI+): m/z 380.1 (M+H).

Example 147: (S)-12-fluoro-4-(4-methyloxazol-5-yl)-7a,8,13,14-tetrahydro-7H-[1,2,4]triazolo[4',3':1,6]pyrido[3,2-b]benzofuro[4,3-fg][1,4]oxazonine

Step 1: 4-methyl-2-(triisopropylsilyl)oxazole

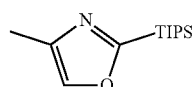

To a solution of 4-methyloxazole (1.50 g, 18.1 mmol, 1.00 eq) in THF (20.0 mL) was added n-BuLi (2.50 M, 7.94 mL, 1.10 eq) at −30° C. under N$_2$. The resulting solution was stirred at −30° C. for 0.5 hr. TIPS-OTf (6.08 g, 19.9 mmol, 5.34 mL, 1.10 eq) was added at −10° C. under N$_2$ and the resulting solution was stirred at 25° C. for 12 h. Saturated aqueous NH$_4$Cl solution (15.0 mL) was added, the mixture was extracted with EtOAc (10.0 mL*3), the combined organic layers were washed with brine (10.0 mL), dried over Na$_2$SO$_4$, filtered, and under vacuum. The crude product was purified by column chromatography on basic A$_2$O$_3$(PE:EtOAc=1:0 to 10:1). 4-methyl-2-(triisopropylsilyl)oxazole (3.50 g, 14.6 mmol, 81% yield) was obtained as a yellow oil. $^1$H NMR CDCl$_3$ 400 MHz δ=ppm 7.49 (s, 1H), 2.21 (s, 3H), 1.44-1.36 (m, 3H), 1.12 (d, J=7.6 Hz, 18H).

402

Step 2: 4-methyl-5-(tributylstannyl)-2-(triisopropylsilyl)oxazole

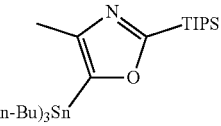

To the solution of 4-methyl-2-(triisopropylsilyl)oxazole (0.200 g, 835 umol, 1.00 eq) in THF (4.00 mL) was added n-BuLi (2.50 M, 368 uL, 1.10 eq) dropwise at −78° C. under N$_2$ and the resulting solution was stirred at −78° C. for 0.5 hr. Tributyl(chloro)stannane (299 mg, 919 umol, 247 uL, 1.10 eq) was added at −78° C. and the resulting solution was stirred at −78° C. for 1 hr, then at 15° C. for 2 hr. MeOH (2.00 mL) was added and the mixture was concentrated under vacuum. The residue was purified by prep-TLC (PE:EtOAc=10:1). 4-methyl-5-(tributylstannyl)-2-(triisopropylsilyl)oxazole (320 mg, 606 umol, 72% yield) was obtained as a colorless oil.

Step 3: tert-butyl (S)-12-fluoro-4-(4-methyl-2-(triisopropylsilyl)oxazol-5-yl)-7a,13-dihydro-7H-[1,2,4]triazolo[4',3':1,6]pyrido[3,2-b]benzofuro[4,3-fg][1,4]oxazonine-14(8H)-carboxylate

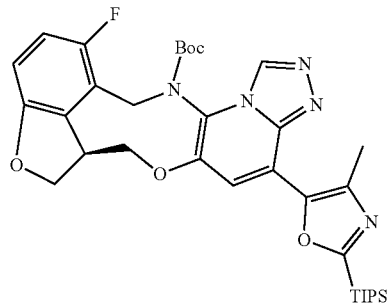

To the solution of 4-methyl-5-(tributylstannyl)-2-(triisopropylsilyl)oxazole (194 mg, 366 umol, 1.20 eq) in dioxane (5.00 mL) were added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14(8H)-carboxylate (150 mg, 305 umol, 1.00 eq), Pd(PPh$_3$)$_4$ (35.3 mg, 30.5 umol, 0.100 eq), LiCl (25.9 mg, 611 umol, 12.5 uL, 2.00 eq) and CuI (23.3 mg, 122 umol, 0.400 eq) under N$_2$. The resulting solution was stirred at 80° C. for 12 hr. The mixture was concentrated under vacuum. The residue was purified by prep-TLC (PE:EtOAc=1:1). tert-butyl (S)-12-fluoro-4-(4-methyl-2-(triisopropylsilyl)oxazol-5-yl)-7a,13-dihydro-7H-[1,2,4]triazolo[4',3':1,6]pyrido[3,2-b]benzofuro[4,3-fg][1,4]oxazonine-14(8H)-carboxylate (180 mg, 277 umol, 90% yield) was obtained as a yellow oil.

403

Step 4: (S)-12-fluoro-4-(4-methyloxazol-S-yl)-7a,8, 13,14-tetrahydro-7H-[1,2,4]triazolo[4',3':1,6]pyrido[3,2-b]benzofuro[4,3-fg][1,4]oxazonine

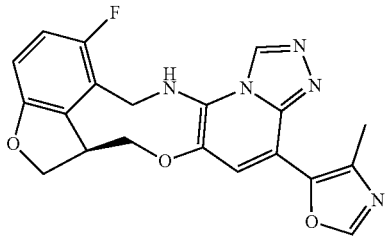 [SMILES: Cc1ncoc1-c1cc2c(n3cnnc13)NCc1c(F)ccc3c1[C@H](CO3)CO2]

To the solution of tert-butyl (S)-12-fluoro-4-(4-methyl-2-(triisopropylsilyl)oxazol-S-yl)-7a,13-dihydro-7H-[1,2,4]triazolo[4',3':1,6]pyrido[3,2-b]benzofuro[4,3-fg][1,4]oxazonine-14 (8H)-carboxylate (180 mg, 277 umol, 1.00 eq) in DCM (1.50 mL) was added TFA (1.50 mL) at 15° C. and the resulting solution was stirred at 15° C. for 4 hr. The mixture was concentrated under vacuum. The residue was purified by prep-HPLC (FA) to obtain (S)-12-fluoro-4-(4-methyl-oxazol-S-yl)-7a,8,13,14-tetrahydro-7H-[1,2,4]triazolo[4',3':1,6]pyrido[3,2-b]benzofuro[4,3-fg][1,4]oxazonine (29.1 mg, 64.7 umol, 23% yield, 97.7% purity, formate salt) as a yellow solid. $^1$H NMR CDCl$_3$ 400 MHz δ=ppm 8.95 (br s, 1H), 7.93 (s, 1H), 7.32 (s, 1H), 6.87 (t, J=9.2 Hz, 1H), 6.69-6.66 (m, 1H), 5.30 (br s, 1H), 5.15-5.09 (m, 1H), 4.90-4.86 (m, 1H), 4.68-4.63 (m, 2H), 4.29-4.26 (m, 1H), 3.94-3.87 (m, 2H), 2.52 (s, 3H). LCMS (ESI+): m/z 394.1 (M+H).

Example 148: (S)-4-(2-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine Step 1: tert-butyl (S)-4-(2-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

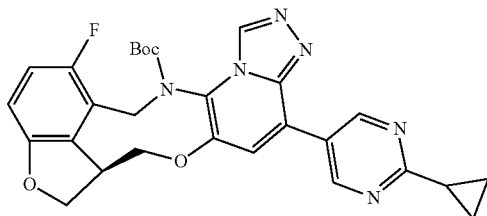

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq) in dioxane (5.00 mL) and water (0.500 mL) were added 2-cyclopropyl-S—(4,4,5,5-tetramethyl-1,3,2-dioxaborolan-2-yl)pyrimidine (150 mg, 609 umol, 2.00 eq), Na$_2$CO$_3$ (64.7 mg, 611 umol, 2.00 eq) and Pd(dppf)Cl$_2$ (22.3 mg, 30.5 umol, 0.100 eq) at 20° C. under nitrogen atmosphere. The mixture was stirred at 80° C. for 12 h under nitrogen atmosphere. The reaction mixture was concentrated. The residue was purified by prep-TLC (SiO$_2$, Petroleum ether/Ethyl acetate=0/1). tert-butyl (S)-4-(2-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (260 mg, crude) was obtained as a yellow oil.

Step 2: (S)-4-(2-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine

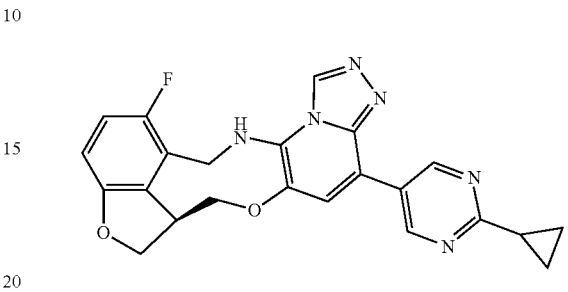

A solution of tert-butyl (S)-4-(2-cyclopropylpyrimidin-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (160 mg, 302 umol, 1.00 eq) in HFIP (5.00 mL) was stirred at 100° C. for 2 h. LC-MS indicated incomplete conversion. The mixture was stirred at 100° C. for additional 6 h. LC-MS showed that the reaction was complete. The reaction mixture was concentrated under reduced pressure. The residue was dissolved in DMSO (3.00 mL). The mixture was purified by prep-HPLC (column: Welch Xtimate C18 150*25 mm*5 um; mobile phase: [water (0.2% FA)—ACN]; B %: 30%-60%, 10 min). The product-containing fraction was concentrated under reduced pressure to remove most of MeCN at 30° C. and the aqueous phase was lyophilized. (S)-4-(2-cyclopropylpyrimidin-S-yl)-12-fluoro-7a,8,13,14-tetrahydro-7H-[1,2,4]triazolo[4',3':1,6]pyrido[3,2-b]benzofuro[4,3-fg][1,4]oxazonine (67.6 mg, 142 umol, 46% yield, 99.5% purity, formate salt) was obtained as a yellow solid. $^1$H NMR DMSO-d6 400 MHz δ=ppm 9.47 (s, 1H), 9.39 (s, 2H), 7.87 (s, 1H), 7.70 (br t, J=6.1 Hz, 1H), 6.95 (t, J=9.5 Hz, 1H), 6.69 (dd, J=8.6, 3.7 Hz, 1H), 4.95-4.75 (m, 2H), 4.58-4.49 (m, 2H), 4.22 (br dd, J=9.5, 2.8 Hz, 1H), 4.03 (br d, J=9.2 Hz, 1H), 3.99-3.90 (m, 1H), 2.29-2.20 (m, 1H), 1.10-1.02 (m, 4H). LCMS (ESI+): m/z 431.1 (M+H).

Example 149: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-3-amine Step 1: 2-methyl-3-nitro-S-(4,4,5,5-tetramethyl-1,3,2-dioxaborolan-2-yl)pyridine

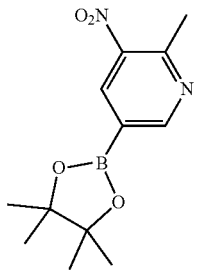

To a solution of 5-bromo-2-methyl-3-nitropyridine (1.00 g, 4.61 mmol, 1.00 eq) in dioxane (15.0 mL) were added 4,4,5,5-tetramethyl-2-(4,4,5,5-tetramethyl-1,3,2-dioxaborolan-2-yl)-1,3,2-dioxaborolane (1.75 g, 6.91 mmol, 1.50 eq), KOAc (905 mg, 9.22 mmol, 2.00 eq) and Pd(dppf)Cl2 (337 mg, 461 umol, 0.100 eq) at 20° C. under nitrogen atmosphere. The mixture was stirred at 80° C. for 12 h under nitrogen atmosphere. Water (10.0 mL) was added to the mixture, the mixture was extracted with ethyl acetate (8.00 mL*3), the combined organic layers were dried over Na₂SO₄, filtered, and concentrated under reduced pressure. The residue was purified by column chromatography (SiO₂, Petroleum ether/Ethyl acetate=1/0 to 1/1). 2-Methyl-3-nitro-S—(4,4,5,5-tetramethyl-1,3,2-dioxaborolan-2-yl)pyridine (1.15 g, 4.35 mmol, 94% yield) was obtained as a white solid.

Step 2: 2-methyl-S-(4,4,5,5-tetramethyl-1,3,2-dioxaborolan-2-yl)pyridin-3-amine

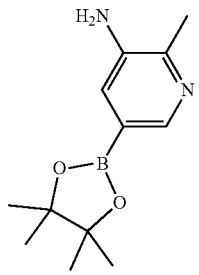

To a solution of 2-methyl-3-nitro-S-(4,4,5,5-tetramethyl-1,3,2-dioxaborolan-2-yl)pyridine (1.15 g, 4.35 mmol, 1.00 eq) in MeOH (25.0 mL) was added 10% Pd/C (2.32 g, 50.0% purity) under nitrogen atmosphere. The suspension was degassed and purged with H₂ 5 times. The mixture was stirred under H₂ (15 Psi) at 20° C. for 4 h. LC-MS showed 2-methyl-3-nitro-S—(4,4,5,5-tetramethyl-1,3,2-dioxaborolan-2-yl)pyridine was consumed completely and one main peak with the desired mass was detected. The reaction mixture was filtered and the filter was concentrated under reduced pressure to give 2-methyl-S-(4,4,5,5-tetramethyl-1,3,2-dioxaborolan-2-yl)pyridin-3-amine (850 mg, crude) as a yellow oil.

Step 3: tert-butyl (S)-4-(5-amino-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

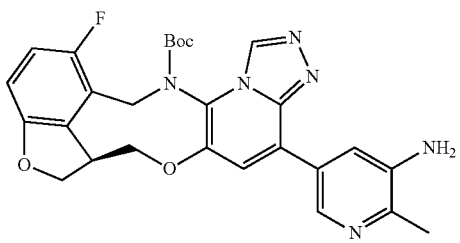 [SMILES: Cc1ncc(-c2cc3c(n4cnnc24)N(C(=O)OC(C)(C)C)Cc2c(F)ccc4c2[C@H](CO4)CO3)cc1N]

To a solution of 2-methyl-S-(4,4,5,5-tetramethyl-1,3,2-dioxaborolan-2-yl)pyridin-3-amine (143 mg, 611 umol, 2.00 eq) in water (0.700 mL) and EtOH (4.90 mL) were added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq), KOAc (59.9 mg, 610 umol, 2.00 eq) and 4-ditert-butylphosphanyl-N,N-dimethyl-aniline; dichloropalladium (21.6 mg, 30.5 umol, 21.6 uL, 0.100 eq) at 20° C. under nitrogen atmosphere. The mixture was stirred at 80° C. for 12 hr under nitrogen atmosphere. The reaction mixture was concentrated. The residue was purified by prep-TLC (SiO₂, Ethyl acetate/MeOH=10/1). tert-Butyl (S)-4-(5-amino-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (138 mg, 266 umol, 87% yield) was obtained as a yellow solid.

Step 4: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-3-amine

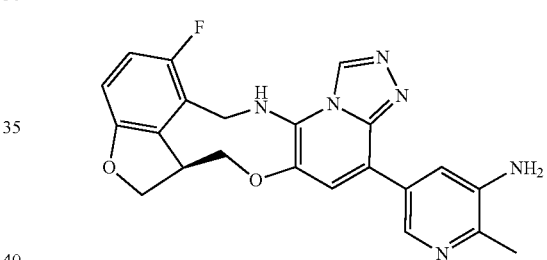

A solution of tert-butyl (S)-4-(5-amino-6-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (110 mg, 212 umol, 1.00 eq) in HFIP (5.00 mL) was stirred at 100° C. for 15 h. The reaction mixture was concentrated under reduced pressure. The residue was dissolved in DMSO (3.00 mL). The mixture was purified by prep-HPLC (column: Phenomenex Gemini-NX 80*40 mm*3 um; mobile phase: [water (10 mM NH₄HCO₃)—ACN]; B %: 10%-40%, 8 min). The product-containing fraction was concentrated under reduced pressure to remove most of MeCN at 30° C. and the aqueous phase was lyophilized. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-3-amine (37.3 mg, 89.1 umol, 42% yield, 99.9% purity) was obtained as a yellow solid. ¹H NMR DMSO-d₆ 400 MHz δ=ppm 9.43 (s, 1H), 8.35 (s, 1H), 7.78 (s, 1H), 7.56 (s, 1H), 7.50 (br t, J=6.2 Hz, 1H), 6.95 (t, J=9.5 Hz, 1H), 6.68 (dd, J=8.6, 3.7 Hz, 1H), 5.10 (s, 2H), 4.95-4.72 (m, 2H), 4.59-4.47 (m, 2H), 4.22 (br dd, J=9.6, 3.0 Hz, 1H), 4.02 (br d, J=8.9 Hz, 1H), 3.95-3.87 (m, 1H), 2.31 (s, 3H). LCMS (ESI+): m/z 419.1 (M+H).

Example 150: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-ol Step 1: 6-methyl-S-(4,4,5,5-tetramethyl-1,3,2-dioxaborolan-2-yl)pyridin-2-ol

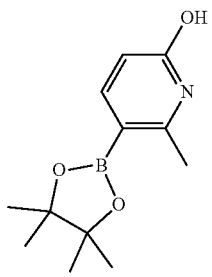

To a solution of 5-bromo-6-methylpyridin-2-ol (1.00 g, 5.32 mmol, 1.00 eq) in dioxane (12.0 mL) were added 4,4,5,5-tetramethyl-2-(4,4,5,5-tetramethyl-1,3,2-dioxaborolan-2-yl)-1,3,2-dioxaborolane (2.02 g, 7.95 mmol, 1.50 eq), KOAc (1.04 g, 10.6 mmol, 2.00 eq) and Pd(dppf)Cl$_2$ (390 mg, 533 umol, 0.100 eq) at 20° C. under nitrogen atmosphere. The mixture was stirred at 80° C. for 12 hr under nitrogen atmosphere. Water (15.0 mL) was added to the mixture, the mixture was extracted with ethyl acetate (10.0 mL*3), the combined organic layers were dried over Na$_2$SO$_4$, filtered, and concentrated under reduced pressure. The residue was purified by MPLC (SiO$_2$, Petroleum ether/Ethyl acetate=1/0 to 1/1). 6-Methyl-S-(4,4,5,5-tetramethyl-1,3,2-dioxaborolan-2-yl)pyridin-2-ol (690 mg, crude) was obtained as a yellow solid.

Step 2: tert-butyl (S)-12-fluoro-4-(6-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

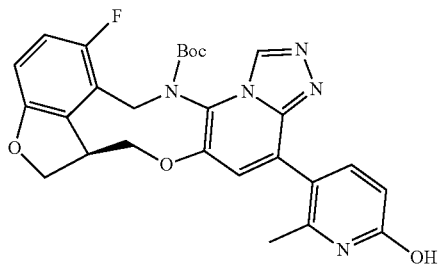 [SMILES: Cc1nc(O)ccc1-c1cc2c(n3cnnc13)N(C(=O)OC(C)(C)C)Cc1c(F)ccc3c1[C@H](CO3)CO2]

To a solution of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (120 mg, 244 umol, 1.00 eq) in dioxane (5.00 mL) and water (0.500 mL) were added 6-methyl-S—(4,4,5,5-tetramethyl-1,3,2-dioxaborolan-2-yl)pyridin-2-ol (230 mg, 977 umol, 4.00 eq), Na$_2$CO$_3$ (51.8 mg, 489 umol, 2.00 eq) and Pd(dppf)Cl$_2$ (17.9 mg, 24.4 umol, 0.100 eq) at 20° C. under nitrogen atmosphere. The mixture was stirred at 80° C. for 12 h under nitrogen atmosphere. LC-MS showed tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate was remained and one main peak with the desired mass was detected. The reaction mixture was concentrated under reduced pressure. The residue was purified by prep-TLC (SiO$_2$, Ethyl acetate/MeOH=5/1). tert-Butyl (S)-12-fluoro-4-(6-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (95.0 mg, 183 umol, 74% yield) was obtained as a yellow solid.

Step 3: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-ol

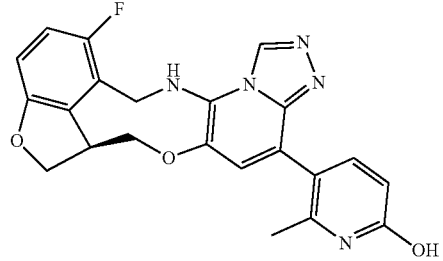 [SMILES: Cc1nc(O)ccc1-c1cc2c(n3cnnc13)NCc1c(F)ccc3c1[C@H](CO3)CO2]

To a solution of tert-butyl (S)-12-fluoro-4-(6-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (200 mg, 385 umol, 1.00 eq) in DCM (2.00 mL) was added TFA (3.08 g, 27.0 mmol, 2.00 mL, 70.2 eq) at 20° C. The mixture was stirred at 20° C. for 1 hr. The reaction mixture was concentrated under reduced pressure. The residue was dissolved in DMSO (2.00 mL). The mixture was purified by acidic prep-HPLC (column: Luna Omega 5 u Polar C18 100A; mobile phase: [water (0.04% HCl)-ACN]; B %: 15%-40%, 7 min). The product-containing fraction was concentrated under reduced pressure to remove most of MeCN at 30° C. and the aqueous phase was lyophilized. (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-ol (104 mg, 228 umol, 59% yield, 100% purity, HCl salt) was obtained as a yellow solid. $^1$H NMR CD$_3$OD 400 MHz δ=ppm 9.53 (s, 1H), 7.94 (s, 1H), 7.70 (d, J=9.2 Hz, 1H), 6.98-6.88 (m, 1H), 6.72-6.64 (m, 2H), 5.19 (d, J=14.7 Hz, 1H), 4.95 (br d, J=14.8 Hz, 1H), 4.76 (br dd, J=10.0, 4.3 Hz, 1H), 4.63 (t, J=9.5 Hz, 1H), 4.32 (dd, J=9.7, 3.2 Hz, 1H), 4.13-4.05 (m, 1H), 3.953-3.85 (m, 1H), 2.25 (s, 3H). LCMS (ESI+): m/z 420.1 (M+H).

Example 151: (S)-12-fluoro-4-(3-methyl-1H-pyrazol-1-yl)-7a,8,13,14-tetrahydro-7H-[1,2,4]triazolo[4',3':1,6]pyrido[3,2-b]benzofuro[4,3-fg][1,4]oxazonine

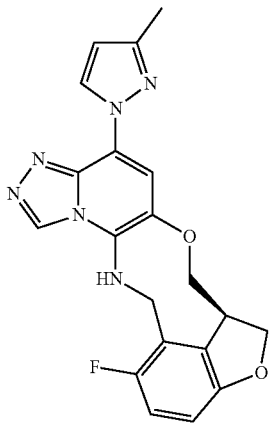 [SMILES: Cc1ccn(-c2cc3c(n4cnnc24)NCc2c(F)ccc4c2[C@H](CO4)CO3)n1]

3-Methyl-1H-pyrazole (0.0492 mL, 0.611 mmol) was added to a mixture of tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (Example 17; 150 mg, 0.305 mmol), $K_3PO_4$ (130 mg, 0.611 mmol), CuI (5.81 mg, 0.0305 mmol), and trans-N,N'-dimethylcyclohexane-1,2-diamine (0.0193 mL, 0.122 mmol) in toluene (0.600 mL) under $N_2$. The mixture was heated at 115° C. for 18 h. The mixture was concentrated under reduced pressure. The residue was purified by silica gel chromatography (12.0 g cartridge) eluting with EtOAc in hexanes (0-100%) to afford tert-butyl (S)-12-fluoro-4-(3-methyl-1H-pyrazol-1-yl)-7a,13-dihydro-7H-[1,2,4]triazolo[4',3':1,6]pyrido[3,2-b]benzofuro[4,3-fg][1,4]oxazonine-14 (8H)-carboxylate as a solid (60 mg, 31%). m/z (ES+) [M+H]⁺: 493.16. HPLC (A05) $t_R$=2.78 min.

The solid was diluted with HFIP (3.00 mL) and stirred at 80° C. for 16 h. The solution was concentrated under reduced pressure, and the residue was purified by reverse phase chromatography (BEH C18 30×150 ACN/AmBicarb 19 min, 35-55%) to provide the title compound as a solid (5.77 mg). ¹H NMR (500 MHz, DMSO-$d_6$) δ 9.50 (s, 1H), 8.96 (d, J=2.1 Hz, 1H), 7.72 (s, 1H), 7.42 (t, J=6.0 Hz, 1H), 6.93 (dd, J=10.3, 8.7 Hz, 1H), 6.67 (dd, J=8.7, 3.8 Hz, 1H), 6.35 (d, J=2.4 Hz, 1H), 4.86 (dd, J=14.9, 5.7 Hz, 1H), 4.75 (dd, J=15.3, 6.4 Hz, 1H), 4.58-4.47 (m, 2H), 4.24 (dd, J=9.6, 3.5 Hz, 1H), 4.09-3.98 (m, 1H), 3.86 (t, J=11.5 Hz, 1H), 2.29 (s, 3H). m/z (ES+) [M+H]⁺: 393.2. HPLC (BEH C18 5-100% ACN/AmForm 10 mM pH4) $t_R$=1.46 min.

Example 152: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpicolinamide

Step 1: 5-bromo-N,N-dimethylpicolinamide

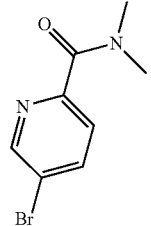

To a solution of 5-bromopicolinic acid (1.00 g, 4.95 mmol, 1.00 eq), N-methylmethanamine (484 mg, 5.94 mmol, 1.20 eq, HCl salt) in DMF (10 mL) was added DIPEA (1.28 g, 9.90 mmol, 1.72 mL, 2.00 eq) and HATU (2.26 g, 5.94 mmol, 1.2 eq) at 25° C. The mixture was stirred at 25° C. for 10 h. LCMS showed 5-bromopicolinic acid was consumed completely and the product was detected. To the mixture was added water (20 mL), the mixture was extracted with EtOAc (20 mL*3). The combined organic layers were dried over $Na_2SO_4$, filtered, and concentrated under reduced pressure. The residue was purified by MPLC ($SiO_2$, PE:EtOAc=1:0 to PE:EtOAc=1:1). 5-Bromo-N,N-dimethylpicolinamide (560 mg, 2.44 mmol, 49% yield) was obtained as a yellow oil.

Step 2: N,N-dimethyl-S-(4,4,5,5-tetramethyl-1,3,2-dioxaborolan-2-yl)picolinamide

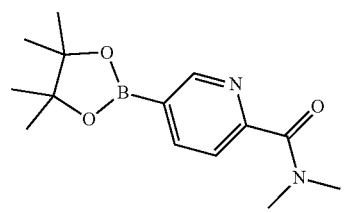

To a solution of 5-bromo-N,N-dimethylpicolinamide (500 mg, 2.18 mmol, 1.00 eq) and 4,4,4',4',5,5,5',5'-octamethyl-2,2'-bi(1,3,2-dioxaborolane) (831 mg, 3.27 mmol, 1.50 eq) in dioxane (5.00 mL) was added KOAc (643 mg, 6.55 mmol, 3.00 eq) and Pd(dppf)$Cl_2$·DCM (89.1 mg, 109 umol, 0.0500 eq) under nitrogen atmosphere at 25° C. The mixture was stirred at 80° C. for 10 h under nitrogen atmosphere. LCMS showed that the reaction was complete. The mixture was concentrated under reduced pressure. The residue was purified by MPLC ($SiO_2$, PE:EtOAc=1:0 to EtOAc:MeOH=5:1) to give N,N-dimethyl-S-(4,4,5,5-tetramethyl-1,3,2-dioxaborolan-2-yl)picolinamide (100 mg, crude) as a yellow oil.

411

Step 3: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpicolinamide

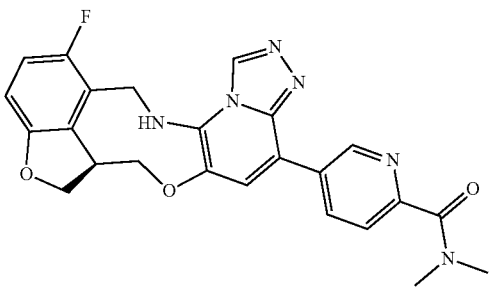 [SMILES: CN(C)C(=O)c1ccc(-c2cc3c(n4cnnc24)NCc2c(F)ccc4c2[C@H](CO4)CO3)cn1]

To a solution of N,N-dimethyl-S-(4,4,5,5-tetramethyl-1,3,2-dioxaborolan-2-yl)picolinamide (74.1 mg, 268 umol, 1.50 eq), (S)-4-bromo-12-fluoro-7a,8,13,14-tetrahydro-7H-[1,2,4]triazolo[4',3':1,6]pyrido[3,2-b]benzofuro[4,3-fg][1,4]oxazonine (70.0 mg, 179 umol, 1.00 eq) and NaHCO₃ (75.2 mg, 895 umol, 34.8 uL, 5.00 eq) in dioxane (1.00 mL) and water (0.100 mL) was added Pd(dppf)Cl₂ (13.1 mg, 17.9 umol, 0.100 eq) under nitrogen at 25° C. The resulting mixture was stirred at 80° C. under nitrogen for 3 hr. The reaction mixture was concentrated under reduced pressure. The residue was dissolved in MeOH (2 mL) and silica-thiol (180 mg, modified silicon gel for eliminating Pd, irregular silica gel, 100-200 mesh, Chlorides (Cl), %≤0.004, particle size distribution 45-75 um) was added at 20° C. and the mixture was stirred at 20° C. for 3 h. The suspension was filtered, the filtrate was concentrated, and obtained residue was purified by acidic prep-HPLC (column: Phenomenex Luna C18 150*30 mm*5 um; mobile phase: [water (0.04% HCl) —ACN]; B %: 20%-50%, 10 min). The product-containing fraction was concentrated under reduced pressure to remove most of MeCN at 30° C. and the aqueous phase was lyophilized. (S)-5-(12-fluoro-7a,8,13,14-tetrahydro-7H-[1,2,4]triazolo[4',3':1,6]pyrido[3,2-b]benzofuro[4,3-fg][1,4]oxazonin-4-yl)-N,N-dimethylpicolinamide (40.6 mg, 80.56 umol, 45% yield, 98.6% purity, HCl salt) was obtained as a yellow solid. 1H NMR CD3OD 400 MHz δ=ppm 9.62 (s, 1H), 9.00 (br s, 1H), 8.41 (br d, J=7.9 Hz, 1H), 8.21 (s, 1H), 7.93 (br d, J=7.8 Hz, 1H), 6.90 (t, J=9.5 Hz, 1H), 6.67 (dd, J=8.6, 3.7 Hz, 1H), 5.19 (d, J=14.7 Hz, 1H), 5.03-4.94 (m, 1H), 4.85-4.74 (m, 1H), 4.62 (br t, J=9.2 Hz, 1H), 4.33 (br d, J=8.6 Hz, 1H), 4.11-4.03 (m, 1H), 4.02-3.94 (m, 1H), 3.18 (s, 3H), 3.13 (s, 3H). LCMS (ESI+): m/z 461.2 (M+H).

412

Example 153: (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)-N-methylpropanamide Step 1: tert-butyl (S,E)-4-(6-(3-ethoxy-3-oxoprop-1-en-1-yl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

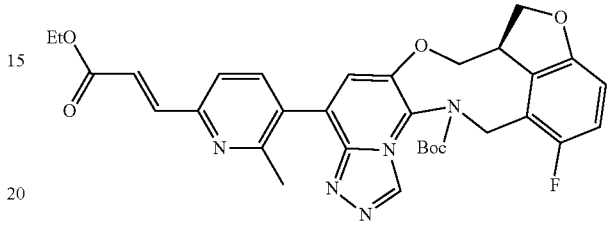

To a stirred solution of ethyl (E)-3-(6-methyl-S-(4,4,5,5-tetramethyl-1,3,2-dioxaborolan-2-yl)pyridin-2-yl)acrylate (678 mg, 2.14 mmol, 3.50 eq) and tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (300 mg, 611 umol, 1.00 eq) in dioxane (8.00 mL) and H₂O (1.60 mL) were added Na₂CO₃ (129 mg, 1.22 mmol, 2.00 eq) and Pd(dppf)Cl₂ (44.7 mg, 61.1 umol, 0.100 eq) at 15° C. The resulting mixture was stirred at 80° C. for 2 h under N₂. LCMS indicated incomplete conversion. The mixture was stirred at 80° C. for 12 h. LCMS showed that the reaction was complete. The mixture was concentrated in vacuo. The mixture was purified by MPLC (SiO₂, PE/EtOAc=1/0 to 0/1) to give tert-butyl (S,E)-4-(6-(3-ethoxy-3-oxoprop-1-en-1-yl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (200 mg, 332 umol, 54% yield) as a yellow oil.

Step 2: tert-butyl (S)-4-(6-(3-ethoxy-3-oxopropyl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

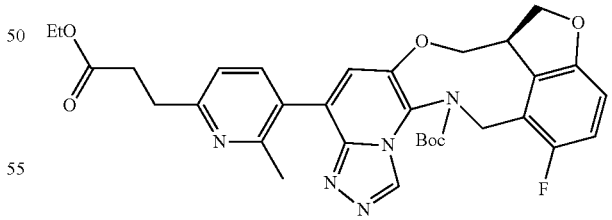

To a stirred solution of tert-butyl (S,E)-4-(6-(3-ethoxy-3-oxoprop-1-en-1-yl)-2-methylpyridin-3-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (180 mg, 299 umol, 1.00 eq) in MeOH (10.0 mL) was added 10% Pd/C (50.0 mg, 50% purity) at 15° C. under N₂. The resulting mixture was stirred at 15° C. under H₂ (15 psi) for 12 h. The mixture was filtered and the filtrate was concentrated in vacuo. tert-Butyl (S)-4-(6-(3-ethoxy-3-oxopropyl)-2-methylpyridin-3-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate (150 mg, crude) was obtained as a yellow oil.

Step 3: (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)propanoic Acid

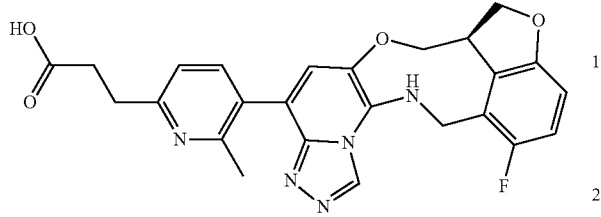

To a stirred solution of tert-butyl (S)-4-(6-(3-ethoxy-3-oxopropyl)-2-methylpyridin-3-yl)-12-fluoro-7a,13-dihydro-7H-[1,2,4]triazolo[4',3':1,6]pyrido[3,2-b]benzofuro[4,3-fg] [1,4]oxazonine-14 (8H)-carboxylate (150 mg, 248 umol, 1.00 eq) in water (1.00 mL) and MeOH (2.00 mL) was added NaOH (19.9 mg, 497 umol, 2.00 eq) at 15° C. The resulting mixture was stirred at 15° C. for 12 h. The mixture was concentrated in vacuo to remove MeOH. The aqueous phase was acidified with aqueous HCl solution (2.00 M) to pH=2-3 and the aqueous layer was concentrated in vacuo. (S)-3-(5-(14-(tert-butoxycarbonyl)-12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)propanoic acid (130 mg, crude, HCl salt) was obtained as a yellow solid.

Step 4: (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)-N-methylpropanamide

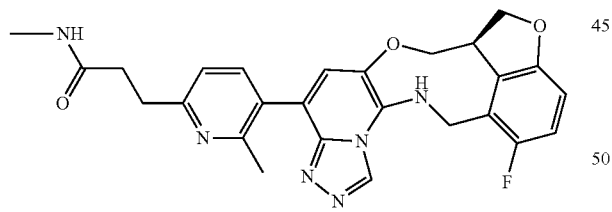

To a stirred solution of (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)propanoic acid (120 mg, 252 umol, 1.00 eq, HCl salt), methanamine hydrochloride (34.1 mg, 505 umol, 2.00 eq) and DIPEA (196 mg, 1.51 mmol, 264 uL, 6.00 eq) in DMF (3.00 mL) was added HATU (192 mg, 505 umol, 2.00 eq) at 15° C. The resulting mixture was stirred at 30° C. for 12 h. The mixture was purified by neutral prep-HPLC (column: Waters Xbridge Prep OBD C18 150*40 mm*10 um; mobile phase: [water (10 mM NH4HCO3)—ACN]; B %: 10%-40%, 8 min). (S)-3-(5-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-2-yl)-N-methylpropanamide (37.7 mg, 75.9 umol, 30% yield, 98.3% purity) was obtained as a yellow solid. 1H NMR CDCl3 400 MHz δ =ppm 8.88 (s, 1H), 7.63 (d, J=7.9 Hz, 1H), 7.11 (d, J=8.0 Hz, 1H), 7.06 (s, 1H), 6.90 (t, J=9.4 Hz, 1H), 6.76 (br s, 1H), 6.69 (dd, J=8.7, 3.9 Hz, 1H), 5.18-5.03 (m, 2H), 4.85 (br dd, J=12.7, 4.0 Hz, 1H), 4.71-4.58 (m, 2H), 4.27 (dd, J=9.7, 3.2 Hz, 1H), 4.02-3.91 (m, 1H), 3.88-3.80 (m, 1H), 3.14 (t, J=7.0 Hz, 2H), 2.81 (d, J=4.8 Hz, 3H), 2.68 (t, J=7.0 Hz, 2H), 2.47 (s, 3H). LCMS (ESI+): m/z 489.2 (M+H).

Example 154

Step 1: 3-bromo-2-methylpyridin-4-amine

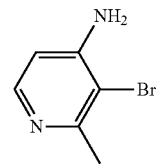

A solution of 2-methylpyridin-4-amine (3.00 g, 27.7 mmol, 1.00 eq) in 40.0% HBr (30.0 mL) aqueous solution was stirred at 70° C. and a solution of H2O2 (12.6 g, 55.5 mmol, 10.7 mL, 15.0% purity, 2.00 eq) was added dropwise over 1 hr period at such a rate that the temperature of the reaction mixture remained at 70° C. The mixture was stirred for another 1 h at 70° C. The mixture was poured on to crushed ice (40.0 g). The pH was adjusted to 7 with solid NaHCO3. The mixture was extracted with EtOAc (50.0 mL*3). The combined organic layers were dried over Na2SO4, filtered and concentrated under reduced pressure. The residue was purified by column chromatography (SiO2, Petroleum ether/Ethyl acetate=1/0 to 0/1). 3-Bromo-2-methylpyridin-4-amine (3.00 g, crude) was obtained as a yellow solid. 1H NMR CD3OD 400 MHz δ=ppm 7.76 (d, J=5.8 Hz, 1H), 6.52 (d, J=5.8 Hz, 1H), 2.48 (s, 3H).

Step 2: 3-bromo-2-methylpyridin-4-ol

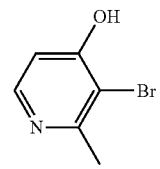

H2SO4 (2.10 g, 21.4 mmol, 1.14 mL, 4.00 eq) (98% purity) and 3-bromo-2-methylpyridin-4-amine (1.00 g, 5.35 mmol, 1.00 eq) were added successively to H2O (8.00 mL) at 0° C., and then NaNO2 (553 mg, 8.02 mmol, 1.50 eq) in H2O (8.00 mL) was added dropwise to maintain the temperature between 0-5° C. After stirring at 15° C. for 1 hr, the reaction mixture was heated at 95° C. for additional 2 h. The mixture was poured on to crushed ice (20.0 g) and the pH was adjusted to 8 with solid NaHCO3. The mixture was concentrated under reduced pressure to give a residue. The residue was purified by column chromatography (SiO2, Petroleum ether/Ethyl acetate=1/0 to 0/1 and then Ethyl acetate/Methanol=1/0 to 10/1). 3-Bromo-2-methylpyridin-4-ol (1.80 g, crude) was obtained as a yellow solid.

Step 3: tert-butyl (S)-12-fluoro-4-(4-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

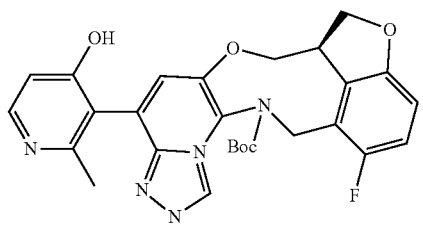

The reaction was set up in two parallel batches. To a solution of tert-butyl (S)-12-fluoro-4-(tributylstannyl)-7a,13-dihydro-7H-[1,2,4]triazolo[4',3':1,6]pyrido[3,2-b]benzofuro[4,3-fg][1,4]oxazonine-14 (8H)-carboxylate (50.0 mg, 71.3 umol, 1.00 eq) in DMF (3.00 mL) were added 4-ditert-butylphosphanyl-N,N-dimethyl-aniline dichloropalladium (5.05 mg, 7.13 umol, 5.05 uL, 0.100 eq) and 3-bromo-2-methylpyridin-4-ol (26.8 mg, 143 umol, 2.00 eq) at 20° C. The mixture was stirred at 110° C. for 12 h under $N_2$. The batches were combined and concentrated under reduced pressure to remove solvent. The residue was purified by prep-TLC ($SiO_2$, Ethyl acetate/MeOH=5/1). tert-butyl (S)-12-fluoro-4-(4-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, crude) was obtained as a yellow solid.

Step 4: (S)-3-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-4-ol

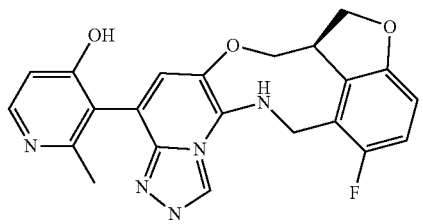

To a solution of tert-butyl (S)-12-fluoro-4-(4-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (80.0 mg, 154 umol, 1.00 eq) in DCM (2.00 mL) was added TFA (0.750 mL) at 20° C. The mixture was stirred at 20° C. for 2 h. The reaction mixture was concentrated under reduced pressure to remove solvent. The residue was purified by prep-HPLC (column: Welch Xtimate C18 150*25 mm*5 um; mobile phase: [water (0.04% HCl)-ACN]; B %: 20%-40%, 8 min). (S)-3-(12-fluoro-7a,8,13,14-tetrahydro-7H-[1,2,4]triazolo[4',3':1,6]pyrido[3,2-b]benzofuro[4,3-fg][1,4]oxazonin-4-yl)-2-methylpyridin-4-ol (28.0 mg, 61.4 umol, 40% yield, 100% purity, HCl salt) was obtained as an off-white solid. 1H NMR CD3OD 400 MHz δ=ppm 9.53 (s, 1H), 8.44 (br s, 1H), 8.01 (s, 1H), 7.23 (br dd, J=18.5, 6.6 Hz, 1H), 6.93 (t, J=9.4 Hz, 1H), 6.68 (dd, J=8.7, 3.9 Hz, 1H), 5.20 (br dd, J=14.6, 6.4 Hz, 1H), 4.98-4.92 (m, 1H), 4.73 (br s, 1H), 4.62 (br t, J=9.5 Hz, 1H), 4.30 (dd, J=9.7, 3.1 Hz, 1H), 4.07 (br s, 1H), 3.89 (br s, 1H), 2.63 (s, 1.5H), 2.53 (s, 1.5H). 1H NMR DMSO-d6 400 MHz δ=ppm 14.77 (br s, 1H), 9.77 (s, 1H), 8.49 (br s, 1H), 8.44 (d, J=7.2 Hz, 1H), 7.78 (br s, 1H), 7.31 (br s, 1H), 6.99 (t, J=9.6 Hz, 1H), 6.72 (dd, J=8.6, 3.7 Hz, 1H), 5.01-4.91 (m, 1H), 4.85 (br s, 1H), 4.59-4.42 (m, 2H), 4.30-4.16 (m, 1H), 4.08 (br s, 1H), 3.83 (br s, 1H), 2.38 (br s, 3H). LCMS (ESI+): m/z 420.2 (M+H).

Example 200

Step 1: 5-bromo-6-methylpyridin-3-amine

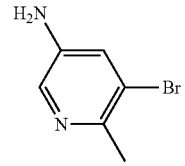

To a solution of 3-bromo-2-methyl-S-nitropyridine (5.00 g, 23.0 mmol, 1.00 eq) and $NH_4Cl$ (6.25 g, 117 mmol, 5.07 eq) in MeOH (100 mL) and $H_2O$ (100 mL) was added Fe (5.15 g, 92.2 mmol, 4.00 eq) at 25° C., and the mixture was stirred at 90° C. for 2 h. LCMS showed that 3-bromo-2-methyl-S-nitropyridine was consumed completely and the desired mass was detected. The mixture was filtered, and the filtrate was concentrated under reduced pressure to remove MeOH and then extracted with EtOAc (50.0 mL*3). The combined organic layers were dried over $Na_2SO_4$ and concentrated under reduced pressure to give 5-bromo-6-methylpyridin-3-amine (3.91 g, crude) as a yellow solid.

Step 2: 5-bromo-6-methylpyridin-3-ol

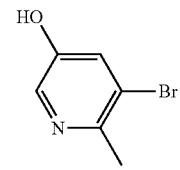

To a mixture of 5-bromo-6-methylpyridin-3-amine (3.40 g, 18.2 mmol, 1.00 eq), trifluoroborane hydrofluoride (21.6 g, 98.3 mmol, 15.3 mL, 40.0% purity, 5.41 eq) and $H_2O$ (15.0 mL) was added drop-wise a solution of $NaNO_2$ (1.38 g, 20.0 mmol, 1.10 eq) in $H_2O$ (15.0 mL) at 0° C. The mixture was stirred at 0° C. for 1 h. Water (15.0 mL) was added to the mixture which was then stirred at 100° C. for 12 h. The pH of the mixture was adjusted with $NaHCO_3$ to 8. The precipitate was filtered off and dried under reduced pressure. 5-Bromo-6-methylpyridin-3-ol (3.34 g, crude) was obtained as a brown solid.

Step 3: 6-methyl-S-(4,4,5,5-tetramethyl-1,3,2-dioxaborolan-2-yl)pyridin-3-ol

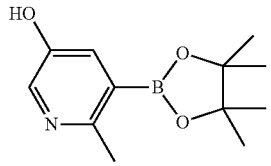 [SMILES: Cc1ncc(O)cc1B1OC(C)(C)C(C)(C)O1]

To a solution of 5-bromo-6-methylpyridin-3-ol (3.34 g, 17.8 mmol, 1.00 eq) in dioxane (100 mL) was added 4,4,5,5-tetramethyl-2-(4,4,5,5-tetramethyl-1,3,2-dioxaborolan-2-yl)-1,3,2-dioxaborolane (6.77 g, 26.7 mmol, 1.50 eq), KOAc (3.49 g, 35.5 mmol, 2.00 eq) and Pd(dppf)Cl2 (1.30 g, 1.78 mmol, 0.100 eq) at 25° C. The mixture was stirred at 100° C. for 12 h under nitrogen. The mixture was concentrated under reduced pressure to afford a crude product which was used in the next step directly. 6-Methyl-S-(4,4,5,5-tetramethyl-1,3,2-dioxaborolan-2-yl)pyridin-3-ol (4.20 g, crude) was obtained as brown solid.

Step 4: tert-butyl (S)-12-fluoro-4-(5-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

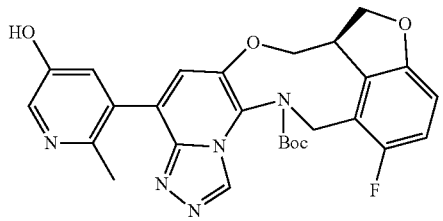 [SMILES: Cc1ncc(O)cc1-c1cc2c(n3cnnc13)N(C(=O)OC(C)(C)C)Cc1c(F)ccc3c1[C@H](CO3)CO2]

The reaction was set up in 5 parallel batches. To a solution of 6-methyl-S—(4,4,5,5-tetramethyl-1,3,2-dioxaborolan-2-yl)pyridin-3-ol (120 mg, 509 umol, 5.00 eq) in H$_2$O (0.300 mL) and dioxane (2.00 mL) were added KOAc (20.0 mg, 204 umol, 2.00 eq), tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (50.0 µmg, 102 umol, 1.00 eq) and 4-ditert-butylphosphanyl-N,N-dimethyl-aniline dichloropalladium (10.8 mg, 15.3 umol, 10.8 uL, 0.150 eq) at 25° C., and the mixture was stirred at 90° C. under nitrogen for 12 h. The batches were combined. The obtained mixture was concentrated under reduced pressure. The residue was purified by prep-TLC (SiO$_2$, Ethyl acetate:Methanol=10:1). tert-Butyl (S)-12-fluoro-4-(5-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (200 mg, 385 umol, 76% yield) was obtained as a brown solid.

Step 5: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-3-ol

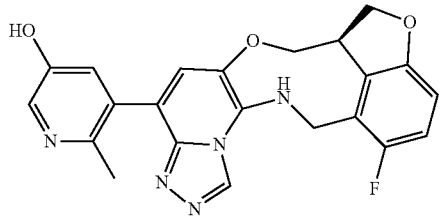 [SMILES: Cc1ncc(O)cc1-c1cc2c(n3cnnc13)NCc1c(F)ccc3c1[C@H](CO3)CO2]

A solution of tert-butyl (S)-12-fluoro-4-(5-hydroxy-2-methylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (200 mg, 385 umol, 1.00 eq) in HFIP (2.00 mL) was stirred at 100° C. for 2 h. The mixture was concentrated under reduced pressure. The residue was dissolved in MeCN (4.00 mL) and the mixture was purified by prep-HPLC (column: Phenomenex Luna C18 200*40 mm*10 um; mobile phase: [water (0.2% FA)—ACN]; B %: 1%-50%, 8 min). The product-containing fraction was concentrated under reduced pressure to remove most of MeCN at 30° C. and the aqueous phase was lyophilized. (S)—S-(12-Fluoro-7a,8,13,14-tetrahydro-7H-[1,2,4]triazolo[4',3':1,6]pyrido[3,2-b]benzofuro[4,3-fg][1,4]oxazonin-4-yl)-6-methylpyridin-3-ol (65.0 mg, 140 umol, 36.3% yield, 100% purity, formate salt) was obtained as a yellow solid. 1H NMR DMSO-d6 400 MHz δ=ppm 9.42 (s, 1H), 8.15 (s, 1H), 8.05 (d, J=2.8 Hz, 1H), 7.49 (br t, J=6.4 Hz, 1H), 7.30 (s, 1H), 7.19 (d, J=2.8 Hz, 1H), 7.00-6.94 (m, 1H), 6.70 (dd, J=8.6, 3.9 Hz, 1H), 4.97-4.87 (m, 1H), 4.84-4.73 (m, 1H), 4.54 (t, J=9.5 Hz, 1H), 4.47 (br d, J=7.3 Hz, 1H), 4.21 (dd, J=9.7, 3.4 Hz, 1H), 4.09-3.98 (m, 1H), 3.91-3.80 (m, 1H), 2.25 (s, 3H). LCMS (ESI+): m/z 420.2 (M+H).

Example 155: (S)-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)methanol

Step 1: 3-(tributylstannyl)picolinaldehyde

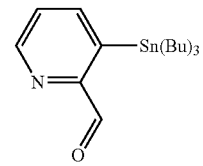

The reaction was set up in 2 parallel batches. To the solution of N,N',N'-trimethylethane-1,2-diamine (572 mg, 5.60 mmol, 728 uL, 1.20 eq) in THF (10.0 mL) was added n-BuLi (2.50 M, 1.87 mL, 1.00 eq) at −20° C. under nitrogen. The resulting solution was stirred at −20° C. for 15 min followed by addition of pyridine-2-carbaldehyde (0.500 g, 4.67 mmol, 1.00 eq) was added at −20° C. and the solution was stirred at −20° C. for 15 min. Another portion of n-BuLi (2.50 M, 2.80 mL, 1.50 eq) was added at −20° C., the resulting solution was stirred at −20° C. for 0.5 hr, and tributyl(chloro)stannane (4.56 g, 14.0 mmol, 3.77 mL, 3.00 eq) was added at −40° C. The reaction mixture was stirred at −40° C. for 1 h. The reaction batches were combined, the obtained mixture was poured into cold (0° C.) HCl (1.00 M; 10.0 mL), and the mixture was extracted with EtOAc (20.0 mL*3). The combined organic layers were washed with brine (10.0 mL), dried over Na$_2$SO$_4$, and concentrated under vacuum. The crude product was purified by MPLC (PE: EtOAc=1:0 to 10:1). 3-(Tributylstannyl)picolinaldehyde (2.20 g, 5.55 mmol, 59.5% yield) was obtained as a yellow oil which was used directly in the next step.

Step 2: tert-butyl (S)-12-fluoro-4-(2-formylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

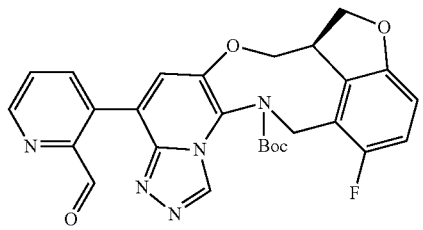 [SMILES: CC(C)(C)OC(=O)N1Cc2c(F)ccc3c2[C@H](CO3)COc2cc(-c3cccnc3C=O)c3nncn3c21]

The reaction was set up in 9 parallel batches. To the solution of tert-butyl (S)-12-fluoro-4-(2-(hydroxymethyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (100 mg, 204 umol, 1.00 eq) and crude 3-(tributylstannyl)picolinaldehyde (242 mg, 611 umol, 3.00 eq) in dioxane (5.00 mL) was added Pd(t-Bu3P)2 (15.6 mg, 30.5 umol, 0.150 eq) and the resulting solution was stirred at 120° C. for 12 h under nitrogen. LCMS showed tert-butyl (S)-12-fluoro-4-(2-(hydroxymethyl)pyridin-3-yl)-7a,13-dihydro-7H-[1,2,4]triazolo[4',3':1,6]pyrido[3,2-b]benzofuro [4,3-fg][1,4]oxazonine-14 (8H)-carboxylate was remained, and the desired ms was detected on LCMS. The parallel reactions were combined and the obtained mixture was concentrated under vacuum. The crude product was purified by prep-TLC (SiO$_2$, EtOAc:MeOH=10:1). Crude tert-Butyl (S)-12-fluoro-4-(2-formylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate was obtained as a brown oil which was used directly in the next step.

Step 3: tert-butyl (S)-12-fluoro-4-(2-(hydroxymethyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate

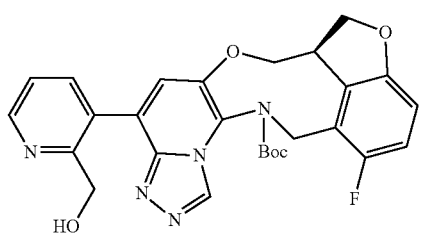 [SMILES: CC(C)(C)OC(=O)N1Cc2c(F)ccc3c2[C@H](CO3)COc2cc(-c3cccnc3CO)c3nncn3c21]

To the solution of tert-butyl (S)-12-fluoro-4-(2-formylpyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (110 mg, 213 umol, 1.00 eq) in MeOH (2.00 mL) was added NaBH$_4$ (9.65 mg, 255 umol, 1.20 eq) at 10° C., and the resulting solution was stirred at 10° C. for 0.5 h. The mixture solution was concentrated under vacuum to give tert-butyl (S)-12-fluoro-4-(2-(hydroxymethyl)pyridin-3-yl)-7a,13-dihydro-7H-[1,2,4]triazolo[4',3':1,6]pyrido[3,2-b] benzofuro[4,3-fg][1,4]oxazonine-14 (8H)-carboxylate (110 mg, crude) as a brown oil which was used directly in the next step.

Step 4: (S)-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)methanol

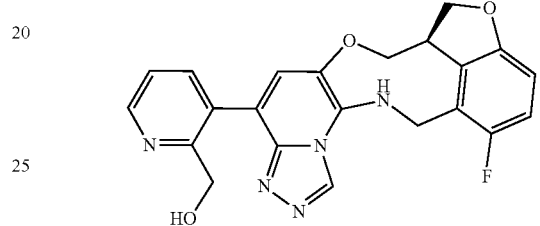

The solution of tert-butyl (S)-12-fluoro-4-(2-(hydroxymethyl)pyridin-3-yl)-7a,13-dihydro-7H-[1,2,4]triazolo[4',3':1,6]pyrido[3,2-b]benzofuro[4,3-fg][1,4]oxazonine-14 (8H)-carboxylate (140 mg, 269 umol, 1.00 eq) in HCl/MeOH (3.00 mL; 4.00 M) was stirred at 10° C. for 1 h. The mixture was concentrated under vacuum to give a crude product which was purified by prep-HPLC (column: Phenomenex luna C18 80*40 mm*3 um; mobile phase: [water (0.04% HCl)-ACN]; B %: 13%-27%). QC indicated insufficient purity and the material was purified by prep-HPLC again (column: Phenomenex luna C18 80*40 mm*3 um; mobile phase: [water (0.04% HCl)-ACN]; B %: 10%-25%) to obtain (S)-(3-(12-fluoro-7a,8,13,14-tetrahydro-7H-[1,2,4]triazolo[4',3':1,6]pyrido[3,2-b]benzofuro[4,3-fg][1,4]oxazonin-4-yl)pyridin-2-yl)methanol (21.4 mg, 45.9 umol, 17% yield, 97.7% purity, HCl salt) as a yellow solid. 1H NMR CD3OD 400 MHz δ=ppm 9.58 (s, 1H), 8.90 (d, J=6.0 Hz, 1H), 8.61 (d, J=7.6 Hz, 1H), 8.16-8.13 (m, 1H), 8.08 (s, 1H), 6.95-6.90 (m, 1H), 6.68 (dd, J=8.4, 3.6 Hz, 1H), 5.23-5.19 (m, 1H), 4.98-4.87 (m, 1H), 4.87 (s, 2H), 4.77-4.76 (m, 1H), 4.62 (t, J=9.6 Hz, 1H), 4.33-4.29 (m, 1H), 4.13-4.10 (m, 1H), 3.95-3.92 (m, 1H). LCMS (ESI+): m/z 420.1 (M+H).

Example 156: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-ol Step 1: 1-methyl-1H-pyrazol-4-ol

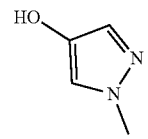

To a solution of 1-methyl-4-(4,4,5,5-tetramethyl-1,3,2-dioxaborolan-2-yl)-1H-pyrazole (5.00 g, 24.0 mmol, 1.00 eq) in THF (120 mL) were added NaOH (3.00 M, 16.0 mL, 2.00 eq) and H$_2$O$_2$ (5.45 g, 48.1 mmol, 4.62 mL, 30% purity, 2.00 eq) at 0° C., and the mixture was stirred at 0° C. for 3 h. To the mixture was added HCl (12.0 M, 3.72 mL) and the mixture was extracted with a mixture of DCM and MeOH (9:1, 40.0 mL*4). The combined organic layers were dried over Na$_2$SO$_4$ and concentrated under reduced pressure. 1-Methyl-1H-pyrazol-4-ol (5.10 g, crude) was obtained as a yellow oil.

Step 2: 4-(benzyloxy)-1-methyl-1H-pyrazole

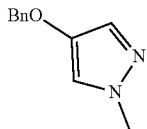

To a solution of 1-methyl-1H-pyrazol-4-ol (2.00 g, 20.4 mmol, 1.00 eq) in DMF (20.0 mL) was added NaH (815 mg, 20.4 mmol, 60% purity, 1.00 eq) at 0° C., the mixture was stirred at 25° C. for 30 mins. BnBr (5.23 g, 30.6 mmol, 3.63 mL, 1.50 eq) was added to the mixture at 25° C. and the mixture was stirred at 25° C. for 2 h. Water (20.0 mL) was added, the mixture was extracted with EtOAc (30.0 mL*3), the combined organic layers were dried over Na$_2$SO$_4$, filtered, and the filtrate was concentrated under vacuum. The residue was purified by column chromatography (SiO$_2$, Petroleum ether/Ethyl acetate=1/0 to 0/1). 4-(Benzyloxy)-1-methyl-1H-pyrazole (800 mg, 4.25 mmol, 21% yield) was obtained as a yellow oil.

Step 3: (4-(benzyloxy)-1-methyl-1H-pyrazol-S-yl) boronic Acid

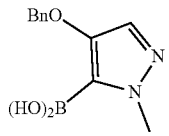

To the solution of 4-(benzyloxy)-1-methyl-1H-pyrazole (750 mg, 3.98 mmol, 1.00 eq) in THF (10.0 mL) was added n-BuLi (2.50 M, 1.59 mL, 1.00 eq) drop-wise at −78° C. under nitrogen. The reaction mixture was stirred at −78° C. for 1 hr. Tri-isopropyl borate (749 mg, 3.98 mmol, 916 uL, 1.00 eq) was added at −78° C., and the resulting solution was stirred at −78° C. under nitrogen for 1 hr, and then at 15° C. for 12 h. LCMS indicated incomplete conversion. To the mixture was added n-BuLi (2.50 M, 1.59 mL, 1.00 eq) drop-wise at −78° C. under nitrogen, and the resulting solution was stirred at −78° C. under N$_2$ for 1 hr followed by addition of tri-isopropyl borate (749 mg, 3.98 mmol, 91.0 uL, 1.00 eq) at −78° C. The reaction mixture was stirred at −78° C. under nitrogen for 1 hr, then at 15° C. for 12 h. LCMS showed showed that the conversion was complete. MeOH (5.00 mL) was added. The mixture was concentrated under reduced pressure to give (4-(benzyloxy)-1-methyl-1H-pyrazol-S-yl)boronic acid (1.24 g, crude) as a white solid, which was used to the next step directly.

Step 4: tert-butyl (S)-4-(3-(benzyloxy)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate

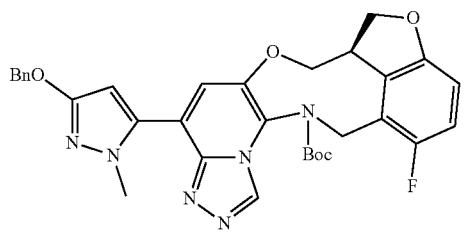 [SMILES: Cn1nc(OCc2ccccc2)cc1-c1cc2c(n3cnnc13)N(C(=O)OC(C)(C)C)Cc1c(F)ccc3c1[C@H](CO3)CO2]

Two parallel reactions were set up. To a solution of (4-(benzyloxy)-1-methyl-1H-pyrazol-S-yl)boronic acid (354 mg, 1.53 mmol, 5.00 eq) in dioxane (5.00 mL) and H$_2$O (1.00 mL) were added tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (150 mg, 305 umol, 1.00 eq), 4-ditert-butylphosphanyl-N,N-dimethyl-aniline dichloropalladium (32.4 mg, 45.8 umol, 32.4 uL, 0.150 eq) and KOAc (59.9 mg, 611 umol, 2.00 eq) at 25° C., and the reaction mixture was stirred at 90° C. under N$_2$ for 12 h. The batches were combined. The mixture was concentrated under reduced pressure and the residue was purified by prep-TLC (SiO$_2$, Ethyl acetate:Methanol=20:1). tert-Butyl (S)-4-(3-(benzyloxy)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (280 mg, crude) was obtained as a yellow solid.

Step 5: tert-butyl (S)-12-fluoro-4-(3-hydroxy-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate

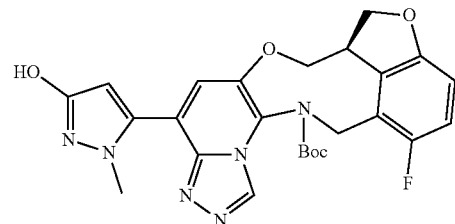 [SMILES: Cn1nc(O)cc1-c1cc2c(n3cnnc13)N(C(=O)OC(C)(C)C)Cc1c(F)ccc3c1[C@H](CO3)CO2]

To a solution of tert-butyl (S)-4-(3-(benzyloxy)-1-methyl-1H-pyrazol-S-yl)-12-fluoro-7a,13-dihydro-7H-[1,2,4]triazolo[4',3':1,6]pyrido[3,2-b]benzofuro[4,3-fg][1,4]oxazonine-14 (8H)-carboxylate (280 mg, 468 umol, 1.00 eq) in MeOH (3.00 mL) was added 10% Pd/C (300 mg, 50% purity) under N$_2$ atmosphere at 25° C. The suspension was degassed and purged with hydrogen 3 times. The mixture was stirred under hydrogen (15 Psi) at 40° C. for 1 h. The mixture filtered and the filtrate was concentrated under reduced pressure to give tert-butyl (S)-12-fluoro-4-(3-hydroxy-1-methyl-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate (220 mg, crude) as a yellow solid which was used to the next step directly.

Step 6: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-ol

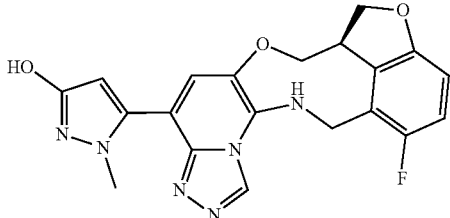

A solution of tert-butyl (S)-12-fluoro-4-(3-hydroxy-1-methyl-1H-pyrazol-S-yl)-7a,13-dihydro-7H-[1,2,4]triazolo[4',3':1,6]pyrido [3,2-b]benzofuro[4,3-fg][1,4]oxazonine-14 (8H)-carboxylate (220 mg, 432 umol, 1.00 eq) in DCM (1.00 mL) and TFA (1.00 mL) was stirred at 25° C. for 1.5 h. The mixture was concentrated under reduced pressure. The residue was dissolved in MeCN (4.00 mL) and the mixture was purified by prep-HPLC (column: Phenomenex Luna C18 200*40 mm*10 um; mobile phase: [water (0.2% FA)—ACN]; B %: 10%-50%, 8 min). The product-containing fraction was concentrated under reduced pressure to remove most of MeCN at 30° C. and the aqueous phase was lyophilized. (S)—S-(12-Fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-3-ol (50.0 mg, 110 umol, 25.4% yield, 100% purity, formate) was obtained as a white solid. 1H NMR CD3OD 400 MHz δ=ppm 9.31 (s, 1H), 7.45 (s, 1H), 7.18 (s, 1H), 6.87 (t, J=9.6 Hz, 1H), 6.63 (dd, J=8.6, 3.7 Hz, 1H), 5.07 (d, J=14.8 Hz, 1H), 4.84 (d, J=14.8 Hz, 1H), 4.62-4.53 (m, 2H), 4.27 (dd, J=9.7, 3.1 Hz, 1H), 4.05-3.95 (m, 1H), 3.92-3.84 (m, 1H), 3.71 (s, 3H). LCMS (ESI+): m/z 409.1 (M+H).

Example 157: (S)-1-(4-(12-fluoro-7a,8,13,14-tetrahydro-7H-[1,2,4]triazolo[4',3':1,6]pyrido[3,2-b]benzofuro[4,3-fg][1,4]oxazonin-4-yl)-3,6-dihydropyridin-1 (2H)-yl)ethan-1-one Step 1: 4-(4,4,5,5-tetramethyl-1,3,2-dioxaborolan-2-yl)-1,2,3,6-tetrahydropyridine

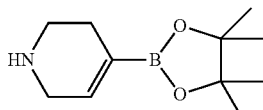

To a solution of tert-butyl 4-(4,4,5,5-tetramethyl-1,3,2-dioxaborolan-2-yl)-3,6-dihydropyridine-1 (2H)-carboxylate (1.00 g, 3.23 mmol, 1.00 eq) in EtOAc (5.00 mL) was added HCl/EtOAc (4.00 M, 10.0 mL, 12.4 eq) at 0° C., the mixture was stirred at 25° C. for 2 h. The reaction was concentrated to afford 4-(4,4,5,5-tetramethyl-1,3,2-dioxaborolan-2-yl)-1,2,3,6-tetrahydropyridine (820 mg, crude, HCl salt) as a white solid.

Step 2: 1-(4-(4,4,5,5-tetramethyl-1,3,2-dioxaborolan-2-yl)-3,6-dihydropyridin-1 (2H)-yl)ethan-1-one

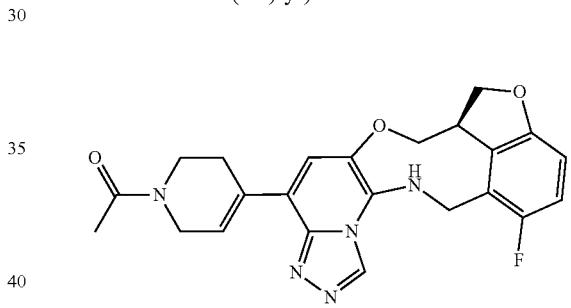

To a solution of 4-(4,4,5,5-tetramethyl-1,3,2-dioxaborolan-2-yl)-1,2,3,6-tetrahydropyridine (820 mg, 3.34 mmol, 1.00 eq, HCl) in DCM (12.0 mL) was added DIPEA (1.73 g, 13.4 mmol, 2.33 mL, 4.00 eq) and acetyl chloride (393 mg, 5.01 mmol, 357 uL, 1.50 eq) at 0° C., and the mixture was stirred at 20° C. for 12 h. The reaction was concentrated. The residue was diluted with H₂O (100 mL) and extracted with EtOAc (50.0 mL*3). The combined organic layers were washed with brine (10.0 mL), dried over Na₂SO₄, filtered, and concentrated under reduced pressure. 1-(4-(4,4,5,5-tetramethyl-1,3,2-dioxaborolan-2-yl)-3,6-dihydropyridin-1 (2H)-yl)ethan-1-one (850 mg, crude) was obtained as a brown solid.

Step 3: (S)-1-(4-(12-fluoro-7a,8,13,14-tetrahydro-7H-[1,2,4]triazolo[4',3':1,6]pyrido[3,2-b]benzofuro [4,3-fg][1,4]oxazonin-4-yl)-3,6-dihydropyridin-1 (2H)-yl)ethan-1-one To a solution of (S)-4-bromo-12-fluoro-7a,8,13,14-tetrahydro-7H-[1,2,4]triazolo[4',3':1,6]pyrido[3,2-b]benzofuro [4,3-fg][1,4]oxazonine (100 mg, 256 umol, 1.00 eq) in dioxane (2.00 mL) and H₂O (0.200 mL) were added 1-(4-(4,4,5,5-tetramethyl-1,3,2-dioxaborolan-2-yl)-3,6-dihydropyridin-1 (2H)-yl)ethan-1-one (128 mg, 511 umol, 2.00 eq), Na₂CO₃ (54.2 mg, 511 umol, 2.00 eq) and Pd(dppf)Cl₂ (18.7 mg, 25.6 umol, 0.100 eq) at 20° C. under N₂, and the mixture was stirred at 80° C. for 2 h under N₂ atmosphere. The reaction was filtered and the filtrate concentrated. The residue was dissolved in MeOH (3.00 mL) and silica-thiol (300 mg, modified silicon gel for eliminating Pd, irregular silica gel, 100-200 mesh, Chlorides (Cl), %≤0.004, particle size distribution 45-75 um) was added at 20° C. and stirred at 20° C. for 12 h. The suspension was filtered and the filtrate was concentrated and purified by acidic prep-HPLC (column: Phenomenex Luna C18 200*40 mm*10 um; mobile phase: [water (0.2% FA)—ACN]; B %: 20%-60%, 8 min). The product-containing fraction was concentrated under reduced pressure to remove most of MeCN at 30° C. and the aqueous phase was lyophilized. (S)-1-(4-(12-Fluoro-7a,8,13,14-tetrahydro-7H-[1,2,4]triazolo[4',3':1,6]pyrido[3,2-b]benzofuro [4,3-fg][1,4]oxazonin-4-yl)-3,6-dihydropyridin-1 (2H)-yl)ethan-1-one (66.4 mg, 138 umol, 54% yield, 100% purity, formate) was obtained as a yellow solid. 1H NMR DMSO-d6 400 MHz δ=ppm 9.29 (s, 1H), 7.29 (br s, 1H), 7.21-7.10 (m, 2H), 6.91-6.84 (m, 1H), 6.62 (dd, J=8.8, 3.9 Hz, 1H), 4.91-4.81 (m, 1H), 4.79-4.70 (m, 1H), 4.50 (t, J=9.2 Hz, 1H), 4.43 (dd, J=10.5, 4.4 Hz, 1H), 4.23-4.09 (m, 3H), 3.97 (br d, J=8.8 Hz, 1H), 3.89-3.80 (m, 1H), 3.63 (br s, 2H), 2.63 (br s, 2H), 2.02 (s, 3H). LCMS (ESI+): m/z 436.2 (M+H).

Example 158: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-4-ol Step 1: 1-methyl-3-((triisopropylsilyl)oxy)-1H-pyrazole

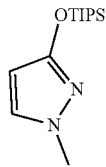

To 1-methyl-1H-pyrazol-3-ol (500 mg, 5.10 mmol, 1.00 eq) and imidazole (694 mg, 10.2 mmol, 2.00 eq) in DCM (10.0 mL) was added triisopropylsilyl trifluoromethanesulfonate (2.34 g, 7.65 mmol, 2.05 mL, 1.50 eq) at 0° C. The mixture was stirred at 10° C. for 4 h under N₂. The mixture was concentrated under reduce pressure to remove most of DCM and H₂O (3.00 mL) was added. The mixture was extracted with ethyl acetate (10.0 mL*3). The combined organic layers were dried with anhydrous Na₂SO₄, filtered, and concentrated under reduce pressure. The residue was purified by column chromatography (SiO₂, Petroleum ether/Ethyl acetate=1/0 to 2/1). 1-Methyl-3-((triisopropylsilyl)oxy)-1H-pyrazole (1.10 g, 4.32 mmol, 85% yield) was obtained as a colorless oil.

Step 2: 1-methyl-S-(tributylstannyl)-1H-pyrazol-3-ol

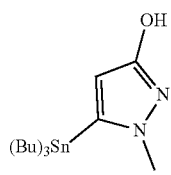

To 1-methyl-3-((triisopropylsilyl)oxy)-1H-pyrazole (900 mg, 3.54 mmol, 1.00 eq) in THF (3.00 mL) was added t-BuLi (1.30 M, 8.16 mL, 3.00 eq) at −78° C. under N₂. The mixture was stirred at −78° C. for 0.5 hr under N₂. Then tributyl(chloro)stannane (3.45 g, 10.6 mmol, 2.85 mL, 3.00 eq) was added into the mixture which was then stirred at −78° C. for 1 hr under N₂. MeOH (5.00 mL) was added to the mixture and it was concentrated under reduced pressure. The residue was purified by column chromatography (SiO₂, Petroleum ether/Ethyl acetate=1/0 to 0/1). 1-Methyl-S-(tributylstannyl)-1H-pyrazol-3-ol (600 mg, 1.55 mmol, 43.8% yield) was obtained as a colorless oil.

Step 3: 1-methyl-S-(tributylstannyl)-3-((triisopropylsilyl)oxy)-1H-pyrazole

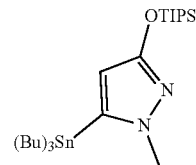

To 1-methyl-S-(tributylstannyl)-1H-pyrazol-3-ol (600 mg, 1.55 mmol, 1.00 eq) and imidazole (211 mg, 3.10 mmol, 2.00 eq) in DCM (10.0 mL) was added triisopropylsilyl trifluoromethanesulfonate (712 mg, 2.32 mmol, 625 uL, 1.50 eq) at 0° C. The mixture was stirred at 10° C. for 12 h under N₂. LC-MS showed minimal conversion. Additional triisopropylsilyl trifluoromethanesulfonate (712 mg, 2.32 mmol, 625 uL, 1.50 eq) was added to the mixture under N₂, and it was stirred at 10° C. for 12 h. TLC (SiO₂, petroleum ether:ethyl acetate=1:1) indicated complete conversion. The mixture was concentrated under reduce pressure to remove most of DCM, H₂O (10.0 mL) was added into the mixture which was then extracted with ethyl acetate (10.0 mL*3). The combined organic layers were dried with anhydrous Na₂SO₄, filtered, concentrated under reduce pressure. 1-Methyl-S-(tributylstannyl)-3-((triisopropylsilyl)oxy)-1H-pyrazole (300 mg, crude) was obtained as colorless oil.

Step 4: tert-butyl (S)-12-fluoro-4-(1-methyl-4-((triisopropylsilyl)oxy)-1H-pyrazol-S-yl)-7a,13-dihydro-7H-[1,2,4]triazolo[4',3':1,6]pyrido[3,2-b]benzofuro[4,3-fg][1,4]oxazonine-14 (8H)-carboxylate

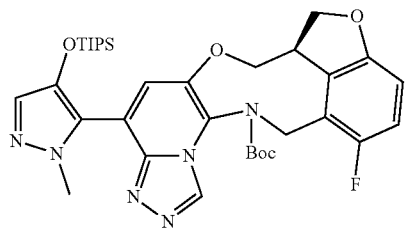

The reaction was set up in two parallel batches. To tert-butyl (S)-4-bromo-12-fluoro-7a,13-dihydro-7H-[1,2,4]triazolo[4',3':1,6]pyrido[3,2-b]benzofuro[4,3-fg][1,4]oxazonine-14 (8H)-carboxylate (40.0 mg, 81.4 umol, 1.00 eq) and 1-methyl-S-(tributylstannyl)-3-((triisopropylsilyl)oxy)-1H-pyrazole (66.4 mg, 122 umol, 1.50 eq) in dioxane (1.00 mL) were added Pd(PPh₃)4 (9.41 mg, 8.14 umol, 0.100 eq), LiCl (6.90 mg, 163 umol, 3.33 uL, 2.00 eq) and CuI (6.20 mg, 32.6 umol, 0.400 eq) at 10° C. The mixture was stirred at 100° C. for 12 h under N₂. The batches were combined. The obtained mixture was filtered and the filtrate was concentrated under reduced pressure. The residue was purified by prep-TLC (SiO₂, Petroleum ether/Ethyl acetate=1/3). tert-Butyl (S)-12-fluoro-4-(1-methyl-4-((triisopropylsilyl)oxy)-1H-pyrazol-S-yl)-7a,13-dihydro-7H-[1,2,4]triazolo[4',3':1, 6]pyrido[3,2-b]benzofuro[4,3-fg][1,4]oxazonine-14 (8H)-carboxylate (90.0 mg, 135 umol, 83% yield) was obtained as a yellow oil.

Step 5: (S)—S-(12-fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-4-ol

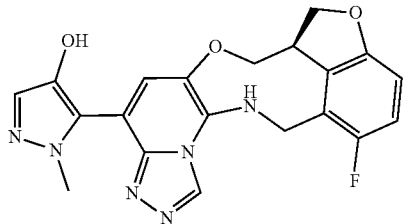 [SMILES: Cn1ncc(O)c1-c1cc2c(n3cnnc13)NCc1c(F)ccc3c1[C@H](CO3)CO2]

To tert-butyl (S)-12-fluoro-4-(1-methyl-4-((triisopropylsilyl)oxy)-1H-pyrazol-S-yl)-7a,13-dihydro-7H-[1,2,4]triazolo[4',3':1,6]pyrido[3,2-b]benzofuro[4,3-fg] [1,4]oxazonine-14 (8H)-carboxylate (155 mg, 233 umol, 1.00 eq) in DCM (3.00 mL) was added TFA (1.54 g, 13.5 mmol, 1.00 mL, 57.9 eq) at 10° C. The mixture was stirred at 10° C. for 2 h. The mixture was concentrated under reduce pressure to give a residue. The crude product was purified by prep-HPLC (HCl conditions). (S)—S-(12-Fluoro-7a,8,13,14-tetrahydro-7H-[1,2,4]triazolo[4',3':1,6]pyrido[3,2-b]benzofuro[4,3-fg][1,4]oxazonin-4-yl)-1-methyl-1H-pyrazol-4-ol (40.3 mg, 90.2 umol, 39% yield, 99.6% purity, HCl salt) was obtained as a yellow solid. 1H NMR CD3OD 400 MHz δ=ppm 9.51 (s, 1H), 8.02 (s, 1H), 6.92 (dd, J=10.1, 8.8 Hz, 1H), 6.68 (dd, J=8.7, 3.9 Hz, 1H), 5.90 (s, 1H), 5.20 (d, J=14.8 Hz, 1H), 4.95 (br d, J=14.8 Hz, 1H), 4.76 (br dd, J=9.6, 3.9 Hz, 1H), 4.62 (t, J=9.4 Hz, 1H), 4.31 (dd, J=9.8, 3.4 Hz, 1H), 4.11-4.00 (m, 1H), 3.97-3.85 (m, 1H), 3.61 (s, 3H) LCMS (ESI+): m/z 409.1 (M+H) Example 159: Histone methyltransferase assay Effect of compounds of the present disclosure on EZH2/PRC2 complex methyltransferase functional activity was measured using the radioisotope-based HotSpot assay described by Horiuchi, K. Y., et al. Assay Drug Dev Technol. 11(4):227-36 (2013). Briefly, compounds were prepared in a 10-point 3-fold serial dilution in DMSO from a 10 mM stock in ECHO qualified plate using Assist Plus (Integra Biosciences) liquid handler. Four microliters of EZH2/PRC2 complex (12.5 nM) and core histone substrate (0.0625 mg/mL) mix in assay buffer (50 mM Tris-HCl (pH 8.0), 0.01% Brij35, 1 mM EDTA, 1 mM DTT, 1% DMSO) were transferred into a 384-well assay plate by hand. Nanoliter quantities of each compound's concentration series were transferred into the enzyme/substrate mix using (Echo 550, LabCyte Inc. Sunnyvale, Calif.) acoustic dispenser and pre-incubated for 20 min at room temperature. The methylation reaction was initiated by the addition of 1 µl of 5 µM S-Adenosyl-L-[methyl-$^3$H]methionine (3H-SAM) and incubated at 30° C. for 1 h. The final concentration of the EZH2/PRC2 complex, core histone substrate and $^3$H-SAM were 10 nM, 0.05 mg/ml, and 1 µM respectively. The % activity of test samples were calculated with reference to positive (no compound) and negative (no EZH2/PRC2) controls on the plate using Excel (Microsoft). The resulting values were exported to Prism (GraphPad software) to generate concentration response curves and $IC_{50}$ values using the four-parameter logistic equation.

Example 160: EED Binding SPR Assay

Biotinylated EED Protein Production
Biotinylated AVI-tagged EED was produced using standard molecular biology techniques. A pGEX plasmid with a GST-preScission-cleavage-site-AVI-EED(76-441) sequence was placed into E. coli BL21(DE3) cells and co-expressed with pGro7. The E. coli were grown in shaker flasks in LB with ampicillin at 37° C. at 110 rpm to an $OD_{600}$=0.7. At this time the temperature was lowered to 15° C. and IPTG was added to 0.3 mM. The cells were allowed to express overnight. Cells were then harvested.

For purification, the E. coli cell pellet was lysed into a buffer of 50 mM Tris pH 8.0, 500 mM NaCl, 5% glycerol and 5 mM DTT. The lysate was loaded onto a GSTrap FF column from GE Healthcare. After washing, the bound protein was eluted with 50 mM Tris pH 8.0, 500 mM NaCl, 5% glycerol, 5 mM DTT and 15 mM GSH. The collected fractions were combined and incubated with PreScission enzyme overnight at 4° C. The cleaved protein was then passed through a GSTrap FF column in a buffer of 50 mM Tris pH 8.0, 500 mM NaCl, 5% glycerol and 5 mM DTT. The cleaved protein was confirmed through mass spectrometry. The AVI-EED(76-441) was then buffer exchanged into 50 mM Bicine pH 8.3, 10 mM ATP, 10 mM magnesium acetate and 50 µM D-Biotin. 3 mg of BirA enzyme was added to the system and incubated at 4° C. for 2 hours to biotinylate the AVI-EED(76-441). The biotinylated-AVI-EED(76-441) was then buffer exchanged into 20 mM Tris pH 8.0 and 400 mM NaCl and passed through a size exclusion column of Superdex 200 16/60 Increase. The purified monomeric biotinylated-AVI-EED(76-441) was confirmed through SDS-PAGE, LC-MS and analytical size exclusion chromatography.

Surface Plasmon Resonance Assay
All surface plasmon resonance (SPR) assays were performed using a GE Biacore S200 utilizing GE Biotin CAPture chips. Capturing of CAP reagents was performed with a flow rate of 2 µL/min for 90 seconds. For protein capturing, a solution of 50 µg/mL of biotinylated AVI-tagged EED (76-441) in 10 mM HEPES pH 7.4, 150 mM NaCl, 0.05% Tween 20 and 2% DMSO (Running Buffer) was flowed over the chip with a flow rate of 5 µL/min for a contact time of 30 seconds. Final readings were 2200-2400 RU. For compounds, 7 concentrations were made with 3-dilutions using the Running Buffer for a total of 300 µL of each concentration in a 96-well microplate. During the binding experiments, a flow rate of 50 µL was used for an association time of 90 seconds followed by a disassociation time of 180 seconds. The compartment temperature was set at 10° C. with the chip at 25° C. During regeneration the flow rate was set to 30 µL/min for 30 seconds. All fittings were done using a 1:1 binding model.

Example 161: H3K27Me3 and HbF
Immunocytochemistry Assay and Hemoglobin
ELISA Assay Generation of a P-Gp Expressing HEK293T Cell Line
A plasmid encoding the human ABCB1 gene under the control of a CMV promoter was purchased from Origene (Cat# RC216080). The HEK293T cells were purchased from ATCC (Cat# CRL-3216) and were cultured for expansion in the recommended conditions. The HEK293T cells were transfected with 2 ug of the pCMV-ABCB1 plasmid using Lipofectamine 3000 following recommendations from the manufacturer (ThermoFisher Scientific, Cat#L3000008).

After 24h, cells were dissociated, and 5000 cells were seeded on a 10 cm tissue culture dish. On the next day, fresh media containing 5 nM Vinblastine (Sigma, Cat#V1377) was added, and media containing compound was replenished every 72h. After surviving cells reached confluency, cells were passaged, and lines were maintained in the presence of 2.5 nM Vinblastine until further characterization.

Tissue Culture

P-gp expressing HEK293T, HUDEP2, and Human Mobilized Peripheral Blood Primary CD34+ cells were cultured for use in an H3K27me3 immunocytochemistry assay. HUDEP2 and Human Mobilized Peripheral Blood Primary CD34+ cells were cultured for use in an HbF immunocytochemistry assay. P-gp expressing HEK293T cells were maintained and passaged every 3-4 days by plating 300,000 viable cells in a T-25 culture flask containing 6 mLs of 293 Passaging Media comprised of DMEM (ThermoFisher #10566016), 10% fetal bovine serum (ThermoFisher #A3160502), 1% penicillin-streptomycin (ThermoFisher #15140122), and 2.5 nM Vinblastine (Sigma #V1377). To evaluate the inhibitory effect of the compounds of the present disclosure and their brain penetrant properties via P-gp mediated efflux, the H3K27me3 immunocytochemistry assay was conducted in the presence or absence of 250 nM of the P-gp inhibitor, elacridar. Poor brain penetrant compounds were expected to show higher potencies in the presence of Elacridar. However, brain penetrant compounds would show similar potencies irrespective of whether Elacridar is present or not. In these experiments plates without elacridar were seeded with P-gp expressing HEK293T cells at 1000 viable cells per well in a poly-d-lysine coated 384-well plate (Corning Cat#356697) in 45 µL of 293 Assay Media comprised of DMEM (ThermoFisher #10566016), 10% fetal bovine serum (ThermoFisher #A3160502), 1% penicillin-streptomycin (ThermoFisher #15140122). A replicate set of plates were seeded under the same conditions with 45 µL of 293 Assay Media supplemented with 250 nM of Elacridar to inhibit P-gp activity. Compounds were serially diluted at 10× concentration in 293 Media, and 5 µL transferred to their respective wells on both sets of plates for a total volume of 50 µL per well. The compound treated HEK293T cells were allowed to incubate for 4 days at 37° C., 85% relative humidity, and 5% $CO_2$ before proceeding to ICC Fix and Stain protocol.

HUDEP2 cells were maintained and passaged every 2-3 days by seeding 300,000 viable cells/mL in a culture flask containing HUDEP2 Growth Media comprised of StemSpan SFEM (Stemcell Technologies #09650), 50 ng/mL human stem cell factor (Stemcell Technologies #78062.2), 3 IU/mL erythropoietin (ThermoFisher #PHC2054), 1 µM dexamethasone (Sigma #D2915), and 1 pg/mL doxycycline (Sigma #D3072). HUDEP2 cells were differentiated towards erythroid lineage by seeding at 25,000 viable cells/well in 96-well V-Bottom plates (Corning #3894) containing 135 µL HUDEP2 Differentiation Media comprised of Iscove's Modified Dulbecco's Medium (Stemcell Technologies #36150), 1% L-glutamine (ThermoFisher #25030081), 2% penicillin-streptomycin (ThermoFisher #15140122), 330 µg/mL holo-human transferrin (Sigma #T0665), 2 IU/mL heparin (Stemcell Technologies #07980), 10 µg/mL recombinant human insulin (Sigma #91077C), 3 IU/mL erythropoietin (ThermoFisher #PHC2054), 100 ng/mL human stem cell factor (Stemcell Technologies #78062.2), and 4% fetal bovine serum (ThermoFisher #$A_{3160502}$). Chemical probes for treatment were resuspended in 100 µL of Iscove's Modified Dulbecco's Medium (Stemcell Technologies #36150) to a 10× concentration, and 15 µL of 10× concentrated chemical probes were added to each well for a total well volume of 150 µL. HUDEP2 cells were left to incubate at 37° C., 85% relative humidity, and 5% $CO_2$ for 3 days. On Day 3, assay plates containing HUDEP2 cells were centrifuged at 500×g for 5 minutes. After centrifugation cells were pelleted to the bottom of the well, and 100 µL of media aspirated from the well without disturbing the cells. Then 90 µL of fresh HUDEP2 Differentiation Media and 10 µL of 10× concentrated chemical probes were added back each well. For the H3K27me3 assay, cells were harvested on Day 4 of treatment. The HUDEP2 cells were centrifuged at 500×g for 5 minutes and all media was aspirated from the well. Then 150 µL of phosphate buffered saline (ThermoFisher #10010023) was added to each well to resuspend the cells. Finally, 50 µL of the HUDEP2 cell suspension from each well was transferred to a poly-d-lysine coated 384-well plate (Corning Cat#356697) and centrifuged at 1000×g for 5 minutes before proceeding to ICC Fix and Stain Protocol. Assay plates for the HbF assay were returned to the incubator until Day 5, where the media was exchanged and chemical probes added exactly as on Day 3. On Day 7 of the HbF assay, the HUDEP2 cells were harvested in the same manner as described for the H3K27me3 assay before proceeding to ICC Fix and Stain Protocol.

Human Mobilized Peripheral Blood Primary CD34+ cells were expanded from thaw by seeding 100,000 viable cells/mL in a culture flask containing CD34+ Expansion Media comprised of StemSpan SFEMII (Stemcell Technologies #09655), 1% erythroid expansion supplement (Stemcell Technologies #02692), and 1 µM dexamethasone (Sigma #D2915). The cells were supplemented by adding an additional 1× culture volume of CD34+ Expansion Media on Day 3 after thaw. After 7 days of expansion, Primary CD34+ cells were differentiated towards erythroid lineage by seeding at 15,000 viable cells/well in 96-well V-Bottom plates (Corning #3894) containing 135 µL CD34+ Differentiation Media comprised of StemSpan SFEMII (Stemcell Technologies #09655), 3% normal human serum (Sigma #H4522), 3 IU/mL erythropoietin (ThermFisher #PHC2054). Chemical probes for treatment were resuspended in 100 µL of Iscove's Modified Dulbecco's Medium (Stemcell Technologies #36150) to a 10× concentration, and 15 µL of 10× concentrated chemical probe was added to each well for a total well volume of 150 µL. Primary CD34+ cells were left to incubate at 37° C., 85% relative humidity, and 5% $CO_2$ for 3 days. On Day 3, assay plates containing Primary CD34+ cells were centrifuged at 500×g for 5 minutes. After centrifugation cells were pelleted to the bottom of the well, and 100 µL of media aspirated from the well without disturbing the cells. Then 90 µL of fresh CD34+ Differentiation Media and 10 µL of 10× concentrated chemical probes were added back each well. For the H3K27me3 assay, cells were harvested on Day 4 of treatment. The Primary CD34+ cells were centrifuged at 500×g for 5 minutes and all media was aspirated from the well. Then 150 µL of phosphate buffered saline (ThermoFisher #10010023) was added to each well to resuspend the cells. Finally, 50 µL of the Primary CD34+ cell suspension from each well was transferred to a poly-d-lysine coated 384-well plate (Corning Cat#356697) and centrifuged at 1000×g for 5 minutes before proceeding to ICC Fix and Stain Protocol. Assay plates for the HbF assay were returned to the incubator until Day 5, where the media was exchanged and chemical probes added exactly as on Day 3. On Day 7 of the HbF assay, the Primary CD34+ cells were harversted in the same manner as described for the H3K27me3 assay before proceeding to ICC Fix and Stain Protocol.

The Fix and Stain Protocol was the same for HEK293T, HUDEP2, and Primary CD34+ cell assays except the specific primary and secondary antibodies used for detection. Following 4 days of compound treatment, the respective plates were washed once with L of PBS (ThermoFisher #10010023) and fixed with 25 µL of 4% paraformaldehyde (ThermoFisher #28908) for 10 minutes at room temperature. The plates were then washed three times with 25 µL of PBS. Subsequent to that, the cells were permeabilized and blocked for 1 hour at room temperature in 25 µL of Perm/Block buffer comprised of 1×PBS, 1% bovine serum albumin (ThermoFisher #$A_{3294}$), 10% fetal bovine serum (ThermoFisher #$A_{3160502}$), 0.3M glycine (Sigma #G7126), and 0.1% tween-20 (Sigma #P7949). This was followed by additional washing (three times) of the plates with 25 µL of 0.1% tween in PBS.

For the H3K27me3 assay, the cells were incubated overnight at 4° C. with 25 µL of H3K27me3 Primary Antibody (Cell Signaling #9733) diluted 1:200 in 0.1% tween-20 in PBS. On the next day, the cells were washed again three times with 25 µL of 0.1% tween-20 in PBS and incubated at room temperature in the dark for 1 hour with 25 µL Secondary Antibody Solution comprised of Donkey Anti-Rabbit 488 (ThermoFisher #$A_{21206}$) and Hoechst (ThermoFisher #H3570) diluted 1:2000 in 0.1% tween in PBS. Finally, the cells were washed three times with 25 µL of PBS and sealed with a foil (BioRad #MSB1001) for imaging on the ThermoFisher CellInsight CX7.

Plates for the HbF assay were treated similarly as described above except that HbF Primary Antibody (ThermoFisher #MHFHO1-4) diluted 1:40 in 0.1% tween-20 in PBS and Hoescht (ThermoFisher #H3570) diluted 1:2000 in 0.1% tween-20 in PBS were used for detection.

H3K27me3 and HbF immunocytochemistry assay

The plates were then scanned on the CX7 at 10× magnification, and 9 images were acquired per well. The software algorithm then identified nuclei and calculated a total nuclei count using the Hoechst staining on channel 1. After nuclei were identified, the algorithm calculated the average nuclear intensity of the H3K27me3 or HbF staining on channel 2. Data for total nuclei count was reported as a percentage of negative control (% DMSO). Data for average nuclear intensity of H3K27me3 or HbF was reported as a controls normalized percent inhibition (($\sigma_{Pos}$-Sample$_i$/$\sigma_{Pos}$-$\sigma_{Neg}$)*100). A threshold for HbF positivity was set and HbF data was also reported at % HbF+ out of total number of cells.

Hemoglobin ELISA Assay

HUDEP2 cells were cultured as described above. Briefly, 100,000 cells were grown in differentiation media and treated with compound for 7 days with media and compound changed on Day 3 and Day 5. Cells were pelleted by centrifugation (900×g for 5 minutes), resuspended in 100 uL of lysis buffer (50 mM Tris buffered saline, pH8.0; 0.05% Tween 20 (Sigma Chemical #T9039) to generate cell lysates and frozen at −80 C. The cell lysates were analyzed for protein content per well using bicinchoninic acid (BCA) assay (Pierce BCA kit #23225), total hemoglobin content per well using enzyme-linked immunosorbent (ELISA) assays (Bethyl Laboratories #E80-134) and fetal hemoglobin (HbF) content per well using ELISA assays (Bethyl Laboratories #E80-136).

BCA assays were run to calculate the total protein content and determine the amount of lysate to load onto the total hemoglobin and HbF assays. In general, 100 uL of BCA buffer was added to a well of a clear 96-well plate. 2 uL of cell lysate was loaded to the well. Sample was incubated at 37 degrees Celsius for 30 minutes and analyzed on an Envision plate reader (PerkinElmer). Protein content was calculated using bovine serum albumin as a standard.

Total hemoglobin and HbF ELISA assays were performed following the protocol recommended by the manufacturer. In general, each sample was analyzed for total hemoglobin and HbF content. 1 µl of affinity purified antibody (Total hemoglobin:$A_{80}$-134A, HbF:$A_{80}$-136A) to 100 µl Coating Buffer (0.05M carbonate-bicarbonate in water) for each well to be coated (example: for 100 wells dilute 100 µl to 10 ml) in the ELISA plates. Plates were incubated at room temperature for 60 minutes. The well was then washed 5 times with 100 uL of wash buffer (50 mM Tris buffered saline, pH8.0; 0.05% Tween 20). 200 uL of blocking buffer (50 mM Tris buffered saline, pH8.0; 1% bovine serum albumin) was added to each well and incubated for 1 hour at room temperature. The well was then washed 5 times with 100 uL of wash buffer. Cell lysates were diluted in 50 mM Tris buffered saline, pH8.0; 0.05% Tween 20; 1% bovine serum albumin and the appropriate amount of material was added to be within the linear range of the total hemoglobin or HbF standard curve (Total hemoglobin calibrator:Bethyl RC80-135-5; Fetal hemoglobin calibrator:Bethyl RC80-135-5). Samples were incubated at room temperature for 1 hour with shaking (300 rpm). The well was then washed 5 times with 100 uL of wash buffer. Detection antibody (Total hemoglobin:$A_{80}$-134P and HbF:$A_{80}$-136P) was diluted 1:100,000 in 50 mM Tris buffered saline, pH8.0; 0.05% Tween 20; 1% bovine serum albumin and 100 uL was added per corresponding well. Samples were incubated for 1 hour at room temperature with shaking (300 rpm). The well was then washed 5 times with 100 uL of wash buffer. 100 uL of TMB One Component HRP reagent was added to the well and incubated for 15 minutes in the dark at room temperature. 100 uL of stop solution (Bethyl Laboratories #E115) was then added to each well, directly into the TMB solution. The absorbance was measured on an Envision plate reader at 450 nm.

Table 2 below describes inhibitory effects of compounds of Formula I on the HMT enzyme where "+++++" indicates a measured $IC_{50}$ value <0.025 µM; "++++" indicates a measured $IC_{50}$ value from 0.025 µM to 0.050 µM of the disclosed compound; "+++" indicates a measured $IC_{50}$ value from 0.050 µM to 0.10 µM of the disclosed compound; "++" indicates a measured $IC_{50}$ value from 0.10 µM to 0.50 µM of the disclosed compound; and "+" indicates a measured $IC_{50}$ value >0.50 µM of the disclosed compound.

TABLE 2

| Compounds with an $IC_{50}$ value <0.025 µM | Compounds with an $IC_{50}$ value from 0.025 µM to 0.050 µM | Compounds with an $IC_{50}$ value from 0.050 µM to 0.10 µM | Compounds with an $IC_{50}$ value from 0.10 µM to 0.50 µM | Compounds with an $IC_{50}$ value >0.50 µM |
|---|---|---|---|---|
| 1, 3, 4, 7, 8, 9, 10, 12, 13, 15, 16, 17, 18, 19, 20, 21, 22, | 5, 26, 176 | 14 | 11 | 6, 185, 198 |

TABLE 2-continued

| Compounds with an IC$_{50}$ value <0.025 μM | Compounds with an IC$_{50}$ value from 0.025 μM to 0.050 μM | Compounds with an IC$_{50}$ value from 0.050 μM to 0.10 μM | Compounds with an IC$_{50}$ value from 0.10 μM to 0.50 μM | Compounds with an IC$_{50}$ value >0.50 μM |
|---|---|---|---|---|
| 23, 24, 25, 27, 28, 29, 30, 31, 32, 33, 34, 35, 36, 38, 39, 40, 41, 42, 43, 44, 48, 49, 51, 53, 57, 59, 60, 62, 63, 68, 69, 70, 71, 72, 85, 86, 89, 94, 102, 115, 121, 125, 126, 130, 131, 132, 133, 145, 146, 157, 164, 165, 167, 168, 169, 172, 175, 186, 189 | | | | |

Table 3 below describes the equilibrium dissociation constant (K$_D$) as measured by surface plasmon resonance (SPR) of compounds of Formula I where "+++++" indicates a measured K$_D$ concentration <0.0025 KM; "++++" indicates a measured K$_D$ concentration from 0.0025 M to 0.0050 μM of the disclosed compound; "+++" indicates a measured K$_D$ concentration from 0.0050 μM to 0.010 μM of the disclosed compound; "++" indicates a measured K$_D$ concentration from 0.010 μM to 0.050 μM of the disclosed compound; and "+" indicates a measured K$_D$ concentration >0.050 μM of the disclosed compound.

TABLE 3

| Compounds with an K$_D$ value <0.0025 μM | Compounds with an K$_D$ value from 0.0025 μM to 0.0050 μM | Compounds with an K$_D$ value from 0.0050 μM to 0.010 μM | Compounds with an K$_D$ value from 0.010 μM to 0.050 μM | Compounds with an K$_D$ value >0.050 μM |
|---|---|---|---|---|
| 1, 3, 8, 9, 13, 15, 16, 17, 18, 19, 20, 22, 23, 27, 28, 29, 30, 31, 32, 33, 34, 35, 36, 40, 41, 42, 43, 44, 45, 47, 49, 50, 51, 52, 53, 54, 57, 58, 59, 60, 61, 62, 63, 66, 67, 68, 69, 70, 71, 72, 73, 75, 76, 77, 80, 84, 85, 86, 87, 88, 89, 90, 91, 92, 93, 94, 95, 96, 97, 99, 100, 102, 103, 104, 106, 108, 109, 114, 115, 116, 117, 118, 119, 123, 124, 125, 126, 127, 128, 129, 130, 131, 132, 133, 134, 135, 137, 139, 145, 146, 147, 148, 151, 152, 155, 156, 157, 158, 160, 163, 164, 167, 168, 169, 170, 171, 172, 175, 178, 179, 186, 187, 188, 189, 190, 191, 193, 194, 195, 196, 197 | 12, 21, 24, 37, 38, 46, 48, 55, 56, 64, 74, 81, 82, 110, 111, 112, 136, 142, 144, 150, 153, 154, 162, 166 | 5, 10, 25, 78, 79, 83, 105, 122, 143, 161, 174 | 4, 7, 14, 26, 39, 65, 98, 101, 107, 113, 120, 121, 138, 141, 149, 159, 165, 176, 177, 192, 197 | 6, 11, 140 |

Table 4 below describes inhibitory activity of compounds of Formula on human P-glycoprotein HEK cells (HEK-P-gp) where "+++++" indicates a measured $IC_5$ value <0.025 µM; "++++" indicates a measured $IC_{50}$ value from 0.025 µM to 0.050 µM of the disclosed compound; "+++" indicates a measured $IC_{50}$ value from 0.050 µM to 0.10 µM of the disclosed compound; "++" indicates a measured $IC_{50}$ value from 0.10 µM to 0.50 µM of the disclosed compound; and "+" indicates a measured $IC_{50}$ value >0.50 µM of the disclosed compound.

TABLE 4

| Compounds with an $IC_{50}$ value <0.025 µM | Compounds with an $IC_{50}$ value from 0.025 µM to 0.050 µM | Compounds with an $IC_{50}$ value from 0.050 µM to 0.10 µM | Compounds with an $IC_{50}$ value from 0.10 µM to 0.50 µM | Compounds with an $IC_{50}$ value >0.50 µM |
|---|---|---|---|---|
| 8, 17, 18, 19, 23, 29, 32, 33, 34, 35, 36, 42, 43, 57, 69, 70, 71, 85, 102, 130, 131, 145, 146, 152, 157, 164, 167, 168, 169, 189, 190, 195, 197 | 13, 15, 40, 49, 50, 53, 62, 66, 80, 86, 87, 88, 89, 90, 94, 115, 124, 126, 162, 172, 193, 196 | 12, 20, 21, 27, 28, 30, 31, 38, 44, 46, 48, 51, 59, 60, 68, 72, 73, 75, 92, 96, 106, 125, 133, 135, 151, 156, 186, 191, 194 | 1, 16, 22, 39, 41, 45, 47, 52, 55, 63, 74, 77, 84, 91, 93, 95, 99, 100, 104, 105, 109, 110, 111, 112, 114, 117, 118, 119, 120, 122, 129, 137, 141, 142, 143, 144, 150, 154, 155, 160, 163, 170, 178, 184, 188 | 3, 4, 5, 6, 7, 9, 10, 11, 14, 24, 25, 26, 37, 54, 56, 58, 61, 64, 65, 67, 76, 78, 79, 81, 82, 83, 97, 98, 101, 107, 108, 113, 116, 121, 123, 127, 128, 132, 134, 136, 138, 139, 140, 147, 148, 149, 153, 158, 159, 161, 165, 166, 171, 175, 176, 177, 179, 181, 182, 183, 185, 187, 192 |

Table 5 below describes inhibitory activity of compounds of Formula I on human P-glycoprotein HEK cells (HEK-P-gp) pretreated with elacridar where "+++++" indicates a measured $IC_{50}$ value <0.025 µM; "++++" indicates a measured $IC_{50}$ value from 0.025 µM to 0.050 µM of the disclosed compound; "+++" indicates a measured $IC_{50}$ value from 0.050 µM to 0.10 µM of the disclosed compound; "++" indicates a measured $IC_{50}$ value from 0.10 µM to 0.50 µM of the disclosed compound; and "+" indicates a measured $IC_{50}$ value >0.50 µM of the disclosed compound.

TABLE 5

| Compounds with an $IC_{50}$ value <0.025 µM | Compounds with an $IC_{50}$ value from 0.025 µM to 0.050 µM | Compounds with an $IC_{50}$ value from 0.050 µM to 0.10 µM | Compounds with an $IC_{50}$ value from 0.10 µM to 0.50 µM | Compounds with an $IC_{50}$ value >0.50 µM |
|---|---|---|---|---|
| 1, 8, 13, 15, 17, 18, 19, 23, 29, 31, 32, 33, 34, 35, 36, 41, 42, 43, 44, 49, 57, 59, 60, 62, 63, 69, 70, 71, 72, 85, 86, 89, 94, 102, 115, 126, 130, 131, 133, 145, 146, 152, 156, 157, 164, 167, 168, 169, 172, 189, 190 | 12, 20, 21, 22, 27, 28, 30, 40, 50, 53, 68, 80, 84, 87, 88, 90, 92, 106, 125, 127, 129, 132, 163, 172, 186 | 9, 16, 47, 48, 51, 52, 66, 73, 75, 77, 78, 91, 93, 95, 96, 110, 117, 118, 119, 124, 135, 151, 158, 162, 178, 186, 193, 194, 195, 196, 197 | 3, 7, 10, 24, 38, 39, 45, 46, 54, 55, 56, 74, 79, 97, 100, 104, 105, 109, 111, 112, 114, 116, 120, 122, 137, 138, 139, 142, 143, 144, 147, 148, 150, 154, 155, 160, 170, 175, 179, 184, 188, 191 | 4, 5, 6, 11, 14, 25, 26, 37, 58, 61, 64, 65, 67, 76, 81, 82, 83, 98, 99, 101, 107, 108, 113, 121, 123, 128, 134, 136, 140, 141, 149, 153, 159, 161, 165, 166, 171, 176, 177, 181, 182, 183, 185, 187, 192 |

Table 6 below describes half-maximal effective concentration ($EC_{50}$) of compounds of Formula I in the fetal hemoglobin (HbF) upregulation assay of HUDEP2 cells where "+++++" indicates a measured $EC_{50}$ value <0.025 µM; "++++" indicates a measured $EC_{50}$ value from 0.025 µM to 0.050 µM of the disclosed compound; "+++" indicates a measured $EC_{50}$ value from 0.050 µM to 0.10 µM of the disclosed compound; "++" indicates a measured $EC_{50}$ value from 0.10 µM to 0.50 µM of the disclosed compound; and "+" indicates a measured $EC_{50}$ value >0.50 µM of the disclosed compound.

TABLE 6

| Compounds with an $EC_{50}$ value <0.025 µM | Compounds with an $EC_{50}$ value from 0.025 µM to 0.050 µM | Compounds with an $EC_{50}$ value from 0.050 µM to 0.10 µM | Compounds with an $EC_{50}$ value from 0.10 µM to 0.50 µM |
| --- | --- | --- | --- |
| 17, 33, 71, 115 | 8, 28, 29, 31, 57, 69, 70, 72, 184 | 13, 18, 19, 36, 49 | 23, 30, 62 |

Table 7 below describes half-maximal effective concentration ($EC_{50}$) of compounds of Formula I in the fetal hemoglobin (HbF) upregulation assay of CD34+ cells where "+++++" indicates a measured $EC_{50}$ value <0.025 µM; "++++" indicates a measured $EC_{50}$ value from 0.025 µM to 0.050 µM of the disclosed compound; "+++" indicates a measured $EC_{50}$ value from 0.050 µM to 0.10 µM of the disclosed compound; "++" indicates a measured $EC_{50}$ value from 0.10 µM to 0.50 µM of the disclosed compound; and "+" indicates a measured $EC_{50}$ value >0.50 µM of the disclosed compound.

TABLE 7

| Compounds with an $EC_{50}$ value <0.025 µM | Compounds with an $EC_{50}$ value from 0.050 µM to 0.10 µM | Compounds with an $EC_{50}$ value from 0.10 µM to 0.50 µM |
| --- | --- | --- |
| 17, 131, 164 | 8, 18, 33, 57, 69, 70, 71, 89, 115, 130, 146 | 15, 20, 28, 85, 94 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound having the formula Ih-a:

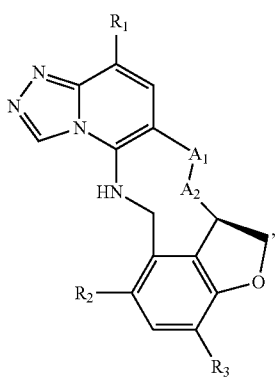

(Ih-a)

or a pharmaceutically acceptable salt thereof, wherein $A_1$ is —O—;

$A_2$ is —CH$_2$—;

$R_2$ and $R_3$ are each independently selected, for each occurrence, from the group consisting of: H, halogen, —OH, and $C_1$ alkyl, wherein the $C_1$ alkyl is optionally substituted with one or more halogens; and $R_1$ is selected from the group consisting of:

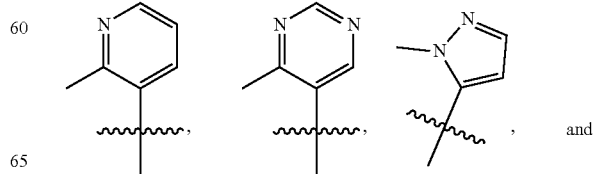

and

2. The compound of claim 1, wherein R₁ is

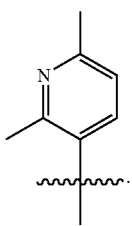

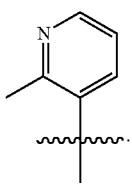 [SMILES: *c1cccnc1C]

3. The compound of claim 2, wherein R₂ is selected from the group consisting of H, C₁ alkyl, and halogen.

4. A compound represented by:

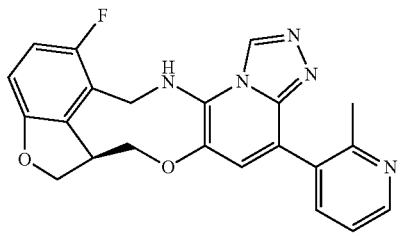 [SMILES: Cc1ncccc1-c1cc2c(n3cnnc13)NCc1c(F)ccc3c1[C@H](CO3)CO2]

or a pharmaceutically acceptable salt thereof.

5. A compound represented by:

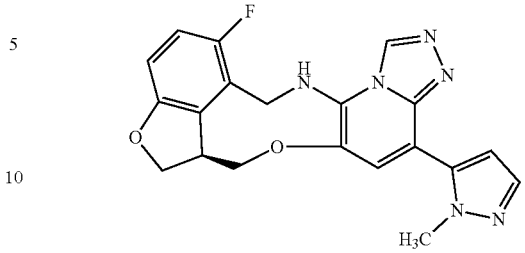

or a pharmaceutically acceptable salt thereof.

6. A pharmaceutical composition comprising the compound of claim 1 and a pharmaceutically acceptable carrier.

7. A pharmaceutical composition comprising the compound of claim 5 and a pharmaceutically acceptable carrier.

8. A pharmaceutical composition comprising the compound of claim 4 and a pharmaceutically acceptable carrier.

9. A method of treating sickle cell disease in a subject in need thereof, comprising administering to the subject an effective amount of the compound of claim 1.

10. A method of treating sickle cell disease in a subject in need thereof, comprising administering to the subject an effective amount of a compound according to the formula:

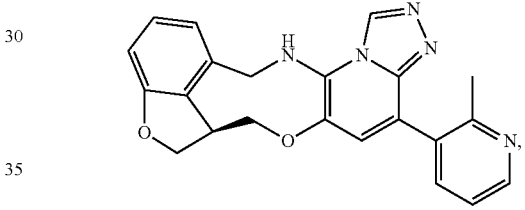

or a pharmaceutically acceptable salt thereof.

* * * * *